US009580719B2

(12) United States Patent
Retallack et al.

(10) Patent No.: US 9,580,719 B2

(45) **Date of Patent: *Feb. 28, 2017**

(54) METHOD FOR RAPIDLY SCREENING MICROBIAL HOSTS TO IDENTIFY CERTAIN STRAINS WITH IMPROVED YIELD AND/OR QUALITY IN THE EXPRESSION OF HETEROLOGOUS PROTEINS

(75) Inventors: Diane M. Retallack, Poway, CA (US); Charles H. Squires, Poway, CA (US); Thomas M. Ramseier, Carmel, IN (US); Russell J. Coleman, San Diego, CA (US); Jane C. Schneider, San Diego, CA (US); Charles D. Hershberger, Fremont, CA (US)

(73) Assignee: PFENEX, INC., San Diego, CA (US)

(*) Notice: Subject to any disclaimer, the term of this patent is extended or adjusted under 35 U.S.C. 154(b) by 475 days.

This patent is subject to a terminal disclaimer.

(21) Appl. No.: 12/610,207

(22) Filed: Oct. 30, 2009

(65) Prior Publication Data

US 2010/0137162 A1 Jun. 3, 2010

Related U.S. Application Data

(63) Continuation-in-part of application No. 12/109,554, filed on Apr. 25, 2008, now Pat. No. 9,394,571.

(60) Provisional application No. 60/914,361, filed on Apr. 27, 2007.

(51) Int. Cl.
*C12N 15/78* (2006.01)

(52) U.S. Cl.
CPC .................................... *C12N 15/78* (2013.01)

(58) Field of Classification Search
None
See application file for complete search history.

(56) References Cited

U.S. PATENT DOCUMENTS

| | | | |
|---|---|---|---|
| 3,844,893 | A | 10/1974 | Hitzman |
| 3,878,093 | A | 4/1975 | Kanani et al. |
| 4,169,010 | A | 9/1979 | Marwil |
| 4,432,895 | A | 2/1984 | Tamowski |
| 4,511,503 | A | 4/1985 | Olson et al. |
| 4,551,433 | A | 11/1985 | DeBoer |
| 4,595,658 | A | 6/1986 | Zinder et al. |
| 4,637,980 | A | 1/1987 | Auerbach et al. |
| 4,680,264 | A | 7/1987 | Puhler et al. |
| 4,695,455 | A | 9/1987 | Bames et al. |
| 4,695,462 | A | 9/1987 | Bames et al. |
| 4,755,465 | A | 7/1988 | Gray et al. |
| 4,861,595 | A | 8/1989 | Bames et al. |
| 4,888,274 | A | 12/1989 | Radding et al. |
| 4,963,495 | A | 10/1990 | Chang et al. |
| 5,023,171 | A | 6/1991 | Ho et al. |
| 5,043,430 | A | 8/1991 | Yoshikawa |
| 5,055,294 | A | 10/1991 | Gilroy |
| 5,082,783 | A | 1/1992 | Ernst et al. |
| 5,084,559 | A | 1/1992 | Profy |
| 5,085,862 | A | 2/1992 | Klein et al. |
| 5,128,130 | A | 7/1992 | Gilroy et al. |
| 5,151,350 | A | 9/1992 | Colbert et al. |
| 5,165,927 | A | 11/1992 | Kaslow |
| 5,169,760 | A | 12/1992 | Wilcox |
| 5,169,772 | A | 12/1992 | Zimmerman et al. |
| 5,173,616 | A | 12/1992 | Hinooka |
| 5,232,840 | A | 8/1993 | Olins |
| 5,264,365 | A | 11/1993 | Georgiou et al. |
| 5,281,532 | A | 1/1994 | Rammler et al. |
| 5,292,507 | A | 3/1994 | Charley |
| 5,292,658 | A | 3/1994 | Cormier et al. |
| 5,348,867 | A | 9/1994 | Georgiou et al. |
| 5,399,684 | A | 3/1995 | Davie et al. |
| 5,418,155 | A | 5/1995 | Cormier et al. |

(Continued)

FOREIGN PATENT DOCUMENTS

| | | |
|---|---|---|
| EP | 0121352 | 10/1984 |
| EP | 0155189 | 9/1985 |

(Continued)

OTHER PUBLICATIONS

Wu et al., 2002, Cell-biological applications of transfected-cell microarrays, Trends in Cell Biology, 12(10): 485-488.*

Asai et al., "DNA microarray analysis of Bacillus subtilis sigma factors of extraplasmic function family," FEMS Microbiol. Ltrs. 220(1):155-160 (2003).

Baneyx, F., "Recombinant Protein Expression in *E. coli*," Curr. Op. Biotech. 10:411-421 (1999).

Baneyx, F. and Georgiou, G., "Construction and Characterization of *Escherichia coli* Strains Deficient in Multiple Secreted Proteases: Protease III Degrades High-Molecular-Weight Substrates In Vivo," J. Bacteriol. 173(8):2696-2703 (1991).

Choi et al., "Enhanced Production of Insulin-Like Growth Factor I Fusion Protein in *Escherichia coli* by Coexpression of the Down-Regulated Genes Identified by Transcriptome Profiling," App. Envir. Microbiol. 69:4737-4742 (2003).

(Continued)

*Primary Examiner* — Mindy G Brown

(74) *Attorney, Agent, or Firm* — Wilson Sonsini Goodrich & Rosati

(57) ABSTRACT

The present invention provides an array for rapidly identifying a host cell population capable of producing a heterologous protein with improved yield and/or quality. The array comprises one or more host cell populations that have been genetically modified to increase the expression of one or more target genes involved in protein production, decrease the expression of one or more target genes involved in protein degradation, or both. One or more of the strains in the array may express the heterologous protein of interest in a periplasm compartment or may secrete the heterologous protein extracellularly through an outer cell wall. The strain arrays are useful for screening for improved expression of any protein of interest including therapeutic proteins, hormones, growth factors, extracellular receptors or ligands, proteases, kinases, blood proteins, chemokines, cytokines, antibodies and the like.

38 Claims, 76 Drawing Sheets

(56) References Cited

U.S. PATENT DOCUMENTS 5,441,934 A 8/1995 Krapcho et al.
5,508,192 A 4/1996 Georgiou et al.
5,527,883 A 6/1996 Thompson et al.
5,558,862 A 9/1996 Corbin et al.
5,559,015 A 9/1996 Capage et al.
5,571,694 A 11/1996 Makoff et al.
5,595,898 A 1/1997 Robinson et al.
5,610,044 A 3/1997 Lam et al.
5,621,074 A 4/1997 Bjorn et al.
5,622,846 A 4/1997 Kiener et al.
5,641,671 A 6/1997 Bos et al.
5,641,870 A 6/1997 Rinderknecht et al.
5,643,774 A 7/1997 Ligon et al.
5,662,898 A 9/1997 Ligon et al.
5,677,127 A 10/1997 Hogan et al.
5,683,888 A 11/1997 Campbell
5,686,282 A 11/1997 Lam et al.
5,686,283 A 11/1997 Gaffney et al.
5,698,425 A 12/1997 Ligon et al.
5,698,435 A 12/1997 Robinson et al.
5,710,031 A 1/1998 Gaffney et al.
5,728,574 A 3/1998 Legg
5,731,280 A 3/1998 Nielsen et al.
5,736,379 A 4/1998 Davie et al.
5,741,663 A 4/1998 Russell
5,741,668 A 4/1998 Ward et al.
5,756,087 A 5/1998 Ligon et al.
5,757,051 A 5/1998 Wu et al.
5,766,926 A 6/1998 Blanchette et al.
5,773,600 A 6/1998 Burnette
5,776,730 A 7/1998 Stuart et al.
5,777,079 A 7/1998 Tsien et al.
5,795,759 A 8/1998 Rosazza et al.
5,804,387 A 9/1998 Cormack et al.
5,824,472 A 10/1998 Betlach et al.
5,834,250 A 11/1998 Wells et al.
5,840,554 A 11/1998 Thompson et al.
5,869,038 A 2/1999 Leifert et al.
5,876,995 A 3/1999 Bryan
5,891,688 A 4/1999 Gaffney et al.
5,914,233 A 6/1999 Mundy et al.
5,914,254 A 6/1999 Mascarenhas et al.
5,919,445 A 7/1999 Chao
5,922,576 A 7/1999 He et al.
5,925,558 A 7/1999 Tsien et al.
5,932,435 A 8/1999 Atkins et al.
5,942,387 A 8/1999 Hollinshead
5,948,681 A 9/1999 Scanlin et al.
5,948,889 A 9/1999 de Boer et al.
5,952,208 A 9/1999 Darzins et al.
5,952,236 A 9/1999 Thompson et al.
5,955,348 A 9/1999 Ligon et al.
5,958,713 A 9/1999 Thastrup et al.
5,968,738 A 10/1999 Anderson et al.
5,968,773 A 10/1999 Heddle et al.
5,968,779 A 10/1999 Campfield et al.
5,985,577 A 11/1999 Bulinski
5,989,808 A 11/1999 Young et al.
5,993,778 A 11/1999 Firestein et al.
5,994,071 A 11/1999 Ross et al.
5,994,077 A 11/1999 Valdivia et al.
6,001,557 A 12/1999 Wilson et al.
6,013,447 A 1/2000 Nilsen et al.
6,015,557 A 1/2000 Tobinick et al.
6,020,192 A 2/2000 Muzyczka et al.
6,025,192 A 2/2000 Beach et al.
6,027,881 A 2/2000 Pavlakis
6,037,133 A 3/2000 Li
6,040,138 A 3/2000 Lockhart et al.
6,051,383 A 4/2000 Thomashow et al.
6,054,321 A 4/2000 Tsien et al.
6,060,247 A 5/2000 Miller et al.
6,066,476 A 5/2000 Tsien et al.
6,071,738 A 6/2000 Johnson et al.
6,077,707 A 6/2000 Tsien et al.
6,080,576 A 6/2000 Zambrowicz et al.
6,083,690 A 7/2000 Harris et al.
6,090,919 A 7/2000 Cormack et al.
6,093,808 A 7/2000 Li
6,096,717 A 8/2000 Jarvik
6,096,865 A 8/2000 Michaels
6,110,711 A 8/2000 Serafini et al.
6,117,670 A 9/2000 Ligon et al.
6,121,247 A 9/2000 Huang et al.
6,124,128 A 9/2000 Tsien et al.
6,130,313 A 10/2000 Li et al.
6,133,429 A 10/2000 Davis et al.
6,136,538 A 10/2000 Olivo et al.
6,136,539 A 10/2000 Basbaum et al.
6,136,566 A 10/2000 Sands et al.
6,140,132 A 10/2000 Tsien et al.
6,146,826 A 11/2000 Chalfie et al.
6,150,176 A 11/2000 Tsien et al.
6,153,409 A 11/2000 Bentley et al.
6,156,313 A 12/2000 Burton et al.
6,156,552 A 12/2000 Okkels et al.
6,172,188 B1 1/2001 Thastrup et al.
6,180,343 B1 1/2001 Anderson et al.
6,184,440 B1 2/2001 Shoseyov et al.
6,194,194 B1 2/2001 Molloy
6,197,928 B1 3/2001 Tsien et al.
6,203,986 B1 3/2001 Singer et al.
6,204,023 B1 3/2001 Robinson et al.
6,210,910 B1 4/2001 Walt et al.
6,210,922 B1 4/2001 Cote et al.
6,214,563 B1 4/2001 Negulescu et al.
6,214,567 B1 4/2001 Allen-Hoffmann et al.
6,218,185 B1 4/2001 Shirk et al.
6,221,612 B1 4/2001 Knapp et al.
6,225,082 B1 5/2001 Carson et al.
6,228,639 B1 5/2001 Gaitanaris
6,232,107 B1 5/2001 Bryan et al.
6,246,543 B1 6/2001 Baumgart et al.
6,248,550 B1 6/2001 Tsien et al.
6,248,558 B1 6/2001 Lin et al.
6,251,384 B1 6/2001 Tan et al.
6,251,582 B1 6/2001 Littman et al.
6,251,602 B1 6/2001 Young et al.
6,251,677 B1 6/2001 Wilson et al.
6,255,071 B1 7/2001 Beach et al.
6,255,558 B1 7/2001 Haseloff et al.
6,258,560 B1 7/2001 Leung et al.
6,261,760 B1 7/2001 Fielding et al.
6,261,776 B1 7/2001 Pirrung et al.
6,265,548 B1 7/2001 Pavlakis et al.
6,268,201 B1 7/2001 Alland et al.
6,268,549 B1 7/2001 Sailland et al.
6,270,958 B1 8/2001 Olivo et al.
6,274,354 B1 8/2001 Wilson et al.
6,277,625 B1 8/2001 Huang et al.
6,280,934 B1 8/2001 Madden et al.
6,284,496 B1 9/2001 Litman et al.
6,284,519 B1 9/2001 Young et al.
6,291,175 B1 9/2001 Sevigny et al.
6,291,177 B1 9/2001 Madden et al.
6,303,373 B1 10/2001 Bogan et al.
6,316,181 B1 11/2001 Fillmore et al.
6,319,669 B1 11/2001 Tsien et al.
6,329,172 B1 12/2001 Rhee et al.
6,344,316 B1 2/2002 Lockhart et al.
6,372,225 B1 4/2002 Matsuda et al.
6,403,957 B1 6/2002 Fodor et al.
6,410,229 B1 6/2002 Lockhart et al.
6,420,108 B2 7/2002 Mack et al.
6,447,770 B1 9/2002 Raaijmakers et al.
6,451,536 B1 9/2002 Fodor et al.
6,495,357 B1 12/2002 Fuglsang et al.
6,506,559 B1 1/2003 Fire et al.
6,509,181 B1 1/2003 Danielsen et al.
6,524,827 B2 2/2003 Moller et al.
6,528,298 B1 3/2003 Svendsen et al.
6,532,462 B2 3/2003 Balaban
6,551,784 B2 4/2003 Fodor et al.
6,558,939 B1 5/2003 Madsen et al.

(56) References Cited

U.S. PATENT DOCUMENTS

| | | | | |
|---|---|---|---|---|
| 6,567,540 | B2 | 5/2003 | Balaban et al. | |
| 6,573,099 | B2 | 6/2003 | Graham | |
| 6,576,424 | B2 | 6/2003 | Fodor et al. | |
| 6,600,031 | B1 | 7/2003 | Fodor et al. | |
| 6,607,885 | B1 | 8/2003 | Larossa et al. | |
| 6,608,018 | B1 | 8/2003 | Shinohara | |
| 6,617,143 | B1 | 9/2003 | Fukuyama | |
| 6,642,030 | B1 | 11/2003 | English et al. | |
| 6,673,580 | B2 | 1/2004 | Koren et al. | |
| 6,687,692 | B1 | 2/2004 | Balaban et al. | |
| 6,696,561 | B1 | 2/2004 | Pompujus et al. | |
| 6,800,738 | B1 | 10/2004 | Carter et al. | |
| 6,979,556 | B2 | 12/2005 | Simmons et al. | |
| 7,112,324 | B1 | 9/2006 | Dorken et al. | |
| 7,175,840 | B2 | 2/2007 | Kim et al. | |
| 7,189,389 | B2 | 3/2007 | Yanai et al. | |
| 7,217,796 | B2 | 5/2007 | Wang et al. | |
| 7,235,641 | B2 | 6/2007 | Kufer et al. | |
| 7,270,993 | B2 | 9/2007 | Smit et al. | |
| 7,338,794 | B2 | 3/2008 | Gaertner et al. | |
| 7,381,804 | B2 | 6/2008 | Osslund | |
| 7,399,463 | B2 | 7/2008 | Shirley et al. | |
| 7,411,050 | B2 | 8/2008 | Anderson | |
| 7,416,849 | B2 | 8/2008 | Allen et al. | |
| 7,427,596 | B2 | 9/2008 | Keyt et al. | |
| 7,439,063 | B2 | 10/2008 | Digicaylioglu et al. | |
| 7,439,323 | B2 | 10/2008 | Bielicki | |
| 7,445,772 | B2 | 11/2008 | West et al. | |
| 7,452,971 | B2 | 11/2008 | Vitetta et al. | |
| 7,459,540 | B1 | 12/2008 | Thomason et al. | |
| 7,491,697 | B2 | 2/2009 | Beals et al. | |
| 7,504,237 | B2 | 3/2009 | Jensen et al. | |
| 7,524,931 | B2 | 4/2009 | Van Den Hazel et al. | |
| 7,537,771 | B2 | 5/2009 | Williamson et al. | |
| 7,544,519 | B2 | 6/2009 | Hsu et al. | |
| 7,547,821 | B2 | 6/2009 | Moloney et al. | |
| 7,553,940 | B2 | 6/2009 | Fares et al. | |
| 7,553,941 | B2 | 6/2009 | Fares et al. | |
| 7,556,817 | B2 | 7/2009 | Steward et al. | |
| 7,560,112 | B2 | 7/2009 | Chen et al. | |
| 7,563,443 | B2 | 7/2009 | Grant et al. | |
| 7,566,566 | B2 | 7/2009 | Alitalo et al. | |
| 7,566,769 | B2 | 7/2009 | Browning et al. | |
| 7,575,923 | B2 | 8/2009 | Dorken et al. | |
| 7,576,190 | B2 | 8/2009 | Glaesner et al. | |
| 7,582,607 | B2 | 9/2009 | Frye et al. | |
| 7,585,942 | B2 | 9/2009 | Harrison et al. | |
| 7,618,799 | B2 | 11/2009 | Coleman et al. | |
| 7,985,564 | B2 | 7/2011 | Retallack et al. | |
| 8,288,127 | B2 | 10/2012 | Schneider et al. | |
| 8,603,824 | B2 | 12/2013 | Ramseier et al. | |
| 9,109,229 | B2 | 8/2015 | Ramseier et al. | |
| 2003/0013150 | A1 | 1/2003 | Manosroi et al. | |
| 2003/0044906 | A1 | 3/2003 | Habermann et al. | |
| 2003/0064435 | A1 | 4/2003 | Weiner et al. | |
| 2003/0108923 | A1 | 6/2003 | Tuschl et al. | |
| 2003/0114409 | A1 | 6/2003 | Mello et al. | |
| 2003/0157069 | A1 | 8/2003 | Lyman et al. | |
| 2003/0180937 | A1 | 9/2003 | Georgiou et al. | |
| 2004/0028705 | A1 | 2/2004 | Ballard et al. | |
| 2004/0138127 | A1 | 7/2004 | Davidson et al. | |
| 2004/0157289 | A1 | 8/2004 | Salerno et al. | |
| 2004/0180378 | A1 | 9/2004 | Tozer et al. | |
| 2005/0186666 | A1 | 8/2005 | Schneider et al. | |
| 2005/0214321 | A1 | 9/2005 | Rasochova et al. | |
| 2006/0040352 | A1 * | 2/2006 | Retallack et al. | ........... 435/69.1 |
| 2006/0062784 | A1 | 3/2006 | Grant et al. | |
| 2006/0110747 | A1 | 5/2006 | Ramseier et al. | |
| 2006/0115470 | A1 | 6/2006 | Silence et al. | |
| 2006/0149041 | A1 | 7/2006 | Silence | |
| 2006/0193852 | A1 | 8/2006 | Dorken et al. | |
| 2006/0211088 | A1 | 9/2006 | Hermans et al. | |
| 2006/0234346 | A1 | 10/2006 | Retallack et al. | |
| 2006/0246477 | A1 | 11/2006 | Hermans et al. | |
| 2007/0077249 | A1 | 4/2007 | Silence et al. | |
| 2007/0123479 | A1 | 5/2007 | Kufer et al. | |
| 2007/0178082 | A1 | 8/2007 | Silence et al. | |
| 2007/0224205 | A1 | 9/2007 | Powell et al. | |
| 2007/0237769 | A1 | 10/2007 | Silence et al. | |
| 2007/0269422 | A1 | 11/2007 | Beirnaert et al. | |
| 2008/0096223 | A1 | 4/2008 | De Groot et al. | |
| 2008/0107601 | A1 | 5/2008 | Lauwereys et al. | |
| 2008/0107673 | A1 | 5/2008 | Ballard et al. | |
| 2008/0193974 | A1 | 8/2008 | Coleman et al. | |
| 2008/0267949 | A1 | 10/2008 | Revets et al. | |
| 2008/0269070 | A1 | 10/2008 | Ramseier et al. | |
| 2009/0022721 | A1 | 1/2009 | Silence et al. | |
| 2009/0028880 | A1 | 1/2009 | Beirnaert et al. | |
| 2009/0062143 | A1 | 3/2009 | Ramseier et al. | |
| 2009/0074770 | A1 | 3/2009 | Lasters et al. | |
| 2009/0148438 | A1 | 6/2009 | Nuttal et al. | |
| 2009/0191186 | A1 | 7/2009 | Bebbington et al. | |
| 2009/0226432 | A1 | 9/2009 | Lutterbuse et al. | |
| 2009/0226444 | A1 | 9/2009 | Rau et al. | |
| 2009/0238829 | A1 | 9/2009 | Silence et al. | |
| 2009/0252681 | A1 | 10/2009 | Laeremans et al. | |
| 2014/0162279 | A1 | 6/2014 | Ramseier et al. | |

FOREIGN PATENT DOCUMENTS

| | | | | | |
|---|---|---|---|---|---|
| EP | 0177343 | A1 | 4/1986 | | |
| EP | 0288451 | A2 | 10/1988 | | |
| EP | 0 404 097 | | 12/1990 | | |
| EP | 0207459 | B1 | 3/1991 | | |
| EP | 1709170 | | 10/2006 | | |
| FR | 2567540 | | 1/1986 | | |
| JP | 2001-299360 | A | 10/2001 | | |
| JP | 2004502929 | A | 1/2004 | | |
| JP | 2006-501811 | | 1/2006 | | |
| JP | H9-506508 | | 6/2009 | | |
| KR | 10-2003-0074654 | | 9/2003 | | |
| WO | WO-87-05937 | | 10/1987 | | |
| WO | WO-87-05938 | | 10/1987 | | |
| WO | WO-89-10971 | | 11/1989 | | |
| WO | WO-90-03438 | A1 | 4/1990 | | |
| WO | WO-92-15673 | | 9/1992 | | |
| WO | WO-93-11161 | | 6/1993 | | |
| WO | WO-95-03395 | | 2/1995 | | |
| WO | WO-95-07463 | | 3/1995 | | |
| WO | WO-96-17943 | | 6/1996 | | |
| WO | WO-97-22687 | A1 | 6/1997 | | |
| WO | WO-98-14605 | | 4/1998 | | |
| WO | WO-98-24919 | | 6/1998 | | |
| WO | WO-98-26277 | | 6/1998 | | |
| WO | WO-99-09834 | | 3/1999 | | |
| WO | WO-99-15650 | | 4/1999 | | |
| WO | WO-99-49019 | | 9/1999 | | |
| WO | WO-99-53035 | | 10/1999 | | |
| WO | WO-00-15761 | | 3/2000 | | |
| WO | WO-00-29604 | | 5/2000 | | |
| WO | WO-00-59537 | | 10/2000 | | |
| WO | WO-01-21662 | | 3/2001 | | |
| WO | WO-01-27258 | | 4/2001 | | |
| WO | WO 01/32844 | | * | 5/2001 | ............... C12N 9/00 |
| WO | WO-01-32844 | A1 | 5/2001 | | |
| WO | WO 02-02794 | | 1/2002 | | |
| WO | WO-02-14551 | | 2/2002 | | |
| WO | WO-02-16940 | | 2/2002 | | |
| WO | WO-02-40696 | | 5/2002 | | |
| WO | WO-02-48376 | A2 | 6/2002 | | |
| WO | WO-02-068660 | | 9/2002 | | |
| WO | WO-03-006477 | | 1/2003 | | |
| WO | WO-03-012052 | | 2/2003 | | |
| WO | WO-03-023015 | | 3/2003 | | |
| WO | WO-03-056022 | | 7/2003 | | |
| WO | WO-03-064435 | | 8/2003 | | |
| WO | WO-03-064621 | | 8/2003 | | |
| WO | WO-03-068926 | A2 | 8/2003 | | |
| WO | WO-03-070966 | | 8/2003 | | |
| WO | WO-03-079007 | | 9/2003 | | |
| WO | WO-03-089455 | A2 | 10/2003 | | |
| WO | WO-2004-005221 | A2 | 1/2004 | | |
| WO | WO-2004-006657 | | 1/2004 | | |
| WO | WO-2004-011628 | | 2/2004 | | |

(56) References Cited

FOREIGN PATENT DOCUMENTS

| | | | | |
|---|---|---|---|---|
| WO | WO-2004-055206 | | 7/2004 | |
| WO | WO-2004-087864 | | 10/2004 | |
| WO | WO-2005-014639 A2 | | 2/2005 | |
| WO | WO-2005-052151 A1 | | 6/2005 | |
| WO | WO-2005-069913 | | 8/2005 | |
| WO | WO-2005-089093 | | 9/2005 | |
| WO | WO-2005-103077 | | 11/2005 | |
| WO | WO-2005-115622 | | 12/2005 | |
| WO | WO 2006/014899 | * | 2/2006 | ............. C12P 21/06 |
| WO | WO-2006-059701 | | 6/2006 | |
| WO | WO-2006-066001 | | 6/2006 | |
| WO | WO-2008-017906 | | 2/2008 | |
| WO | WO-2008-134461 | | 7/2008 | |
| WO | WO-2008-094986 | | 8/2008 | |

OTHER PUBLICATIONS

Eymann et al., "Bacillis subtilis functional genomics: global characterization of the stringent response by proteome and transcriptome analysis," J. Bacteriol. 184(9):25002520 (2002).

Fathallah-Shaykh, H.M., "Microarrays: applications and pitfalls," Arch. Neurol. 62(11):1669-1672 (2005).

Gill et al., "Genomic Analysis of High-Cell-Density Recombinant *Escherichia coli* Fermentaion and "Cell Conditioning" for Improved Recombinant Protein Yield," Biotech. Bioengin. 72:85-95 (2001).

Gottesman, PRoteases and their targets in *Escherichia coli*, Ann. Rev. Genet. 30:465-506 (1996).

Gottesman et al., "The ClpXP and ClpAP proteases degrade proteins with carboxyl-terminal peptide tails added by the SsrA-tagging system," Genes Dev. 12:1338-1347 (1998).

Han et al., "Engineering *Escherichia coli* for Increased Productivity of Serine_Rich Proteins Based on Proteome Profiling," Applied Env. Microbiol. 69(10):5772-5781 (2003).

Herman et al., "Degradation of carboxyl-terminal-tagged cytoplasmic proteins by the *Escherichia coli* protease HflB," Genes Dev. 12:1348-1355 (1998).

Kabir et al., Gene expression patterns for metabolic pathway in pgi knockout *Escherichia coli* with and without phb genes based on RT-PCT, J. Biotech. 105(1-2):11-31 (2003).

Lee et al., "Global analysis of transcriptomes and proteomes of a parent strain and an L-threonine-overproducing mutant strain," J. Bacteriol. 185(18):5442-5451 (2003).

Lee et al., "Effect of overproduction in *Escherichia coli*," JBC 267:2849-2852 (1992).

Nishihara et al., "Chaperone coexpression plasmids: differential and synergistic roles of DnaK-DnaJ-GrpE and GroEl-GroES in assisting folding of an allergen of Japanese cedar pollen, Cryj2, in *Escherichia coli*," Appl. Environ. Microbiol. 64:1694 (1998).

Park et al., "Secretory production of recombinant protein by a high density culture of a protease negative mutant *Escherichia coli* strain," Biotech. Progr. 15:164-167 (1999).

Sabina et al., "Interfering with Different Steps of Protein Synthesis Explored by Transcriptional Profiling of *Escherichia coli* K-12," J. Bacteriol. 185:6158-6170 (2003).

Thomas, J.G. et al., "Molecular Chaperones, Folding Catalysts, and the Recovery of Active Recombinant Proteins from *E. coli*—To Fold or to Refold," Applied Biochem. Biotechnol. 66:197-238 (1997).

Wall, G.J. and Pluckthun, A., "Effects of Overexpressing Folding Modulators on the in vivo Folding of Heterologous Proteins in *Escherichia coli*," Curr. Op. Biotechnol. 6:507-516 (1995).

Wei et al., "High-density microarray-mediated gene expression profiling of *Escherichia coli*," J. Bacteriol. 183(2):545-556 (2001).

PCT/US08/61483 Search Report dated Nov. 7, 2008.

PCT/US05/26390 Search Report dated Jul. 17, 2006.

Abdullah et al., "System-48" high-throughput cloning and protein expression analysis," Methods Mol Biol 498:117-127 (2009).

Akao et al., "Purification and Characterization of a Peptide Essential for Formation of Streptolysin S by *Streptococcus pyogenes*," Infection and Immunity 60(11):4777-4780 (1992).

Amitani et al., "Purification and Characterization of Factors Produced by Aspergillus fumigatus Which Affect Human Ciliated Respiratory Epithelium," Infection and Immunity 63(9):3266-3271 (1995).

Aricescu et al., "Eukaryotic expression: developments for structural proteomics," Acta Cryst D62:1114-1124 (2006).

Aricescu et al., "A time—and cost-efficient system for high-level protein production in mammalian cells," Acta Cryst D62:1243-1250 (2006).

Bahia et al., "Optimisation of insect cell growth in deep-well blocks: development of a high-throughput insect cell expression screen," Protein Expression and Purification 39:61-70 (2005).

Baldwin et al., "Subunit Vaccine against the Seven Serotypes of Botulism," Infection and Immunity 76(3):1314-1318 (2008).

Bebbington and Yarranton, "Antibodies for the treatment of bacterial infections: current experience and future prospects," Curr Op Biotech 19(6):613-619 (2008).

Boettner et al., "High-throughput screening for expression of heterologous proteins in the yeast *Pichia pastoris*," J Biotech 99:51-62 (2002).

Buzzi et al., "CRM197: reduction of atherosclerosis stenoses in carotids of three elderly patients," Therapy 4(3):293-298 (2007).

Calvete et al., "The disulfide bond pattern of catrocollastatin C, a disintegrin-like/cysteine-rich protein isolated from Crotalus atrox venom," Protein Science 9:1365-1373 (2000).

Cosman, D., "A Family of Ligands for the TNF Receptor Superfamily," Stem Cells 12:440-455 (1994).

Damasceno et al., "Cooverexpression of chaperones for enhanced secretion of a single-chain antibody fragment in Pichia pastoris," Appl Microbiol Biotechnol 74:381-389 (2007).

Duetz et al., "Methods for Intense Aeration, Growth, Storage, and Replication of Bacterial Strains in Microtiter Plates," Appl Env Microbiol 66(6):2641-2646 (2000).

Duetz and Witholt, "Oxygen transfer by orbital shaking of square vessels and deepwell microtiter platesof various dimensions," Biochem Eng J 17:181-185 (2004).

Edmond et al., "Optimized and automated protocols for high-throughput screening of amylosucrase libraries," J Biomol Screen 12:715-723 (2007).

Fang et al., "Development of a high-throughput yeast two-hybrid screening system to study protein-protein interactions in plants," Mol Genet Genomics 267:142-153 (2002).

Fischer and Montal, "Crucial Role of the Disulfide Bridge between Botulinum Neurotoxin Light and Heavy Chains in Protease Translocation across Membranes," J Biol Chem 282(40):29604-29611 (2007).

Georgopoulos, "Toothpicks, Serendipity and the Emergence of the *Escherichia coli* DnaK (Hsp70) and GroEL (Hsp60) Chaperone Machines," Genetics 174:1699-1707 (2006).

Giannini et al., "The amino-acid sequence of two non-toxic mutants of diphtheria toxin: CRM45 and CRM 197," Nucl Acids Res 12(10):4063-4069 (1984).

Gonzalez Barrios et al., "Autoinducer 2 controls biofilm formation in *Escherichia coli* through a novel motility quorum-sensing regulator (MqsR, B3022)," J Bacteriol 188:305-316 (2006).

Halling et al., "Genomic cloning and characterization of a ricin gene from Ricinus communis," Nucl Acids Res 13(22):8019-8033 (1985).

Holz et al., "A micro-scale process for high-throughput expression of cDNAs in the yeast *Saccharomyces cerevisiae*," Protein Expression and Purification 25:372-378 (2002).

Hsu et al., "Engineering the Assembly Pathway of the Baculovirus-Insect Cell Expression System," Annals New York Academy of Sciences 721:208-217 (1994).

Jarvis et al., "Influence of different signal peptides and prosequences on expression and secretion of human tissue plasminogen activator in the baculovirus system," J Biol Chem 268:16754-16762 (1993).

Kim et al., "Glycosyltransferase—a specific marker for the discrimination of Bacillus anthracis from the Bacillus cereus group," J Med Microbiol57:279-286 (2008).

(56) References Cited

OTHER PUBLICATIONS

Larsen et al., "Expression of Candida antarctica lipase B in *Pichia pastoris* and various *Escherichia coli* systems," Protein Expression and Purification 62:90-97 (2008).
Makarenkova et al., "Dendritic cells and natural killer cells interact via multiple TNF family molecules," J Leukocyte Biol 77:408-413 (2005).
Mitamura et al., "Diphtheria Toxin Binds to the Epidermal Growth Factor (EGF)-like Domain of Human Heparin-binding EGF-like Growth Factor/Diphetheria Toxin Receptor and Inhibits Specifically Its Mitogenic Activity," J Biol Chem 270(3):1015-1019 (1995).
Montgomerie et al., "Improving the accuracy of protein secondary structure prediction using structural alignment," BMC Bioinformatics 7:301 (2006).
Naamati et al., "ClanTox: a classifier of short animal toxins," Nucl Acids Res 37:W363-W368 (2009).
Niwa et al., "Bimodal protein solubility distribution revealed by an aggregation analysis of the entire ensemble of *Escherichia coli* proteins," PNAS 106(11):4201-4206 (2009).
Novak et al., "Bacterial growth properties at low optical densities," Antonie Van Leeuwenhoek 96(3):267-274 (2009).
Orr et al., "Expression and Immunogenecitity of a Mutant Diphtheria Toxin Molecule, CRM 197, and Its Fragments in *Salmonella typhi* Vaccine Strain CVD 908-htrA," Infection and Immunity 67(8):4290-4294 (1999).
Papini et al., "Cell Penetration of Diphtheria Toxin," J Biol Chem 268(3):1567-1574 (1993).
Randolph et al., "Amino acid sequence of fibrolase, a direct-acting fibrinolytic enzyme from Agkistrodon contortrix contortrix venom," Protein Science 1:590-600 (1992).
Schiavo et al., "An Intact Interchain Disulfide Bond Is Required for the Neurotoxicity of Tetanus Toxin," Infection and Immunity 58(12):4136-4141 (1990).
Shu et al., "The structure of spider toxin huwentoxin-II with unique disulfide linkage: Evidence for structural evolution," Protein Science 11:245-252 (2002).
Smialowski et al., "Protein solubility: sequence based prediction and experimental verification," Bioinformatics 23(19):2536-2542 (2007).
Tsai and Rapoport, "Unfolded cholera toxin is transferred to the ER membrane and released from protein disulfide isomerase upon oxidation by Erol," J Cell Biol 159(2):207-215 (2002).
Tsunawaki et al., "Fungal Metabolite Gliotoxin Inhibits Assembly of the Human Respiratory Burst NADPH Oxidase," Infection and Immunity 72(6):3373-3382 (2004).
Usami et al., "Primary structure of two-chain botrocetin, a von Willebrand factor modulator purified from the venom of Bothrops jararaca," PNAS USA 90:928-932 (1993).
Vad et al., "Engineering of a Pichia pastoris expression system for secretion of high amounts of intact human parathyroid hormone," J Biotechnology 116:251-260 (2005).
Yuan et al., "Discovery of a Distinct Superfamily of Kunitz-Type Toxin (KTT) from Tarantulas," PLoS One 3(10):e3414 (2008).
Zhang et al., "Enhanced Secretion of Heterologous Proteins in Pichia pastoris Following Overexpression of *Saccharomyces cerevisiae* Chaperone Proteins," Biotechnol Prog 22:1090-1095 (2006).
EP11173331.7 Office action dated Nov. 6, 2013.
Japanese Patent Application 2007-523707 Office Action dated Feb. 28, 2014.
Korean Patent Application 10-2013-7002343 Office Action dated Feb. 25, 2014.
U.S. Appl. No. 11/038,901 Office Action mailed Dec. 17, 2013.
U.S. Appl. No. 11/400,840 Office Action mailed Mar. 28, 2014.
Canadian Patent Application CA2553503 Exam Report dated Apr. 29, 2014.
Canadian Patent Application CA2685326 Office Action dated May 22, 2014.
Japanese Patent Application 2006-549690 Office Action mailed Mar. 11, 2014.
Japanese Patent Application 2011-132011 Office Action mailed Mar. 25, 2014.
Korean Patent Application 10-2009-7024636 Office Action dated Nov. 26, 2014 (with English language reporting letter from the foreign associate).
U.S. Appl. No. 11/038,901 Supp. RR mailed Oct. 10, 2014.
U.S. Appl. No. 14/071,273 Non Final Office Action mailed Oct. 9, 2014.
Canadian Patent Application No. 2,685,326 Office Action mailed Jul. 30, 2015.
EP Application No. 05705852.1 Invitation pursuant to Article 94(3) dated May 26, 2015.
European Patent Application No. 11176612.7 Communication dated Nov. 20, 2015.
India Patent Application No. 6791/DELNP/2009 First Examination Report dated May 26, 2015.
U.S. Appl. No. 11/038,901 Office Action mailed May 4, 2015.
U.S. Appl. No. 11/400,840 Office Action dated Apr. 30, 2015.
U.S. Appl. No. 11/400,840 Office Action dated Jan. 12, 2016.
U.S. Appl. No. 12/109,554 Office Action dated Nov. 6, 2015.
Ada, Gordon, et al., Overview of Host Defense Mechanisms with Special Reference to Viral Infections, Gamma Interferon in Antiviral Defense, 1997, Chapter 1, pp. 1-18, R.G. Landes Group.
Ahn Jung Hoon, et al., Homologous Expression of the Lipase and ABC Transporter Gene Cluster, tIiDEFA, Enhances Lipase Secretion in *Psuedomonas* spp., Appl. Environ. Microbiol., Dec. 2001, pp. 5506-5511, vol. 67, No. 12, American Society for Microbiology.
Akao, et al., "Unique synthetic peptides stimulating streptolysin S production in *Streptococci*," 1999, J. Biochem. 125(1):27-30.
Altschul, Stephen F., et al., Basic Alignment Search Tool, J. Mol. Biol., 1990, pp. 403-410, vol. 215.
Ames, et al., "Simple, Rapid, and Quantitive Release of Periplasmic Proteins by Chloroform," 1984, J. Bacteriol., 160(3): 1181-1183.
Andersen, D.C., et al., "Production technologies for monoclonal antibodies and their fragments," Current Opinion in Biotechnology, London, GB, vol. 15, No. 5, Oct. 1, 2004, pp. 456-462.
Anderson, et al., "A homologue of the TNF receptor and its ligand enhance T-cell growth and dendritic-cell function," 1997, Nature 390 (6656), 175-179.
Anderson, Kevin P., et al., Enhancement of a Secondary Antibody Response to Vesicular Stomatitis Virus G Protein by IFN-γ Treatment at Primary Immunization. The Journal of Immunology, 1988, pp. 3599-3604, vol. 140, No. 10, The American Association of Immunologists.
Appa Rao, et al., "High-Level expression of ovine growth hormone in *Escherichia coli*: single-step purification and characterization," Protein Expr Purif, 1997, vol. 1, No. 2, pp. 201-208.
Ariga, et al.,"Release of Thermophilic α-amylase from Transformed *Escherichia coli* by Addition of Glycine," 1989, J. Ferm. Bioeng., 68:243-246.
Arthur, et al., High Level expression of interleukin-1beta in a recombinant *Escherichia coli* strain for use in a controlled bioreactor, Journal of Biotechnology, Elsevier Science Publishers, 1990, vol. 13, No. 1, pp. 29-46.
Asami, et al., "Synchronized disruption of *Escherichia coli* cells by T4 Phage Infection." 1997, J. Ferment and Bioeng., 83: pp. 511-516.
AU Patent Application 2005206951 Office Action issued Jan. 16, 2009.
AU Patent Application 2005269527 Office Action issued Nov. 3, 2010.
AU Patent Application 2008245696 Office Action issued Oct. 24, 2012.
Babiuk, L.A., et al., Symposium Immunobiology of Cytokines and Their Application in Disease Prevention in Dairy Cattle, J. Dairy Sci., 1991, vol. 74, pp. 4385-4398, Veterinary Infectious Disease Organization.
Bagdasarian, M. and Timmis, K., "Host: Vector Systems for Gene Cloning in Pseudomonas." 1982, Curr. Topics Microbial. Immunol , pp. 47-67, vol. 96.
Bagdasarian, M., et al., Specific-purpose plasmid cloning vectors II. Broad host range, high copy number, RSF1010-derived vectors, and a host-vector system for gene cloning in *Pseudomonas*, 1981, Gene, pp. 237-247, vol. 16, Elsevier/North-Holland Biomedical Press.

(56) References Cited

OTHER PUBLICATIONS

Baldwin, G.S., Comparison of Transferrin Sequences From Different Species. 1993, Comp. Biocherm Physiol., vol. 106B. No. 1, Pergamon Press Ltd., pp. 203-218.
Bardwell, et al., "Pathways of Disulfide Bond Formation in Proteins in Vivo," 1994, Phosphate Microorg. Chapter 45, pp. 270-275.
Bellini, et al., "Production processes of recombinant IL-lbeta from Bacillus subtilis: comparison between intracellular and exocellular expression," Journal of Biotechnology, Elsevier Science, 1991, vol. 18, No. 3, pp. 177-192.
Benoist & Chambon, "In vivo sequence requirements of the SV40 early promoter region," 1981, Nature 290:304-310.
Berrow, N.S. et al., "Recombinant protein expression and solubility screening in *Escherichia coli*: a comparative study." 2006, Biological Crystallography. 62: 1218-1226.
Blattner, et al., "The Complete Genome Sequence for *Escherichia coli* K-12." 1997, Science 277 (5331): 1453-74.
Bohnsack, R.N. "Site-directed mutagenesis using positive antibiotic selection." 1996, Meth. Mol. Biol. 57,1-12.
Brosius Jurgen, "Toxicity of an overproduced foreign gene product in *Escherichia coli* and its use in plasmid vectors for the selection of transcription terminators." 1984, Gene 27(2): 161-72.
Broxmeyer, H.E., Monocyte-Macrophage-Derived Acidic Isoferritins: Nomal Feedback Regulators of Granulocyte-Macrophage Progenitor Cells In Vitro, Blood, 1982, pp. 595-607, vol. 60, American Society of Hematology.
Butte, A. "The use and analysis of microarray data." 2002, Nat Rev Drug Discov 1:951-60.
Canadian Patent Application CA2553503 Exam Report dated May 10, 2011.
Canadian Patent Application CA2553503 Exam Report dated May 2, 2012.
Canadian Patent Application CA2553503 Exam Report dated May 2, 2013.
Canadian Patent Application CA2574953 Office Action dated Jun. 27, 2012.
Canadian Patent Application CA2574953 Office Action dated Jul. 23, 2013.
Carrier, M.I., et al., Expression of Human IL-1B in *Salmonella typhimurium* a Model System for the Delivery of Recombinant Therapeutic Proteins in Vivo, The Journal of Immunology, 1992, pp. 1176-1181, vol. 148, No. 4, The American Association of Immunologists.
Carter et al., "High Level *Escherichia coli* expression and production of a bivalent humanized antibody fragment." 1992, Bio/ Technology, 10: 163-167.
Casavant, et al., "Use of a site-specific recombination-based biosensor for detecting bioavailable toluene and related compounds on roots." Environmental Microbiology, Apr. 2003, pp. 238-249, vol. 5, No. 4, Society for Applied Microbiology.
Cerretti, Douglas Pat., et al., Cloning, Sequence, and Expression of Bovine Interferon-γ, The Journal of Immunology, 1986, pp. 4561-4564, vol. 136, No. 12, The American Association of Immunologists.
Chalfie, et al., "Green fluorescent protein as a marker for gene expression." 1994, Science 263(5148):802-805.
Chang and Cohen "Construction and Characterization of Amplifiable Multiopy DNA Cloning Vehicles Derived from the P15A Cryptic Miniplasmid." 1978, Journal of Bacteriology, vol. 134, No. 3, p. 1141-1156.
Chew, et al., "Production of Recombinant Proteins. Novel Microbial and Eucaryotic Expression Systems," 2005, G. Gellissen, Weinheim, Wiley-VCH: 45-66.
Chiou et al., "Cobra venom cardiotoxin (cytotoxin) isoforms and neurotoxin: Comparative potency of protein kinase C inhibition and cancer cell cytotoxicity and modes of enzyme inhibition," 1993, Biochemistry, 32 (8), pp. 2062-2067.
Cho, Won-Kyung, et al., "Production and In Vitro Refolding of a Single-Chain Antibody Specific for Human Plasma Apolipoprotein A-I". Journal of Biotechnology, 2000, pp. 169-178, vol. 77, Elsevier Science B.V.
Clark-Curtiss, Josephine, et al., "Analysis of Recombinant DNA Using *Escherichia coli* Minicells." Methods in Enzymology, 1983, vol. 101, pp. 347-362, Academic Press, Inc.
CN200580032245 Office Action dated Apr. 12, 2012.
CN200880022208 Secord Office Action dated Jul. 16, 2012.
Dabora and Cooney, "Intracellular lytic enzyme systems and their use for disruption of *Escherichia coli.*" 1990, Advances in Biochemical Engineering/Biotechnology, vol. 43, A. Fiechter, ed. (Springer-Verlag: Berlin), pp. 11-30.
Dammeyer et al., "Efficient production of soluble recombinant single chain Fv fragments by a *Pseudomonas putida* strain KT2440 cell factory." 2011, Microbial Cell Factories, vol. 10, pp. 1-8.
Davis and ES Mingioli "Mutants of *Escherichia coli* Requiring Methionin or Vitamin B12." (1950) J. Bact. 60:17-28.
Davis, Bernard D., et al., Mutants of *Escherichia coli* Requiring Methionine or Vitamin B12, 1950, J. Bact., pp. 1728, vol. 60.
De Marco, Ario, et al., Native folding of aggregation-prone recombinant proteins in *Escherichia coli* by osmolytes, plasmid- or benzyl alcohol-overexpressed molecular chaperones, 2005, Cell Stress and Chaperones, 10(4), pp. 329-339, Cell Stress Society International.
Deng, W.P. and Nickoloff, J.A., "Site-directed mutagenesis of virtually any plasmid by eliminating a unique site," 1992, Anal. Biochem. 200, 81.
Dolinski, et al., "Peptidyl-prolyl isomerases—an overview of the cyclophilin, FKBP and parvulin families in Guidebook to Molecular Chaperones and Protein-Folding Catalysts." (1997) Gething M-J Ed. Oxford University Press Inc. New York. pp. 359-369.
Doudoroff, M., et al., Gram-Negative Aerobic Rods and Cocci, 1974, Bergey's Manual of Determinative Bacteriology, edited by Buchanan and Gibbons, pp. 217-289.
Dulebohn, D., "Trans-Translation: The tmRNA-Mediated Surveillance Mechanism for Ribosome Rescue, Directed Protein Degradation, and Nonstop mRNA Decay," Biochemistry, 2007, 46 (16): 4681-4693.
Elbashir, et al., "Duplexes of 21-nucleotide RNAs mediate RNA interference in cultured mammalian cells," 2001, Nature 411(6836): 494-8.
Elbashir, et al., "RNA interference is mediated by 21-and 22-nucleotide RNAs," 2001, Genes & Development 15(2):188-200.
EP 05705852 Supplementary European Search Report dated Mar. 18, 2008.
EP05705852 European Search Report dated Oct. 5, 2011.
EP05774619 Examination Report dated Oct. 29, 2010.
EP05774619 International Search Report dated Apr. 4, 2009.
EP08746833.6 Exam Report dated Feb. 15, 2012.
EP11173331.7 Examination Report issued Dec. 19, 2012.
EP11173331.7 Extended search report dated Apr. 18, 2012.
EP11173331.7 Partial Search Report dated Dec. 27, 2011.
EP11176612 Extended European Search Report dated Jul. 18, 2012.
EP11176612 Partial European Search Report dated Jan. 25, 2012.
EP12198545 Extended European Search Report dated Jun. 14, 2013.
Espejo, A., "Protein-domain microarrays Processes," 2004, Mol Biol., 264:173-81.
Fire, ,A. et al. "Potent and specific genetic interference by double-stranded RNA in Caenorhabdtis elegans,." 1998, Nature 391:806-11.
Fleer et al., "High-level secretion of correctly processed recombinant human interleukin-1 beta in *Kluyveromyces lactis.*" Gene, Elsevier, 1991, vol. 107, No. 2, pp. 285-295.
Foss, FM, 2001, "Interleukin-2 fusion toxin: targeted therapy for cutaneous T cell lymphoma," Ann N Y Acad Sci. 941:166-76.
Fox, L.K., et al., The Effect of Interferon-γ Intramammary Administration on Mammary Phagocyte Function, J. Vet. Med., 1990, pp. 28-30. Paul Parey Scientific Publishers.
Fransen, Lucie, et al., Recombinant Tumor Necrosis Factor: Species Specificity for a Variety of Human and Murine Transformed Cell Lines, Cellular Immunology, 1986, vol. 100, Academic Press, Inc., pp. 260-267.

(56) References Cited

OTHER PUBLICATIONS

French et al., "Development of a simple method for the recovery of recombinant proteins from the *Escherichia coli* periplasm." 1996, Enzyme and Microb. Tech., 19:332-338.
Friedman, Robert M., et al., Interferon with Special Emphasis on the Immune System, Advances in Immunology, pp. 97-140, 1983, vol. 34, Academic Press Inc.
Frishman, Dmitrij, et al., Starts of bacterial genes: estimating the reliability of computer predictions, Gene, 1999, vol. 234, Elsevier Science B.V., pp. 257-265.
Furlong and Sundstrom, "Immobilized cell bioreactors for producing immobilized protein bioadsorbers," 1989, Developments in Industrial Microbiology, vol. 30, pp. 141-148.
Gaertner, Frank H., CellCap: An Encapsulation System for Insecticidal Biotoxin Proteins, Advanced Engineered Pesticides, 1993, pp. 73-83, Marcel Dekker, New York.
Gaertner, Frank H., et al., Amended recombinant cells (ARCs(TM)): An economical and surprisingly effective production and delivery vehicle for recombinant bovine IFN-γ, Journal of Controlled Release, Oct. 2005, vol. 107, Elsevier B.V., pp. 189-202.
Gardiner et al., "Bioinformatic and expression analysis of the putative gliotoxin biosynthetic gene cluster of Aspergillus fumigatus," 2005, FEMS Microbiol. Lett. 248(2):241-248.
Gardy, et al., 2005 PSORTb v.2.0 expanded prediction of bacterial protein subcellular localization and insights gained from comparative proteome analysis. Bioinformatics 21(5): 617-623.
Gellison, ed. Production of Recombinant Proteins, Novel Microbial and Eukaryotic Expression Systems, Wiley-VCH 2005, pp. 47-48.
Gene Ontology Consortium 2004, The Gene Ontology (GO) database and informatics resource, Nucleic Acids Research 32: D258-D261.
Georgiou, et al., "Preparative expression of secreted proteins in bacteria: status report and future prospects," 2005, Current Opinion in Biotechnology, vol. 16, pp. 538-545.
Gillette, W.K., et al., Pooled ORF Expression Technology (POET), Molecular and Cellular Proteomics, 4: 1657-1652 (2005).
Goeddel, et al., "Expression in *Escherichia coli* of chemically synthesized genes for human insulin," Jan. 1979, Proc. Nat. Acad. Sci. USA, vol. 76, No. 1, pp. 106-110.
Gough, R.E., et al., Further Studies on the Adjuvant Effect of an Interferon Inducer (BRL 5907) on Newcastle Disease and Avian Influenza Inactivated Vaccines, Research in Veterinary Science, 1975, vol. 19, pp. 185-188.
Graslund, S. et al., Protein production and purification, Nature Methods, 5:135-146 (2008).
Graupner, S. & Wackernagel, W., "A broad-host-range expression vector series including a Ptac test plasmid and its application in the expression of the dod gene of *Serratia marcescens* (coding for ribulose-5-phosphate 3-epimerase) in *Pseudomonas stutzeri,*" 2000, Biomolecular Engineering, vol. 17, Elsevier Science B.V., pp. 11-16.
Gray, et al, "Structure of the human immune interferon gene." (1982) Nature 298:859-63.
Gray, et al. "Pseudomonas Aeruginosa Secretes and Correctly Processes Human Growth Hormone." (Bio/Technology, Feb. 1984, pp. 161-165).
Greenfield, L., et al., "Nucleotide sequence of the structural gene for diphtheria toxin carried by corynebacteriophage beta," 1983, Proc. Natl. Acad. Sci. USA, 80(22):6853-6857.
Gresser, Ion, et al., Anti-Tumor Effects of Interferon in Mice Injected with Interferon Sensitive and Interferon-Resistant Friend Leukemia Cells. VI. Adjuvant Therapy After Surgery in the Inhibition of Liver and Spleen Metastases, Int. J. Cancer, 1987, vol. 39, Alan R. Liss, Inc., pp. 789-792.
Gruss, P., et al., "Simian virus 40 tandem repeated sequences as an element of the early promoter," 1981, Proc. Nat. Acad. Sci. USA 78:943-947.
Gubler, U., et al., "Recombinant Human Interleukin 1-Alpha Purification and Biological Characterization," Journal of Immunology, 1986, vol. 136, No. 7, pp. 2492-2497.
Guzman, M., et al., "Tight Regulation, Modulation and High-Level Expression by Vectors Containing the Arabinose PBAD Promoter," 1995, Journal of Bacteriology 177(14):4121-30.
Gygi, et al., "Quantitative analysis of complex protein mixtures using isotope-coded affinity tags," Nat. Biotech, Oct. 1999, 17:994-999.
Hamilton, et al., "New Method for generating deletions and gene replacements in *Escherichia coli*," 1989, Journal of Bacteriology 171(9): 4617-4622.
Hancock and I. Poxton, "Isolation and Purification of Cell Walls," 1988, Bacterial Cell Surface Techniques, Chapter 3, p. 55, John Wiley & Sons Ltd.
Hayase N., et al., "Secretion of Human Epidermal Growth Factor (EGF) in Autotrophic Culture by a Recombinant Hydrogen-Utilizing Bacterium, *Pseudomonas psedollava*, Carrying Broad-Host-Range EGF Secretion Vector pKSEGF2." Applied and Environmental Microbiology, Sep. 1994, pp. 3336-3342, vol. 60, No. 9, American Society for Microbiology.
Heffron, F., et al., "Translocation of a plasmid DNA sequence which mediates ampicillin resistance: Molecular nature and specificity of Insertion," Sep. 1975, Proc. Nat. Acad. Sci., vol. 72, No. 9, pp. 3623-3627.
Heim and Tsien, "Engineering green fluorescent protein for improved brightness, longer wavelengths and fluorescence resonance energy transfer," 1996, Curr. Biol.6:178-182.
Hochuli, Erich, "Purification of Recombinant Proteins with Metal Chelate Absorbent," 1990, Genetic Engineering, vol. 12, pp. 87-91.
Hockney, Robert C., "Recent developments in heterologous protein production in *Escherichia coli*," 1994, Trends BioTechnology, 12, pp. 456-463.
Holliday, R., "A Mechanism for Gene Conversion in Fungi," Genet Res. 5:282, 1964.
Holliger, et al., "Diabodies: small bivalent and bispecific antibody fragments," 1993, Proc. Natl. Acad. Sci. USA, 90:6444-6448.
Holtwick, R., et al., "A novel rolling-circle-replicating plasmid from Pseudomonas putida P8: molecular characterization and use as a vector," 2001, Microbiology, vol. 147, Pt. 2, pp. 337-344.
Horton, et al., "Gene splicing by overlap extension: tailor-made genes using the polymerase cabin reaction," 1990, BioTechniques 8(5): 528-30, 532, 534-5.
Hsieh, et al., "Pairing of homologous DNA sequences by proteins: evidence for three-stranded DNA," 1990, Genes & Development 4: 1951-1963.
Hsiung et al., "Use of Bacteriocin Release Protein in *E. coli* for Excretion of Human Growth Hormone into the Culture Medium," 1989, Bio/Technology 7:267-71.
Ikehata, O., et al., Primary structure of nitrile hydratase deduced from the nucleotide sequence of a *Rhodococcus* species and its expression in *Escherichia coli*, 1989, Eur. J. Biochem, pp. 563-570, vol. 181.
Indian Patent Application 3608/DELNP/20 Exam Reported dated Apr. 29, 2011.
Indian Patent Application 523/DELNP/07 Office Action issued Sep. 6, 2012.
Ishii, T., et al., Elastase gene expression in non-elastase-producing *Pseudomonas aeruginosa* strains using novel shuttle vector systems, 1994, FEMS Microbiology Letters, vol. 116, Federation of European Microbiological Societies, pp. 307-314.
Japanese Patent Application 2006-549690 Office Action mailed Sep. 11, 2012.
Japanese Patent Application 2011-132011 Office Action mailed Jul. 9, 2013.
Japanese Patent Application 2007-523707 Office Action dated May 17, 2011.
Japanese Patent Application 2010-506503 Office Action dated Jun. 5, 2012.
Japanese Patent Application 2010-506503 Office Action dated May 14, 2013.
Jeong K.J. and Lee S.Y., "Excretion of Human β-Endorphin into Culture Medium by Using Outer Membrance Protein F as a Fusion Partner in Recombinant *Escherichia coli*," 2002, Appl. Environ. Microbio 68: vol. 10, pp. 4979-4985.

(56) References Cited

OTHER PUBLICATIONS

Jin, H., et al., "Soluble periplasmic production of human granulocyte colony-stimulating factor (G-CSF) in *Pseudomonas fluorescens*," 2011, Protein Expression and Purification, vol. 78, No. 1, pp. 69-77.
Jones, Jonathan D.G., et al., An Efficient Mobilizable Cosrnid Vector, pRK7813, and its Use in a Rapid Method for Markler Exchange in Pseudomonas Flourescens Strain HV37a, Gene, 1987, Elsevier Science Publishers B.V., pp. 299-306.
Joseph-Liazun et al., "Human recombinant interleukin-1β isolated from *Escherichia coli* by simple osmotic shock," 1990, Gene 86:291-295.
Kaster, K.R. et al., "Analysis of a bacterial hygromycin B resistance gene by transcriptional and translational fusions and by DNA sequencing," 1983, Nucleic Acids Res. (19):6895-911.
Keown, et al., "Methods for Introducing DNA into Mammalian Cells," Processes in Enzymology, 1990, vol. 185, pp. 527-537.
Khoury, G. and Gruss, P., "Enhancer Elements," 1983, Cell, vol. 33:313-314.
Knight Jr., E., Antiviral and Cell Growth Inhibitory Activities Reside in the Same Glycoprotein of Human Fibroblast Interferon, Nature, 1976, vol. 262, Nature Publishing Group, pp. 302-303.
Knight, et al., Construction and initial characterization of a mouse-human chimeric anti-TNF antibody, Mol Immunol. Nov. 1993;30(16):1443-53.
Kodama, T., et al., "The Initial Phosphate Burst in ATP Hydrolysis by Myosin and Subfragment-1 as Studied by a Modified Malachite Green Method for Determination of Inorganic Phosphate," 1986, J. Biochem., vol. 99, pp. 1465-1472.
Korean Patent Application 10-2006-7014191 Office Action dated Apr. 24, 2012.
Korean Patent Application 10-2006-7014191 Office Action dated Sep. 8, 2011 (English Translation only).
Korean Patent Application 10-2007-7004418 Exam Report dated Dec. 22, 2011.
Korean Patent Application 10-2007-7004418 Exam Report dated Nov. 26, 2012.
Korean Patent Application 10-2007-7004418 Final Rejection dated Sep. 11, 2012.
Korean Patent Application 10-2012-7013463 Office Action dated Sep. 2, 2012 (Office action in Korean only).
Korean Patent Application 10-2007-7004418 Exam Report dated Jun. 25, 2013(Office action in Korean only).
Kumar, et al., "The highly efficient productions of full-length and mutant rat brain calcium-binding proteins (calbindins-28K) in a bacterial expression system," Arch Biochem Biophys, 1994, vol. 308, No. 1, pp. 311-317.
Kunkel, T.A., et al., Rapid and efficient site-specific mutagenesis without phenotypic slection, 1987, Meth. Enzymol 154, p. 367.
Kunkel, Thomas A., "Rapid and efficient site-specific mutagenesis without phenotypic selection," 1985, Proc. Natl. Acad. Sci. USA, vol. 82, pp. 488-492.
Lawn, R., et al., "The sequence of human serum albumin cDNA and its expression in *E. coli*," 1981, Nucleic Acids Research, vol. 9, No. 22, IRL Press Limited, London, pp. 6103-6114.
Lee, M.H., "Bacterial Expression and in Vitro Refolding of a Single-Chain Fv Antibody Specific for Human Plasma Apolipoprotein B-100," 2002, Protein Expression and Purification, vol. 25, Elsevier Science USA, pp. 166-173.
Lewis, M.K. and Thompson, D.V., "Efficient site directed in vitro mutagenesis using ampicillin selection," 1990, Nucl. Acids Res. 18, No. 12, pp. 3439-3443.
Lloubes, R. et al., "Colincin A lysis protein promotes extracellular release of active human growth hormone accumulated in *Escherichia coli* cytoplasm," 1993, Biochimie 75, pp. 451-458.
Lockhart, et al., "Expression monitoring by hybridization to high-density oligonucleotide arrays," 1996, Nat Biotechnol 14:1675-80.
Lofthouse, S.A., et al., Cytokines as Adjuvants for Ruminant Vaccines, International Journal of Parasitology, 1996, vol. 26, No. 8/9, Elsevier Science, pp. 835-842.
Lombardo, et al, "*Escherichia coli* PapD in Guidebook to Molecular Chaperones and Protein Folding Catalysts," Gething M-J Ed. Oxford University Press Inc. New York, 1997, pp. 463-465.
Lombillo, Vivian A., Antibodies to the Kinesin Motor Domain and CENP-E Inhibit Microtubule Depolymerization-dependent Motion of Chromosomes In Vitro, 1995, The Journal of Cell Biology, vol. 128, Nos. 1 & 2, The Rockefeller University Press, pp. 107-115.
Lopez, et al., "Homologous recombination intermediates between two duplex DNA catalysed by human cell extracts," 1987, Nucleic Acids Res. 15:5643-5655.
Lundell et al., "Cytoplasmic and periplasmic expression of a highly basic protein, human interleukin 4, in *Escherichia coli*," 1990, J. Indust. Microbio. 5: pp. 215-228.
Lushnikov, A.A., et al., "Shuttle Vector for *Escherichia coli, Pseudomonas putida* and *Pseudomonas aeruginosa*," 1985, Basic Life Sci., vol. 30, pp. 657-662.
MacBeath, G. & Schreiber, SL, "Printing proteins as microarrays for high-throughput function determination," 2000, Science 289:1760-1763.
Magnan, et al., SOLpro: accurate sequence-based prediction of protein solubility, 2009, Bioinformatics 25(17): 2200-2207.
Manduchi, E., et al., "Comparison of different labeling processes for two-channel high-density microarray experiments," 2002, Physiol Genomics 10:169-79.
Manoil, Colin, "Tagging Exported Proteins Using *Escherichia coli* Alkaline Phosphatase Gene Fusions," 2000, Methods in Enzymol, 326: 35-47.
Martineau, Pierre, et al., Expression of an Antibody Fragment at High Levels in the Bacterial Cytoplasm, J. Mol. Biol., 1998, Academic Press, pp. 117-127.
McCarthy, et al., "Translational Control of Prokaryotic Gene Expression," 1990, Trends in Genetics 6:78-85.
Menne, et al., "A comparison of signal sequence prediction methods ising a t test set of signal peptides," 2000, Bioinformatics, vol. 16, No. 8, pp. 741-742.
Messing et al., "Genetic Engineering of Plants: An Agricultural Perspective," 1983, Edited by Kosuge et al., eds., pp. 211-227.
Mezghani-Abdelmoula, et al., "Invasive Behavior and Depolarization Effect of Pseudomonas Fluorescens on Rat Cerebellar Granule Neurons," African Journal of Clinical and Experimental Microbiology, Jan. 2005, pp. 1-13.
Michalski, Wojtek, et al., Recombinant Chicken IFN-γ Express in *Escherichia coli*: Analysis of C-Terminal Truncation and Effect on Biologic Activity, Journal of Interferon and Cytokine Research, 1999, vol. 19, Mary Ann Liebert, lnc., pp. 383-392.
Miksch, G., et al, "The kil gene of the ColE1 plasmid of *Escherichia coli* controlled by a growth-phase-dependant promoter mediates the secretion of a heterologous periplasmic protein during the stationary phase," 1997, Arch. Microbiol. 167:143-150.
Missiakas, D., et al., "Indentification and characterization of HsIV HsIU (ClpQ ClpY) proteins involved in overall proteolysis of misfolded proteins in *Escherichia coli*," 1996, Embo J. 15:6899-909.
Morrison, D.A., Transformation in *Escherichia coli*: Cryogenic Preservation of Competent Cells, Journal of Bacteriology, Oct. 1977, vol. 132, No. I, American Society for Microbiology, pp. 349-351.
Mukhija, Reema, et al., High-Level Production and One-Step Purification of Biologically Active Human Growth Hormone in *Escherichia coli*, Gene, 1995, vol. 165, Elsevier Science B.V., pp. 303-306.
Mukhopadhyay, Pradip, et al., "Construction of a Stable Shuttle Vector for High-Frequency Transformation in Pseudomonas syringae pv. Syringae," Journal of Bacteriology, Jan. 1990, vol. 172, No. 1, American Society for Microbiology, pp. 477-480.
Mulder et al., "InterPro, progress and status in 2005," Nucleic Acids Res., 2005, 33, Database Issue: D201-5.
Nagahari, Kenji, et al., "RSF1010 Plasmid as a Potentially Useful Vector in *Pseudomonas* Species," Journal of Bacteriology, Mar. 1978, vol. 133, No. 3, American Society for Microbiology, pp. 1527-1529.

(56) References Cited

OTHER PUBLICATIONS

Nagahira, et al., Humanization of a mouse neutralizing monoclonal antibody against tumor necrosis factor-alpha (TNF-alpha), J Immunol Methods, Jan. 1, 1999;222(1-2):83-92.
Naglak and Wang, "Recovery of a foreign protein from the periplasm of *Escherichia coli* by chemical permeabilization," 1990, Enzyme Microb. Technol., 12: 603-611.
Nakamaye, K. and Eckstein F., "Inhibition of restriction endoneuclease Nci I cleavage by phosphorothioate groups and its application to oligonucleotide-directed mutagenesis," 1986, Nucl. Acids Res. 14, 9679-98.
Nakashima, Nobutaka, et al., "Cell-free protein synthesis using cell extract of Pseudomonas fluorescens and CspA promoter," Biochemical and Biophysical Research Communications, Jun. 2004, vol. 319, No. 2., Elsevier, pp. 671-676.
Nedospasov, et al., "Tandem arrangement of genes coding for tumor necrosis factor (TNF-alpha) and lymphotoxin (TNF-beta) in the human genome," 1986, Cold Spring Harb. Symp. Quant. Biol. 51 Pt 1, pp. 611-624.
Needleman, Saul B., et al., "A General Method Applicable to the Search for Similarities in the Amino Acid Sequence of Two Proteins," J. Mol. Biol., 1970, vol. 48, pp. 443-453.
Neu and Heppel, "The release of enzymes from *Escherichia coli* by osmotic shock and during the formation of spheroplasts," (1965) J. Biol. Chem., 240:3685-3692.
Neu and Heppel, "The Release of Ribonuclease into the Medium when *Escherichia coli* Cells are converted to Spheroplasts," 1964, J. Biol. Chem 239: 3893-3900.
Nielsen, Iienrik, et al., Short Communication—"Identification of Prokaryotic and Eukaryotic Signal Peptides and Prediction of their Cleavage Sites," Protein Engineering, 1997, vol. 10, No. I, Oxford University Press, pp. 1-6.
Nieto, C., et al., "Cloning Vectors, Derived From a Naturally Occurring Plasmid of Pseudomonas Savastanoi, Specifically Tailored for Genetic Manipulation in Pseudomonas," Gene, 1990, vol. 87, Elsevier, pp. 145-149.
Niwa, et al., "An Efficient Gene-Trap Method Using Poly A Trap Vectors and Characterization of Gene-Trap Events," 1993, J. Biochem 113:343-349.
Nomine, Yves, et al., "Formation of Soluble Inclusion Bodies by HPV E6 Oncoprotein Fused to Maltose-Binding Protein, Protein Expression and Purification," 2001, vol. 23, Academic Press, pp. 22-32.
Nossal and Heppel, "The Release of Enzymes by Osmotic Shock from *Escherichia coli* in exponential phase," 1966, J. Biol. Chem., 241: 3055-3062.
Olekhnovich, Igor N., el al., "Controlled-Expression Shuttle Vector for Pseudomonads Based on the trpIBA genes of Pseudomonas Putida," Gene, 1994, vol. 140, Elsevier Science, pp. 63-65.
Opdenakker, G., et al., Interaction of Interferon With Other Cytokines, Experientia, 1989, vol. 45, Birkhauser Verlag, Switzerland, pp. 513-520.
Patra, Ashok K., et al., "Optimization of Inclusion Body Solubilization and Renaturation of Recombinant Human Growth Hormone from *Escherichia coli*," Protein Expression and Purification, 2000, vol. 18, Academic Press, pp. 182-192.
PCT/US05/01549 International Search Report mailed Jul. 19, 2005.
Pearson, William R., et al., "Improved Tools for Biological Sequence Comparison," Proc. Natl. Acad. Sci., Apr. 1988, vol. 85, pp. 2444-2448.
Peluso, P., et al., "Optimizing antibody immobilization strategies for the construction of protein microarrays," 2003, Anal Biochem 312:113-124.
Perussia, Bice, et al., "Immune Interferon Induces the Receptor for Monomeric IgG1 on Human Monocytic and Myeloid Cells," J. Exp. Med., 1983, vol. 158, Rockefeller University Press, pp. 1092-1113.
Pestka, Sidney, et al., "Interferons and Their Actions," Annu. Rev. Biochem., 1987, vol. 56, Annual Reviews, Inc., pp. 727-777.
Pierce, et al., "Expression and Recovery of cominant periplasmically secreted or amyase derived from Streptomyces thermoviolaceus," 1995, Icheme Research Event 2: 995-997.
Pighetti, Gina M., et al., Specific Immune Responses of Dairy Cattle Atter Primary Inoculation with Recombinant Bonvine Interferon-y as an Adjuvant When Vaccinating Against Mastitis, American Journal of Veterinary Research, 1996, vol. 57, No. 6, pp. 819-824.
Pilon, et al., "High-Level expression and efficient recovery of ubiquitin fusion proteins from *Escherichia coli*," Biotechnol Prog., 1996, vol. 12, No. 3, pp. 331-337.
Puehler, et al., 1984, Advanced Molecular Genetics New York, Heidelberg, Berlin, Tokyo, Springer Verlag.
Quevillon, et al., "InterProScan: protein domains identifier," 2005, Nucleic Acids Research 33: W116-W120.
Radding, C.M., "Homologous pairing and strand exchange in genetic recombination," 1982, Ann. Rev. Genet. 16: 405.
Ralph, Peter, "Human B Cell-Inducing Factor(s) for Production of lgM, IgG and 19A; Independence From IL 2(1)," The Journal of Immunology, Apr. 1984, vol. 132, No. 4, The American Society of Immunologists, pp. 1858-1862.
Ranson, et al., "Chaperonins," 1998, BioChem. J. 333, 233-242.
Rao, et al., "Stable three-stranded DNA made by RecA protein," 1991, PNAS 88: pp. 2984-2988.
Rawlings et al., "MEROPS: the peptidase database," 2006, Nucleic Acids Res., vol. 34, D270-D272, Database issue doi:10.1093/nar/gkj089.
Retallack, Diane , et al., "Reliable protein production in a Pseudomonas fluorescens expression system," Protein Expression and Purification, 2012, vol. 81, No. 2, pp. 157-165.
Retallack, Diane, et al., "Pseudomonas fluorescens—a robust expression platform for pharmaceutical protein production," Microbial Cell Factories, 2006, vol. 5 (Suppl. 1), BioMed Central, p. S28.
Retallack, Diane, et al., "Transport of heterologous proteins to the periplasmic space of Pseudomonas fluorescens using a variety of native signal sequences," Biotechnology Letters, 2007, vol. 29, Springer Science+Business Media B.V., pp. 1483-1491.
Riesenberg, D., et al., "High Cell Density Cultivation of *Escherichia coli* at Controlled Specific Growth Rate," Journal of Biotechnology, 1991, vol. 20, Elsevier Science Publishers, B.V, pp. 17-28.
Rosenberg, et al., "Vectors for selective expression of cloned DNAs by T7 RNA polymerase," 1987, Gene, 56(1): 125-35.
Ruiz-Taylor, LA, et al., "Monolayers of derivatized poly(L-lysine)-grafted poly(ethylene glycol) on metal oxides as a class of biomolecular interfaces," 2001, Proc Natl Acad Sci USA, 98:852-857.
Ruiz-Taylor, LA, et al., "X-ray photoelectron spectroscopy and radiometry studies of biotin-derivatized poly(L-lysine)-grafted-poly(ethylene glycol) monolayers on metal oxides," 2001, Langmuir, 7313-7322.
Saiki, Osamu, et al., Induction of Human Immunoglobulin Secretion—I. Synergistic Effect of B Cell Mitogen Cowan I Plus T Cell Mitogens or Factors, The Journal of Immunology, Sep. 1981, vol. 127, No. 3, The American Association of Immunologists, pp. 1044-1047.
Sanchez-Romero & V. De Lorenzo, Manual of Industrial Microbiology and Biotechnology, 1999, A. Demain & J. Davies, eds., pp. 460-474.
Schein, C.H., "Production of Soluble recombinant Proteins in Bacteria," Bio/Technology, 1989, 7:1141-1149.
Schena, M. et al., "Quantitative monitoring of gene expression patterns with a complementary DNA microarray," 1995, Science 270:467-70.
Schneider et al., (2005) "Auxotrophic markers pyrF and proC can replace antibiotic markers on protein productions plasmids in high-cell-density Pseudomonas fluorescens fermentation," 2005a, Biotechnology Progress 21(2): 343-348.
Schweizer, Herbert P., et al., Vector Design and Development of Host Systems for Pseudomonas, Genetic Engineering, 2001, vol. 23, Kluwer Academic/Plenum Publishers, pp. 69-81.

(56) References Cited

OTHER PUBLICATIONS

Schweizer, Herbert P., Vectors to Express Foreign Genes and Techniques to Monitor Gene Expression in Pseudomonads, Current Opinion in Biotechnology, 2001, vol. 12, Elsevier Science Ltd., pp. 439-445.
Service, R.F. et al., "Tapping DNA for structures produces a trickle," 2002, Science 298:948-950.
SG200906987-3 Exam Report dated Sep. 26, 2011.
Shine and Dalgarno, "The 3'-terminal sequence of *Escherichia coli* ribosomal RNA: complementarity to nonsense triplets and ribosome binding sites," 1974, Proc. Natl. Sci. USA 71:1342-1346.
Shokri, et al., "Growth rate-dependent changes in *Escherichia coli* membrane structure and protein leakage," 2002, App. Microbiol. Biotechnol 58:386-392.
Simmons, et al., "Expression of full-length immunoglobins in *Escherichia coli*: rapid and efficient production of aglycosylated," 2002, J. Immun. Meth. 263:133-147.
Singleton, et al., 2000, "Cloning, expression, and characterization of pyrrolidone carboxyl peptidase from the archaeon Thermococcus litoralis" Extremophiles 4(5), 297-303.
Singleton, Paul & Sainsbury, Diana: "Dictionary of Microbiology," 1978, John Wiley & Sons Ltd., Chichester, UK, XP002667935, pp. 332-333.
Slater, Robert J., and Williams,Ross, "The Expression of Foreign DNA in Bacteria," 2000, Molecular Biology and Biotechnology, Fourth Edition, Chapter 4, The Royal Society of Chemistry, Cambridge, UK, pp. 125-154.
Smith & Waterman, Michael S., Comparison of Biosequences, 1981, Adv. Appl. Math 2:482-489.
Smits, et al., "New Alkane-responsive expression vectors for *Escherichia coli* and pseudomonas," Plasmid, 2001, vol. 46, pp. 16-24.
Song, K.Y., et al., "Accurate modification of a chromosomal plasmid by homologous recombination in human cells," 1987, Proc. Natl. Acad. Sci. USA 84:6820-6824.
Sordillo, L.M., Controlling Acute *Escherichia coli* Mastitis During the Periparturient Period with Recombinant Bovine Interferon-Gamma, Veterinary Microbiology, 1991, vol. 28, pp. 189-198.
Southern, P. and P. Berg, "Transformation of mammalian cells to antibiotic resistance with a bacterial gene under control of the SV40 early region promoter," 1982, J. Mol. Appl. Genet. 1:327-341.
Squires, et al., "Heterologous protein production in P. Fluorescens," Bioprocess International, 2004, vol. 2, No. 11, pp. 54-56, 58-59.
Stabel, et al., "Periplasmic location of *Brucella abortus* Cu/Zn superoxide dismutase," 1994, Veterinary Microbiol. 38: 307-314.
Stauber, et al., "Development and applications of enhanced green fluorescent protein mutants." (1998) Biotechniques 24(3):462-471.
Steidler, L., et al., Mucosal Delivery of Murine Interleukin-2 (IL-2) and IL-6 by Recombinant Strains of Lactococcus Lactis Coexpressing Antigen and Cytokine, Infection and Immunity, 1998, vol. 66, No. 7, pp. 3183-3189.
Steidler, L., In Situ Delivery of Cytokines by Genetically Engineered Lactococcus Lactis, Antonie van Leeuwenhoek, 2002, vol. 82, pp. 323-331.
Steinbeck, M.J., et al., Activation of Bovine Neutrophils by Recombinant Interferon-y, Cell. Immunol., 1986, vol. 98, pp. 137-144.
Stewart, Russell J., et al., Direction of Microtubule Movement is an Intrinsic Property of the Motor Dotrnins of Kinesin Heavy Chain and *Drosophila* Ned Protein, Proc. Natl. Acad. Sci., 1993, vol. 90, pp. 5209-5213.
Studier, F.W. and B.A. Moffatt, "Use of bacteriophage T7 RNA polymerase to direct selective high-level expression of cloned genes," 1986, Journal of Molecular Biology, 189(1):113-30.
Suzek, Baris E., et al., "A Probalistic Method for Identifying Start Codons in Bacterial Genomes," Bioinformatics, 2001, vol. 17, No. 12, Oxford University Press, pp. 1123-1130.
Taguchi, et al., "Comparison of secretory expression in *Escherichia coli* and *Streptomyces* subtilisin inhibtor (SSI) gene," 1990, Biochimica Biophysica Acta 1049: 278-85.
Takara Bio Inc., Product Information Bulletin, "Chaperone Plasmid Set," pp. 1-8, Catalog #3340, Version 0401, Mar. 22, 2013.
Tanji, et al., "Controlled Expression of Lysis Genes Encoded in T4 Phage for the Gentle Disruption of *Escherichia coli* cells," 1998, J. Ferment and Bioeng., 85:74-78.
Taub, Dennis D., "Cytokine, growth factor, and chemokine ligand database," Current Protocols in Immunology, 2004, XP002677096, DOI: 10.1002/047114273 5.im0629s61, [Retrieved from the Internet: URL:http://onlinelibrary.wiley.com/doi/10.1002/0471142735.im0629s61/full [retrieved on Jun. 1, 2012].
Taylor, J.W. et al., "The use of phosphorothioate-modified DNA in restriction enzyme reactions to prepare nicked DNA," 1985, Nucl. Acids Res. 13, No. 24, pp. 8749-8764.
Te Riele H., et al., "Consecutive inactivation of both alleles of the pim-1 proto-oncogene by homologous recombination in embryonic stem cells," 1990, Nature 348:649-651.
Toogood, H.S., et al., "A thermostable L-aminoacylase from Thermococcus litoralis: cloning, overexpression, characterization, and applications in biotransformations," 2002, Extremophiles 6(2), pp. 111-122.
Tsuda & Nakazawa, "A mutagenesis system utilizing a Tn1722 derivative containing an *Escherichia coli*-specific vector plasmid: application to *Pseudomonas* species," 1993, Gene 136 (1-2): 257-62.
U.S. Appl. No. 12/109,554 Final Office Action mailed Jun. 15, 2011.
U.S. Appl. No. 12/109,554 Non Final Office Action mailed Dec. 30, 2010.
U.S. Appl. No. 11/189,375 Non Final Office Action dated Sep. 14, 2012.
U.S. Appl. No. 11/038,901 Final Office Action mailed Feb. 27, 2008.
U.S. Appl. No. 11/038,901 Final Office Action mailed Sep. 17, 2009.
U.S. Appl. No. 11/038,901 Non Final Office Action mailed Apr. 15, 2011.
U.S. Appl. No. 11/038,901 Non Final Office Action mailed Aug. 6, 2008.
U.S. Appl. No. 11/038,901 Non-Final Office Action mailed Jul. 27, 2007.
U.S. Appl. No. 11/038,901 Office Action mailed Nov. 25, 2011.
U.S. Appl. No. 11/189,375 Final Office Action mailed Jun. 16, 2010.
U.S. Appl. No. 11/189,375 Final Office Action mailed Mar. 19, 2009.
U.S. Appl. No. 11/189,375 Non Final Office Action mailed Feb. 7, 2008.
U.S. Appl. No. 11/189,375 Non Final Office Action mailed Sep. 9, 2009.
U.S. Appl. No. 11/189,375 Final Office Action mailed Mar. 29, 2013.
U.S. Appl. No. 11/400,840 Office Action mailed Dec. 24, 2009.
U.S. Appl. No. 11/400,840 Office Action mailed Feb. 14, 2008.
U.S. Appl. No. 11/400,840 Office Action mailed Sep. 17, 2008.
Vale, Ronald D., et al., "Identification of a Novel Force-Generating Protein, Kinesin, Involved in Microtubule-Based Motility," Cell, Aug. 1985, vol. 42, MIT, pp. 39-50.
Vera, Andrea, et al., "The Conformational Quality of Insoluble Recombinant Proteins Is Enhanced at Low Growth Temperatures," Biotechnology and Engineering, Apr. 15, 2007, vol. 96, No. 6, pp. 1101-1106.
Vincentelli, Renaud, et al., "Medium-Scale Structural Genomics: Strategies for Protein Expression and Crystallization," Ace. Chem. Res., 2003, vol. 36, No. 3, pp. 165-172.
Vinogradov, Alexi A, et al., Solubilization and Refolding of Inclusion Body Proteins in Reverse Micelles, Analytical Biochemistry, 2003, Elsevier Science, pp. 234-238.
Wackemagel, et al., "The periplasmic endonuclease I of *Escherichia coli* has amino-acid sequence homology to the extracellular Dnases of Vibrio cholerae and aeromonas hydrophila," 1995, Gene 154: 55-59.
Wan and Baneyx, "ToIAIII Co-overexpression facilitates the recovery of periplasmic recombinant proteins into the growth medium of *Escherichia coli*," 1998, Protein Expression Purif 14:3-22.

(56) References Cited

OTHER PUBLICATIONS

Waterman, Michael. S., Comparison of Biosequences, Advances in Applied Mathematics, 1981, vol. 2, Academic Press, Inc., pp. 482-489.
Wesolowski, et al., 2009, "Single domain antibodies: promising experimental and therapeutic tools in infection and immunity," Med Microbiol Immunol. 198(3): 157-174.
Wilson, D.S., et al., "The use of mRNA display to select high-affinity protein-binding peptides," 2001, Proc Nat Acad Sci USA 98:3750-3755.
Witholt, et al., "How does lysozyme penetrate through the bacterial outer membrane?" 1976, Biochim. Biophys. Acta, 443: 534-544.
Wood, David O., et al., "Versatile Cloning Vector for *Pseudomonas aeruginosal*," Journal of Bacteriology, Mar. 1981, vol. 14, No. 3, pp. 1448-1451.
Yang, Funmei, et al., Human Transferrin: cDNA Characterization and Chromosomal Localization, Proc. Natl. Acad. Sci. USA, May 1984, vol. 81, pp. 2752-2756.
Yasuda, et al., "Osteoclast differentiation factor is a ligand for osteoprotegerin/osteoclastogenesis-inhibitory factor and is identical to TRANCE/RANKL," 1998, Proc. Natl. Acad. Sci. U.S.A. 95(7), 3597-3602.
Yilma T., et al., Enhancement of Primary and Secondary Immune Responses by Interferon-Gamma, Adv. Exp. Med. Biol., 1989, pp. 145.152, vol. 251.
Yilma, T.K., et al., Expression of an Adjuvant Gene (Interferon-y) an Infectious Vaccinia Virus Recombinants, Vaccines, 1987, vol. 87, pp. 393-396.
Yoshida, et al., "A new strategy of gene trapping in ES cells using 3'RACE," 1995, Transgenic Research 4:277-287.
Zapata, et al., "Engineering linear F(ab')2 fragments for efficient production in *Escherichia coli* and enhanced antiproliferative activity," 1995, Protein Eng. 8(10): 1057-1062.
Zhu, H. et al., "Global analysis of protein activities using proteome chips," 2001, Science Express.
Zinder and Arndt, "Production of Protoplasts of *Escherichia coli* by Lysozyme Treatment.," Proc. Mathl. Acad. Sci. USA, 1956, 42: 586-590.
Zuffa, A., et al., Protection of Cattle Vaccinated with Inactivated Oil-Adjuvant Infectious Bovine Rhino Trachetis Vaccine Against Experimental Infection, Zbl. Vet. Med. G., 1989, vol. 27, pp. 725-733.

* cited by examiner

SEQ ID NO: 138 RXF01181.1

ATGTCACTAAATTTCCCGCTGTTGCTGGTCATTGCCGTTGCCGTCTGTGGTCTCCTGGCGTTGCTCGATCTGG
TGTTCTTCGCCCCGCGTCGTCGGGCGGCCATTGCTTCCTATCAGGGCAGCGTCAGCCAGCCCGATGCGGTG
GTGGTCGAGAAGCTGAACAAAGAGCCCTTGCTGGTTGAGTACGGCAAGTCGTTCTTCCCGGTGTTGTTCATC
GTGCTGGTGTTGCGCTCGTTTCTGGTAGAGCCGTTCCAGATCCCTTCGGGGTCGATGAAACCGACCCTGGAC
GTGGGCGACTTCATCCTGGTGAACAAGTTTTCCTACGGCATTCGTCTGCCGGTGATCGACAAGAAAGTCATCC
CCGTGGGTGACCCGCAGCGCGGCGATGTGATGGTGTTCCGCTACCCAAGCGACCCGAACGTCAACTACATC
AAGCGTGTGGTCGGCCTGCCGGGCGACGTGGTGCGCTACACCAGTGACAAGCGCCTGTTCATCAACGGTGA
GTCGGTGGCCGAGAAGCTGCTGGGCGCCGAGCCGAACACCCTGGGCAGCGCCGAGCTGTACCAGGAAAAA
CTCGGCGCGGTGGAGCACCAAATCCGCAAGGAAATGAGCCGCTACCGTGCGATGCCGGATGGCCAGTGGAA
AGTGCCTGCCGGGCACTACTTTATGATGGGCGACAACCGCGACAACTCCAACGACAGCCGCTACTGGGATGA
CCCCAACATTCCCAAAGACCTGCTGGGCATGGTGCCCGACGAGAACATTGTCGGCAAAGCCTTCGCGGTCTG
GATGAGTTGGCCGGAACCCAAGCTCAGCCACCTGCCGAACTTCTCGCGGGTCGGGCTGATCAAGTAA

SEQ ID NO: 139 RXF03364.1

ATGATCAAGACCCCCGCACAGTTGGCCGTAATGCGTGAAGCCGGGCGCCTGTTGGCGCAGGTCTTCGACAT
GCTCGACGGCTTCGTCGCCGCCGGCCGCTCTACCCTGGAGCTGGACAGCGCCGTCGAAGCCTTCATCCGCA
ATGACCTCAAGGCCCGCCCTGCCAGCCTGGGGCAGTACGACTACCCCTTCTGCATCAACACCTCGATCAACG
AAGTGGTGTGCCACGGCATGCCCAGCGCCAAGCAATTGCTCAAGGACGGCGACATCATCAACATCGACATCA
CCCTGGAAAAAGGCGGCTTCATTGCCGACTCCAGCAAGATGTACATGATCGGCAACGTGACGCCCAAGGCCA
GGCGCCTGGTGGACATGACCTTCGAGGCGATGTGGGCCGGTATCCGCCAGGTCAAGCCCGGCGCGCGCCT
GGGCGATATCGGCCATGCGATCCAGAGCCACGCGCAAGCCAATGGCTACAGCGTGGTGCGCGAATACTGCG
GCCACGGCATCGGCCGGCAAATGCACGAAGAACCGCAAATCCTGCACTTCGGCCGCCCCGGCACCGGCCTG
GAACTGCGCGAAGGCATGGTGTTTACCATCGAGCCGATGCTCAACCAGGGCAGCGCCAAAACCCGCAGCCT
GAAAGACGGTTGGACGGTGGTCACCAAGGACAACAGCCTCTCGGCGCAATGGGAACATACCGTGGCGGTGA
CGGCGGATGGGTTTGAAGTGCTGACCTTGCAAACCCCTCAAAACCTTCACACCCTGTAG

SEQ ID NO: 140 RXF03376.1

ATGGCTCTACTGCAAATCGCCGAACCCGGCCAAAGCCCTCAACCGCACCAGCGTCGCCTGGCGGTCGGGAT
TGACCTGGGCACCACCAATTCCCTGGTTGCTGCCTTGCGCAGCGGCCTGTCCGAGCCACTGCCTGACGCCG
ATGGGCAGGTGATCCTGCCGTCCGCCGTGCGTTATCACGCCGACCGCACTGAAGTGGGCGAATCGGCCAAA
TTGGCCGCGTCCGCAGACCCTTTGAACACGGTGTTGTCGGTCAAGCGCTTGATGGGTCGTGGGTTGTCCGAC
GTCAAGCAATTGGGCGACCAACTGCCGTACCGCTTTGTCGGCGGTGAATCCCATATGCCGTTCATCGACACC
GTCCAGGGGCCCAAGAGCCCGGTGGAAGTGTCGGCTGATATCCTCAAGGTGCTGCGCCAGCGTGCAGAAAG
CACCCTGGGCGGTGAGCTGGTAGGGGCGGTGATCACTGTTCCGGCGTATTTCGATGACGCCCAGCGCCAAG
CCACCAAGGATGCGGCGAAACTTGCCGGCTTGAACGTGCTGCGCTTGCTCAACGAACCGACTGCGGCGGCG
GTGGCCTACGGCCTCGATCAGCACGCTGAAGGCCTGGTCGCTATTTATGACCTGGGCGGCGGCACCTTCGA
TATTTCGATCCTGCGCCTGACCGGCGGTGTGTTCGAAGTGCTCGCGACCGGCGGCGACAGCGCCCTGGGTG
GCGATGATTTCGATCACGCTATTGCTGGCTGGATCATCAGCAGTGCTGGCTTATCGGCCGACCTGGACCCAG
GCGCGCAGCGCAACCTGCTGCAAACTGCCTGCGCGGCCAAAGAGGCGCTGACTGACGCTGCTTCTGTTGAA
GTGTCCTACGGTGACTGGTCGGCACAGCTGACCCGCGAAGCCTTTGATGCGCTGATCGAGCCGATGGTCGC
CCGCAGCCTCAAAGCCTGTCGTCGTGCTGTGCGTGATTCCGGTATCGAGTTGGAAGACGTCGGTGCAGTGGT
CATGGTCGGCGGTTCCACCCGCGTGCCGCGCGTGCGCGAAGCGGTCGCCGAAGCCTTTGGGCGCCAACCG
CTGACCGAAATCGACCCGGATCAAGTGGTCGCCATCGGCGCTGCCATCCAGGCCGATACCCTGGCTGGTAA
CAAACGCGATGGCGGCGAATTGCTGTTGCTCGACGTGATCCCGTTGTCCCTGGGCCTGGAAACCATGGGTG
GCCTGATGGAGAAGGTGATTCCGCGCAACACCACCATTCCCGTCGCCCGTGCCCAGGACTTTTCTACCTACA
AAGACGGCCAGACAGCGATGATGATTCATGTGCTGCAAGGTGAGCGCGAGCTGATCAGCGACTGCCGTTCC
CTGGCGCGCTTTGAATTGCGTGGCATTCCGGCGATGGTGGCCGGTGCCGCCAAGATTCGCGTGACCTTCCA
GGTCGATGCCGATGGCTTGCTCAGCGTGGCTGCGCGTGAGCTGGCTTCGGGCGTGGAGGCCAGCATCCAG
GTCAAGCCGTCCTACGGCCTCACCGATGGCGAAATCGCCAAGATGCTCAAGGATTCGTTCCAGTATGCCGGT
GACGATAAGGTCGCCCGTGTATTACGCGAGCAGCAAGTAGATGCCCAGCGCCTGCTCGAAGCGGTGCAGGG
TGCCCTTGAAGCCGATGGCGAGCGCCTGCTGGATGCCGAAGAACGCATGGTCATTGACCTGCAAATGCAGG
AACTGGCCGAACTGATGAAAGGCAACGATGGCTACGCCATCGAGCAACAGACCAAGCGCCTGTCGCAAGTG
ACTGATGCCTTTGCCGCCCGCCGTATGGATCAGACGGTTAAAGCCGCGCTGGCGGGCCGCAACCTGAATGA
AATTGAGGAATAA

FIGURE 5-1

SEQ ID NO: 141 RXF04693.1
ATGACCGTTACCTTGAAAACCGCCGAAGACATCGCAGGCATGCGCGTTGCCGGCAAACTGGCTGCCGACGT
GCTGGAAATGATCGCCGAACACGTCAAGCCCGGCGTCACCACCGAAGCGCTGGACCGCATCTGCCACAACT
ATATAGTCGACGTGCAAAAAGCCATCCCTGCCCCGCTGAATTACAAAGGCTTCCCCAAGTCGATCTGCACCTC
GATCAACCACGTGGTCTGCCACGGCATTCCCGGTGACAAGCCACTGAAGGACGGCGACACCCTGAACATCG
ACGTCACGGTGATCAAGGACGGCTACCACGGCGACACCAGCCGCATGTTCCACGTCGGCAATGTACCGGTG
TGGGCCGAGCGCCTGTCCCAGGTCACCCAGGAATGCATGTACAAGGCCATCGAAATCGTCAAGCCCGGCTG
CCGCCTGGGTGACATCGGTGAAGTGATCCAGAAGCACGCGGAAAAGAACGGTTTCTCGGTGGTGCGCGAAT
TCTGCGGCCACGGTATCGGCAAAGTGTTCCACGAAGAGCCGCAGATCCTGCACTACGGCCGCGCCGGAACC
GGCATGGAACTCAAGGCAGGCATGACCTTCACCATCGAGCCGATGATCAACCAGGGCAAGGCCGACACCAA
GGTGCTGGGCGACGGCTGGACCGCCATCACCAAGGACCGCAAGCTCTCGGCCCAGTGGGAACACACCCTG
CTGGTCACCGACACCGGCTATGAGATTTTCACCCTGCGCGCCGACGACACCATCCCACGCGTTTCGGCCTGA

SEQ ID NO: 142 RXF05319.1
ATGCAAAAAACCAGTGCCACGCTGCTGATAATCGATGACGACGAAGTAGTGCGCGCGAGCCTCGCGGCCTAC
TTGGAAGACAGTGGCTTCAGCGTCCTGCAGGCCAGTAATGGCCAACAGGGTCTCCAGGTATTCGAGCGCGA
CAAGCCCGACCTTGTGATCTGCGACCTTCGCATGCCCCAGATGGGCGGCCTGGAGCTGATTCGCCAGGTGA
CCGACCTTGCCCCGCAAACGCCGGTGATTGTCGTGTCCGGTGCCGGTGTCATGAACGATGCCGTTGAAGCC
TTGCGCCTGGGCGCCGCCGATTACCTGATCAAACCCCTGGAAGACCTGGCCGTGCTGGAGCACTCGGTGCG
CCGCGCCCTGGACCGTGCACGCCTGCTCCTGGAAAACCAGCGCTACCGCGAAAAGCTCGAGACCGCCAACC
GCGAACTTGAAGCCAGCCTGAACCTGCTGCAGGAAGACCAGAACGCCGGTCGCCAGGTGCAGATGAACATG
CTGCCGGTCAGCCCCTGGACCACCGACGAATTCAAGTTCGCCCACCAGATCATCCCGTCGTTGTACCTGTCG
GGTGATTTTGTCGACTATTTCCGCGTCGATGAGCGGCGCGTAGCGTTCTACCTGGCCGACGTTTCCGGCCAC
GGCGCGTCTTCAGCGTTTGTGACCGTGTTGTTGAAGTTCATGACCACACGGCTGTTGGTCGAGTCCAAGCGC
AATGGCACCTTGCCGGAGTTCACCCCCTCCGAGGTGCTGGGCCACATCAACCGAGGCCTGATCAGCTGCAA
GCTGGGCAAGCACGTGACGATGGTCGGCGGCGTGATCGACGAAGAAACCGGTCTTTTGACCTACAGTATTG
GCGGTCACCTGCCGATGCCTGTTTTATACACTCCTGACAGTGTGCGCTACCTGGAAGGGCGTGGCCTGCCCG
TAGGCTTGTTTAACGAAGCCACGTACGAAGACCACATCCTAGAATTGCCGCCGACCTTCAGCCTGACGCTGC
TGTCCGACGGAATTCTGGACCTTCTTCCAGAGCCTACACTCAAAGAGAAAGAAGCCGCCTTGCCCCAAAAGG
TCAAGTCGGCGGGCGGCAGCCTGGATGGCCTGCGGCAGGTTTTTGGATTGGCCACGCTAGGGGAGATGCC
GGATGATATCGCCCTATTGGTGTTGAGCAGGAATCTTTGA

SEQ ID NO: 143 RXF05445.1
ATGAGCTTTTTTATCTCTAACGCCATGGCTGACGCCGCTGCGCCTGCTGCTGCCGGCCCTATGGGCGGTGGT
TTCGAGTGGATTTTCCTGGTCGGCTTCCTGGTCATCTTCTACCTGATGATCTGGCGTCCACAGGCCAAGCGC
GCCAAAGAGCAGAAAAACCTGCTGGGCAGCCTGCAAAAAGGCGACGAAGTCGTGACCACTGGCGGCATCGC
CGGCAAGATCACCAAGGTTTCCGATGCTTTCGTGGTACTGGAAGTCTCCGACACCGTGGAAATGAAGTTCCA
GAAGGGCGCCATCGCCGCCACGCTGCCTAAAGGCACGCTCAAAGCGATCTAA

SEQ ID NO: 144 RXF08122.2
ATGTCCGCACCTCTTGTAATCCCCTGCCCACATTGCAACGGCCTCAACCGCATCCCCGGCGAACGCCTGGGT
GACGCGCCCAAGTGTGGGCGTTGCAAGCAGTCGGTGTTGCTGAGCAAACCCTTTGATTTGAAACAGGGTGAC
TATGCCAGCCAGATCAAGGGCGACCTGCCGCTTTTGGTCGATGTGTGGGCCGACTGGTGCGGGCCGTGCAA
GTCGTTTGCGCCGGTATTCGAACAGGCCGCCGGGCAGTTGGAAGGCAAGTGCCGGCTGGCGAAGCTGGACA
GTGAAGCTAACCAGCACCTGTCGGCGCAGTTGGGGATTCGCTCGATTCCCAGTTTGATTCTGTTCAAGAACG
GCCGCGAAGTGGCGCGCCAGAGTGGGGCATTCCCGTTGCCGCAGTTGATGAGCTGGTTGCGTAGCCAGGG
GGTGTAA

FIGURE 5-2

SEQ ID NO: 145 RXF06751.1
ATGGCCTACGATTTTGACCTGTATGTAATTGGCGCCGGTTCTGGCGGTGTTCGCGCGGCGCGCTTTGCCGCT
GGCTTTGGCGCCAAGGTGGCCGTGGCGGAGAGCCGCTACCTGGGTGGCACCTGCGTGAACGTCGGCTGTG
TGCCAAAGAAGCTGTTGGTGTATGGCGCGCATTTTGCCGAGGATTTTGAGCAGGCCAGTGGCTTTGGCTGGT
CCCTGGGCGAGGCGAACTTTGATTGGGCGACCTTGATCGCCAACAAGGATCGCGAGATCAACCGCCTCAATG
GCATCTATCGCAACCTGTTGGTCAACAGCGGCGTGACCCTGCATGAAGGGCATGCACGCCTGGTTGATGCCC
ACCAGGTGGAGATTAACGGTGAGCGCTTCACTGCCAAGCACATCCTGATCGCCACCGGCGGCTGGCCGCAG
ATCCCTGAGATTCCAGGGCGCGAGCACGCCATTGGTTCCAATGAGGCATTCTTCCTCAAAGAGCTACCTAAG
CGCGTGCTGGTAGTGGGCGGTGGCTATATCGCCGTCGAGTTCGCCGGCATCTTCCACGGCTTGGGTGCACA
AACTTCATTGCTGTATCGCGGCGACTTGTTCTTGCGCGGCTTTGATGGCTCGGTGCGCAAGCATCTGCAAGA
AGAGCTGACCAAGCGCGGCCTGGACTTGCAGTTCAATGCCGACATCGAGCGCATCGATAAGCAAGCCGACG
GCAGCCTCAAGGCCACGTTGAAGGATGGTCGCGTGCTGGAAGCCGATTGTGTGTTCTACGCCACCGGCCGC
CGCCCAATGCTGGATAACCTGGGCCTGGAAAACACCGGGGTCAAACTGGACGAGCGCGGTTTCGTCGCGGT
GGATGATCTCTACCAGACCGCCGAGCCGTCGATCCTGGCGATTGGCGATGTGATTGGTCGTGTGCAGCTGAC
GCCGGTGGCTCTGGCTGAAGGCATGGCCGTGGCGCGGCGGTTGTTCAAGCCCGAGCAATACCGGCCGGTG
GATTACGCCAATATCGCGACGGCGGTGTTCAGCCTGCCAAATATCGGCACAGTCGGTCTGACGGAAGAGGAT
GCACGCAAGCACGGCCACAACGTGCAGATCTTTGAAAGCCGTTTCCGGCCGATGAAGCTGACCCTCACCGAT
TGCCAGGAAAAGACCCTGATGAAGCTGGTGGTCGACGCCGACACCGACAAAGTGCTGGGTTGCCACATGGT
CGGCCCGGATGCGGGTGAAATCGTGCAAGGGCTGGCGATCGCGCTCAAGGCGGGCGCGACTAAGCAGCAT
TTCGACGAAACCATCGGCGTGCATCCTACGGCGGCGGAAGAATTCGTCACCATGCGCACGCCCGTGGCGGA
CTGA

SEQ ID NO: 146 RXF00922.1
TTGAGCGAACTTCTCAACCGCCGCCTGGCCCTGCTCGGCAAGCGCGAACACCTCTCCCTGCTAGAGCAGTG
CTTGCACGGCATCGAGCGCGAATGCCTGCGCGTCACCAGTGAGGGTCGCCTGGCACAAACGCCACACCCCG
AAGCATTGGGCGCCGCGTTGACCAACGAACAGATCACCACTGACTACTCGGAATCTCTGCTGGAGTTCATCA
CCCCAGCCCTGCCCAACCCGGCCGAGACCCTGAGCAGCCTGGACAAGATCCATCGCTTTGCCTACTCCAAG
CTGGGCAGCGAATACCTCTGGAGCCCCTCGATGCCGTGCCCGTTGCCGGCCGAGGAAGATATACCGATTGC
CTACTACGGCACCTCCAATATCGGTCAGCTCAAGTACGTGTACCGCAAGGGCCTGGCCCTGCGTTACGGCAA
GACCATGCAGTGCATCGCAGGCATCCACTACAACTTTTCCCTCCCGGAAGCGTTGTGGCCGTTGCTCAAGGA
AACAGAAGGGTTTGTCGGCACCGACCGTGACTATCAGTCCACGGCCTACATCGCGCTGATCCGTAATTTCCG
ACGCTACAGTTGGCTGTTGATGTACCTGTTCGGTGCCTCGCCAGCCCTGGACGCCGGCTTCCTGCGGGGGC
GCTCGCACCAGCTTGAAGTCCTCGACGCCGACACCCTGTACCTGCCCTACGCCACCAGCCTGCGCATGAGC
GACCTGGGTTACCAGAGCAATGCCCAGGCCGGCCTGACGCCGTGCTACAACGACTTGGCCAGCTACACCGA
TAGCCTGCGCGAAGCGGTGGCAACGCCCTACGCGCCGTACGTTGAAGTCGGCACGCACAAGGATGGCGAGT
GGGTGCAGCTGAACACCAACATCCTGCAGATCGAAAACGAGTACTACTCCAACATCCGTCCCAAGCGCGTGA
CCTACACTGGCGAGCGGCCGATCCAGGCGTTGATGGCCCGCGGCATCCAGTACATCGAAGTGCGCTGCCTG
GACATCAACCCGTTCTTGCCGATGGGTATCGACCTGCCGGAATCACGTTTCCTCGACGCGTTCCTGCTGTACT
GCGCACTGAACGACAGCCCGCTGTTCGCCAACAACGAGTGCGGCAACGCCAGCTCCAACTTCCTCAGCGTG
GTCAAGGAAGGCCGCCGTCCGGGCCTGCAATTGCAGCGTGACGGCCAGCCGGTGGACATGAAGGAGTGGG
CGGCCGAGTTGCTGGAGAAGATTGCCCCGCTGGCCGCCCTGCTCGATCAGAGCCATGGCATCACTGAGCAC
AGCGAGGCACTGGACGCCCAGTTGGCCAAGGTCAAGGACCCGTCCCTGACGCCGTCGGCCCAGGTATTGGC
GGCCATGGCCGAGCGCAAGGATAGCTTTGCGCAGTTCTCCCTGCATCAAAGCGAAGTGCATGCTGAATACTT
CCGCAAGGAGCCTTTGGCGCCTGAGGAACAAGCGCACTTTGAAGAACTGGCCCGTGCGTCGCTGGCGCAAC
AGGCGGAGCTGGAGCAGAACGAAGTGGGCGATTTCGACGTGTTTGTCGGCTCGTACCAGGCAAGCATCCTG
GCCATCAGCAACTAA

SEQ ID NO: 147 RXF03204.1
ATGATTGACGACATGCGTTTAGGCAGGGAGCGGCGCTTTCTGGTGTTGCTGGGCATCATCTGCCTGGCGCTG
ATTGGCGGGGCGCTGTACATGCAAGTGGTGCTGGGAGAAGCACCGTGCCCGCTGTGCATTCTGCAGCGCTA
CGCCTTGCTGCTGATTGCGCTCTTCGCGTTCATCGGCGCCGCCATGCGCACCAAGGGCGCGCTGACGTTCTT
TGAAGGGTTGGTGGTGCTCAGCGCCTTGGGTGGCGTGGCTGCGGCCGGCCATCACGTGTACACCCAGTTCT
TCCCCCAGGTCAGCTGCGGTATCGATGTGTTGCAACCGATCGTCGACGACCTGCCCCTGGCCAAGGTGTTTC
CCCTGGGCTTCCAGGTCGACGGCTTCTGCAGCACCCCCTACCCACCGATTCTCGGCCTGTCTCTGGCCCAAT
GGGCACTGGTGGCATTCGTGCTGACGGCGATCCTGGTGCCCCTATGCATCTATCGCAACCGTCACCCCAAAG
CCTGA

FIGURE 5-3

SEQ ID NO: 148 RXF04886.2

ATGCGGCATCTGTTTACCTTTCTGCTGGTGTTGTTCGCGGGATTCGCCCAGGCAGCGCCGGGCAGCCCCTTC
GAAACCAAACCCGACTTCCTCCCGGTGGGCAAAGCCTTCGCCTTTACCTCCGAACGTCTTGAAAGCGGCGAA
ACCCAGCTGTTTTGGCAGATTGCCGACGGTTACTACCTGTACCAGCAGCGCATGAAGTTCGACGGCCTGGCC
GAAAAGCCCGTGCTGCCCGAGGGTGAAGCCCATAGCGACGAGTTCTTTGGCGAGCAGCAAGTGTATCGCCA
GGGCCTGGAAGTGAAGATCCCCGCCGGCACCACCGGCCAGGTCAAGCTCGGCTGGCAGGGCTGCGCCGAT
GCGGGCCTGTGCTATCCACCGCAGTCGATCACCGTGGACCTGGGCGGCAACCCGGCCGTCGCCGCCACCG
CGCAAGCCCAGGATCAAAGCCTGGCCAGCGGCCTGCAACAGCGCAGCCTGGGGTGGAGCCTGCTGGTGTT
CTTCGGCCTGGGCCTGCTGTTGGCGTTTGCGCCTTGCTCGTTGCCGATGCTGCCGATCCTCGCCGGCCTGG
TGGTGGGCAGTGGCGCCAGCCCGCGCCGTGGCTTTGCCCTGGCCGGCAGCTACGTCGTGTGCATGGCGCT
GGTATATGCCGCCTTGGGGGTGATGGCCGCGTTGCTCGGCGCCAACCTTGCCGCACTTTTGCAAACGCCGT
GGATCCTCGGCAGCTTTGCGGCGTTGTTCGTGCTGCTCGCTCTGCCGATGTTCGGCTTCTTTGAATTGCAACT
GCCCGCCTTCCTGCGCGACCGCCTCGATAACGTCAGCCGCCAGCAAAGCGGTGGCAGCCTGGTGGGTGCC
GGTGTGCTCGGCGCGTTGTCCGGCCTGCTGGTGGGACCGTGCATGACCGCGCCCCTGGCTGGCGCCCTGC
TGTACATCGCCCAGAGCGGCAATGCGCTGCACGGTGGCCTGATCCTGTTTGCCATGGGCATCGGTATCGGC
ATTCCCCTGTTGTTGCTGGTGACCGTGGGCAATCGCTTCCTGCCCAAGCCGGGCACCTGGATGAACGTGCTC
AAGGGCATCTTCGGTTTCCTGTTCCTGGGCACTGCGGTGCTGATGATTCGCCCGGTGGTCGGCGACAGCCT
GTGGATCGGCCTGTGGGGCGCCTTGGCGCTGGTGATGGCGTACTGTGGCTGGGCGCTGGCCCGTGAGTCC
GGCCTGGCGGCCAAGGTATTTGGCGCCGGTTCCCTGGTGCTGGGCCTGTGGGGCGCGGTGCTGGTGGTGG
GTGCGGCCGGTGGCAGCGATGAGCTGTGGCAACCGTTGAAGGTCTACAGCGGCTCTCGGGTCGCCGATGCA
CCCAGCGCTCACGATGCCTTCACCACGGTCAGCGATCCGGCAGTATTGCAAAGCCAACTCGACAGCGCCAA
GGCCCAGGGCCAGTGGGTGCTGTTGGACTACTACGCCGACTGGTGCGTGTCGTGCAAGATCATGGAAAAAC
AGGTGTTCGGCAAACCCGAGGTGATGGACGCGCTCAAAGACGTGCGCCTGTTACGCCTGGACGTCACCGCC
GACAACGCCGCCAGCCGCGAGCTGCTGGGCCGCTACAAAGTGCCGGGGCCACCGAGCTTCGTGTGGATCG
GCCCGGACGGTGAAGAACGCCGCGCCCAACGCATCACCGGCGAAGTAGACGCCGCCGCCTTCCTGCAACG
CTGGACACAAACCCGAGACGCGCGCTGA

SEQ ID NO: 149 RXF05426.1

ATGCTGAACAAATACCCTCTGTGGAAATACGTACTGATCCTGGCGGTGCTGGCGATCGGCTTTATTTATTCCG
CTCCCAATCTCTATCCTGATGACCCGGCGATCCAGATCTCTGGCGCCAGCACTTCGCTGCAGGTCAATCAGG
CTGATCTGGACCGTGCGAGCAAAGCGCTCAACGACGCGGGTATCCAGGTTAAAGCGGCAACCTTGGCAGCT
GGTTCCAAAGGCGGCTTGTTGCGCCTGACCAAGCAAGAAGACCAATTGCCGGCCAAAGATGTCGTACGCAAG
GTCATGGGTGATGACTACGTTGTCGCGCTCAACCTGGCCCAGACCACGCCACAATGGCTGCGCAGCATTGG
CGCGCACCCGATGAAGCTGGGTCTGGACTTGTCCGGTGGTGTGCACTTCCTGCTGGAAGTCGACATGGACA
AGGCCCTGGACGCACGTCTGAAAGTCTACGAAGGCGACGTGAAGAGCCTGCTGCGCAAAGAGAAGCTGCGC
TATCGCAGCCTGCCGCAGCTCAACGGTGCCATTCAGCTGGGCTTTGCTGACGAAGCATCCCGCGAACAGGC
CCGTGCGCTTATCCGCAAGAACTTCAATGATTTCGACATCGTGCCTGCCGACCTCAATGGTCAAGCGGTACTG
CGTCTGGCGATGAGCCCGGCCAAGATCGCCGAAATCCGCGAATACTCCATCAAGCAGAACTTGACCACGGTG
CGTAACCGCGTCAACGAGCTGGGTGTGGCCGAGCCGATCGTGCAGCGCCAGGGCGCCAACCGTATCGTGG
TTGAGTTGCCGGGCGTACAGGACACCGCTGAAGCCAAGCGTATCCTCGGCAAGACCGCCAACCTGGAGTTC
CGTCTCGCGGCAGACCCAGGCGCTACGCGTGCCACTTCCGAAGAGTTCGAATTCCGTGAAGGCAACCGTCC
TCCTGCGTTGATCGAGCGTGGTTTGATCATCACCGGTGACCAGGTGACCGACGCCAAGGCCGGTTTCGGCG
AGCACGGTACGCCTGAAGTGAACATCCGCCTGGATGGCCATGGCGGCGAACTGATGAGCCGCGCCACGCGC
AGCAACGTCGGTCGCAGCATGGCAGTGATCTTCATCGAGCAGCGCCCGGTGACCACCTACACCAAGCAGAT
GGTCAACGGCGTCGAGAAAGACGTGCCGGTGCAGACCTTCAAGGAAGAGAAGAAGATCATCAGCCTGGCGA
CCATCCAGTCGCCGCTGGGTGCTCAGTTCCGTATCACTGGCCTGAACGGCCAGGGCGAGTCGTCCGAGCTG
GCGTTGCTGCTGCGTGCCGGTGGCCTGGCTGCACCGATGTACTTCGCTGAAGAGCGTACCATTGGCCCGAG
CCTGGGTGCCGACAACATCACCAAGGGTGTCGATGCGGCGCTGTGGGGCATGTTGTTCGTGTCGCTGTTCAT
CATCGCCATCTACCGCTTCTTTGGTGTGATCGCCACCGTTGCCCTGGCGGGCAACATGGTGATGTTGCTGGC
TCTGATGTCGTTGCTGGGTGCCACACTGACCCTGCCAGGTATTGCCGGTATCGTACTCACCATGGGTATGGC
GGTGGATGCCAACGTGCTGATCTTCTCGCGGATTCGTGAAGAGATCGCCGCCGGCATGACCGTGCAGCGTG
CAATCAACGAAGGCTTCGGCCGGGCATTTACCGCGATCCTCGACTCCAACCTGACCACGCTGTTGGTCGGCG
GGATTCTCTTCGCCATGGGCACAGGCCCGGTGAAAGGCTTTGCGGTGACCATGTCCCTCGGGATCTTTACCT
CGATGTTCACGGCCATCATGGTGACCCGCGCAATGGTCAACCTGATCTTTGGCGGGCGTGACTTCAAGAAGT
TGTGGATTTAA

FIGURE 5-4

SEQ ID NO: 150 RXF05432.1
ATGTTACGTACAATCAACTTCATGGGCGTTCGCAACGTTGCGTTCGGCGTCACCGTGCTCCTTACCGTTCTGG
CGTTGTTCAGCTGGTTCCATAAGGGTCTGAACTACGGCCTGGACTTCACCGGCGGTACGCTCATCGAGCTGA
CCTACGAGAAGCCGGCCGACGTTACCCTGGTGCGCAGCGAGCTGGTCAAGGCCGGCTATCACGAAGCCGTG
GTACAGAGCTTTGGTGCCACCACCGACCTGCTGGTGCGTATGCCTGGCGAAGACCCGCAACTGGGTCACCA
GGTAGCCGAGGCCTTGCAAAAGGTCGGCGGCGATAACCCTGCGTCGGTCAAACGCGTCGAGTTCGTCGGCC
CGCAAGTGGGTGAAGAACTGCGCGATCAGGGCGGCCTCGGCATGCTGATGGCGCTGGTCGGCATCATGATC
TACCTGGCGTTCCGCTTTCAGTGGAAGTTCGGTGTCGGCGCCATTGTGTCGCTGATCCACGACGTGGTCGTC
ACCGTGGGTATCCTGGCCTACTTCCAGATCACCTTCGACCTGACCGTATTGGCAGCTGTGCTGGCGATCATT
GGTTACTCGCTCAACGACACCATCGTGGTATTCGACCGAGTTCGTGAGAACTTCCGTGTACTGCGCAAGGCG
ACGTTGATCGAGAACATCAACATCTCCACCACCCAGACCCTGCTGCGGACCATGGCGACGTCGATCTCCACC
TTGCTGGCGATTGCTGCGCTGATGATCTTCGGCGGCGACAACCTGTGGGGCTTCTCCCTGGCGCTGTTTATC
GGCGTTCTGGCGGGTACCTACTCGTCGATCTACATCGCCAACGTGGTGCTGATCTGGCTGAACCTCAACAGC
GAAGACTTGATCCCTCCTGCCGCTACCGACAAGGAGGTCGACGACCGTCCTTGA

SEQ ID NO: 151 RXF00458.2
ATGAGAATCCTCGGCATTTTATGCCTGCTACTCACATTGAACGGCTGCAGCTCCTTACTGTTCTACCCCGAGC
CCGGCCTGCCCTTCACTCCGGAAAAAGCCCACCTGCAATACCGCGACGTCACGCTCACCACCGCAGACGGG
GTGAAGCTGCACGCTTGGTGGTTGCCAGCCAAAGCGGGTGTGCCACTCAAAGGCACCATCCTGCATTTGCAC
GGCAACGGCGGTAACCTCGCCTGGCACCTGGGGGGCAGTTGGTGGTTGCCGGAGCAGGGTTATCAAGTGTT
GTTGCTGGACTATCGCGGCTATGGGCTGTCGGAAGGCAAGCCATCGTTGCCGGCGGTCTACCAGGATATCG
ACGCCGCATTCGGCTGGATCGACAAGGCGCCTGAAACCCAGGGTAAACCGCTGATTATTCTCGGGCAAAGCC
TGGGCGGTGCACTGGCGGTGCATTACCTGGCAGCCCACCCGGAGCGTCAAGCCCAACTCAAAGCTCTGGTA
CTGGACGGCGTGCCAGCCAGTTATCGTGACGTAGGACAATTCGCCTTGAGCACTTCCTGGTTAACCTGGCCG
TTGCAGGTGCCGCTGTCATGGCTGGTGCCCGACGCCGACAGTGCGATCAATGCCATGCCCCGCGTGACCGG
CGTGCCCAAGCTGCTGTTCCACAGCCTGGATGATCCCATCGTGCCGGTGGCCAATGGCATCCGCCTGTATCA
GGCCGCACCGCCGCCCAGGGTGTTGCAACTGACCCGTGGCGGCCATGTGCAGACCTTTGCCGATAAAACCT
GGCAGACCGTGATGCTGCGTTACCTGGACGACCCGCAGCACTTCAACGGCTTGCGCCGCCTGGGCGAAATT
CCGAATTACCCTATTCCTAAAGTTGATTCATCAGAGAGCCCGCAATGA

SEQ ID NO: 152 RXF01957.2
ATGTCCATGACTCCCCGCGAAATCGTCCATGAACTCAATCGCCATATCATCGGCCAGGACGATGCCAAGCGC
GCCGTTGCCATTGCGCTGCGTAACCGCTGGCGCCGGATGCAACTGCCGGAAGAACTGCGCGTTGAAGTAAC
GCCCAAGAACATCCTGATGATCGGCCCCACCGGCGTGGGTAAAACCGAGATCGCCCGGCGCCTGGCCAAAC
TGGCCAATGCACCGTTCATCAAGGTCGAAGCGACCAAGTTCACCGAAGTCGGCTATGTGGGCCGCGATGTCG
AGTCGATCATTCGTGACCTGGCTGACGCCGCCCTGAAGATGCTGCGCGAACAGGAAGTAACCAAGGTCAGC
CACCGCGCCGAAGACGCCGCTGAAGAGCGCATCCTCGACGCCCTGTTGCCACCGGCACGCATGGGTTTCAA
CGAAGACGCCGCACCGGCTACCGATTCCAACACTCGCCAGCTGTTCCGCAAGCGCCTGCGTGAAGGCCAGC
TGGATGACAAGGAAATCGAGATCGAAGTGGCTGAAGTGTCCGGCGTGGATATTTCTGCCCCGCCTGGCATGG
AAGAAATGACCAGCCAGCTGCAGAACCTGTTCGCCAACATGGGCAAGGGCAAGAAGAAAAGCCGCAAGCTCA
AGGTGAAAGAGGCGCTCAAGCTCGTGCGCGACGAAGAAGCCGGGCGCCTGGTCAATGAGGAAGAACTCAAG
GCCAAGGCCCTGGAAGCGGTCGAGCAACATGGCATCGTGTTTATCGACGAGATCGACAAAGTGGCCAAGCG
AGGCAACTCAGGCGGCGTGGATGTGTCCCGCGAAGGCGTGCAGCGCGATTTGCTGCCGCTGATCGAGGGCT
GCACGGTCAACACCAAGCTGGGCATGGTCAAGACTGACCACATCCTGTTTATCGCTTCCGGTGCTTTCCACCT
GAGCAAGCCCAGCGACCTGGTGCCCGAGCTGCAAGGCCGCTTGCCGATTCGGGTGGAGCTCAAGGCGCTG
ACGCCGGGCGACTTCGAGCGCATCCTCAGCGAGCCGCATGCCTCGCTCACCGAGCAGTACCGCGAGTTGCT
GAAAACCGAAGGGCTGGGTATCGAATTCCAGGCAGACGGGATCAAGCGCCTGGCGGAGATCGCCTGGCAGG
TCAACGAGAAGACCGAGAACATCGGTGCCCGTCGCCTGCATACCTTGCTTGAGCGCCTGCTGGAGGAAGTGT
CCTTCAGTGCCGGCGACATGGCCGGTGCGCAGAATGGCGAAGCGATCAAGATCGATGCTGATTACGTCAACA
GCCACTTGGGCGAATTGGCGCAGAACGAAGATCTGTCTCGTTATATCCTGTAA

FIGURE 5-5

SEQ ID NO: 153 RXF04497.2

GTGAAGTCCTCTCATGCCGATGCGAACTCGGCGGCAGACAACCAGGCCTCGACAGGATCCAAGTTGCTTAAT
CTTTCCGCTCCGCTGGTAGGTGACCGCACTGGCCTGCAGCGACTGTATGGATCGAGCCTGAACTCCGGACT
GCTTCAACTAGGGGAAGTGAATTCTGGCAAAGTGGTTATCGCTCGTTGTTCCCCGAAGGCAGAGGAAGATAC
CAAACCGGCAGCGGATGAGCCCAAGCCGAATGGTGACACCAAGCCAGTAACGGATAAGCCCAAGCCGGGCG
GCTTCTCCACGCCAGTAACAGATAGGCCCAAGCCACGCGGCGGCACCAAGGAGCCGGTGGTTGAGCAGCCC
AAGCCAGAGGGCACCAAGCAGCCAGTGGTTGAGCAGCCCAAGCCAGAGGGCACCAAGCAGCCAGTGGTAG
ATCAGCCCAAGCCAGAAGGTACCAAGGGGCCGGTGGTTGAGCAGCCCAAGCCCGAGGGCACCAAACAGCCA
GTGGTAGATCAGCCCAAGCCAGCGGGCACTAAGCAGCCAGTGGTAGATCAGCCCAAGCCAGCGGGCACTAA
GCAGCCAGTGGTAGATCAGCCCAAGCCAGCGGGCACTAAGCAGCCAGTGGTAGATCAGCCCAAGCCAGCGG
GCACTAAGCAGCCAGTGGTAGATCAGCCCAAGCCAGCAGGCACTAAGCAGCCAGTGGTAGAGCAGCCCAAG
CCAGAGGGCACCAAGCAGCCAGTGGTTGACCGGCCCAAGCCAGAGGGCACCAAGCAGCCAGTGGTAGATCA
GCCCAAGCCAGAAGGCACCAAGCAGCCAGTGGTAGATCAGCCCAAGCCAGAAGGCACCAAGCAGCCAGTCG
TTGACCGGCCCAGGCCAGGCGGCGACCCCCGGACCGATGACACCACCTACGGATTCAATTCAAATACTGGC
AAGCGGGAAACCACCCTGACGTCCGCGTCCGATAAGCCAGAGTTCAACATCTGGGATGAGCGTGGGAACGA
TACGTTTGATTTCTCTGGCTTCAAGCAGGATCAAATCATCAACTTGCGTGGCGGTGCGTTTTCCAGTGTAGGC
GGGATGAGGGAAAACGTTCGCATCGGTGAGAAGACGGTGATCGAAAATGCCGTGGGTGGCCACGGTAACGA
CCGCATCATAGGTAACAGTGCCGATAACGTGCTTACCGGTGGCGCGGGAGCCGATACGTTGGTGGGCGGCG
GCGGCTGGAATACCTTCAAGTTCAATGCCTTTAGTGATTCAACCCGCGCCAATGCCGACTTGCTGTTGGACTT
CAACACAGGGCAAGACAAGATCGACCTCTCGCAGATGGCGCTCGACGGCAAGGTATCGTTGAACTTCGTCGA
TAACTACACGGGGAAGGCGGGCGACACCATCATCAAGTTTAACCCGCTGTCTGGCCGTTATTTGCTGGCGAT
AGACTTGGACGGAGATGGCAAGACCGACTTCCTGATCAAGAGTACCCGAATGATCAGTCCGGAAGATGTCAT
AGGGCTCAACATTAAAGATGGCGGTTATCTTTGA

SEQ ID NO: 154 RXF04587.1

ATGTTAAACCGCGAGCTCGAAGTCACCCTCAATCTTGCCTTCAAGGAGGCTCGTTCGAAGCGTCATGAATTCA
TGACCGTCGAACACCTTTTGCTGGCACTTTTGGATAACGAAGCTGCCGCCACCGTTCTACGTGCGTGCGGCG
CCAACCTTGACAAGCTCAAGCATGACCTGCAGGAGTTTATCGACTCCACCACGCCACTGATCCCCGTGCATG
ACGAGGACCGCGAAACCCAGCCAACCCTGGGCTTCCAGCGGGTATTGCAGCGTGCTGTGTTCCACGTACAG
AGCTCCGGTAAGCGTGAGGTCACAGGCGCGAATGTACTTGTGGCAATTTTCAGCGAACAGGAAAGCCAGGCC
GTGTTTCTGCTCAAGCAGCAGAGCGTTGCCCGTATTGATGTGGTCAACTACATCGCCCACGGTATCTCCAAG
GTGCCTGGGCACGGCGATCATTCCGAGGGTGAGCAGGACATGCAGGACGAGGAGGGCGGCGAGTCTTCTT
CTTCCAGCAACCCGCTGGATGCCTATGCAAGTAACCTCAATGAAATGGCGCGCCAGGGGCGGATCGATCCG
CTAGTGGGGCGTGAGCATGAGGTTGAGCGTGTAGCGCAGATCCTGGCGCGTCGTCGCAAGAACAACCCATT
GCTGGTGGGCGAGGCGGGCGTGGGTAAAACCGCGATTGCCGAAGGCCTGGCCAAGCGCATTGTCGACAAC
CAGGTGCCAGACCTGCTGGCCAGCAGTGTCGTCTACTCCCTTGACCTGGGCGCGTTGCTCGCCGGGACCAA
GTACCGTGGCGATTTCGAGAAGCGCTTCAAGGCGTTGCTCGGCGAGCTGAAAAAACGCCCGCAGGCCATCC
TGTTCATCGACGAGATCCATACCATCATTGGCGCCGGTGCGGCTTCCGGTGGGGTGATGGACGCTTCCAACC
TGCTCAAGCCACTGCTGTCCTCCGGTGATATCCGCTGCATTGGTTCGACCACGTTCCAGGAATTTCGCGGCA
TCTTCGAGAAAGACCGCGCCCTGGCGCGTCGCTTCCAGAAAGTTGACGTGTCCGAGCCCTCGGTTGAAGACA
CCATCGGCATCCTGCGCGGGCTCAAGGGGCGTTTTGAAGCGCACCATGGCATCGAGTACACCGATGAGGCC
CTGCGTGCGGCGGCTGAGCTGGCGTCGCGCTACATCAACGACCGGCACATGCCAGACAAAGCCATCGATGT
GATCGACGAGGCGGGTGCCTACCAGCGCCTGCAGCCGGTCGAGAAGCGCGTGAAGCGCATCGACGTGCCT
CAGGTCGAGGACATCGTGGCCAAGATCGCGCGGATTCCGCCAAAACACGTCACCAGTTCCGACAAGGAGTT
GCTGCGTAACCTGGAGCGCGACCTCAAGCTCACCGTGTTTGGTCAGGATGCGGCCATCGACTCGCTGTCCA
CGGCGATCAAGTTGTCCCGTGCGGGCCTCAAGTCGCCGGACAAGCCAGTCGGTTCGTTCCTGTTCGCAGGC
CCGACCGGCGTCGGCAAGACCGAGGCGGCTCGCCAGTTGGCCAAGGCCATGGGCATCGAGCTGGTGCGTT
TCGACATGTCCGAGTACATGGAGCGCCACACGGTGTCGCGTTTGATCGGCGCGCCTCCGGGCTATGTCGGC
TTCGATCAGGGCGGCCTGTTGACCGAGGCGATCACCAAGCAGCCACACTGCGTATTGCTGCTCGACGAAATC
GAAAAGGCTCACCCGGAAGTCTTCAACCTGCTGTTGCAGGTCATGGACCACGGCACCCTGACCGACAACAAC
GGGCGCAAGGCAGACTTCCGCAACGTGATCGTGATCATGACCACCAACGCCGGTGCTGAAACCGCGGCGCG
TGCTTCGATCGGCTTTACGCATCAGGATCACTCGTCTGATGCCATGGAAGTGATCAAGAAGAGCTTCACGCC
GGAGTTCCGCAACCGCCTGGACACCATTATCCAGTTTGGTCGCCTCAGCCATGAGGTCATCAAAAGCGTGGT
GGACAAGTTCCTCACCGAGCTTCAAGCGCAGTTGGAAGACAAGCGCGTGCAGCTGGATGTGACGGAAGCGG
CCCGCAGTTGGATCGCAGAGGGCGGCTACGATGCGGCAATGGGCGCACGCCCAATGGCGCGTCTGATCCA
GGACAAGATCAAGCGGCCATTGGCCGAAGAGATCCTGTTCGGCGAACTCTCCGACCATGGCGGCGTGGTGC
ACATCGACCTGAAGGACGGCGAGCTGACCTTCGAGTTCGAGACCACGGCGGAAATGGCCTGA

FIGURE 5-6

SEQ ID NO: 155 RXF04654.2

ATGACTGACACCCGCAACGGCGAGGACAACGGCAAGCTGCTCTATTGCTCCTTCTGTGGCAAAAGCCAGCAT
GAAGTACGCAAATTGATTGCCGGCCCCTCGGTGTTTATCTGCGACGAATGCGTCGACCTGTGCAATGACATC
ATCCGTGAGGAGGTGCAGGAAGCCCAGGCCGAGAGCAGTGCGCATAAATTACCTTCGCCTAAAGAAATCAGT
GGCATCCTTGACCAATACGTCATTGGTCAAGAGCGTGCAAAAAAGGTTCTGGCCGTAGCGGTGTACAACCAC
TACAAGCGCTTGAACCAGCGTGACAAGAAAGGTGACGAGGTTGAACTCGGCAAGAGCAACATCTTGCTGATC
GGTCCTACAGGCTCGGGTAAAACCCTGCTTGCAGAAACCCTCGCTCGCCTGCTGAACGTTCCGTTCACCATC
GCCGACGCCACCACCCTCACCGAGGCTGGCTACGTGGGTGAAGATGTCGAGAACATCATTCAGAAACTGCTG
CAGAAGTGCGACTACGACGTAGAGAAAGCCCAGATGGGTATTGTCTACATCGACGAGATCGACAAGATCTCG
CGCAAGTCGGACAACCCGTCGATCACTCGGGACGTTTCCGGTGAAGGCGTGCAGCAGGCCCTGTTGAAGCT
GATCGAAGGCACGGTTGCGTCCGTACCGCCGCAAGGTGGTCGCAAGCACCCGCAGCAGGAATTCCTTCAGG
TTGATACGCGCAACATCCTGTTCATTTGTGGCGGTGCGTTCTCGGGTCTCGAGAAGGTGATTCAGCAGCGTT
CCACCCGTGGCGGCATTGGTTTCAGTGCGGAAGTGCGTAGCAAGGAAGAAGGCAAGAAGGTGGGCGAGTCC
CTGCGTGAAGTCGAGCCTGACGATTTGGTCAAGTTCGGTCTGATCCCGGAATTCGTTGGCCGTCTGCCGGTC
CTGGCCACGTTGGACGAGTTGGATGAGGCGGCTTTGATCCAGATCCTCACCGAACCGAAAAACGCCCTGACC
AAGCAATACGGCAAATTGTTCGAGATGGAAGGTGTAGACCTGGAGTTCCGTACCGACGCGCTGAAATCGGTG
GCCAAGCGGGCACTGGAGCGCAAGACCGGTGCACGTGGTCTGCGTTCTATCCTCGAAGGCGTGTTGCTCGA
CACCATGTACGAAATCCCCTCGCAGTCCGAGGTGAGTAAAGTGGTGATCGACGAAAGCGTTATCGAAGGCAA
GTCCAAGCCGCTGTATATCTATGAAAACAGTGAGCCGGCTGCCAAGGCTGCACCCGACGCGTAA

SEQ ID NO: 156 RXF04892.1

ATGCGGTGTTTGGCCTGCACGTATGGGCCGGTGTGCCTGCCGGGGCAAATCGCCTATCGCCCGGGCCCGAC
TTTGGCCAGCTCCGATGACCTGCGCATCAAAATCCTCGGCAAACAGACCCACGCCGGCCGCCCCTGGGACG
GTATCGACCCGATCACCGTCGGCGCGCAAACCATTGTCGGCCTGCAGACCGTGGTCAGCCGCCGTACCGAT
ATTTCGTCATTCCCCTCTGTGGTGAGCATCGGCACCATCAACGGTGGCACTCGCTACAACATCATCCCCGAGT
CGGTGGACATGAGCGGCACCCTTCGCTCCTACGACTACGGCATTCGTCAGAAGCTGCATGCAGACGTGCGT
CAAACCGTAGAGAAAATCGCCGAAAGCGGTGGCGCCAAGGCCGAAGTGACAATCATCGAGAAGTACGACCC
CACCATCAACAACCCGGCGCTGACCGAGAAAATGCTGCCGAGCCTGCGTTGGGCGGCTCAGGATGATGTGG
TGCAAGGCCCATTGGTAGGTGGCGCCGAAGACTTCTCGTTCTATGCCAAGGAAGCGCCGGGGCTGTTTGTGT
TCCTGGGGGTGACCCCAAGGGACCAGGACATGAGCAAGGCGGCGCCGAATCACAACCCAGGGTTCTTTGTG
GATGAGTCGGCATTGGTGGTGGGCGTGAGGACACTGGCGTCGTTGGCGACGGATTACCTTTACACCCACAC
CCCCCTGTAG

SEQ ID NO: 157 XFRNA203

GGGGCCGTTTAGGATTCGACGCCGGTCGCGAAACTTTAGGTGCATGCCGAGTTGGTAACAGAACTCGTAAAT
CCACTGTTGCAACTTCTTATAGTTGCCAATGACGAAAACTACGGCCAGGAATTCGCTCTCGCTGCGTAAGCAG
CCTTAGCCCTGAGCTTCTGGTACCTTCGGGTCCAGCAATCACCAGGGGATGTCTGTAAACCCAAAGTGATTGT
CATATAGAACAGAATCGCCGTGCAGTACGTTGTGGACGAAGCGGCTAAAACTTACACAACTCGCCCAAAGCA
CCCTGCCCTTCGGGTCGCTGAGGGTTAACTTAATAGAAACGGCTACGCATGTAGTACCGACAGCGGAGTACT
GGCGGACGGGGGTTCAAATCCCCCCGGCTCCACCAC

FIGURE 5-7

SEQUENCE LISTING

```
<110> Coleman, Russell J.
      Retallack, Diane M.
      Schneider, Jane C.
      Ramseier, Thomas M.
      Hershberger, Charles D.
      Lee, Stacey L.
      Resnick, Sol M.


<120> BACTERIAL LEADER SEQUENCES FOR INCREASED
  EXPRESSION

<130> 043292/339398

<160> 50

<170> FastSEQ for Windows Version 4.0

<210> 1
<211> 72
<212> DNA
<213> Artificial Sequence

<220>
<223> mutant phosphate binding protein leader sequence
      (pbp*)

<221> CDS
<222> (1)...(72)

<400> 1
atg aaa ctg aaa cgt ttg atg gcg gca atg act ttt gtc gct gct ggc   48
Met Lys Leu Lys Arg Leu Met Ala Ala Met Thr Phe Val Ala Ala Gly
 1               5                  10                  15

gtt gcg acc gtc aac gcg gtg gcc                                   72
Val Ala Thr Val Asn Ala Val Ala
             20


<210> 2
<211> 24
<212> PRT
<213> Artificial Sequence

<220>
<223> mutant phosphate binding protein leader sequence
      (pbp*)

<400> 2
Met Lys Leu Lys Arg Leu Met Ala Ala Met Thr Phe Val Ala Ala Gly
 1               5                  10                  15
Val Ala Thr Val Asn Ala Val Ala
            20
```

FIGURE 6 - 1

```
<210> 3
<211> 66
<212> DNA
<213> Pseudomonas fluorescens

<220>
<221> CDS
<222> (1)...(66)

<400> 3
atg cgt aat ctg atc ctc agc gcc gct ctc gtc act gcc agc ctc ttc   48
Met Arg Asn Leu Ile Leu Ser Ala Ala Leu Val Thr Ala Ser Leu Phe
 1               5                  10                  15

ggc atg acc gca caa gct                                           66
Gly Met Thr Ala Gln Ala
             20


<210> 4
<211> 22
<212> PRT
<213> Pseudomonas fluorescens

<400> 4
Met Arg Asn Leu Ile Leu Ser Ala Ala Leu Val Thr Ala Ser Leu Phe
 1               5                  10                  15
Gly Met Thr Ala Gln Ala
            20


<210> 5
<211> 63
<212> DNA
<213> Pseudomonas fluorescens

<220>
<221> CDS
<222> (1)...(63)

<400> 5
atg cgc ttg acc cag att att gcc gcc gca gcc att gcg ttg gtt tcc   48
Met Arg Leu Thr Gln Ile Ile Ala Ala Ala Ala Ile Ala Leu Val Ser
 1               5                  10                  15

acc ttt gcg ctc gcc                                               63
Thr Phe Ala Leu Ala
             20


<210> 6
<211> 21
<212> PRT
<213> Pseudomonas fluorescens
```

FIGURE 6 - 2

```
<400> 6
Met Arg Leu Thr Gln Ile Ile Ala Ala Ala Ala Ile Ala Leu Val Ser
 1               5                  10                  15
Thr Phe Ala Leu Ala
            20


<210> 7
<211> 99
<212> DNA
<213> Bacillus coagulans

<220>
<221> CDS
<222> (1)...(99)

<400> 7
atg agc aca cga atc ccc cgc cga caa tgg ctg aaa ggc gcc tcg ggc    48
Met Ser Thr Arg Ile Pro Arg Arg Gln Trp Leu Lys Gly Ala Ser Gly
 1               5                  10                  15

ctg ctg gcc gcc gcg agc ctg ggc cgg ttg gcc aac cgc gag gcg cgc    96
Leu Leu Ala Ala Ala Ser Leu Gly Arg Leu Ala Asn Arg Glu Ala Arg
             20                  25                  30

gcc                                                                99
Ala



<210> 8
<211> 33
<212> PRT
<213> Bacillus coagulans

<400> 8
Met Ser Thr Arg Ile Pro Arg Arg Gln Trp Leu Lys Gly Ala Ser Gly
 1               5                  10                  15
Leu Leu Ala Ala Ala Ser Leu Gly Arg Leu Ala Asn Arg Glu Ala Arg
            20                  25                  30
Ala



<210> 9
<211> 75
<212> DNA
<213> Pseudomonas fluorescens

<220>
<221> CDS
<222> (1)...(75)

<400> 9
atg tcg tgc aca cgt gca ttc aaa cca ctg ctg ctg atc ggc ctg gcc    48
Met Ser Cys Thr Arg Ala Phe Lys Pro Leu Leu Leu Ile Gly Leu Ala
 1               5                  10                  15
```

FIGURE 6 - 3

```
aca ctg atg tgt tcc cat gca ttc gct                                 75
Thr Leu Met Cys Ser His Ala Phe Ala
             20                  25


<210> 10
<211> 25
<212> PRT
<213> Pseudomonas fluorescens

<400> 10
Met Ser Cys Thr Arg Ala Phe Lys Pro Leu Leu Leu Ile Gly Leu Ala
 1               5                  10                  15
Thr Leu Met Cys Ser His Ala Phe Ala
            20                  25


<210> 11
<211> 72
<212> DNA
<213> Pseudomonas fluorescens

<220>
<221> CDS
<222> (1)...(72)

<400> 11
atg ctt ttt cgc aca tta ctg gcg agc ctt acc ttt gct gtc atc gcc     48
Met Leu Phe Arg Thr Leu Leu Ala Ser Leu Thr Phe Ala Val Ile Ala
 1               5                   10                  15

ggc tta ccg tcc acg gcc cac gcg                                     72
Gly Leu Pro Ser Thr Ala His Ala
             20


<210> 12
<211> 24
<212> PRT
<213> Pseudomonas fluorescens

<400> 12
Met Leu Phe Arg Thr Leu Leu Ala Ser Leu Thr Phe Ala Val Ile Ala
 1               5                  10                  15
Gly Leu Pro Ser Thr Ala His Ala
            20


<210> 13
<211> 69
<212> DNA
<213> Pseudomonas fluorescens

<220>
<221> CDS
<222> (1)...(69)
```

FIGURE 6 - 4

```
<400> 13
atg ccg cct cgt tct atc gcc gca tgt ctg ggg ctg ctg ggc ttg ctc    48
Met Pro Pro Arg Ser Ile Ala Ala Cys Leu Gly Leu Leu Gly Leu Leu
 1               5                   10                  15

atg gct acc cag gcc gcc gcc                                        69
Met Ala Thr Gln Ala Ala Ala
             20


<210> 14
<211> 23
<212> PRT
<213> Pseudomonas fluorescens

<400> 14
Met Pro Pro Arg Ser Ile Ala Ala Cys Leu Gly Leu Leu Gly Leu Leu
 1               5                  10                  15
Met Ala Thr Gln Ala Ala Ala
            20


<210> 15
<211> 63
<212> DNA
<213> Pseudomonas fluorescens

<220>
<221> CDS
<222> (1)...(63)

<400> 15
atg cgc ctc gct gcc cta ccg cta ttg ctt gcc cct ctc ttt att gcg    48
Met Arg Leu Ala Ala Leu Pro Leu Leu Leu Ala Pro Leu Phe Ile Ala
 1               5                   10                  15

ccg atg gcc gtt gcg                                                63
Pro Met Ala Val Ala
             20


<210> 16
<211> 21
<212> PRT
<213> Pseudomonas fluorescens

<400> 16
Met Arg Leu Ala Ala Leu Pro Leu Leu Leu Ala Pro Leu Phe Ile Ala
 1               5                  10                  15
Pro Met Ala Val Ala
            20


<210> 17
<211> 63
<212> DNA
```

FIGURE 6 - 5

```
<213> Pseudomonas fluorescens

<220>
<221> CDS
<222> (1)...(63)

<400> 17
atg aag ttc aaa cag ctg atg gcg atg gcg ctt ttg ttg gcc ttg agc   48
Met Lys Phe Lys Gln Leu Met Ala Met Ala Leu Leu Leu Ala Leu Ser
 1               5                  10                  15

gct gtg gcc cag gcc                                               63
Ala Val Ala Gln Ala
            20


<210> 18
<211> 21
<212> PRT
<213> Pseudomonas fluorescens

<400> 18
Met Lys Phe Lys Gln Leu Met Ala Met Ala Leu Leu Leu Ala Leu Ser
 1               5                  10                  15
Ala Val Ala Gln Ala
            20


<210> 19
<211> 63
<212> DNA
<213> Pseudomonas fluorescens

<220>
<221> CDS
<222> (1)...(63)

<400> 19
atg aat aga tct tcc gcg ttg ctc ctc gct ttt gtc ttc ctc agc ggc   48
Met Asn Arg Ser Ser Ala Leu Leu Leu Ala Phe Val Phe Leu Ser Gly
 1               5                  10                  15

tgc cag gcc atg gcc                                               63
Cys Gln Ala Met Ala
            20


<210> 20
<211> 21
<212> PRT
<213> Pseudomonas fluorescens

<400> 20
Met Asn Arg Ser Ser Ala Leu Leu Leu Ala Phe Val Phe Leu Ser Gly
 1               5                  10                  15
Cys Gln Ala Met Ala
            20
```

FIGURE 6 - 6

```
<210> 21
<211> 99
<212> DNA
<213> Pseudomonas fluorescens

<220>
<221> CDS
<222> (1)...(99)

<400> 21
atg caa aac cgc act gtg gaa atc ggt gtc ggc ctt ttc ttg ctg gct    48
Met Gln Asn Arg Thr Val Glu Ile Gly Val Gly Leu Phe Leu Leu Ala
 1               5                  10                  15

ggc atc ctg gct tta ctg ttg ttg gcc ctg cga gtc agc ggc ctt tcg    96
Gly Ile Leu Ala Leu Leu Leu Leu Ala Leu Arg Val Ser Gly Leu Ser
             20                  25                  30

gcc                                                                99
Ala



<210> 22
<211> 33
<212> PRT
<213> Pseudomonas fluorescens

<400> 22
Met Gln Asn Arg Thr Val Glu Ile Gly Val Gly Leu Phe Leu Leu Ala
 1               5                  10                  15
Gly Ile Leu Ala Leu Leu Leu Leu Ala Leu Arg Val Ser Gly Leu Ser
             20                  25                  30
Ala



<210> 23
<211> 117
<212> DNA
<213> Pseudomonas fluorescens

<220>
<221> CDS
<222> (1)...(117)

<400> 23
atg tct ctt cgt aat atg aat atc gcc ccg agg gcc ttc ctc ggc ttc    48
Met Ser Leu Arg Asn Met Asn Ile Ala Pro Arg Ala Phe Leu Gly Phe
 1               5                  10                  15

gcg ttt att ggc gcc ttg atg ttg ttg ctc ggt gtg ttc gcg ctg aac    96
Ala Phe Ile Gly Ala Leu Met Leu Leu Leu Gly Val Phe Ala Leu Asn
             20                  25                  30
```

FIGURE 6 - 7

```
cag atg agc aaa att cgt gcg                                          117
Gln Met Ser Lys Ile Arg Ala
        35


<210> 24
<211> 39
<212> PRT
<213> Pseudomonas fluorescens

<400> 24
Met Ser Leu Arg Asn Met Asn Ile Ala Pro Arg Ala Phe Leu Gly Phe
1               5                   10                  15
Ala Phe Ile Gly Ala Leu Met Leu Leu Leu Gly Val Phe Ala Leu Asn
            20                  25                  30
Gln Met Ser Lys Ile Arg Ala
        35


<210> 25
<211> 30
<212> DNA
<213> Artificial Sequence

<220>
<223> oligonucleotide primer

<400> 25
aattactagt aggaggtaca ttatgcgctt                                    30

<210> 26
<211> 30
<212> DNA
<213> Artificial Sequence

<220>
<223> oligonucleotide primer

<400> 26
tatactcgag ttatttaacc tgtttcagta                                    30

<210> 27
<211> 5
<212> PRT
<213> Artificial Sequence

<220>
<223> First 5 amino acids of the predicted protein
      sequence for the processed form of dsbC-Skp

<400> 27
Ala Asp Lys Ile Ala
1               5


<210> 28
<211> 10
```

```
<212> PRT
<213> Artificial Sequence

<220>
<223> First 10 amino acids of the predicted protein
      sequence for the unprocessed form of dsbC-Skp



<400> 28
Met Arg Leu Thr Gln Ile Ile Ala Ala Ala
 1               5                  10


<210> 29
<211> 10
<212> PRT
<213> Artificial Sequence

<220>
<223> First 10 amino acids of the predicted protein
      sequence for the processed form of dsbC-Skp




<400> 29
Ala Asp Lys Ile Ala Ile Val Asn Met Gly
 1               5                  10


<210> 30
<211> 63
<212> DNA
<213> Pseudomonas fluorescens

<220>
<221> CDS
<222> (1)...(63)

<400> 30
atg aag aag tcc acc ttg gct gtg gct gta acg ttg ggc gca atc gcc   48
Met Lys Lys Ser Thr Leu Ala Val Ala Val Thr Leu Gly Ala Ile Ala
 1               5                   10                  15

cag caa gca ggc gct                                               63
Gln Gln Ala Gly Ala
             20


<210> 31
<211> 21
<212> PRT
<213> Pseudomonas fluorescens

<400> 31
Met Lys Lys Ser Thr Leu Ala Val Ala Val Thr Leu Gly Ala Ile Ala
```

FIGURE 6 - 9

```
 1               5                   10                  15
Gln Gln Ala Gly Ala
            20


<210> 32
<211> 72
<212> DNA
<213> Pseudomonas fluorescens

<220>
<221> CDS
<222> (1)...(72)

<400> 32
atg aaa ctg aaa aac acc ttg ggc ttg gcc att ggt tct ctt att gcc    48
Met Lys Leu Lys Asn Thr Leu Gly Leu Ala Ile Gly Ser Leu Ile Ala
 1               5                   10                  15

gct act tct ttc ggc gtt ctg gca                                    72
Ala Thr Ser Phe Gly Val Leu Ala
             20


<210> 33
<211> 24
<212> PRT
<213> Pseudomonas fluorescens

<400> 33
Met Lys Leu Lys Asn Thr Leu Gly Leu Ala Ile Gly Ser Leu Ile Ala
 1               5                   10                  15
Ala Thr Ser Phe Gly Val Leu Ala
            20


<210> 34
<211> 72
<212> DNA
<213> Pseudomonas fluorescens

<220>
<221> CDS
<222> (1)...(72)

<400> 34
atg aaa ctg aaa cgt ttg atg gcg gca atg act ttt gtc gct gct ggc    48
Met Lys Leu Lys Arg Leu Met Ala Ala Met Thr Phe Val Ala Ala Gly
 1               5                   10                  15

gtt gcg acc gcc aac gcg gtg gcc                                    72
Val Ala Thr Ala Asn Ala Val Ala
             20


<210> 35
<211> 24
```

<212> PRT
<213> Pseudomonas fluorescens

<400> 35
Met Lys Leu Lys Arg Leu Met Ala Ala Met Thr Phe Val Ala Ala Gly
1 5 10 15
Val Ala Thr Ala Asn Ala Val Ala
20

<210> 36
<211> 60
<212> DNA
<213> Pseudomonas fluorescens

<220>
<221> CDS
<222> (1)...(60)

<400> 36
atg ttt gcc aaa ctc gtt gct gtt tcc ctg ctg act ctg gcg agc ggc 48
Met Phe Ala Lys Leu Val Ala Val Ser Leu Leu Thr Leu Ala Ser Gly
1 5 10 15 cag ttg ctt gct 60
Gln Leu Leu Ala
20

<210> 37
<211> 20
<212> PRT
<213> Pseudomonas fluorescens

<400> 37
Met Phe Ala Lys Leu Val Ala Val Ser Leu Leu Thr Leu Ala Ser Gly
1 5 10 15
Gln Leu Leu Ala
20

<210> 38
<211> 51
<212> DNA
<213> Pseudomonas fluorescens

<220>
<221> CDS
<222> (1)...(51)

<400> 38
atg atc aaa cgc aat ctg ctg gtt atg ggc ctt gcc gtg ctg ttg agc 48
Met Ile Lys Arg Asn Leu Leu Val Met Gly Leu Ala Val Leu Leu Ser
1 5 10 15 gct 51
Ala

<210> 39
<211> 17
<212> PRT
<213> Pseudomonas fluorescens

<400> 39
Met Ile Lys Arg Asn Leu Leu Val Met Gly Leu Ala Val Leu Leu Ser
 1               5                  10                  15
Ala

<210> 40
<211> 69
<212> DNA
<213> Pseudomonas fluorescens

<220>
<221> CDS
<222> (1)...(69)

<400> 40
atg cag aac tat aaa aaa ttc ctt ctg gcc gcg gcc gtc tcg atg gcg   48
Met Gln Asn Tyr Lys Lys Phe Leu Leu Ala Ala Ala Val Ser Met Ala
 1               5                  10                  15 ttc agc gcc acg gcc atg gca   69
Phe Ser Ala Thr Ala Met Ala
             20

<210> 41
<211> 23
<212> PRT
<213> Pseudomonas fluorescens

<400> 41
Met Gln Asn Tyr Lys Lys Phe Leu Leu Ala Ala Ala Val Ser Met Ala
 1               5                  10                  15
Phe Ser Ala Thr Ala Met Ala
             20

<210> 42
<211> 93
<212> DNA
<213> Pseudomonas fluorescens

<220>
<221> CDS
<222> (1)...(93)

<400> 42
atg atc cgt gac aac cga ctc aag aca tcc ctt ctg cgc ggc ctg acc   48

```
Met Ile Arg Asp Asn Arg Leu Lys Thr Ser Leu Leu Arg Gly Leu Thr
 1               5                  10                  15

ctc acc cta ctc agc ctg acc ctg ctc tcg ccc gcg gcc cat tct       93
Leu Thr Leu Leu Ser Leu Thr Leu Leu Ser Pro Ala Ala His Ser
             20                  25                  30



<210> 43
<211> 31
<212> PRT
<213> Pseudomonas fluorescens

<400> 43
Met Ile Arg Asp Asn Arg Leu Lys Thr Ser Leu Leu Arg Gly Leu Thr
 1               5                  10                  15
Leu Thr Leu Leu Ser Leu Thr Leu Leu Ser Pro Ala Ala His Ser
             20                  25                  30


<210> 44
<211> 5
<212> PRT
<213> Artificial Sequence

<220>
<223> N-terminal amino acid sequence of processed azurin
      and ibp



<400> 44
Ala Gln Val Gln Leu
 1               5


<210> 45
<211> 1317
<212> DNA
<213> Bacillus coagulans

<220>
<221> CDS
<222> (1)...(1317)

<400> 45
atg agc aca cga atc ccc cgc cga caa tgg ctg aaa ggc gcc tcg ggc   48
Met Ser Thr Arg Ile Pro Arg Arg Gln Trp Leu Lys Gly Ala Ser Gly
 1               5                  10                  15

ctg ctg gcc gcc gcg agc ctg ggc cgg ttg gcc aac cgc gag gcg cgc   96
Leu Leu Ala Ala Ala Ser Leu Gly Arg Leu Ala Asn Arg Glu Ala Arg
             20                  25                  30

gcc gcc gaa gcg agc gcc gcc gcg ccg ctc gac act ggc tcg ctg ggc   144
```

```
Ala Ala Glu Ala Ser Ala Ala Ala Pro Leu Asp Thr Gly Ser Leu Gly
        35                  40                  45

gcc tcg ccg cgc gcg acg ctc gac gcc tgc ctg caa aaa gcc gtc gac     192
Ala Ser Pro Arg Ala Thr Leu Asp Ala Cys Leu Gln Lys Ala Val Asp
    50                  55                  60

gac ggc acg ctc aag agc gtg gtg gcg atg gcc gcc acc gag cgc ggg     240
Asp Gly Thr Leu Lys Ser Val Val Ala Met Ala Ala Thr Glu Arg Gly
65                  70                  75                  80

ctc gcc tac cag ggc gcg cgc ggc ccg gcc aac gcg gcc ggc gag ccg     288
Leu Ala Tyr Gln Gly Ala Arg Gly Pro Ala Asn Ala Ala Gly Glu Pro
                85                  90                  95

atc ggc ccc gat acg gtg ttc tgg atg ctg tcg atg acc aag gcg atc     336
Ile Gly Pro Asp Thr Val Phe Trp Met Leu Ser Met Thr Lys Ala Ile
            100                 105                 110

acc gcc acc gcc tgc atg cag ctg atc gag cag ggc cgg ctc ggg ctc     384
Thr Ala Thr Ala Cys Met Gln Leu Ile Glu Gln Gly Arg Leu Gly Leu
        115                 120                 125

gac cag ccc gcc gcc gag atc ctg ccg caa ctg aag gcg ccg cag gtg     432
Asp Gln Pro Ala Ala Glu Ile Leu Pro Gln Leu Lys Ala Pro Gln Val
    130                 135                 140

ctg gag ggc ttc gac gcc gcc ggc cag ccc agg ctg cgc ccg gcg cgc     480
Leu Glu Gly Phe Asp Ala Ala Gly Gln Pro Arg Leu Arg Pro Ala Arg
145                 150                 155                 160

cgc gcg atc acg gtg cgc cac ctg ctc acg cat acc tcg ggc tat acc     528
Arg Ala Ile Thr Val Arg His Leu Leu Thr His Thr Ser Gly Tyr Thr
                165                 170                 175

tac agc atc tgg agc gag gcg ctg ggc cgc tac gaa cag gtc acg ggc     576
Tyr Ser Ile Trp Ser Glu Ala Leu Gly Arg Tyr Glu Gln Val Thr Gly
            180                 185                 190

atg ccc gac atc ggc tac tcg ctg aac ggc gcc ttc gcg gcc ccg ctc     624
Met Pro Asp Ile Gly Tyr Ser Leu Asn Gly Ala Phe Ala Ala Pro Leu
        195                 200                 205

gaa ttc gag ccc ggc gag cgc tgg caa tac ggc atc ggc atg gat tgg     672
Glu Phe Glu Pro Gly Glu Arg Trp Gln Tyr Gly Ile Gly Met Asp Trp
    210                 215                 220

gtg ggc aag ctg gtg gag gcg gtg acc gac cag tcg ctg gaa gtg gcg     720
Val Gly Lys Leu Val Glu Ala Val Thr Asp Gln Ser Leu Glu Val Ala
225                 230                 235                 240

ttc cgc gag cgg atc ttc gcg ccg ctc ggc atg cac gat acg ggc ttc     768
Phe Arg Glu Arg Ile Phe Ala Pro Leu Gly Met His Asp Thr Gly Phe
                245                 250                 255

ctg atc ggc agc gcg caa aag cgc cgc gtc gcc acg ctg cat cgg cgc     816
Leu Ile Gly Ser Ala Gln Lys Arg Arg Val Ala Thr Leu His Arg Arg
```

FIGURE 6 - 14

```
            260                 265                 270

cag gcc gat ggc tcg ctg acg ccg gaa ccc ttc gag acc aac cag cgg    864
Gln Ala Asp Gly Ser Leu Thr Pro Glu Pro Phe Glu Thr Asn Gln Arg
        275                 280                 285

ccc gag ttc ttc atg ggc ggc ggc ggg ctg ttc agc acc ccg cgc gac    912
Pro Glu Phe Phe Met Gly Gly Gly Gly Leu Phe Ser Thr Pro Arg Asp
    290                 295                 300

tac ctc gcc ttc ctg cag atg ctg ctg aac ggc ggc gcc tgg cgc ggc    960
Tyr Leu Ala Phe Leu Gln Met Leu Leu Asn Gly Gly Ala Trp Arg Gly
305                 310                 315                 320

gag cgg ctg ctg cgg ccc gac acc gtg gcg agc atg ttc cgc aac cag    1008
Glu Arg Leu Leu Arg Pro Asp Thr Val Ala Ser Met Phe Arg Asn Gln
                325                 330                 335

atc ggc gat ctt cag gtt cgc gaa atg aag acc gcc cag ccg gcc tgg    1056
Ile Gly Asp Leu Gln Val Arg Glu Met Lys Thr Ala Gln Pro Ala Trp
            340                 345                 350

tcg aac agc ttc gac caa ttc ccc ggc gcg acg cac aag tgg ggg ctg    1104
Ser Asn Ser Phe Asp Gln Phe Pro Gly Ala Thr His Lys Trp Gly Leu
        355                 360                 365

tcc ttc gat ctc aac agc gag ccg ggg ccg cac ggg cgc ggc gcc ggc    1152
Ser Phe Asp Leu Asn Ser Glu Pro Gly Pro His Gly Arg Gly Ala Gly
    370                 375                 380

tcg ggt agc tgg gcc ggc ctg ctg aac acc tac ttc tgg atc gat ccc    1200
Ser Gly Ser Trp Ala Gly Leu Leu Asn Thr Tyr Phe Trp Ile Asp Pro
385                 390                 395                 400

gcc aag cgc gtg acg ggg gcg ctg ttc acg cag atg ctg ccg ttc tac    1248
Ala Lys Arg Val Thr Gly Ala Leu Phe Thr Gln Met Leu Pro Phe Tyr
                405                 410                 415

gac gcg cgc gtg gtc gat ctc tac ggg cgc ttc gag cgc ggg ctc tac    1296
Asp Ala Arg Val Val Asp Leu Tyr Gly Arg Phe Glu Arg Gly Leu Tyr
            420                 425                 430

gac ggg ctg ggc cgc gcc tga                                        1317
Asp Gly Leu Gly Arg Ala  *
        435


<210> 46
<211> 438
<212> PRT
<213> Bacillus coagulans

<400> 46
Met Ser Thr Arg Ile Pro Arg Arg Gln Trp Leu Lys Gly Ala Ser Gly
 1               5                  10                  15
Leu Leu Ala Ala Ala Ser Leu Gly Arg Leu Ala Asn Arg Glu Ala Arg
            20                  25                  30
```

FIGURE 6 - 15

```
Ala Ala Glu Ala Ser Ala Ala Ala Pro Leu Asp Thr Gly Ser Leu Gly
        35                  40                  45
Ala Ser Pro Arg Ala Thr Leu Asp Ala Cys Leu Gln Lys Ala Val Asp
    50                  55                  60
Asp Gly Thr Leu Lys Ser Val Val Ala Met Ala Ala Thr Glu Arg Gly
65                  70                  75                  80
Leu Ala Tyr Gln Gly Ala Arg Gly Pro Ala Asn Ala Ala Gly Glu Pro
                85                  90                  95
Ile Gly Pro Asp Thr Val Phe Trp Met Leu Ser Met Thr Lys Ala Ile
            100                 105                 110
Thr Ala Thr Ala Cys Met Gln Leu Ile Glu Gln Gly Arg Leu Gly Leu
        115                 120                 125
Asp Gln Pro Ala Ala Glu Ile Leu Pro Gln Leu Lys Ala Pro Gln Val
    130                 135                 140
Leu Glu Gly Phe Asp Ala Ala Gly Gln Pro Arg Leu Arg Pro Ala Arg
145                 150                 155                 160
Arg Ala Ile Thr Val Arg His Leu Leu Thr His Thr Ser Gly Tyr Thr
                165                 170                 175
Tyr Ser Ile Trp Ser Glu Ala Leu Gly Arg Tyr Glu Gln Val Thr Gly
            180                 185                 190
Met Pro Asp Ile Gly Tyr Ser Leu Asn Gly Ala Phe Ala Ala Pro Leu
        195                 200                 205
Glu Phe Glu Pro Gly Glu Arg Trp Gln Tyr Gly Ile Gly Met Asp Trp
    210                 215                 220
Val Gly Lys Leu Val Glu Ala Val Thr Asp Gln Ser Leu Glu Val Ala
225                 230                 235                 240
Phe Arg Glu Arg Ile Phe Ala Pro Leu Gly Met His Asp Thr Gly Phe
                245                 250                 255
Leu Ile Gly Ser Ala Gln Lys Arg Arg Val Ala Thr Leu His Arg Arg
            260                 265                 270
Gln Ala Asp Gly Ser Leu Thr Pro Glu Pro Phe Glu Thr Asn Gln Arg
        275                 280                 285
Pro Glu Phe Phe Met Gly Gly Gly Gly Leu Phe Ser Thr Pro Arg Asp
    290                 295                 300
Tyr Leu Ala Phe Leu Gln Met Leu Leu Asn Gly Gly Ala Trp Arg Gly
305                 310                 315                 320
Glu Arg Leu Leu Arg Pro Asp Thr Val Ala Ser Met Phe Arg Asn Gln
                325                 330                 335
Ile Gly Asp Leu Gln Val Arg Glu Met Lys Thr Ala Gln Pro Ala Trp
            340                 345                 350
Ser Asn Ser Phe Asp Gln Phe Pro Gly Ala Thr His Lys Trp Gly Leu
        355                 360                 365
Ser Phe Asp Leu Asn Ser Glu Pro Gly Pro His Gly Arg Gly Ala Gly
    370                 375                 380
Ser Gly Ser Trp Ala Gly Leu Leu Asn Thr Tyr Phe Trp Ile Asp Pro
385                 390                 395                 400
Ala Lys Arg Val Thr Gly Ala Leu Phe Thr Gln Met Leu Pro Phe Tyr
                405                 410                 415
Asp Ala Arg Val Val Asp Leu Tyr Gly Arg Phe Glu Arg Gly Leu Tyr
            420                 425                 430
Asp Gly Leu Gly Arg Ala
        435

<210> 47
<211> 324
<212> DNA
```

FIGURE 6 - 16

```
<213> Escherichia coli

<220>
<221> CDS
<222> (1)...(324)

<400> 47
agc gat aaa att att cac ctg act gac gac agt ttt gac acg gat gta    48
Ser Asp Lys Ile Ile His Leu Thr Asp Asp Ser Phe Asp Thr Asp Val
 1               5                  10                  15

ctc aaa gcg gac ggg gcg atc ctc gtc gat ttc tgg gca gag tgg tgc    96
Leu Lys Ala Asp Gly Ala Ile Leu Val Asp Phe Trp Ala Glu Trp Cys
            20                  25                  30

ggt ccg tgc aaa atg atc gcc ccg att ctg gat gaa atc gct gac gaa   144
Gly Pro Cys Lys Met Ile Ala Pro Ile Leu Asp Glu Ile Ala Asp Glu
        35                  40                  45

tat cag ggc aaa ctg acc gtt gca aaa ctg aac atc gat caa aac cct   192
Tyr Gln Gly Lys Leu Thr Val Ala Lys Leu Asn Ile Asp Gln Asn Pro
    50                  55                  60

ggc act gcg ccg aaa tat ggc atc cgt ggt atc ccg act ctg ctg ctg   240
Gly Thr Ala Pro Lys Tyr Gly Ile Arg Gly Ile Pro Thr Leu Leu Leu
 65                 70                  75                  80

ttc aaa aac ggt gaa gtg gcg gca acc aaa gtg ggt gca ctg tct aaa   288
Phe Lys Asn Gly Glu Val Ala Ala Thr Lys Val Gly Ala Leu Ser Lys
                85                  90                  95

ggt cag ttg aaa gag ttc ctc gac gct aac ctg gcg                   324
Gly Gln Leu Lys Glu Phe Leu Asp Ala Asn Leu Ala
            100                 105


<210> 48
<211> 108
<212> PRT
<213> Escherichia coli

<400> 48
Ser Asp Lys Ile Ile His Leu Thr Asp Asp Ser Phe Asp Thr Asp Val
 1               5                  10                  15
Leu Lys Ala Asp Gly Ala Ile Leu Val Asp Phe Trp Ala Glu Trp Cys
            20                  25                  30
Gly Pro Cys Lys Met Ile Ala Pro Ile Leu Asp Glu Ile Ala Asp Glu
        35                  40                  45
Tyr Gln Gly Lys Leu Thr Val Ala Lys Leu Asn Ile Asp Gln Asn Pro
    50                  55                  60
Gly Thr Ala Pro Lys Tyr Gly Ile Arg Gly Ile Pro Thr Leu Leu Leu
65                  70                  75                  80
Phe Lys Asn Gly Glu Val Ala Ala Thr Lys Val Gly Ala Leu Ser Lys
                85                  90                  95
Gly Gln Leu Lys Glu Phe Leu Asp Ala Asn Leu Ala
            100                 105
```

FIGURE 6 - 17

```
<210> 49
<211> 63
<212> DNA
<213> Pseudomonas fluorescens

<220>
<221> CDS
<222> (1)...(63)

<400> 49
atg aga aac ctt ctt cga gga atg ctt gtc gtt att tgc tgt atg gca    48
Met Arg Asn Leu Leu Arg Gly Met Leu Val Val Ile Cys Cys Met Ala
 1               5                   10                  15

ggg ata gcg gcg gcg                                                 63
Gly Ile Ala Ala Ala
            20


<210> 50
<211> 21
<212> PRT
<213> Pseudomonas fluorescens

<400> 50
Met Arg Asn Leu Leu Arg Gly Met Leu Val Val Ile Cys Cys Met Ala
 1               5                  10                  15
Gly Ile Ala Ala Ala
            20
```

SEQUENCE LISTING

```
<110>  Retallack, Diane M.
       Schneider, Jane C.
       Ramseier, Thomas Martin

<120>  Improved Expression Systems with Sec-System Secretion

<130>  00588-105021 (DOW 104)

<140>  US 10/996,007
<141>  2004-11-22

<150>  US 60/524,124
<151>  2003-11-21

<160>  120

<170>  PatentIn version 3.4

<210>  1
<211>  20
<212>  PRT
<213>  Pseudomonas fluorescens

<400>  1

Asn Thr Leu Gly Leu Ala Ile Gly Ser Leu Ile Ala Ala Thr Ser Phe
1               5                   10                  15


Gly Val Leu Ala
            20


<210>  2
<211>  22
<212>  PRT
<213>  Pseudomonas spp.

<400>  2

Met Arg Pro Ser Ile His Arg Thr Ala Ile Ala Ala Val Leu Ala Thr
1               5                   10                  15


Ala Phe Val Ala Gly Thr
            20


<210>  3
<211>  72
<212>  DNA
<213>  Artificial Sequence
```

FIGURE 7-1

```
<220>
<223>  Synthetic


<220>
<221>  CDS
<222>  (1)..(72)

<400>  3
atg aaa ctg aaa cgt ttg atg gcg gca atg act ttt gtc gct gct ggc        48
Met Lys Leu Lys Arg Leu Met Ala Ala Met Thr Phe Val Ala Ala Gly
1               5                   10                  15

gtt gcg acc gcc aac gcg gtg gcc                                        72
Val Ala Thr Ala Asn Ala Val Ala
            20


<210>  4
<211>  24
<212>  PRT
<213>  Artificial Sequence

<220>
<223>  Synthetic Construct

<400>  4

Met Lys Leu Lys Arg Leu Met Ala Ala Met Thr Phe Val Ala Ala Gly
1               5                   10                  15


Val Ala Thr Ala Asn Ala Val Ala
            20


<210>  5
<211>  63
<212>  DNA
<213>  Artificial Sequence

<220>
<223>  Synthetic


<220>
<221>  CDS
<222>  (1)..(63)

<400>  5
atg aag aag tcc acc ttg gct gtg gct gta acg ttg ggc gca atc gcc        48
Met Lys Lys Ser Thr Leu Ala Val Ala Val Thr Leu Gly Ala Ile Ala
1               5                   10                  15
```

FIGURE 7-2

```
cag caa gca ggc gct                                                   63
Gln Gln Ala Gly Ala
            20


<210>  6
<211>  21
<212>  PRT
<213>  Artificial Sequence

<220>
<223>  Synthetic Construct

<400>  6

Met Lys Lys Ser Thr Leu Ala Val Ala Val Thr Leu Gly Ala Ile Ala
1               5                   10                  15


Gln Gln Ala Gly Ala
            20


<210>  7
<211>  60
<212>  DNA
<213>  Artificial Sequence

<220>
<223>  Synthetic


<220>
<221>  CDS
<222>  (1)..(60)

<400>  7
atg ttt gcc aaa ctc gtt gct gtt tcc ctg ctg act ctg gcg agc ggc       48
Met Phe Ala Lys Leu Val Ala Val Ser Leu Leu Thr Leu Ala Ser Gly
1               5                   10                  15

cag ttg ctt gct                                                       60
Gln Leu Leu Ala
            20


<210>  8
<211>  20
<212>  PRT
<213>  Artificial Sequence

<220>
<223>  Synthetic Construct
```

```
Met Phe Ala Lys Leu Val Ala Val Ser Leu Leu Thr Leu Ala Ser Gly
1               5                   10                  15


Gln Leu Leu Ala
            20
```

<210> 9
<211> 69
<212> DNA
<213> Artificial Sequence

<220>
<223> Synthetic

<220>
<221> CDS
<222> (1)..(69)

<400> 9

```
atg cag aac tat aaa aaa ttc ctt ctg gcc gcg gcc gtc tcg atg gcg       48
Met Gln Asn Tyr Lys Lys Phe Leu Leu Ala Ala Ala Val Ser Met Ala
1               5                   10                  15

ttc agc gcc acg gcc atg gca                                           69
Phe Ser Ala Thr Ala Met Ala
            20
```

<210> 10
<211> 23
<212> PRT
<213> Artificial Sequence

<220>
<223> Synthetic Construct

<400> 10

```
Met Gln Asn Tyr Lys Lys Phe Leu Leu Ala Ala Ala Val Ser Met Ala
1               5                   10                  15


Phe Ser Ala Thr Ala Met Ala
            20
```

<212> DNA
<213> Artificial Sequence

<220>
<223> Synthetic

<220>
<221> CDS
<222> (1)..(96)

<400> 11
```
atg atg atc cgt gac aac cga ctc aag aca tcc ctt ctg cgc ggc ctg       48
Met Met Ile Arg Asp Asn Arg Leu Lys Thr Ser Leu Leu Arg Gly Leu
1               5                   10                  15

acc ctc acc cta ctc agc ctg acc ctg ctc tcg ccc gcg gcc cat tct       96
Thr Leu Thr Leu Leu Ser Leu Thr Leu Leu Ser Pro Ala Ala His Ser
            20                  25                  30
```

<210> 12
<211> 32
<212> PRT
<213> Artificial Sequence

<220>
<223> Synthetic Construct

<400> 12
```
Met Met Ile Arg Asp Asn Arg Leu Lys Thr Ser Leu Leu Arg Gly Leu
1               5                   10                  15

Thr Leu Thr Leu Leu Ser Leu Thr Leu Leu Ser Pro Ala Ala His Ser
            20                  25                  30
```

<210> 13
<211> 51
<212> DNA
<213> Artificial Sequence

<220>
<223> Synthetic

<220>
<221> CDS
<222> (1)..(51)

<400> 13
```
atg atc aaa cgc aat ctg ctg gtt atg ggc ctt gcc gtg ctg ttg agc       48
```

FIGURE 7-5

```
Met Ile Lys Arg Asn Leu Leu Val Met Gly Leu Ala Val Leu Leu Ser
1               5                   10                  15

gct                                                                51
Ala



<210>  14
<211>  17
<212>  PRT
<213>  Artificial Sequence

<220>
<223>  Synthetic Construct

<400>  14

Met Ile Lys Arg Asn Leu Leu Val Met Gly Leu Ala Val Leu Leu Ser
1               5                   10                  15


Ala



<210>  15
<211>  22
<212>  PRT
<213>  Artificial Sequence

<220>
<223>  Synthetic

<400>  15

Leu Lys Arg Leu Met Ala Ala Met Thr Phe Val Ala Ala Gly Val Ala
1               5                   10                  15


Thr Ala Asn Ala Val Ala
            20


<210>  16
<211>  23
<212>  PRT
<213>  Artificial Sequence

<220>
<223>  Synthetic

<400>  16
```

Met Lys Leu Lys Arg Leu Met Ala Ala Met Thr Phe Val Ala Ala Gly
1               5                   10                  15

Val Ala Thr Ala Asn Ala Val
            20

<210> 17
<211> 22
<212> PRT
<213> Artificial Sequence

<220>
<223> Synthetic

<400> 17

Met Lys Leu Lys Arg Leu Met Ala Ala Met Thr Phe Val Ala Ala Gly
1               5                   10                  15

Val Ala Thr Ala Asn Ala
            20

<210> 18
<211> 21
<212> PRT
<213> Artificial Sequence

<220>
<223> Synthetic

<400> 18

Met Lys Leu Lys Arg Leu Met Ala Ala Met Thr Phe Val Ala Ala Gly
1               5                   10                  15

Val Ala Thr Ala Asn
            20

<210> 19
<211> 20
<212> PRT
<213> Artificial Sequence

<220>
<223> Synthetic

Met Lys Leu Lys Arg Leu Met Ala Ala Met Thr Phe Val Ala Ala Gly
1 5 10 15

Val Ala Thr Ala
20

<210> 20
<211> 19
<212> PRT
<213> Artificial Sequence

<220>
<223> Synthetic

<400> 20

Met Lys Leu Lys Arg Leu Met Ala Ala Met Thr Phe Val Ala Ala Gly
1 5 10 15

Val Ala Thr

<210> 21
<211> 18
<212> PRT
<213> Artificial Sequence

<220>
<223> Synthetic

<400> 21

Met Lys Leu Lys Arg Leu Met Ala Ala Met Thr Phe Val Ala Ala Gly
1 5 10 15

Val Ala

<210> 22
<211> 17
<212> PRT
<213> Artificial Sequence

<220>
<223> Synthetic

```
Met Lys Leu Lys Arg Leu Met Ala Ala Met Thr Phe Val Ala Ala Gly
1               5                   10                  15


Val



<210>  23
<211>  16
<212>  PRT
<213>  Artificial Sequence

<220>
<223>  Synthetic

<400>  23

Met Lys Leu Lys Arg Leu Met Ala Ala Met Thr Phe Val Ala Ala Gly
1               5                   10                  15


<210>  24
<211>  15
<212>  PRT
<213>  Artificial Sequence

<220>
<223>  Synthetic

<400>  24

Met Lys Leu Lys Arg Leu Met Ala Ala Met Thr Phe Val Ala Ala
1               5                   10                  15


<210>  25
<211>  14
<212>  PRT
<213>  Artificial Sequence

<220>
<223>  Synthetic

<400>  25

Met Lys Leu Lys Arg Leu Met Ala Ala Met Thr Phe Val Ala
1               5                   10


<210>  26
<211>  19
<212>  PRT
<213>  Artificial Sequence
```

FIGURE 7-9

<220>
<223> Synthetic

<400> 26

Lys Ser Thr Leu Ala Val Ala Val Thr Leu Gly Ala Ile Ala Gln Gln
1               5                   10                  15

Ala Gly Ala

<210> 27
<211> 20
<212> PRT
<213> Artificial Sequence

<220>
<223> Synthetic

<400> 27

Met Lys Lys Ser Thr Leu Ala Val Ala Val Thr Leu Gly Ala Ile Ala
1               5                   10                  15

Gln Gln Ala Gly
            20

<210> 28
<211> 19
<212> PRT
<213> Artificial Sequence

<220>
<223> Synthetic

<400> 28

Met Lys Lys Ser Thr Leu Ala Val Ala Val Thr Leu Gly Ala Ile Ala
1               5                   10                  15

Gln Gln Ala

<210> 29
<211> 18
<212> PRT
<213> Artificial Sequence

FIGURE 7-10

<220>
<223> Synthetic

<400> 29

Met Lys Lys Ser Thr Leu Ala Val Ala Val Thr Leu Gly Ala Ile Ala
1 5 10 15

Gln Gln

<210> 30
<211> 17
<212> PRT
<213> Artificial Sequence

<220>
<223> Synthetic

<400> 30

Met Lys Lys Ser Thr Leu Ala Val Ala Val Thr Leu Gly Ala Ile Ala
1 5 10 15

Gln

<210> 31
<211> 16
<212> PRT
<213> Artificial Sequence

<220>
<223> Synthetic

<400> 31

Met Lys Lys Ser Thr Leu Ala Val Ala Val Thr Leu Gly Ala Ile Ala
1 5 10 15

<210> 32
<211> 15
<212> PRT
<213> Artificial Sequence

<220>
<223> Synthetic

Met Lys Lys Ser Thr Leu Ala Val Ala Val Thr Leu Gly Ala Ile
1 5 10 15

<210> 33
<211> 14
<212> PRT
<213> Artificial Sequence

<220>
<223> Synthetic

<400> 33

Met Lys Lys Ser Thr Leu Ala Val Ala Val Thr Leu Gly Ala
1 5 10

<210> 34
<211> 13
<212> PRT
<213> Artificial Sequence

<220>
<223> Synthetic

<400> 34

Met Lys Lys Ser Thr Leu Ala Val Ala Val Thr Leu Gly
1 5 10

<210> 35
<211> 12
<212> PRT
<213> Artificial Sequence

<220>
<223> Synthetic

<400> 35

Met Lys Lys Ser Thr Leu Ala Val Ala Val Thr Leu
1 5 10

<210> 36
<211> 11
<212> PRT
<213> Artificial Sequence

<223> Synthetic

<400> 36

Met Lys Lys Ser Thr Leu Ala Val Ala Val Thr
1 5 10

<210> 37
<211> 21
<212> PRT
<213> Artificial Sequence

<220>
<223> Synthetic

<400> 37

Met Tyr Lys Ser Thr Leu Ala Val Ala Val Thr Leu Gly Ala Ile Ala
1 5 10 15

Gln Gln Ala Gly Ala
20

<210> 38
<211> 21
<212> PRT
<213> Artificial Sequence

<220>
<223> Synthetic

<400> 38

Met Lys Lys Ser Ser Leu Ala Val Ala Val Thr Leu Gly Ala Ile Ala
1 5 10 15

Gln Gln Ala Gly Ala
20

<210> 39
<211> 21
<212> PRT
<213> Artificial Sequence

<220>
<223> Synthetic

Met Lys Lys Ser Thr Leu Ala Leu Ala Val Thr Leu Gly Ala Ile Ala
1 5 10 15

Gln Gln Ala Gly Ala
20

<210> 40
<211> 22
<212> PRT
<213> Artificial Sequence

<220>
<223> Synthetic

<400> 40

Met Lys Lys Ser Thr Leu Ala Val Ala Val Arg Thr Leu Gly Ala Ile
1 5 10 15

Ala Gln Gln Ala Gly Ala
20

<210> 41
<211> 21
<212> PRT
<213> Artificial Sequence

<220>
<223> Synthetic

<400> 41

Met Lys Lys Ser Thr Leu Ala Val Ala Val Thr Leu Gly Val Ile Ala
1 5 10 15

Gln Gln Ala Gly Ala
20

<210> 42
<211> 21
<212> PRT
<213> Artificial Sequence

<220>
<223> Synthetic

Met Lys Lys Ser Thr Leu Ala Val Ala Val Thr Leu Gly Ala Leu Ala
1               5                   10                  15

Gln Gln Ala Gly Ala
            20

<210>  43
<211>  18
<212>  PRT
<213>  Artificial Sequence

<220>
<223>  Synthetic

<400>  43

Ala Lys Leu Val Ala Val Ser Leu Leu Thr Leu Ala Ser Gly Gln Leu
1               5                   10                  15

Leu Ala

<210>  44
<211>  19
<212>  PRT
<213>  Artificial Sequence

<220>
<223>  Synthetic

<400>  44

Met Phe Ala Lys Leu Val Ala Val Ser Leu Leu Thr Leu Ala Ser Gly
1               5                   10                  15

Gln Leu Leu

<210>  45
<211>  18
<212>  PRT
<213>  Artificial Sequence

<220>
<223>  Synthetic

Met Phe Ala Lys Leu Val Ala Val Ser Leu Leu Thr Leu Ala Ser Gly
1               5                   10                  15

Gln Leu

<210> 46
<211> 17
<212> PRT
<213> Artificial Sequence

<220>
<223> Synthetic

<400> 46

Met Phe Ala Lys Leu Val Ala Val Ser Leu Leu Thr Leu Ala Ser Gly
1               5                   10                  15

Gln

<210> 47
<211> 16
<212> PRT
<213> Artificial Sequence

<220>
<223> Synthetic

<400> 47

Met Phe Ala Lys Leu Val Ala Val Ser Leu Leu Thr Leu Ala Ser Gly
1               5                   10                  15

<210> 48
<211> 15
<212> PRT
<213> Artificial Sequence

<220>
<223> Synthetic

<400> 48

Met Phe Ala Lys Leu Val Ala Val Ser Leu Leu Thr Leu Ala Ser
1               5                   10                  15

FIGURE 7-16

<210> 49
<211> 14
<212> PRT
<213> Artificial Sequence

<220>
<223> Synthetic

<400> 49

Met Phe Ala Lys Leu Val Ala Val Ser Leu Leu Thr Leu Ala
1 5 10

<210> 50
<211> 13
<212> PRT
<213> Artificial Sequence

<220>
<223> Synthetic

<400> 50

Met Phe Ala Lys Leu Val Ala Val Ser Leu Leu Thr Leu
1 5 10

<210> 51
<211> 12
<212> PRT
<213> Artificial Sequence

<220>
<223> Synthetic

<400> 51

Met Phe Ala Lys Leu Val Ala Val Ser Leu Leu Thr
1 5 10

<210> 52
<211> 11
<212> PRT
<213> Artificial Sequence

<220>
<223> Synthetic

<400> 52

Met Phe Ala Lys Leu Val Ala Val Ser Leu Leu
1 5 10

FIGURE 7-17

<210> 53
<211> 10
<212> PRT
<213> Artificial Sequence

<220>
<223> Synthetic

<400> 53

Met Phe Ala Lys Leu Val Ala Val Ser Leu
1 5 10

<210> 54
<211> 20
<212> PRT
<213> Artificial Sequence

<220>
<223> Synthetic

<400> 54

Met Leu Arg Lys Leu Val Ala Val Ser Leu Leu Thr Leu Ala Ser Gly
1 5 10 15

Gln Leu Leu Ala
20

<210> 55
<211> 20
<212> PRT
<213> Artificial Sequence

<220>
<223> Synthetic

<400> 55

Met Ile Arg Lys Leu Val Ala Val Ser Leu Leu Thr Leu Ala Ser Gly
1 5 10 15

Gln Leu Leu Ala
20

```
<212>  PRT
<213>  Artificial Sequence

<220>
<223>  Synthetic

<400>  56

Met Phe Ala Lys Ala Val Ala Val Ser Leu Leu Thr Leu Ala Ser Gly
1               5                   10                  15


Gln Leu Leu Ala
            20


<210>  57
<211>  20
<212>  PRT
<213>  Artificial Sequence

<220>
<223>  Synthetic

<400>  57

Met Phe Ala Lys Leu Ala Ala Val Ser Leu Leu Thr Leu Ala Ser Gly
1               5                   10                  15


Gln Leu Leu Ala
            20


<210>  58
<211>  20
<212>  PRT
<213>  Artificial Sequence

<220>
<223>  Synthetic

<400>  58

Met Phe Ala Lys Leu Ile Ser Ala Ser Leu Leu Thr Leu Ala Ser Gly
1               5                   10                  15


Gln Leu Leu Ala
            20


<210>  59
<211>  20
```

<212> PRT
<213> Artificial Sequence

<220>
<223> Synthetic

<400> 59

Met Phe Ala Lys Leu Val Ala Val Ser Leu Ile Thr Leu Ala Ser Gly
1 5 10 15

Gln Leu Leu Ala
20

<210> 60
<211> 20
<212> PRT
<213> Artificial Sequence

<220>
<223> Synthetic

<400> 60

Met Phe Ala Lys Leu Val Ala Val Ser Leu Leu Ser Leu Ala Ser Gly
1 5 10 15

Gln Leu Leu Ala
20

<210> 61
<211> 20
<212> PRT
<213> Artificial Sequence

<220>
<223> Synthetic

<400> 61

Met Phe Ala Lys Leu Val Ala Val Ser Leu Leu Thr Leu Leu Ser Gly
1 5 10 15

Gln Leu Leu Ala
20

<212> PRT
<213> Artificial Sequence

<220>
<223> Synthetic

<400> 62

Met Phe Ala Lys Leu Val Ala Val Ser Leu Leu Thr Leu Phe Ser Gly
1 5 10 15

Gln Leu Leu Ala
20

<210> 63
<211> 20
<212> PRT
<213> Artificial Sequence

<220>
<223> Synthetic

<400> 63

Met Phe Ala Lys Leu Val Ala Val Ser Leu Leu Thr Leu Ala Ser Ala
1 5 10 15

Gln Leu Leu Ala
20

<210> 64
<211> 20
<212> PRT
<213> Artificial Sequence

<220>
<223> Synthetic

<400> 64

Met Phe Ala Lys Leu Val Ala Val Ser Leu Leu Thr Leu Ala Ser Gly
1 5 10 15

Ser Leu Leu Ala
20

<212> PRT
<213> Artificial Sequence

<220>
<223> Synthetic

<400> 65

Met Phe Ala Lys Leu Val Ala Val Ser Leu Leu Thr Leu Ala Ser Gly
1 5 10 15

Pro Leu Leu Ala
20

<210> 66
<211> 20
<212> PRT
<213> Artificial Sequence

<220>
<223> Synthetic

<400> 66

Met Phe Ala Lys Leu Val Ala Val Ser Leu Leu Thr Leu Ala Ser Gly
1 5 10 15

Gln Val Leu Ala
20

<210> 67
<211> 20
<212> PRT
<213> Artificial Sequence

<220>
<223> Synthetic

<400> 67

Met Phe Ala Lys Leu Val Ala Val Ser Leu Leu Thr Leu Ala Ser Gly
1 5 10 15

Gln Val Phe Ala
20

<212> PRT
<213> Artificial Sequence

<220>
<223> Synthetic

<400> 68

Asn Tyr Lys Lys Phe Leu Leu Ala Ala Ala Val Ser Met Ala Phe Ser
1 5 10 15

Ala Thr Ala Met Ala
20

<210> 69
<211> 22
<212> PRT
<213> Artificial Sequence

<220>
<223> Synthetic

<400> 69

Met Gln Asn Tyr Lys Lys Phe Leu Leu Ala Ala Ala Val Ser Met Ala
1 5 10 15

Phe Ser Ala Thr Ala Met
20

<210> 70
<211> 21
<212> PRT
<213> Artificial Sequence

<220>
<223> Synthetic

<400> 70

Met Gln Asn Tyr Lys Lys Phe Leu Leu Ala Ala Ala Val Ser Met Ala
1 5 10 15

Phe Ser Ala Thr Ala
20

```
<212>  PRT
<213>  Artificial Sequence

<220>
<223>  Synthetic

<400>  71

Met Gln Asn Tyr Lys Lys Phe Leu Leu Ala Ala Ala Val Ser Met Ala
1               5                   10                  15


Phe Ser Ala Thr
            20


<210>  72
<211>  19
<212>  PRT
<213>  Artificial Sequence

<220>
<223>  Synthetic

<400>  72

Met Gln Asn Tyr Lys Lys Phe Leu Leu Ala Ala Ala Val Ser Met Ala
1               5                   10                  15


Phe Ser Ala



<210>  73
<211>  18
<212>  PRT
<213>  Artificial Sequence

<220>
<223>  Synthetic

<400>  73

Met Gln Asn Tyr Lys Lys Phe Leu Leu Ala Ala Ala Val Ser Met Ala
1               5                   10                  15


Phe Ser



<210>  74
<211>  17
```

<212> PRT
<213> Artificial Sequence

<220>
<223> Synthetic

<400> 74

Met Gln Asn Tyr Lys Lys Phe Leu Leu Ala Ala Ala Val Ser Met Ala
1 5 10 15

Phe

<210> 75
<211> 16
<212> PRT
<213> Artificial Sequence

<220>
<223> Synthetic

<400> 75

Met Gln Asn Tyr Lys Lys Phe Leu Leu Ala Ala Ala Val Ser Met Ala
1 5 10 15

<210> 76
<211> 15
<212> PRT
<213> Artificial Sequence

<220>
<223> Synthetic

<400> 76

Met Gln Asn Tyr Lys Lys Phe Leu Leu Ala Ala Ala Val Ser Met
1 5 10 15

<210> 77
<211> 14
<212> PRT
<213> Artificial Sequence

<220>
<223> Synthetic

```
Met Gln Asn Tyr Lys Lys Phe Leu Leu Ala Ala Ala Val Ser
1               5                   10


<210>  78
<211>  13
<212>  PRT
<213>  Artificial Sequence

<220>
<223>  Synthetic

<400>  78

Met Gln Asn Tyr Lys Lys Phe Leu Leu Ala Ala Ala Val
1               5                   10


<210>  79
<211>  30
<212>  PRT
<213>  Artificial Sequence

<220>
<223>  Synthetic

<400>  79

Ile Arg Asp Asn Arg Leu Lys Thr Ser Leu Leu Arg Gly Leu Thr Leu
1               5                   10                  15


Thr Leu Leu Ser Leu Thr Leu Leu Ser Pro Ala Ala His Ser
            20                  25                  30


<210>  80
<211>  31
<212>  PRT
<213>  Artificial Sequence

<220>
<223>  Synthetic

<400>  80

Met Met Ile Arg Asp Asn Arg Leu Lys Thr Ser Leu Leu Arg Gly Leu
1               5                   10                  15


Thr Leu Thr Leu Leu Ser Leu Thr Leu Leu Ser Pro Ala Ala His
            20                  25                  30
```

FIGURE 7-26

```
<210>  81
<211>  30
<212>  PRT
<213>  Artificial Sequence

<220>
<223>  Synthetic

<400>  81

Met Met Ile Arg Asp Asn Arg Leu Lys Thr Ser Leu Leu Arg Gly Leu
1               5                   10                  15


Thr Leu Thr Leu Leu Ser Leu Thr Leu Leu Ser Pro Ala Ala
            20                  25                  30


<210>  82
<211>  29
<212>  PRT
<213>  Artificial Sequence

<220>
<223>  Synthetic

<400>  82

Met Met Ile Arg Asp Asn Arg Leu Lys Thr Ser Leu Leu Arg Gly Leu
1               5                   10                  15


Thr Leu Thr Leu Leu Ser Leu Thr Leu Leu Ser Pro Ala
            20                  25


<210>  83
<211>  28
<212>  PRT
<213>  Artificial Sequence

<220>
<223>  Synthetic

<400>  83

Met Met Ile Arg Asp Asn Arg Leu Lys Thr Ser Leu Leu Arg Gly Leu
1               5                   10                  15


Thr Leu Thr Leu Leu Ser Leu Thr Leu Leu Ser Pro
            20                  25
```

FIGURE 7-27

<210> 84
<211> 27
<212> PRT
<213> Artificial Sequence

<220>
<223> Synthetic

<400> 84

```
Met Met Ile Arg Asp Asn Arg Leu Lys Thr Ser Leu Leu Arg Gly Leu
1               5                   10                  15


Thr Leu Thr Leu Leu Ser Leu Thr Leu Leu Ser
            20                  25
```

<210> 85
<211> 26
<212> PRT
<213> Artificial Sequence

<220>
<223> Synthetic

<400> 85

```
Met Met Ile Arg Asp Asn Arg Leu Lys Thr Ser Leu Leu Arg Gly Leu
1               5                   10                  15


Thr Leu Thr Leu Leu Ser Leu Thr Leu Leu
            20                  25
```

<210> 86
<211> 25
<212> PRT
<213> Artificial Sequence

<220>
<223> Synthetic

<400> 86

```
Met Met Ile Arg Asp Asn Arg Leu Lys Thr Ser Leu Leu Arg Gly Leu
1               5                   10                  15


Thr Leu Thr Leu Leu Ser Leu Thr Leu
            20                  25
```

FIGURE 7-28

<210> 87
<211> 24
<212> PRT
<213> Artificial Sequence

<220>
<223> Synthetic

<400> 87

Met Met Ile Arg Asp Asn Arg Leu Lys Thr Ser Leu Leu Arg Gly Leu
1 5 10 15

Thr Leu Thr Leu Leu Ser Leu Thr
20

<210> 88
<211> 23
<212> PRT
<213> Artificial Sequence

<220>
<223> Synthetic

<400> 88

Met Met Ile Arg Asp Asn Arg Leu Lys Thr Ser Leu Leu Arg Gly Leu
1 5 10 15

Thr Leu Thr Leu Leu Ser Leu
20

<210> 89
<211> 22
<212> PRT
<213> Artificial Sequence

<220>
<223> Synthetic

<400> 89

Met Met Ile Arg Asp Asn Arg Leu Lys Thr Ser Leu Leu Arg Gly Leu
1 5 10 15

Thr Leu Thr Leu Leu Ser
20

FIGURE 7-29

<210> 90
<211> 15
<212> PRT
<213> Artificial Sequence

<220>
<223> Synthetic

<400> 90

Lys Arg Asn Leu Leu Val Met Gly Leu Ala Val Leu Leu Ser Ala
1 5 10 15

<210> 91
<211> 16
<212> PRT
<213> Artificial Sequence

<220>
<223> Synthetic

<400> 91

Met Ile Lys Arg Asn Leu Leu Val Met Gly Leu Ala Val Leu Leu Ser
1 5 10 15

<210> 92
<211> 15
<212> PRT
<213> Artificial Sequence

<220>
<223> Synthetic

<400> 92

Met Ile Lys Arg Asn Leu Leu Val Met Gly Leu Ala Val Leu Leu
1 5 10 15

<210> 93
<211> 14
<212> PRT
<213> Artificial Sequence

<220>
<223> Synthetic

<400> 93

Met Ile Lys Arg Asn Leu Leu Val Met Gly Leu Ala Val Leu
1 5 10

FIGURE 7-30

<210> 94
<211> 13
<212> PRT
<213> Artificial Sequence

<220>
<223> Synthetic

<400> 94

Met Ile Lys Arg Asn Leu Leu Val Met Gly Leu Ala Val
1 5 10

<210> 95
<211> 12
<212> PRT
<213> Artificial Sequence

<220>
<223> Synthetic

<400> 95

Met Ile Lys Arg Asn Leu Leu Val Met Gly Leu Ala
1 5 10

<210> 96
<211> 11
<212> PRT
<213> Artificial Sequence

<220>
<223> Synthetic

<400> 96

Met Ile Lys Arg Asn Leu Leu Val Met Gly Leu
1 5 10

<210> 97
<211> 10
<212> PRT
<213> Artificial Sequence

<220>
<223> Synthetic

Met Ile Lys Arg Asn Leu Leu Val Met Gly
1 5 10

<210> 98
<211> 9
<212> PRT
<213> Artificial Sequence

<220>
<223> Synthetic

<400> 98

Met Ile Lys Arg Asn Leu Leu Val Met
1 5

<210> 99
<211> 8
<212> PRT
<213> Artificial Sequence

<220>
<223> Synthetic

<400> 99

Met Ile Lys Arg Asn Leu Leu Val
1 5

<210> 100
<211> 7
<212> PRT
<213> Artificial Sequence

<220>
<223> Synthetic

<400> 100

Met Ile Lys Arg Asn Leu Leu
1 5

<210> 101
<211> 834
<212> DNA
<213> Artificial Sequence

<220>
<223> Synthetic

FIGURE 7-32

```
<220>
<221>  CDS
<222>  (1)..(834)

<400>  101
atg aaa ctg aaa cgt ttg atg gcg gca atg act ttt gtc gct gct ggc      48
Met Lys Leu Lys Arg Leu Met Ala Ala Met Thr Phe Val Ala Ala Gly
1               5                   10                  15

gtt gcg acc gcc aac gcg gtg gcc gcc cag gtg cag ctg cag gag tcg      96
Val Ala Thr Ala Asn Ala Val Ala Ala Gln Val Gln Leu Gln Glu Ser
            20                  25                  30

ggc cca gga ctg gtg aag cct tcg gag acc ctg tcc ctc acc tgc act     144
Gly Pro Gly Leu Val Lys Pro Ser Glu Thr Leu Ser Leu Thr Cys Thr
        35                  40                  45

gtc tct ggt ggt tcc atc agt agt tat cac tgg agc tgg atc cgg cag     192
Val Ser Gly Gly Ser Ile Ser Ser Tyr His Trp Ser Trp Ile Arg Gln
    50                  55                  60

ccc cca ggg aag gga ctg gag tgg att ggg tat atc tat tac agt ggg     240
Pro Pro Gly Lys Gly Leu Glu Trp Ile Gly Tyr Ile Tyr Tyr Ser Gly
65                  70                  75                  80

agc acc aac tac aac ccc tcc ctc aag aat cga gtc acc ata tct gta     288
Ser Thr Asn Tyr Asn Pro Ser Leu Lys Asn Arg Val Thr Ile Ser Val
                85                  90                  95

gac acg tcc aag aac cag ttc tcc ctg aac ctg agg tct gtg acc gct     336
Asp Thr Ser Lys Asn Gln Phe Ser Leu Asn Leu Arg Ser Val Thr Ala
            100                 105                 110

gca gac acg gcc gtg tat tac tgt gcg cga gga acg tat ggc cca gcc     384
Ala Asp Thr Ala Val Tyr Tyr Cys Ala Arg Gly Thr Tyr Gly Pro Ala
        115                 120                 125

gga gat gct ttt gat atc tgg ggg caa ggg acc acg gtc acc gtc tcg     432
Gly Asp Ala Phe Asp Ile Trp Gly Gln Gly Thr Thr Val Thr Val Ser
    130                 135                 140

agt ggt gga ggc ggt tca ggc gga ggt ggc agc ggc ggt ggc gga tcg     480
Ser Gly Gly Gly Gly Ser Gly Gly Gly Gly Ser Gly Gly Gly Gly Ser
145                 150                 155                 160

gac atc cag atg acc cag tct cct tcc acc ctg tct gca tct att gga     528
Asp Ile Gln Met Thr Gln Ser Pro Ser Thr Leu Ser Ala Ser Ile Gly
                165                 170                 175

gac aga gtc acc atc acc tgc cgg gcc agt gag ggt att tat cac tgg     576
Asp Arg Val Thr Ile Thr Cys Arg Ala Ser Glu Gly Ile Tyr His Trp
            180                 185                 190
```

FIGURE 7-33

```
ttg gcc tgg tat cag cag aag cca ggg aaa gcc cct aaa ctc ctg atc      624
Leu Ala Trp Tyr Gln Gln Lys Pro Gly Lys Ala Pro Lys Leu Leu Ile
        195                 200                 205

tat aag gcc tct agt tta gcc agt ggg gcc cca tca agg ttc agc ggc      672
Tyr Lys Ala Ser Ser Leu Ala Ser Gly Ala Pro Ser Arg Phe Ser Gly
    210                 215                 220

agt gga tct ggg aca gat ttc act ctc acc atc agc agc ctg cag cct      720
Ser Gly Ser Gly Thr Asp Phe Thr Leu Thr Ile Ser Ser Leu Gln Pro
225                 230                 235                 240

gat gat ttt gca act tat tac tgc caa caa tat agt aat tat ccg ctc      768
Asp Asp Phe Ala Thr Tyr Tyr Cys Gln Gln Tyr Ser Asn Tyr Pro Leu
                245                 250                 255

act ttc ggc gga ggg acc aag ctg gag atc aaa cgt gcg gcc gca cat      816
Thr Phe Gly Gly Gly Thr Lys Leu Glu Ile Lys Arg Ala Ala Ala His
            260                 265                 270

cac cat cat cac cat taa                                              834
His His His His His
        275


<210>  102
<211>  277
<212>  PRT
<213>  Artificial Sequence

<220>
<223>  Synthetic Construct

<400>  102

Met Lys Leu Lys Arg Leu Met Ala Ala Met Thr Phe Val Ala Ala Gly
1               5                   10                  15


Val Ala Thr Ala Asn Ala Val Ala Ala Gln Val Gln Leu Gln Glu Ser
            20                  25                  30


Gly Pro Gly Leu Val Lys Pro Ser Glu Thr Leu Ser Leu Thr Cys Thr
        35                  40                  45


Val Ser Gly Gly Ser Ile Ser Ser Tyr His Trp Ser Trp Ile Arg Gln
    50                  55                  60


Pro Pro Gly Lys Gly Leu Glu Trp Ile Gly Tyr Ile Tyr Tyr Ser Gly
65                  70                  75                  80
```

FIGURE 7-34

```
Ser Thr Asn Tyr Asn Pro Ser Leu Lys Asn Arg Val Thr Ile Ser Val
                85                  90                  95

Asp Thr Ser Lys Asn Gln Phe Ser Leu Asn Leu Arg Ser Val Thr Ala
            100                 105                 110

Ala Asp Thr Ala Val Tyr Tyr Cys Ala Arg Gly Thr Tyr Gly Pro Ala
        115                 120                 125

Gly Asp Ala Phe Asp Ile Trp Gly Gln Gly Thr Thr Val Thr Val Ser
    130                 135                 140

Ser Gly Gly Gly Gly Ser Gly Gly Gly Gly Ser Gly Gly Gly Gly Ser
145                 150                 155                 160

Asp Ile Gln Met Thr Gln Ser Pro Ser Thr Leu Ser Ala Ser Ile Gly
                165                 170                 175

Asp Arg Val Thr Ile Thr Cys Arg Ala Ser Glu Gly Ile Tyr His Trp
            180                 185                 190

Leu Ala Trp Tyr Gln Gln Lys Pro Gly Lys Ala Pro Lys Leu Leu Ile
        195                 200                 205

Tyr Lys Ala Ser Ser Leu Ala Ser Gly Ala Pro Ser Arg Phe Ser Gly
    210                 215                 220

Ser Gly Ser Gly Thr Asp Phe Thr Leu Thr Ile Ser Ser Leu Gln Pro
225                 230                 235                 240

Asp Asp Phe Ala Thr Tyr Tyr Cys Gln Gln Tyr Ser Asn Tyr Pro Leu
                245                 250                 255

Thr Phe Gly Gly Gly Thr Lys Leu Glu Ile Lys Arg Ala Ala Ala His
            260                 265                 270

His His His His His
        275

<210>  103
```

<211> 33
<212> DNA
<213> Artificial Sequence

<220>
<223> Synthetic

<400> 103
gctctagagg aggtaactta tgaaactgaa acg 33

<210> 104
<211> 24
<212> DNA
<213> Artificial Sequence

<220>
<223> Synthetic

<400> 104
ctgcacctgg gcggccaccg cgtt 24

<210> 105
<211> 24
<212> DNA
<213> Artificial Sequence

<220>
<223> Synthetic

<400> 105
aacgcggtgg ccgcccaggt gcag 24

<210> 106
<211> 52
<212> DNA
<213> Artificial Sequence

<220>
<223> Synthetic

<400> 106
acgcgtcgac ttattaatgg tgatgatggt gatgtgcggc cgcacgttga tc 52

<210> 107
<211> 30
<212> DNA
<213> Artificial Sequence

<220>
<223> Synthetic

FIGURE 7-36

<400> 107
gggaatggtt gggaaggcca ccgcgttggc 30

<210> 108
<211> 50
<212> DNA
<213> Artificial Sequence

<220>
<223> Synthetic

<400> 108
agagaactag taaaaaggag aaatccatgg ctacaggctc ccggacgtcc 50

<210> 109
<211> 38
<212> DNA
<213> Artificial Sequence

<220>
<223> Synthetic

<400> 109
agagactcga gtcattagaa gccacagctg ccctccac 38

<210> 110
<211> 30
<212> DNA
<213> Artificial Sequence

<220>
<223> Synthetic

<400> 110
gccaacgcgg tggccttccc aaccattccc 30

<210> 111
<211> 48
<212> DNA
<213> Artificial Sequence

<220>
<223> Synthetic

<400> 111
agagactcga gtcattagaa gccacagctg ccctccacag agcggcac 48

```
<211>  645
<212>  DNA
<213>  Artificial Sequence

<220>
<223>  Synthetic


<220>
<221>  CDS
<222>  (1)..(645)

<400>  112
atg aaa ctg aaa cgt ttg atg gcg gca atg act ttt gtc gct gct ggc        48
Met Lys Leu Lys Arg Leu Met Ala Ala Met Thr Phe Val Ala Ala Gly
1               5                   10                  15

gtt gcg acc gcc aac gcg gtg gcc ttc cca acc att ccc tta tcc agg        96
Val Ala Thr Ala Asn Ala Val Ala Phe Pro Thr Ile Pro Leu Ser Arg
            20                  25                  30

cct ttt gac aac gct atg ctc cgc gcc cat cgt ctg cac cag ctg gcc       144
Pro Phe Asp Asn Ala Met Leu Arg Ala His Arg Leu His Gln Leu Ala
        35                  40                  45

ttt gac acc tac cag gag ttt gaa gaa gcc tat atc cca aag gaa cag       192
Phe Asp Thr Tyr Gln Glu Phe Glu Glu Ala Tyr Ile Pro Lys Glu Gln
    50                  55                  60

aag tat tca ttc ctg cag aac ccc cag acc tcc ctc tgt ttc tca gag       240
Lys Tyr Ser Phe Leu Gln Asn Pro Gln Thr Ser Leu Cys Phe Ser Glu
65                  70                  75                  80

tct att ccg aca ccc tcc aac agg gag gaa aca caa cag aaa tcc aac       288
Ser Ile Pro Thr Pro Ser Asn Arg Glu Glu Thr Gln Gln Lys Ser Asn
                85                  90                  95

cta gag ctg ctc cgc atc tcc ctg ctg ctc atc cag tcg tgg ctg gag       336
Leu Glu Leu Leu Arg Ile Ser Leu Leu Leu Ile Gln Ser Trp Leu Glu
            100                 105                 110

ccc gtg cag ttc ctc agg agt gtc ttc gcc aac agc ctg gtg tac ggc       384
Pro Val Gln Phe Leu Arg Ser Val Phe Ala Asn Ser Leu Val Tyr Gly
        115                 120                 125

gcc tct gac agc aac gtc tat gac ctc cta aag gac cta gag gaa ggc       432
Ala Ser Asp Ser Asn Val Tyr Asp Leu Leu Lys Asp Leu Glu Glu Gly
    130                 135                 140

atc caa acg ctg atg ggg agg ctg gaa gat ggc agc ccc cgg act ggg       480
Ile Gln Thr Leu Met Gly Arg Leu Glu Asp Gly Ser Pro Arg Thr Gly
145                 150                 155                 160

cag atc ttc aag cag acc tac agc aag ttc gac aca aac tca cac aac       528
```

FIGURE 7-38

```
Gln Ile Phe Lys Gln Thr Tyr Ser Lys Phe Asp Thr Asn Ser His Asn
                165                 170                 175

gat gac cta ctc aag aac tac ggg ctg ctc tac tgc ttc agg aag gac       576
Asp Asp Leu Leu Lys Asn Tyr Gly Leu Leu Tyr Cys Phe Arg Lys Asp
            180                 185                 190

atg gac aag gtc gag aca ttc ctg cgc atc gtg cag tgc cgc tct gtg       624
Met Asp Lys Val Glu Thr Phe Leu Arg Ile Val Gln Cys Arg Ser Val
        195                 200                 205

gag ggc agc tgt ggc ttc taa                                           645
Glu Gly Ser Cys Gly Phe
    210


<210>  113
<211>  214
<212>  PRT
<213>  Artificial Sequence

<220>
<223>  Synthetic Construct

<400>  113

Met Lys Leu Lys Arg Leu Met Ala Ala Met Thr Phe Val Ala Ala Gly
1               5                   10                  15


Val Ala Thr Ala Asn Ala Val Ala Phe Pro Thr Ile Pro Leu Ser Arg
            20                  25                  30


Pro Phe Asp Asn Ala Met Leu Arg Ala His Arg Leu His Gln Leu Ala
        35                  40                  45


Phe Asp Thr Tyr Gln Glu Phe Glu Glu Ala Tyr Ile Pro Lys Glu Gln
    50                  55                  60


Lys Tyr Ser Phe Leu Gln Asn Pro Gln Thr Ser Leu Cys Phe Ser Glu
65                  70                  75                  80


Ser Ile Pro Thr Pro Ser Asn Arg Glu Glu Thr Gln Gln Lys Ser Asn
                85                  90                  95


Leu Glu Leu Leu Arg Ile Ser Leu Leu Leu Ile Gln Ser Trp Leu Glu
            100                 105                 110
```

FIGURE 7-39

```
Pro Val Gln Phe Leu Arg Ser Val Phe Ala Asn Ser Leu Val Tyr Gly
        115                 120                 125

Ala Ser Asp Ser Asn Val Tyr Asp Leu Leu Lys Asp Leu Glu Glu Gly
    130                 135                 140

Ile Gln Thr Leu Met Gly Arg Leu Glu Asp Gly Ser Pro Arg Thr Gly
145                 150                 155                 160

Gln Ile Phe Lys Gln Thr Tyr Ser Lys Phe Asp Thr Asn Ser His Asn
                165                 170                 175

Asp Asp Leu Leu Lys Asn Tyr Gly Leu Leu Tyr Cys Phe Arg Lys Asp
            180                 185                 190

Met Asp Lys Val Glu Thr Phe Leu Arg Ile Val Gln Cys Arg Ser Val
        195                 200                 205

Glu Gly Ser Cys Gly Phe
    210


<210>  114
<211>  13
<212>  PRT
<213>  Artificial Sequence

<220>
<223>  Synthetic

<400>  114

Ala Asp Lys Ile Ala Ile Val Asn Met Gly Ser Leu Phe
1               5                   10


<210>  115
<211>  17
<212>  PRT
<213>  Artificial Sequence

<220>
<223>  Synthetic

<400>  115

Gln Gln Val Ala Gln Lys Thr Gly Val Ser Asn Thr Leu Glu Asn Glu
1               5                   10                  15
```

FIGURE 7-40

Phe

<210> 116
<211> 10
<212> PRT
<213> Artificial Sequence

<220>
<223> Synthetic

<400> 116

```
Phe Pro Thr Ile Pro Leu Ser Arg Pro Phe
1               5                   10
```

<210> 117
<211> 277
<212> PRT
<213> Artificial Sequence

<220>
<223> Synthetic

<400> 117

```
Met Lys Leu Lys Asn Thr Leu Gly Leu Ala Ile Gly Ser Leu Ile Ala
1               5                   10                  15

Ala Thr Ser Phe Gly Val Leu Ala Ala Gln Val Gln Leu Gln Glu Ser
            20                  25                  30

Gly Pro Gly Leu Val Lys Pro Ser Glu Thr Leu Ser Leu Thr Cys Thr
        35                  40                  45

Val Ser Gly Gly Ser Ile Ser Ser Tyr His Trp Ser Trp Ile Arg Gln
    50                  55                  60

Pro Pro Gly Lys Gly Leu Glu Trp Ile Gly Tyr Ile Tyr Tyr Ser Gly
65                  70                  75                  80

Ser Thr Asn Tyr Asn Pro Ser Leu Lys Asn Arg Val Thr Ile Ser Val
                85                  90                  95
```

FIGURE 7-41

```
Asp Thr Ser Lys Asn Gln Phe Ser Leu Asn Leu Arg Ser Val Thr Ala
            100                 105                 110

Ala Asp Thr Ala Val Tyr Tyr Cys Ala Arg Gly Thr Tyr Gly Pro Ala
        115                 120                 125

Gly Asp Ala Phe Asp Ile Trp Gly Gln Gly Thr Thr Val Thr Val Ser
    130                 135                 140

Ser Gly Gly Gly Gly Ser Gly Gly Gly Gly Ser Gly Gly Gly Gly Ser
145                 150                 155                 160

Asp Ile Gln Met Thr Gln Ser Pro Ser Thr Leu Ser Ala Ser Ile Gly
                165                 170                 175

Asp Arg Val Thr Ile Thr Cys Arg Ala Ser Glu Gly Ile Tyr His Trp
            180                 185                 190

Leu Ala Trp Tyr Gln Gln Lys Pro Gly Lys Ala Pro Lys Leu Leu Ile
        195                 200                 205

Tyr Lys Ala Ser Ser Leu Ala Ser Gly Ala Pro Ser Arg Phe Ser Gly
    210                 215                 220

Ser Gly Ser Gly Thr Asp Phe Thr Leu Thr Ile Ser Ser Leu Gln Pro
225                 230                 235                 240

Asp Asp Phe Ala Thr Tyr Tyr Cys Gln Gln Tyr Ser Asn Tyr Pro Leu
                245                 250                 255

Thr Phe Gly Gly Gly Thr Lys Leu Glu Ile Lys Arg Ala Ala Ala His
            260                 265                 270

His His His His His
        275


<210>  118
<211>  277
<212>  PRT
<213>  Artificial Sequence

<220>
```

<223> Synthetic

<400> 118

```
Met Lys Leu Lys Arg Leu Met Ala Ala Met Thr Phe Val Ala Ala Gly
1               5                   10                  15

Val Ala Thr Ala Asn Ala Val Ala Ala Gln Val Gln Leu Gln Glu Ser
            20                  25                  30

Gly Pro Gly Leu Val Lys Pro Ser Glu Thr Leu Ser Leu Thr Cys Thr
        35                  40                  45

Val Ser Gly Gly Ser Ile Ser Ser Tyr His Trp Ser Trp Ile Arg Gln
    50                  55                  60

Pro Pro Gly Lys Gly Leu Glu Trp Ile Gly Tyr Ile Tyr Tyr Ser Gly
65                  70                  75                  80

Ser Thr Asn Tyr Asn Pro Ser Leu Lys Asn Arg Val Thr Ile Ser Val
                85                  90                  95

Asp Thr Ser Lys Asn Gln Phe Ser Leu Asn Leu Arg Ser Val Thr Ala
            100                 105                 110

Ala Asp Thr Ala Val Tyr Tyr Cys Ala Arg Gly Thr Tyr Gly Pro Ala
        115                 120                 125

Gly Asp Ala Phe Asp Ile Trp Gly Gln Gly Thr Thr Val Thr Val Ser
    130                 135                 140

Ser Gly Gly Gly Gly Ser Gly Gly Gly Gly Ser Gly Gly Gly Gly Ser
145                 150                 155                 160

Asp Ile Gln Met Thr Gln Ser Pro Ser Thr Leu Ser Ala Ser Ile Gly
                165                 170                 175

Asp Arg Val Thr Ile Thr Cys Arg Ala Ser Glu Gly Ile Tyr His Trp
            180                 185                 190

Leu Ala Trp Tyr Gln Gln Lys Pro Gly Lys Ala Pro Lys Leu Leu Ile
        195                 200                 205
```

FIGURE 7-43

Tyr Lys Ala Ser Ser Leu Ala Ser Gly Ala Pro Ser Arg Phe Ser Gly
210 215 220

Ser Gly Ser Gly Thr Asp Phe Thr Leu Thr Ile Ser Ser Leu Gln Pro
225 230 235 240

Asp Asp Phe Ala Thr Tyr Tyr Cys Gln Gln Tyr Ser Asn Tyr Pro Leu
245 250 255

Thr Phe Gly Gly Gly Thr Lys Leu Glu Ile Lys Arg Ala Ala Ala His
260 265 270

His His His His His
275

<210> 119
<211> 161
<212> PRT
<213> Artificial Sequence

<220>
<223> Synthetic

<400> 119

Met Lys Lys Trp Leu Leu Ala Ala Gly Leu Gly Leu Ala Leu Ala Thr
1 5 10 15

Ser Ala Gln Ala Ala Asp Lys Ile Ala Ile Val Asn Met Gly Ser Leu
20 25 30

Phe Gln Gln Val Ala Gln Lys Thr Gly Val Ser Asn Thr Leu Glu Asn
35 40 45

Glu Phe Lys Gly Arg Ala Ser Glu Leu Gln Arg Met Glu Thr Asp Leu
50 55 60

Gln Ala Lys Met Lys Lys Leu Gln Ser Met Lys Ala Gly Ser Asp Arg
65 70 75 80

Thr Lys Leu Glu Lys Asp Val Met Ala Gln Arg Gln Thr Phe Ala Gln
85 90 95

FIGURE 7-44

```
Lys Ala Gln Ala Phe Glu Gln Asp Arg Ala Arg Arg Ser Asn Glu Glu
            100                 105                 110

Arg Gly Lys Leu Val Thr Arg Ile Gln Thr Ala Val Lys Ser Val Ala
        115                 120                 125

Asn Ser Gln Asp Ile Asp Leu Val Val Asp Ala Asn Ala Val Ala Tyr
    130                 135                 140

Asn Ser Ser Asp Val Lys Asp Ile Thr Ala Asp Val Leu Lys Gln Val
145                 150                 155                 160

Lys


<210>  120
<211>  140
<212>  PRT
<213>  Artificial Sequence

<220>
<223>  Synthetic

<400>  120

Ala Asp Lys Ile Ala Ile Val Asn Met Gly Ser Leu Phe Gln Gln Val
1               5                   10                  15

Ala Gln Lys Thr Gly Val Ser Asn Thr Leu Glu Asn Glu Phe Lys Gly
            20                  25                  30

Arg Ala Ser Glu Leu Gln Arg Met Glu Thr Asp Leu Gln Ala Lys Met
        35                  40                  45

Lys Lys Leu Gln Ser Met Lys Ala Gly Ser Asp Arg Thr Lys Leu Glu
    50                  55                  60

Lys Asp Val Met Ala Gln Arg Gln Thr Phe Ala Gln Lys Ala Gln Ala
65                  70                  75                  80

Phe Glu Gln Asp Arg Ala Arg Arg Ser Asn Glu Glu Arg Gly Lys Leu
                85                  90                  95
```

FIGURE 7-45

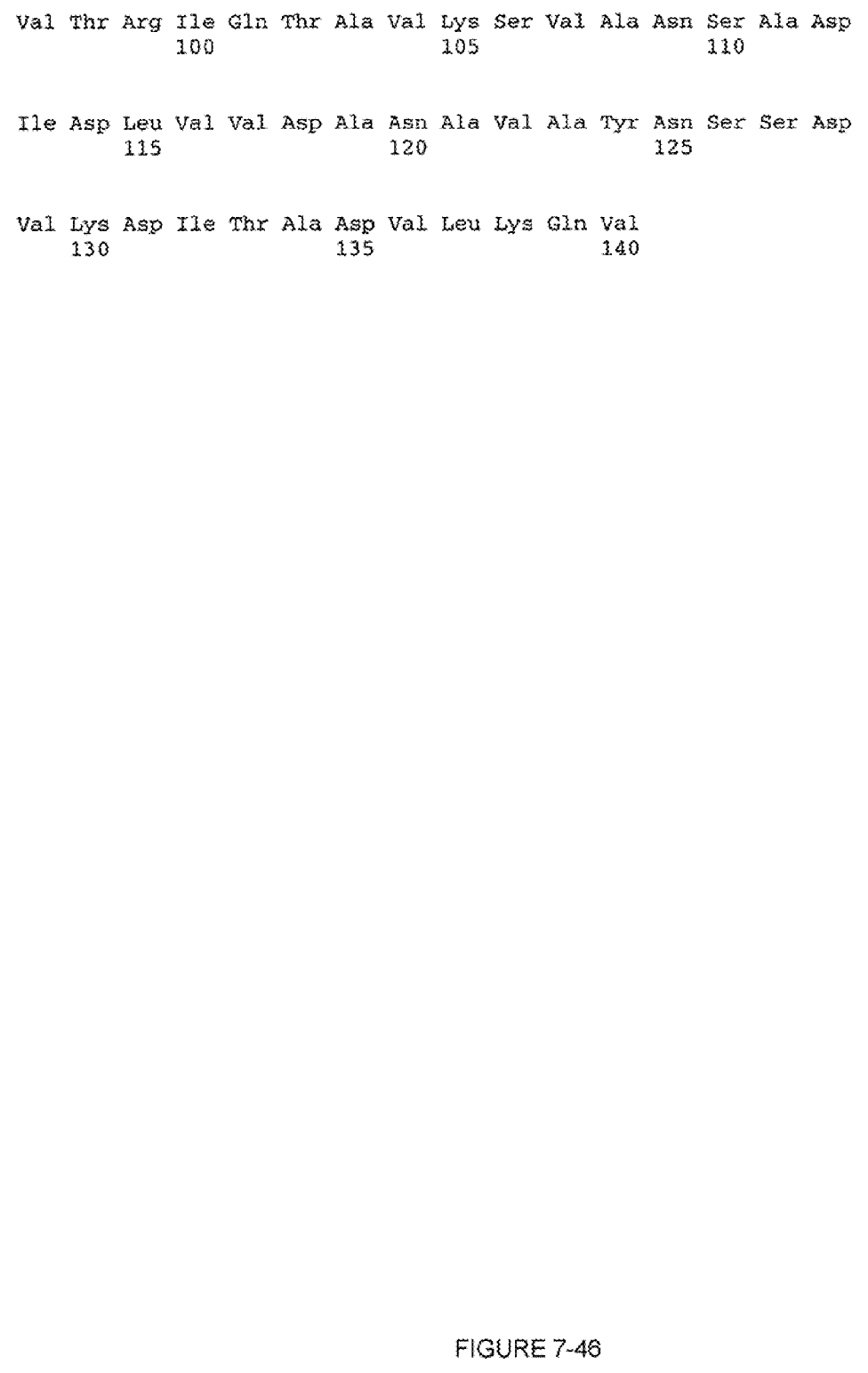

```
Val Thr Arg Ile Gln Thr Ala Val Lys Ser Val Ala Asn Ser Ala Asp
            100                 105                 110

Ile Asp Leu Val Val Asp Ala Asn Ala Val Ala Tyr Asn Ser Ser Asp
        115                 120                 125

Val Lys Asp Ile Thr Ala Asp Val Leu Lys Gln Val
    130                 135                 140
```

FIGURE 7-46

METHOD FOR RAPIDLY SCREENING MICROBIAL HOSTS TO IDENTIFY CERTAIN STRAINS WITH IMPROVED YIELD AND/OR QUALITY IN THE EXPRESSION OF HETEROLOGOUS PROTEINS

CROSS-REFERENCE TO RELATED APPLICATIONS

This application is a Continuation-in-Part of U.S. application Ser. No. 12/109,554, filed Apr. 25, 2008, incorporated by reference herein, which claims the benefit of U.S. Provisional Application No. 60/914,361, filed Apr. 27, 2007, incorporated by reference herein.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of 38194701.txt, a creation date of Oct. 30, 2009 and a size of 352 KB. The sequence listing filed via EFS-Web is part of the specification and is herein incorporated by reference in its entirety.

FIELD OF THE INVENTION

This invention relates to the field of protein production, particularly to identifying optimal host cells for large-scale production of properly processed heterologous proteins.

BACKGROUND OF THE INVENTION

More than 150 recombinantly produced proteins and polypeptides have been approved by the U.S. Food and Drug Administration (FDA) for use as biotechnology drugs and vaccines, with another 370 in clinical trials. Unlike small molecule therapeutics that are produced through chemical synthesis, proteins and polypeptides are most efficiently produced in living cells. However, current methods of production of recombinant proteins in bacteria often produce improperly folded, aggregated or inactive proteins, and many types of proteins require secondary modifications that are inefficiently achieved using known methods.

Numerous attempts have been developed to increase production of properly folded proteins in recombinant systems. For example, investigators have changed fermentation conditions (Schein (1989) Bio/Technology, 7:1141-1149), varied promoter strength, or used overexpressed chaperone proteins (Hockney (1994) Trends Biotechnol. 12:456-463), which can help prevent the formation of inclusion bodies.

Strategies have been developed to excrete proteins from the cell into the supernatant. For example, U.S. Pat. No. 5,348,867; U.S. Pat. No. 6,329,172; PCT Publication No. WO 96/17943; PCT Publication No. WO 02/40696; and U.S. Application Publication 2003/0013150. Other strategies for increased expression are directed to targeting the protein to the periplasm. Some investigations focus on non-Sec type secretion (see for e.g. PCT Publication No. WO 03/079007; U.S. Publication No. 2003/0180937; U.S. Publication No. 2003/0064435; and, PCT Publication No. WO 00/59537). However, the majority of research has focused on the secretion of exogenous proteins with a Sec-type secretion system.

A number of secretion signals have been described for use in expressing recombinant polypeptides or proteins. See, for example, U.S. Pat. No. 5,914,254; U.S. Pat. No. 4,963,495; European Patent No. 0 177 343; U.S. Pat. No. 5,082,783; PCT Publication No. WO 89/10971; U.S. Pat. No. 6,156,552; U.S. Pat. Nos. 6,495,357; 6,509,181; 6,524,827; 6,528,298; 6,558,939; 6,608,018; 6,617,143; U.S. Pat. Nos. 5,595,898; 5,698,435; and 6,204,023; U.S. Pat. No. 6,258,560; PCT Publication Nos. WO 01/21662, WO 02/068660 and U.S. Application Publication 2003/0044906; U.S. Pat. No. 5,641,671; and European Patent No. EP 0 121 352.

Heterologous protein production often leads to the formation of insoluble or improperly folded proteins, which are difficult to recover and may be inactive. Furthermore, the presence of specific host cell proteases may degrade the protein of interest and thus reduce the final yield. There is no single factor that will improve the production of all heterologous proteins. As a result, there is a need in the art for identifying improved large-scale expression systems capable of secreting and properly processing recombinant polypeptides to produce transgenic proteins in properly processed form.

SUMMARY OF THE INVENTION

The present invention provides compositions and methods for rapidly identifying a host cell population capable of producing at least one heterologous polypeptide according to a desired specification with improved yield and/or quality. The compositions comprise two or more host cell populations that have been genetically modified to increase the expression of one or more target genes involved in protein production, decrease the expression of one or more target genes involved in protein degradation, express a heterologous gene that affects the protein product, or a combination. The ability to express a polypeptide of interest in a variety of modified host cells provides a rapid and efficient means for determining an optimal host cell for the polypeptide of interest. The desired specification will vary depending on the polypeptide of interest, but includes yield, quality, activity, and the like.

It is recognized that the host cell populations may be modified to express many combinations of nucleic acid sequences that affect the expression levels of endogenous sequences and/or exogenous sequences that facilitate the expression of the polypeptide of interest. In one embodiment, two or more of the host cell populations has been genetically modified to increase the expression of one or more target genes involved in one or more of the proper expression, processing, and/or translocation of a heterologous protein of interest. In another embodiment, the target gene is a protein folding modulator. In another embodiment, the protein folding modulator is selected from the list in Table 1.

In another embodiment, one or more of the host cell populations has been genetically modified to decrease the expression of one or more target genes involved in proteolytic degradation. In another embodiment, the target gene is a protease. In another embodiment, the protease is selected from the list in Table 2.

In one embodiment, nucleotide sequences encoding the proteins of interest are operably linked to a *P. fluorescens* Sec system secretion signal as described herein. One or more of the strains in the array may express the heterologous protein of interest in a periplasm compartment. In certain embodiments, one or more strains may also secrete the heterologous protein extracellularly through an outer cell wall.

Host cells include eukaryotic cells, including yeast cells, insect cells, mammalian cells, plant cells, etc., and prokaryotic cells, including bacterial cells such as *P. fluorescens, E. coli*, and the like.

As indicated, the library of host cell populations can be rapidly screened to identify certain strain(s) with improved yield and/or quality of heterologously expressed protein. The strain arrays are useful for screening for improved expression of any protein of interest, including therapeutic proteins, hormones, a growth factors, extracellular receptors or ligands, proteases, kinases, blood proteins, chemokines, cytokines, antibodies and the like.

The invention includes a method of assembling an array of expression systems for testing expression of at least one heterologous protein, said method comprising: placing in separate addressable locations at least 10 nonidentical test expression systems, said at least 10 nonidentical test expression systems each comprising a different combination of a) a Pseudomonad or *E. coli* host cell population, and b) at least one expression vector encoding the at least one heterologous protein, wherein the array includes at least 5 different host cell populations and at least 2 different expression vectors, and further wherein at least 3 of said at least 5 different host cell populations are deficient in their expression of at least one protease; and wherein at least one of the nonidentical test expression systems overexpresses the at least one heterologous protein.

In embodiments, the at least 2 different expression vectors each encode a different heterologous protein. In other embodiments, the array includes at least 5 different expression vectors, and wherein each of said at least 5 different expression vectors encodes a different heterologous protein. In embodiments, at least one expression vector encodes 2 different heterologous proteins. In other embodiments, at least 20 nonidentical test expression systems are placed in separate addressable locations, and wherein the array includes at least 10 different host cell populations and at least 2 different expression vectors, and further wherein at least 5 of said at least 10 different host cell populations are deficient in their expression of at least one protease. In other embodiments at least 50 nonidentical test expression systems are placed in separate addressable locations, and wherein the array includes at least 20 different host cell populations and at least 3 different expression vectors, and further wherein at least 10 of said at least 20 different host cell populations are deficient in their expression of at least one protease. In related embodiments, the overexpression of the heterologous protein in the at least one nonidentical test expression system is an increase in yield, of about 1.5-fold to an about 100-fold, relative to the yield in an indicator expression system. In other embodiments, the overexpression is a yield of the heterologous protein in the at least one nonidentical test expression system of about 10 mg/liter to about 2000 mg/liter. In related embodiments, the increase in yield is about 1.5-fold to about 2-fold, about 2-fold to about 3-fold, about 3-fold to about 4-fold, about 4-fold to about 5-fold, about 5-fold to about 6 fold, about 6-fold to about 7-fold, about 7-fold to about 8-fold, about 8-fold to about 9-fold, about 9-fold to about 10-fold, about 10-fold to about 15-fold, about 15-fold to about 20-fold, about 20-fold to about 25-fold, about 25-fold to about 30-fold, about 30-fold to about 35-fold, about 35-fold to about 40-fold, about 45-fold to about 50-fold, about 50-fold to about 55-fold, about 55-fold to about 60-fold, about 60-fold to about 65-fold, about 65-fold to about 70-fold, about 70-fold to about 75-fold, about 75-fold to about 80-fold, about 80-fold to about 85-fold, about 85-fold to about 90-fold, about 90-fold to about 95-fold, or about 95-fold to about 100-fold. In other related embodiments, the yield of the heterologous protein is about 10 mg/liter to about 20 mg/liter, about 20 mg/liter to about 50 mg/liter, about 50 mg/liter to about 100 mg/liter, about 100 mg/liter to about 200 mg/liter, about 200 mg/liter to about 300 mg/liter, about 300 mg/liter to about 400 mg/liter, about 400 mg/liter to about 500 mg/liter, about 500 mg/liter to about 600 mg/liter, about 600 mg/liter to about 700 mg/liter, about 700 mg/liter to about 800 mg/liter, about 800 mg/liter to about 900 mg/liter, about 900 mg/liter to about 1000 mg/liter, about 1000 mg/liter to about 1500 mg/liter, or about 1500 mg/liter to about 2000 mg/liter. Included are embodiments wherein the indicator expression system comprises a second nonidentical test expression system in the array or a standard expression system. In other embodiments, the yield of the heterologous protein is a measure of the amount of soluble heterologous protein, the amount of recoverable heterologous protein, the amount of properly processed heterologous protein, the amount of properly folded heterologous protein, the amount of active heterologous protein, and/or the total amount of heterologous protein. The invention includes methods wherein the optimal expression system is selected from among the test expression systems based on the increased yield of the heterologous protein in the test expression system relative to that in the indicator expression system. In certain embodiments, an optimal expression system is selected from among the test expression systems based on the yield of the heterologous protein in the test expression system.

The invention also includes methods for selecting an optimal expression system comprising using the array assembled using the methods of the invention, and an array assembled using the methods of the invention. In embodiments, at least 2 of said at least 5 different expression systems overexpress at least one folding modulator. In other embodiments, the at least one folding modulator is selected from the folding modulators listed herein in Table 1 and Table 2. In embodiments, the at least one folding modulator is expressed from a plasmid. In certain embodiments, at least one host cell population is defective in at least one to about eight proteases. In other embodiments, the at least one to about eight proteases are selected from the proteases listed in Table 1 and Table 2. In embodiments, the methods of the invention include determining the number of cysteine residues in, the presence of clustered prolines in, the requirement of an N terminal methionine for activity of, or the presence of a small amino acid in the plus two position of, the heterologous protein. In certain embodiments, when the heterologous protein has more than two cysteine residues, at least one of said at least 2 different expression systems overexpressing a folding modulator overexpresses a disulfide isomerase/oxidoreductase. In embodiments, the disulfide isomerase/oxidoreductase is encoded on a plasmid. In embodiments, when the heterologous protein has more than four cysteine residues, at least one of said at least 2 different expression vectors encoding the heterologous protein contains a periplasmic secretion leader sequence. In other embodiments, when the heterologous protein has more than four cysteine residues, at least one of said at least 2 different expression vectors encoding the heterologous protein contains a high or medium ribosome binding sequence. In embodiments, said at least one of said at least 2 different expression vectors encoding the heterologous protein and containing a periplasmic secretion leader sequence is included in at least one expression system that overexpresses at least one periplasmic chaperone, and at least one expression system that overexpresses at least one cytoplasmic chaperone. In other embodiments, when the heterologous protein has fewer than four cysteine residues, at least one of said at least 2 different expression vectors encoding the heterologous protein does not contain a periplasmic secretion leader sequence, and further wherein said at least one of said at least 2 different expression vectors encoding the heterologous protein and not containing a periplasmic secretion leader sequence is included in at least one expression system that overexpresses at least one cytoplasmic chaperone. In other embodiments, when clustered prolines are present, at least one expression system that overexpresses at least one 2+ peptidyl-prolyl cis-trans isomerase (PPIase) is included in the array. In certain embodiments, the 2+ peptidyl-prolyl cis-trans isomerase (PPIase) is encoded on a plasmid. In other embodiments, when the N-terminal methionine is required, at least one expression system comprising a host cell population that has at least one defect in at least one methionyl amino peptidase, is included in the array. In embodiments, when a small amino acid is present in the plus two position of the heterologous protein, at least one expression system comprising a host cell population that has at least one defect in at least one amino peptidase, is included in the array.

In embodiments, the small amino acid is selected from the group consisting of: glycine, alanine, valine, serine, threonine, aspartic acid, asparagine, and proline. In embodiments, the heterologous protein is a toxin. In specific embodiments, the toxin is a vertebrate or invertebrate animal toxin, a plant toxin, a bacterial toxin, a fungal toxin, or variant thereof. In other embodiments, the heterologous protein is a cytokine, growth factor or hormone, or receptor thereof. In certain embodiments, the heterologous protein is an antibody or antibody derivative. In specific embodiments, the antibody or antibody derivative is a humanized antibody, modified antibody, nanobody, bispecific antibody, single-chain antibody, Fab, Domain antibody, shark single domain antibody, camelid single domain antibody, linear antibody, diabody, or BiTE molecule. In other embodiments, the heterologous protein is a human therapeutic protein or therapeutic enzyme, a non-natural protein, a fusion protein, a chaperone, a pathogen protein or pathogen-derived antigen, a lipoprotein, a reagent protein, or a biocatalytic enzyme. In embodiments of the invention, at least 10% of the heterologous protein is insoluble when expressed in an indicator strain, or wherein the heterologous protein is predicted to be insoluble using a protein solubility prediction tool.

The invention additionally includes a method for selecting an optimal expression system for overexpressing at least one heterologous protein, said method comprising: assembling an array by placing in separate addressable locations at least 10 nonidentical test expression systems, said at least 10 nonidentical test expression systems each comprising a different combination of a) Pseudomonad or *E. coli* host cell population, and b) at least one expression vector encoding the at least one heterologous protein, wherein the array includes at least 5 different host cell populations and at least 2 different expression vectors, and further wherein at least 3 of said at least 10 different host cell populations are deficient in their expression of at least one protease; measuring the yield of the heterologous protein expressed; and selecting at least one optimal expression system from among the test expression systems based on the yield of the heterologous protein measured. In embodiments, the yield of the heterologous protein is about 1.5-fold to an about 100-fold higher in the at least one optimal expression system relative to that in an indicator expression system. In other embodiments, the yield of the heterologous protein in the at least one optimal expression system is about 10 mg/liter to about 2000 mg/liter. In certain embodiments, the indicator expression system comprises a second nonidentical test expression system in the array or a standard expression system. In embodiments, the yield of the heterologous protein is a measure of the amount of soluble heterologous protein, the amount of recoverable heterologous protein, the amount of properly processed heterologous protein, the amount of properly folded heterologous protein, the amount of active heterologous protein, and/or the total amount of heterologous protein.

The invention also includes an array of expression systems for testing expression of at least one heterologous protein, said array comprising: at least 10 nonidentical test expression systems in separate addressable locations, said at least 10 nonidentical test expression systems each comprising a different combination of a) a Pseudomonad or *E. coli* host cell population, and b) at least one expression vector encoding at least one heterologous protein, wherein the array includes at least 5 different host cell populations and at least 2 different expression vectors, and further wherein at least 3 of said at least 5 different host cell populations are deficient in their expression of at least one protease; and wherein at least one of the nonidentical test expression systems overexpresses the heterologous protein.

BRIEF DESCRIPTION OF THE FIGURES

FIG. 5 provides the sequences of the elements of SEQ ID NOS: 138-157, including open reading frames for folding modulators and proteases.

FIG. 6 provides sequences, including leader sequences, also provided herein in the sequence listing. These sequences are disclosed in U.S. Patent App. Pub. No. 2008/0193974, "Bacterial leader sequences for increased expression."

FIG. 7 provides sequences, including leader sequences, also provided herein in the sequence listing as SEQ ID NOS:208-327. These sequences are disclosed in U.S. Patent App. Pub. No. US2006/0008877, "Expression systems with Sec-secretion."

DETAILED DESCRIPTION

Figure 1A:
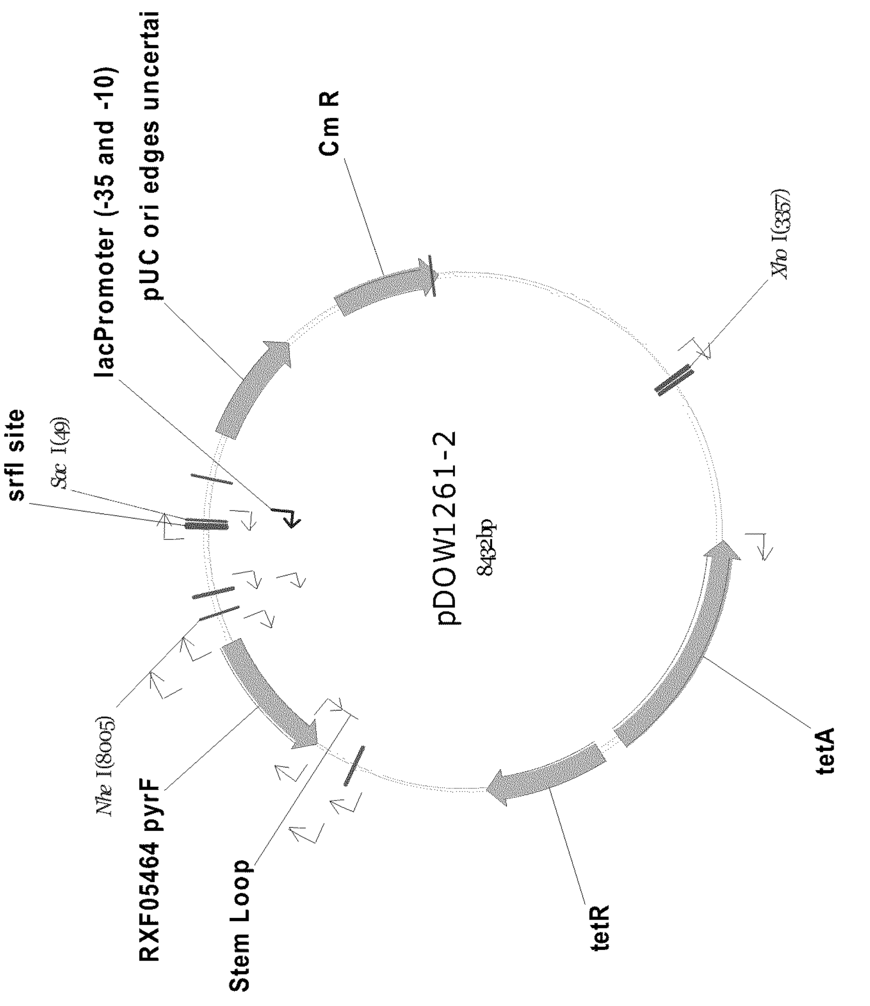
FIG. 1A depicts plasmid pDOW1261-2 used for engineering genomic deletion in *P. fluorescens*.

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements.

Many modifications and other embodiments of the inventions set forth herein will come to mind to one skilled in the art to which these inventions pertain having the benefit of the teachings presented in the foregoing descriptions and the associated drawings.

Therefore, it is to be understood that the inventions are not to be limited to the specific embodiments disclosed and that modifications and other embodiments are intended to be included within the scope of the invention. Although specific terms are employed herein, they are used in a generic and descriptive sense only and not for purposes of limitation.

Overview

Compositions and methods for identifying an optimal host strain, e.g, a *Pseudomonas fluorescens* host strain, for producing high levels of properly processed heterologous polypeptides in a host cell are provided. In particular, a library (or "array") of host strains is provided, wherein each strain (or "population of host cells") in the library has been genetically modified to modulate the expression of one or more target genes in the host cell. An "optimal host strain" or "optimal expression system" can be identified or selected based on the quantity, quality, and/or location of the expressed protein of interest compared to other populations of phenotypically distinct host cells in the array. Thus, an optimal host strain is the strain that produces the polypeptide of interest according to a desired specification. While the desired specification will vary depending on the polypeptide being produced, the specification includes the quality and/or quantity of protein, whether the protein is sequestered or secreted, protein folding, and the like. For example, the optimal host strain or optimal expression system produces a yield, characterized by the amount of soluble heterologous protein, the amount of recoverable heterologous protein, the amount of properly processed heterologous protein, the amount of properly folded heterologous protein, the amount of active heterologous protein, and/or the total amount of heterologous protein, of a certain absolute level or a certain level relative to that produced by an indicator strain, i.e., a strain used for comparison.

"Heterologous," "heterologously expressed," or "recombinant" generally refers to a gene or protein that is not endogenous to the host cell or is not endogenous to the location in the native genome in which it is present, and has been added to the cell by infection, transfection, microinjection, electroporation, microprojection, or the like.

One or more of the host cell populations in the array is modified to modulate the expression of one or more target genes in the host cell. By "target gene" is intended a gene that affects heterologous protein production in a host cell. Target genes that affect heterologous protein production include genes encoding proteins that modulate expression, activity, solubility, translocation, proteolytic degradation and/or cleavage of the heterologous protein. For example, a target gene may encode at least one of a host cell protease, a protein folding modulator, a transcription factor, a translation factor, a secretion modulator, or any other protein involved in the proper transcription, translation, processing, and/or translocation of a heterologous protein of interest. A "target protein" refers to the protein or polypeptide resulting from expression of the target gene. Expression and/or activity of a target gene or genes is increased or decreased, depending on the function of the target gene or protein. For example, expression of one or more host cell proteases may be decreased, whereas expression of one or more protein folding modulators may be increased.

The arrays described herein are useful for rapidly identifying an optimal host cell for production of a heterologous protein or peptide of interest. Heterologous protein production often leads to the formation of insoluble or improperly folded proteins, which are difficult to recover and may be inactive. Furthermore, the presence of specific host cell proteases may degrade the protein of interest and thus reduce the final yield. There is no single host cell population that will optimally produce all polypeptides or proteins of interest. Thus, using the compositions and methods of the invention, an optimal host cell can be rapidly and efficiently identified from the library of modified cell populations. The optimal host strain can then be used to produce sufficient amounts of the protein of interest or for commercial production. Likewise, a host strain can be modified for expression of the protein of interest based on the optimal host strain.

In one embodiment, the method includes obtaining an array comprising at least a first and a second population of *P. fluorescens* cells, wherein each population is selected from the group consisting of (i) a population of *P. fluorescens* cells that has been genetically modified to reduce the expression of at least target gene involved in protein degradation; (ii) a population of *P. fluorescens* cells that has been genetically modified to increase the expression of at least one target gene involved in protein production; and, (iii) a population of *P. fluorescens* cells that has been genetically modified to reduce the expression of at least one target gene involved in protein degradation and to increase the expression of at least one target gene involved in protein production; introducing into at least one cell of each population an expression construct comprising at least one gene encoding at least one heterologous protein of interest; maintaining said cells under conditions sufficient for the expression of said protein of interest in at least one population of cells; and selecting the optimal population of cells in which the heterologous protein of interest is produced; wherein each population in the array is non-identical and wherein each population is physically separate from one from another; wherein the heterologous protein of interest exhibits one or more of improved expression, improved activity, improved solubility, improved translocation, or reduced proteolytic degradation or cleavage in the optimal population of cells compared to other populations in the array.

The array may further comprise a population of host cells (e.g., *P. fluorescens* host cells) that has not been genetically modified to alter the expression of a host cell protease or a protein folding modulator. This population may be a wild-type strain, or may be a strain that has been genetically modified to alter the expression of or more genes not involved in protein production, processing, or translocation (e.g., may be genetically modified to express, for example, a selectable marker gene).

In one embodiment, each population of *P. fluorescens* host cells is phenotypically distinct (i.e., "non-identical") one from another. By "phenotypically distinct" is intended that each population produces a measurably different amount of one or more target proteins. In this embodiment, each strain has been genetically modified to alter the expression of one or more different target genes. Where the expression of more than one target gene is modulated in a population of host cells, then the combination of target genes is phenotypically distinct from other populations in the library. An array comprising a plurality of phenotypically distinct populations of host cells according to the present invention is one that provides a diverse population from which to select one or more strains useful for producing a heterologous protein or peptide of interest. It will be understood by one of skill in the art that such an array may also comprise replicates (e.g., duplicates, triplicates, etc.) of any one or more populations of host cells.

In embodiments, structural characteristics of the recombinant protein guide the selection of expression vector elements. The expression vector elements can in turn influence selection of the host cell population. For example, a recombinant protein having multiple cysteine residues can have a propensity to misfold improper due to disulfide mispairing. Using the methods of the present invention, an array that includes at least one expression vector having a periplasmic secretion leader is assembled, and in turn that expression vector is paired with a host cell population that overexpresses a periplasmic chaperone. The host strain element thus can act synergistically with the vector element to increase expression of the recombinant protein. Thus, in embodiments, an array of the present invention is assembled using different combinations of potentially synergistic expression vector and host cell elements.

In embodiments, a heterologous protein containing more than one disulfide bond, or more than two cysteine residues, can be screened in expression systems wherein the host strain is, e.g., a disulfide isomerase/oxidoreductase pathway overexpressor. In addition to the number of cysteine residues available to form disulfide bonds, a heterologous protein can be evaluated to determine the presence of clustered prolines, the requirement of an N terminal methionine for activity, or the presence of a small amino acid in the plus two position. In embodiments, identification of the presence of clustered prolines or several prolines within relatively close proximity indicates the use of a 2+ peptidyl-prolyl cis-trans isomerase (PPIase) overexpression host cell population. In other embodiments, a host cell population that has at least one defect in at least one methionyl amino peptidase is included in the array when the heterologous protein is determined to require an N-terminal methionine. In still other embodiments, a host cell population that has at least one defect in at least one amino peptidase is included in an expression system of the array when the presence of a small amino acid in the plus two position of the heterologous protein is identified.

The heterologous protein can also be evaluated for a propensity for protease degradation, and a host cell populations having one or more protease mutations used in the array. Furthermore, if a cleavage site for a specific protease is identified, a host having a mutation in the protease(s) which cleaves at that site can be included in the array. Useful host cell populations can contain multiple protease mutations, multiple folding modulators, or both protease mutations and folding modulators. In embodiments, a host cell population that has at least one to at least eight different protease mutations is used in an expression system of the array.

Variation of the expression systems of the invention at multiple interdependent levels allows fine-tuning of expression, which in conjunction with rapid screening capabilities provides a powerful tool for identifying overexpression systems for any protein.

Arrays

Provided herein is an array of host cell populations (i.e. "strain array") which can be rapidly screened to identify certain strain(s) with improved yield and/or quality of heterologous protein. As used herein, the term "strain array" refers to a plurality of addressed or addressable locations (e.g., wells, such as deep well or microwells). The location of each of the microwells or groups of microwells in the array is typically known, so as to allow for identification of the optimal host cell for expression of the heterologous protein of interest.

The strain array comprises a plurality of phenotypically distinct host strains. The arrays may be low-density arrays or high-density arrays and may contain about 2 or more, about 4 or more, about 8 or more, about 12 or more, about 16 or more, about 20 or more, about 24 or more, about 32 or more, about 40 or more, about 48 or more, about 64 or more, about 72 or more, about 80 or more, about 96 or more, about 192 or more, about 384 or more host cell populations.

The host cell populations of the invention can be maintained and/or screened in a multi-well or deep well vessel. The vessel may contain any desired number of wells, however, a miniaturized cell culture microarray platform is useful for screening each population of host cells individually and simultaneously using minimal reagents and a relatively small number of cells. A typical multi-well, microtiter vessel useful in this assay is a multi-well plate including, without limitation, 10-well plates, 28-well plates, 96-well plates, 384-well plates, and plates having greater than 384 wells. Alternatively, an array of tubes, holders, cartridges, minitubes, microfuge tubes, cryovials, square well plates tubes, plates, slants, or culture flasks may also be used, depending on the volume desired.

The vessel may be made of any material suitable for culturing and/or screening a host cell of interest, e.g., *Pseudomonas*. For example, the vessel can be a material that can be easily sterilized such as plastic or other artificial polymer material, so long as the material is biocompatible. Any number of materials can be used, including, but not limited to, polystyrene; polypropylene; polyvinyl compounds (e.g. polyvinylchloride); polycarbonate (PVC); polytetrafluoroethylene (PTFE); polyglycolic acid (PGA); cellulose; glass, fluoropolymers, fluorinated ethylene propylene, polyvinylidene, polydimethylsiloxane, silicon, and the like.

Automated transformation of cells and automated colony pickers will facilitate rapid screening of desired cells. The arrays may be created and/or screened using a spotter device (e.g., automated robotic devices) as known in the art.

Target Genes

The strain array of the present invention comprises a plurality of phenotypically and genotypically distinct host cell populations, wherein each population in the array has been genetically modified to modulate the expression of one or more target genes in the host cell. By "target gene" is intended a gene that affects heterologous protein production in a host cell. A target gene may encode a host cell protease or an endogenous or exogenous protein folding modulator, transcription factor, translation factor, secretion modulator, or any other gene involved in the proper expression, processing, and/or translocation of a heterologous protein of interest. A "target protein" refers to the protein or polypeptide resulting from expression of the target gene. Expression and/or activity of a target gene or genes is increased or decreased, depending on the function of the target gene or protein. A target gene can be endogenous to the host cell, or can be a gene that is heterologously expressed in each of the host cell populations in the array.

In one embodiment, the target gene or genes is at least one protein folding modulator, putative protein folding modulator, or a cofactor or subunit of a folding modulator. In some embodiments, the target gene or genes can be selected from a chaperone protein, a foldase, a peptidyl prolyl isomerase and a disulfide bond isomerase. In some embodiments, the target gene or genes can be selected from htpG, cbpA, dnaJ, dnaK and fkbP. Exemplary protein folding modulators from *P. fluorescens* are listed in Table 1.

In other embodiments, the target gene comprises at least one putative protease, a protease-like protein, or a cofactor or subunit of a protease. For example, the target gene or genes can be a serine, threonine, cysteine, aspartic or metallopeptidase. In one embodiment, the target gene or genes can be selected from hslV, hslU, clpA, clpB and clpX. The target gene can also be a cofactor of a protease. Exemplary proteases from *P. fluorescens* are listed in Table 2. Proteases from a variety of organisms can be found in the MEROPS Peptidase Database maintained by the Welcome Trust Sanger Institute, Cambridge, UK (Rawlings et. al., 2006, Nucleic Acids Research 34 (Database issue): D270-2).

Protein Folding Modulators

Another major obstacle in the production of heterologous proteins in host cells is that the cell often is not adequately equipped to produce either soluble or active protein. While the primary structure of a protein is defined by its amino acid sequence, the secondary structure is defined by the presence of alpha helices or beta sheets, and the ternary structure by covalent bonds between adjacent protein stretches, such as disulfide bonds. When expressing heterologous proteins, particularly in large-scale production, the secondary and tertiary structure of the protein itself is of critical importance. Any significant change in protein structure can yield a functionally inactive molecule, or a protein with significantly reduced biological activity. In many cases, a host cell expresses protein folding modulators (PFMs) that are necessary for proper production of active heterologous protein. However, at the high levels of expression generally required to produce usable, economically satisfactory biotechnology products, a cell often cannot produce enough native protein folding modulator or modulators to process the heterologously-expressed protein.

In certain expression systems, overproduction of heterologous proteins can be accompanied by their misfolding and segregation into insoluble aggregates. In bacterial cells these aggregates are known as inclusion bodies. In *E. coli*, the network of folding modulators/chaperones includes the Hsp70 family. The major Hsp70 chaperone, DnaK, efficiently prevents protein aggregation and supports the refolding of damaged proteins. The incorporation of heat shock proteins into protein aggregates can facilitate disaggregation. However, proteins processed to inclusion bodies can, in certain cases, be recovered through additional processing of the insoluble fraction. Proteins found in inclusion bodies typically have to be purified through multiple steps, including denaturation and renaturation. Typical renaturation processes for inclusion body targeted proteins involve attempts to dissolve the aggregate in concentrated denaturant and subsequent removal of the denaturant by dilution. Aggregates are frequently formed again in this stage. The additional processing adds cost, there is no guarantee that the in vitro refolding will yield biologically active product, and the recovered proteins can include large amounts of fragment impurities.

The recent realization that in vivo protein folding is assisted by molecular chaperones, which promote the proper isomerization and cellular targeting of other polypeptides by transiently interacting with folding intermediates, and by foldases, which accelerate rate-limiting steps along the folding pathway, has provided additional approaches to combat the problem of inclusion body formation (see for e.g. Thomas J G et al. (1997) *Appl Biochem Biotechnol* 66:197-238).

In certain cases, the overexpression of chaperones has been found to increase the soluble yields of aggregation-prone proteins (see Baneyx, F. (1999) *Curr. Opin. Biotech.* 10:411-421 and references therein). The beneficial effect associated with an increase in the intracellular concentration of these chaperones appears highly dependent on the nature of the overproduced protein, and may not require overexpression of the same protein folding modulator(s) for all heterologous proteins.

Protein folding modulators, including chaperones, disulfide bond isomerases, and peptidyl-prolyl cis-trans isomerases (PPIases) are a class of proteins present in all cells which aid in the folding, unfolding and degradation of nascent polypeptides.

Chaperones act by binding to nascent polypeptides, stabilizing them and allowing them to fold properly. Proteins possess both hydrophobic and hydrophilic residues, the former are usually exposed on the surface while the latter are buried within the structure where they interact with other hydrophilic residues rather than the water which surrounds the molecule. However in folding polypeptide chains, the hydrophilic residues are often exposed for some period of time as the protein exists in a partially folded or misfolded state. It is during this time when the forming polypeptides can become permanently misfolded or interact with other misfolded proteins and form large aggregates or inclusion bodies within the cell. Chaperones generally act by binding to the hydrophobic regions of the partially folded chains and preventing them from misfolding completely or aggregating with other proteins. Chaperones can even bind to proteins in inclusion bodies and allow them to disaggregate (Ranson et. al. 1998). The GroES/EL, DnaKJ, Clp, Hsp90 and SecB families of folding modulators are all examples of proteins with chaperone like activity.

Another important type of folding modulator is the disulfide bond isomerases. These proteins catalyze a very specific set of reactions to help folding polypeptides form the proper intra-protein disulfide bonds. Any protein that has more than two cysteines is at risk of forming disulfide bonds between the wrong residues. The disulfide bond formation family consists of the Dsb proteins which catalyze the formation of disulfide bonds in the non-reducing environment of the periplasm. When a periplasmic polypeptide misfolds disulfide bond isomerase, DsbC is capable of rearranging the disulfide bonds and allowing the protein to reform with the correct linkages.

The proline residue is unique among amino acids in that the peptidyl bond immediately preceding it can adopt either a cis or trans conformation. For all other amino acids this is not favored due to steric hindrance. Peptidyl-prolyl cis-trans isomerases (PPIases) catalyze the conversion of this bond from one form to the other. This isomerization may aid in protein folding, refolding, assembly of subunits and trafficking in the cell (Dolinski, et. al. 1997).

In addition to the general chaperones which seem to interact with proteins in a non-specific manner, there are also chaperones which aid in the folding of specific targets. These protein-specific chaperones form complexes with their targets, preventing aggregation and degradation and allowing time for them to assemble into multi-subunit structures. The PapD chaperone is one well known example of this type (Lombardo et. al. 1997).

Folding modulators also include, for example, HSP70 proteins, HSP110/SSE proteins, HSP40 (DNAJ-related) proteins, GRPE-like proteins, HSP90 proteins, CPN60 and CPN10 proteins, Cytosolic chaperoning, HSP100 proteins, Small HSPs, Calnexin and calreticulin, PDI and thioredoxin-related proteins, Peptidyl-prolyl isomerases, Cyclophilin PPIases, FK-506 binding proteins, Parvulin PPIases, Individual chaperoning, Protein specific chaperones, or intramolecular chaperones. Folding modulators are generally described in "Guidebook to Molecular Chaperones and Protein-Folding Catalysts" (1997) ed. M. Gething, Melbourne University, Australia.

The best characterized molecular chaperones in the cytoplasm of *E. coli* are the ATP-dependent DnaK-DnaJ-GrpE and GroEL-GroES systems. Based on in vitro studies and homology considerations, a number of additional cytoplasmic proteins have been proposed to function as molecular chaperones in *E. coli*. These include ClpB, HtpG and IbpA/B, which, like DnaK-DnaJ-GrpE and GroEL-GroES, are heat-shock proteins (Hsps) belonging to the stress regulon. The trans conformation of X-Pro bonds is energetically favored in nascent protein chains; however, approximately 5% of all prolyl peptide bonds are found in a cis conformation in native proteins. The trans to cis isomerization of X-Pro bonds is rate limiting in the folding of many polypeptides and is catalyzed in vivo by peptidyl prolyl cis/trans isomerases (PPIases). Three cytoplasmic PPIases, SlyD, SlpA and trigger factor (TF), have been identified to date in *E. coli*. TF, a 48 kDa protein associated with 50S ribosomal subunits that has been postulated to cooperate with chaperones in *E. coli* to guarantee proper folding of newly synthesized proteins. At least five proteins (thioredoxins 1 and 2, and glutaredoxins 1, 2 and 3, the products of the trxA, trxC, grxA, grxB and grxC genes, respectively) are involved in the reduction of disulfide bridges that transiently arise in cytoplasmic enzymes. Thus, target genes can be disulfide bond forming proteins or chaperones that allow proper disulfide bond formation.

TABLE 1

*P. fluorescens* strain MB214 protein folding modulators

| ORF ID | GENE | FUNCTION | FAMILY | LOCATION |
|---|---|---|---|---|
| | | GroES/EL | | |
| RXF02095.1 | groES | Chaperone | Hsp10 | Cytoplasmic |
| RXF06767.1::Rxf02090 | groEL | Chaperone | Hsp60 | Cytoplasmic |
| RXF01748.1 | ibpA | Small heat-shock protein (sHSP) IbpA PA3126; Acts as a holder for GroESL folding | Hsp20 | Cytoplasmic |
| RXF03385.1 | hscB | Chaperone protein hscB | Hsp20 | Cytoplasmic |
| | | Hsp70 (DnaK/J) | | |
| RXF05399.1 | dnaK | Chaperone | Hsp70 | Periplasmic |
| RXF06954.1 | dnaK | Chaperone | Hsp70 | Cytoplasmic |
| RXF03376.1 | hscA | Chaperone | Hsp70 | Cytoplasmic |
| RXF03987.2 | cbpA | Curved dna-binding protein, dnaJ like activity | Hsp40 | Cytoplasmic |
| RXF05406.2 | dnaJ | Chaperone protein dnaJ | Hsp40 | Cytoplasmic |
| RXF03346.2 | dnaJ | Molecular chaperones (DnaJ family) | Hsp40 | Non-secretory |
| RXF05413.1 | grpE | heat shock protein GrpE PA4762 | GrpE | Cytoplasmic |
| | | Hsp100 (Clp/Hsl) | | |
| RXF04587.1 | clpA | atp-dependent clp protease atp-binding subunit clpA | Hsp100 | Cytoplasmic |
| RXF08347.1 | clpB | ClpB protein | Hsp100 | Cytoplasmic |
| RXF04654.2 | clpX | atp-dependent clp protease atp-binding subunit clpX | Hsp100 | Cytoplasmic |
| RXF04663.1 | clpP | atp-dependent Clp protease proteolytic subunit (ec 3.4.21.92) | MEROPS peptidase family S14 | Cytoplasmic |
| RXF01957.2 | hslU | atp-dependent hsl protease atp-binding subunit hslU | Hsp100 | Cytoplasmic |
| RXF01961.2 | hslV | atp-dependent hsl protease proteolytic subunit | MEROPS peptidase subfamily T1B | Cytoplasmic |
| | | Hsp33 | | |
| RXF04254.2 | yrfI | 33 kDa chaperonin (Heat shock protein 33 homolog) (HSP33). | Hsp33 | Cytoplasmic |
| | | Hsp90 | | |
| RXF05455.2 | htpG | Chaperone protein htpG | Hsp90 | Cytoplasmic |
| | | SecB | | |
| RXF02231.1 | secB | secretion specific chaperone SecB | SecB | Non-secretory |
| | | Disulfide Bond Isomerases | | |
| RXF07017.2 | dsbA | disulfide isomerase | DSBA oxido-reductase | Cytoplasmic |

TABLE 1-continued

| *P. fluorescens* strain MB214 protein folding modulators | | | | |
|---|---|---|---|---|
| ORF ID | GENE | FUNCTION | FAMILY | LOCATION |
| RXF08657.2 | dsbA/dsbC/dsbG/fernA | disulfide isomerase | DSBA oxido-reductase | Cytoplasmic |
| RXF01002.1 | dsbA/dsbC | disulfide isomerase | DSBA oxido-reductase/Thioredoxin | Periplasmic |
| RXF03307.1 | dsbC | disulfide isomerase | Glutaredoxin/Thioredoxin | Periplasmic |
| RXF04890.2 | dsbG | disulfide isomerase | Glutaredoxin/Thioredoxin | Periplasmic |
| RXF03204.1 | dsbB | Disulfide bond formation protein B (Disulfide oxidoreductase). | DSBA oxido-reductase | Periplasmic |
| RXF04886.2 | dsbD | Thiol:disulfide interchange protein dsbD | DSBA oxido-reductase | Periplasmic |
| Peptidyl-prolyl cis-trans isomerases | | | | |
| RXF03768.1 | ppiA | Peptidyl-prolyl cis-trans isomerase A (ec 5.2.1.8) | PPIase: cyclophilin type | Periplasmic |
| RXF05345.2 | ppiB | Peptidyl-prolyl cis-trans isomerase B. | PPIase: cyclophilin type | Cytoplasmic |
| RXF06034.2 | fklB | Peptidyl-prolyl cis-trans isomerase FklB. | PPIase: FKBP type | OuterMembrane |
| RXF06591.1 | fklB/fkbP | fk506 binding protein Peptidyl-prolyl cis-trans isomerase (EC 5.2.1.8) | PPIase: FKBP type | Periplasmic |
| RXF05753.2 | fklB; fkbP | Peptidyl-prolyl cis-trans isomerase (ec 5.2.1.8) | PPIase: FKBP type | OuterMembrane |
| RXF01833.2 | slyD | Peptidyl-prolyl cis-trans isomerase SlyD. | PPIase: FKBP type | Non-secretory |
| RXF04655.2 | tig | Trigger factor, ppiase (ec 5.2.1.8) | PPIase: FKBP type | Cytoplasmic |
| RXF05385.1 | yaad | Probable FKBP-type 16 kDa peptidyl-prolyl cis-trans isomerase (EC 5.2.1.8) (PPiase) (Rotamase). | PPIase: FKBP type | Non-secretory |
| RXF00271.1 | | Peptidyl-prolyl cis-trans isomerase (ec 5.2.1.8) | PPIase: FKBP type | Non-secretory |
| pili assembly chaperones (papD like) | | | | |
| RXF06068.1 | cup | Chaperone protein cup | pili assembly papD | Periplasmic |
| RXF05719.1 | ecpD | Chaperone protein ecpD | pili assembly papD | Signal peptide |
| RXF05319.1 | ecpD | Hnr protein | pili assembly chaperone | Periplasmic |
| RXF03406.2 | ecpD; csuC | Chaperone protein ecpD | pili assembly papD | Signal peptide |
| RXF04296.1 | ecpD; cup | Chaperone protein ecpD | pili assembly papD | Periplasmic |
| RXF04553.1 | ecpD; cup | Chaperone protein ecpD | pili assembly papD | Periplasmic |
| RXF04554.2 | ecpD; cup | Chaperone protein ecpD | pili assembly papD | Periplasmic |
| RXF05310.2 | ecpD; cup | Chaperone protein ecpD | pili assembly papD | Periplasmic |
| RXF05304.1 | ecpD; cup | Chaperone protein ecpD | pili assembly papD | Periplasmic |
| RXF05073.1 | gltF | Gram-negative pili assembly chaperone periplasmic function | pili assembly papD | Signal peptide |
| Type II Secretion Complex | | | | |
| RXF05445.1 | YacJ | Histidinol-phosphate aminotransferase (ec 2.6.1.9) | Class-II pyridoxal-phosphate-dependent aminotransferase family. Histidinol-phosphate amino-transferase subfamily. | Membrane |
| RXF05426.1 | SecD | Protein translocase subunit secd | Type II secretion complex | Membrane |
| RXF05432.1 | SecF | protein translocase subunit secf | Type II secretion complex | Membrane |

TABLE 1-continued

| *P. fluorescens* strain MB214 protein folding modulators | | | | |
|---|---|---|---|---|
| ORF ID | GENE | FUNCTION | FAMILY | LOCATION |
| Disulfide Bond Reductases | | | | |
| RXF08122.2 | trxC | Thioredoxin 2 | Disulfide Bond Reductase | Cytoplasmic |
| RXF06751.1 | Gor | Glutathione reductase (EC 1.8.1.7) (GR) (GRase) PA2025 | Disulfide Bond Reductase | Cytoplasmic |
| RXF00922.1 | gshA | Glutamate--cysteine ligase (ec 6.3.2.2) PA5203 | Disulfide Bond Reductase | Cytoplasmic |

Protease

Unwanted degradation of heterologously-expressed protein presents an obstacle to the efficient use of certain expression systems. When a cell is modified to produce large quantities of a target protein, the cell is placed under stress and often reacts by inducing or suppressing other proteins. The stress that a host cell undergoes during production of heterologous proteins can increase expression of, for example, specific proteins or cofactors to cause degradation of the overexpressed heterologous protein. The increased expression of compensatory proteins can be counterproductive to the goal of expressing high levels of active, full-length heterologous protein. Decreased expression or lack of adequate expression of other proteins can cause misfolding and aggregation of the heterologously-expressed protein. While it is known that a cell under stress will change its profile of protein expression, not all heterologously expressed proteins will modulate expression of the same proteins in a particular host cell.

Thus, the optimal host strain, e.g., *P. fluorescens* host strain, can be identified using an array comprising a plurality of host cell populations that have been genetically engineered to decrease the expression of one or more protease enzymes. In one embodiment, one or more host cell populations is modified by reducing the expression of, inhibiting or removing at least one protease from the genome. The modification can also be to more than one protease. In a related embodiment, the cell is modified by reducing the expression of a protease cofactor or protease protein. In another embodiment, the host cell is modified by inhibition of a promoter for a protease or related protein, which can be a native promoter. Alternatively, the gene modification can be to modulate a protein homologous to the target gene.

The array comprising the modified host strains can be screened by expressing the heterologous protein(s) of interest and assessing the quality and/or quantity of protein production as discussed infra. Alternatively, an isolate of the heterologous protein of interest can be independently incubated with lysate collected from each of the protease-deficient host cell populations and the level of proteolytic degradation can be used to identify the optimal host cell. In this embodiment, the optimal host cell population is that which results in the least amount of heterologous protein degradation. Thus, in one embodiment, lysate from the optimal host cell population can be degraded by less than about 50% of the heterologous protein, less than about 45%, less than about 40%, less than about 35%, less than about 30%, less than about 25%, less than about 20%, less than about 10%, less than about 5%, less than about 4%, about 3%, about 2%, about 1%, or less of the protein.

Exemplary target protease genes include those proteases classified as Aminopeptidases; Dipeptidases; Dipeptidyl-peptidases and tripeptidyl peptidases; Peptidyl-dipeptidases; Serine-type carboxypeptidases; Metallocarboxypeptidases; Cysteine-type carboxypeptidases; Omegapeptidases; Serine proteinases; Cysteine proteinases; Aspartic proteinases; Metallo proteinases; or Proteinases of unknown mechanism.

Aminopeptidases include cytosol aminopeptidase (leucyl aminopeptidase), membrane alanyl aminopeptidase, cystinyl aminopeptidase, tripeptide aminopeptidase, prolyl aminopeptidase, arginyl aminopeptidase, glutamyl aminopeptidase, x-pro aminopeptidase, bacterial leucyl aminopeptidase, thermophilic aminopeptidase, clostridial aminopeptidase, cytosol alanyl aminopeptidase, lysyl aminopeptidase, x-trp aminopeptidase, tryptophanyl aminopeptidase, methionyl aminopeptidas, d-stereospecific aminopeptidase, aminopeptidase ey. Dipeptidases include x-his dipeptidase, x-arg dipeptidase, x-methyl-his dipeptidase, cys-gly dipeptidase, glu-glu dipeptidase, pro-x dipeptidase, x-pro dipeptidase, met-x dipeptidase, non-stereospecific dipeptidase, cytosol non-specific dipeptidase, membrane dipeptidase, beta-ala-his dipeptidase. Dipeptidyl-peptidases and tripeptidyl peptidases include dipeptidyl-peptidase i, dipeptidyl-peptidase ii, dipeptidyl peptidase iii, dipeptidyl-peptidase iv, dipeptidyl-dipeptidase, tripeptidyl-peptidase I, tripeptidyl-peptidase II. Peptidyl-dipeptidases include peptidyl-dipeptidase a and peptidyl-dipeptidase b. Serine-type carboxypeptidases include lysosomal pro-x carboxypeptidase, serine-type D-ala-D-ala carboxypeptidase, carboxypeptidase C, carboxypeptidase D. Metallocarboxypeptidases include carboxypeptidase a, carboxypeptidase B, lysine(arginine) carboxypeptidase, gly-X carboxypeptidase, alanine carboxypeptidase, muramoylpentapeptide carboxypeptidase, carboxypeptidase h, glutamate carboxypeptidase, carboxypeptidase M, muramoyltetrapeptide carboxypeptidase, zinc d-ala-d-ala carboxypeptidase, carboxypeptidase A2, membrane pro-x carboxypeptidase, tubulinyl-tyr carboxypeptidase, carboxypeptidase t. Omegapeptidases include acylaminoacyl-peptidase, peptidyl-glycinamidase, pyroglutamyl-peptidase I, beta-aspartyl-peptidase, pyroglutamyl-peptidase II, n-formylmethionyl-peptidase, pteroylpoly-[gamma]-glutamate carboxypeptidase, gamma-glu-X carboxypeptidase, acylmuramoyl-ala peptidase. Serine proteinases include chymotrypsin, chymotrypsin c, metridin, trypsin, thrombin, coagulation factor Xa, plasmin, enteropeptidase, acrosin, alpha-lytic protease, glutamyl, endopeptidase, cathepsin G, coagulation factor viia, coagulation factor ixa, cucumisi, prolyl oligopeptidase, coagulation factor xia, brachyurin, plasma kallikrein, tissue kallikrein, pancreatic elastase, leukocyte elastase, coagulation factor xiia, chymase, complement component c1r55, complement component c1s55, classical-complement pathway c3/c5 convertase, complement factor I, complement factor D, alternative-complement pathway c3/c5 convertase, cerevisin, hypodermin C, lysyl endopeptidase, endopeptidase 1a, gamma-reni, venombin ab, leucyl endopeptidase, tryptase, scutelarin, kexin, subtilisin, oryzin, endopeptidase k, thermomycolin, thermitase, endopeptidase SO, T-plasminogen activator, protein C, pancreatic endopeptidase E, pancreatic elastase ii, IGA-specific serine endopeptidase, U-plasminogen, activator, venombin A, furin, myeloblastin, semenogelase, granzyme A or cytotoxic T-lymphocyte proteinase 1, granzyme B or cytotoxic T-lymphocyte proteinase 2, streptogrisin A, treptogrisin B, glutamyl endopeptidase II, oligopeptidase B, *limulus* clotting factor c, *limulus* clotting factor, *limulus* clotting enzyme, omptin, repressor lexa, bacterial leader peptidase I, togavirin, flavirin. Cysteine proteinases include cathepsin B, papain, ficin, chymopapain, asclepain, clostripain, streptopain, actinide, cathepsin 1, cathepsin H, calpain, cathepsin t, glycyl, endopeptidase, cancer procoagulant, cathepsin S, picornain 3C, picornain 2A, caricain, ananain, stem bromelain, fruit bromelain, legumain, histolysain, interleukin 1-beta converting enzyme. Aspartic proteinases include pepsin A, pepsin B, gastricsin, chymosin, cathepsin D, neopenthesin, renin, retropepsin, pro-opiomelanocortin converting enzyme, aspergillopepsin I, aspergillopepsin II, penicillopepsin, rhizopuspepsin, endothiapepsin, mucoropepsin, candidapepsin, saccharopepsin, rhodotorulapepsin, physaropepsin, acrocylindropepsin, polyporopepsin, pycnoporopepsin, scytalidopepsin a, scytalidopepsin b, xanthomonapepsin, cathepsin e, barrierpepsin, bacterial leader peptidase I, pseudomonapepsin, plasmepsin. Metallo proteinases include atrolysin a, microbial collagenase, leucolysin, interstitial collagenase, neprilysin, envelysin, iga-specific metalloendopeptidase, procollagen N-endopeptidase, thimet oligopeptidase, neurolysin, stromelysin 1, meprin A, procollagen C-endopeptidase, peptidyl-lys metalloendopeptidase, astacin, stromelysin, 2, matrilysin gelatinase, aeromonolysin, pseudolysin, thermolysin, bacillolysin, aureolysin, coccolysin, mycolysin, beta-lytic metalloendopeptidase, peptidyl-asp metalloendopeptidase, neutrophil collagenase, gelatinase B, leishmanolysin, saccharolysin, autolysin, deuterolysin, serralysin, atrolysin B, atrolysin C, atroxase, atrolysin E, atrolysin F, adamalysin, horrilysin, ruberlysin, bothropasin, bothrolysin, ophiolysin, trimerelysin I, trimerelysin II, mucrolysin, pitrilysin, insulysin, O-syaloglycoprotein endopeptidase, russellysin, mitochondrial, intermediate, peptidase, dactylysin, nardilysin, magnolysin, meprin B, mitochondrial processing peptidase, macrophage elastase, choriolysin, toxilysin. Proteinases of unknown mechanism include thermopsin and multicatalytic endopeptidase complex.

Certain proteases can have both protease and chaperone-like activity. When these proteases are negatively affecting protein yield and/or quality it can be useful to delete them, and they can be overexpressed when their chaperone activity may positively affect protein yield and/or quality. These proteases include, but are not limited to: Hsp100 (Clp/Hsl) family members RXF04587.1 (clpA), RXF08347.1, RXF04654.2 (clpX), RXF04663.1, RXF01957.2 (hslU), RXF01961.2 (hslV); Peptidyl-prolyl cis-trans isomerase family member RXF05345.2 (ppiB); Metallopeptidase M20 family member RXF04892.1 (aminohydrolase); Metallopeptidase M24 family members RXF04693.1 (methionine aminopeptidase) and RXF03364.1 (methionine aminopeptidase); and Serine Peptidase S26 signal peptidase I family member RXF01181.1 (signal peptidase).

TABLE 2

*P. fluorescens* strain MB214 proteases

| | Family | ORF ID | Gene | Function | Location |
|---|---|---|---|---|---|
| Aspartic Peptidases | A8 (signal peptidase II family) | RXF05383.2 | | Lipoprotein signal peptidase (ec 3.4.23.36) | Cytoplasmic Membrane |
| | A24 (type IV prepilin peptidase family) | RXF05379.1 | | type 4 prepilin peptidase pild (ec 3.4.99.—) | Cytoplasmic Membrane |
| Cysteine Peptidases | C15 (pyroglutamyl peptidase I family) | RXF02161.1 | | Pyrrolidone-carboxylate peptidase (ec 3.4.19.3) | Cytoplasmic |
| | C40 | RXF01968.1 | | invasion-associated protein, P60 | Signal peptide |
| | | RXF04920.1 | | invasion-associated protein, P60 | Cytoplasmic |
| | | RXF04923.1 | | phosphatase-associated protein papq | Signal peptide |
| | C56 (PfpI endopeptidase family) | RXF01816.1 | | protease I (ec 3.4.—.—) | Non-secretory |
| Metallopeptidases | M1 | RXF08773.1 | | Membrane alanine aminopeptidase (ec 3.4.11.2) | Non-secretory |
| | M3 | RXF00561.2 | prlC | Oligopeptidase A (ec 3.4.24.70) | Cytoplasmic |
| | | RXF04631.2 | | Zn-dependent oligopeptidases | Cytoplasmic |
| | M4 (thermolysin family) | RXF05113.2 | | Extracellular metalloprotease precursor (ec 3.4.24.—) | Extracellular |
| | M41 (FtsH endopeptidase family) | RXF05400.2 | | Cell division protein ftsH (ec 3.4.24.—) | Cytoplasmic Membrane |
| | M10 | RXF04304.1 | | Serralysin (ec 3.4.24.40) | Extracellular |
| | | RXF04500.1 | | Serralysin (ec 3.4.24.40) | Extracellular |
| | | RXF01590.2 | | Serralysin (ec 3.4.24.40) | Extracellular |
| | | RXF04497.2 | | Serralysin (ec 3.4.24.40) | Extracellular |
| | | RXF04495.2 | | Serralysin (ec 3.4.24.40) | Extracellular |
| | | RXF02796.1 | | Serralysin (ec 3.4.24.40) | Extracellular |
| | M14 (carboxypeptidase A family) | RXF09091.1 | | Zinc-carboxypeptidase precursor (ec 3.4.17.—) | Cytoplasmic |
| | M16 (pitrilysin family) | RXF03441.1 | | Coenzyme pqq synthesis protein F (ec 3.4.99.—) | Non-secretory |
| | | RXF01918.1 | | zinc protease (ec 3.4.99.—) | Signal peptide |
| | | RXF01919.1 | | zinc protease (ec 3.4.99.—) | Periplasmic |
| | | RXF03699.2 | | processing peptidase (ec 3.4.24.64) | Signal peptide |

TABLE 2-continued

*P. fluorescens* strain MB214 proteases

| | Family | ORF ID | Gene | Function | Location |
|---|---|---|---|---|---|
| | M17 (leucyl aminopeptidase family) | RXF00285.2 | | Cytosol aminopeptidase (ec 3.4.11.1) | Non-secretory |
| | M18 | RXF07879.1 | | Aspartyl aminopeptidase (ec 3.4.11.21) | Cytoplasmic |
| | M20 | RXF00811.1 | dapE | Succinyl-diaminopimelate desuccinylase (ec 3.5.1.18) | Cytoplasmic |
| | | RXF04052.2 | | Xaa-His dipeptidase (ec 3.4.13.3) | Signal peptide |
| | | RXF01822.2 | | Carboxypeptidase G2 precursor (ec 3.4.17.11) | Signal peptide |
| | | RXF09831.2:: RXF04892.1 | | N-acyl-L-amino acid amidohydrolase (ec 3.5.1.14) | Signal peptide |
| | M28 (aminopeptidase Y family) | RXF03488.2 | | Alkaline phosphatase isozyme conversion protein precursor (ec 3.4.11.—) | OuterMembrane |
| | M42 (glutamyl aminopeptidase family) | RXF05615.1 | | Deblocking aminopeptidase (ec 3.4.11.—) | Non-secretory |
| | M22 | RXF05817.1 | | O-sialoglycoprotein endopeptidase (ec 3.4.24.57) | Extracellular |
| | | RXF03065.2 | | Glycoprotease protein family | Non-secretory |
| | M23 | RXF01291.2 | | Cell wall endopeptidase, family M23/M37 | Signal peptide |
| | | RXF03916.1 | | Membrane proteins related to metalloendopeptidases | Signal peptide |
| | | RXF09147.2 | | Cell wall endopeptidase, family M23/M37 | Signal peptide |
| | M24 | RXF04693.1 | | Methionine aminopeptidase (ec 3.4.11.18) | Cytoplasmic |
| | | RXF03364.1 | | Methionine aminopeptidase (ec 3.4.11.18) | Non-secretory |
| | | RXF02980.1 | | Xaa-Pro aminopeptidase (ec 3.4.11.9) | Cytoplasmic |
| | | RXF06564.1 | | Xaa-Pro aminopeptidase (ec 3.4.11.9) | Cytoplasmic |
| | M48 (Ste24 endopeptidase family) | RXF05137.1 | | Heat shock protein HtpX | Cytoplasmic Membrane |
| | | RXF05081.1 | | Zinc metalloprotease (ec 3.4.24.—) | Signal peptide |
| | M50 (S2P protease family) | RXF04692.1 | | Membrane metalloprotease | Cytoplasmic Membrane |
| Serine Peptidases | S1 (chymotrypsin family) | RXF01250.2 | | protease do (ec 3.4.21.—) | Periplasmic |
| | | RXF07210.1 | | protease do (ec 3.4.21.—) | Periplasmic |
| | S8 (subtilisin family) | RXF06755.2 | | serine protease (ec 3.4.21.—) | Non-secretory |
| | | RXF08517.1 | | serine protease (ec 3.4.21.—) | Extracellular |
| | | RXF08627.2 | | extracellular serine protease (ec 3.4.21.—) | Signal peptide |
| | | RXF06281.1 | | Extracellular serine protease precursor (ec 3.4.21.—) | Non-secretory |
| | | RXF08978.1 | | extracellular serine protease (ec 3.4.21.—) | OuterMembrane |
| | | RXF06451.1 | | serine protease (ec 3.4.21.—) | Signal peptide |
| | S9 (prolyl oligopeptidase family) | RXF02003.2 | | Protease ii (ec 3.4.21.83) | Periplasmic |
| | | RXF00458.2 | | Hydrolase | Non-secretory |
| | S11 (D-Ala-D-Ala carboxypeptidase A family) | RXF04657.2 | | D-alanyl-D-alanine-endopeptidase (ec 3.4.99.—) | Periplasmic |
| | | RXF00670.1 | | D-alanyl-D-alanine carboxypeptidase (ec 3.4.16.4) | Cytoplasmic Membrane |
| | S13 (D-Ala-D-Ala peptidase C family) | RXF00133.1 | | D-alanyl-meso-diaminopimelate endopeptidase (ec 3.4.—.—) | OuterMembrane |
| | | RXF04960.2 | | D-alanyl-meso-diaminopimelate endopeptidase (ec 3.4.—.—) | Signal peptide |
| | S14 (ClpP endopeptidase family) | RXF04567.1 | clpP | atp-dependent Clp protease proteolytic subunit (ec 3.4.21.92) | Non-secretory |
| | | RXF04663.1 | clpP | atp-dependent Clp protease proteolytic subunit (ec 3.4.21.92) | Cytoplasmic |
| | S16 (Ion protease family) | RXF04653.2 | | atp-dependent protease La (ec 3.4.21.53) | Cytoplasmic |
| | | RXF08653.1 | | atp-dependent protease La (ec 3.4.21.53) | Cytoplasmic |
| | | RXF05943.1 | | atp-dependent protease La (ec 3.4.21.53) | Cytoplasmic |
| | S24 (LexA family) | RXF00449.1 | | LexA repressor (ec 3.4.21.88) | Non-secretory |
| | | RXF03397.1 | | LexA repressor (ec 3.4.21.88) | Cytoplasmic |
| | S26 (signal peptidase I family) | RXF01181.1 | | Signal peptidase I (ec 3.4.21.89) | Cytoplasmic Membrane |

TABLE 2-continued

| *P. fluorescens* strain MB214 proteases | | | | | |
|---|---|---|---|---|---|
| | Family | ORF ID | Gene | Function | Location |
| | S33 | RXF05236.1 | pip3 | Proline iminopeptidase (ec 3.4.11.5) | Non-secretory |
| | | RXF04802.1 | pip1 | Proline iminopeptidase (ec 3.4.11.5) | Non-secretory |
| | | RXF04808.2 | pip2 | Proline iminopeptidase (ec 3.4.11.5) | Cytoplasmic |
| | S41 (C-terminal processing peptidase family) | RXF06586.1 | | Tail-specific protease (ec 3.4.21.—) | Signal peptide |
| | | RXF01037.1 | | Tail-specific protease (ec 3.4.21.—) | Signal peptide |
| | S45 | RXF07170.1 | pacB2 | Penicillin acylase (ec 3.5.1.11) | Signal peptide |
| | | RXF06399.2 | pacB1 | Penicillin acylase ii (ec 3.5.1.11) | Signal peptide |
| | S49 (protease IV family) | RXF06993.2 | | possible protease sohb (ec 3.4.—.—) | Non-secretory |
| | | RXF01418.1 | | protease iv (ec 3.4.—.—) | Non-secretory |
| | S58 (DmpA aminopeptidase family) | RXF06308.2 | | D-aminopeptidase (ec 3.4.11.19) | Cytoplasmic Membrane |
| Threonine Peptidases | T1 (proteasome family) | RXF01961.2 | hslV | atp-dependent protease hslV (ec 3.4.25.—) | Cytoplasmic |
| | T3 (gamma-glutamyltransferase family) | RXF02342.1 | ggt1 | Gamma-glutamyltranspeptidase (ec 2.3.2.2) | Periplasmic |
| | | RXF04424.2 | ggt2 | Gamma-glutamyltranspeptidase (ec 2.3.2.2) | Periplasmic |
| Unclassified Peptidases | U32 | RXF00428.1 | | protease (ec 3.4.—.—) | Cytoplasmic |
| | | RXF02151.2 | | protease (ec 3.4.—.—) | Cytoplasmic |
| | U61 | RXF04715.1 | | Muramoyltetrapeptide carboxypeptidase (ec 3.4.17.13) | Non-secretory |
| | U62 | RXF04971.2 | pmbA | PmbA protein | Cytoplasmic |
| | | RXF04968.2 | | TldD protein | Cytoplasmic |
| Non MEROPS Proteases | | RXF00325.1 | | Repressor protein C2 | Non-secretory |
| | | RXF02689.2 | | Microsomal dipeptidase (ec 3.4.13.19) | Cytoplasmic |
| | | RXF02739.1 | | membrane dipeptidase (3.4.13.19) | Signal peptide |
| | | RXF03329.2 | | Hypothetical Cytosolic Protein | Cytoplasmic |
| | | RXF02492.1 | | Xaa-Pro dipeptidase (ec 3.4.13.9) | Cytoplasmic |
| | | RXF04047.2 | | caax amino terminal protease family | Cytoplasmic Membrane |
| | | RXF08136.2 | | protease (transglutaminase-like protein) | Cytoplasmic |
| | | RXF09487.1 | | Zinc metalloprotease (ec 3.4.24.—) | Non-secretory |

Additional Protein Modification Enzymes

In another embodiment, the target gene comprises a gene involved in proper protein processing and/or modification. Common modifications include disulfide bond formation, glycosylation, acetylation, acylation, phosphorylation, and gamma-carboxylation, all of which can regulate protein folding and biological activity. A non-exhaustive list of several classes of enzymes involved in protein processing is found in Table 3. One of skill in the art will recognize how to identify a target gene useful in the host cell chosen for the array, or useful with the heterologous protein of interest, from among the classes of protein modification enzymes listed in Table 3. The target gene may be endogenous to the host cell utilized, may be endogenous to the organism from which the heterologous protein of interest is derived, or may be known to facilitate proper processing of a heterologously expressed protein of interest. It is also recognized that any gene involved in protein production can be targeted according to desired specifications for the heterologous protein of interest.

In embodiments, a target gene is a tmRNA tag-coding region. tmRNAs can add tags to proteins to target for degradation by a process called trans-translation as described, e.g. by Dulebohn, D., 2007 "Trans-Translation: The tmRNA-Mediated Surveillance Mechanism for Ribosome Rescue, Directed Protein Degradation, and Nonstop mRNA Decay", incorporated herein by reference. An exemplary tmRNA sequence is provided as XFRNA203 (SEQ ID NO:157). The sequence of the molecule is shown below, with the tag coding sequence underlined and the TAA stop codon in bold. Deletion or mutation of tmRNA sequences can result in improved heterologous protein yield.

5'-GGGGCCGTTTAGGATTCGACGCCGGTCGCGAAACTTTAGGTGCATGC

CGAGTTGGTAACAGAACTCGTAAATCCACTGTTGCAACTTCTTATAGTTG

CCAATGACGAAAACTACGGCCAGGAATTCGCTCTCGCTGCGTAAGCAGCC

TTAGCCCTGAGCTTCTGGTACCTTCGGGTCCAGCAATCACCAGGGGATGT

CTGTAAACCCAAAGTGATTGTCATATAGAACAGAATCGCCGTGCAGTACG

TTGTGGACGAAGCGGCTAAAACTTACACAACTCGCCCAAAGCACCCTGCC

CTTCGGGTCGCTGAGGGTTAACTTAATAGAAACGGCTACGCATGTAGTAC

CGACAGCGGAGTACTGGCGGACGGGGGTTCAAATCCCCCCGGCTCCACCA

C-3'

TABLE 3

| Classes of enzymes involved in protein processing | |
|---|---|
| Class | Examples |
| Glycosyltransferases (EC 2.4.1.18) | α-glucan-branching glycosyltransferase<br>enzymatic branching factor<br>branching glycosyltransferase<br>enzyme Q<br>glucosan transglycosylase<br>glycogen branching enzyme<br>amylose isomerase<br>plant branching enzyme<br>α-1,4-glucan:α-1,4-glucan-6-glycosyltransferase<br>starch branching enzyme<br>UDP-N-acetyl-D-galactosamine:polypeptide N-acetylgalactosaminyltransferase<br>GDP-fucose protein O-fucosyltransferase 2<br>O-GlcNAc transferase |
| Histone acetyltransferase (EC 2.3.1.48) | nucleosome-histone acetyltransferase<br>histone acetokinase<br>histone acetylase<br>histone transacetylase<br>histone deacetylase |
| Protein kinase (EC 2.7) | non-specific serine/threonine protein kinase<br>Fas-activated serine/threonine kinase<br>Goodpasture antigen-binding protein kinase<br>IκB kinase<br>cAMP-dependent protein kinase<br>cGMP-dependent protein kinase<br>protein kinase C<br>polo kinase<br>cyclin-dependent kinase<br>mitogen-activated protein kinase<br>mitogen-activated protein kinase kinase kinase<br>receptor protein serine/threonine kinase<br>dual-specificity kinase |
| Phosphatase (EC 3.1.3.48) | protein-tyrosine-phosphatase<br>phosphotyrosine phosphatase<br>phosphoprotein phosphatase (phosphotyrosine)<br>phosphotyrosine histone phosphatase<br>protein phosphotyrosine phosphatase<br>tyrosylprotein phosphatase<br>phosphotyrosine protein phosphatase<br>phosphotyrosylprotein phosphatase<br>tyrosine O-phosphate phosphatase<br>PPT-phosphatase<br>PTPase<br>[phosphotyrosine]protein phosphatase<br>PTP-phosphatase |

Methods for Modulating the Expression of Target Genes

One or more host cell populations of the array can be modified by any technique known in the art, for example by a technique wherein at least one target gene is knocked out of the genome, or by mutating at least one target gene to reduce expression of the gene, by altering at least one promoter of at least one target gene to reduce expression of the target gene, or by coexpressing (with the heterologous protein or polypeptide of interest) the target gene or an inhibitor of the target gene in the host genome. As discussed supra, the target gene can be endogenous to the host cell populations in the array, or can be heterologously expressed in each of the host cell populations.

The expression of target genes can be increased, for example, by introducing into at least one cell in a host population an expression vector comprising one or more target genes involved in protein production. The target gene expression can also be increased, for example, by mutating a promoter of a target gene. A host cell or organism that expresses a heterologous protein can also be genetically modified to increase the expression of at least one target gene involved in protein production and decrease the expression of at least one target gene involved in protein degradation.

The genome may be modified to modulate the expression of one or more target genes by including an exogenous gene or promoter element in the genome or in the host with an expression vector, by enhancing the capacity of a particular target gene to produce mRNA or protein, by deleting or disrupting a target gene or promoter element, or by reducing the capacity of a target gene to produce mRNA or protein. The genetic code can be altered, thereby affecting transcription and/or translation of a target gene, for example through substitution, deletion ("knock-out"), co-expression, or insertion ("knock-in") techniques. Additional genes for a desired protein or regulatory sequence that modulate transcription of an existing target sequence can also be inserted.

Genome Modification

The genome of the host cell can be modified via a genetic targeting event, which can be by insertion or recombination, for example homologous recombination. Homologous recombination refers to the process of DNA recombination based on sequence homology. Homologous recombination permits site-specific modifications in endogenous genes and thus novel alterations can be engineered into a genome (see, for example Radding (1982) *Ann. Rev. Genet.* 16: 405; U.S. Pat. No. 4,888,274).

Various constructs can be prepared for homologous recombination at a target locus. Usually, the construct can include at least 10 bp, 20 bp, 30 bp, 40 bp, 50 bp, 70 bp, 100 bp, 500 bp, 1 kbp, 2 kbp, 4 kbp, 5 kbp, 10 kbp, 15 kbp, 20 kbp, or 50 kbp of sequence homologous with the identified locus. Various considerations can be involved in determining the extent of homology of target gene sequences, such as, for example, the size of the target locus, availability of sequences, relative efficiency of double cross-over events at the target locus and the similarity of the target sequence with other sequences.

The modified gene can include a sequence in which DNA substantially isogenic flanks the desired sequence modifications with a corresponding target sequence in the genome to be modified. The "modified gene" is the sequence being introduced into the genome to alter the expression of a protease or a protein folding modulator in the host cell. The "target gene" is the sequence that is being replaced by the modified gene. The substantially isogenic sequence can be at least about 95%, 97-98%, 99.0-99.5%, 99.6-99.9%, or 100% identical to the corresponding target sequence (except for the desired sequence modifications). The modified gene and the targeted gene can share stretches of DNA at least about 10, 20, 30, 50, 75, 150 or 500 base pairs that are 100% identical.

Nucleotide constructs can be designed to modify the endogenous, target gene product. The modified gene sequence can have one or more deletions, insertions, substitutions or combinations thereof designed to disrupt the function of the resultant gene product. In one embodiment, the alteration can be the insertion of a selectable marker gene fused in reading frame with the upstream sequence of the target gene.

The genome can also be modified using insertional inactivation. In this embodiment, the genome is modified by recombining a sequence in the gene that inhibits gene product formation. This insertion can either disrupt the gene by inserting a separate element, or remove an essential portion of the gene. In one embodiment, the insertional deletion also includes insertion of a gene coding for resistance to a particular stressor, such as an antibiotic, or for growth in a particular media, for example for production of an essential amino acid.

The genome can also be modified by use of transposons, which are genetic elements capable of inserting at sites in prokaryote genomes by mechanisms independent of homologous recombination. Transposons can include, for example, Tn7, Tn5, or Tn10 in *E. coli*, Tn554 in *S. aureus*, IS900 in *M. paratuberculosis*, IS492 from *Pseudomonas atlantica*, IS116 from *Streptomyces* and IS900 from *M. paratuberculosis*. Steps believed to be involved in transposition include cleavage of the end of the transposon to yield 3'OH; strand transfer, in which transposase brings together the 3'OH exposed end of transposon and the identified sequence; and a single step transesterification reaction to yield a covalent linkage of the transposon to the identified DNA. The key reaction performed by transposase is generally thought to be nicking or strand exchange, the rest of the process is done by host enzymes.

In one embodiment, the expression or activity of a target gene or protein is increased by incorporating a genetic sequence encoding the target protein or homolog thereof into the genome by recombination. In another embodiment, a promoter is inserted into the genome to enhance the expression of the target gene or homolog. In another embodiment, the expression or activity of a target gene or homolog thereof is decreased by recombination with an inactive gene. In another embodiment, a sequence that encodes a different gene, which can have a separate function in the cell or can be a reporter gene such as a resistance marker or an otherwise detectable marker gene, can be inserted into the genome through recombination. In yet another embodiment, a copy of at least a portion of the target gene that has been mutated at one or more locations is inserted into the genome through recombination. The mutated version of the target gene may not encode a protein, or the protein encoded by the mutated gene may be rendered inactive, the activity may be modulated (either increased or decreased), or the mutant protein can have a different activity when compared to the native protein.

There are strategies to knock out genes in bacteria, which have been generally exemplified in *E. coli*. One route is to clone a gene-internal DNA fragment into a vector containing an antibiotic resistance gene (e.g. ampicillin). Before cells are transformed via conjugative transfer, chemical transformation or electroporation (Puehler, et al. (1984) Advanced Molecular Genetics New York, Heidelberg, Berlin, Tokyo, Springer Verlag), an origin of replication, such as the vegetative plasmid replication (the oriV locus) is excised and the remaining DNA fragment is re-ligated and purified (Sambrook, et al. (2000) Molecular cloning: A laboratory manual, third edition Cold Spring Harbor, N.Y., Cold Spring Harbor Laboratory Press). Alternatively, antibiotic-resistant plasmids that have a DNA replication origin can be used. After transformation, the cells are plated onto e.g. LB agar plates containing the appropriate antibiotics (e.g. 200 micrograms/mL ampicillin). Colonies that grow on the plates containing the antibiotics presumably have undergone a single recombination event (Snyder, L., W. Champness, et al. (1997) Molecular Genetics of Bacteria Washington D.C., ASM Press) that leads to the integration of the entire DNA fragment into the genome at the homologous locus. Further analysis of the antibiotic-resistant cells to verify that the desired gene knock-out has occurred at the desired locus is e.g. by diagnostic PCR (McPherson, M. J., P. Quirke, et al. (1991) PCR: A Practical Approach New York, Oxford University Press). Here, at least two PCR primers are designed: one that hybridizes outside the DNA region that was used for the construction of the gene knock-out; and one that hybridizes within the remaining plasmid backbone. Successful PCR amplification of the DNA fragment with the correct size followed by DNA sequence analysis will verify that the gene knock-out has occurred at the correct location in the bacterial chromosome. The phenotype of the newly constructed mutant strain can then be analyzed by, e.g., SDS polyacrylamide gel electrophoresis (Simpson, R. J. (2003) Proteins and Proteomics—A Laboratory Manual. Cold Spring Harbor, N.Y., Cold Spring Harbor Laboratory Press).

An alternate route to generate a gene knock-out is by use of a temperature-sensitive replicon, such as the pSC101 replicon to facilitate gene replacement (Hamilton, et al. (1989) *Journal of Bacteriology* 171(9): 4617-22). The process proceeds by homologous recombination between a gene on a chromosome and homologous sequences carried on a plasmid temperature sensitive for DNA replication. After transformation of the plasmid into the appropriate host, it is possible to select for integration of the plasmid into the chromosome at 44° C. Subsequent growth of these cointegrates at 30° C. leads to a second recombination event, resulting in their resolution. Depending on where the second recombination event takes place, the chromosome will either have undergone a gene replacement or retain the original copy of the gene.

Other strategies have been developed to inhibit expression of particular gene products. For example, RNA interference (RNAi), particularly using small interfering RNA (siRNA), has been extensively developed to reduce or even eliminate expression of a particular gene product. siRNAs are short, double-stranded RNA molecules that can target complementary mRNAs for degradation. RNAi is the phenomenon in which introduction of a double-stranded RNA suppresses the expression of the homologous gene. dsRNA molecules are reduced in vivo to 21-23 nt siRNAs which are the mediators of the RNAi effect. Upon introduction, double stranded RNAs get processed into 20-25 nucleotide siRNAs by an RNase III-like enzyme called Dicer (initiation step). Then, the siRNAs assemble into endoribonuclease-containing complexes known as RNA-induced silencing complexes (RISCs), unwinding in the process. The siRNA strands subsequently guide the RISCs to complementary RNA molecules, where they cleave and destroy the cognate RNA (effecter step). Cleavage of cognate RNA takes place near the middle of the region bound by the siRNA strand. RNAi has been successfully used to reduce gene expression in a variety of organisms including zebrafish, nematodes (*C. elegans*), insects (*Drosophila melanogaster*), planaria, cnidaria, trypanosomes, mice and mammalian cells.

The genome can also be modified by mutation of one or more nucleotides in an open reading frame encoding a target gene. Techniques for genetic mutation, for instance site directed mutagenesis, are well known in the art. Some approaches focus on the generation of random mutations in chromosomal DNA such as those induced by X-rays and chemicals.

Coexpression

In one embodiment, one or more target genes in the host cell can be modified by including one or more vectors that encode the target gene(s) to facilitate coexpression of the target gene with the heterologous protein or peptide. In another embodiment, the host cell is modified by enhancing a promoter for a target gene, including by adding an exogenous promoter to the host cell genome.

In another embodiment, one or more target genes in the host cell is modified by including one or more vectors that encode an inhibitor of a target gene, such as a protease inhibitor to inhibit the activity of a target protease. Such an inhibitor can be an antisense molecule that limits the expression of the target gene, a cofactor of the target gene or a homolog of the target gene. Antisense is generally used to refer to a nucleic acid molecule with a sequence complementary to at least a portion of the target gene. In addition, the inhibitor can be an interfering RNA or a gene that encodes an interfering RNA. In Eukaryotic organisms, such an interfering RNA can be a small interfering RNA or a ribozyme, as described, for example, in Fire, A. et al. (1998) Nature 391:806-11, Elbashir et al. (2001) Genes & Development 15(2):188-200, Elbashir et al. (2001) *Nature* 411 (6836):494-8, U.S. Pat. No. 6,506,559 to Carnegie Institute, U.S. Pat. No. 6,573,099 to Benitec, U.S. patent application Nos. 2003/0108923 to the Whitehead Inst., and 2003/0114409, PCT Publication Nos. WO03/006477, WO03/012052, WO03/023015, WO03/056022, WO03/064621 and WO03/070966.

The inhibitor can also be another protein or peptide. The inhibitor can, for example, be a peptide with a consensus sequence for the target protein. The inhibitor can also be a protein or peptide that can produce a direct or indirect inhibitory molecule for the target protein in the host. For example, protease inhibitors can include Amastatin, E-64, Antipain, Elastatinal, APMSF, Leupeptin, Bestatin, Pepstatin, Benzamidine, 1,10-Phenanthroline, Chymostatin, Phosphoramidon, 3,4-dichloroisocoumarin, TLCK, DFP, TPCK. Over 100 naturally occurring protein protease inhibitors have been identified so far. They have been isolated in a variety of organisms from bacteria to animals and plants. They behave as tight-binding reversible or pseudo-irreversible inhibitors of proteases preventing substrate access to the active site through steric hindrance. Their size are also extremely variable from 50 residues (e.g BPTI: Bovine Pancreatic Trypsin Inhibitor) to up to 400 residues (e.g alpha-1PI: alpha-1 Proteinase Inhibitor). They are strictly class-specific except proteins of the alpha-macroglobulin family (e.g alpha-2 macroglobulin) which bind and inhibit most proteases through a molecular trap mechanism.

An exogenous vector or DNA construct can be transfected or transformed into the host cell. Techniques for transfecting and transforming eukaryotic and prokaryotic cells respectively with exogenous nucleic acids are well known in the art. These can include lipid vesicle mediated uptake, calcium phosphate mediated transfection (calcium phosphate/DNA co-precipitation), viral infection, particularly using modified viruses such as, for example, modified adenoviruses, microinjection and electroporation. For prokaryotic transformation, techniques can include heat shock mediated uptake, bacterial protoplast fusion with intact cells, microinjection and electroporation. Techniques for plant transformation include *Agrobacterium* mediated transfer, such as by *A. tumefaciens*, rapidly propelled tungsten or gold microprojectiles, electroporation, microinjection and polyethelyne glycol mediated uptake. The DNA can be single or double stranded, linear or circular, relaxed or supercoiled DNA. For various techniques for transfecting mammalian cells, see, for example, Keown et al. (1990) Processes in Enzymology Vol. 185, pp. 527-537.

An expression construct encoding a target gene or an enhancer or inhibitor thereof can be constructed as described below for the expression constructs comprising the heterologous protein or polypeptide of interest. For example, the constructs can contain one, or more than one, internal ribosome entry site (IRES). The construct can also contain a promoter operably linked to the nucleic acid sequence encoding at least a portion of the target gene, or a cofactor of the target gene, a mutant version of at least a portion of the target gene, or in some embodiments, an inhibitor of the target gene. Alternatively, the construct can be promoterless. In cases in which the construct is not designed to incorporate into the cellular DNA/genome, the vector typically contains at least one promoter element. In addition to the nucleic acid sequences, the expression vector can contain selectable marker sequences. The expression constructs can further contain sites for transcription initiation, termination, and/or ribosome binding sites. The identified constructs can be inserted into and can be expressed in any prokaryotic or eukaryotic cell, including, but not limited to bacterial cells, such as *P. fluorescens* or *E. coli*, yeast cells, mammalian cells, such as CHO cells, or plant cells.

The construct can be prepared in accordance with processes known in the art. Various fragments can be assembled, introduced into appropriate vectors, cloned, analyzed and then manipulated further until the desired construct has been achieved. Various modifications can be made to the sequence, to allow for restriction analysis, excision, identification of probes, etc. Silent mutations can be introduced, as desired. At various stages, restriction analysis, sequencing, amplification with the polymerase chain reaction, primer repair, in vitro mutagenesis, etc. can be employed. Processes for the incorporation of antibiotic resistance genes and negative selection factors will be familiar to those of ordinary skill in the art (see, e.g., WO 99/15650; U.S. Pat. No. 6,080,576; U.S. Pat. No. 6,136,566;

Niwa, et al., J. Biochem. 113:343-349 (1993); and Yoshida, et al., Transgenic Research, 4:277-287 (1995)).

The construct can be prepared using a bacterial vector, including a prokaryotic replication system, e.g. an origin recognizable by a prokaryotic cell such as *P. fluorescens* or *E. coli*. A marker, the same as or different from the marker to be used for insertion, can be employed, which can be removed prior to introduction into the host cell. Once the vector containing the construct has been completed, it can be further manipulated, such as by deletion of certain sequences, linearization, or by introducing mutations, deletions or other sequences into the homologous sequence. In one embodiment, the target gene construct and the heterologous protein construct are part of the same expression vector, and may or may not be under the control of the same promoter element. In another embodiment, they are on separate expression vectors. After final manipulation, the construct can be introduced into the cell.

Cell Growth Conditions

The cell growth conditions for the host cells described herein include that which facilitates expression of the protein of interest in at least one strain in the array (or at least a proportion of cells thereof), and/or that which facilitates fermentation of the expressed protein of interest. As used herein, the term "fermentation" includes both embodiments in which literal fermentation is employed and embodiments in which other, non-fermentative culture modes are employed. Growth, maintenance, and/or fermentation of the populations of host cells in the array may be performed at any scale. However, where multiple populations of host cells are screened simultaneously, the scale will be limited by the number of different populations and the capacity to grow and test multiple populations of host cells. In one embodiment, the fermentation medium may be selected from among rich media, minimal media, and mineral salts media. In another embodiment either a minimal medium or a mineral salts medium is selected. In still another embodiment, a minimal medium is selected. In yet another embodiment, a mineral salts medium is selected.

Mineral salts media consists of mineral salts and a carbon source such as, e.g., glucose, sucrose, or glycerol. Examples of mineral salts media include, e.g., M9 medium, *Pseudomonas* medium (ATCC 179), Davis and Mingioli medium (see, B D Davis & E S Mingioli (1950) in *J. Bact.* 60:17-28). The mineral salts used to make mineral salts media include those selected from among, e.g., potassium phosphates, ammonium sulfate or chloride, magnesium sulfate or chloride, and trace minerals such as calcium chloride, borate, and sulfates of iron, copper, manganese, and zinc. No organic nitrogen source, such as peptone, tryptone, amino acids, or a yeast extract, is included in a mineral salts medium. Instead, an inorganic nitrogen source is used and this may be selected from among, e.g., ammonium salts, aqueous ammonia, and gaseous ammonia. A preferred mineral salts medium will contain glucose as the carbon source. In comparison to mineral salts media, minimal media can also contain mineral salts and a carbon source, but can be supplemented with, e.g., low levels of amino acids, vitamins, peptones, or other ingredients, though these are added at very minimal levels.

In one embodiment, media can be prepared using the components listed in Table 4 below. The components can be added in the following order: first $(NH_4)HPO_4$, $KH_2PO_4$ and citric acid can be dissolved in approximately 30 liters of distilled water; then a solution of trace elements can be added, followed by the addition of an antifoam agent, such as Ucolub N 115. Then, after heat sterilization (such as at approximately 121° C.), sterile solutions of glucose $MgSO_4$ and thiamine-HCL can be added. Control of pH at approximately 6.8 can be achieved using aqueous ammonia. Sterile distilled water can then be added to adjust the initial volume to 371 minus the glycerol stock (123 mL). The chemicals are commercially available from various suppliers, such as Merck.

TABLE 4

| Medium composition | |
|---|---|
| Component | Initial concentration |
| $KH_2PO_4$ | 13.3 g $l^{-1}$ |
| $(NH_4)_2HPO_4$ | 4.0 g $l^{-1}$ |
| Citric Acid | 1.7 g $l^{-1}$ |
| $MgSO_4$—$7H_2O$ | 1.2 g $l^{-1}$ |
| Trace metal solution | 10 ml $l^{-1}$ |
| Thiamin HCl | 4.5 mg $l^{-1}$ |
| Glucose-$H_2O$ | 27.3 g $l^{-1}$ |
| Antifoam Ucolub N115 | 0.1 ml $l^{-1}$ |
| Feeding solution | |
| $MgSO_4$—$7H_2O$ | 19.7 g $l^{-1}$ |
| Glucose-$H_2O$ | 770 g $l^{-1}$ |
| $NH_3$ | 23 g |
| Trace metal solution | |
| 6 g $l^{-1}$ Fe(III) citrate 1.5 g $l^{-1}$ $MnCl_2$—$4H_2O$ 0.8 g $l^{-1}$ $ZmCH_2COOl_2$—$2H_2O$ 0.3 g $l^{-1}$ $H_3BO_3$ 0.25 g $l^{-1}$ $Na_2MoO_4$—$2H_2O$ 0.25 g $l^{-1}$ $CoCl_26H_2O$ 0.15 g $l^{-1}$ $CuCl_22H_2O$ 0.84 g $l^{-1}$ ethylene Dinitrilo-tetracetic acid $Na_2$ sah $2H_2O$ (Tritriplex III, Merck) | |

In the present invention, growth, culturing, and/or fermentation of the transformed host cells is performed within a temperature range permitting survival of the host cells, preferably a temperature within the range of about 4° C. to about 55° C., inclusive. Thus, e.g., the terms "growth" (and "grow," "growing"), "culturing" (and "culture"), and "fermentation" (and "ferment," "fermenting"), as used herein in regard to the host cells of the present invention, inherently means "growth," "culturing," and "fermentation," within a temperature range of about 4° C. to about 55° C., inclusive. In addition, "growth" is used to indicate both biological states of active cell division and/or enlargement, as well as biological states in which a non-dividing and/or non-enlarging cell is being metabolically sustained, the latter use of the term "growth" being synonymous with the term "maintenance."

The host cells of the array should be grown and maintained at a suitable temperature for normal growth of that cell type. Such normal growth temperatures may be readily selected based on the known growth requirements of the selected host cell. Preferably, during the establishment of the culture and particularly during course of the screening, the cell culture is incubated in a controlled $CO_2/N_2$ humidity suitable for growth of the selected cells before and after transformation with the heterologous protein or polypeptide of interest. The humidity of the incubation is controlled to minimize evaporation from the culture vessel, and permit the use of smaller volumes. Alternatively, or in addition to controlling humidity, the vessels may be covered with lids in order to minimize evaporation. Selection of the incubation temperature depends primarily upon the identity of the host cells utilized. Selection of the percent humidity to control evaporation is based upon the selected volume of the vessel and concentration and volume of the cell culture in the vessel, as well as upon the incubation temperature. Thus, the humidity may vary from about 10% to about 80%. It should be understood that selection of a suitable conditions is well within the skill of the art.

Screening

The strain array described herein can be screened for the optimal host cell population in which to express a heterologous protein of interest. The optimal host cell population can be identified or selected based on the quantity, quality, and/or location of the expressed protein of interest. In one embodiment, the optimal host cell population is one that results in an increased yield of the protein or polypeptide of interest within the host cell compared to other populations of phenotypically distinct host cells in the array, e.g., an indicator expression system.

An indicator expression system is any heterologous protein expression system that is used for comparison of protein expression. An indicator expression system can be a) a second test expression system present in the same array or b) a standard expression system. A second test expression system refers to any test expression system on the array that is different from the expression system on the array that is being compared to the indicator expression system. A standard expression system is a heterologous protein expression system used as a standard, for example, one comprising a host from which the test expression system for comparison was derived, the host transformed with a heterologous protein expression vector that does not contain a secretion leader. In other embodiments the vector is the same as that used in the test expression system. A standard expression system for use in a *Pseudomonas* expression array of the invention, can be, e.g., a DC454 expression system. A DC454 expression system refers to a DC454 host transformed with an expression vector encoding the heterologous protein. In other embodiments, the standard expression system contains expression elements (e.g., protease mutations, folding modulator overexpression constructs, secretion leaders) not present in a wild type expression system, but fewer or different expression elements than does the test expression system that is being compared. A standard expression system for use in an *E. coli* expression array of the invention can be, e.g., BL21(DE3), or any other appropriate strain selected by one of skill in the art for the experiment at hand. A null strain refers to a wild type host cell population transformed with a vector that does not express the heterologous protein.

The increased production alternatively can be an increased level of properly processed protein or polypeptide per gram of protein produced, or per gram of host protein. The increased production can also be an increased level of recoverable protein or polypeptide produced per gram of heterologous protein or per gram of host cell protein. The increased production can also be any combination of an increased level of total protein, increased level of properly processed or properly folded protein, or increased level of active or soluble protein. In this embodiment, the term "increased" or "improved" is relative to the level of protein or polypeptide that is produced, properly processed, soluble, and/or recoverable when the protein or polypeptide of interest is expressed in one or more other populations of host cells in the array. The increased production may optimize the efficiency of the cell or organism by for example, decreasing the energy expenditure, increasing the use of available resources, or decreasing the requirements for growth supplements in growth media. The increased production may also be the result of a decrease in proteolyic degradation of the expressed protein.

In one embodiment, at least one strain in the array produces at least 0.1 mg/ml correctly processed protein. A correctly processed protein has an amino terminus of the native protein. In another embodiment, at least one strain produces 0.1 to 10 mg/ml correctly processed protein in the cell, including at least about 0.2, about 0.3, about 0.4, about 0.5, about 0.6, about 0.7, about 0.8, about 0.9 or at least about 1.0 mg/ml correctly processed protein. In another embodiment, the total correctly processed protein or polypeptide of interest produced by at least one strain in the array is at least 1.0 mg/ml, at least about 2 mg/ml, at least about 3 mg/ml, about 4 mg/ml, about 5 mg/ml, about 6 mg/ml, about 7 mg/ml, about 8 mg/ml, about 10 mg/ml, about 15 mg/ml, about 20 mg/ml, about 25 mg/ml, about 30 mg/ml, about 35 mg/ml, about 40 mg/ml, about 45 mg/ml, at least about 50 mg/ml, or greater. In some embodiments, the amount of correctly processed protein produced is at least about 5%, about 10%, about 15%, about 20%, about 25%, about 30%, about 40%, about 50%, about 60%, about 70%, about 80%, about 90%, about 95%, about 96%, about 97%, about 98%, at least about 99%, or more of total heterologous protein in a correctly processed form.

An improved expression of a protein or polypeptide of interest can also refer to an increase in the solubility of the protein. The protein or polypeptide of interest can be produced and recovered from the cytoplasm, periplasm or extracellular medium of the host cell. The protein or polypeptide can be insoluble or soluble. The protein or polypeptide can include one or more targeting (e.g., signal or leader) sequences or sequences to assist purification, as discussed supra.

The term "soluble" as used herein means that the protein is not precipitated by centrifugation at between approximately 5,000 and 20,000× gravity when spun for 10-30 minutes in a buffer under physiological conditions. Soluble proteins are not part of an inclusion body or other precipitated mass. Similarly, "insoluble" means that the protein or polypeptide can be precipitated by centrifugation at between 5,000 and 20,000× gravity when spun for 10-30 minutes in a buffer under physiological conditions. Insoluble proteins or polypeptides can be part of an inclusion body or other precipitated mass. Some proteins, e.g., membrane proteins, can fractionate with the insoluble proteins, though they are active. Therefore, it is understood that an insoluble protein is not necessarily inactive. The term "inclusion body" is meant to include any intracellular body contained within a cell wherein an aggregate of proteins or polypeptides has been sequestered.

In another embodiment, the optimal host cell population produces an increased amount of the protein of interest that is transported to the periplasm or secreted into the extracellular space of the host cell. In one embodiment, at least one strain in the array produces at least 0.1 mg/ml protein in the periplasmic compartment. In another embodiment, at least one strain produces 0.1 to 10 mg/ml periplasmic protein in the cell, or at least about 0.2, about 0.3, about 0.4, about 0.5, about 0.6, about 0.7, about 0.8, about 0.9 or at least about 1.0 mg/ml periplasmic protein. In one embodiment, the total protein or polypeptide of interest produced by at least one strain in the array is at least 1.0 mg/ml, at least about 2 mg/ml, at least about 3 mg/ml, about 4 mg/ml, about 5 mg/ml, about 6 mg/ml, about 7 mg/ml, about 8 mg/ml, about 10 mg/ml, about 15 mg/ml, about 20 mg/ml, at least about 25 mg/ml, or greater. In some embodiments, the amount of periplasmic protein produced is at least about 5%, about 10%, about 15%, about 20%, about 25%, about 30%, about 40%, about 50%, about 60%, about 70%, about 80%, about 90%, about 95%, about 96%, about 97%, about 98%, about 99%, or more of total protein or polypeptide of interest produced.

At least one strain in the array of the invention can also lead to increased yield of the protein or polypeptide of interest. In one embodiment, at least one strain produces a protein or polypeptide of interest as at least about 5%, at least about 10%, about 15%, about 20%, about 25%, about 30%, about 40%, about 45%, about 50%, about 55%, about 60%, about 65%, about 70%, about 75%, or greater of total cell protein (tcp). "Percent total cell protein" is the amount of protein or polypeptide in the host cell as a percentage of aggregate cellular protein. Methods for the determination of the percent total cell protein are well known in the art.

In a particular embodiment, at least one host cell population in the array can have a heterologous protein production level of at least 1% tcp and a cell density of at least 40 mg/ml, when grown (i.e. within a temperature range of about 4° C. to about 55° C., including about 10° C., about 15° C., about 20° C., about 25° C., about 30° C., about 35° C., about 40° C., about 45° C., and about 50° C.) in a mineral salts medium. In a particularly preferred embodiment, the expression system will have a protein or polypeptide expression level of at least 5% tcp and a cell density of at least 40 g/L, when grown (i.e. within a temperature range of about 4° C. to about 55° C., inclusive) in a mineral salts medium.

In practice, heterologous proteins targeted to the periplasm are often found in the broth (see European Patent No. EP 0 288 451), possibly because of damage to or an increase in the fluidity of the outer cell membrane. The rate of this "passive" secretion may be increased by using a variety of mechanisms that permeabilize the outer cell membrane, including: colicin (Miksch et al. (1997) *Arch. Microbiol.* 167: 143-150); growth rate (Shokri et al. (2002) *App Miocrobiol Biotechnol* 58:386-392); TolIII overexpression (Wan and Baneyx (1998) *Protein Expression Purif.* 14: 13-22); bacteriocin release protein (Hsiung et al. (1989) *Bio/Technology* 7: 267-71), colicin A lysis protein (Lloubes et al. (1993) *Biochimie* 75: 451-8) mutants that leak periplasmic proteins (Furlong and Sundstrom (1989) Developments in Indus. *Microbio.* 30: 141-8); fusion partners (Jeong and Lee (2002) *Appl. Environ. Microbio.* 68: 4979-4985); or, recovery by osmotic shock (Taguchi et al. (1990) *Biochimica Biophysica Acta* 1049: 278-85). Transport of engineered proteins to the periplasmic space with subsequent localization in the broth has been used to produce properly folded and active proteins in *E. coli* (Wan and Baneyx (1998) *Protein Expression Purif.* 14: 13-22; Simmons et al. (2002) *J. Immun. Meth.* 263: 133-147; Lundell et al. (1990) *J. Indust. Microbio.* 5: 215-27).

The method may also include the step of purifying the protein or polypeptide of interest from the periplasm or from extracellular media. The heterologous protein or polypeptide can be expressed in a manner in which it is linked to a tag protein and the "tagged" protein can be purified from the cell or extracellular media.

In some embodiments, the protein or polypeptide of interest can also be produced by at least one strain in the array in an active form. The term "active" means the presence of biological activity, wherein the biological activity is comparable or substantially corresponds to the biological activity of a corresponding native protein or polypeptide. In the context of proteins this typically means that a polynucleotide or polypeptide comprises a biological function or effect that has at least about 20%, about 50%, preferably at least about 60-80%, and most preferably at least about 90-95% activity compared to the corresponding native protein or polypeptide using standard parameters. However, in some embodiments, it may be desirable to produce a polypeptide that has altered or improved activity compared to the native protein (e.g, one that has altered or improved immunoreactivity, substrate specificity, etc). An altered or improved polypeptide may result from a particular conformation created by one or more of the host cell populations of the array.

The determination of protein or polypeptide activity can be performed utilizing corresponding standard, targeted comparative biological assays for particular proteins or polypeptides which can be used to assess biological activity.

The recovery of active protein or polypeptide of interest may also be improved in the optimal host strain compared to one or more other strains in the array of the invention. Active proteins can have a specific activity of at least about 20%, at least about 30%, at least about 40%, about 50%, about 60%, at least about 70%, about 80%, about 90%, or at least about 95% that of the native protein or polypeptide from which the sequence is derived. Further, the substrate specificity ($k_{cat}/K_m$) is optionally substantially similar to the native protein or polypeptide. Typically, $k_{cat}/K_m$ will be at least about 30%, about 40%, about 50%, about 60%, about 70%, about 80%, at least about 90%, at least about 95%, or greater. Methods of assaying and quantifying measures of protein and polypeptide activity and substrate specificity ($k_{cat}/K_m$), are well known to those of skill in the art.

Measurement of Protein Activity

The activity of the heterologously-expressed protein or polypeptide of interest can be compared with a previously established native protein or polypeptide standard activity. Alternatively, the activity of the protein or polypeptide of interest can be determined in a simultaneous, or substantially simultaneous, comparative assay with the native protein or polypeptide. For example, in vitro assays can be used to determine any detectable interaction between a protein or polypeptide of interest and a target, e.g. between an expressed enzyme and substrate, between expressed hormone and hormone receptor, between expressed antibody and antigen, etc. Such detection can include the measurement of calorimetric changes, proliferation changes, cell death, cell repelling, changes in radioactivity, changes in solubility, changes in molecular weight as measured by gel electrophoresis and/or gel exclusion methods, phosphorylation abilities, antibody specificity assays such as ELISA assays, etc. In addition, in vivo assays include, but are not limited to, assays to detect physiological effects of the heterologously expressed protein or polypeptide in comparison to physiological effects of the native protein or polypeptide, e.g. weight gain, change in electrolyte balance, change in blood clotting time, changes in clot dissolution and the induction of antigenic response. Generally, any in vitro or in vivo assay can be used to determine the active nature of the protein or polypeptide of interest that allows for a comparative analysis to the native protein or polypeptide so long as such activity is assayable. Alternatively, the proteins or polypeptides produced in at least one strain in the array of the present invention can be assayed for the ability to stimulate or inhibit interaction between the protein or polypeptide and a molecule that normally interacts with the protein or polypeptide, e.g. a substrate or a component of a signal pathway with which the native protein normally interacts. Such assays can typically include the steps of combining the protein with a substrate molecule under conditions that allow the protein or polypeptide to interact with the target molecule, and detect the biochemical consequence of the interaction with the protein and the target molecule.

Assays that can be utilized to determine protein or polypeptide activity are described, for example, in Ralph, P. J., et al. (1984) *J. Immunol.* 132:1858 or Saiki et al. (1981) *J. Immunol.* 127:1044, Steward, W. E. II (1980) *The Interferon Systems*. Springer-Verlag, Vienna and New York, Broxmeyer, H. E., et al. (1982) *Blood* 60:595, *Molecular Cloning: A Laboratory Manual"*, 2d ed., Cold Spring Harbor Laboratory Press, Sambrook, J., E. F. Fritsch and T. Maniatis eds., 1989, and *Methods in Enzymology: Guide to Molecular Cloning Techniques*, Academic Press, Berger, S. L. and A. R. Kimmel eds., 1987, A K Patra et al., *Protein Expr Purif,* 18(2): p/182-92 (2000), Kodama et al., *J. Biochem.* 99: 1465-1472 (1986); Stewart et al., *Proc. Nat'l Acad. Sci.* USA 90: 5209-5213 (1993); (Lombillo et al., *J. Cell Biol.* 128:107-115 (1995); (Vale et al., *Cell* 42:39-50 (1985). Activity can be compared between samples of heterologously expressed protein derived from one or more of the other host cell populations in the array, or can be compared to the activity of a native protein, or both. Activity measurements can be performed on isolated protein, or can be performed in vitro in the host cell.

In another embodiment, protein production and/or activity may be monitored directly in the culture by fluorescence or spectroscopic measurements on, for example, a conventional microscope, luminometer, or plate reader. Where the protein of interest is an enzyme whose substrate is known, the substrate can be added to the culture media wherein a fluorescent signal is emitted when the substrate is converted by the enzyme into a product. In one embodiment, the expression construct encoding the heterologous protein or polypeptide of interest further encodes a reported protein. By "reporter protein" is meant a protein that by its presence in or on a cell or when secreted in the media allows the cell to be distinguished from a cell that does not contain the reporter protein. Production of the heterologous protein of interest results in a detectable change in the host cell population. The reporter molecule can be firefly luciferase and GFP or any other fluorescence molecule, as well as beta-galactosidase gene (beta.gal) and chloramphenicol and acetyltransferase gene (CAT). Assays for expression produced in conjunction with each of these reporter gene elements are well-known to those skilled in the art.

The reporter gene can encode a detectable protein or an indirectly detectable protein, or the reporter gene can be a survival gene. In a preferred embodiment, the reporter protein is a detectable protein. A "detectable protein" or "detection protein" (encoded by a detectable or detection gene) is a protein that can be used as a direct label; that is, the protein is detectable (and preferably, a cell comprising the detectable protein is detectable) without further manipulation. Thus, in this embodiment, the protein product of the reporter gene itself can serve to distinguish cells that are expressing the detectable gene. In this embodiment, suitable detectable genes include those encoding autofluorescent proteins.

As is known in the art, there are a variety of autofluorescent proteins known; these generally are based on the green fluorescent protein (GFP) from Aequorea and variants thereof; including, but not limited to, GFP, (Chalfie, et al. (1994) *Science* 263(5148):802-805); enhanced GFP (EGFP; Clontech—Genbank Accession Number U55762)), blue fluorescent protein (BFP; Quantum Biotechnologies, Inc., Montreal, Canada); Stauber (1998) *Biotechniques* 24(3): 462-471; Heim and Tsien (1996) *Curr. Biol.* 6:178-182), enhanced yellow fluorescent protein (EYFP; Clontech Laboratories, Inc., Palo Alto, Calif.) and red fluorescent protein. In addition, there are recent reports of autofluorescent proteins from *Renilla* and *Ptilosarcus* species. See WO 92/15673; WO 95/07463; WO 98/14605; WO 98/26277; WO 99/49019; U.S. Pat. No. 5,292,658; U.S. Pat. No. 5,418,155; U.S. Pat. No. 5,683,888; U.S. Pat. No. 5,741,668; U.S. Pat. No. 5,777,079; U.S. Pat. No. 5,804,387; U.S. Pat. No. 5,874,304; U.S. Pat. No. 5,876,995; and U.S. Pat. No. 5,925,558; all of which are expressly incorporated herein by reference.

Isolation of Protein or Polypeptide of Interest

To measure the yield, solubility, conformation, and/or activity of the protein of interest, it may be desirable to isolate the protein from one or more strains in the array. The isolation may be a crude, semi-crude, or pure isolation, depending on the requirements of the assay used to make the appropriate measurements. The protein may be produced in the cytoplasm, targeted to the periplasm, or may be secreted into the culture or fermentation media. To release proteins targeted to the periplasm, treatments involving chemicals such as chloroform (Ames et al. (1984) *J. Bacteriol.,* 160: 1181-1183), guanidine-HCl, and Triton X-100 (Naglak and Wang (1990) *Enzyme Microb. Technol.,* 12: 603-611) have been used. However, these chemicals are not inert and may have detrimental effects on many heterologous protein products or subsequent purification procedures. Glycine treatment of *E. coli* cells, causing permeabilization of the outer membrane, has also been reported to release the periplasmic contents (Ariga et al. (1989) *J. Ferm. Bioeng.,* 68: 243-246). The most widely used methods of periplasmic release of heterologous protein are osmotic shock (Nosal and Heppel (1966) *J. Biol. Chem.,* 241: 3055-3062; Neu and Heppel (1965) *J. Biol. Chem.,* 240: 3685-3692), hen Egg white (HEW)-lysozyme/ethylenediamine tetraacetic acid (EDTA) treatment (Neu and Heppel (1964) *J. Biol. Chem.,* 239: 3893-3900; Witholt et al. (1976) *Biochim. Biophys. Acta,* 443: 534-544; Pierce et al. (1995) ICheme Research. Event, 2: 995-997), and combined HEW-lysozyme/osmotic shock treatment (French et al. (1996) *Enzyme and Microb. Tech.,* 19: 332-338). The French method involves resuspension of the cells in a fractionation buffer followed by recovery of the periplasmic fraction, where osmotic shock immediately follows lysozyme treatment.

Typically, these procedures include an initial disruption in osmotically-stabilizing medium followed by selective release in non-stabilizing medium. The composition of these media (pH, protective agent) and the disruption methods used (chloroform, HEW-lysozyme, EDTA, sonication) vary among specific procedures reported. A variation on the HEW-lysozyme/EDTA treatment using a dipolar ionic detergent in place of EDTA is discussed by Stabel et al. (1994) *Veterinary Microbiol.,* 38: 307-314. For a general review of use of intracellular lytic enzyme systems to disrupt *E. coli*, see Dabora and Cooney (1990) in *Advances in Biochemical Engineering/Biotechnology*, Vol. 43, A. Fiechter, ed. (Springer-Verlag: Berlin), pp. 11-30.

Conventional methods for the recovery of proteins or polypeptides of interest from the cytoplasm, as soluble protein or refractile particles, involved disintegration of the bacterial cell by mechanical breakage. Mechanical disruption typically involves the generation of local cavitation in a liquid suspension, rapid agitation with rigid beads, sonication, or grinding of cell suspension (*Bacterial Cell Surface Techniques*, Hancock and Poxton (John Wiley & Sons Ltd, 1988), Chapter 3, p. 55).

HEW-lysozyme acts biochemically to hydrolyze the peptidoglycan backbone of the cell wall. The method was first developed by Zinder and Arndt (1956) *Proc. Natl. Acad. Sci. USA,* 42: 586-590, who treated *E. coli* with egg albumin (which contains HEW-lysozyme) to produce rounded cellular spheres later known as spheroplasts. These structures retained some cell-wall components but had large surface areas in which the cytoplasmic membrane was exposed. U.S. Pat. No. 5,169,772 discloses a method for purifying heparinase from bacteria comprising disrupting the envelope of the bacteria in an osmotically-stabilized medium, e.g., 20% sucrose solution using, e.g., EDTA, lysozyme, or an organic compound, releasing the non-heparinase-like proteins from the periplasmic space of the disrupted bacteria by exposing the bacteria to a low-ionic-strength buffer, and releasing the heparinase-like proteins by exposing the low-ionic-strength-washed bacteria to a buffered salt solution.

Many different modifications of these methods have been used on a wide range of expression systems with varying degrees of success (Joseph-Liazun et al. (1990) *Gene,* 86: 291-295; Carter et al. (1992) *Bio/Technology,* 10: 163-167). Efforts to induce recombinant cell culture to produce lysozyme have been reported. EP 0 155 189 discloses a means for inducing a recombinant cell culture to produce lysozymes, which would ordinarily be expected to kill such host cells by means of destroying or lysing the cell wall structure.

U.S. Pat. No. 4,595,658 discloses a method for facilitating externalization of proteins transported to the periplasmic space of bacteria. This method allows selective isolation of proteins that locate in the periplasm without the need for lysozyme treatment, mechanical grinding, or osmotic shock treatment of cells. U.S. Pat. No. 4,637,980 discloses producing a bacterial product by transforming a temperature-sensitive lysogen with a DNA molecule that codes, directly or indirectly, for the product, culturing the transformant under permissive conditions to express the gene product intracellularly, and externalizing the product by raising the temperature to induce phage-encoded functions. Asami et al. (1997) *J. Ferment. and Bioeng.,* 83: 511-516 discloses synchronized disruption of *E. coli* cells by T4 phage infection, and Tanji et al. (1998) *J. Ferment. and Bioeng.,* 85: 74-78 discloses controlled expression of lysis genes encoded in T4 phage for the gentle disruption of *E. coli* cells.

Upon cell lysis, genomic DNA leaks out of the cytoplasm into the medium and results in significant increase in fluid viscosity that can impede the sedimentation of solids in a centrifugal field. In the absence of shear forces such as those exerted during mechanical disruption to break down the DNA polymers, the slower sedimentation rate of solids through viscous fluid results in poor separation of solids and liquid during centrifugation. Other than mechanical shear force, there exist nucleolytic enzymes that degrade DNA polymer. In *E. coli*, the endogenous gene endA encodes for an endonuclease (molecular weight of the mature protein is approx. 24.5 kD) that is normally secreted to the periplasm and cleaves DNA into oligodeoxyribonucleotides in an endonucleolytic manner. It has been suggested that endA is relatively weakly expressed by *E. coli* (Wackemagel et al. (1995) *Gene* 154: 55-59).

If desired, the proteins produced using one or more strains in the array of this invention may be isolated and purified to substantial purity by standard techniques well known in the art, including, but not limited to, ammonium sulfate or ethanol precipitation, acid extraction, anion or cation exchange chromatography, phosphocellulose chromatography, hydrophobic interaction chromatography, affinity chromatography, nickel chromatography, hydroxylapatite chromatography, reverse phase chromatography, lectin chromatography, preparative electrophoresis, detergent solubilization, selective precipitation with such substances as column chromatography, immunopurification methods, and others. For example, proteins having established molecular adhesion properties can be reversibly fused with a ligand. With the appropriate ligand, the protein can be selectively adsorbed to a purification column and then freed from the column in a relatively pure form. The fused protein is then removed by enzymatic activity. In addition, protein can be purified using immunoaffinity columns or Ni-NTA columns. General techniques are further described in, for example, R. Scopes, *Protein Purification*: Principles and Practice, Springer-Verlag: N.Y. (1982); Deutscher, *Guide to Protein Purification*, Academic Press (1990); U.S. Pat. No. 4,511,503; S. Roe, *Protein Purification Techniques: A Practical Approach* (Practical Approach Series), Oxford Press (2001); D. Bollag, et al., Protein Methods, Wiley-Lisa, Inc. (1996); A K Patra et al., *Protein Expr Purif,* 18(2): p/182-92 (2000); and R. Mukhija, et al., *Gene* 165(2): p. 303-6 (1995). See also, for example, Ausubel, et al. (1987 and periodic supplements); Deutscher (1990) "Guide to Protein Purification," *Methods in Enzymology* vol. 182, and other volumes in this series; Coligan, et al. (1996 and periodic Supplements) *Current Protocols in Protein Science* Wiley/Greene, NY; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See also, for example., Hochuli (1989) *Chemische Industrie* 12:69-70; Hochuli (1990) "Purification of Recombinant Proteins with Metal Chelate Absorbent" in Setlow (ed.) *Genetic Engineering, Principle and Methods* 12:87-98, Plenum Press, NY; and Crowe, et al. (1992) QIAexpress: The High Level Expression & Protein Purification System QUIAGEN, Inc., Chatsworth, Calif.

Detection of the expressed protein is achieved by methods known in the art and include, for example, radioimmunoassays, Western blotting techniques or immunoprecipitation.

Certain proteins expressed by the strains in the array of this invention may form insoluble aggregates ("inclusion bodies"). Several protocols are suitable for purification of proteins from inclusion bodies. For example, purification of inclusion bodies typically involves the extraction, separation and/or purification of inclusion bodies by disruption of the host cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension is typically lysed using 2-3 passages through a French Press. The cell suspension can also be homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies can be solubilized, and the lysed cell suspension typically can be centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art.

The heterologously-expressed proteins present in the supernatant can be separated from the host proteins by standard separation techniques well known to those of skill in the art. For example, an initial salt fractionation can separate many of the unwanted host cell proteins (or proteins derived from the cell culture media) from the protein or polypeptide of interest. One such example can be ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

The molecular weight of a protein or polypeptide of interest can be used to isolated it from proteins of greater and lesser size using ultrafiltration through membranes of different pore size (for example, Amicon or Millipore membranes). As a first step, the protein mixture can be ultrafiltered through a membrane with a pore size that has a lower molecular weight cut-off than the molecular weight of the protein of interest. The retentate of the ultrafiltration can then be ultrafiltered against a membrane with a molecular cut off greater than the molecular weight of the protein of interest. The protein or polypeptide of interest will pass through the membrane into the filtrate. The filtrate can then be chromatographed as described below.

The expressed proteins or polypeptides of interest can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

Renaturation and Refolding

Where heterologously expressed protein is produced in a denatured form, insoluble protein can be renatured or refolded to generate secondary and tertiary protein structure conformation. Protein refolding steps can be used, as necessary, in completing configuration of the heterologous product. Refolding and renaturation can be accomplished using an agent that is known in the art to promote dissociation/association of proteins. For example, the protein can be incubated with dithiothreitol followed by incubation with oxidized glutathione disodium salt followed by incubation with a buffer containing a refolding agent such as urea.

The protein or polypeptide of interest can also be renatured, for example, by dialyzing it against phosphate-buffered saline (PBS) or 50 mM Na-acetate, pH 6 buffer plus 200 mM NaCl. Alternatively, the protein can be refolded while immobilized on a column, such as the Ni NTA column by using a linear 6M-1M urea gradient in 500 mM NaCl, 20% glycerol, 20 mM Tris/HCl pH 7.4, containing protease inhibitors. The renaturation can be performed over a period of 1.5 hours or more. After renaturation the proteins can be eluted by the addition of 250 mM imidazole. Imidazole can be removed by a final dialyzing step against PBS or 50 mM sodium acetate pH 6 buffer plus 200 mM NaCl. The purified protein can be stored at 4° C. or frozen at −80° C.

Other methods include, for example, those that may be described in M H Lee et al., *Protein Expr. Purif.,* 25(1): p. 166-73 (2002), W. K. Cho et al., *J. Biotechnology,* 77(2-3): p. 169-78 (2000), Ausubel, et al. (1987 and periodic supplements), Deutscher (1990) "Guide to Protein Purification," *Methods in Enzymology* vol. 182, and other volumes in this series, Coligan, et al. (1996 and periodic Supplements) *Current Protocols in Protein Science* Wiley/Greene, NY, S. Roe, *Protein Purification Techniques: A Practical Approach* (Practical Approach Series), Oxford Press (2001); D. Bollag, et al., Protein Methods, Wiley-Lisa, Inc. (1996)

Expression Vectors

A heterologous protein of interest can be produced in one or more of the host cells disclosed herein by introducing into each strain an expression vector encoding the heterologous protein of interest. In one embodiment, the vector comprises a polynucleotide sequence encoding the protein of interest operably linked to a promoter capable of functioning in the chosen host cell, as well as all other required transcription and translation regulatory elements.

The term "operably linked" refers to any configuration in which the transcriptional and any translational regulatory elements are covalently attached to the encoding sequence in such disposition(s), relative to the coding sequence, that in and by action of the host cell, the regulatory elements can direct the expression of the coding sequence.

The heterologous protein of interest can be expressed from polynucleotides in which the heterologous polypeptide coding sequence is operably linked to transcription and translation regulatory elements to form a functional gene from which the host cell can express the protein or polypeptide. The coding sequence can be a native coding sequence for the heterologous polypeptide, or may be a coding sequence that has been selected, improved, or optimized for use in the selected expression host cell: for example, by synthesizing the gene to reflect the codon use bias of a host species. In one embodiment of the invention, the host species is a *P. fluorescens*, and the codon bias of *P. fluorescens* is taken into account when designing the polypeptide coding sequence. The gene(s) are constructed within or inserted into one or more vector(s), which can then be transformed into the expression host cell.

Other regulatory elements may be included in a vector (also termed "expression construct"). The vector will typically comprise one or more phenotypic selectable markers and an origin of replication to ensure maintenance of the vector and to, if desirable, provide amplification within the host. Additional elements include, but are not limited to, for example, transcriptional enhancer sequences, translational enhancer sequences, other promoters, activators, translational start and stop signals, transcription terminators, cistronic regulators, polycistronic regulators, or tag sequences, such as nucleotide sequence "tags" and "tag" polypeptide coding sequences, which facilitates identification, separation, purification, and/or isolation of an expressed polypeptide.

In another embodiment, the expression vector further comprises a tag sequence adjacent to the coding sequence for the protein or polypeptide of interest. In one embodiment, this tag sequence allows for purification of the protein.

The tag sequence can be an affinity tag, such as a hexa-histidine affinity tag (SEQ ID NO: 158). In another embodiment, the affinity tag can be a glutathione-5-transferase molecule. The tag can also be a fluorescent molecule, such as YFP or GFP, or analogs of such fluorescent proteins. The tag can also be a portion of an antibody molecule, or a known antigen or ligand for a known binding partner useful for purification.

A protein-encoding gene according to the present invention can include, in addition to the protein coding sequence, the following regulatory elements operably linked thereto: a promoter, a ribosome binding site (RBS), a transcription terminator, translational start and stop signals. Useful RBSs can be obtained from any of the species useful as host cells in expression systems according to the present invention, preferably from the selected host cell. Many specific and a variety of consensus RBSs are known, e.g., those described in and referenced by D. Frishman et al., Gene 234(2):257-65 (8 Jul. 1999); and B. E. Suzek et al., Bioinformatics 17(12): 1123-30 (December 2001). In addition, either native or synthetic RBSs may be used, e.g., those described in: EP 0207459 (synthetic RBSs); O. Ikehata et al., Eur. J. Biochem. 181(3):563-70 (1989) (native RBS sequence of AAGGAAG). Further examples of methods, vectors, and translation and transcription elements, and other elements useful in the present invention are described in, e.g.: U.S. Pat. No. 5,055,294 to Gilroy and U.S. Pat. No. 5,128,130 to Gilroy et al.; U.S. Pat. No. 5,281,532 to Rammler et al.; U.S. Pat. Nos. 4,695,455 and 4,861,595 to Barnes et al.; U.S. Pat. No. 4,755,465 to Gray et al.; and U.S. Pat. No. 5,169,760 to Wilcox.

Transcription of the DNA encoding the heterologous protein of interest is increased by inserting an enhancer sequence into the vector or plasmid. Typical enhancers are cis-acting elements of DNA, usually about from 10 to 300 bp in size that act on the promoter to increase its transcription. Examples include various *Pseudomonas* enhancers.

Generally, the heterologous expression vectors will include origins of replication and selectable markers permitting transformation of the host cell and a promoter derived from a highly-expressed gene to direct transcription of a downstream structural sequence. Such promoters can be derived from operons encoding the enzymes such as 3-phosphoglycerate kinase (PGK), acid phosphatase, or heat shock proteins, among others. Where signal sequences are used, the heterologous coding sequence is assembled in appropriate phase with translation initiation and termination sequences, and the signal sequence capable of directing compartmental accumulation or secretion of the translated protein. Optionally the heterologous sequence can encode a fusion enzyme including an N-terminal identification polypeptide imparting desired characteristics, e.g., stabilization or simplified purification of expressed heterologous product. The fusion polypeptide can also comprise one or more target proteins or inhibitors or enhances thereof, as discussed supra.

Vectors are known in the art for expressing heterologous proteins in host cells, and any of these may be used for expressing the genes according to the present invention. Such vectors include, e.g., plasmids, cosmids, and phage expression vectors. Examples of useful plasmid vectors include, but are not limited to, the expression plasmids pBBR1MCS, pDSK519, pKT240, pML122, pPS10, RK2, RK6, pRO1600, and RSF1010. Other examples of such useful vectors include those described by, e.g.: N. Hayase, in Appl. Envir. Microbiol. 60(9):3336-42 (September 1994); A. A. Lushnikov et al., in Basic Life Sci. 30:657-62 (1985); S. Graupner & W. Wackemagel, in Biomolec. Eng. 17(1): 11-16. (October 2000); H. P. Schweizer, in Curr. Opin. Biotech. 12(5):439-45 (October 2001); M. Bagdasarian & K. N. Timmis, in Curr. Topics Microbiol. Immunol. 96:47-67 (1982); T. Ishii et al., in FEMS Microbiol. Lett. 116(3): 307-13 (Mar. 1, 1994); I. N. Olekhnovich & Y. K. Fomichev, in Gene 140(1):63-65 (Mar. 11, 1994); M. Tsuda & T. Nakazawa, in Gene 136(1-2):257-62 (Dec. 22, 1993); C. Nieto et al., in Gene 87(1):145-49 (Mar. 1, 1990); J. D. Jones & N. Gutterson, in Gene 61(3):299-306 (1987); M. Bagdasarian et al., in Gene 16(1-3):237-47 (December 1981); H. P. Schweizer et al., in Genet. Eng. (NY) 23:69-81 (2001); P. Mukhopadhyay et al., in J. Bact. 172(1):477-80 (January 1990); D. O. Wood et al., in J. Bact. 145(3):1448-51 (March 1981); and R. Holtwick et al., in Microbiology 147(Pt 2):337-44 (February 2001).

Further examples of expression vectors that can be useful in a host cell of the invention include those listed in Table 5 as derived from the indicated replicons.

TABLE 5

Examples of Useful Expression Vectors

| Replicon | Vector(s) |
|---|---|
| PPS10 | PCN39, PCN51 |
| RSF1010 | PKT261-3 |
| | PMMB66EH |
| | PEB8 |
| | PPLGN1 |
| | PMYC1050 |
| RK2/RP1 | PRK415 |
| | PJB653 |
| PRO1600 | PUCP |
| | PBSP |

The expression plasmid, RSF1010, is described, e.g., by F. Heffron et al., in Proc. Nat'l Acad. Sci. USA 72(9):3623-27 (September 1975), and by K. Nagahari & K. Sakaguchi, in J. Bact. 133(3):1527-29 (March 1978). Plasmid RSF1010 and derivatives thereof are particularly useful vectors in the present invention. Exemplary useful derivatives of RSF1010, which are known in the art, include, e.g., pKT212, pKT214, pKT231 and related plasmids, and pMYC1050 and related plasmids (see, e.g., U.S. Pat. Nos. 5,527,883 and 5,840,554 to Thompson et al.), such as, e.g., pMYC1803. Plasmid pMYC1803 is derived from the RSF1010-based plasmid pTJS260 (see U.S. Pat. No. 5,169,760 to Wilcox), which carries a regulated tetracycline resistance marker and the replication and mobilization loci from the RSF1010 plasmid. Other exemplary useful vectors include those described in U.S. Pat. No. 4,680,264 to Puhler et al.

In one embodiment, an expression plasmid is used as the expression vector. In another embodiment, RSF1010 or a derivative thereof is used as the expression vector. In still another embodiment, pMYC1050 or a derivative thereof, or pMYC4803 or a derivative thereof, is used as the expression vector.

The plasmid can be maintained in the host cell by inclusion of a selection marker gene in the plasmid. This may be an antibiotic resistance gene(s), where the corresponding antibiotic(s) is added to the fermentation medium, or any other type of selection marker gene known in the art, e.g., a prototrophy-restoring gene where the plasmid is used in a host cell that is auxotrophic for the corresponding trait, e.g., a biocatalytic trait such as an amino acid biosynthesis or a nucleotide biosynthesis trait, or a carbon source utilization trait.

The promoters used in accordance with the present invention may be constitutive promoters or regulated promoters. Common examples of useful regulated promoters include those of the family derived from the lac promoter (i.e. the lacZ promoter), especially the tac and trc promoters described in U.S. Pat. No. 4,551,433 to DeBoer, as well as Ptac16, Ptac17, PtacII, PlacUV5, and the T7lac promoter. In one embodiment, the promoter is not derived from the host cell organism. In certain embodiments, the promoter is derived from an *E. coli* organism.

Common examples of non-lac-type promoters useful in expression systems according to the present invention include, e.g., those listed in Table 6.

TABLE 6

Examples of non-lac Promoters

| Promoter | Inducer |
|---|---|
| $P_R$ | High temperature |
| $P_L$ | High temperature |
| Pm | Alkyl- or halo-benzoates |
| Pu | Alkyl- or halo-toluenes |
| Psal | Salicylates |

See, e.g.: J. Sanchez-Romero & V. De Lorenzo (1999) Manual of Industrial Microbiology and Biotechnology (A. Demain & J. Davies, eds.) pp. 460-74 (ASM Press, Washington, D.C.); H. Schweizer (2001) Current Opinion in Biotechnology, 12:439-445; and R. Slater & R. Williams (2000 Molecular Biology and Biotechnology (J. Walker & R. Rapley, eds.) pp. 125-54 (The Royal Society of Chemistry, Cambridge, UK)). A promoter having the nucleotide sequence of a promoter native to the selected bacterial host cell may also be used to control expression of the transgene encoding the target polypeptide, e.g, a *Pseudomonas* anthranilate or benzoate operon promoter (Pant, Pben). Tandem promoters may also be used in which more than one promoter is covalently attached to another, whether the same or different in sequence, e.g., a Pant-Pben tandem promoter (interpromoter hybrid) or a Plac-Plac tandem promoter, or whether derived from the same or different organisms.

Regulated promoters utilize promoter regulatory proteins in order to control transcription of the gene of which the promoter is a part. Where a regulated promoter is used herein, a corresponding promoter regulatory protein will also be part of an expression system according to the present invention. Examples of promoter regulatory proteins include: activator proteins, e.g., *E. coli* catabolite activator protein, MalT protein; AraC family transcriptional activators; repressor proteins, e.g., *E. coli* Lad proteins; and dual-function regulatory proteins, e.g., *E. coli* NagC protein. Many regulated-promoter/promoter-regulatory-protein pairs are known in the art. In one embodiment, the expression construct for the target protein(s) and the heterologous protein of interest are under the control of the same regulatory element.

Promoter regulatory proteins interact with an effector compound, i.e. a compound that reversibly or irreversibly associates with the regulatory protein so as to enable the protein to either release or bind to at least one DNA transcription regulatory region of the gene that is under the control of the promoter, thereby permitting or blocking the action of a transcriptase enzyme in initiating transcription of the gene. Effector compounds are classified as either inducers or co-repressors, and these compounds include native effector compounds and gratuitous inducer compounds. Many regulated-promoter/promoter-regulatory-protein/effector-compound trios are known in the art. Although an effector compound can be used throughout the cell culture or fermentation, in a preferred embodiment in which a regulated promoter is used, after growth of a desired quantity or density of host cell biomass, an appropriate effector compound is added to the culture to directly or indirectly result in expression of the desired gene(s) encoding the protein or polypeptide of interest.

By way of example, where a lac family promoter is utilized, a lacI gene can also be present in the system. The lacI gene, which is (normally) a constitutively expressed gene, encodes the Lac repressor protein (LacD protein) which binds to the lac operator of these promoters. Thus, where a lac family promoter is utilized, the lacI gene can also be included and expressed in the expression system. In the case of the lac promoter family members, e.g., the tac promoter, the effector compound is an inducer, preferably a gratuitous inducer such as IPTG (isopropyl-D-1-thiogalactopyranoside, also called "isopropylthiogalactoside").

For expression of a protein or polypeptide of interest, any plant promoter may also be used. A promoter may be a plant RNA polymerase II promoter. Elements included in plant promoters can be a TATA box or Goldberg-Hogness box, typically positioned approximately 25 to 35 basepairs upstream (5') of the transcription initiation site, and the CCAAT box, located between 70 and 100 basepairs upstream. In plants, the CCAAT box may have a different consensus sequence than the functionally analogous sequence of mammalian promoters (Messing et al. (1983) In: *Genetic Engineering of Plants*, Kosuge et al., eds., pp. 211-227). In addition, virtually all promoters include additional upstream activating sequences or enhancers (Benoist and Chambon (1981) *Nature* 290:304-310; Gruss et al. (1981) *Proc. Nat. Acad. Sci.* 78:943-947; and Khoury and Gruss (1983) *Cell* 27:313-314) extending from around −100 bp to −1,000 bp or more upstream of the transcription initiation site.

Expression Systems

It may be desirable to target the protein or polypeptide of interest to the periplasm of one or more of the populations of host cells in the array, or into the extracellular space. In one embodiment, the expression vector further comprises a nucleotide sequence encoding a secretion signal sequence polypeptide operably linked to the nucleotide sequence encoding the protein or polypeptide of interest. In some embodiments, no modifications are made between the signal sequence and the protein or polypeptide of interest. However, in certain embodiments, additional cleavage signals are incorporated to promote proper processing of the amino terminal of the polypeptide.

The vector can have any of the characteristics described above. In one embodiment, the vector comprising the coding sequence for the protein or polypeptide of interest further comprises a signal sequence, e.g., a secretion signal sequence.

Therefore, in one embodiment, this isolated polypeptide is a fusion protein of the secretion signal and a protein or polypeptide of interest. However, the secretion signal can also be cleaved from the protein when the protein is targeted to the periplasm. In one embodiment, the linkage between the Sec system secretion signal and the protein or polypeptide is modified to increase cleavage of the secretion signal.

Secretion signals useful in the compositions and methods of the present invention are known in the art and are provided herein and in U.S. Pat. App. Pub. Nos. 2006/0008877 and 2008/0193974, both incorporated herein by reference in there entirety. These sequences can promote the targeting of an operably linked polypeptide of interest to the periplasm of Gram-negative bacteria or into the extracellular environment. Use of secretion signal leader sequences can increase production of recombinant proteins in bacteria that produce improperly folded, aggregated or inactive proteins. Additionally, many types of proteins require secondary modifications that are inefficiently achieved using known methods. Secretion leader utilization can increase the harvest of properly folded proteins by secreting the protein from the intracellular environment. In Gram-negative bacteria, a protein secreted from the cytoplasm can end up in the periplasmic space, attached to the outer membrane, or in the extracellular broth. These methods also avoid formation of inclusion bodies, which constitute aggregated proteins. Secretion of proteins into the periplasmic space also has the well-known effect of facilitating proper disulfide bond formation (Bardwell et al. (1994) Phosphate Microorg. 270-5; Manoil (2000) Methods in Enzymol. 326: 35-47). Other benefits of secretion of recombinant protein include: more efficient isolation of the protein; proper folding and disulfide bond formation of the transgenic protein, leading to an increase in yield represented by, e.g., the percentage of the protein in active form, reduced formation of inclusion bodies and reduced toxicity to the host cell, and an increased percentage of the recombinant protein in soluble form. The potential for excretion of the protein of interest into the culture medium can also potentially promote continuous, rather than batch culture for protein production.

Certain secretion leader sequences useful in the compositions and methods of the present invention are shown in Table 7 below. As understood by those of skill in the art, these sequences and others described in the art can retain function or have improved function when amino acid changes are made. Furthermore, it is understood that the nucleic acid sequences encoding these leaders can in come cases vary without effect on the function of the leader. Additional leader sequences are provided in the sequence listings.

TABLE 7

Exemplary Leader Sequences

| Leader Sequence | Abbrev | Amino Acid Sequence | SEQ ID NO |
|---|---|---|---|
| Porin E1 | PorE | MKKSTLAVAVTLGAIAQQAGA | |
| Outer membrane porin F | OprF | MKLKNTLGLAIGSLIAATSFGVLA | |
| Periplasmic phosphate binding protein | Pbp | MKLKRLMAAMTFVAAGVATANAVA | |
| Azurin | Azu | MFAKLVAVSLLTLASGQLLA | |
| Lipoprotein B RXF04720 | Lip | MIKRNLLVMGLAVLLSA | |
| Lysine-arginine-ornithine-binding protein | Lao | MQNYKKFLLAAAVSMAFSATAMA | |
| Iron(III) binding protein | Ibp | MIRDNRLKTSLLRGLTLTLLSLTLLSPAAHS | |
| PB signal sequence mutant | Pbp-A20V | MKLKRLMAAMTFVAAGVATVNAVA | |
| DsbA | DsbA | MRNLILSAALVTASLFGMTAQA | |
| DsbC | DsbC | MRLTQIIAAAAIALVSTFALA | |
| tolB (PCR amplified from MB214 genomic) | tolB | MRNLLRGMLVVICCMAGIAAA | |
| Tetratricopeptide repeat family protein | tpr | MNRSSALLLAFVFLSGCQAMA | |
| Methyl-accepting chemotaxis protein | | MSLRNMNIAPRAFLGFAFIGALMLLLGVFALNQMSKIRA | |
| Toluene tolerance protein ttg2C | ttg2C | MQNRTVEIGVGLFLLAGILALLLLALRVSGLSA | |
| FlgI RXF05262 | FlgI | MKFKQLMAMALLLALSAVAQA | |
| EcpD, CupC2 bacterial pili assembly chaperone RXF04554 | cupC2 | MPPRSIAACLGLLGLLMATQAAA | |

TABLE 7-continued

| Exemplary Leader Sequences | | | |
|---|---|---|---|
| Leader Sequence | Abbrev | Amino Acid Sequence | SEQ ID NO |
| EcpD, CupB2 RXF05310 | cupB2 | MLFRTLLASLTFAVIAGLPSTAHA | |
| EcpD, CupA2 RXF04296 | cupA2 | MSCTRAFKPLLLIGLATLMCSHAFA | |
| NikA Periplasmic dipeptide transport protein RXF08966 | nikA | MRLAALPLLLAPLFIAPMAVA | |
| Bce (*Bacillus coagulans*) | bce | MSTRIPRRQWLKGASGLLAAASLGRLANREARA | |
| IBP S31A | | MIRDNRLKTSLLRGLTLTLLSLTLLSPAAHA | |

In embodiments, the expression vector contains an optimal ribosome binding sequence. Modulating translation strength by altering the translation initiation region of a protein of interest can be used to improve the production of heterologous cytoplasmic proteins that accumulate mainly as inclusion bodies due to a translation rate that is too rapid. Secretion of heterologous proteins into the periplasmic space of bacterial cells can also be enhanced by optimizing rather than maximizing protein translation levels such that the translation rate is in sync with the protein secretion rate.

The translation initiation region has been defined as the sequence extending immediately upstream of the ribosomal binding site (RBS) to approximately 20 nucleotides downstream of the initiation codon (McCarthy et al. (1990) Trends in Genetics 6:78-85, herein incorporated by reference in its entirety). In prokaryotes, alternative RBS sequences can be utilized to optimize translation levels of heterologous proteins by providing translation rates that are decreased with respect to the translation levels using the canonical, or consensus, RBS sequence (AGGAGG; SEQ ID NO:1) described by Shine and Dalgarno (Proc. Natl. Acad. Sci. USA 71:1342-1346, 1974). By "translation rate" or "translation efficiency" is intended the rate of mRNA translation into proteins within cells. In most prokaryotes, the Shine-Dalgarno sequence assists with the binding and positioning of the 30S ribosome component relative to the start codon on the mRNA through interaction with a pyrimidine-rich region of the 16S ribosomal RNA. The RBS (also referred to herein as the Shine-Dalgarno sequence) is located on the mRNA downstream from the start of transcription and upstream from the start of translation, typically from 4 to 14 nucleotides upstream of the start codon, and more typically from 8 to 10 nucleotides upstream of the start codon. Because of the role of the RBS sequence in translation, there is a direct relationship between the efficiency of translation and the efficiency (or strength) of the RBS sequence.

In some embodiments, modification of the RBS sequence results in a decrease in the translation rate of the heterologous protein. This decrease in translation rate may correspond to an increase in the level of properly processed protein or polypeptide per gram of protein produced, or per gram of host protein. The decreased translation rate can also correlate with an increased level of recoverable protein or polypeptide produced per gram of recombinant or per gram of host cell protein. The decreased translation rate can also correspond to any combination of an increased expression, increased activity, increased solubility, or increased translocation (e.g., to a periplasmic compartment or secreted into the extracellular space). In this embodiment, the term "increased" is relative to the level of protein or polypeptide that is produced, properly processed, soluble, and/or recoverable when the protein or polypeptide of interest is expressed under the same conditions, and wherein the nucleotide sequence encoding the polypeptide comprises the canonical RBS sequence. Similarly, the term "decreased" is relative to the translation rate of the protein or polypeptide of interest wherein the gene encoding the protein or polypeptide comprises the canonical RBS sequence. The translation rate can be decreased by at least about 5%, at least about 10%, at least about 15%, at least about 20%, about 25%, about 30%, about 35%, about 40%, about 45%, about 50%, about 55%, about 60%, about 65%, about 70, at least about 75% or more, or at least about 2-fold, about 3-fold, about 4-fold, about 5-fold, about 6-fold, about 7-fold, or greater.

In some embodiments, the RBS sequence variants described herein can be classified as resulting in high, medium, or low translation efficiency. In one embodiment, the sequences are ranked according to the level of translational activity compared to translational activity of the canonical RBS sequence. A high RBS sequence has about 60% to about 100% of the activity of the canonical sequence. A medium RBS sequence has about 40% to about 60% of the activity of the canonical sequence. A low RBS sequence has less than about 40% of the activity of the canonical sequence.

Examples of RBS sequences are shown in Table 8. The sequences were screened for translational strength using COP-GFP as a reporter gene and ranked according to percentage of consensus RBS fluorescence. Each RBS variant was placed into one of three general fluorescence ranks: High ("Hi"—100% Consensus RBS fluorescence), Medium ("Med"—46-51% of Consensus RBS fluorescence), and Low ("Lo"—16-29% Consensus RBS fluorescence).

TABLE 8

| RBS Sequences | | |
|---|---|---|
| Consensus | AGGAGG | High |
| RBS2 | GGAGCG | Med |
| RBS34 | GGAGCG | Med |
| RBS41 | AGGAGT | Med |
| RBS43 | GGAGTG | Med |
| RBS48 | GAGTAA | Low |
| RBS1 | AGAGAG | Low |
| RBS35 | AAGGCA | Low |
| RBS49 | CCGAAC | Low |

Methods for identifying optimal ribosome binding sites are described in U.S. Pat. App. No. 2009/062143, "Translation initiation region sequences for optimal expression of heterologous proteins," incorporated herein by reference in its entirety.

One or more genes encoding heterologous proteins can be expressed from the same expression vector, as desired. For example, one might choose to express an antibody heavy chain and light chain from the same vector. The same promoter and regulatory sequences can be used to drive expression of both genes (e.g., in tandem), or the genes can be expressed separately on the same expression vector. In embodiments of the invention, at least two genes are encoded on separate expression vectors within the same expression system. The at least two genes are related or unrelated.

In the context of the array, it can be convenient and informative to test the expression of a group of heterologous proteins in parallel in the same array. This can be accomplished by providing several series of expression systems. One series contains expression vectors encoding at least one heterologous protein to be compared with at least one other heterologous protein in another series of expression systems. For example, a group of variants of the same protein can be tested on the same array in several series of expression systems. In each series of expression systems, the expression vector encodes the same variant. Such an approach could also be useful for testing a library of binding proteins, e.g., antibodies. In embodiments, the proteins tested in parallel are related; in others, they are not.

Prior to cloning into an expression vector, the protein coding sequence can be optimized if desired. The sequence is cloned into a series of expression vectors containing, e.g., secretion leader sequences and other appropriate promoters or regulatory sequences as described herein. These sequence elements can be selected based on an analysis of the heterologous protein amino acid sequence as described herein.

The CHAMPION™ pET expression system provides a high level of protein production. Expression is induced from the strong T7lac promoter. This system takes advantage of the high activity and specificity of the bacteriophage T7 RNA polymerase for high level transcription of the gene of interest. The lac operator located in the promoter region provides tighter regulation than traditional T7-based vectors, improving plasmid stability and cell viability (Studier and Moffatt (1986) *J Molecular Biology* 189(1): 113-30; Rosenberg, et al. (1987) *Gene* 56(1): 125-35). The T7 expression system uses the T7 promoter and T7 RNA polymerase (T7 RNAP) for high-level transcription of the gene of interest. High-level expression is achieved in T7 expression systems because the T7 RNAP is more processive than native *E. coli* RNAP and is dedicated to the transcription of the gene of interest. Expression of the identified gene is induced by providing a source of T7 RNAP in the host cell. This is accomplished by using a BL21 *E. coli* host containing a chromosomal copy of the T7 RNAP gene. The T7 RNAP gene is under the control of the lacUV5 promoter which can be induced by IPTG. T7 RNAP is expressed upon induction and transcribes the gene of interest.

The pBAD expression system allows tightly controlled, titratable expression of protein or polypeptide of interest through the presence of specific carbon sources such as glucose, glycerol and arabinose (Guzman, et al. (1995) J Bacteriology 177(14): 4121-30). The pBAD vectors are uniquely designed to give precise control over expression levels. Heterologous gene expression from the pBAD vectors is initiated at the araBAD promoter. The promoter is both positively and negatively regulated by the product of the araC gene. AraC is a transcriptional regulator that forms a complex with L-arabinose. In the absence of L-arabinose, the AraC dimer blocks transcription. For maximum transcriptional activation two events are required: (i) L-arabinose binds to AraC allowing transcription to begin, and, (ii) The cAMP activator protein (CAP)-cAMP complex binds to the DNA and stimulates binding of AraC to the correct location of the promoter region.

The trc expression system allows high-level, regulated expression in *E. coli* from the trc promoter. The trc expression vectors have been optimized for expression of eukaryotic genes in *E. coli*. The trc promoter is a strong hybrid promoter derived from the tryptophane (trp) and lactose (lac) promoters. It is regulated by the lacO operator and the product of the lacIQ gene (Brosius, J. (1984) Gene 27(2): 161-72).

Transformation of the host cells with the vector(s) disclosed herein may be performed using any transformation methodology known in the art, and the bacterial host cells may be transformed as intact cells or as protoplasts (i.e. including cytoplasts). Exemplary transformation methodologies include poration methodologies, e.g., electroporation, protoplast fusion, bacterial conjugation, and divalent cation treatment, e.g., calcium chloride treatment or CaCl/Mg2+ treatment, or other well known methods in the art. See, e.g., Morrison, *J. Bact.*, 132:349-351 (1977); Clark-Curtiss & Curtiss, *Methods in Enzymology,* 101:347-362 (Wu et al., eds, 1983), Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

Proteins of Interest

The methods and compositions of the present invention are useful for identifying a *P. fluorescens* strain that is optimal for producing high levels of a properly processed protein or polypeptide of interest. The arrays are useful for screening for production of a protein or polypeptide of interest of any species and of any size. However, in certain embodiments, the protein or polypeptide of interest is a therapeutically useful protein or polypeptide. In some embodiments, the protein can be a mammalian protein, for example a human protein, and can be, for example, a growth factor, a cytokine, a chemokine or a blood protein. The protein or polypeptide of interest can be processed in a similar manner to the native protein or polypeptide. In certain embodiments, the protein or polypeptide of interest is less than 100 kD, less than 50 kD, or less than 30 kD in size. In certain embodiments, the protein or polypeptide of interest is a polypeptide of at least about 5, 10, 15, 20, 30, 40, 50 or 100 or more amino acids.

The coding sequence for the protein or polypeptide of interest can be a native coding sequence for the polypeptide, if available, but will more preferably be a coding sequence that has been selected, improved, or optimized for use in an expressible form in the strains of the array: for example, by optimizing the gene to reflect the codon use bias of a *Pseudomonas* species such as *P. fluorescens* or other suitable organism. For gene optimization, one or more rare codons may be removed to avoid ribosomal stalling and minimize amino acid misincorporation. One or more gene-internal ribosome binding sites may also be eliminated to avoid truncated protein products. Long stretches of C and G nucleotides may be removed to avoid RNA polymerase slippage that could result in frame-shifts. Strong gene-internal stem-loop structures, especially the ones covering the ribosome binding site, may also be eliminated.

In other embodiments, the protein when produced also includes an additional targeting sequence, for example a sequence that targets the protein to the periplasm or the extracellular medium. In one embodiment, the additional targeting sequence is operably linked to the carboxy-terminus of the protein. In another embodiment, the protein includes a secretion signal for an autotransporter, a two partner secretion system, a main terminal branch system or a fimbrial usher porin.

The gene(s) that result are constructed within or are inserted into one or more vectors, and then transformed into each of the host cell populations in the array. Nucleic acid or a polynucleotide said to be provided in an "expressible form" means nucleic acid or a polynucleotide that contains at least one gene that can be expressed by the one or more of the host cell populations of the invention.

Extensive sequence information required for molecular genetics and genetic engineering techniques is widely publicly available. Access to complete nucleotide sequences of mammalian, as well as human, genes, cDNA sequences, amino acid sequences and genomes can be obtained from GenBank. GenBank is maintained by the National Institutes of Health, Bethesda, Md., and can be accessed at ncbi.nlm.nih.gov/Entrez within the NIH website. Additional information can also be obtained from GeneCards, an electronic encyclopedia integrating information about genes and their products and biomedical applications, made available by the Department of Molecular Genetics, the Weizmann Institute of Science, Rehovot, Israel. Nucleotide sequence information also can be obtained from the EMBL Nucleotide Sequence Database made available on the worldwide web by the European Bioinformatics Institute (Hinxton, Cambridge, UK) or from the DNA Databank of Japan (Research Organization of Information and Systems, National Institute of Genetics, Center for Information Biology and DNA Data Bank of Japan, 1111 Yata, Mishima, Shizuoka 411-8540, Japan). Additional sites for information on amino acid sequences include the Protein Information Resource website established by the National Biomedical Research Foundation, which includes Swiss-Prot.

Examples of proteins that can be expressed in this invention include molecules such as, e.g., renin, a growth hormone, including human growth hormone; bovine growth hormone; growth hormone releasing factor; parathyroid hormone; thyroid stimulating hormone; lipoproteins; α-1-antitrypsin; insulin A-chain; insulin B-chain; proinsulin; thrombopoietin; follicle stimulating hormone; calcitonin; luteinizing hormone; glucagon; clotting factors such as factor VIIIC, factor IX, tissue factor, and von Willebrands factor; anti-clotting factors such as Protein C; atrial naturietic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; a serum albumin such as human serum albumin; mullerian-inhibiting substance; relaxin A-chain; relaxin B-chain; prorelaxin; mouse gonadotropin-associated polypeptide; a microbial protein, such as beta-lactamase; Dnase; inhibin; activin; vascular endothelial growth factor (VEGF); receptors for hormones or growth factors; integrin; protein A or D; rheumatoid factors; a neurotrophic factor such as brain-derived neurotrophic factor (BDNF), neurotrophin-3, -4, -5, or -6 (NT-3, NT-4, NT-5, or NT-6), or a nerve growth factor such as NGF-β; cardiotrophins (cardiac hypertrophy factor) such as cardiotrophin-1 (CT-1); platelet-derived growth factor (PDGF); fibroblast growth factor such as aFGF and bFGF; epidermal growth factor (EGF); transforming growth factor (TGF) such as TGF-alpha and TGF-β, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; anti-HER-2 antibody; superoxide dismutase; T-cell receptors; surface membrane proteins; decay accelerating factor; viral antigen such as, for example, a portion of the AIDS envelope; transport proteins; homing receptors; addressins; regulatory proteins; antibodies; and fragments of any of the above-listed polypeptides.

In certain embodiments, the protein or polypeptide can be selected from IL-1, IL-1a, IL-1b, IL-2, IL-3, IL-4, IL-5, IL-6, IL-7, IL-8, IL-9, IL-10, IL-11, IL-12, IL-12elasti, IL-13, IL-15, IL-16, IL-18, IL-18BPa, IL-23, IL-24, VIP, erythropoietin, GM-CSF, G-CSF, M-CSF, platelet derived growth factor (PDGF), MSF, FLT-3 ligand, EGF, fibroblast growth factor (FGF; e.g., α-FGF (FGF-1), β-FGF (FGF-2), FGF-3, FGF-4, FGF-5, FGF-6, or FGF-7), insulin-like growth factors (e.g., IGF-1, IGF-2); tumor necrosis factors (e.g., TNF, Lymphotoxin), nerve growth factors (e.g., NGF), vascular endothelial growth factor (VEGF); interferons (e.g., IFN-α, IFN-β, IFN-γ); leukemia inhibitory factor (LIF); ciliary neurotrophic factor (CNTF); oncostatin M; stem cell factor (SCF); transforming growth factors (e.g., TGF-α, TGF-β1, TGF-β2, TGF-β3); TNF superfamily (e.g., LIGHT/TNFSF14, STALL-1/TNFSF13B (BLy5, BAFF, THANK), TNFalpha/TNFSF2 and TWEAK/TNFSF12); or chemokines (BCA-1/BLC-1, BRAK/Kec, CXCL16, CXCR3, ENA-78/LIX, Eotaxin-1, Eotaxin-2/MPIF-2, Exodus-2/SLC, Fractalkine/Neurotactin, GROalpha/MGSA, HCC-1, I-TAC, Lymphotactin/ATAC/SCM, MCP-1/MCAF, MCP-3, MCP-4, MDC/STCP-1/ABCD-1, MIP-1.quadrature., MIP-1.quadrature., MIP-2.quadrature./GRO.quadrature., MIP-3.quadrature./Exodus/LARC, MIP-3/Exodus-3/ELC, MIP-4/PARC/DC-CK1, PF-4, RANTES, SDF1, TARC, TECK, microbial toxins, ADP ribosylating toxins, microbial or viral antigens).

In one embodiment of the present invention, the protein of interest can be a multi-subunit protein or polypeptide. Multisubunit proteins that can be expressed include homomeric and heteromeric proteins. The multisubunit proteins may include two or more subunits that may be the same or different. For example, the protein may be a homomeric protein comprising 2, 3, 4, 5, 6, 7, 8, 9, 10, 11, 12 or more subunits. The protein also may be a heteromeric protein including 2, 3, 4, 5, 6, 7, 8, 9, 10, 11, 12, or more subunits. Exemplary multisubunit proteins include: receptors including ion channel receptors; extracellular matrix proteins including chondroitin; collagen; immunomodulators including MHC proteins, full chain antibodies, and antibody fragments; enzymes including RNA polymerases, and DNA polymerases; and membrane proteins.

In another embodiment, the protein of interest can be a blood protein. The blood proteins expressed in this embodiment include but are not limited to carrier proteins, such as albumin, including human and bovine albumin, transferrin, recombinant transferrin half-molecules, haptoglobin, fibrinogen and other coagulation factors, complement components, immunoglobulins, enzyme inhibitors, precursors of substances such as angiotensin and bradykinin, insulin, endothelin, and globulin, including alpha, beta, and gamma-globulin, and other types of proteins, polypeptides, and fragments thereof found primarily in the blood of mammals. The amino acid sequences for numerous blood proteins have been reported (see, S. S. Baldwin (1993) Comp. Biochem Physiol. 106b:203-218), including the amino acid sequence for human serum albumin (Lawn, L. M., et al. (1981) Nucleic Acids Research, 9:6103-6114.) and human serum transferrin (Yang, F. et al. (1984) Proc. Natl. Acad. Sci. USA 81:2752-2756).

In another embodiment, the protein of interest can be an enzyme or co-factor. The enzymes and co-factors expressed in this embodiment include but are not limited to aldolases, amine oxidases, amino acid oxidases, aspartases, B12 dependent enzymes, carboxypeptidases, carboxyesterases, carboxylyases, chemotrypsin, CoA requiring enzymes, cyanohydrin synthetases, cystathione synthases, decarboxylases, dehydrogenases, alcohol dehydrogenases, dehydratases, diaphorases, dioxygenases, enoate reductases, epoxide hydrases, fumerases, galactose oxidases, glucose isomerases, glucose oxidases, glycosyltrasferases, methyltransferases, nitrile hydrases, nucleoside phosphorylases, oxidoreductases, oxynitilases, peptidases, glycosyltrasferases, peroxidases, enzymes fused to a therapeutically active polypeptide, tissue plasminogen activator; urokinase, reptilase, streptokinase; catalase, superoxide dismutase; Dnase, amino acid hydrolases (e.g., asparaginase, amidohydrolases); carboxypeptidases; proteases, trypsin, pepsin, chymotrypsin, papain, bromelain, collagenase; neuramimidase; lactase, maltase, sucrase, and arabinofuranosidases.

In another embodiment, the protein of interest can be a single chain, Fab fragment and/or full chain antibody or fragments or portions thereof. A single-chain antibody can include the antigen-binding regions of antibodies on a single stably-folded polypeptide chain. Fab fragments can be a piece of a particular antibody. The Fab fragment can contain the antigen binding site. The Fab fragment can contain 2 chains: a light chain and a heavy chain fragment. These fragments can be linked via a linker or a disulfide bond.

In other embodiments, the protein of interest is a protein that is active at a temperature from about 20 to about 42° C. In one embodiment, the protein is active at physiological temperatures and is inactivated when heated to high or extreme temperatures, such as temperatures over 65° C.

In one embodiment, the protein of interest is a protein that is active at a temperature from about 20 to about 42° C., and/or is inactivated when heated to high or extreme temperatures, such as temperatures over 65° C.; is, or is substantially homologous to, a native protein, such as a native mammalian or human protein and not expressed from nucleic acids in concatameric form, where the promoter is not a native promoter in to the host cell used in the array but is derived from another organism, such as *E. coli*.

The heterologous protein(s) expressed using the compositions and methods of the invention can be any protein wished to be overexpressed, e.g., a protein that has been found to to be difficult to express. Such a protein may have been found to form inclusion bodies, aggregate, be degraded, or otherwise be produced in an unsatisfactory manner in previous attempts at overexpression. The protein may have been predicted to be insoluble based on analysis of the amino acid sequence. It is known to those of skill in the art that the propensity for a protein to be insoluble can be evaluated using prediction tools available to those of skill in the art. Prediction tools include, e.g., PROSO, described by Smialowski, et al., 2007, "Protein solubility: sequence based prediction and experimental verification," Bioinformatics 23(19):2536. PROSO can be used to assess the chance that a protein will be soluble upon heterologous expression in *E. coli*. The sequence-based approach classifies proteins as "soluble" or "insoluble." Another tool is SOLpro, described by Magnan, et al., 2009, "SOLpro: accurate sequence-based prediction of protein solubility," Bioinformatics 25(17):2200-2207. SOLpro predicts the propensity of a protein to be soluble upon overexpression in *E. coli*. It is integrated in the SCRATCH suite of predictors and is available for download as a standalone application and for use at the Scratch proteomics website.

Table 9 lists exemplary heterologous proteins that can be expressed using the methods and arrays of the present invention, and includes examples of references and sequence information relating to proteins listed. The lists of exemplary proteins and exemplary sequences provided, in Table 8 and elsewhere herein, are in no way intended to be limiting. It is understood that the compositions and methods of the invention can be used in the expression of any desired protein.

TABLE 9

Exemplary Heterologous Proteins

| Protein Class | Exemplary Protein | Exemplary References/Sequences (incorporated herein by reference) |
|---|---|---|
| Vertebrate and Invertebrate Animal Toxins | ω-Agatoxin<br>μ-Agatoxin | Swiss-Prot Acc. No. P15969 (omega agatoxin 1A)<br>Swiss-Prot: P15970 (omega agatoxin 1B) |
| | Agitoxin | |
| | Allopumiliotoxin 267A | |
| | ω-Atracotoxin-HV1 | |
| | δ-Atracotoxin-Hv1b | |
| | Batrachotoxin (Dendrobatidae frogs) | |

TABLE 9-continued

| Exemplary Heterologous Proteins | | |
|---|---|---|
| Protein Class | Exemplary Protein | Exemplary References/Sequences (incorporated herein by reference) |
| | Botrocetin (*Bothrops jararaca*) | Usami, et al., 1993, "Primary structure of two-chain botrocetin, a von Willebrand factor modulator purified from the venom of *Bothrops jararaca*," Proc. Natl. Acad. Sci. USA 90: 928-932 |
| | Bufotoxins (Arenobufagin, Bufotalin, Bufotenin · Cinobufagin, Marinobufagin) | |
| | Bungarotoxin (Alpha-Bungarotoxin, Beta-Bungarotoxin) | |
| | Calcicludine | |
| | Calciseptine | |
| | Cardiotoxin III | |
| | Catrocollastatin C (*Crotalus atrox*) | Calvete, et al., 2000, "The disulfide bond pattern of catrocollastatin C, a disintegrin-like/cysteine-rich protein isolated from *Crotalus atrox* venom," Protein Science 9: 1365-1373 |
| | Charybdotoxin | |
| | Ciguatera | |
| | Cobra venom cytotoxins | Chiou, et al., 1993, "Cobra venom cardiotoxin (cytotoxin) isoforms and neurotoxin: Comparative potency of protein kinase C inhibition and cancer cell cytotoxicity and modes of enzyme inhibition," Biochemistry, 32 (8), pp 2062-2067 |
| | Conotoxin | |
| | Echinoidin (*Anthocidaris crassispina*) | |
| | Eledoisin | |
| | Epibatidine | |
| | Fibrolase (*Agkistrodon contortrix contortrix*) | Randolph, et al., 1992, "Amino acid sequence of fibrolase, a direct-acting fibrinolytic enzyme from *Agkistrodon contortrix contortrix* venom," Protein Science 1 590-600 |
| | Hefutoxin | |
| | Histrionicotoxin | |
| | Huwentoxin-I | |
| | Huwentoxin-II (*Selenocosmia huwena*) | Shu, et al., 2002, "The structure of spider toxin huwentoxin-II with unique disulfide linkage: Evidence for structural evolution," Protein Science 11: 245-252 |
| | J-ACTX-Hv1c | |
| | Kunitz-Type Toxins, e.g. Dendrotoxin-K, Dendrotoxin 1 | Yuan, et al., 2008, "Discovery of a distinct superfamily of Kunitz-type toxin (KTT) from tarantulas," PLoS one 3(10): e3414, doi: 10.1371/journal.pone.0003414 |
| | Latrotoxin (Alpha-latrotoxin) | |
| | Margatoxin | |
| | Maurotoxin | |
| | Onchidal | |
| | PhTx3 | |
| | Pumiliotoxin 251D | |
| | Rattlesnake lectin | |
| | Robustoxin | |
| | Saxitoxin | |
| | Scyllatoxin | |
| | Slotoxin | |
| | Stromatoxin | |
| | Taicatoxin | |
| | Tarichatoxin | |
| | Tetrodotoxin (e.g., toads, Tetraodontiformes fish, Naticidae sea snails, newts, *Vibrio* bacteria) | |
| Plant toxins | Ricin (*Ricinus communis*) | GenBank Nucleotide Acc. No. DQ661048 (Ricin A chain)<br>Halling, et al., 1985, "Genomic cloning and characterization of a ricin gene from *Ricinus communis*" Nucleic Acids Res. 13(22): 8019-33 (Sequence on p. 8025) |
| | Gelonin (Gelonium multiflorum) | GenBank Acc. No. L12243 |

TABLE 9-continued

| Exemplary Heterologous Proteins | | |
|---|---|---|
| Protein Class | Exemplary Protein | Exemplary References/Sequences (incorporated herein by reference) |
| Fungal toxins | Aflatoxin<br>Amatoxin (Alpha-amanitin, Beta-amanitin, Gamma-amanitin, Epsilon-amanitin)<br>Citrinin<br>Cytochalasin<br>Ergotamine<br>Fumagillin<br>Fumonisin (Fumonisin B1, Fumonisin B2) | |
| | Gliotoxin | GenBank Acc. No. AAW03299 (gliotoxin)<br>Gardiner, et al., 2005, "Bioinformatic and expression analysis of the putative gliotoxin biosynthetic gene cluster of *Aspergillus fumigatus*, FEMS Microbiol. Lett. 248(2): 241-248<br>Tsunawaki, et al., 2004, "Fungal metabolite gliotoxin inhibits assembly of the human respiratory burst NADPH oxidase," Infection and Immunity 72(6): 3373-3382 |
| | Helvolic Acid<br>Ibotenic acid<br>Muscimol<br>Ochratoxin<br>Patulin<br>Sterigmatocystin<br>Trichothecene<br>Vomitoxin<br>Zeranol<br>Zearalenone | |
| Bacterial toxins | *Bacillus anthracis* toxins: e.g., Anthrax toxin, Adenylate cyclase, rPA | Swiss-Prot Acc. No. P13423.2 (rPA, Protective Antigen) |
| | *Bacillus thuringiensis*: Cry toxins | GenBank accession numbers for Cry proteins listed in, e.g., Table 1 of U.S. Pat. No. 6,642,030, "Nucleic acid compositions encoding modified *Bacillus thuringiensis* coleopteran-toxic crystal proteins" |
| | *Bordetella pertussis*: *Pertussis* toxin<br>*Pertussis* toxin variants | EMBL M13223 (*pertussis* toxin operon of 5 ORFs)<br>U.S. Pat. No. 5,085,862, "Genetic detoxification of *pertussis* toxin"<br>U.S. Pat. No. 5,165,927, "Composition with modified *pertussis* toxin"<br>U.S. Pat. No. 5,773,600, "DNA encoding *pertussis* toxin muteins" |
| | *Clostridium botulinum*: *Botulinum* toxins | Fischer, et al., 2007, "Crucial role of the disulfide bridge between *botulinum* neurotoxin light and heavy chains in protease translocation across membranes," J. Biol. Chem. 282(40): 29604-11, Epub,<br>Baldwin, et al., 2008, "Subunit vaccine against the seven serotypes of botulism," Infection and Immunity 76(3): 1314-1318 |
| | *Clostridium difficile*: Toxin A, B<br>Wild type, variants, mutants | Swiss-Prot Acc. No. P16154 (wild type Toxin A, strain VPI)<br>Swiss-Prot Acc. No. P18177 (wild type Toxin B, strain VPI)<br>US Pat. App. Pub. Nos. 2004/0028705 and 2008/0107673, "Mutants of *clostridium difficile* toxin B and methods of use" |
| | *Clostridium perfringens*: Alpha toxin, Enterotoxin | |
| | *Clostridium tetani*: Tetanus toxin | GenBank Acc. No. 1A8D_A<br>U.S. Pat. No. 5,571,694, "Expression of tetanus toxin fragment C in yeast"<br>U.S. Pat. No. 6,372,225, "Tetanus toxin functional fragment antigen and tetanus vaccine"<br>Schiavo, et al., 1990, "An intact interchain disulfide bond is required for the neurotoxicity of tetanus toxin," Infection and Immunity 58(12): 4136-4141<br>U.S. Pat. No. 7,556,817, "Clostridial toxin activatable Clostridial toxins" |

TABLE 9-continued

| Exemplary Heterologous Proteins | | |
|---|---|---|
| Protein Class | Exemplary Protein | Exemplary References/Sequences (incorporated herein by reference) |
| | *Corynebacterium beta*: Diphtheria toxin (DT) | GenBank Acc. No. K01722 (DT nucleotide)<br>GenBank Acc. No. AAA32182 (DT protein)<br>Greenfield, et al., 1983, "Nucleotide sequence of the structural gene for diphtheria toxin carried by corynebacteriophage beta," Proc. Natl. Acad. Sci. U.S.A. 80(22): 6853-6857<br>Papini, et al., 1993, "Cell penetration of diphtheria toxin. Reduction of the interchain disulfide bridge is the rate-limiting step of translocation in the cytosol," J. Biol. Chem. 268(3): 1567-74 |
| | Diphtheria toxin variants, e.g., CRM45, CRM176, CRM197 | GenBank Acc. No. 1007216A (CRM197)<br>GenBank Acc. No. 1007216B (CRM45)<br>U.S. Pat. No. 7,585,942, "Diphtheria toxin variant"<br>Orr, et al., 1999, "Expression and Immunogenicity of a Mutant Diphtheria Toxin Molecule, CRM 197, and Its Fragments in *Salmonella typhi* Vaccine Strain CVD 908-htrA," Infection and Immunity 67(8): 4290-4294<br>Giannini, et al., 1984, "The amino-acid sequence of two non-toxic mutants of diphtheria toxin: CRM45 and CRM197," Nucleic Acids Research 12(10): 4063-4069 |
| | *E. coli*:<br>Verotoxin/Shiga-like toxin<br>Heat-stable enterotoxin<br>Heat-labile enterotoxin<br>Enterotoxins | GenBank Acc. No. AAA24685 (Heat-labile enterotoxin A prepeptide)<br>GenBank Acc. No. AAC60441 (Heat-labile enterotoxin B subunit; LTc B subunit) |
| | *Listeria monocytogenes*:<br>Listeriolysin O | |
| | *Mycobacterium tuberculosis*: Cord factor | |
| | *Pseudomonas* exotoxin | |
| | *Salmonella* endotoxin, exotoxin | |
| | *Shigella disinteriae*: Shiga toxin | |
| | *Staphylococcus aureus*:<br>Alpha/beta/delta toxin<br>Exfoliatin Toxin<br>Toxic shock syndrome toxin<br>Enterotoxins<br>Leukocidin (Panton-Valentine leukocidin) | |
| | *Streptococcus pyogenes*:<br>Streptolysin S | Akao, et al., 1999, "Unique synthetic peptides stimulating streptolysin S production in streptococci," J. Biochem. 125(1): 27-30<br>Akao, et al., 1992, "Purification and characterization of a peptide essential for formation of streptolysin S by *Streptococcus pyogenes*," Infection and Immunity 60(11): 4777-4780 |
| | *Vibrio cholerae*: Cholera toxin | GenBank Acc. No. ACH70471<br>Tsai, et al., 2002, "Unfolded cholera toxin is transferred to the ER membrane and released from protein disulfide isomerase upon oxidation by Ero1," J. Cell Biology 159(2): 207-215 |
| Toxin-like proteins | | "ClanTox: a classifier of short animal toxins," Nucleic Acids Research 37, Web Server issue W363-W368 doi: 10.1093/nar/gkp299. |
| Cytokines (Receptors and Ligands) | Interferon alpha 2a | Swiss-Prot P01563<br>(mature form amino acids 24-188) |
| | Interferon alpha 2b | GenBank Acc. No. NP_000596<br>(mature form amino acids 24-188)<br>U.S. Pat. No. 7,189,389, "Pharmaceutical composition of human interferon-alpha 2 and interferon-alpha 8 subtypes" |
| | Interferon beta | GenBank Acc. No. ABS89222<br>U.S. Pat. No. 7,399,463, "HSA-free formulations of interferon-beta" |

TABLE 9-continued

Exemplary Heterologous Proteins

| Protein Class | Exemplary Protein | Exemplary References/Sequences (incorporated herein by reference) |
|---|---|---|
| | Interferon gamma | GenBank Acc. No. NP_000610 (mature form aa 24-166)<br>U.S. Pat. No. 7,524,931, "Full-length interferon gamma polypeptide variants"<br>U.S. Pat. No. 7,504,237, "Polynucleotides encoding interferon gamma polypeptides" |
| | Interleukin 1 beta | GenBank Acc. No. NP_000567 (mature form aa 117-269) |
| | Interleukin 6 | GenBank Acc. No. AAC41704<br>U.S. Pat. No. 7,560,112, "Anti-il-6 antibodies, compositions, methods and uses" |
| | Tumor Necrosis Factor Family, e.g.,<br>TNFα<br>TNFβ (formerly LTα)<br>LTβ<br>TRELL<br>FasL<br>CD40L<br>CD30L<br>CD27L<br>4-1BBL<br>TNF-related apoptosis-inducing ligand (TRAIL)<br>RANKL (also TRANCE)<br>GITRL<br>TNF-2<br>TFRP<br>OX40L | GenBank Acc. No. CAA26669.1 (human TNF-alpha)<br>(mature form aa 77-233)<br>PCT WO 2005/103077<br>Amino acid sequences for human TNF, LT-α, LT-β, FasL, TFRP, TRAIL, CD27L, CD30L, CD40L, and 4-1BBL and TRELL provided by, e.g., U.S. Pat. No. 7,566,769," Tumor necrosis factor related ligand"<br>GenBank Acc. No. AAA61198 (human tumor necrosis factor)<br>Wang, et al., 1985, "Molecular cloning of the complementary DNA for human tumor necrosis factor," Science 228 (4696), 149-154<br>GenBank Acc. No. AAA61200 (human tumor necrosis factor)<br>Nedospasov, et al., 1986, "Tandem arrangement of genes coding for tumor necrosis factor (TNF-alpha) and lymphotoxin (TNF-beta) in the human genome," Cold Spring Harb. Symp. Quant. Biol. 51 Pt 1, 611-624<br>U.S. Pat. No. 7,544,519, "Fhm a novel member of the TNF ligand supergene family: materials and methods for interaction modulators"<br>Mouse and human RANKL sequences provided in, e.g., U.S. Pat. No. 7,411,050, "Monoclonal blocking antibody to human RANKL"<br>GenBank Acc. No. AB008426 (mouse RANKL)<br>Yasuda, et al., 1998, "Osteoclast differentiation factor is a ligand for osteoprotegerin/osteoclastogenesis-inhibitory factor and is identical to TRANCE/RANKL," Proc. Natl. Acad. Sci. U.S.A. 95(7), 3597-3602<br>Anderson, et al., 1997, "A homologue of the TNF receptor and its ligand enhance T-cell growth and dendritic-cell function," Nature 390 (6656), 175-179 |
| Antibodies/Antibody Derivatives | Modified anti-TNF-alpha antibody<br>Infliximab (Remicade) | U.S. Pat. No. 6,015,557, "Tumor necrosis factor antagonists for the treatment of neurological disorders"<br>Nagahira, et al., Humanization of a mouse neutralizing monoclonal antibody against tumor necrosis factor-alpha (TNF-alpha), J Immunol Methods. 1999 Jan 1; 222(1-2): 83-92<br>Knight, et al., Construction and initial characterization of a mouse-human chimeric anti-TNF antibody. Mol Immunol. 1993 Nov; 30(16): 1443-53. |
| | Golimumab (Simponi)<br>Adalimumab (Humira) | |
| | Diabodies | EP 0 404 097, "Bispecific and oligospecific, mono- and oligovalent receptors, production and applications thereof"<br>WO 93/11161, "Multivalent antigen-binding proteins"<br>Hollinger et al., Proc. Natl. Acad. Sci. USA, 90: 6444-6448 (1993)); |

TABLE 9-continued

| Exemplary Heterologous Proteins | | |
|---|---|---|
| Protein Class | Exemplary Protein | Exemplary References/Sequences (incorporated herein by reference) |
| | Linear antibodies | U.S. Pat. No. 5,641,870, "Low pH hydrophobic interaction chromatography for antibody purification"<br>Zapata et al., 1995, "Engineering linear F(ab')2 fragments for efficient production in Escherichia coli and enhanced antiproliferative activity," Protein Eng. 8(10): 1057-1062 |
| | Nanobodies<br>Single-domain antibodies (e.g., shark IgNAR or VNAR, camelid)<br>Heterospecific antibodies<br>Trivalent antibodies | U.S. Pat. App. Pub. No. 2007/0178082 and 2009/0238829, "Stabilized single domain antibodies"<br>U.S. Pat. App. Pub. No. 2006/0149041 and 2006/0149041 "Therapeutic polypeptides, homologues thereof, fragments thereof and for use in modulating platelet-mediated aggregation"<br>U.S. Pat. App. Pub. No. 2009/0252681 "Nanobodies and Polypeptides Against EGFR and IGF-IR"<br>U.S. Pat. App. Pub. No. 2009/0074770, "Amino acid sequences that bind to serum proteins in a manner that is essentially independent of the pH, compounds comprising the same, and uses thereof"<br>U.S. Pat. App. Pub. No. 2009/0028880, "Serum albumin binding proteins"<br>U.S. Pat. App. Pub. No. 2009/0022721, 2007/0077249, and 2007/0237769 "Single domain antibodies directed against tumour necrosis factor-alpha and uses therefor"<br>U.S. Pat. App. Pub. No. 2008/0267949 "Peptides capable of binding to serum proteins"<br>U.S. Pat. App. Pub. No. 2008/0107601 "Nanobodies Against Amyloid-Beta and Polypeptides Comprising the Same for the Treatment of Degenerative Neural Diseases Such as Alzheimer's Disease"<br>U.S. Pat. App. Pub. No. 2008/0096223 "Methods And Assays For Distinguishing Between Different Forms Of Diseases And Disorders Characterized By Thrombocytopenia And/Or By Spontaneous Interaction Between Von Willebrand Factor (Vwf) And Platelets"<br>U.S. Pat. App. Pub. No. 2007/0269422 "Serum albumin binding proteins with long half-lives"<br>U.S. Pat. App. Pub. No. 2006/0246477 and 2006/0211088 "Method for generating variable domain sequences of heavy chain antibodies"<br>U.S. Pat. App. Pub. No. 2006/0115470 "Camelidae antibodies against immunoglobulin e and use thereof for the treatment of allergic disorders"<br>Wesolowski, et al., 2009, "Single domain antibodies: promising experimental and therapeutic tools in infection and immunity," Med Microbiol Immunol. 198(3): 157-174<br>US Pat. App. Pub. No. 2009/0148438, "Binding Moieties Based on Shark Ignar Domains" |
| | BiTE molecules | U.S. Pat. No. 7,235,641, "Bispecific antibodies"<br>U.S. Pat. No. 7,575,923 and 7,112,324, "CD19xCD3 specific polypeptides and uses thereof"<br>US Pat. App. Pub. No. 2006/0193852 "Novel CD19xCD3 specific polypeptides and uses thereof"<br>US Pat. App. Pub. No. 2007/0123479 "Pharmaceutical compositions comprising bispecific anti-cd3, anti-cd19 antibody constructs for the treatment of b-cell related disorders" |

TABLE 9-continued

| Exemplary Heterologous Proteins | | |
|---|---|---|
| Protein Class | Exemplary Protein | Exemplary References/Sequences (incorporated herein by reference) |
| | | US Pat. App. Pub. Nos. 2009/0226444 and 2009/0226432, "Pharmaceutical Antibody Compositions with Resistance To Soluble CEA" |
| | Domain antibodies (dAbs) | U.S. Pat. No. 7,563,443, "Monovalent anti-CD40L antibody polypeptides and compositions thereof" US Pat. App. Pub. No. 2006/0062784 "Compositions monovalent for CD40L binding and methods of use" |
| | scFV | GenBank Acc. No. CAA12399.1 |
| | Anti-beta-galactosidase | GenBank Acc. No. CAA12398 |
| | Humanized/Modified antibodies | U.S. Pat. App. Pub. No. 2009/0191186, "Antibodies to the PcrV Antigen of *Pseudomonas aeruginosa*" Bebbington, et al., 2008, "Antibodies for the treatment of bacterial infections: current experience and fugure prospects," Current Opin. in Biotech. 19(6): 613-619 |
| Growth Factors/Hormones | Activin A (Inhibin A) | Swiss-Prot Acc. No. P08476.2 (Inhibin beta A chain/Activin beta-A chain) US 575751, "Activin-A mutants" |
| | Epidermal growth factor (EGF) | Swiss-Prot Acc. No. P01133.2 (mature form aa 971-1023) |
| | Erythropoietin | Swiss-Prot Acc. No. P01588 (mature form aa 28-193) U.S. Pat. No. 7,553,941, "Long-acting polypeptides and methods of producing same" |
| | Fibroblast growth factors 1, 2, 21 (FGF-1, 2, 21) | GenBank Acc. No. NP_061986 U.S. Pat. No. 7,459,540, "Fibroblast growth factor-like polypeptides" U.S. Pat. No. 7,576,190, "FGF-21 fusion proteins" U.S. Pat. No. 7,491,697, "Muteins of fibroblast growth factor 21" U.S. Pat. No. 7,582,607, "Muteins of fibroblast growth factor 21" GenBank Acc. Nos. AAH18404 and ABI75345 |
| | Granulocyte Colony Stimulating Factor | GenBank Acc. No. ABI85510.1 U.S. Pat. No. 7,381,804, "G-CSF analog compositions and methods" |
| | Growth Hormone Cytoplasmic Secreted Variants | GenBank NP_000506.2 (mature form aa 27-217) U.S. Pat. No. 7,553,941, "Long-acting polypeptides and methods of producing same" U.S. Pat. No. 7,553,940, "Long-acting EPO polypeptides and derivatives thereof and methods thereof" |
| | Hepatocyte growth factor (HGF) | GenBank Acc. No. BAA14348 |
| | Keratinocyte growth factor (KGF) | |
| | Leukemia Inhibitory Factor | GenBank Acc. No. AAA51699 (mature form aa 25-213) U.S. Pat. No. 7,445,772, "Heterodimeric four helix bundle cytokines" |
| | Nerve growth factor (NGF) | |
| | Platelet derived growth factor (PDGF) | |
| | Thrombopoietin | Swiss-Prot Acc. No. P40225 (amino acids 22-353) U.S. Pat. No. 6,673,580, "Identification and modification of immunodominant epitopes in polypeptides" |
| | Transforming growth factor-alpha (TGF-alpha) | |
| | Transforming growth factor-beta (TGF-beta) | |
| | Vascular endothelial growth factor (VEGF) | GenBank Acc. No. CAA44447 U.S. Pat. No. 7,427,596, "Variants of vascular endothelial cell growth factor, their uses, and processes for their production" U.S. Pat. No. 7,566,566, "Materials and methods involving hybrid vascular endothelial growth factor DNAs and proteins" |

TABLE 9-continued

Exemplary Heterologous Proteins

| Protein Class | Exemplary Protein | Exemplary References/Sequences (incorporated herein by reference) |
|---|---|---|
| Human Therapeutic Proteins | ApoA1 and ApoA1 Milano | GenBank Acc. No. CAT02154<br>GenBank Acc. No. ACK12192<br>U.S. Pat. No. 7,439,323, "Cysteine-containing peptides having antioxidant properties"<br>WO 2008/017906<br>(mature form aa 25-267) |
| | Insulin | Swiss-Prot Acc. No. P01308 |
| | Proinsulin | U.S. Pat. No. 7,547,821, "Methods for the production of insulin in plants" |
| | Insulin-like Growth Factor | Swiss-Prot. Acc. No. P01343 (IA)<br>U.S. Pat. No. 7,439,063, "Neuroprotective synergy of erythropoietin and insulin-like growth factors"<br>Swiss-Prot. Acc. No. P05019 (IB)<br>U.S. Pat. No. 7,217,796, "Neutralizing human anti-IGFR antibody" |
| | Kringle Domains of Human Plasminogen | GenBank Acc. No. AAA36451<br>(amino acids 469-562)<br>U.S. Pat. No. 7,175,840, "Compositions for gene therapy of rheumatoid arthritis including a gene encoding an anti-angiogenic protein or parts thereof"<br>US Pat. App. Pub. No. 2004/0138127, "Novel antiangiogenic peptides, polypeptides encoding same and methods for inhibiting angiogenesis" |
| Chaperones | Hsp 90 (human) | Swiss-Prot Acc. No. P07900 |
| | BiP (human) | |
| | GRP94 (human) | |
| | GRP170 (human) | |
| | Calnexin (human) | |
| | Calreticulin (human) | |
| | HSP47 (human) | |
| | ERp29 (human) | |
| | Protein disulfide isomerase (PDI) (human) | |
| | Peptidyl prolyl cis-trans-isomerase (PPI) (human) | |
| | ERp57 (human) | |
| Fusion Proteins/ Non-natural Proteins | Ontak (Eisai) | Foss, FM, 2001, "Interleukin-2 fusion toxin: targeted therapy for cutaneous T cell lymphoma," Ann N Y Acad Sci. 941: 166-76. |
| | Etanercept (Enbrel) | |
| | Anthrax rPA fusions | U.S. Pat. No. 7,537,771, "Expression system" |
| Therapeutic Enzymes | Nucleoside deaminase | GenBank Acc. No. NP_000013.2 |
| | Antimicrobial glycosidase-lysostaphin | GenBank Acc. No. AAB53783<br>(aa 249-493) |
| | Bovine aprotinin | U.S. Pat. No. 5,621,074, "Aprotinin analogs" |
| | Butyrylcholine esterase | GenBank Acc. No. AAA98113.1<br>U.S. Pat. No. 6,291,175, "Methods for treating a neurological disease by determining BCHE genotype" |
| | Ornithine carbamoyltransferase | |
| | Streptokinase C | GenBank Acc. No. P00779 |
| Biocatalytic Enzymes | Carboxylic acid reductase (*Nocardia*) | U.S. Pat. No. 5,795,759, "Carboxylic acid reductase, and methods of using same" |
| | DszA<br>DszB<br>DszC<br>DszD<br>(*Rhodococcus*) | U.S. Pat. No. 6,071,738, "Conversion of organosulfur compounds to oxyorganosulfur compounds for desulfurization of fossil fuels"<br>U.S. Pat. No. 5,952,208, "Dsz gene expression in *pseudomonas* hosts" |
| | L-aminoacylase (*Thermococcus litoralis*) | Toogood, et al., 2002, "A thermostable L-aminoacylase from *Thermococcus litoralis*: cloning, overexpression, characterization, and applications in biotransformations," Extremophiles 6(2): 1431-0651<br>Singleton, et al., 2000, "Cloning, expression, and characterization of pyrrolidone carboxyl peptidase from the archaeon *Thermococcus litoralis*" Extremophiles 4 (5), 297-303 |

TABLE 9-continued

| Exemplary Heterologous Proteins | | |
|---|---|---|
| Protein Class | Exemplary Protein | Exemplary References/Sequences (incorporated herein by reference) |
| Pathogen Proteins/Antigens | *Chlamydia trachomatis* major outer membrane protein (MOMP) | GenBank Acc. No. ABB51004 (mature form aa 23-393) |
| | Cowpea Chlorotic Mottle Virus coat protein | GenBank Acc. No. NP_613277<br>US Pat. App. Pub. No. 2005/0214321, "Recombinant icosahedral virus like particle production in pseudomonads" |
| | *Salmonella* flagellin and variants thereof | GenBank Acc. No. AAA27067 (*Salmonella enterica* subsp. *enterica* serovar *Typhi*)<br>GenBank Acc. No. AAL20871 (*Salmonella enterica* subsp. *enterica* serovar *Typhimurium* str. LT2)<br>US 2007/0224205, "Compositions that include hemagglutinin, methods of making and methods of use thereof" |
| | HIV Gag | GenBank Acc. No. AAB50258.1 (HIV-1 Gag) |
| | HIV Vpr | Swiss-Prot Acc. No. P12520.2 |
| | HIV Nef | GenBank Acc. No. AAA44993 (HIV-1 Nef) |
| | Influenza Hemagglutinin | GenBank Acc. No. ABW06108.1 (Influenza A HA) |
| | *P. falciparum* circumsporozoite protein | GenBank Acc. No. CAB38998 |
| Reagent Proteins, Other Proteins | Alpha-1-anti-trypsin | U.S. Pat. No. 5,399,684, "DNA sequences expressing mammalian alpha-1-antitrypsin"<br>U.S. Pat. No. 5,736,379, "DNA sequences expressing mammalian alpha$_1$ antitrypsin" |
| | Horseradish Peroxidase C | GenBank Acc. No. CAA00083 |
| | LRP6 sub-domains | Swiss-Prot Acc. No. O75581 (amino acids 20-1370 and subdomians thereof)<br>U.S. Pat. No. 7,416,849, "HBM variants that modulate bone mass and lipid levels" |
| | Protein A, Cysteinyl Protein A | U.S. Pat. No. 5,151,350, "Cloned genes encoding recombinant protein A"<br>U.S. Pat. No. 5,084,559, "Protein A domain mutants" |
| | Streptavidin | GenBank Acc. No. CAA00084 |

In embodiments of the present invention, expression systems that successfully overexpress toxin proteins are identified. Toxin proteins contemplated for expression include, but are not limited to, animal toxins, plant toxins, fungal toxins, and bacterial toxins. Toxin proteins frequently contain structural elements, for example disulfide bonds, that lead to misfolding and insolubility in overexpression efforts. Kunitz-type toxins (KTTs), found in the venom of animals including spiders, snakes, cone snails, and sea anemones, usually have a peptide chain of around 60 amino acids and are stabilized by three disulfide bridges. Botrocetin, a toxin from snake venom that causes platelet aggregation by inducing binding of von Willebrand factor (vWF) to platelet glycoprotein Ib (GPIb), is present in a two-chain form containing both intrachain and interchain disulfide bonds. The Botrocetin two-chain form was reported to be about thirty times more active than the single chain form (Usami, et al., 1993). Catrocollastatin C, a snake venom toxin that impairs platelet aggregation by inhibiting fibrinogen binding to the αIIbβ3 integrin, contains 28 cysteine residues that form 14 disulfide bonds (Calvete, et al., 2000).

Toxin-like proteins have been identified in non-venomous contexts and shown to act as cell activity modulators. Toxin-like proteins include proteases, protease inhibitors, cell antigens, growth factors, etc. A toxin classification tool, ClanTox, available from The Sudarsky Center for Computational Biology at The Hebrew University of Jerusalem in Israel (HUJI) on the HUJI website, predicts whether a given protein is a toxin or toxin-like protein. The server also provides other information, including the presence of a signal peptide, the number of cysteine residues, and associated functional annotations. The tool is described by Naamati, et al., 2009, "ClanTox: a classifier of short animal toxins," Nucleic Acids Research 37, Web Server issue W363-W368 doi:10.1093/nar/gkp299.

Embodiments of the present invention contemplate the expression of antibodies or antibody fragments. Many forms of antibody fragments are known in the art and encompassed herein. "Antibody fragments" comprise only a portion of an intact antibody, generally including an antigen binding site of the intact antibody and thus retaining the ability to bind antigen. Examples of antibody fragments encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single arm of an antibody; (vi) the dAb fragment (Ward et al., Nature 341, 544-546 (1989)) which consists of a VH domain; (vii) isolated CDR regions; (viii) F(ab')$_2$ fragments, a bivalent fragment including two Fab' fragments linked by a disulfide bridge at the hinge region; (ix) single chain antibody molecules (e.g., single chain Fv; scFv) (Bird et al., Science 242:423-426 (1988); and Huston et al., PNAS (USA) 85:5879-5883 (1988)); (x) "diabodies" with two antigen binding sites, comprising a heavy chain variable domain (VH) connected to a light chain variable domain (VL) in the same polypeptide chain (see, e.g., EP 404,097; WO 93/11161; and Hollinger et al., Proc. Natl. Acad. Sci. USA, 90:6444-6448 (1993)); (xi) "linear antibodies" comprising a pair of tandem Fd segments (VH-$CH_1$-VH-$CH_1$) which, together with complementary light chain polypeptides, form a pair of antigen binding regions (Zapata et al. Proteifz *Eng.* 8(10): 1057-1062 (1995); and U.S. Pat. No. 5,641,870).

Moreover, embodiments of the present invention may include expression of antibody fragments that are modified to improve their stability and or to create antibody complexes with multivalency. For many medical applications, antibody fragments must be sufficiently stable against denaturation or proteolysis conditions, and the antibody fragments should ideally bind the target antigens with high affinity. A variety of techniques and materials have been developed to provide stabilized and or multivalent antibody fragments. An antibody fragment may be fused to a dimerization domain. In one embodiment, the antibody fragments expressed using the compositions and methods of the present invention are dimerized by the attachment of a dimerization domain, such as leucine zippers.

Fusion proteins and other non-natural proteins are also contemplated for expression using the methods and compositions of the invention. A non-natural protein can be, e.g., an engineered protein or a protein obtained by molecular modeling. An example of a fusion protein is Ontak (Eisai Corporation), also called denileukin diftitox or interleukin-2 (IL-2) fusion protein. Ontak was made by replacing the receptor-binding domain of diphtheria toxin with IL-2, the receptor for which is overexpressed in leukemia cells. IL-2 acts to carry the protein inhibitory function of diphtheria toxin to the targeted leukemia cells. Another fusion, Etanercept (Enbrel), links the human gene for soluble TNF receptor 2 to the gene for the Fc component of human immunoglobulin G1.

It is understood that the compositions and methods of the invention can be used to express variants and mutants of the proteins listed herein, regardless of whether specifically noted. Furthermore, as previously described, sequence information required for molecular genetics and genetic engineering techniques relating to many known proteins is widely available, e.g., from GenBank or other sources known to those of skill in the art. The GenBank data herein are provided by way of example. It is understood that if a GenBank accession number is not expressly provided herein, one of skill in the art can identify a desired gene or protein sequence by searching the GenBank database or the published literature.

It is generally recognized that a search of the GenBank database for a particular protein or gene can yield multiple hits. This can be due, e.g., to multiple listings of the same sequence, the occurrence of analogous genes or proteins in different species, or to the listing of truncated, partial, or variant sequences. One knowledgeable in the art will be aware that information relating to the sequence entry is provided in the accompanying information within the record, for example, in a published report cited in the record. Therefore, one of skill in the art, when searching for a sequence to use in the methods and compositions of the invention, will be able to identify the desired sequence from among a list of multiple results.

It is common knowledge in the art that proteins can be functionally equivalent despite differences in amino acid sequence. Substitution of an amino acid by a different amino acid having similar chemical properties and size (e.g., a conservative substitution) often does not significantly change protein function. Even nonconservative amino acid substitutions can be made with no effect on function, for example, when the change is made in a part of the protein that is not critical for function.

A "conservative amino acid substitution" is one in which the amino acid residue is replaced with an amino acid residue having a similar side chain, or similar physicochemical characteristics (e.g., electrostatic, hydrogen bonding, isosteric, hydrophobic features). The amino acids may be naturally occurring or non-natural (unnatural). Families of amino acid residues having similar side chains are known in the art. These families include amino acids with basic side chains (e.g. lysine, arginine, histidine), acidic side chains (e.g., aspartic acid, glutamic acid), uncharged polar side chains (e.g., glycine, asparagine, glutamine, serine, threonine, tyrosine, methionine, cysteine), nonpolar side chains (e.g., alanine, valine, leucine, isoleucine, proline, phenylalanine, tryptophan), beta-branched side chains (e.g., threonine, valine, isoleucine) and aromatic side chains (e.g., tyrosine, phenylalanine, tryptophan, histidine). Substitutions may also include non-conservative changes. Substitutions may also include changes that result in an increased resistance to proteolysis, for example, changes that eliminate a protease recognition site in the recombinant protein.

It is also known to one of skill in the art that proteins having the same amino acid sequence can be encoded by different nucleotide sequences due to the redundancy in the genetic code. The present invention thus includes the use of protein sequences that are different from the sequences provided or referenced herein, or available from public sources, but that are functionally equivalent nonetheless. Also included are proteins that have the same amino acid sequences but are encoded by different nucleotide sequences.

Codon usage or codon preference is well known in the art. The selected coding sequence may be modified by altering the genetic code thereof to match that employed by the bacterial host cell, and the codon sequence thereof may be enhanced to better approximate that employed by the host. Genetic code selection and codon frequency enhancement may be performed according to any of the various methods known to one of ordinary skill in the art, e.g., oligonucleotide-directed mutagenesis. Useful on-line InterNet resources to assist in this process include, e.g.: (1) the Codon Usage Database of the Kazusa DNA Research Institute (2-6-7 Kazusa-kamatari, Kisarazu, Chiba 292-0818 Japan); and (2) the Genetic Codes tables available from the NCBI Taxonomy database on the NIH website. For example, *Pseudomonas* species are reported as utilizing Genetic Code Translation Table 11 of the NCBI Taxonomy site, and as exhibiting the codon usage frequency as shown at the Kazusa site.

Equivalence in protein function can be evaluated by any of a number of assays suitable for the particular protein, as known in the art and described elsewhere herein. For example, the function of an antibody can be evaluated by measuring its binding to its target antigen, and enzymes can be evaluated by activity assay.

Host Cell

In one embodiment the invention provides an array of *P. fluorescens* host cells from which to optimally produce a heterologous protein or peptide of interest. *P. fluorescens* has been demonstrated to be an improved platform for production of a variety of proteins and several efficient secretion signals have been identified from this organism (see, e.g., U.S. Pat. App. Pub. No. 2006/0008877 and 2008/0193974).

The Pseudomonads system offers advantages for commercial expression of polypeptides and enzymes, in comparison with other bacterial expression systems. In particular, *P. fluorescens* has been identified as an advantageous expression system. *P. fluorescens* encompasses a group of common, nonpathogenic saprophytes that colonize soil, water and plant surface environments. Commercial enzymes derived from *P. fluorescens* have been used to reduce environmental contamination, as detergent additives, and for stereoselective hydrolysis. *P. fluorescens* is also used agriculturally to control pathogens. U.S. Pat. No. 4,695,462 describes the expression of recombinant bacterial proteins in *P. fluorescens*.

It is contemplated that alternate host cells, particularly *E. coli*, which utilizes expression elements described herein in a manner similar to *P. fluorescens*, or a multiplicity of different host cells, can be used to generate an array comprising a plurality of phenotypically distinct host cells that have been genetically modified to modulate the expression of one or more target genes, as discussed supra. The host cell can be any organism in which target genes can be altered. Methods of identifying target genes homologous to those listed in Tables 1 and 2 are known in the art. Further, one of skill in the art would understand how to identify target genes that are native to or useful in a host cell of interest. Many of these proteins are well known in the art. See, for example, U.S. Patent Application Publication No. 2006/0110747).

Host cells can be selected from "Gram-negative Proteobacteria Subgroup 18." "Gram-negative Proteobacteria Subgroup 18" is defined as the group of all subspecies, varieties, strains, and other sub-special units of the species *Pseudomonas fluorescens*, including those belonging, e.g., to the following (with the ATCC or other deposit numbers of exemplary strain(s) shown in parenthesis): *Pseudomonas fluorescens* biotype A, also called biovar 1 or biovar I (ATCC 13525); *Pseudomonas fluorescens* biotype B, also called biovar 2 or biovar II (ATCC 17816); *Pseudomonas fluorescens* biotype C, also called biovar 3 or biovar III (ATCC 17400); *Pseudomonas fluorescens* biotype F, also called biovar 4 or biovar IV (ATCC 12983); *Pseudomonas fluorescens* biotype G, also called biovar 5 or biovar V (ATCC 17518); *Pseudomonas fluorescens* biovar VI; *Pseudomonas fluorescens* Pf0-1; *Pseudomonas fluorescens* Pf-5 (ATCC BAA-477); *Pseudomonas fluorescens* SBW25; and *Pseudomonas fluorescens* subsp. *cellulosa* (NCIMB 10462).

The host cell can be selected from "Gram-negative Proteobacteria Subgroup 19." "Gram-negative Proteobacteria Subgroup 19" is defined as the group of all strains of *Pseudomonas fluorescens* biotype A. A particularly preferred strain of this biotype is *P. fluorescens* strain MB101 (see U.S. Pat. No. 5,169,760 to Wilcox), and derivatives thereof. An example of a preferred derivative thereof is *P. fluorescens* strain MB214, constructed by inserting into the MB101 chromosomal asd (aspartate dehydrogenase gene) locus, a native *E. coli* PlacI-lacI-lacZYA construct (i.e. in which PlacZ was deleted).

Additional *P. fluorescens* strains that can be used in the present invention include *Pseudomonas fluorescens* Migula and *Pseudomonas fluorescens* Loitokitok, having the following ATCC designations: [NCIB 8286]; NRRL B-1244; NCIB 8865 strain CO1; NCIB 8866 strain CO2; 1291 [ATCC 17458; IFO 15837; NCIB 8917; LA; NRRL B-1864; pyrrolidine; PW2 [ICMP 3966; NCPPB 967; NRRL B-899]; 13475; NCTC 10038; NRRL B-1603 [6; IFO 15840]; 52-1C; CCEB 488-A [BU 140]; CCEB 553 [EM 15/47]; IAM 1008 [AHH-27]; IAM 1055 [AHH-23]; 1 [IFO 15842]; 12 [ATCC 25323; NIH 11; den Dooren de Jong 216]; 18 [IFO 15833; WRRL P-7]; 93 [TR-10]; 108 [52-22; IFO 15832]; 143 [IFO 15836; PL]; 149 [2-40-40; IFO 15838]; 182 [IFO 3081; PJ 73]; 184 [IFO 15830]; 185 [W2 L-1]; 186 [IFO 15829; PJ 79]; 187 [NCPPB 263]; 188 [NCPPB 316]; 189 [PJ227; 1208]; 191 [IFO 15834; PJ 236; 22/1]; 194 [Klinge R-60; PJ 253]; 196 [PJ 288]; 197 [PJ 290]; 198 [PJ 302]; 201 [PJ 368]; 202 [PJ 372]; 203 [PJ 376]; 204 [IFO 15835; PJ 682]; 205 [PJ 686]; 206 [PJ 692]; 207 [PJ 693]; 208 [PJ 722]; 212. [PJ 832]; 215 [PJ 849]; 216 [PJ 885]; 267 [B-9]; 271 [B-1612]; 401 [C71A; IFO 15831; PJ 187]; NRRL B-3178 [4; IFO. 15841]; KY 8521; 3081; 30-21; [IFO 3081]; N; PYR; PW; D946-B83 [BU 2183; FERM-P 3328]; P-2563 [FERM-P 2894; IFO 13658]; IAM-1126 [43F]; M-1; A506 [A5-06]; A505 [A5-05-1]; A526 [A5-26]; B69; 72; NRRL B-4290; PMW6 [NCIB 11615]; SC 12936; A1 [IFO 15839]; F 1847 [CDC-EB]; F 1848 [CDC 93]; NCIB 10586; P17; F-12; AmMS 257; PRA25; 6133D02; 6519E01; Ni; SC15208; BNL-WVC; NCTC 2583 [NCIB 8194]; H13; 1013 [ATCC 11251; CCEB 295]; IFO 3903; 1062; or Pf-5.

In one embodiment, the host cell can be any cell capable of producing a protein or polypeptide of interest, including a *P. fluorescens* cell as described above. The most commonly used systems to produce proteins or polypeptides of interest include certain bacterial cells, particularly *E. coli*, because of their relatively inexpensive growth requirements and potential capacity to produce protein in large batch cultures. Yeasts are also used to express biologically relevant proteins and polypeptides, particularly for research purposes. Systems include *Saccharomyces cerevisiae* or *Pichia pastoris*. These systems are well characterized, provide generally acceptable levels of total protein production and are comparatively fast and inexpensive. Insect cell expression systems have also emerged as an alternative for expressing recombinant proteins in biologically active form. In some cases, correctly folded proteins that are post-translationally modified can be produced. Mammalian cell expression systems, such as Chinese hamster ovary cells, have also been used for the expression of proteins or polypeptides of interest. On a small scale, these expression systems are often effective. Certain biologics can be derived from proteins, particularly in animal or human health applications. In another embodiment, the host cell is a plant cell, including, but not limited to, a tobacco cell, corn, a cell from an *Arabidopsis* species, potato or rice cell.

In another embodiment, the host cell can be a prokaryotic cell such as a bacterial cell including, but not limited to, an *Escherichia* or a *Pseudomonas* species. Typical bacterial cells are described, for example, in "Biological Diversity: Bacteria and Archaeans," a chapter of the On-Line Biology Book, provided by Dr. M. J. Farabee of the Estrella Mountain Community College, Arizona, USA. In certain embodiments, the host cell can be a Pseudomonad cell, and can typically be a *P. fluorescens* cell. In other embodiments, the host cell can also be an *E. coli* cell. In another embodiment the host cell can be a eukaryotic cell, for example an insect cell, including but not limited to a cell from a *Spodoptera, Trichoplusia, Drosophila* or an *Estigmene* species, or a mammalian cell, including but not limited to a murine cell, a hamster cell, a monkey cell, a primate cell or a human cell.

In one embodiment, the host cell can be a member of any of the bacterial taxa. The cell can, for example, be a member of any species of eubacteria. The host can be a member of any one of the taxa: Acidobacteria, Actinobacteira, Aquificae, Bacteroidetes, Chlorobi, Chlamydiae, Choroflexi, Chrysiogenetes, Cyanobacteria, Deferribacteres, Deinococcus, Dictyoglomi, Fibrobacteres, Firmicutes, Fusobacteria, Gemmatimonadetes, Lentisphaerae, Nitrospirae, Planctomycetes, Proteobacteria, Spirochaetes, Thermodesulfobacteria, Thermomicrobia, Thermotogae, *Thermus* (Thermales), or Verrucomicrobia. In an embodiment of a eubacterial host cell, the cell can be a member of any species of eubacteria, excluding Cyanobacteria.

The bacterial host can also be a member of any species of Proteobacteria. A proteobacterial host cell can be a member of any one of the taxa Alphaproteobacteria, Betaproteobacteria, Gammaproteobacteria, Deltaproteobacteria, or Epsilonproteobacteria. In addition, the host can be a member of any one of the taxa Alphaproteobacteria, Betaproteobacteria, or Gammaproteobacteria, and a member of any species of Gammaproteobacteria.

In one embodiment of a Gamma Proteobacterial host, the host will be member of any one of the taxa Aeromonadales, Alteromonadales, Enterobacteriales, Pseudomonad ales, or Xanthomonadales; or a member of any species of the Enterobacteriales or Pseudomonad ales. In one embodiment, the host cell can be of the order Enterobacteriales, the host cell will be a member of the family Enterobacteriaceae, or may be a member of any one of the genera *Erwinia*, *Escherichia*, or *Serratia*; or a member of the genus *Escherichia*. Where the host cell is of the order Pseudomonad ales, the host cell may be a member of the family Pseudomonadaceae, including the genus *Pseudomonas*. Gamma Proteobacterial hosts include members of the species *Escherichia coli* and members of the species *Pseudomonas fluorescens*.

Other *Pseudomonas* organisms may also be useful. Pseudomonads and closely related species include Gram-negative Proteobacteria Subgroup 1, which include the group of Proteobacteria belonging to the families and/or genera described as "Gram-Negative Aerobic Rods and Cocci" by R. E. Buchanan and N. E. Gibbons (eds.), Bergey's Manual of Determinative Bacteriology, pp. 217-289 (8th ed., 1974) (The Williams & Wilkins Co., Baltimore, Md., USA) (hereinafter "Bergey (1974)"). Table 10 presents these families and genera of organisms.

TABLE 10

Families and Genera Listed in the Part, "Gram-Negative Aerobic Rods and Cocci" (in Bergey (1974))

| | |
|---|---|
| Family I. Pseudomonaceae | *Gluconobacter* |
| | *Pseudomonas* |
| | *Xanthomonas* |
| | *Zoogloea* |
| Family II. Azotobacteraceae | *Azomonas* |
| | *Azotobacter* |
| | *Beijerinckia* |
| | *Derxia* |
| Family III. Rhizobiaceae | *Agrobacterium* |
| | *Rhizobium* |
| Family IV. Methylomonadaceae | *Methylococcus* |
| | *Methylomonas* |
| Family V. Halobacteriaceae | *Halobacterium* |
| | *Halococcus* |
| Other Genera | *Acetobacter* |
| | *Alcaligenes* |
| | *Bordetella* |
| | *Brucella* |
| | *Francisella* |
| | *Thermus* |

"Gram-negative Proteobacteria Subgroup 1" also includes Proteobacteria that would be classified in this heading according to the criteria used in the classification. The heading also includes groups that were previously classified in this section but are no longer, such as the genera *Acidovorax, Brevundimonas, Burkholderia, Hydrogenophaga, Oceanimonas, Ralstonia*, and *Stenotrophomonas*, the genus *Sphingomonas* (and the genus *Blastomonas*, derived therefrom), which was created by regrouping organisms belonging to (and previously called species of) the genus *Xanthomonas*, the genus *Acidomonas*, which was created by regrouping organisms belonging to the genus *Acetobacter* as defined in Bergey (1974). In addition hosts can include cells from the genus *Pseudomonas, Pseudomonas enalia* (ATCC 14393), *Pseudomonas nigrifaciensi* (ATCC 19375), and *Pseudomonas putrefaciens* (ATCC 8071), which have been reclassified respectively as *Alteromonas haloplanktis, Alteromonas nigrifaciens*, and *Alteromonas putrefaciens*. Similarly, e.g., *Pseudomonas acidovorans* (ATCC 15668) and *Pseudomonas testosteroni* (ATCC 11996) have since been reclassified as *Comamonas acidovorans* and *Comamonas testosteroni*, respectively; and *Pseudomonas nigrifaciens* (ATCC 19375) and *Pseudomonas piscicida* (ATCC 15057) have been reclassified respectively as *Pseudoalteromonas nigrifaciens* and *Pseudoalteromonas piscicida*. "Gram-negative Proteobacteria Subgroup 1" also includes Proteobacteria classified as belonging to any of the families: Pseudomonad aceae, Azotobacteraceae (now often called by the synonym, the "Azotobacter group" of Pseudomonad aceae), Rhizobiaceae, and Methylomonadaceae (now often called by the synonym, "Methylococcaceae"). Consequently, in addition to those genera otherwise described herein, further Proteobacterial genera falling within "Gram-negative Proteobacteria Subgroup 1" include: 1) *Azotobacter* group bacteria of the genus *Azorhizophilus;* 2) Pseudomonad aceae family bacteria of the genera *Cellvibrio, Oligella*, and *Teredinibacter;* 3) Rhizobiaceae family bacteria of the genera *Chelatobacter, Ensifer, Liberibacter* (also called "*Candidatus Liberibacter*"), and *Sinorhizobium*; and 4) Methylococcaceae family bacteria of the genera *Methylobacter, Methylocaldum, Methylomicrobium, Methylosarcina*, and *Methylosphaera*.

In another embodiment, the host cell is selected from "Gram-negative Proteobacteria Subgroup 2." "Gram-negative Proteobacteria Subgroup 2" is defined as the group of Proteobacteria of the following genera (with the total numbers of catalog-listed, publicly-available, deposited strains thereof indicated in parenthesis, all deposited at ATCC, except as otherwise indicated): *Acidomonas* (2); *Acetobacter* (93); *Gluconobacter* (37); *Brevundimonas* (23); *Beyerinckia* (13); *Derxia* (2); *Brucella* (4); *Agrobacterium* (79); *Chelatobacter* (2); *Ensifer* (3); *Rhizobium* (144); *Sinorhizobium* (24); *Blastomonas* (1); *Sphingomonas* (27); *Alcaligenes* (88); *Bordetella* (43); *Burkholderia* (73); *Ralstonia* (33); *Acidovorax* (20); *Hydrogenophaga* (9); *Zoogloea* (9); *Methylobacter* (2); *Methylocaldum* (1 at NCIMB); *Methylococcus* (2); *Methylomicrobium* (2); *Methylomonas* (9); *Methylosarcina* (1); *Methylosphaera; Azomonas* (9); *Azorhizophilus* (5); *Azotobacter* (64); *Cellvibrio* (3); *Oligella* (5); *Pseudomonas* (1139); *Francisella* (4); *Xanthomonas* (229); *Stenotrophomonas* (50); and *Oceanimonas* (4).

Exemplary host cell species of "Gram-negative Proteobacteria Subgroup 2" include, but are not limited to the following bacteria (with the ATCC or other deposit numbers of exemplary strain(s) thereof shown in parenthesis): *Acidomonas methanolica* (ATCC 43581); *Acetobacter aceti* (ATCC 15973); *Gluconobacter oxydans* (ATCC 19357); *Brevundimonas diminuta* (ATCC 11568); *Beijerinckia indica* (ATCC 9039 and ATCC 19361); *Derxia gummosa* (ATCC 15994); *Brucella melitensis* (ATCC 23456), *Brucella abortus* (ATCC 23448); *Agrobacterium tumefaciens*

(ATCC 23308), *Agrobacterium radiobacter* (ATCC 19358), *Agrobacterium rhizogenes* (ATCC 11325); *Chelatobacter heintzii* (ATCC 29600); *Ensifer adhaerens* (ATCC 33212); *Rhizobium leguminosarum* (ATCC 10004); *Sinorhizobium fredii* (ATCC 35423); *Blastomonas natatoria* (ATCC 35951); *Sphingomonas paucimobilis* (ATCC 29837); *Alcaligenes faecalis* (ATCC 8750); *Bordetella pertussis* (ATCC 9797); *Burkholderia cepacia* (ATCC 25416); *Ralstonia pickettii* (ATCC 27511); *Acidovorax facilis* (ATCC 11228); Hydrogenophagaflava (ATCC 33667); *Zoogloea ramigera* (ATCC 19544); *Methylobacter luteus* (ATCC 49878); *Methylocaldum gracile* (NCIMB 11912); *Methylococcus capsulatus* (ATCC 19069); *Methylomicrobium agile* (ATCC 35068); *Methylomonas methanica* (ATCC 35067); *Methylosarcina fibrata* (ATCC 700909); *Methylosphaera hansonii* (ACAM 549); *Azomonas agilis* (ATCC 7494); *Azorhizophilus paspali* (ATCC 23833); *Azotobacter chroococcum* (ATCC 9043); *Cellvibrio mixtus* (UQM 2601); *Oligella urethralis* (ATCC 17960); *Pseudomonas aeruginosa* (ATCC 10145), *Pseudomonas fluorescens* (ATCC 35858); *Francisella tularensis* (ATCC 6223); *Stenotrophomonas maltophilia* (ATCC 13637); *Xanthomonas campestris* (ATCC 33913); and *Oceanimonas doudoroffli* (ATCC 27123).

In another embodiment, the host cell is selected from "Gram-negative Proteobacteria Subgroup 3." "Gram-negative Proteobacteria Subgroup 3" is defined as the group of Proteobacteria of the following genera: *Brevundimonas; Agrobacterium; Rhizobium; Sinorhizobium; Blastomonas; Sphingomonas; Alcaligenes; Burkholderia; Ralstonia; Acidovorax; Hydrogenophaga; Methylobacter; Methylocaldum; Methylococcus; Methylomicrobium; Methylomonas; Methylosarcina; Methylosphaera; Azomonas; Azorhizophilus; Azotobacter Cellvibrio; Oligella; Pseudomonas; Teredinibacter; Francisella; Stenotrophomonas; Xanthomonas*; and *Oceanimonas.*

In another embodiment, the host cell is selected from "Gram-negative Proteobacteria Subgroup 4." "Gram-negative Proteobacteria Subgroup 4" is defined as the group of Proteobacteria of the following genera: *Brevundimonas; Blastomonas; Sphingomonas; Burkholderia; Ralstonia; Acidovorax; Hydrogenophaga; Methylobacter; Methylocaldum; Methylococcus; Methylomicrobium; Methylomonas; Methylosarcina; Methylosphaera; Azomonas; Azorhizophilus; Azotobacter; Cellvibrio; Oligella; Pseudomonas; Teredinibacter; Francisella; Stenotrophomonas; Xanthomonas*; and *Oceanimonas.*

In another embodiment, the host cell is selected from "Gram-negative Proteobacteria Subgroup 5." "Gram-negative Proteobacteria Subgroup 5" is defined as the group of Proteobacteria of the following genera: *Methylobacter; Methylocaldum; Methylococcus; Methylomicrobium; Methylomonas; Methylosarcina; Methylosphaera; Azomonas; Azorhizophilus; Azotobacter; Cellvibrio; Oligella; Pseudomonas; Teredinibacter; Francisella; Stenotrophomonas; Xanthomonas*; and *Oceanimonas.*

The host cell can be selected from "Gram-negative Proteobacteria Subgroup 6." "Gram-negative Proteobacteria Subgroup 6" is defined as the group of Proteobacteria of the following genera: *Brevundimonas; Blastomonas; Sphingomonas; Burkholderia; Ralstonia; Acidovorax; Hydrogenophaga; Azomonas; Azorhizophilus; Azotobacter; Cellvibrio; Oligella; Pseudomonas; Teredinibacter; Stenotrophomonas; Xanthomonas*; and *Oceanimonas.*

The host cell can be selected from "Gram-negative Proteobacteria Subgroup 7." "Gram-negative Proteobacteria Subgroup 7" is defined as the group of Proteobacteria of the following genera: *Azomonas; Azorhizophilus; Azotobacter; Cellvibrio; Oligella; Pseudomonas; Teredinibacter; Stenotrophomonas; Xanthomonas*; and *Oceanimonas.*

The host cell can be selected from "Gram-negative Proteobacteria Subgroup 8." "Gram-negative Proteobacteria Subgroup 8" is defined as the group of Proteobacteria of the following genera: *Brevundimonas; Blastomonas; Sphingomonas; Burkholderia; Ralstonia; Acidovorax; Hydrogenophaga; Pseudomonas; Stenotrophomonas; Xanthomonas*; and *Oceanimonas.*

The host cell can be selected from "Gram-negative Proteobacteria Subgroup 9." "Gram-negative Proteobacteria Subgroup 9" is defined as the group of Proteobacteria of the following genera: *Brevundimonas; Burkholderia; Ralstonia; Acidovorax; Hydrogenophaga; Pseudomonas; Stenotrophomonas*; and *Oceanimonas.*

The host cell can be selected from "Gram-negative Proteobacteria Subgroup 10." "Gram-negative Proteobacteria Subgroup 10" is defined as the group of Proteobacteria of the following genera: *Burkholderia; Ralstonia; Pseudomonas; Stenotrophomonas*; and *Xanthomonas.*

The host cell can be selected from "Gram-negative Proteobacteria Subgroup 11." "Gram-negative Proteobacteria Subgroup 11" is defined as the group of Proteobacteria of the genera: *Pseudomonas; Stenotrophomonas*; and *Xanthomonas*. The host cell can be selected from "Gram-negative Proteobacteria Subgroup 12." "Gram-negative Proteobacteria Subgroup 12" is defined as the group of Proteobacteria of the following genera: *Burkholderia; Ralstonia; Pseudomonas*. The host cell can be selected from "Gram-negative Proteobacteria Subgroup 13." "Gram-negative Proteobacteria Subgroup 13" is defined as the group of Proteobacteria of the following genera: *Burkholderia; Ralstonia; Pseudomonas*; and *Xanthomonas*. The host cell can be selected from "Gram-negative Proteobacteria Subgroup 14." "Gram-negative Proteobacteria Subgroup 14" is defined as the group of Proteobacteria of the following genera: *Pseudomonas* and *Xanthomonas*. The host cell can be selected from "Gram-negative Proteobacteria Subgroup 15." "Gram-negative Proteobacteria Subgroup 15" is defined as the group of Proteobacteria of the genus *Pseudomonas.*

The host cell can be selected from "Gram-negative Proteobacteria Subgroup 16." "Gram-negative Proteobacteria Subgroup 16" is defined as the group of Proteobacteria of the following *Pseudomonas* species (with the ATCC or other deposit numbers of exemplary strain(s) shown in parenthesis): *Pseudomonas abietaniphila* (ATCC 700689); *Pseudomonas aeruginosa* (ATCC 10145); *Pseudomonas alcaligenes* (ATCC 14909); *Pseudomonas anguilliseptica* (ATCC 33660); *Pseudomonas citronellolis* (ATCC 13674); *Pseudomonas flavescens* (ATCC 51555); *Pseudomonas mendocina* (ATCC 25411); *Pseudomonas nitroreducens* (ATCC 33634); *Pseudomonas oleovorans* (ATCC 8062); *Pseudomonas pseudoalcaligenes* (ATCC 17440); *Pseudomonas resinovorans* (ATCC 14235); *Pseudomonas straminea* (ATCC 33636); *Pseudomonas agarici* (ATCC 25941); *Pseudomonas alcaliphila; Pseudomonas alginovora; Pseudomonas andersonii; Pseudomonas asplenii* (ATCC 23835); *Pseudomonas azelaica* (ATCC 27162); *Pseudomonas beyerinckii* (ATCC 19372); *Pseudomonas borealis; Pseudomonas boreopolis* (ATCC 33662); *Pseudomonas brassicacearum; Pseudomonas butanovora* (ATCC 43655); *Pseudomonas cellulosa* (ATCC 55703); *Pseudomonas aurantiaca* (ATCC 33663); *Pseudomonas chlororaphis* (ATCC 9446, ATCC 13985, ATCC 17418, ATCC 17461); *Pseudomonas fragi* (ATCC 4973); *Pseudomonas lundensis* (ATCC 49968); *Pseudomonas taetrolens* (ATCC 4683); *Pseudomonas cissicola* (ATCC 33616); *Pseudomonas coronafaciens; Pseudomonas diterpeniphila; Pseudomonas elongata* (ATCC 10144); *Pseudomonasflectens* (ATCC 12775); *Pseudomonas azotoformans; Pseudomonas brenneri; Pseudomonas cedrella; Pseudomonas corrugata* (ATCC 29736); *Pseudomonas extremorientalis; Pseudomonas fluorescens* (ATCC 35858); *Pseudomonas gessardii; Pseudomonas libanensis; Pseudomonas mandelii* CC 700871); *Pseudomonas marginalis* CC 10844); *Pseudomonas migulae; Pseudomonas mucidolens* (ATCC 4685); *Pseudomonas orientalis; Pseudomonas rhodesiae; Pseudomonas synxantha* (ATCC 9890); *Pseudomonas tolaasii* (ATCC 33618); *Pseudomonas veronii* (ATCC 700474); *Pseudomonas frederiksbergensis; Pseudomonas geniculata* (ATCC 19374); *Pseudomonas gingeri; Pseudomonas graminis; Pseudomonas grimontii; Pseudomonas halodenitrificans; Pseudomonas halophila; Pseudomonas hibiscicola* (ATCC 19867); *Pseudomonas huttiensis* (ATCC 14670); *Pseudomonas hydrogenovora; Pseudomonas jessenii* (ATCC 700870); *Pseudomonas kilonensis; Pseudomonas lanceolata* (ATCC 14669); *Pseudomonas lini; Pseudomonas marginate* (ATCC 25417); *Pseudomonas mephitica* (ATCC 33665); *Pseudomonas denitrificans* (ATCC 19244); *Pseudomonas pertucinogena* (ATCC 190); *Pseudomonas pictorum* (ATCC 23328); *Pseudomonas psychrophila; Pseudomonas filva* (ATCC 31418); *Pseudomonas monteilii* (ATCC 700476); *Pseudomonas mosselii; Pseudomonas oryzihabitans* (ATCC 43272); *Pseudomonas plecoglossicida* (ATCC 700383); *Pseudomonas putida* (ATCC 12633); *Pseudomonas reactans; Pseudomonas spinosa* (ATCC 14606); *Pseudomonas balearica; Pseudomonas luteola* (ATCC 43273); *Pseudomonas stutzeri* (ATCC 17588); *Pseudomonas amygdali* (ATCC 33614); *Pseudomonas avellanae* (ATCC 700331); *Pseudomonas caricapapayae* (ATCC 33615); *Pseudomonas cichorii* (ATCC 10857); *Pseudomonas ficuserectae* (ATCC 35104); *Pseudomonas fuscovaginae; Pseudomonas meliae* (ATCC 33050); *Pseudomonas syringae* (ATCC 19310); *Pseudomonas viridiflava* (ATCC 13223); *Pseudomonas thermocarboxydovorans* (ATCC 35961); *Pseudomonas thermotolerans; Pseudomonas thivervalensis; Pseudomonas vancouverensis* (ATCC 700688); *Pseudomonas wisconsinensis*; and *Pseudomonas xiamenensis.*

The host cell can be selected from "Gram-negative Proteobacteria Subgroup 17." "Gram-negative Proteobacteria Subgroup 17" is defined as the group of Proteobacteria known in the art as the "fluorescent Pseudomonads" including those belonging, e.g., to the following *Pseudomonas* species: *Pseudomonas azotoformans; Pseudomonas brenneri; Pseudomonas cedrella; Pseudomonas corrugata; Pseudomonas extremorientalis; Pseudomonas fluorescens; Pseudomonas gessardii; Pseudomonas libanensis; Pseudomonas mandelii; Pseudomonas marginalis; Pseudomonas migulae; Pseudomonas mucidolens; Pseudomonas orientalis; Pseudomonas rhodesiae; Pseudomonas synxantha; Pseudomonas tolaasii*; and *Pseudomonas veronii.*

Other suitable hosts include those classified in other parts of the reference, such as Gram (+) Proteobacteria. In one embodiment, the host cell is an *E. coli.* The genome sequence for *E. coli* has been established for *E. coli* MG1655 (Blattner, et al. (1997) The complete genome sequence of *Escherichia coli* K-12, Science 277(5331): 1453-74) and DNA microarrays are available commercially for *E. coli* K12 (MWG Inc, High Point, N.C.). *E. coli* can be cultured in either a rich medium such as Luria-Bertani (LB) (10 g/L tryptone, 5 g/L NaCl, 5 g/L yeast extract) or a defined minimal medium such as M9 (6 g/L $Na_2HPO_4$, 3 g/L $KH_2PO_4$, 1 g/L $NH_4C1$, 0.5 g/L NaCl, pH 7.4) with an appropriate carbon source such as 1% glucose. Routinely, an over night culture of *E. coli* cells is diluted and inoculated into fresh rich or minimal medium in either a shake flask or a fermentor and grown at 37° C.

A host cell can also be of mammalian origin, such as a cell derived from a mammal including any human or non-human mammal. Mammals can include, but are not limited to primates, monkeys, porcine, ovine, bovine, rodents, ungulates, pigs, swine, sheep, lambs, goats, cattle, deer, mules, horses, monkeys, apes, dogs, cats, rats, and mice.

A host cell may also be of plant origin. Cells from any plant can be selected in which to screen for the production of a heterologous protein of interest. Examples of suitable plant include, but are not limited to, alfalfa, apple, apricot, *Arabidopsis*, artichoke, arugula, asparagus, avocado, banana, barley, beans, beet, blackberry, blueberry, broccoli, brussels sprouts, cabbage, canola, cantaloupe, carrot, cassaya, castorbean, cauliflower, celery, cherry, chicory, cilantro, citrus, clementines, clover, coconut, coffee, corn, cotton, cranberry, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, linseed, mango, melon, mushroom, nectarine, nut, oat, oil palm, oil seed rape, okra, olive, onion, orange, an ornamental plant, palm, papaya, parsley, parsnip, pea, peach, peanut, pear, pepper, persimmon, pine, pineapple, plantain, plum, pomegranate, poplar, potato, pumpkin, quince, radiata pine, radiscchio, radish, rapeseed, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf, turnip, a vine, watermelon, wheat, yams, and zucchini. In some embodiments, plants useful in the method are *Arabidopsis*, corn, wheat, soybean, and cotton.

Kits

The present invention also provides kits useful for identifying a host strain, e.g. a *P. fluorescens* host strain, optimal for producing a heterologous protein or polypeptide of interest. The kit comprises a plurality of phenotypically distinct host cells, wherein each population has been genetically modified to increase the expression of one or more target genes involved in protein production, to decrease the expression of one or more target genes involved in protein degradation, or both. The array may further comprise one or more populations of cells that have not been genetically modified to modulate the expression of either a gene involved in protein production or a gene involved in protein degradation. These kits may also comprise reagents sufficient to facilitate growth and maintenance of the cell populations as well as reagents and/or constructs for expression of a heterologous protein or polypeptide of interest. The populations of host cells may be provided in the kit in any manner suitable for storage, transport, and reconstitution of cell populations. The cell populations may be provided live in a tube, on a plate, or on a slant, or may be preserved either freeze-dried or frozen in a tube or vial. The cell populations may contain additional components in the storage media such as glycerol, sucrose, albumin, or other suitable protective or storage agents.

The following examples are offered by way of illustration and not by way of limitation.

EXPERIMENTAL EXAMPLES

Overview

Heterologous protein production often leads to the formation of insoluble or improperly folded proteins, which are difficult to recover and may be inactive. Furthermore, the presence of specific host cell proteases may degrade the protein of interest and thus reduce the final yield. There is no single factor that will improve the production of all heterologous proteins. Thus, a method was sought to identify factors specific to a particular heterologous protein from a pool of likely candidates.

Using Systems Biology tools, the *P. fluorescens* genome was mined to identify host cell protein folding modulator and protease genes. Then, global gene expression analyses were performed to prioritize upregulated targets, and, thereafter, novel protein production strains were constructed. As a result, a "Pfēnex Strain Array" was assembled consisting of a plurality of phenotypically distinct *P. fluorescens* host strains that are deficient in host-cell proteases or allow the co-overexpression of protein folding modulators. This strain array can be used to screen for factors that specifically enhance the yield or quality of certain heterologous proteins. Providing a plurality of phenotypically distinct host strains increases the chance of success of identifying a host strain that will increase the production of any individual heterologous protein of interest.

This invention provides an improvement in the production of heterologous proteins in *Pseudomonas fluorescens*. Having available a library of host strains in the same genetic background allows the rapid screening and identification of factors that increase the yield and/or quality of heterologously expressed proteins. The genome sequence of *P. fluorescens* has been annotated and targeted host cell folding modulators and proteases have been identified. Folding modulators assist in the proper folding of proteins and include chaperones, chaperonins, peptidyl-proline isomerases (PPIases), and disulfide bond formation proteins. Proteases can degrade the protein of interest and thus affect heterologous protein yield and quality. Using background knowledge from the literature and DNA microarray analyses to identify likely targets, a list of about 80 target genes was assembled. In host cells that have the same genetic background, these genes were either removed from the genome or cloned into plasmids to enable co-overexpression along with heterologous proteins. The resulting strains were arrayed in 96-well format and, after transformation of plasmids that express the heterologous protein of interest, were screened for improved protein yield and/or quality.

Example 1

Identification of Folding Modulator Genes in the Genome of *P. fluorescens* Strain MB214

Folding modulators are a class of proteins present in all cells which aid in the folding, unfolding and degradation of nascent and heterologous polypeptides. Folding modulators include chaperones, chaperonins, peptidyl-prolyl cis-trans isomerases, and proteins involved in protein disulfide bond formation. As a first step to construct novel production strains with the ability to help fold heterologous proteins, the *P. fluorescens* genome was mined to identify host cell folding modulator genes.

Each of the 6,433 predicted ORFs of the *P. fluorescens* MB214 genome was analyzed for the possibility that they encoded a folding modulator using the following method. Several folding modulators of interest had already been identified by Dow researchers by analysis of the genome annotation (Ramseier et. al. 2001). Homologs of these starting proteins were identified using protein/protein BLAST with the starting protein as the query and a database of all MB214 translated ORFs as the subject. Those translated ORFs which matched the query proteins with significant homology were added to the list for further analysis. Significant homology is defined here as having an e-score of 1e-30 or less with allowances made for human judgment based on the length and quality of the alignment. The intention of this study was to be very inclusive to maximize the chance that all potential folding modulators would be identified.

More ORFs were added to the list based on their curated function from the previous annotation containing the keyword "chaperone". Finally, the ORFs were analyzed by the protein signature family searching program InterProScan (Quevillon et. al. 2005) against the InterPro Database version 7.0 (Mulder et. al. 2005). The ORFs were assigned protein families by the InterProScan software as well as Gene Ontology (GO) categories associated with those families (Gene Ontology Consortium. 2004). Using these automatic GO assignments, all of the ORFs which had been assigned the GO terms "GO:0006457 Biological Process: protein folding" or "GO:0003754 Molecular Function: chaperone activity" were added to the list for further analysis.

The list was then analyzed to remove ORFs which had a low probability of encoding folding modulators. Again, the intent of this study was to be very inclusive but many of the ORFs assigned to the list by these semi-automated methods could be easily identified as not coding for folding modulators based on limited criteria and human judgment.

The most common reason for excluding a certain ORF was the weak evidence that this ORF is actually a folding modulator, i.e. ORFs which had been assigned to the list based on the previous annotation where the reasoning for annotating the ORF as a folding modulator was either unclear or contradictory. InterProScan is actually a conglomerate of different programs and some of these programs are considered to be more reliable than others. If an ORF was assigned to the list based solely on the output of the ScanRegExp or ProfileScan components then it was removed. The final list of *P. fluorescens* folding modulators has 43 members and is shown in Table 1.

Example 2

Identification of Protease Genes in the Genome of *P. fluorescens* Strain MB214

Proteases are enzymes that hydrolyze peptide bonds and are necessary for the survival of all living creatures. However, their role in the cell means that proteases can be detrimental to recombinant protein yield and/or quality in any heterologous protein expression system, which also includes the Pfenex Expression Technology™. As a first step to construct novel production strains that have protease genes removed from the genome, the *P. fluorescens* genome was mined to identify host cell protease genes.

Each of the 6,433 predicted ORFs of the *P. fluorescens* MB214 genome were analyzed for the possibility that they encoded a protease using the following method. The MEROPS database is manually curated by researchers at the Wellcome Trust Sanger Institute, Cambridge, UK (Rawlings et. al., 2006, Nucleic Acids Research 34 (Database issue): D270-2. It is a comprehensive list of proteases discovered both through laboratory experiments as well as by homology to known protease families. One of the strengths of the database is the MEROPS hierarchical classification scheme. In this system, homologs which share the same function are grouped together into families. Families are grouped into clans based on evolutionary relatedness that again are based on similar structural characteristics. The method makes great use of the database to identify protease homologs within the *P. fluorescens* genome.

Homologs to the MEROPS database were identified using protein/protein BLAST with each MB214 translated ORF as the query and a database of all of the MEROPS proteins as the subject. Those translated ORFs, which matched the query proteins with significant homology, were added to the list for further analysis. Significant homology in this case is defined here as having an e-score of $1e^{-60}$ or less with allowances made for human judgment based on the length and quality of the alignment. This step yielded 109 potential proteases for the list.

The ORFs were also analyzed by the protein signature family searching program InterProScan (Quevillon et. al. 2005) against the InterPro Database version 7.0 (Mulder et. al. 2005). The ORFs were assigned protein families by the InterProScan software as well as Gene Ontology (GO) categories associated with those families (Gene Ontology Consortium. 2004). Using these automatic GO assignments, all of the ORFs which had been assigned a GO name that contained the strings "peptidase", "protease" or "proteolysis" were added to the list for further analysis. This step yielded an additional 70 potential proteases that had not been identified in the previous step.

More ORFs were added to the list based on their curated function from the previous annotation (Ramseier et. al. 2001) containing the keywords "peptidase" or "protease". This step yielded 32 potential proteases that again had not been identified in the previous steps.

The list was then analyzed to remove ORFs which had a low probability of encoding proteases. Again, the intent of this study was to be very inclusive but many of the ORFs assigned to the list by these semi-automated methods could be easily identified as not coding for proteases based on limited criteria and human judgment. The two most common reasons for excluding genes were the weak evidence that a certain ORF is actually a protease, or that a particular gene showed greatest homology with another protein known to be protease homolog but not a protease itself. The final list of *P. fluorescens* proteases has 90 members and is shown in Table 2.

Example 3

In Silico Cellular Location Prediction of the Folding Modulator and Protease Proteins One of the strengths of the Pfenex Expression Technology™ is its ability to control the cellular compartment to which a particular heterologous protein can be segregated. Thus, the cellular compartments where the identified host cell folding modulator and protease proteins are located were predicted. To make these predictions, two programs were chosen. PsortB 2.0 combines the results of 12 separate algorithms, which predict the subcellular location of a given peptide. The majority of the algorithms rely on detecting homology between the query protein and proteins of known subcellular localization. PsortB also includes algorithms such as HMMTOP and SignalP, which detect the presence of transmembrane folding domains or type I secretion signal sequences, respectively, using Hidden Markov Models (HMM). In addition to the PsortB results, SignalP HMM was used to predict the presence of type I secretion signal sequences. This was necessary because the output of PsortB can be vague when a signal sequence is detected but no other specific information indicating the subcellular location is given. In these cases, PsortB indicates that the subcellular localization of the protein is unknown, because it really could segregate to any one of the cytoplasmic membrane, periplasm, outer membrane or extracellular compartments. However, it is informative enough to know that the protein is probably not located in the cytoplasm to make it worth noting that in the table. Thus, Table 2 lists the results of the PsortB algorithm except in cases where that result was unknown. In these cases the result of SignalP HMM alone is given with "Signal Peptide" indicating that a signal peptide was detected and "Non Secretory" indicating that no signal peptide was detected.

Example 4

Construction of Plasmids that Enable the Co-Overexpression of Folding Modulators Folding modulator genes were cloned into a plasmid derivative of pCN (Nieto et al. 1990), which is compatible with another plasmid that routinely is used to express the heterologous protein of interest (Squires et al. 2004; Chew et al. 2005). The construction of a mannitol-inducible grpE-dnaKJ-containing plasmid is exemplified. Other folding modulators either as a single gene or as multiple genes when organized in operons were cloned similarly as outlined below.

Employing genomic DNA isolated from *P. fluorescens* MB214 (DNeasy; Qiagen, Valencia, Calif.) as a template and primers RC199 (5-ATATACTAGTAGGAGGTAACT-TATGGCTGACGAACAGACGCA-3') (SEQ ID NO:1) and RC200 (5'-ATATTCTAGATTACAGGTCGC-CGAAGAAGC-3') (SEQ ID NO:2), the grpE-dnaKJ genes were amplified using PfuTurbo (Stratagene, La Jolla, Calif.) as per the manufacturer's recommendations. The resulting 4 kb PCR product was digested with SpeI and XbaI (restriction sites underlined in the primers above) and ligated into pDOW2236 which is a derivative of pDOW1306-6 (Schneider et al. 2005b) to create pDOW2240 containing the grpE-dnaKJ operon under control of the tac promoter. Plasmid pDOW2240 was then digested with SpeI and HindIII and the resulting grpE-dnaKJ-containing 4.0 kb DNA fragment was gel-purified using Qiaquick (Qiagen, Valencia, Calif.) and ligated into pDOW2247, which is a derivative of pCN carrying the *P. fluorescens* mannitol-regulated promoter (Schneider et al. 2005a), that was also digested with SpeI and HindIII. The resulting plasmid, pDOW3501, contained the grpE-dnaKJ operon under the control of the mannitol promoter. Plasmid pDOW3501 was then transformed into DC388 and other uracil-auxotrophic strains by selecting on M9 glucose plates supplemented with 250 ug/ml uracil.

Example 5

Construction of *P. fluorescens* Strains with Genomic Deletions of Protease Genes Plasmids that enabled the creation of genomic deletions were constructed by amplification of 500-1000 bp DNA fragments both 5' and 3' of the gene to be deleted. The resulting 5' PCR product typically ends with the translational initiation codon (ATG or GTG or TGT) of the gene to be deleted while the 3' PCR product typically begins with the stop codon (TAA or TGA or TAG) of the gene to be deleted.

Figure 1B:
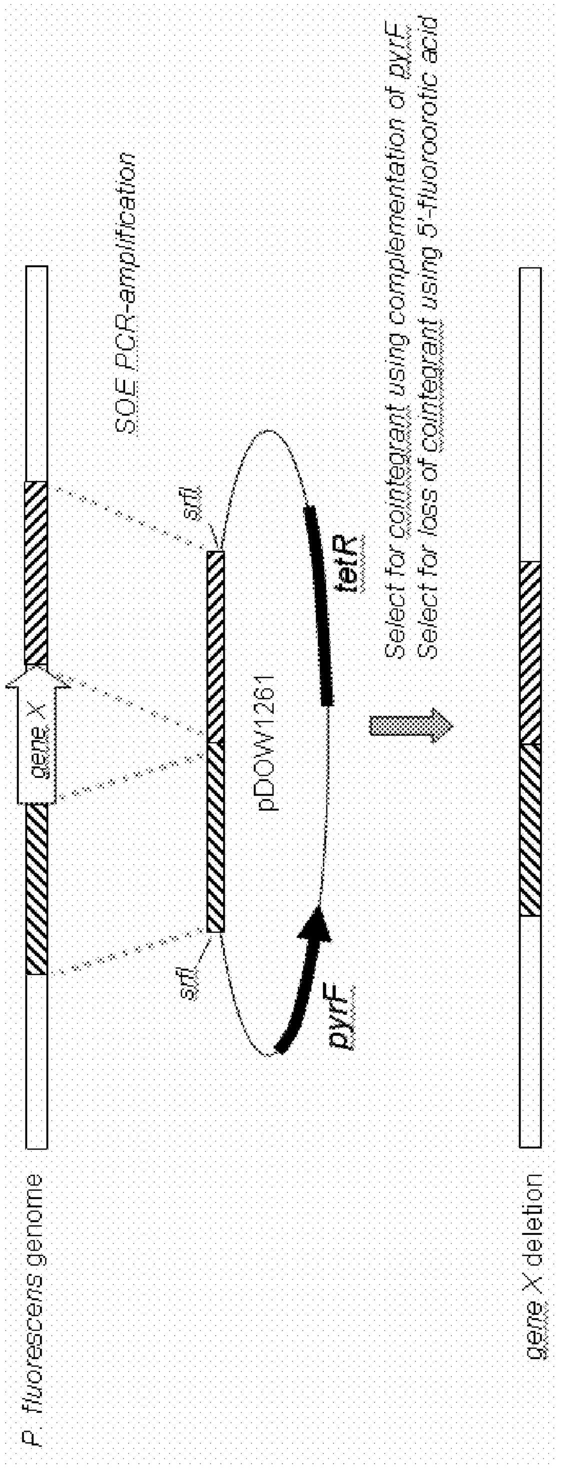
FIG. 1B is a schematic drawing of the constructions of a gene X deletion.

These two PCR products were fused together through an additional amplification step then cloned into pDOW1261 (FIG. 1) (Chew et al. 2005) using SOE PCR (Horton et al. 1990).

Example 6

Figure 2:
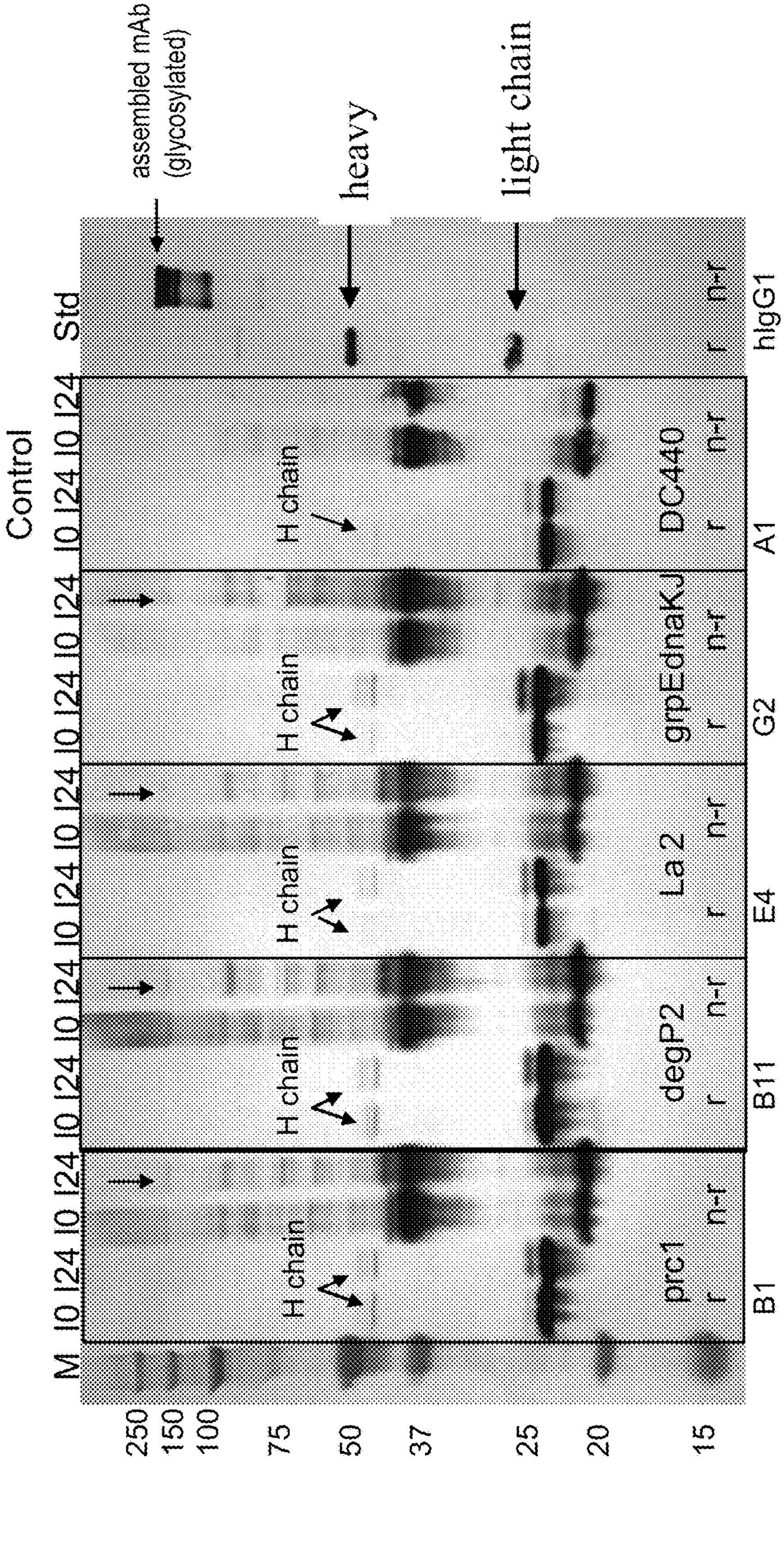
FIG. 2 is a Western blot analysis of soluble cells fractions prepared at 0 and 24 hours post-induction (I0 and I24, respectively) in Δprc1, ΔdegP2, ΔLa2 and the grpEdnaKJ co-expression strains (Example 6). The top arrows point to the fully assembled monoclonal antibody in the co-expressed strains but not in the control (DC440). r=recombinant; n-r=nonrecombinant.

High-Through-Put Growth and Analysis of Heterologous Protein Expression in *P. fluorescens* Strains: Monoclonal Antibody Plasmid pDOW2787 encodes the monoclonal antibody (mAb) gal2; the heavy chain is expressed with a Pbp secretion leader and under control of the tac promoter. The light chain is expressed with an OprF secretion leader and under control of the mannitol promoter. The plasmid was electroporated into competent cells of 63 strains carrying either a directed gene deletion or pDOW2247 carrying a folding modulator for co-expression, and five control strains containing a wild type strain. Cells were cultured in replicate deep-well blocks containing growth medium with glycerol by shaking at 300 rpm. Protein expression was induced at 24 hrs with 0.1 mM isopropyl β-D-thiogalactopyranoside (IPTG) and 1% mannitol. At 24 hrs post-induction, aliquots were lysed, antigen-binding of the antigen was measured to quantitate amounts of active antibody. The value was divided by $OD_{600}$ to measure cell specific activity. Strains Δprc1, ΔdegP2, ΔLa2, ΔclpP, and Δprc2, Δprc2, the grpEdnaKJ co-expression strain, Δtig, ΔclpX, and Δlon were all 2.4-fold or more higher than the control strains, which was statistically significant ($p<0.5$). Soluble cells fractions were prepared from Δprc1, ΔdegP2, ΔLa2 and the grpEdnaKJ co-expression strain and subjected to Western analysis (FIG. 2). A band with a size consistent with fully assembled antibody was detected in the four test strains, but not in the control.

Example 7

High Throughput Evaluation of Protein Expression in *E. coli* and *P. fluorescens*

Construction of C-Terminal his-Tag Expression Clones

Seven open reading frames (ORFs) were amplified for ligation into the NheI-XhoI sites of the periplasmic vector pDOW3718: Map2K3, ApoAI, hGH, gal2 scFV, gal13 scFv, EPO, and IL2. Primers were designed with a NheI restriction site on the 5' primer and a XhoI restriction site on the 3' primer. PCR reactions were performed using Platinum PCR Supermix (Invitrogen cat#1306-016) and PCR products digested with NheI and XhoI in NEBuffer 2 (New England Biolabs), incubating 37° C. overnight, then purified using Qiaquick Extraction kit (Qiagen). The digested products were then ligated to NheI-XhoI digested pDOW3718 using T4 DNA ligase (NEB). Ligation products were transformed into electrocompetent *P. fluorescens* DC454 and transformants were selected on LB agar supplemented with 250 μg/mL uracil and 30 μg/mL tetracycline.

The same seven ORFs were also amplified and prepared for ligation into the NcoI-XhoI sites of pET22b (Novagen) for expression in *E. coli*. Primers were designed with an NcoI restriction site on the 5' primer, and XhoI restriction site (HindIII for MAP2K3 and SalI for ApoAI) on the 3' primer. PCR reactions and restriction digestion were performed as described above with the exception that restriction enzymes NcoI, HindIII, SalI and XhoI were used as required. The digested products were ligated to NcoI-XhoI digested pET22b using T4 DNA ligase (NEB), and the ligation products were transformed into chemically competent *E. coli* Top 10 cells. Transformants were selected in LB agar ampicillin plates (Teknova). Plasmid DNA was prepared (Qiagen) and screened for insert by PCR using T7 promoter and T7 terminator primers. Positive clones were sequenced to confirm insert sequence. One confirmed cloned plasmid for each was subsequently transformed into BL21 (DE3) (Invitrogen) for expression analysis.

High Throughput Expression Analysis

The *P. fluorescens* strains were grown using a high throughput expression protocol. Briefly, seed cultures, grown in LB medium supplemented with 250 ug/mL uracil and 15 mg/mL tetracycline, were used to inoculate 0.5 mL of defined minimal salts medium without yeast extract (Teknova 3H1130) supplemented with 250 ug/mL uracil and 15 mg/mL, tetracycline and 5% glycerol as the carbon source in a 2.0 mL deep 96-well microtiter plate. Following an initial growth phase at 30° C. (24 hours), expression via the Ptac promoter was induced with 0.3 mM isopropyl-β-D-1-thiogalactopyranoside (IPTG).

The *E. coli* strains were grown in a 2.0 mL deep 96-well plate using Overnight Express™ autoinduction medium (Novagen). Briefly, seed cultures grown in LB medium supplemented with 100 μg/mL ampicillin (LBAmp) were used to inoculate 0.5 mL of LBAmp+Overnight Express™ prepared according to the manufacturer's protocol. The cultures were allowed to grow for 24 hours.

Cultures were sampled at the time of induction (I0), and at 24 hours post induction (I24). Cell density was measured by optical density at 600 nm ($OD_{600}$), and 25 μL of whole broth was removed at 124 and stored at −20° C. for later processing. The remainder of the culture (~400 μL) was transferred to Eppendorf tubes and centrifuged 20,000×g for 2 minutes. The cell free broth fractions were removed to a 96-well plate and stored at −20° C. as were the cell pellets.

SDS-PAGE and Western Analyses

Soluble and insoluble fractions from culture samples were generated using Easy Lyse™ (Epicentre Technologies cat#RP03750). The 250 μL whole broth sample was lysed by adding 175 mL of Easy Lyse™ buffer, incubating with gentle rocking at room temperature for 30 minutes. The lysate was centrifuged at 14,000 rpm for 20 minutes (4° C.) and the supernatant removed. The supernatant was saved as the soluble fraction. The pellet (insoluble fraction) was then resuspended in an equal volume of lysis buffer and resuspended by pipetting up and down. For selected clones, cell free broth samples were thawed and analyzed without dilution. Samples were mixed 1:1 with 2× Laemmli sample buffer containing β-mercaptoethanol (BioRad cat#161-0737) and boiled for 5 minutes prior to loading 204 on a Bio-Rad Criterion 4-12% Criterion XT gel (BioRad cat#345-0124) and electrophoresis in 1×MES buffer (cat.#161-0789). Gels were stained with Simply Blue Safe Stain (Invitrogen cat# LC6060) according to the manufacturer's protocol and imaged using the Alpha Innotech Imaging system.

Soluble and insoluble fractions prepared and separated by SDS-PAGE as described above were transferred to nitrocellulose (BioRad cat#162-0232) using 1× transfer buffer (Invitrogen cat# NP0006) prepared according to manufacturer's protocol, for 1.5-2 hours at 100 V. After transfer, the blot was washed briefly in 1×PBS and then blocked overnight in Blocker Casein in PBS (Pierce cat#37528) at 4° C. The diluent was poured off and more diluent was added containing a 1:5,000 dilution of anti-histidine-HRP antibody. The blots were incubated 2 hours at room temperature. The diluent/antibody solution was then poured off and the blots washed in 1×PBST (Sigma #P-3563) with vigorous shaking for 5 minutes. The PBST was changed and washing was repeated twice. For development, the blots were removed from the PBST solution and immersed in prepared solution using the Immunopure Metal Enhanced DAB Substrate Kit (Pierce cat#34065). The blots were incubated with gentle shaking for 10 minutes and then removed from the solution and allowed to dry on paper. The blots were imaged, and densitometry was performed using an Alpha Innotech FluorImager.

HTP Expression Analysis of *E. coli* and *P. fluorescens* Recombinant Strains

*P. fluorescens* and *E. coli* strains were grown in 0.5 mL cultures in a 96 well format to evaluate expression of a variety of human proteins as well as 2 single chain antibodies. Each protein was cloned into the *P. fluorescens* periplasmic expression vector pDOW3718, and the *E. coli* periplasmic expression vector pET22B in frame with a C-terminal 6× histidine tag. *P. fluorescens* cultures were grown in Dow's standard high throughput medium, and *E. coli* cultures were grown in the autoinduction medium Overnight Express™. Growth of *P. fluorescens* expression strains was observed to reach $A_{600}$ units of 20-25 at the time of induction and ~25-45 post induction.

Figure 3:
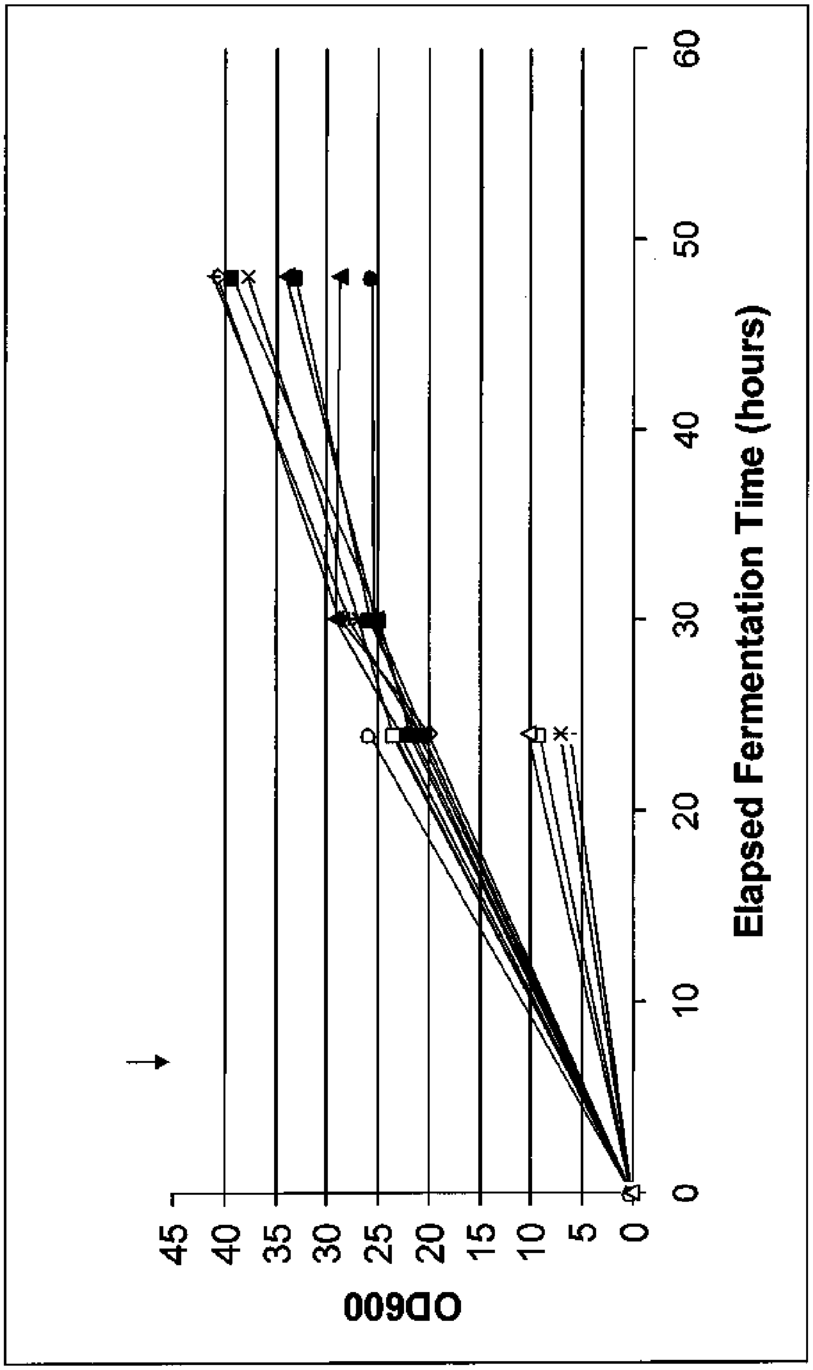
FIG. 3 shows growth curves for *P. fluorescens* (filled symbols) and *E. coli* (open symbols) expression clones observed during growth in a 96-well format. Elapsed fermentation time in hours is shown on the X-axis and optical density measured at 600 nm ($A_{600}$) is shown on the Y-axis. The arrow indicates time of induction of *P. fluorescens* cultures.

FIG. 3 shows growth curves for *P. fluorescens* (filled symbols) and *E. coli* (open symbols) expression clones. Elapsed fermentation time in hours is shown on the X-axis and optical density measured at 600 nm ($A_{600}$) is shown on the Y-axis. The arrow indicates time of induction of *P. fluorescens* cultures.

Figure 4:
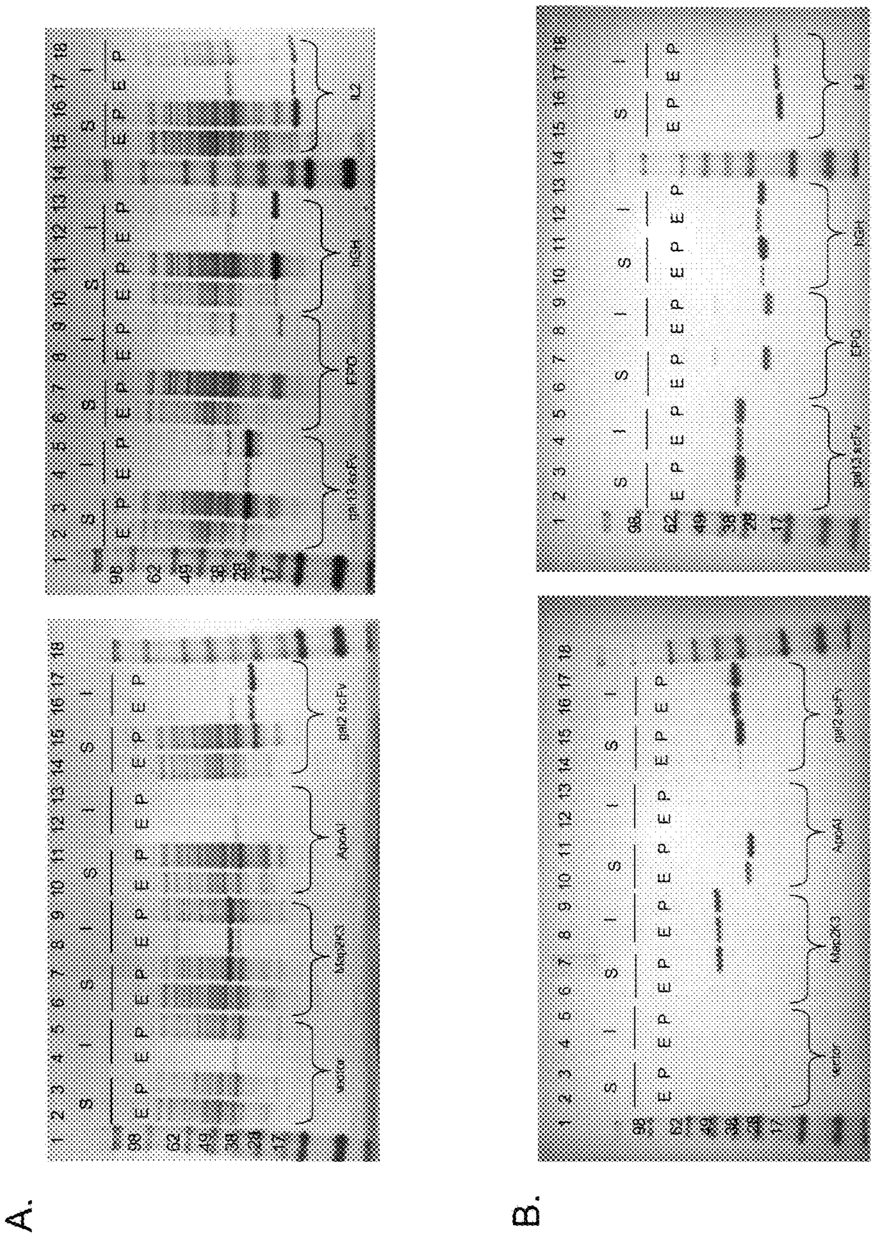
FIG. 4 shows SDS-PAGE (A) and Western blot (B) analysis of analyses of soluble (S) and insoluble (I) samples following 24 hours induction of *E. coli* (E) or *P. fluorescens* (P) cultures. Molecular weight markers are indicated in the first lane. Proteins expressed are indicated at the bottom of the gel image.

The *E. coli* constructs reached an $A_{600}$ of ~5-10 units at the time of harvest, with the exception of 1 strain, which reached an $A_{600}$ of ~25 units after 24 hours of growth in autoinduction medium (FIG. 3, open circle). SDS-PAGE and Western analyses (FIG. 4) showed expression of recombinant protein for *P. fluorescens* in all cases tested, and for *E. coli* in all but one case tested (Epo). Differences in expression levels and solubility between strains were readily detectable. *P. fluorescens* showed an advantage in solubility for MAP2K3, Gal2 and Gal13 scFvs (1), hGH and IL2. Moreover, an advantage in secretion leader processing in *P. fluorescens* was observed for ApoAI, Gal2 scFv, hGH and I12. In *E. coli*, the pelB leader appeared to be unprocessed from these proteins by SDS-PAGE and Western analyses.

Example 8

High-Through-Put Growth and Analysis of Heterologous Protein Expression in *P. fluorescens* Strains: Increasing Expression of Interferon Alpha 2a Construction of Protein Expression Plasmids Standard cloning methods are used in the construction of plasmids that overexpress Interferon alpha 2a. The fragment containing the coding sequences is subcloned into 16 different expression vectors. The expression vectors each contain a periplasmic secretion leader, as shown in Table 11.

TABLE 11

Expression vectors

| Expression Vector | Secretion Leader |
|---|---|
| pDOW5201 | Pbp |
| pDOW5206 | DsbA |
| pDOW5209 | Azu |
| pDOW5217 | LAO |
| pDOW5220 | Ibp S31A |
| pDOW5223 | TolB |
| pDOW5226 | Trc |
| pDOW5235 | FlgI |
| pDOW5238 | CupC2 |
| pDOW5241 | CupB2 |
| pDOW5244 | CupA2 |
| pDOW5247 | nikA |
| pDOW5256 | PorE |
| pDOW5259 | pbpA20V |
| pDOW5262 | DsbC |
| pDOW5265 | Bce |

For the subcloning, a plasmid containing the coding sequence for a heterologous protein to be overexpressed is digested with appropriate restriction enzymes. The expression vectors are digested with the same restriction enzymes. The insert and vector DNA is ligated overnight with T4 DNA ligase (New England Biolabs; M0202S), then electroporated into competent *P. fluorescens* DC454 cells. The transformants are plated on M9 glucose agar (Teknova) and screened for an insert by PCR. Positive clones are selected and sequence-confirmed on both strands. Each sequence-confirmed plasmid is transformed into selected *P. fluorescens* host strains in a 96-well format, to obtain an expression system comprising the host strain and an expression vector. Expression of the coding gene is driven by an appropriate promoter, e.g., Ptac.

Transformation into the *P. fluorescens* host strains DC485 and DC487 is performed as follows: twenty five microliters of competent cells are thawed and transferred into a 96-well electroporation plate (BTX ECM630 Electroporator), and 1 μl miniprep plasmid DNA is added to each well. Cells are electroporated and subsequently resuspended in 75 μl HTP media with trace minerals, transferred to 96-well deep well plate with 400 μl M9 salts 1% glucose medium, and incubated at 30° C. with shaking for 48 hours.

Growth and Expression in 96-Well Format

Expression of the recombinant protein is evaluated under standard induction conditions at the HTP 96-well plate scale. The expression systems, each containing one of each of the 16 expression constructs, are grown in triplicate and expression from the heterologous gene promoter is induced. A standard expression system, e.g., DC454 transformed with one of the heterologous protein expression vectors used, is included on the array. A null strain comprising DC432 null strain containing a vector without an expression insert is also included.

Ten microliters of seed culture is transferred into triplicate 96-well deep well plates, each well containing 500 μl of HTP-YE medium, and incubated as before for 24 hours. Isopropyl βD-1 thiogalactopyranoside (IPTG) is added to each well for a final concentration of 0.3 mM to induce recombinant protein expression, 1% mannitol is used to induce expression of genes (e.g., encoding folding modulators or proteases having potential chaperone activity) present on secondary expression vectors, and the temperature is reduced to 25° C. Twenty four hours after induction, cells are normalized to $OD_{600}$=20. Samples can be normalized in phosphate buffered saline, pH 7.4 to a final volume of 4000 μL, in cluster tubes, e.g., using the Biomek FX liquid-handling system (Beckman Coulter), and frozen at −80° C. for later processing.

Sample Preparation and SDS-CGE

Soluble and insoluble fractions are prepared from the cultures by sonication followed by centrifugation. Frozen, normalized culture broth (200-400 μL) is sonicated for 10 minutes. The lysates are centrifuged at 14,000 rpm for 20 minutes (4° C.) and the supernatants removed by pipet (soluble fraction). The pellets are then resuspended in 200 μL of phosphate buffered saline (PBS), pH 7.4. Insoluble samples are prepared for SDS capillary gel electrophoresis (CGE) (Caliper Life Sciences, Protein Express LabChip Kit, Part 760301), in the presence of dithiothreitol (DTT).

An overview of growth before induction and 24 hours after induction are analyzed by the statistical analysis software JMP. The mean $OD_{600}$ for each expression strain after an initial 24-hour growth period and following the 24 hour induction period are determined.

Soluble and insoluble fractions are analyzed by SDS-CGE to assess expression of the recombinant protein. Strains showing signal above background (e.g., expression from the DC432 null strain) corresponding to induced, soluble protein are noted. Soluble recombinant protein expression and insoluble protein expression are observed. Based on comparison of total and soluble protein yield to those in an indicator strain, expression systems representing a diversity of expression strategies are selected to evaluate at fermentation scale, and an optimal expression system is selected for overexpression of the Interferon alpha 2a.

Example 9

High-Through-Put Growth and Analysis of Heterologous Protein Expression in *P. fluorescens* Strains: Overexpression of a Protein in Table 9

Using a method similar to that described in Example 8, the coding sequence for a heterologous protein listed in Table 9 is cloned into a series of *P. fluorescens* expression vectors. The insert is confirmed by sequencing, and the vectors transformed into *P. fluorescens* host cell populations. The resulting expression strains are grown and protein expression is induced, in a 96-well format. The cultures are evaluated for heterologous protein yield. At least one optimal expression system is selected for overexpression based on the yields observed.

REFERENCES

Chew, L. C., T. M. Ramseier, D. M. Retallack, J. C. Schneider, C. H. Squires and H. W. Talbot (2005). *Pseudomonas fluorescens. Production of Recombinant Proteins. Novel Microbial and Eucaryotic Expression Systems*. G. Gellissen. Weinheim, WILEY-VCH: 45-66

Dolinski, K, Heitman, J. 1997. Peptidyl-prolyl isomerases—an overview of the cyclophilin, FKBP and parvulin families, in Guidebook to Molecular Chaperones and Protein-Folding Catalysts. Gething M-J Ed. Oxford University Press Inc., New York: 359-369

Gardy, J. L., M. R. Laird, F. Chen, S. Rey, C. J. Walsh, M. Ester, and F. S. L. Brinkman 2005 PSORTb v.2.0: expanded prediction of bacterial protein subcellular localization and insights gained from comparative proteome analysis. Bioinformatics 21(5):617-623.

Gene Ontology Consortium. 2004. The Gene Ontology (GO) database and informatics resource. Nucleic Acids Research 32:D258-D261.

Gething M-J Ed. 1997. Guidebook to Molecular Chaperones and Protein-Folding Catalysts. Oxford University Press Inc., New York.

Horton, R. M., Z. Cai, S, N. Ho and L. R. Pease (1990). "Gene splicing by overlap extension: tailor-made genes using the polymerase chain reaction." *BioTechniques* 8(5): 528-30, 532, 534-5

Lombardo, M-J, Thanassi, D G, Hultgren, S J. 1997. *Escherichia coli* PapD. in Guidebook to Molecular Chaperones and Protein-Folding Catalysts. Gething M-J Ed. Oxford University Press Inc., New York: 463-465

Mulder N J, Apweiler R, Attwood T K, Bairoch A, Bateman A, Binns D, Bradley P, Bork P, Bucher P, Cerutti L, Copley R, Courcelle E, Das U, Durbin R, Fleischmann W, Gough J, Haft D, Harte N, Hulo N, Kahn D, Kanapin A, Krestyaminova M, Lonsdale D, Lopez R, Letunic I, Madera M, Maslen J, McDowall J, Mitchell A, Nikolskaya A N, Orchard S, Pagni M, Ponting C P, Quevillon E, Selengut J, Sigrist C J, Silventoinen V, Studholme D J, Vaughan R, Wu C H. 2005. InterPro, Progress and Status in 2005. Nucleic Acids Res. 33, Database Issue:D201-5.

Nieto, C., E. Fernandez-Tresguerres, N. Sanchez, M. Vicente and R. Diaz (1990). "Cloning vectors, derived from a naturally occurring plasmid of *Pseudomonas savastanoi*, specifically tailored for genetic manipulations in *Pseudomonas." Gene* 87(1): 145-9.

Quevillon E., Silventoinen V., Pillai S., Harte N., Mulder N., Apweiler R., Lopez R. (2005) InterProScan: protein domains identifier. Nucleic Acids Research 33: W116-W120.

Ramseier T M, S. C., Payne J, Chew L, Rothman L D, Subramanian M. 2001. The *Pseudomonas fluorescens* MB214 Genome Sequence. CRI CRI2001001442; BIOTECH 01-007. The Dow Chemical Company.

Ranson, N A, White, H E, Saibil, H R. 1998. Chaperonins Biochem. J. 333, 233-242.

Rawlings, N. D., Morton, F. R. & Barrett, A. J. 2006. *MEROPS*: the peptidase database. Nucleic Acids Res 34, D270-D272.

Schneider, J. C., A. F. Jenings, D. M. Mun, P. M. McGovern and L. C. Chew (2005a). "Auxotrophic markers pyrF and proC can replace antibiotic markers on protein production plasmids in high-cell-density *Pseudomonas fluorescens* fermentation." Biotechnology Progress 21(2): 343-348.

Schneider, J. C., B. Rosner and A. Rubio (2005b). Mannitol Induced Promoter Systems in Bacterial Host Cells. USA, The Dow Chemical Company.

Squires, C. H., D. M. Retallack, L. C. Chew, T. M. Ramseier, J. C. Schneider and H. W. Talbot (2004). "Heterologous protein production in *P. fluorescens*." BioProcess International 2(11): 54-56, 58-59.

Graslund, S. et al. Protein production and purification, Nature Methods 5:135-146 (2008)

Berrow, N. S. et al. Recombinant protein expression and solubility screening in *Escherichia coli*: a comparative study. Biological Crystallography. 62: 1218-1226 (2006). Gillette, W. K. et al. Pooled ORF Expression Technology (POET), Molecular and Cellular Proteomics, 4: 1657-1652 (2005).

Service, R. F. Tapping DNA for structures produces a trickle, Science 298:948-950 (2002).

Bussow, K. et al. Structural genomics of human proteins-target selection and generation of a public catalogue of expression clones, Microbial Cell Factories. 4:21-34 (2005).

Abdullah, J. M., A. Joachimiak, and F. R. Collart. 2009. "System 48" high-throughput cloning and protein expression analysis. Methods Mol Biol 498:117-27.

Aricescu, A. R., R. Assenberg, R. M. Bill, D. Busso, V. T. Chang, S. J. Davis, A. Dubrovsky, L. Gustafsson, K. Hedfalk, U. Heinemann, I. M. Jones, D. Ksiazek, C. Lang, K. Maskos, A. Messerschmidt, S. Macieira, Y. Peleg, A. Perrakis, A. Poterszman, G. Schneider, T. K. Sixma, J. L. Sussman, G. Sutton, N. Tarboureich, T. Zeev-Ben-Mordehai, and E. Y. Jones. 2006. Eukaryotic expression: developments for structural proteomics. Acta Crystallogr D Biol Crystallogr 62:1114-24.

Aricescu, A. R., W. Lu, and E. Y. Jones. 2006. A time- and cost-efficient system for high-level protein production in mammalian cells. Acta Crystallogr D Biol Crystallogr 62:1243-50.

Bahia, D., R. Cheung, M. Buchs, S. Geisse, and I. Hunt. 2005. Optimisation of insect cell growth in deep-well blocks: development of a high-throughput insect cell expression screen. Protein Expr Purif 39:61-70.

Boettner, M., B. Prinz, C. Holz, U. Stahl, and C. Lang. 2002. High-throughput screening for expression of heterologous proteins in the yeast *Pichia pastoris*. J Biotechnol 99:51-62.

Damasceno, L. M., K. A. Anderson, G. Ritter, J. M. Cregg, L. J. Old, and C. A. Batt. 2007. Cooverexpression of chaperones for enhanced secretion of a single-chain antibody fragment in *Pichia pastoris*. Appl Microbiol Biotechnol 74:381-9.

Emond, S., G. Potocki-Veronese, P. Mondon, K. Bouayadi, H. Kharrat, P. Monsan, and M. Remaud-Simeon. 2007. Optimized and automated protocols for high-throughput screening of amylosucrase libraries. J Biomol Screen 12:715-23.

Gonzalez Barrios, A. F., R. Zuo, Y. Hashimoto, L. Yang, W. E. Bentley, and T. K. Wood. 2006. Autoinducer 2 controls biofilm formation in *Escherichia coli* through a novel motility quorum-sensing regulator (MqsR, B3022). J Bacteriol 188:305-16.

Holz, C., O. Hesse, N. Bolotina, U. Stahl, and C. Lang. 2002. A micro-scale process for high-throughput expression of cDNAs in the yeast *Saccharomyces cerevisiae*. Protein Expr Purif 25:372-8.

Hsu, T. A., J. J. Eiden, and M. J. Betenbaugh. 1994. Engineering the assembly pathway of the baculovirus-insect cell expression system. Ann N Y Acad Sci 721: 208-17.

Jarvis, D. L., M. D. Summers, A. Garcia, Jr., and D. A. Bohlmeyer. 1993. Influence of different signal peptides and prosequences on expression and secretion of human tissue plasminogen activator in the baculovirus system. J Biol Chem 268:16754-62.

Larsen, M. W., U. T. Bornscheuer, and K. Hult. 2008. Expression of *Candida antarctica* lipase B in *Pichia pastoris* and various *Escherichia coli* systems. Protein Expr Purif 62:90-7.

Novak, M., T. Pfeiffer, M. Ackermann, and S. Bonhoeffer. 2009. Bacterial growth properties at low optical densities. Antonie Van Leeuwenhoek.

Vad, R., E. Nafstad, L. A. Dahl, and O, S. Gabrielsen. 2005. Engineering of a *Pichia pastoris* expression system for secretion of high amounts of intact human parathyroid hormone. J Biotechnol 116:251-60.

Zhang, W., H. L. Zhao, C. Xue, X. H. Xiong, X. Q. Yao, X. Y. Li, H. P. Chen, and Z. M. Liu. 2006. Enhanced secretion of heterologous proteins in *Pichia pastoris* following overexpression of *Saccharomyces cerevisiae* chaperone proteins. Biotechnol Prog 22:1090-5.

Table of SEQ ID NOS:

| PROTEIN FOLDING MODULATOR (RXF #) | SEQ ID NO: | PROTEASE (RXF #) | SEQ ID NO: | LEADER/RELATED SEQUENCE | SEQ ID NO: |
|---|---|---|---|---|---|
| RXF02095.1 | 3 | RXF00133.1 | 46 | Pbp mutant leader - DNA sequence | 159 |
| RXF06767.1 | 4 | RXF00285.2 | 47 | Pbp mutant leader - amino acid sequence | 160 |
| RXF01748.1 | 5 | RXF00325.1 | 48 | DsbA leader - DNA sequence | 161 |
| RXF03385.1 | 6 | RXF00428.1 | 49 | DsbA leader - amino acid sequence | 162 |
| RXF05399.1 | 7 | RXF00449.1 | 50 | DsbC leader - DNA sequence | 163 |
| RXF06954.1 | 8 | RXF00458.2 | 51 | DsbC leader - amino acid sequence | 164 |
| RXF03376.1 | 9 | RXF00561.2 | 52 | Bce leader - DNA sequence | 165 |
| RXF03987.2 | 10 | RXF00670.1 | 53 | Bce leader - amino acid sequence | 166 |
| RXF05406.2 | 11 | RXF00811.1 | 54 | CupA2 leader - DNA sequence | 167 |
| RXF03346.2 | 12 | RXF01037.1 | 55 | CupA2 leader - amino acid sequence | 168 |
| RXF05413.1 | 13 | RXF01181.1 | 56 | CupB2 leader - DNA sequence | 169 |
| RXF04587.1 | 14 | RXF01250.2 | 57 | CupB2 leader - amino acid sequence | 170 |
| RXF08347.1 | 15 | RXF01291.2 | 58 | CupC2 leader - DNA sequence | 171 |
| RXF04654.2 | 16 | RXF01418.1 | 59 | CupC2 leader - amino acid sequence | 172 |

-continued

| Table of SEQ ID NOS: | | | | | |
|---|---|---|---|---|---|
| PROTEIN FOLDING MODULATOR (RXF #) | SEQ ID NO: | PROTEASE (RXF #) | SEQ ID NO: | LEADER/RELATED SEQUENCE | SEQ ID NO: |
| RXF04663.1 | 17 | RXF01590.2 | 60 | NikA leader - DNA sequence | 173 |
| RXF01957.2 | 18 | RXF01816.1 | 61 | NikA leader - amino acid sequence | 174 |
| RXF01961.2 | 19 | RXF01822.2 | 62 | FlgI leader - DNA sequence | 175 |
| RXF04254.2 | 20 | RXF01918.1 | 63 | FlgI leader - amino acid sequence | 176 |
| RXF05455.2 | 21 | RXF01919.1 | 64 | ORF5550 leader - DNA sequence | 177 |
| RXF02231.1 | 22 | RXF01961.2 | 65 | ORF5550 leader - amino acid sequence | 178 |
| RXF07017.2 | 23 | RXF01968.1 | 66 | Ttg2C leader - DNA sequence | 179 |
| RXF08657.2 | 24 | RXF02003.2 | 67 | Ttg2C leader - amino acid sequence | 180 |
| RXF01002.1 | 25 | RXF02151.2 | 68 | Methyl - accepting chemotaxis protein leader - DNA sequence | 181 |
| RXF03307.1 | 26 | RXF02161.1 | 69 | Methyl - accepting chemotaxis protein leader - amino acid sequence | 182 |
| RXF04890.2 | 27 | RXF02342.1 | 70 | oligonucleotide primer | 183 |
| RXF03768.1 | 28 | RXF02492.1 | 71 | oligonucleotide primer | 184 |
| RXF05345.2 | 29 | RXF02689.2 | 72 | First 5 amino acids of the predicted protein sequence for the processed form of dsbC-Skp | 185 |
| RXF06034.2 | 30 | RXF02739.1 | 73 | First 10 amino acids of the predicted protein sequence for the unprocessed form of DsbC-Skp | 186 |
| RXF06591.1 | 31 | RXF02796.1 | 74 | First 10 amino acids of the predicted protein sequence for the processed form of DsbC-Skp | 187 |
| RXF05753.2 | 32 | RXF02980.1 | 75 | Porin E1 precursor leader - DNA sequence | 188 |
| RXF01833.2 | 33 | RXF03065.2 | 76 | Porin E1 precursor leader - amino acid sequence | 189 |
| RXF04655.2 | 34 | RXF03329.2 | 77 | Outer membrane porin F leader - DNA sequence | 190 |
| RXF05385.1 | 35 | RXF03364.1 | 78 | Outer membrane porin F leader - amino acid sequence | 191 |
| RXF00271.1 | 36 | RXF03397.1 | 79 | Periplasmic phosphate binding protein (pbp) leader - DNA sequence | 192 |
| RXF06068.1 | 37 | RXF03441.1 | 80 | Periplasmic phosphate binding protein (pbp) leader - amino acid sequence | 193 |
| RXF05719.1 | 38 | RXF03488.2 | 81 | Azurin leader - DNA sequence | 194 |
| RXF03406.2 | 39 | RXF03699.2 | 82 | Azurin leader - amino acid sequence | 195 |
| RXF04296.1 | 40 | RXF03916.1 | 83 | Lipoprote in B precursor leader - DNA sequence | 196 |
| RXF04553.1 | 41 | RXF04047.2 | 84 | Lipoprote in B precursor leader - amino acid sequence | 197 |
| RXF04554.2 | 42 | RXF04052.2 | 85 | Lysine-arginine-ornithine-binding protein leader - DNA sequence | 198 |
| RXF05310.2 | 43 | RXF04304.1 | 86 | Lysine-arginine-ornithine-binding protein leader - amino acid sequence | 199 |
| RXF05304.1 | 44 | RXF04424.2 | 87 | Iron(III) binding protein leader - DNA sequence | 200 |

-continued

Table of SEQ ID NOS:

| PROTEIN FOLDING MODULATOR (RXF #) | SEQ ID NO: | PROTEASE (RXF #) | SEQ ID NO: | LEADER/RELATED SEQUENCE | SEQ ID NO: |
|---|---|---|---|---|---|
| RXF05073.1 | 45 | RXF04495.2 | 88 | Iron(III) binding protein leader - amino acid sequence | 201 |
| RXF02090 | 137 | RXF04500.1 | 89 | N-terminal amino acid sequence of processed azurin and ibp | 202 |
| RXF01181.1 | 138 | RXF04567.1 | 90 | CDS-1 DNA sequence | 203 |
| RXF03364.1 | 139 | RXF04631.2 | 91 | CDS-1 amino acid sequence | 204 |
| RXF03376.1 | 140 | RXF04653.2 | 92 | TrxA DNA sequence | 205 |
| RXF04693.1 | 141 | RXF04657.2 | 93 | TrxA amino acid sequences | 206 |
| RXF05319.1 | 142 | RXF04663.1 | 94 | TolB leader - DNA sequence | 207 |
| RXF05445.1 | 143 | RXF04692.1 | 95 | TolB leader - amino acid sequence | 208 |
| RXF08122.2 | 144 | RXF04693.1 | 96 | Iron (III) binding protein leader variant S31A - DNA sequence | 329 |
| RXF06751.1 | 145 | RXF04715.1 | 97 | Iron (III) binding protein leader variant S31A - amino acid sequence | 330 |
| RXF00922.1 | 146 | RXF04802.1 | 98 | | |
| RXF03204.1 | 147 | RXF04808.2 | 99 | | |
| RXF04886.2 | 148 | RXF04920.1 | 100 | | |
| RXF05426.1 | 149 | RXF04923.1 | 101 | | |
| RXF05432.1 | 150 | RXF04960.2 | 102 | | |
| | | RXF04968.2 | 103 | | |
| | | RXF04971.2 | 104 | | |
| | | RXF05081.1 | 105 | | |
| | | RXF05113.2 | 106 | | |
| | | RXF05137.1 | 107 | | |
| | | RXF05236.1 | 108 | | |
| | | RXF05379.1 | 109 | | |
| | | RXF05383.2 | 110 | | |
| | | RXF05400.2 | 111 | | |
| | | RXF05615.1 | 112 | | |
| | | RXF05817.1 | 113 | | |
| | | RXF05943.1 | 114 | | |
| | | RXF06281.1 | 115 | | |
| | | RXF06308.2 | 116 | | |
| | | RXF06399.2 | 117 | | |
| | | RXF06451.1 | 118 | | |
| | | RXF06564.1 | 119 | | |
| | | RXF06586.1 | 120 | | |
| | | RXF06755.2 | 121 | | |
| | | RXF06993.2 | 122 | | |
| | | RXF07170.1 | 123 | | |
| | | RXF07210.1 | 124 | | |
| | | RXF07879.1 | 125 | | |
| | | RXF08136.2 | 126 | | |
| | | RXF08517.1 | 127 | | |
| | | RXF08627.2 | 128 | | |
| | | RXF08653.1 | 129 | | |
| | | RXF08773.1 | 130 | | |
| | | RXF08978.1 | 131 | | |
| | | RXF09091.1 | 132 | | |
| | | RXF09147.2 | 133 | | |
| | | RXF09487.1 | 134 | | |
| | | RXF09831.2 | 135 | | |
| | | RXF04892.1 | 136 | | |
| | | RXF00458.2 | 151 | | |
| | | RXF01957.2 | 152 | | |
| | | RXF04497.2 | 153 | | |
| | | RXF04587.1 | 154 | | |
| | | RXF04654.2 | 155 | | |
| | | RXF04892.1 | 156 | | |
| | | XFRNA203 | 157 | | |

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

SEQUENCE LISTING

```
<160> NUMBER OF SEQ ID NOS: 330

<210> SEQ ID NO 1
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1

atatactagt aggaggtaac ttatggctga cgaacagacg ca                        42


<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2

atattctaga ttacaggtcg ccgaagaagc                                      30


<210> SEQ ID NO 3
<211> LENGTH: 291
<212> TYPE: DNA
<213> ORGANISM: Pseudomonas fluorescens

<400> SEQUENCE: 3

atgaagcttc gtcctctgca cgaccgcgtc gtaatccgtc gcagcgaaga agaaaagaaa      60

accgctggcg ggatcgttct gccaggttcg gctgctgaaa aagccaacca cggtgtaatc     120

gtcgctgctg gcccaggcaa aaccctggag aatggtgatg tacgcgcact ggccgtgaaa     180

gtgggtgaca aggttgtttt cggcccttac tccggcagca acactgtgaa agtagacggc     240

gaagacctgc tggtaatggc tgagaacgaa attctcgccg ttctggaaga c              291


<210> SEQ ID NO 4
<211> LENGTH: 762
<212> TYPE: DNA
<213> ORGANISM: Pseudomonas fluorescens

<400> SEQUENCE: 4

atggctgcta aagaagttaa attcggcgac tccgcccgca agaaaatgct cactggcgtc      60

aacgtactgg ctgacgcagt aaaagcgacc ttgggcccga aaggccgtaa cgtgatcatc     120

gagaagagct tcggcgctcc gaccatcacc aaggatggcg tttccgtagc aaaagaaatc     180

gaactggaag accgtttcga gaacatgggc gcgcagctgg tcaaagacgt tgcctcccgt     240

gccaacgatg acgcaggcga cggcaccacc accgctaccg tcctggctca ggcgatcgtc     300

aacgagggct acaaggccgt cgctgccggc atgaacccga tggacctcaa gcgtggcatc     360

gacaaggcga ccatcgccat cgttgccgag ctgaaaaatc tgtccaagcc atgcgccgac     420

accaaggcca tcgctcaggt aggcaccatc tccgccaact ccgacagctc catcggtgac     480

atcattgccg aagccatgga aaaagtcggt aaagaaggcg tgatcaccgt tgaagaaggc     540

tcgggcctgg aaaacgaact gtcggttgta gaaggcatgc agttcgaccg tggctacctg     600
```

tctccgtact tcgtcaacaa gcctgagacc atggttgccg agctggacag cccgctgatc 660
ctgctggtcg acaagaagat ctccaacatt cgcgaaatgc tgccagtact ggaagccgtt 720
gccaaagccg gccgtccatt gctgatcgtt tccgaagacg tg 762

<210> SEQ ID NO 5
<211> LENGTH: 456
<212> TYPE: DNA
<213> ORGANISM: Pseudomonas fluorescens

<400> SEQUENCE: 5
atggctacta ccctgtcgtt ggccccactg ttccgtcaat cggtgggctt tgatcgcttc 60
aatgacctgt tcgagtcggc gctgcgcagc gaggctccga attcctatcc acctcacaat 120
gtggaaaagc acggtgacga cgcgtaccgc attgtcatcg ccgtggctgg cctgaccgag 180
gaggatctgg atatccaggt cgagaggggt gtattgacgg tttctggcgg taaacgcgaa 240
accgacgata aggtcgctta cctgcaccag ggcattgccc aacgtgcgtt ccggttgtcg 300
ttccgcttgg cggaccatat cgaagtacgt ggcgcatccc tgaccaacgg tttgctcaac 360
atcgacctgc tgcgtgaagt gcctgaagag gccaagccaa aacgcatcat gattggtggc 420
gaggccaaac ctgaactgcg tcaggtcagc ttgcag 456

<210> SEQ ID NO 6
<211> LENGTH: 519
<212> TYPE: DNA
<213> ORGANISM: Pseudomonas fluorescens

<400> SEQUENCE: 6
gtgggtactc cttgtcattt cgctttattc gagctgcagc cgagctttcg gctggacctt 60
gagcagcttg ccacgcgcta ccgtgaattg gcgcgtggcg tgcatccgga ccgctttgcc 120
gacgcttccg agcgtgagca acgcttggcg ctggagcaat cggccagcct caacgaagcc 180
tatcagacgc taaaaagccc cccgaaacgc gcacgttatt tactggcgat gacgggcggc 240
gagttgccga tggaagtcac cgtgcatgac ccggacttcc tgatgcagca gatgcagtgg 300
cgcgaagagc tcgaagactt gcaggacgaa gccgatgtgg cgggtgtcgt ggtcttcaag 360
cgccgtctga aggcggccca ggatgagctc aacgaaagct tcgcagcctg ttgggatgat 420
gcggcgcaac gtgagcaggc cgaacgcctg atgcggcgca tgcaattcct cgacaagctc 480
acctacgaag tgcgccagct agaagagcgc ctcgacgat 519

<210> SEQ ID NO 7
<211> LENGTH: 1920
<212> TYPE: DNA
<213> ORGANISM: Pseudomonas fluorescens

<400> SEQUENCE: 7
atgggcaaaa ttatcggtat cgacctgggg actaccaact cctgcgtctc cgtgctggaa 60
aacggcgttg caaaagttat tgaaaacgcc gaaggcgcac gtaccacccc gtcgatcatc 120
gcttacgcca acgacggtga aatcctcgtc ggccaatcgg ccaagcgtca ggcagtgacc 180
aacccgcaca acaccctgta cgcggtaaag cgtctgatcg gtcgtaagtt cgacgaagaa 240
gtcgtacaga aagacatcaa gatggtgcct tacaaaatcg ccaaggccga caacggtgac 300
gcctgggttg aagtgaacgg ccagaagatg tcgccgccac aaatctcggc tgaaatcttg 360
aaaaagatga agaagaccgc cgaagactac ctcggtgaag cagtgactga agcggtgatc 420
accgttccgg cctacttcaa cgacagccag cgtcaggcca ccaaagacgc cggccgcatc 480
gcgggcctgg atgtaaaacg tatcatcaac gaaccaaccg cagctgctct ggcttacggt 540
atggacaagg ccaagggcga tcacaccgtg atcgtttacg acctgggtgg cggtacattc 600
gacgtctccg tgatcgagat cgcagaagtt gacggcgagc accagttcga agtgttggcc 660
accaacggcg acaccttctt gggtggtgaa gactttgaca ttcgtctgat cgactacctc 720
gttgacgaat tcaagaaaga aagcggcatg aacctcaaag gtgacccgct ggccatgcag 780
cgcctgaaag aagccgctga aaaagccaag atcgagctgt cttccgctca gtcgaccgac 840
gtgaacctgc cgtacatcac agcagacgcc actggtccta agcacttgaa cgtgaaaatc 900
tcgcgttcca agctcgaagc gctggttgaa gacctggttc aacgcaccat cgaaccttgc 960
cgcatcgcgc tgaaagactc cggtatcgac gttggctcta tcaacgacgt gatcctggta 1020
ggcggtcaga cccgtatgcc actggttcag aagctggtca ccgaattctt cggcaaagaa 1080
gctcgtaaag acgtgaaccc ggacgaagcc gttgccatgg gtgctgccat ccagggtgcc 1140
gtactggccg gtgacgtgaa agacgtgttg ctgctggacg taagcccgct gaccctgggt 1200
atcgaaacca tgggtggcgt gatgactgcg ctgatcgaga aaaacaccac gattcctacc 1260
aagaaatccc aggtgttctc gactgccgat gacaaccagg gcgccgtgac tatccacgtg 1320
ctgcagggcg agcgtaagca agctgcgcag aacaagtccc tgggcaagtt cgacttggct 1380
gagattccac cagcaccacg tggcgtgcca caaatcgaag tgaccttcga catcgacgcc 1440
aacggcatcc tgcacgtcgg cgcgaaagac aaggccaccg gcaaagagca gaagatcacc 1500
atcaaggcca actccggcct gtctgatgaa gaaattcaac agatgatccg tgatgctgaa 1560
accaatgctg aagccgacaa gaagttcgaa gagttggcgg gcgcccgtaa ccagggtgac 1620
gcgctggttc actcgacgcg caaaatgatc gctgatgctg gcgacaaagt gaccgacgaa 1680
gagaaaaccg caatcgaagc ggcagtggtt gccctggaag ccgccatcaa aggcgacgac 1740
aaggctgcca tcgaagccaa ggttgaggag ctgtcgaaag tctccgcgcc agttgctcag 1800
aaaatgtacg ccgaacaagg ccagccggct gacggcgctg cgcaacaagc agaacctgaa 1860
gccaagcacg acgacgttgt cgatgccgag ttcgaagaag ttaaagacga ccagaagaag 1920

<210> SEQ ID NO 8
<211> LENGTH: 1266
<212> TYPE: DNA
<213> ORGANISM: Pseudomonas fluorescens

<400> SEQUENCE: 8
atgaaaaacg catccccagc ccgtgcctgc ggcatcgact tcggcacgtc caactccacc 60
gtcggctgga tccgccccgg cgaggagacg ctgatcgcgc tggaggacga caagatcaca 120
ttgccgtcag tggtcttttt caacttcgag gagcgccgcc cggtgtacgg tcgcctggcg 180
ctgcacgaat acttggagaa ctacgaaggc cgcctgatgc gctcgctcaa gagcctgctg 240
ggttccaagc tgatcaagca cgacaccagc gtgctcggca ccgccatgcc cttcaccgac 300
ctgctggccc tgtttatcgg ccaactcaag agccgcgccg aagccaacgc cggccgtgag 360
ttcgaagaag tggtgctggg ccgcccggtg ttcttcgtcg atgacgaccc gatggccgac 420
caggaagcgg aaaacaccct ggtggacgtg gcgcgcaaga tcggcttcaa ggacatctcc 480
tttcagtacg aaccgattgc tgctgccttc gactacgagt ccaccatcac caaagaagag 540
ctggtgctga tcgtcgacat cggcggtggt acctccgact tctccctggt gcgcctgtcg 600
ccggagcgtc gtcacaacga caaccgccag agcgacatcc tcgccaccgg cggcgtgcac 660
atcggcggta ccgacttcga caaacagctc tcgctagccg gcatgatgcc gctgttcggc 720
tacggcagcc gcatgaaaag cggcgcctac atgcctacca gccaccacat gaacctggcc 780
acctggcata ccatcaactc ggtgtactca caaaaatccc agctggccct gggcagcatg 840
cgctacgaca tcgaagacac cggcggcatc gaccgcctgt tcaagctgat cgaacagcgc 900
gccgggcact ggctggccat ggaagtggaa gagaccaaga tccagctcac ccaggcagac 960
agccgccacg tgccgctgga ccgcatcgaa gccggcctga gcgtagacct gagccgcgcg 1020
ctgttcgagt cgtccattga caatctgctg gaacgcgtac gcggcagcgt cacgcagttg 1080
ctcaacgacg cctcggtgag cgtggcgcaa gtggacacgg tgttcttcac cggcggctcc 1140
agcggcatcc cggcactgcg ccacagcatc tcggcaatgc tgccgaatgc gcggcatgtg 1200
gaaggcaata tcttcggcag tattggcagt ggtttggcga ttgaggcgag caagcgctac 1260
ggcagc 1266

<210> SEQ ID NO 9
<211> LENGTH: 1860
<212> TYPE: DNA
<213> ORGANISM: Pseudomonas fluorescens

<400> SEQUENCE: 9
atggctctac tgcaaatcgc cgaacccggc caaagccctc aaccgcacca gcgtcgcctg 60
gcggtcggga ttgacctggg caccaccaat tccctggttg ctgccttgcg cagcggcctg 120
tccgagccac tgcctgacgc cgatgggcag gtgatcctgc cgtccgccgt gcgttatcac 180
gccgaccgca ctgaagtggg cgaatcggcc aaattggccg cgtccgcaga ccctttgaac 240
acggtgttgt cggtcaagcg cttgatgggt cgtgggttgt ccgacgtcaa gcaattgggc 300
gaccaactgc cgtaccgctt tgtcggcggt gaatcccata tgccgttcat cgacaccgtc 360
caggggccca agagcccggt ggaagtgtcg gctgatatcc tcaaggtgct gcgccagcgt 420
gcagaaagca ccctgggcgg tgagctggta ggggcggtga tcactgttcc ggcgtatttc 480
gatgacgccc agcgccaagc caccaaggat gcggcgaaac ttgccggctt gaacgtgctg 540
cgcttgctca acgaaccgac tgcggcggcg gtggcctacg gcctcgatca gcacgctgaa 600
ggcctggtcg ctatttatga cctgggcggc ggcaccttcg atatttcgat cctgcgcctg 660
accggcggtg tgttcgaagt gctcgcgacc ggcggcgaca gcgccctggg tggcgatgat 720
ttcgatcacg ctattgctgg ctggatcatc agcagtgctg gcttatcggc cgacctggac 780
ccaggcgcgc agcgcaacct gctgcaaact gcctgcgcgg ccaaagaggc gctgactgac 840
gctgcttctg ttgaagtgtc ctacggtgac tggtcggcac agctgacccg cgaagccttt 900
gatgcgctga tcgagccgat ggtcgcccgc agcctcaaag cctgtcgtcg tgctgtgcgt 960
gattccggta tcgagttgga agacgtcggt gcagtggtca tggtcggcgg ttccacccgc 1020
gtgccgcgcg tgcgcgaagc ggtcgccgaa gcctttgggc gccaaccgct gaccgaaatc 1080
gacccggatc aagtggtcgc catcggcgct gccatccagg ccgataccct ggctggtaac 1140
aaacgcgatg gcggcgaatt gctgttgctc gacgtgatcc cgttgtccct gggcctggaa 1200
accatgggtg gcctgatgga gaaggtgatt ccgcgcaaca ccaccattcc cgtcgcccgt 1260
gcccaggact tttctaccta caaagacggc cagacagcga tgatgattca tgtgctgcaa 1320
ggtgagcgcg agctgatcag cgactgccgt tccctggcgc gctttgaatt gcgtggcatt 1380
ccggcgatgg tggccggtgc cgccaagatt cgcgtgacct tccaggtcga tgccgatggc 1440
ttgctcagcg tggctgcgcg tgagctggct tcgggcgtgg aggccagcat ccaggtcaag 1500

```
ccgtcctacg gcctcaccga tggcgaaatc gccaagatgc tcaaggattc gttccagtat   1560

gccggtgacg ataaggtcgc ccgtgtatta cgcgagcagc aagtagatgc ccagcgcctg   1620

ctcgaagcgg tgcagggtgc ccttgaagcc gatggcgagc gcctgctgga tgccgaagaa   1680

cgcatggtca ttgacctgca aatgcaggaa ctggccgaac tgatgaaagg caacgatggc   1740

tacgccatcg agcaacagac caagcgcctg tcgcaagtga ctgatgcctt tgccgcccgc   1800

cgtatggatc agacggttaa agccgcgctg gcgggccgca acctgaatga aattgaggaa   1860
```

<210> SEQ ID NO 10
<211> LENGTH: 936
<212> TYPE: DNA
<213> ORGANISM: Pseudomonas fluorescens

<400> SEQUENCE: 10

```
atggatttca aagactacta caagattctc ggtgtcgagc cgacggctga cgacaaggag     60

atcaagtcgg cttatcgcaa gctggcgcgt aaatatcacc cggacgtcag caaggaaaag    120

gatgccgaat ccaagttcaa ggatgcgtcc gaggcctatg aagcgctgaa aagtgccgac    180

aaacgcgccg aatacgatga actgcgcaaa tacggccagc atggccagcc gttccagggg    240

ccaccgggtt ggcagagccg tggaggcttt ggtggcggcc aggacgcggg cgatttttcg    300

gactttttca gttcgatctt cggttcgcgc ggcgatgcct tcggtggcgg ccagcgccgt    360

cctaccgggc gcaagggcca ggatgtggag atgcagctca tggtttccct ggaggaaacc    420

ctgtccaccg agtccaagca gatcagcttc caggtgccac agtacgatgc ttccggtcgg    480

catgtgagca acaccaccaa aagcctgaac gtgaagatcc cggccggtgt ggccgatggc    540

gagcgcattc ggctcaaggc ccagggcgcg ccgggcattg gtggcggggc caatggtgat    600

ttgtacctga tcatcaagtt cgcaccccac cccaagttcg aggtggacgg cgaaaacctg    660

atcatcaacc tgccgctggc accctgggaa ctggcgctgg gcacggaagt ggccgtgccg    720

actctcaccg gcaagatcaa cctcaaggtg cctgccggca gccagaacgg ccagcgcatg    780

cgcgccaagg gccatggctt gctgaacaag gccgggcaac gcggctatct gttcatccag    840

ctcaaggcgg tgatgcccaa ggcggcggat gatgaggtca aagcgctgtg ggaggccttg    900

gcacaaaagg ccgcgttcaa tccgcgcgag cagttc                              936
```

<210> SEQ ID NO 11
<211> LENGTH: 1122
<212> TYPE: DNA
<213> ORGANISM: Pseudomonas fluorescens

<400> SEQUENCE: 11

```
atggcaaagc gtgactatta cgaagtattg ggtgtggagc gtggcgccag cgaggcggag     60

ctgaaaaagg cctaccgtcg cctggcgatg aagcaccacc cggaccgtaa tccggataac    120

aaagaatccg aagagatgtt caaagaggcc aacgaggcct acgaatgcct gtgtgatccc    180

aataagcgtg cagcctacga ccagtatggc catgccggtg tcgacccaag catgggcggc    240

ggcggtgccg gttttggtgg tcagaacttc tccgatattt tcggcgacgt attcagcgac    300

ttcttcggcg gtggccgtgg cggtcagcgt ggcggccctc agcgcggcag cgacctgcgt    360

tacaccctgg aactgaacct ggaagaagcc gtgcgcggca ccagtgtcaa tatccgtgtg    420

ccgacgctgg tcaactgcaa gccgtgcgac ggctcgggtg cgaagaaagg ctcctcgccg    480

atcacgtgcc cgacctgcgg cggtattggg caggtgcgca tgcaacaggg cttcttctcg    540
```

```
gtgcagcaaa cctgcccgcg ttgccatggc cagggcaaga tcatttccga tccgtgcgac    600
tcctgccacg gcgaaggccg cgtcgaagag tacaagacgc tgtcggtcaa agtgccggcg    660
ggtgtggata ccggcgatcg tattcgcctg tcgggcgaag gcgaggcggg tgcacagggc    720
ggccctacag gcgacctgta cgtggtgatc aatgtgcgcg agcactcgat cttccagcgt    780
gacggcaagc acttgttctg cgaagtgccg atcagctttg ttgatgcggc cctgggtggc    840
gagctggaga ttccgacgct ggatggtcgg gtcaagctca agattcccga ggggactcaa    900
accggcaagc agttccgcat tcgtggcaaa ggcgttgcgc ccgtgcgtgg tggcggtgct    960
ggcgacctga tgtgtcgtgt ggcggttgaa acccccgtga acctgaatcg tcgtcagcgt   1020
gaactgctgg aagagttccg cagctcgctg gaaggcgatg actcgcactc accgaagacc   1080
acaggcttct tcgacggtgt aaaacgcttc ttcggcgacc tg                      1122
```

<210> SEQ ID NO 12
<211> LENGTH: 234
<212> TYPE: DNA
<213> ORGANISM: Pseudomonas fluorescens

<400> SEQUENCE: 12

```
atgaaagtcg aaccagggct ctaccagcat tacaaggggc cgcagtaccg tgttttcagc     60
gtggcgcgcc actctgaaac cgaagaagaa gtggtgtttt accaagcgct gtatggcgaa    120
tacggctttt gggtgcgccc tttgagcatg ttcctggaga ccgtcgaagt tgacggcgag    180
caggtcccgc gctttgcttt ggtcacggcc gaacccagtc tttttacagg gcaa          234
```

<210> SEQ ID NO 13
<211> LENGTH: 558
<212> TYPE: DNA
<213> ORGANISM: Pseudomonas fluorescens

<400> SEQUENCE: 13

```
atggctgacg aacagacgca ggatacgcaa actccagacg ccaattcggc tgccggtgat     60
gaactggcga ctcgtgtgca agtgctcgaa gagcaattgg ccgctgcgca ggatcaatcg    120
ttgcgtgttg ccgccgatct gcagaacgtc cgccgccgtg ccgagcagga tgtagagaag    180
gctcacaagt tcgcgctgga aaaattcgcc ggtgacctgc tgccgatcat cgacagcctg    240
gagcgtggtc ttgagttgtc caacccggac gacgaaaaca tccgcccaat gcgcgaaggc    300
attgagctga ccctgaaaat gttccaggac accctgaagc gttatcagtt ggaagcgatc    360
gatccgcaag ccggcgagcc gttcaatgct gagcatcacc aagccatggc catgcaggaa    420
agccatgacc tggaacccaa tagcgtgatc aaggtgttcc agaagggtta ccagctcaac    480
ggtcgcctga tgcgcccggc aatggtggtg gtgagcaagg ctcctgcacc cgttgcacct    540
tctattgatg agcaggct                                                  558
```

<210> SEQ ID NO 14
<211> LENGTH: 2268
<212> TYPE: DNA
<213> ORGANISM: Pseudomonas fluorescens

<400> SEQUENCE: 14

```
atgttaaacc gcgagctcga agtcaccctc aatcttgcct tcaaggaggc tcgttcgaag     60
cgtcatgaat tcatgaccgt cgaacacctt ttgctggcac ttttggataa cgaagctgcc    120
gccaccgttc tacgtgcgtg cggcgccaac cttgacaagc tcaagcatga cctgcaggag    180
tttatcgact ccaccacgcc actgatcccc gtgcatgacg aggaccgcga aacccagcca    240
```

```
accctgggct tccagcgggt attgcagcgt gctgtgttcc acgtacagag ctccggtaag    300
cgtgaggtca caggcgcgaa tgtacttgtg gcaattttca gcgaacagga aagccaggcc    360
gtgtttctgc tcaagcagca gagcgttgcc cgtattgatg tggtcaacta catcgcccac    420
ggtatctcca aggtgcctgg gcacggcgat cattccgagg gtgagcagga catgcaggac    480
gaggagggcg gcgagtcttc ttcttccagc aacccgctgg atgcctatgc aagtaacctc    540
aatgaaatgg cgcgccaggg gcggatcgat ccgctagtgg ggcgtgagca tgaggttgag    600
cgtgtagcgc agatcctggc gcgtcgtcgc aagaacaacc cattgctggt gggcgaggcg    660
ggcgtgggta aaaccgcgat tgccgaaggc ctggccaagc gcattgtcga caaccaggtg    720
ccagacctgc tggccagcag tgtcgtctac tcccttgacc tgggcgcgtt gctcgccggg    780
accaagtacc gtggcgattt cgagaagcgc ttcaaggcgt tgctcggcga gctgaaaaaa    840
cgcccgcagg ccatcctgtt catcgacgag atccatacca tcattggcgc cggtgcggct    900
tccggtgggg tgatggacgc ttccaacctg ctcaagccac tgctgtcctc cggtgatatc    960
cgctgcattg gttcgaccac gttccaggaa tttcgcggca tcttcgagaa agaccgcgcc   1020
ctggcgcgtc gcttccagaa agttgacgtg tccgagccct cggttgaaga caccatcggc   1080
atcctgcgcg ggctcaaggg gcgttttgaa gcgcaccatg gcatcgagta caccgatgag   1140
gccctgcgtg cggcggctga gctggcgtcg cgctacatca acgaccggca catgccagac   1200
aaagccatcg atgtgatcga cgaggcgggt gcctaccagc gcctgcagcc ggtcgagaag   1260
cgcgtgaagc gcatcgacgt gcctcaggtc gaggacatcg tggccaagat cgcgcggatt   1320
ccgccaaaac acgtcaccag ttccgacaag gagttgctgc gtaacctgga gcgcgacctc   1380
aagctcaccg tgtttggtca ggatgcggcc atcgactcgc tgtccacggc gatcaagttg   1440
tcccgtgcgg gcctcaagtc gccggacaag ccagtcggtt cgttcctgtt cgcaggcccg   1500
accggcgtcg gcaagaccga ggcggctcgc cagttggcca aggccatggg catcgagctg   1560
gtgcgtttcg acatgtccga gtacatggag cgccacacgg tgtcgcgttt gatcggcgcg   1620
cctccgggct atgtcggctt cgatcagggc ggcctgttga ccgaggcgat caccaagcag   1680
ccacactgcg tattgctgct cgacgaaatc gaaaaggctc acccggaagt cttcaacctg   1740
ctgttgcagg tcatggacca cggcaccctg accgacaaca acgggcgcaa ggcagacttc   1800
cgcaacgtga tcgtgatcat gaccaccaac gccggtgctg aaaccgcggc gcgtgcttcg   1860
atcggcttta cgcatcagga tcactcgtct gatgccatgg aagtgatcaa gaagagcttc   1920
acgccggagt tccgcaaccg cctggacacc attatccagt ttggtcgcct cagccatgag   1980
gtcatcaaaa gcgtggtgga caagttcctc accgagcttc aagcgcagtt ggaagacaag   2040
cgcgtgcagc tggatgtgac ggaagcggcc cgcagttgga tcgcagaggg cggctacgat   2100
gcggcaatgg gcgcacgccc aatggcgcgt ctgatccagg acaagatcaa gcggccattg   2160
gccgaagaga tcctgttcgg cgaactctcc gaccatggcg gcgtggtgca catcgacctg   2220
aaggacggcg agctgacctt cgagttcgag accacggcgg aaatggcc                2268
```

<210> SEQ ID NO 15
<211> LENGTH: 2562
<212> TYPE: DNA
<213> ORGANISM: Pseudomonas fluorescens

<400> SEQUENCE: 15

```
atgcgtattg atcgtttaac cagcaaatta cagttggcat tgtccgactc tcaatctttg     60
```

-continued

```
gcagtgggcc tcgaccaccc ggccatcgaa cctgcgcact tgatgcaggc actcctggaa    120
cagcaaggtg gttctatcaa gcccttgctg atgcaggtgg gctttgacgt taacagcctg    180
cgcaaggagt tgagtaaaga gctcgaccag ctgccgaaaa tccagaatcc caccggcgac    240
gtaaacatgt cccaggactt ggcgcgcctg ctcaaccagg ccgaccgtct ggcccagcag    300
aaaggtgacc agttcatctc cagtgaattg gtgttgctcg ccgccatgga cgacaacagc    360
aagctcggca agttgttgct gggccagggc gtgagcaaaa aggccctgga aaacgccatc    420
aacaacctgc gtggcggcga agcggtgaac gaccccaacc acgaggagtc gcgccaggcc    480
ctggacaaat acaccgtcga cctgaccaag cgtgccgaag agggcaagct ggacccggtg    540
atcggccgcg acgatgaaat tcgtcgcacc attcaggtgt tgcaacgtcg caccaagaat    600
aacccggtgt tgatcggtga acctggcgtg ggtaaaaccg cgattgccga gggcctggcc    660
cagcgcatca ttaatggcga ggtaccagac ggcctcaaag gcaagcgcct gctgtctctg    720
gacatgggct cgttgatcgc cggtgccaag ttccggggtg aattcgaaga gcgcctcaaa    780
tccttgctta acgaattgtc gaagcaggaa gggcagatca ttctgtttat cgacgaattg    840
cacaccatgg tcggcgccgg taagggcgaa ggctccatgg acgccggcaa catgctcaag    900
cccgccttgg cacggggtga gttgcattgc gtcggtgcga ccacgctcaa cgaataccgt    960
cagtacatcg aaaaggacgc agcgcttgag cgtcgcttcc agaaagtcct ggtggaagag   1020
ccgagcgaag aagacaccat cgcgatcctg cgtggcctga aagagcgcta tgaggtccac   1080
cataaagtgg cgatcaccga cggtgcgatc attgcggcgg ccaaattgag ccatcgctat   1140
atcaccgatc gtcagttgcc ggacaaggcg atcgacctga tcgacgaagc ggccagccgt   1200
atccgtatgg agatcgactc caagccggaa gtgctggatc gtctggatcg gcgcctgatt   1260
caactgaaag tcgaatccca ggcgctgaag aaagaagaag acgaagcggc caagaaacgc   1320
ctggaaaaac tccaggaaga aattgtccgc ctggaacgtg agtattcgga cctcgaagaa   1380
atctggacct cggaaaaagc cgaagtacag ggttcggcgc agatccagca aaaaatcgag   1440
cagtcccgcc aggaactgga agccgcgcgc cgcaaaggcg acctgaaccg catggccgag   1500
ttgcagtacg gggtgatccc ggacctggaa cgcagcctgc agatggtcga ccagcacggc   1560
aaacctgaaa accagttgct gcgcagcaag gtgaccgagg aagaaattgc cgaagtggtc   1620
tccaagtgga ccggtattcc cgtgtcgaag atgctcgaag gcgagcgcga caagctgttg   1680
aagatggaaa gcctgctgca tcagcgcgtc atcggccagg aagaggcggt ggtggcggtg   1740
tccaacgccg tacggcgttc gcgggcgggt ttgtccgacc cgaaccgtcc aagcggctcg   1800
ttcatgttcc tcggcccgac cggtgtaggt aagaccgagt tgtgcaaggc cctggccgag   1860
ttcctctttg atacggaaga ggccatggtg cggatcgata tgtccgaatt catggagaaa   1920
cactcggtgg ctcgcctgat cggtgcacca ccaggctatg tgggttacga agagggcggt   1980
tatctgaccg aagccgtgcg gcgtaagcct tactcggtga tcctgctgga tgaggtcgag   2040
aaggcgcacc cggatgtgtt caacatcttg ctgcaggtgc tggaggatgg tcgcttgacg   2100
gacagccacg ggcgtacggt ggacttccgt aatacggtga tcgtgatgac ctccaacctg   2160
ggctcggcgc agatccagga attggtgggt gatcgtgaag cccagcgtgc ggcggtgatg   2220
gacgcgttga ccacgcactt ccgtccggaa ttcatcaacc gggtcgatga agtggtgatc   2280
ttcgagcctc tggcgcggga tcagatcgcg ggcatcaccg agatccagtt gggccgcctg   2340
cgtagccgcc tggctgagcg cgagctggac ctggagctga gcggcgaagc gttggacaag   2400
ctgatcgcgg tcggttacga cccagtgtat ggcgcacggc cacttaaacg tgcgatccag   2460
```

cgctggatcg agaacccact ggcgcagttg atcctgtcgg gcagctttat gcctggcact 2520
cgcgtcacgg cgacggtgaa agacgacgaa atcgtcttcc at 2562

<210> SEQ ID NO 16
<211> LENGTH: 1281
<212> TYPE: DNA
<213> ORGANISM: Pseudomonas fluorescens

<400> SEQUENCE: 16
atgactgaca cccgcaacgg cgaggacaac ggcaagctgc tctattgctc cttctgtggc 60
aaaagccagc atgaagtacg caaattgatt gccggcccct cggtgtttat ctgcgacgaa 120
tgcgtcgacc tgtgcaatga catcatccgt gaggaggtgc aggaagccca ggccgagagc 180
agtgcgcata aattaccttc gcctaaagaa atcagtggca tccttgacca atacgtcatt 240
ggtcaagagc gtgcaaaaaa ggttctggcc gtagcggtgt acaaccacta caagcgcttg 300
aaccagcgtg acaagaaagg tgacgaggtt gaactcggca agagcaacat cttgctgatc 360
ggtcctacag gctcgggtaa aaccctgctt gcagaaaccc tcgctcgcct gctgaacgtt 420
ccgttcacca tcgccgacgc caccaccctc accgaggctg gctacgtggg tgaagatgtc 480
gagaacatca ttcagaaact gctgcagaag tgcgactacg acgtagagaa agcccagatg 540
ggtattgtct acatcgacga gatcgacaag atctcgcgca agtcggacaa cccgtcgatc 600
actcgggacg tttccggtga aggcgtgcag caggccctgt tgaagctgat cgaaggcacg 660
gttgcgtccg taccgccgca aggtggtcgc aagcacccgc agcaggaatt ccttcaggtt 720
gatacgcgca acatcctgtt catttgtggc ggtgcgttct cgggtctcga gaaggtgatt 780
cagcagcgtt ccacccgtgg cggcattggt ttcagtgcgg aagtgcgtag caaggaagaa 840
ggcaagaagg tgggcgagtc cctgcgtgaa gtcgagcctg acgatttggt caagttcggt 900
ctgatcccgg aattcgttgg ccgtctgccg gtcctggcca cgttggacga gttggatgag 960
gcggctttga tccagatcct caccgaaccg aaaaacgccc tgaccaagca atacggcaaa 1020
ttgttcgaga tggaaggtgt agacctggag ttccgtaccg acgcgctgaa atcggtggcc 1080
aagcgggcac tggagcgcaa gaccggtgca cgtggtctgc gttctatcct cgaaggcgtg 1140
ttgctcgaca ccatgtacga aatcccctcg cagtccgagg tgagtaaagt ggtgatcgac 1200
gaaagcgtta tcgaaggcaa gtccaagccg ctgtatatct atgaaaacag tgagccggct 1260
gccaaggctg cacccgacgc g 1281

<210> SEQ ID NO 17
<211> LENGTH: 633
<212> TYPE: DNA
<213> ORGANISM: Pseudomonas fluorescens

<400> SEQUENCE: 17
atgttccgta attcctatat tcagcagaac tctgatatcc aggccgcagg cggcctggtc 60
ccgatggttg tcgagcagtc cgctcgtggc gaacgcgcct acgacatcta ctcgcgcctg 120
ctcaaggagc gagtgatctt tctggttggc ccggtagagg actacatggc caacctgatc 180
tgtgcgcagc tgctgttcct tgaagcggaa aacccggaca aggacatcca tctctacatt 240
aattcgccgg gtggttcggt gactgcgggc atgtcgatct acgacaccat gcagttcatc 300
aagccaaacg tgtcgaccac ctgtattggc caggcgtgca gcatgggcgc cttcctgctg 360
accgcgggtg ccgaaggcaa gcgtttctgc ctgccgaact cgcgcgtgat gattcaccag 420

-continued

```
ccactgggcg gtttccaggg ccaggcgtcg gacatcgaaa tccacgccaa ggaaatcctc    480

ttcattcgtg agcgtctcaa cacgctgatg gccaagcaca gcgggcgcac cctggaagaa    540

atcgagcgcg ataccaaccg tgacaatttc atgagcgctg aagccgccaa ggaatacggg    600

ttgatcgacg cagtgatcga caagcgcccc gca                                  633
```

<210> SEQ ID NO 18
<211> LENGTH: 1335
<212> TYPE: DNA
<213> ORGANISM: Pseudomonas fluorescens

<400> SEQUENCE: 18

```
atgtccatga ctccccgcga aatcgtccat gaactcaatc gccatatcat cggccaggac     60

gatgccaagc gcgccgttgc cattgcgctg cgtaaccgct ggcgccggat gcaactgccg    120

gaagaactgc gcgttgaagt aacgcccaag aacatcctga tgatcggccc caccggcgtg    180

ggtaaaaccg agatcgcccg gcgcctggcc aaactggcca atgcaccgtt catcaaggtc    240

gaagcgacca agttcaccga agtcggctat gtgggccgcg atgtcgagtc gatcattcgt    300

gacctggctg acgccgccct gaagatgctg cgcgaacagg aagtaaccaa ggtcagccac    360

cgcgccgaag acgccgctga agagcgcatc ctcgacgccc tgttgccacc ggcacgcatg    420

ggtttcaacg aagacgccgc accggctacc gattccaaca ctcgccagct gttccgcaag    480

cgcctgcgtg aaggccagct ggatgacaag gaaatcgaga tcgaagtggc tgaagtgtcc    540

ggcgtggata tttctgcccc gcctggcatg gaagaaatga ccagccagct gcagaacctg    600

ttcgccaaca tgggcaaggg caagaagaaa agccgcaagc tcaaggtgaa agaggcgctc    660

aagctcgtgc gcgacgaaga agccgggcgc ctggtcaatg aggaagaact caaggccaag    720

gccctggaag cggtcgagca acatggcatc gtgtttatcg acgagatcga caaagtggcc    780

aagcgaggca actcaggcgg cgtggatgtg tcccgcgaag gcgtgcagcg cgatttgctg    840

ccgctgatcg agggctgcac ggtcaacacc aagctgggca tggtcaagac tgaccacatc    900

ctgtttatcg cttccggtgc tttccacctg agcaagccca gcgacctggt gcccgagctg    960

caaggccgct tgccgattcg ggtggagctc aaggcgctga cgccgggcga cttcgagcgc   1020

atcctcagcg agccgcatgc ctcgctcacc gagcagtacc gcgagttgct gaaaaccgaa   1080

gggctgggta tcgaattcca ggcagacggg atcaagcgcc tggcggagat cgcctggcag   1140

gtcaacgaga agaccgagaa catcggtgcc cgtcgcctgc ataccttgct tgagcgcctg   1200

ctggaggaag tgtccttcag tgccggcgac atggccggtg cgcagaatgg cgaagcgatc   1260

aagatcgatg ctgattacgt caacagccac ttgggcgaat tggcgcagaa cgaagatctg   1320

tctcgttata tcctg                                                      1335
```

<210> SEQ ID NO 19
<211> LENGTH: 528
<212> TYPE: DNA
<213> ORGANISM: Pseudomonas fluorescens

<400> SEQUENCE: 19

```
ttgaccacca tcgtttcagt acgtcgccac ggcaaagttg tcatgggcgg cgacggccag     60

gtttccctgg gcaacaccgt gatgaaaggc aacgccaaga aagtgcgccg cctgtaccac    120

ggccaggtgc ttgccggctt cgcaggcgca accgccgacg cctttaccct gttcgagcgt    180

ttcgaaggcc agcttgagaa acaccagggc cacctggtgc gcgccgctgt ggaactagcc    240

aaagaatggc gcaccgaccg ctccctcagc cgcctggagg ccatgctcgc ggttgcgaac    300
```

aaagacgctt ccctgatcat cactggcaac ggcgacgtgg ttgaacccga gcatggcctg 360
atcgccatgg gttccggcgg cggctacgcc caggctgcgg ccagcgcgct gttgaagaaa 420
accgacctgt cggcccgtga aatcgtcgag accgccctgg gtatcgctgg cgatatctgc 480
gtgttcacca accacaacca gaccattgag gagcaggacc tcgccgag 528

<210> SEQ ID NO 20
<211> LENGTH: 900
<212> TYPE: DNA
<213> ORGANISM: Pseudomonas fluorescens

<400> SEQUENCE: 20
atgactgatc taccggatac cgacttcacc caacgcttca tcttcgatga gagcgatgcc 60
cgcggcgaga tggtttcgtt ggagctcagc tatgccgaag tccttgccaa acacgcctat 120
ccggagccgg tcgcgcaatt gctcggcgag ttgatggccg ccgcggcgct gctggtgggc 180
accatgaagt tcgacggttt gctgatcttg caggcgcgtt ccgaagggcc ggtgcccatg 240
ttgatgatcg agtgctcgag cgagcgcgag atccgtggcc tggctcgtta tgacgctgag 300
cagattgctg cagacgctac cctggccgac ctgatgccca acggcgtcct ggcactgact 360
gtcgacccga ccgaaggcca gcgctaccag ggtattgtcg acctcgacgg ccagaccctg 420
tcggaatgct tcaccaacta cttcgtcatg tcccagcaag tgggcaccaa gttctggctt 480
aacgccgacg gcaagcgcgc tcgcggtttg ctggtgcaac aactgccggc cgatcgcatc 540
aaggatgagg atgaccgtgc cgaaagctgg cggcatatca tcgccctggc cgacaccttg 600
aaggccgaag aactgctggg cctggacaac gaaaccatcc tgcaccgcct ctaccacgaa 660
gaagccgtgc gcctgttcga cgcacaaggc ctgcgcttca attgcagctg ctcgcgcgag 720
cgttccggca acgcgctggt cagtctgggc ctggaagatg cgcaaaatct ggtggtggaa 780
cacggcggcc atatcgagat cgactgccag ttctgcaacc agcgctacct gttcgatgcg 840
gctgatgtag cgcaattgtt cgctggcgca ggcagcgaca ccccttccga cacccgccac 900

<210> SEQ ID NO 21
<211> LENGTH: 1902
<212> TYPE: DNA
<213> ORGANISM: Pseudomonas fluorescens

<400> SEQUENCE: 21
atgagtgtgg aaactcaaaa ggaaaccctg ggcttccaga ccgaggtgaa gcaactgctg 60
cacctcatga tccattcgct gtattccaac aaggaaattt tccttcgcga attgatctcg 120
aacgcctctg acgctgtcga caaattacgt ttcgaagccc tgtccaagcc tgagttgctg 180
gaaggcggcg cggaactgaa gatccgtgtg agctacgaca aagacgccaa aaccgtcacc 240
ctcgaagaca acggtatcgg catgagccgt gacgatgcga tcacccacct ggggaccatc 300
gccaaatccg gcactgcaga tttcatgaag aacctgtcgg gcgaccagaa aaaagactct 360
cacctgatcg gccaattcgg cgtgggcttc tattcggcct tcatcgtcgc cgacaaggtt 420
gaagtcttca gccgccgcgc cggcctcgac gccagcgaag gcgtgcactg ggcctccaag 480
ggcgaaggcg aattcgaaat cgccacgatc gacaaggctg accgcggcac ccgcatcgtg 540
ctgcacctga aagccggtga agatgaattc gccgatggct ggcgcctgcg caacatcatc 600
aagaagtact ccgaccatat cgcgttgccg atcgagttgc ccaaggaaca gaccgttgcc 660
gaaggcgaag aagccccggc ggcggagtgg gaaaccgtca accgcgccag cgccctgtgg 720
acccgtccgc gtaccgagat caaggacgag gaataccagg agttctacaa gcacatcggg 780
cacgattacg agaacccgct gagctggagc cacaacaagg ttgaaggcaa gctcgaatac 840
agctcgctgc tctacgtccc ggcccgtgct ccgttcgacc tgtaccagcg tgaagcgcca 900
aaaggcctga agctctacgt acagcgcgtg ttcgtgatgg accaggcgga atccttcctg 960
ccgctgtacc tgcgctttat caaaggtgtg gtcgactcca acgacctgtc gctgaacgtg 1020
tcgcgggaaa tactgcagaa agacccgatt atcgactcca tgaagtcggc gctgaccaag 1080
cgcgtgctcg acatgctgga aaagctggcg aagaacgagc ctgagcaata caagagcttc 1140
tggaaaaact tcggccaggt catgaaagaa ggcccggcag aagattttgc caacaaggaa 1200
aagattgccg gtttgctgcg ttttgcctcg actcaaggcg aagatggcga gcaggttgtg 1260
tccctggctg attacctggc acgtgccaag gaaggtcagg acaagatcta ctacctgacc 1320
ggcgaaacct acgctcaggt caagaacagc ccgcacctgg aagtgttccg caagaaaggc 1380
atcgaagtgc tgctgctgac cgaccgtatc gatgagtggc tgatgagcta cctcaccgag 1440
ttcgacggca aaaccttcgt cgacgtggcc cgtggtgacc tagacctggg taacctggac 1500
tccgaagaag agaagaaaga agccgaagaa gtcgccaagt ctaaagaggg cctggttgag 1560
cgcatcaagg cttccctggg cgaagcggtg agtgaagtgc gggtttccca ccgcctgacc 1620
gactctcctg cgatcctggc catcggcgag caggacctgg gcatgcagat gcgccagatc 1680
ctggaagcca gcggccagaa agtgccggat tccaagccga tcttcgaatt caacccgtct 1740
cacccgctga tcgagaaact cgatggcgag cagagcgaag agcggtttgg tgacctgtcg 1800
cacatcctct tcgaccaggc cgccctggca gccggcgaca gcttgaagga cccggccgcg 1860
tatgtgcgcc gactgaacaa gctgttggtt gaattgtcgg tt 1902

<210> SEQ ID NO 22
<211> LENGTH: 477
<212> TYPE: DNA
<213> ORGANISM: Pseudomonas fluorescens

<400> SEQUENCE: 22
atgactgatc aacagaacac cgaagcagcg caagaccaag gcccacagtt ctcgctgcag 60
cggatctatg tgcgtgacct gtcgttcgaa gcgccaaaaa gcccggccat cttccgtcag 120
gagtggaccc caagcgttgc gctggacctg aacactcgtc agaaatccct ggaaggtgac 180
ttccacgaag tggtgctgac cctgtcggtc accgtcaaga atggtgaaga agtcgctttc 240
atcgctgaag tgcaacaggc cggtatcttc ctgatccagg gcctggacga agcgtccatg 300
agccacaccc tgggcgcgtt ctgcccgaac atcctgttcc cgtatgcccg tgagaccctg 360
gacagcctgg tcacccgtgg ctcgttcccg gcactgatgc tggcgccggt taacttcgat 420
gccctgtacg ctcaagagct gcagcgcatg caacaggaag gcgcgccgac cgttcag 477

<210> SEQ ID NO 23
<211> LENGTH: 588
<212> TYPE: DNA
<213> ORGANISM: Pseudomonas fluorescens

<400> SEQUENCE: 23
atgagtaaaa ccctggagtt tttctttgat ctcggcagcc ccgccactta cctggcctat 60
acccggttgc cggcgctgtg tgccgaaacc ggcgcacagg tggtgtatca acccatgcta 120
ttgggcggtg tattcaaggc cacgggcaat gcctcgccga tcacggtgcc cgccaagggt 180
cgctacatgc tcgatgacct ggcgcgttac gccaaacgct acaacgtgcc gctcaggttc 240

-continued

```
aacccgcact ttcccatcaa taccttgctg ctgatgcgcg ctgtcaccgg cattcaaatc    300

caccagcctg agcgcttcct cgacttcatc ggctgccttt tccgagcact ctgggtggaa    360

ggccgtcact tgggcgaccc agaggtcgtg gccaatgtgc tcaccgaaca ggggttcgat    420

cccgagcagg tactggccct gtcaaacgat gcagccgtca aggacgctct caaggacaaa    480

accgaacaag ccattaagcg cggcgtgttc ggcgctccca gtttctttgt aggaaaccag    540

ctgttcttcg gccaggaccg tctggacttt gtgcgtgaag cgctcagc                 588
```

<210> SEQ ID NO 24
<211> LENGTH: 651
<212> TYPE: DNA
<213> ORGANISM: Pseudomonas fluorescens

<400> SEQUENCE: 24

```
atgagtactc ccctgaaaat cgatttcgtc agcgacgtat cctgcccctg gtgcatcatc     60

ggcctgcgcg gcttgaccga agccctcgac cagctcggca gcgaggtgca ggccgagatt    120

cattttcaac cgttcgaact gaacccgaac atgcccgccg aaggtcagaa catcgtcgag    180

cacattaccg aaaagtacgg ctccacggct gaagagtccc aggctaatcg tgcgcgtatc    240

cgtgacatgg gcgccgcgtt gggctttgct tttcgcaccg atggccagag ccgtatctac    300

aacaccttcg acgcgcaccg tctgttgcac tgggccgggt tggaaggctt gcagtacaac    360

ctcaaggaag cgctgttcaa ggcgtacttc agcgatggcc aggacccttc cgaccacgcg    420

accttggcga tcatcgccga aagcgtcggg ctggaccttg cgcgcgccgc cgagattctt    480

gccagcgatg aatacgccgc cgaggtccgc gagcaggagc agctgtgggt ttcccgtggg    540

gtgagttcgg tgccgaccat tgtcttcaat gaccaatatg cggtgagcgg tgggcaaccg    600

gctgaagcct tcgtgggtgc gattcgccag atcatcaacg aatccaaatc c             651
```

<210> SEQ ID NO 25
<211> LENGTH: 633
<212> TYPE: DNA
<213> ORGANISM: Pseudomonas fluorescens

<400> SEQUENCE: 25

```
atgcgtaatc tgatcctcag cgccgctctc gtcactgcca gcctcttcgg catgaccgca     60

caagctgccg atgtgccgct tgaagccggt aaaacctatg ttgagctggc taacccggtt    120

cccgttgcag tgccgggcaa gatcgaagtg gtggagctgt tctggtacgg ctgcccgcat    180

tgctacgcct tcgagccgac tatcaaccca tgggctgaaa agctgcccaa ggacgttaac    240

ttccgtcgca ttcccgccat gttcggtggc ccatgggacg cccacggcca gctgttcctg    300

accctggaag ccatgggtgt tgagcacaag gtccacaacg ctgtcttcga agcgatccag    360

aaacaaggca agcgcctgac caagccggac gaaatggctg acttcgttgc cactcagggt    420

gtcgacaagg acaagttcct ggcgaccttc aactccttcg ctatccaggg ccagatcaaa    480

caggccaagg aactcgcgca gaagtacggc gtgcaaggcg ttccaaccct gatcgtcaac    540

ggcaaatacc gtttcgacct gggcagcacc ggtggtcctg aagcgaccct gaacgttgct    600

gaccagctga ttgccaaaga acgcgctgcc aag                                 633
```

<210> SEQ ID NO 26
<211> LENGTH: 729
<212> TYPE: DNA
<213> ORGANISM: Pseudomonas fluorescens

<400> SEQUENCE: 26
atgcgcttga cccagattat tgccgccgca gccattgcgt tggtttccac ctttgcgctc 60
gccgatgatg cggccgagca gaccatccgc aagagcctgg ccaacctggc gctcgacacg 120
cctatcgaaa gcattagcgc cagccccatg gccggcctgt acgaagtcaa gctcaagggc 180
agccgcgtgc tgtacgccag tgccgatggc cagtacatcg tccagggcta cctgttccag 240
ctcaaggacg gcaagccggt caacctgacc gagaaggccg agcgcctggg cgtgtccaag 300
ctgatcaacg gcatcccggt ggctgaaacc gtggtttacc cggccattgg cgaaaccaag 360
acccacatca ccgtgttcac cgacaccacc tgcccgtact gccacaagct gcacgctgaa 420
atcccggcac tgaacaagct gggcgtggaa gtgcgctacg tcgcgttccc gcgccagggc 480
ctgggttcgc cgggtgacga gcagttgcaa gccgtatggt gttcggccga caaaaaggcg 540
gccatggaca agatggtcga cggcaaggaa atcaaatcgg ccaaatgcgc caacccggtt 600
tccaagcagt tcgccctggg ccagtccatt ggtgtgaacg gtacaccggc catcgttttg 660
gccgacggcc aggtgattcc gggctaccag ccggcgccgc aagttgccaa actggcactg 720
ggtgccaag 729

<210> SEQ ID NO 27
<211> LENGTH: 759
<212> TYPE: DNA
<213> ORGANISM: Pseudomonas fluorescens

<400> SEQUENCE: 27
atgcctcgcc tccgccacct gctgaccctg ctgccgttga cgctagccgc tgcgctggcc 60
caggccgaag acctgccggc cccgatcaaa cagatcgaag ccaaaggtgc caagatcatc 120
ggcaaattcg acgcccccag cggcctcacc ggctacgcag cccagtacca gaaccgtggc 180
atggccctgt acttgaccgc cgacggcaaa aacgtcatcg ccggcaacct gtacgacgcc 240
cagggcaatg acctgagcac cgcgcccctg gaaaaactgg tgtacgcgcc gatggccaag 300
gaagtctggg ccaagatgga aaacagcagc tggatccagg acggcgacaa aaacgccccg 360
cgcaccatct acctgttcag cgaccccaac tgcccgtact gcaacatgtt ctgggaacag 420
gcccgcccgt gggtcaaggc cggcaaggtg cagttgcgcc acatcatggt cggcatcatc 480
cgcgaagaca gccccggcaa atccgccgcc ctactcgccg ccaaagaccc gcaaaaagcc 540
ctgcaagacc acgaagcggc cggcaagggc agcaagctca aggcgctgga aaagatcccg 600
gccgaggtag aggccaagct tgatgcgaat atgaagttga tggatgaact ggagttgtcg 660
gcgacgccgg cgattttcta tctggatgac aaagggggt tgcagcagca gcaaggcgcg 720
ccttcgccgg ataagttggt gaagatactg gggccgaag 759

<210> SEQ ID NO 28
<211> LENGTH: 561
<212> TYPE: DNA
<213> ORGANISM: Pseudomonas fluorescens

<400> SEQUENCE: 28
atgctgaaaa aaatcgcctt atttgccggt tccgccttgt tcgctgccaa cctgatggcg 60
gctgagccgg ccaaggcgcc acatgttttg ctcgacacca ccaacggcca gattgaaatc 120
gaactggacc cggtcaaggc gccgatcagc accaagaact tccttgagta cgtcgacagc 180
ggcttctaca ccaatacgat tttccatcgc gtgatcccgg gcttcatggt ccagggcggc 240
ggcttcaccc agcaaatgca acagaaagac acgaaggcac cgatcaagaa cgaggccagc 300

```
aacggcctgc ataacgtgcg cggtacgctg tcgatggccc gcacctcgaa cccgaactcg    360

gccaccagcc aattcttcat caacgtggct gacaatgcct tcctcgaccc gggccgcgat    420

gccggttatg ccgtgttcgc caaagtggtc aagggcatgg acgtcgtcga catcatcgtc    480

aactcccaga ccaccaccaa acaaggcatg cagaacgtgc caatcgatcc tgtgttgatc    540

aagtcggcca agcgcatcga c                                              561
```

<210> SEQ ID NO 29
<211> LENGTH: 504
<212> TYPE: DNA
<213> ORGANISM: Pseudomonas fluorescens

<400> SEQUENCE: 29

```
atgactcaag tcaaactgac caccaaccac ggtgacatcg tcatcgagct gaacgccgat     60

aaagcgccga tcaccgtcgc caacttcatc gaatacgtca aagccggcca ctacgaaaac    120

accgttttcc accgtgtcat cggtaacttc atgatccagg gcggcggttt cgagcctggc    180

atgaaagaaa agaaagacaa gcgtccaagc atccagaacg aagcggacaa cggcctttcc    240

aacgacaagt acaccgtcgc catggcccgt accatggagc cgcattcggc ctccgcgcag    300

ttcttcatca acgtcgccga caacgccttc ctgaaccaca gcggcaaaaa cgtgcagggt    360

tggggctacg cggtgttcgg taaagtcacc caaggcaccg acgttgtcga caagatcaaa    420

ggcgtatcga ccacctccaa ggccggtcac caggacgttc cagccgaaga cgtgatcgtc    480

gagaaagccg agatcatcga agcg                                           504
```

<210> SEQ ID NO 30
<211> LENGTH: 729
<212> TYPE: DNA
<213> ORGANISM: Pseudomonas fluorescens

<400> SEQUENCE: 30

```
atgtccgaag ttaatctgtc caccgacgaa acccgcgtca gctacggtat cggccgtcag     60

ttgggcgacc aactgcgtga caacccgcca ccgggcgtca gcctggacgc gatcctggcc    120

ggcctgaccg acgcgttcgc aggcaagcca agccgtgttg accaagagca aatggcggcc    180

agcttcaaag tgatccgcga aatcatgcaa gccgaagccg ctgccaaggc tgaagctgca    240

gcaggcgctg gcctggcttt cctggcggaa aacgccaagc gtgatggcat caccaccctg    300

gcttccggcc tgcaatttga agtgctgacg gctggtaccg gcgccaagcc gacccgtgaa    360

gaccaagtgc gtactcacta ccacggcacc ctgatcgacg gcactgtgtt cgacagctcc    420

tacgagcgcg gccagcctgc agaattcccg gttggcggcg tgatcgccgg ctggaccgaa    480

gccctgcaac tgatgaatgc cggcagcaaa tggcgcgtgt acgtgccgag cgaactggct    540

tacggcgctc aaggcgttgg cagcatcccg ccgcacagcg ttctgtattc gacgtcgagc    600

tgctcgacgt tctgtaaaac ctgctggtta cctgttggga cgaacgcgtt cgccccaaca    660

ggcgtttgcc agtttcttca tggatggaac ttgccattga gctccgtcgc cgggcgcaac    720

gctcgtgca                                                            729
```

<210> SEQ ID NO 31
<211> LENGTH: 738
<212> TYPE: DNA
<213> ORGANISM: Pseudomonas fluorescens

<400> SEQUENCE: 31

```
atgaaacagc atcggttggc ggcggcggtg gccctggtta gcctggtact tgcgggttgt      60

gattcgcaga ccagcgtaga gctgaaaacc ccggcgcaaa aagcttccta cggcatcggc     120

ctgaacatgg gcaagagcct tgcccaagaa ggcatggacg acctggactc caaagctgtt     180

gcccagggca tcgaagatgc cgtcggcaag aaagagcaga agctcaagga cgatgagctg     240

gttgaagcgt ttgccgcact gcaaaagcgt gctgaagaac gcatgaccaa aatgagcgaa     300

gagtcggcag ccgctggcaa gaaattcctc gaagacaacg ccaagaaaga cggtgtcgtc     360

accaccgctt ccggcctgca gtacaagatc gtgaagaagg ccgacggcgc ccagcctaag     420

ccgaccgacg tggtgactgt tcactacacc ggcaagctca ccaacggcac cacctttgac     480

agctccgtag atcgcggtag cccgatcgac ctgccggtca gcggcgtgat cccgggttgg     540

gtcgaaggcc tgcaactgat gcacgtgggc gagaaggttg agctgtacat cccgtccgac     600

ctggcctacg gcgcccagag cccgagcccg gcgatcccag cgaactccgt gctggtattc     660

gacctggaac tgctgggcat caaggaccca gccaaggcag aagcggctga cgcacctgct     720

gcaccagccg ccaagaag                                                   738
```

```
<210> SEQ ID NO 32
<211> LENGTH: 675
<212> TYPE: DNA
<213> ORGANISM: Pseudomonas fluorescens

<400> SEQUENCE: 32

atgtcgcgtt accttttctt agtgttcggc ttggcgatct gcgtggccga tgcaagcgag      60

caaccttcgt caaacatcac cgacgcaacc ccgcacgacc ttgcctatag cctgggcgca     120

agccttggcg aacggttgcg ccaggaagtc cccgacctgc agatacaggc tctgctcgac     180

ggactcaaac aagcctacca aggcaaacca ctggcgctgg ataaggcgcg catcgaacag     240

atcctctccc agcatgaagc gcagaacacc gccgacgccc aactgccgca aagcgaaaaa     300

gcactggccg ccgaacagca atttctcact cgggaaaaag ccgccgccgg cgttcgtcag     360

ctagccgacg gtatcctgct caccgagctg gcaccgggca ctggcaacaa gccgttggcc     420

agcgatgaag tacaggtgaa atacgtgggc cgactgcctg acgggactgt cttcgacaaa     480

agtacgcaac cgcaatggtt tcgcgtcaac agcgtgatca gcggttggag cagtgcattg     540

caacagatgc cggtgggtgc gaaatggcgc ctggtgattc cttcggccca ggcctatggc     600

gcagacggcg caggtgagtt gatcccaccc tatacgccgc tggtgttcga aatcgaactg     660

ctcggcactc gccac                                                      675
```

```
<210> SEQ ID NO 33
<211> LENGTH: 483
<212> TYPE: DNA
<213> ORGANISM: Pseudomonas fluorescens

<400> SEQUENCE: 33

atgacgatcg ccgctaacaa ggctgtctcc atcgactata ccctgaccaa cgacgctggt      60

gaggtcatcg acagctcctc cggcggcgcg ccgctggttt acctgcaagg cgcaggcaac     120

atcatcccgg gcctggaaaa ggctctggaa ggcaagagcg tcggtgacga actgaccgtc     180

gccgtagaac ctgaagatgc ctacggcgaa tactccgccg aactggtcag taccttgagc     240

cgcagcatgt tcgaaggtgt tgatgagctg gaagtgggca tgcagttcca cgcttcggcg     300

ccggacggcc aaatgcagat cgtcaccatc cgcgacctgg acggcgatga cgtgaccgtt     360

gacggcaacc accctctggc tggccagcgc ctgaacttcc aagtgaagat cgtagccatc     420
```

cgcgacgctt cccaggaaga agtggctcac ggccacgtcc acggtgaagg cggccatcac 480
cat 483

<210> SEQ ID NO 34
<211> LENGTH: 1308
<212> TYPE: DNA
<213> ORGANISM: Pseudomonas fluorescens

<400> SEQUENCE: 34
atgcaagttt ctgttgaaaa tactactgct ctcgagcgcc gcctgagcat caccgtgccg 60
gcagagcgta tcgagactgc ggtcaacaag cgtctgcagc agactgccca aaaggccaag 120
atcgctggtt tccgtccagg caaagtgccg atgagcgaaa tcaagcgtcg ttttggtgcc 180
gatgcgcgcc aggaagctgt aggtgacgtg atccaggctt ctttctacga agccgttgtc 240
gagcaaaagc tgaacccggc tggctcgcct tcgatcgagc ccaagtccct ggaagcgggc 300
aaggacctgg aatacgttgc cgtattcgaa gtgttcccgg aatttgaagt ggccggtttc 360
gacggtatcg aaatcgagcg tctgagcgcc gaagtggctg attcggacct ggacaacatg 420
ctggaaatcc tgcgcaagca gaacactcgt ttcgaagtgg ccgaccgtgc cgcccagaac 480
gaagaccaac tgaacatcga tttcgttggc aaggttgacg gcgaagtctt cgctggcggc 540
tccgccaagg gcactcagct ggtgctgggt tccaaccgca tgatccctgg tttcgaagac 600
ggcctggttg gcgccaaagc cggcgaagag cgcgttctga acctgacgtt ccctgctgac 660
taccagaacc tggacctggc tggcaaagcc gccgagttca ccgtgaccgt caacagcgtt 720
tccgagccta agctgccaga gctgaacgaa gagttcttcg cccagttcgg catcaaggaa 780
accggcatcg aaggcttccg caccgaagtt cgcaagaaca tggagcgtga gctgcgccag 840
gccatcaagt ccaaggtcaa gaaccaggtc atggacggtc tgctggccgc caaccctatc 900
gaagtgccta aggccctgct gtccaacgaa gtggatcgcc tgcgtgttca agcggttcag 960
cagtttggtg gcaacatcaa gcctgaccag ctgccggccg agctgttcga agagcaagcc 1020
aagcgccgcg ttgtgctggg cctgatcgtg gctgaagtgg tcaagcagtt cgacctcaag 1080
ccagacgaag accgcgtccg cgaaatgatc caggaaatgg cttcggccta ccaggagcct 1140
gagcaggtcg tggcttggta ctacaagaat gagcagcaga tgaacgaagt acgttcggtt 1200
gtgctggaag aacaagttgt ggatactgtt ctgcagaagg ctaaggtgac cgataaagcg 1260
gtctcttacg aagaagcagt caaaccggcg gaagcagcac aagccgac 1308

<210> SEQ ID NO 35
<211> LENGTH: 450
<212> TYPE: DNA
<213> ORGANISM: Pseudomonas fluorescens

<400> SEQUENCE: 35
atgactgatc aggtattggc tgagcaacgc atcggccaga acacggaagt cactttgcat 60
tttgcattgc gcctggaaaa tggcgacacg gtcgacagca ccttcgacaa agccccggcg 120
accttcaagg ttggcgacgg taacctgctg cctggttttg aagcggcatt gttcgggttc 180
aaggcgggcg acaagcgcaa cctgcagatc ctgccggaaa acgccttcgg ccagcccaac 240
ccgcaaaacg tgcagatcat cccgcgttcg cagtttgaag gcatggacct gtcggaaggc 300
ttgctggtga tcttcaatga tgcggcgaat accgaattgc ccggagtggt taaagcgttc 360
gatgatgcgc aagtgaccat cgacttcaac catccgttgg ccggtaaaac cttgacgttt 420

-continued

```
gatgttgaaa tcatcgacgt taaagcgctc                                    450


<210> SEQ ID NO 36
<211> LENGTH: 450
<212> TYPE: DNA
<213> ORGANISM: Pseudomonas fluorescens

<400> SEQUENCE: 36

atgcattcca gcgaacggtt caccatcacg ctggccattc ccctgcactt gccaaaccca     60

tccgattctg ggaaaacccc agcccttcac cccttcaatg agaaccccat gagcaacgac    120

gaactgcagg tcaccgacat ccgcctgggc gacggcaaag ccgtggtcaa gggcgcgctg    180

atcaccaccc aatacaccgg caccctggaa gatggcacgg tgttcgattc ctcctgggag    240

cggggcaaac cgttccagtg cgtgatcggc actggccgcg tgatcaaggg gtgggaccag    300

ggcttgatgg gcatgcaggt tggcggcgtg cgcacgttgt atgtaccggc gcacctggcc    360

tatggcgagc gctcgatggg cgcgcatatc aaacccaaca gtaacctgcg tttcgagatc    420

gaattgttgg aagtgctgac gcgggatgat                                    450


<210> SEQ ID NO 37
<211> LENGTH: 759
<212> TYPE: DNA
<213> ORGANISM: Pseudomonas fluorescens

<400> SEQUENCE: 37

atgaaaccaa gttttcgtta cacccacctg gtctattcgc tattagtgtt aactttgagc     60

cagagtgcca gtgcggcaat cggattagat cgtacccgtc tggtatttga gggcagcaaa    120

gacgctgtca gcgtcaacat cgtcaacaat aacacccaat taccttactt agctcaaggc    180

tggattgagg atgaaaaagg tgccaaaatc accactccgt tgattgtgct gccaccggtt    240

caacggctgg agccgggtaa gaaaagtcag gtaaaagtcc aggcgctgcc agcagccaag    300

ttgctgccgc aagaccgcga aactgtctac tacttcaatc taagagaaat tccgccgcgt    360

agtgataaag ccaacacctt gcaaattgcc ttgcagaccc gggtcaaatt gttttaccgg    420

ccagctgcta ttacgcctag tcagcaggat atctccaatc catggcagga gaaactcaca    480

ttgacccgcg atggcgaccg ttatcaggtg cataacccta cgccttatta cgtgactttg    540

gtggatgccc gtagcaataa ggacggagaa accgctccag atttccagcc tgtgatggta    600

ccacctaaag gttccttaca cctgggccca agcgctagag cgcttggcac tacaccttac    660

ctgacctacg ttaacgacta cggcggtcgc ccggtactgg cctttacctg cagtggcaat    720

acctgcgaag taaaaccaga cgctaaaccg agcaatgag                          759


<210> SEQ ID NO 38
<211> LENGTH: 702
<212> TYPE: DNA
<213> ORGANISM: Pseudomonas fluorescens

<400> SEQUENCE: 38

atgacgacga cattctcaaa caccgctgtc ggcctgattg ccttgctctt gatgctcggc     60

gatcaggtaa aagccgacgg tatggtcccg gacacctccg tggtgatcgt gcacgaggcc    120

gaaggcgaag cgtccgtgtc ggtgaccaac accgacagcc agctcgcgct gctgcatgtg    180

accttgcagg acattccgga agacaccgag ccgctgctgg tggtgacgcc gcccctttca    240

cgggtggaag cgtccaaatc ccaactggtg cgtttcattc tgcaaaacca gcagccgtta    300

ctgacccagc ggcttaagcg cgcggtgttc gaaggcatgc cccagggccg cgccgccaca    360
```

gccgccgggc atgcccgcgt gggcgtgacc gtgcgccaga acctgccggt gattgtgcac 420
cccaagggcc tggcgcccaa ccgcacgccc tggaccgacc tgacctggac actgcgcgaa 480
ggccagttac aggtgcgcaa cgacacgccg tacgtggtgc gtctggcgca ggagctgcaa 540
ctgctgcccg gtgacggcaa ggcgttgctg cctcggacct atgtgctgcc cggcgaagcc 600
ttgagcgtgc cggccagcag cagccaggcc aagacggtca ggctgcagcc ggccacggtg 660
tacgggttcg cggtcaaggc ttacgacgca ccaatcagct tc 702

<210> SEQ ID NO 39
<211> LENGTH: 786
<212> TYPE: DNA
<213> ORGANISM: Pseudomonas fluorescens

<400> SEQUENCE: 39
atggggtgtg ctttgcgacg gttatgcacc gtgggtttcg ccttgggggc gttgtgctcg 60
gcggggtttg tacaggcagc cagttcggtg ctgatctggc ccatcgaccc ggtgctggag 120
gccgaccaac aggccagcgc gctgtggctg gagaaccgtg gcaccgagac cgccaacctg 180
cagatccgcg tgtttgcctg gagccagaat ggctttgacg agcagtacca gaaccagcgc 240
gatgtgatcg gcagcccgcc cgtggccaaa atcgagccgg gccagaaaca actggtgcgc 300
ctgacccgca cccgggaagt gccgccggga caggagctgg cctatcgcat catcattgat 360
gaaattccct cggcgcttca ggtgcccacg ccgccggagg gcaagaacac ggcggcggcg 420
attcgctttc agatgcgtta ttcggtgccg ttgtttgcct acggcgccgg cttgtggagc 480
aaggacgacg ctacccgcca acgcgatccc aagggcgcgg gcaagccgca gttgagctgg 540
cagaaggtca acgtggcagg gcgcaactac atcgaggtgc gcaaccaggg cgccgtgcat 600
gcgcggctta ccgatgcgtc attcaaacag ggcgggcaga cccggccgtt ggtggacggt 660
ttgctcggct atgtgctgcc gggcgcgagc atgcgctggc cggtgccgga tgccgtatcg 720
gccgaccagc cgttgcaggt acgcgtcaac ggcgcgccgc aactggaaag cctggcgccc 780
aagcga 786

<210> SEQ ID NO 40
<211> LENGTH: 744
<212> TYPE: DNA
<213> ORGANISM: Pseudomonas fluorescens

<400> SEQUENCE: 40
atgtcgtgca cacgtgcatt caaaccactg ctgctgatcg gcctggccac actgatgtgt 60
tcccatgcat tcgctgcagt ggtgattacc ggtacgcgcc tggtctatcc ggcggaccag 120
aaagaaatca ccgtaaaact gaacaataac ggcacgttgc ccgcactggt ccaatcatgg 180
atcgacaccg gcagcgtcga atcgacaccc accagctcca aggcgccgtt cctattgtcg 240
cccccggtgg cgcgcattga cccgaccaag ggccaaagct tgcgagtgct ctttaccggc 300
gcgcctttgg cgcaggacaa agagtcggtg ttctggctca acgttctcga aatcccgccc 360
aaacccgagg cgggtgcaga cctcaacacg ctgcaaatgg ctttccgttc gcgcatcaag 420
ctgttctatc gcccggtcgg cttgcctgga aatcccaatg aggcggttga gcaggtgcag 480
tggcaattgg ttacggcacg cgatggccaa ggcctggcgc tgaaggcgta caacccgtcg 540
gcgttccacg tctcgctgat cgagttggac ctggtggcgg gtaaccaacg ctatcgcagt 600
gaggacggca tggtcggccc tggggaaacc cggcagttcg cgctgcccac gctcaaggcc 660
aggccgtcga gccaggcaca agtggagttc agcgccatca acgattacgg cgcgttggtc 720
ccgacccgca acacgctgca gccc 744

<210> SEQ ID NO 41
<211> LENGTH: 723
<212> TYPE: DNA
<213> ORGANISM: Pseudomonas fluorescens

<400> SEQUENCE: 41
atgggctgcg ttcccttacc cgaccatgga attaccgtgt tcatgtttct actcagaatg 60
gtgctgctgg cctgcgggtt gctggtgctt gcgccccgc ctgccgatgc ggcgctgaag 120
atcgaaggca cccgcctgat ctatttcggc caggacaagg ccgccggtat cagcgtggtc 180
aaccaggcct cgcgggaagt ggtggtgcaa acctggatca ccggcgagga cgaatcagcc 240
gaccgcaccg tgccctttgc cgccaccgag ccattggtac aactgggcgc cggggagcat 300
cacaagctgc gcatcctgta tgccggtgag ggcttgccca gcgatcggga atcgctgttc 360
tggctcaata tcatggagat cccgctcaag cctgaagacc ccaacagcgt gcagttcgcg 420
atccgccagc ggctcaagct gttctatcgg ccccccgcac tccagggcgg ctcggccgag 480
gcggtgcagc aattggtatg gagcagcgac gggcgcacgg tgacggtcaa caaccccagc 540
gccttccacc tgtcgctggt caacctgcga atcgacagcc agacgctcag cgattacctg 600
ctgctcaagc cccatgaacg caaaaccctg accgcgctcg acgctgtgcc caagggcgcc 660
actctccact tcaccgaaat caccgatatc ggtttgcaag cccgtcatag cacggcgctc 720
aac 723

<210> SEQ ID NO 42
<211> LENGTH: 738
<212> TYPE: DNA
<213> ORGANISM: Pseudomonas fluorescens

<400> SEQUENCE: 42
atgccgcctc gttctatcgc cgcatgtctg gggctgctgg gcttgctcat ggctacccag 60
gccgccgcca gcatttcatt gaatgccacc cgtatcgtgt ttgacggtga ccacaaggaa 120
gccaacatta ccgtgcgtaa tggtaaccag gatgtattga ttcaatcctg ggtcgacatg 180
aacgacgcca gcgccagccg cgcgccgttt gccgtcaccc cgccactggc acgggtattc 240
gccaaggaac aacaactgct gcgcattctg tatgaaggca ccggcatgcc cacggaccgc 300
gagtcggtgg tgtggctcaa tgtgcaggaa atccccaagg ccagcgaggc cgagaacacc 360
ttgcagttgg ccatccgcca acgcatcaag attttctacc gccctgccgg tcttaccggc 420
agcgcgctgc aagcccctgc gcagcttgaa tggacgctgg ccaaacacgg cagccaaacc 480
ctgttgcagg tgaaaaaccc gacattgtac cacgtgtcca tggccgacat caaagtgcag 540
gcggtcttgg ccagcgactc caccatgatt gcgcccggcg agcaaaaaca gtttgcgctc 600
agtgctccag ttgccagtgg gccggtgcag ttgtcgtttt ccagcatcaa tgactacggc 660
gcgcagaatc actacagcgc gccgctgacc agcggcactg cgctaccggc gcatgcgact 720
gaatcgcgcc tcaacccc 738

<210> SEQ ID NO 43
<211> LENGTH: 771
<212> TYPE: DNA
<213> ORGANISM: Pseudomonas fluorescens

<400> SEQUENCE: 43
atgctttttc gcacattact ggcgagcctt acctttgctg tcatcgccgg cttaccgtcc 60
acggcccacg cgggagtggt gatcgatggc acacggcaca tctacccccca gcagcgccgt 120 gaaatcaccc tgcgcctgag caacgacgat aaacgggcac cgcgcctggt ccaggtgtgg 180
ctggatcaag gcgatgccac tccagatccc tcccatagcg acgtgccgtt cagcctctcg 240
cccccagtgt ttcgcctgga tccagggaga agccagggtg tgcggctggt ctacacccag 300
gatccgttgc cgccagatcg agagtccttg ttctggctta atgccttgga ggtccccccg 360
aaaatcagtg cggccgaact cggtgaacaa gcccctgaag ggaatcatct gcagtttgct 420
tttcgtatcc gcaccaaagt gttttttcgc ccccgtcatt tgcctggcag tgcagaccag 480
gcccccgcgc aactgcgctg gagtctgagg cgcaccgagc gcgcagccgt actgcgcgta 540
cacaacccta cggcctttca cgtgaccttc aacgaggtgg cactggcgct gggccctcgg 600
cctgacgccc acctgatacc ggtacaagaa ggcatggtgc cgccaggtgc cagccttgaa 660
ctgcctgtac gcggcaccct gccgacgatc cccgcggacg cccaggtgca tttcaaatac 720
atcaatgatt acggcgcatt ctccgcgccg cagcgagccc ccctgaagtt t 771

<210> SEQ ID NO 44
<211> LENGTH: 867
<212> TYPE: DNA
<213> ORGANISM: Pseudomonas fluorescens

<400> SEQUENCE: 44
atggttggca ggcagcaccg gcaacggcac cttccagatt cccttgaccg cgcgctacat 60
acaaaccggc gccaccgtcc gcccgggcac ggccaacggg ctggcgacct ttactttggc 120
ctatcggtag tcggcgtgat gatccgagtc ttattgacct gcgtgtccgg tctggcactg 180
gcggcatcta tggcgatggt gcaagcggaa atcgtcattg atcgcacccg gcttatttac 240
ccggccacgg cacgggtggt aaccctcacc ctgcgcaacg aggcggacag cccacggctg 300
gtacaggtat ggatcgatga aggcgacccc cagatggcgc cggaattgag tgacgtaccc 360
tttactgtca caccaccgat tctgcgaatg ggccccggca aggctcaagc gttgcgggtg 420
atttatcacc cggtacccag acaagccatg accgatcctc aggaagtggt gtattggctg 480
aatgtgctag ggatacggcc tactgacgcg gcaagccatc aactgcaact ggcgtttcgc 540
acgcgtatca aactgttcct gcgccccaat gcgttgcctg gcagggcgga agatgccgtg 600
gcggcgttgc aatggcaact ggcagacgac cgcccggtgc tgcgggtgcg caacccgagt 660
gcctttcatg tgaccttgtc cagcgtggca ctcaaccttg agggcgtcga ataccgccat 720
gaaaacccac cgatgctggc accgcgctca acggccgagt tgatcatgcc gggttgggtt 780
gtaccgtggc gaggtacgcc gacgctgcgc ttcaccacat tggatgacta tggcgcgacc 840
catgagagca cgcagcgcat aggccgg 867

<210> SEQ ID NO 45
<211> LENGTH: 699
<212> TYPE: DNA
<213> ORGANISM: Pseudomonas fluorescens

<400> SEQUENCE: 45
gtgcgtggtt ttttaataag ttgtgcgctg ctgtggcatc ttttttcag tgctgttgcc 60 gccgccgacg gtatgttgcc ggaaacaaca gtggtggtgc tttatgagga agacggcgaa 120
gccaccttga gtatcaagaa caccgatgcg gggccggcac tgttgcattc cgttgttgag 180

-continued

```
aatgtgcctg aagacctgga gccgctactg attgtcacac cgcctgtcac ccgtgtggag    240

gcgggggata cgcagcttgt gcgctttatc agcaccttga aacagccgct caagacccag    300

cggctcaagc gcgtgtcgtt cgagggcatc ccccaagcgc gtgctgccgg tggtgcgacc    360

atcggcatca ccctgcggca gaatttgccg ctgatcctgc acccccaagg cctgccacgg    420

caccacacgc cctgggagtt gttgacgtgg aagcgcgtcg gggaccggct cagcgtccac    480

aacgacagcg cctatgtagt gcgcctggcg ccagatgtgc aactgctgcc acaaggcacg    540

ctggcgacat tgccgcgcac ttacattttg ccaggtgagg cattggtggc gaagggcgaa    600

ggtccgttgg gcaatgtggc tcaagtagag atccagcccg ccacggtcta cgggttttcg    660

gtagacaact accgagcgcc ggtcatcacc gatgagggt                           699
```

<210> SEQ ID NO 46
<211> LENGTH: 1455
<212> TYPE: DNA
<213> ORGANISM: Pseudomonas fluorescens

<400> SEQUENCE: 46

```
atgcactttg gaaaatggtt tcacaccagc accctgctgg tcggcttgag ttttgtgctg     60

ggcggctgcg ccagcgtctc ccaaacctcc accccggcaa ccctggataa gctgttgagc    120

gacccggcgc tgcaaggcgc caccgtctcg ctgatggtgc gtgatgcccg cacaggcacc    180

acgctgtatc agcacaaccc acgcacccgg ctggtgcccg cgtccaacct caagctgttg    240

accacggcgg cagccatgga tgtattgggg ccgcagtacc gcttcgccac gcaactgctg    300

agcaatggcc tacgccaggg cgaccggctg actggcaacc tgtacctgcg tggcttgggc    360

gacccgagta ttcagtttgc cgactatcag gcgctcgccg cgcaattggc cagccagggc    420

gtgcgccagg tgcagggtga cctggtgttc gacgacactt ggttcgatgc cgagcggctg    480

ggcgtggact ggtcccatga tgatgaaacc acctactacg gcgcgcagat ttcagcgctg    540

accgtggcgc ccaataccga ctttgatgct ggcagcgtgc tggtcaccgc caaggcgccg    600

ttgcacgtcg gctcgccggt cggcgtggag atctacccgc ccaccgacta cctgcaactg    660

aataaccgcg ccgtcagcgg gccgggtaac agctatggga tcaaccgtcg ccatggcacc    720

aacctgctgc agctcagcgg cgcggtggcg cctggccggc agagccagca attgatcagc    780

gtgtgggagc cgacgcaact ggtggccaac ctgtttgagc aagccttggc gcagcagggc    840

atcaaggtgc tggggcgtcg ggtgatgggc ggggcaagtc ctgctggggt gacggtgctg    900

gccgagcacc aatcggcgcc gttgcaggag ctgatcgtgc cgctgctcaa gctctcgaac    960

aacgccatgt ccgaagccgt gctcaaggcc atgggccgcc agacggccag cagcggcacg   1020

gcggcggcgg gcgccgtggc ggtggccgac tttctcaagc gccaggggct ggacaccagc   1080

gctgtgagcc aagtggacgg ctccggcctg tcgcggcgta acctggtgtc gtcgcaaacc   1140

ctcaccgacc tgctgctggc ggccagcaaa caaccctggt tcgacgcctg gtacaacgcg   1200

ctgccggttg ccggcaatgc cgaccgtatg accggcggca gcctgggtta ccgcctgcgc   1260

ggcacggctg cggaaaataa cctgcatgcc aagaccggct ccatggccgg cgtgtcgtca   1320

ttgagcggtt acatcaccga tgctcacggg cgcaagctgg tgttcgcgat gttgaccaac   1380

aactatgtgg tcgctggcgc gcaggtaaaa gccgtggaaa accgcgtcgc cgtggccctg   1440

tcccacagcg aagac                                                    1455
```

<210> SEQ ID NO 47
<211> LENGTH: 1488

<212> TYPE: DNA
<213> ORGANISM: Pseudomonas fluorescens

<400> SEQUENCE: 47
atggaattgg ttgtaaaaag cgttagcccc gaaacgttga aaaccgccac cctcgtggtc 60
gctgtcggcg aaggccgcac actcggcgtc gccgccaagc aactggacga actgagcggc 120
ggcgctatca gcgccgtgct caagcgcggc gacctggccg gcaaagtcgg ccagagcctg 180
ctgctgcaga gcctgcccaa ccttaaggcc gagcgcgttt tgctggtggg cgtgggcaag 240
gatgccgaac tgggcgaccg tccgtttcgc aagatcgtca gcagcatcct caccaccctc 300
aagggcctgg gcggcagcga tgcggtgctg gcactcgatg aaatcgtggt caagggccgc 360
gacagctacg gcaagacccg cctgctggcc gagtcgctgg tggacggcgg ctatattttc 420
gaccagttca agagccagaa agccgaaccc cgcgccctga agaaaatcac cctgctgacc 480
atcaaggctg cccaggctga agtccagcgc gccgtcaccc acgcccaggc catcgctaac 540
ggcatgtcgt tcactcgcga cctgggcaac ctgccgccga acatctgcca cccgacattc 600
ctgggcgaac aggccaaggc actgggcaaa gagttcaagg gcttgaaggt tgaagtgctg 660
gacgagaaga aaatcaagga cctgggcatg ggctcgttct atgccgtggg ccagggcagc 720
gaccagccgc cacgcctgat cgtgatgcaa tacaacggcg gcaagaagtc cgagaaacct 780
tacgccctgg taggtaaagg catcaccttc gacaccggcg gcatcagcct caagccgggt 840
gccggcatgg acgagatgaa gtacgacatg ggcggcgccg ccagcgtgtt cggcaccctg 900
cgtgcggtgc ttgagctcaa gctgccgatc aacctggtgt gcattttggc ctgtgccgag 960
aatatgccga gcggcggcgc ggctcgccca ggcgatatcg tcaccaccat gagcggccag 1020
actgtggaga tcctcaacac cgacgccgaa ggccgcctgg tgctgtgcga cgcactgacc 1080
tacgccgagc gcttcaagcc ccaggccgtg atcgacatcg ccactctgac cggtgcctgc 1140
atcgtggccc tgggctccca cacctcaggc ctgctgggca acaacgacga actgatcgag 1200
caactgctca gcgccggcaa ggccgccgac gaccgcgcct ggcaactgcc gctgttcgat 1260
gagtaccagg aacagctcga cagcccgttc gccgacatcg ccaacatcgg tggccctaaa 1320
gccggcacca tcacggcggc ctgcttcctg tcgcgctttg ccaagaactt caactgggct 1380
cacctggaca tcgccggcac cgcctggacc agcggcggca aggacaaggg cgccactggc 1440
cgtccggtgc ccctgttgac tcaatacctg ctggatcgcg ccaaagct 1488

<210> SEQ ID NO 48
<211> LENGTH: 633
<212> TYPE: DNA
<213> ORGANISM: Pseudomonas fluorescens

<400> SEQUENCE: 48
atggataact ggatagcgtt ggtcaaagcc aacatgaaag accgcaaggt cacacaggat 60
gaactggcgc agcgcctggg catgtcccag ggcggcatcg gccattggct caataaacgc 120
cgtgtgccga gcctggcgga catgaaccgc gtactggccg aactggggtt ggggtatttg 180
gaggtggcgc tggaaattcg tgaacgggcc gcgcaagtgc ctgaacggga atcgcactac 240
aacccgtact ttcgttaccc ggtcaacgac tggaagcagg cctgcgagct gcgtgaggag 300
cgtgcgcctt atagaaccga gcgctacgaa ttgaccgatt accacgcccg aggcaaggca 360
ttctggctgc cagtgagggg agacgccatg accgccccca cgggcatgag cattgcagct 420
ggcatgatga tcctggttga cccggcgatc gcgcccgagc ccggtaaatt agtgctggcc 480
caatgggctg gcaaccccca ggccaccttt cgccaattgc aggaagaaag cggccagcac 540
tacctggtgc cgctcaaccc cacttacccc aaggtgctgc tcaccgacgg ctgtcgcctc 600
ctgggtgtag tggtgcaggc cacggcgaag ttc 633

<210> SEQ ID NO 49
<211> LENGTH: 2043
<212> TYPE: DNA
<213> ORGANISM: Pseudomonas fluorescens

<400> SEQUENCE: 49
atgccgccca ggcatttcgc ggctacaatg cgcgcctcaa ccgtgacaag cctgactaaa 60
aaaactatgt ccttgcccaa gcatcacctg gaattgctca gccctgcccg cgatgtcgcc 120
attgcgcgcg aggctatctt gcacggcgcc gacgccgttt atatcggcgg gccgagcttc 180
ggcgcccgcc ataatgcgtg taacgaggtg agcgatatcg ctcaactggt ggaattcgcc 240
cgccgctacc acgcccgcgt cttcaccacc atcaacacta tcttgcatga caacgagctg 300
gagcccgcac gcaagctgat ccatcagctc tacgatgccg gtgtcgatgc gttgatcgtg 360
caagacctgg gcgtgatgga gctggatatt ccgccgatcg agctgcacgc cagcacccag 420
accgacatcc gcacactggg ccgggccagg tttctcgacc aggccggttt ctcgcagttg 480
gtactggccc gcgagttgaa cctgcaagag attcgcgcca ttgccgatga gaccgatgct 540
gccatcgagt tctttatcca cggcgccctg tgcgtagcct tctccggcca gtgcaatatc 600
tcccacgcgc aaaatggccg cagcgccaac cgtggcgact gctcccaggc ctgccgcctg 660
ccctacacct taaaagatga ccaaggccgc gttgtagcct ttgaaaagca cctgctgtcg 720
atgaaagaca acaaccagag cgccaacctg cgcgccctgg tcgaagcggg cgtgcgttcg 780
ttcaagatcg aaggccgcta caaggacatg ggctatgtga agaacatcac cgcctactac 840
cgccagcgcc tcgacgagat cctcgaagac cgcccggacc tggcccgcgc ttccagcggc 900
cgtaccgcgc acttcttcct gcccgacccg gaaaaaacct tccaccgtgg cagcaccgat 960
tactttgtca gcgaccgcaa gatcgacatc ggcgcctttg acaccccgac cttcaccggg 1020
ctgcccgtgg gcaccgtgga aaaagccggc aagcgcgact tgcaggtggt cacccatgag 1080
ccgctgtcca acggcgacgg cctgaatgta ctgatcaagc gtgaagtggt gggctttcgt 1140
gccaacatcg ccgagcccaa gggtgagttc gaggaagacg gtgagaagcg ctaccgctac 1200
cgcgtcgagc ctaacgaaat gccggccggc ctgcatcaac tgcgccccca tcacccgctc 1260
aaccgcaacc tggaccacaa ctggcaacag gccctgctca agacctcggc cgagcgccgt 1320
atcggcttgt catgggtcgc gcgcctgcgt gaagagcagc tgcaaatcac cgcgaccagc 1380
gaagaaggca tcagcgccag cgttatcctg cccggcccgt ttggcgtggc caacaagccg 1440
gaacaggcgc tggacaccct gcgcgacctg ctcggccagc tcggcaccac cgaataccat 1500
gccacccgca tcgagctgga tgcgccgcag gcgttcttca tccccaactc gcagctcaag 1560
gccttgcgcc gtgaagtgat cgaagcgctg actgccgcac gcgtcgccgc gcacccacgg 1620
ggtgggcgca aggctgaaac ctcgccgccg ccggtttacc ctgaggcgca cttgtcgttc 1680
ctggccaacg tctacaacca gaaggcccgg gacttctacc atcgtcacgg cgtaaagctg 1740
atcgacgcag ccttcgaagc ccacgaagaa accggcgaag tgccggtgat gatcaccaag 1800
cactgcctgc gtttctcgtt caacctgtgc cctaaacagg ccaagggcgt gaccggggtg 1860
aagaccaagg tggcgccgat gcagttgatc catggtgacg aagtgttgac cttgaagttc 1920
gactgcaaac cttgcgagat gcacgtggtg ggcaagatca aggggcatat cctcggcctg 1980
ccgcagccag gcagcgcagt ggagcatttc aacccggaaa accttatcta ccaaggcacg 2040
cac 2043

<210> SEQ ID NO 50
<211> LENGTH: 615
<212> TYPE: DNA
<213> ORGANISM: Pseudomonas fluorescens

<400> SEQUENCE: 50
atgtactcca tgacaaacct gactccccgc cgcaccgcca tcctgacctt cattcgcgag 60
cgcatcgcgc aacaaggcca gcctcccagc ctcgccgaga tcgccgaggc gttcggcttc 120
gcctcgcgca gcgtcgcccg caagcatgtg gtggcgctga ccgaagctgg ctttatcgag 180
gtcaacccca accaggcccg tggcattcgc ttgctaaatc aaccggcgcg tcccgagtgg 240
ctggatgtgc cggtgctcgg ccgcgtggcg gccggtcggc cgattggcgc cgatgccgag 300
gtgcacagcc gcttgcaact ggaccccgct accttcgcca aaacccccga ctacctgctg 360
cgagtgcagg gcgattcgat gattgaagat ggcattctcg atggcgacct ggtgggcgta 420
cgccgcactg tcgaagcctt gaacgggcag attgtggtgg cgcgcctgga cggtgacgtc 480
accatcaagc gtttcgagcg ccacggcgac agggttcgcc tgttgccgcg caacccggcg 540
tatcaaccca tcgtggtcgg gcccgagcag gacctggcca tcgaaggcgt gttctgcggc 600
ctggtgaggc aaggc 615

<210> SEQ ID NO 51
<211> LENGTH: 903
<212> TYPE: DNA
<213> ORGANISM: Pseudomonas fluorescens

<400> SEQUENCE: 51
atgagaatcc tcggcatttt atgcctgcta ctcacattga acggctgcag ctccttactg 60
ttctaccccg agcccggcct gcccttcact ccggaaaaag cccacctgca ataccgcgac 120
gtcacgctca ccaccgcaga cggggtgaag ctgcacgctt ggtggttgcc agccaaagcg 180
ggtgtgccac tcaaaggcac catcctgcat ttgcacggca acggcggtaa cctcgcctgg 240
cacctggggg gcagttggtg gttgccggag cagggttatc aagtgttgtt gctggactat 300
cgcggctatg ggctgtcgga aggcaagcca tcgttgccgg cggtctacca ggatatcgac 360
gccgcattcg gctggatcga caaggcgcct gaaacccagg gtaaaccgct gattattctc 420
gggcaaagcc tgggcggtgc actggcggtg cattacctgg cagcccaccc ggagcgtcaa 480
gcccaactca aagctctggt actggacggc gtgccagcca gttatcgtga cgtaggacaa 540
ttcgccttga gcacttcctg gttaacctgg ccgttgcagg tgccgctgtc atggctggtg 600
cccgacgccg acagtgcgat caatgccatg ccccgcgtga ccggcgtgcc caagctgctg 660
ttccacagcc tggatgatcc catcgtgccg gtggccaatg gcatccgcct gtatcaggcc 720
gcaccgccgc ccagggtgtt gcaactgacc cgtggcggcc atgtgcagac ctttgccgat 780
aaaacctggc agaccgtgat gctgcgttac ctggacgacc cgcagcactt caacggcttg 840
cgccgcctgg gcgaaattcc gaattaccct attcctaaag ttgattcatc agagagcccg 900
caa 903

<210> SEQ ID NO 52
<211> LENGTH: 2049
<212> TYPE: DNA

<213> ORGANISM: Pseudomonas fluorescens

<400> SEQUENCE: 52
gtgagcgcga acaaccctct tttgcagtcc tacgacctgc cgccgttctc ggcgatccgt 60
gccgagcacg tgcagccggc catcgaacag atcctcgccg acaaccgcgt ggcaatcgca 120
gagatcctgc agagccaggg taaaaatccg acgtgggccg gcctggtcct ggccatggac 180
gaactcaatg atcgcctggg tgcggcctgg agcccggtca gccacctcaa tgccgtgtgc 240
aacagcgccg aactgcgcga agcctatgag gcgtgcctgc cggccttgag cgcttactct 300
accgaaatgg gccagaaccg tgagctgttc caggccttcg aagccctggc caacagcccg 360
gaagctgccg gtttcgatgt ggcgcaaaaa accattctgg aacactccct gcgtgacttc 420
cgcctgtcgg gtatcgactt gccgccggag cagcaaaagc gctacgccga ggtgcagagc 480
aagctgtccg agctgggcag caagttctca aaccagttgc tggacgccac ccaggcctgg 540
accaagcacg tcaccgatga agccaccctt gccggtctga ccgactcggc caaggcacaa 600
atggccgccg ccgcccaggc caagggcctc gacggctggc tgatcacctt ggaattcccc 660
agctactacg ccgtcatgac ctacgcccag gaccgtgccc tgcgtgaaga ggtgtacgcc 720
gcctactgca cccgtgcgtc ggaccaaggc ccgaatgccg gtcagaacga taacggcccg 780
gtgatggaac agatcctcga cctgcgtcag gaactggccc aattgttggg ttatgcgtcc 840
ttctccgagc tgagcctggc caccaagatg gccgagtcca gcgaccaggt gctgagcttt 900
ctgcgtgacc tggccaagcg cagcaagccg tttgccgccc aggacctgca acagctcaag 960
gcctatgccg ccgagcaagg ctgccctgat ctgcaaagct gggacagcgg tttctacggc 1020
gaaaaactgc gtgagcagcg ctacagcgtg tcccaggaag cgctacgcgc ctacttcccc 1080
atcgacaaag tgctgggcgg cctgtttgcc attgtgcagc gcctgtacgg catcgagatt 1140
gctgagctca aaggcttcga cacctggcac ccggatgttc gtttgttcga aatcaaggaa 1200
aacggcgagc acgtcgggcg tttcttcttc gacctgtacg cccgcgccaa caagcgtggc 1260
ggtgcctgga tggatggcgc ccgtgaccgc cgccgtaccg ttgatggcgt gctgcaaagc 1320
cccgtcgcca acctggtgtg caacttcacc ccggccgaca gcggcaagcc tgccctgctg 1380
acccacgatg aagtcaccac cctgttccac gaattcggcc atggcttgca tcacctgctc 1440
acccgcgtgg aacatgccgg agtatccggt atcaacggtg tggcgtggga cgcggtggaa 1500
ctgccgagcc aattcatgga gaactggtgc tgggagcctg aaggccttgc gctgatctcc 1560
ggccactacg aaaccggcga gcccctgccc caggacctgc tggagaaaat gctcgcggcg 1620
aaaaacttcc agtccggcct gatgatggtg cgtcagctgg agttctcgct gttcgacttt 1680
gaattgcacg ccacccatgg cgatggtcgc agtgtggccc aggtgctgga aggcgtgcgc 1740
gatgaagtct cggtcatgcg cccaccggcc tacaaccgct tccccaacag cttcgcgcac 1800
atcttcgccg gcggttatgc ggcgggttac tacagctaca agtgggccga agtgctgtcg 1860
gcggacgcgt tctccaagtt tgaagaagac ggcgtgctca atgcccagac cgggcgggcg 1920
ttccgtgaag ccatcctggc ccgtggcggt tcccaggcgc cgatggtgct gttcgtcgac 1980
ttccgcggac gcgcgccgtc gattgacgca ctcttgcgcc acagcggcct gagtgaggac 2040
gcggcagca 2049

<210> SEQ ID NO 53
<211> LENGTH: 1155
<212> TYPE: DNA
<213> ORGANISM: Pseudomonas fluorescens

<400> SEQUENCE: 53
atgaacatca ccaccttagc caaacgcacg tgcctgctta tctcgctgat catcaccccg 60
gccgcctggg cggttgaaat ggtgccggcc tccccgcaac tggccgccaa gtcgtgggtc 120
ctcatggacg ccgccagtgg caacgtgctg gtcgaaaacg gcggtgatgt acgcctgccg 180
cctgccagcc tgaccaagct gatgaccgct tacatcgcga ccctggaaat ccgtcgcggc 240
cagatcggcg agaacgaccc ggtgaccgtc agcgaaaacg cctggcgtac cggtggttcg 300
cggatgttca tcaaggtggg ttcgcaagtc accgtgagcg acctgctgca cggcatcatc 360
atccagtccg gtaacgacgc cagcgtcgcc ctggccgagc acatcgccgg cagcgaagac 420
gccttcgccg acatgatgaa caaaaccgcc ggtgagttgg gcatgaccaa cagccacttc 480
atgaacccaa ctggcttgcc aaacccagag cactattcgt cggctcacga catggcgatc 540
ctggcgcgcg cgatcatccg cgttgacccg gtgcactacg cgatctactc ccagaaggaa 600
ttcttctgga acaacatcaa gcagcctaac cgcaacctgt tgctgtggcg cgacaagacc 660
gtcgatggcc tgaagaccgg ccacaccgac gaagccggct actgcatggt gtcgtccgcc 720
gtacgtgatg gccagcgcct gatcgccgta gtattcggca ccaacagcga gcaggcccgt 780
gcggccgaga cgcaaaaact gctgacttac ggcttccgct tcttcgaaac ccagaccttc 840
taccagaagg gtgctgaact ggcgaccgcg ccggtgtgga agggctcgac ttcgcaagtc 900
aaggccggcc tggccgacga cctgaccctg accatgccta aggccagct gaaaaagctc 960 gccgccagca tgaccctgaa cccgcaattg gttgcgccaa tcgccaaggg tgatgtgatc 1020
ggtaaggtcg aagtgaagct ggacgacaag gtggtgcaca gcgccgacct gatcgcgctg 1080
gacgctgtcg aggaaggtgg tatcttccgc cgcgtatggg atagcatccg tctattcttc 1140
tacggcttgt tcaac 1155

<210> SEQ ID NO 54
<211> LENGTH: 1149
<212> TYPE: DNA
<213> ORGANISM: Pseudomonas fluorescens

<400> SEQUENCE: 54
atgacggccc atgccgacct ttcgccgacc cttcaacttg ccatcgacct gatccgtcgc 60
ccgtcggtca cgccggtcga tgccgattgc cagaagctga tgatgcagcg cctgggcgac 120
gccggttttg cgcttgaacc gatgcgcatc ttcgacgtgg acaatttctg ggccacccat 180
ggcaagcatg aaggtccggt gctgtgcttt gccggtcaca ccgacgtggt gccgaccggc 240
ccggtgcagg cctggcagaa cgacccgttc gacgcgctga tcgatgaaaa cggcatgctc 300
tgcggccgtg gcgcggccga catgaaaggc agcctggcgg cgatgctggt ggcagcggaa 360
cgtttcgtca cggactaccc ggaccacaag ggttcggtcg ccttcctgat caccagcgac 420
gaagaaggcc cggcgcacca tggcaccaag gccgtgatcg aacgcctggc cgcacgcaag 480
gagcgcctgg actggtgcat cgtcggcgag ccgtcgagca ccagcctggt gggtgacgtg 540
gtcaagaacg ggcgccgtgg ctccctcggt gccaccttga ccgtgcgcgg tgtacaaggc 600
cacgtggctt acccgcacct ggcgaagaac ccgatccacc tggccgcacc ggccctggcc 660
gaactcgccg ccgaacattg ggatgacggc aacaccttct ttccgccgac cagcttccag 720
atttccaacc tcaactccgg taccggcgcc accaacgtga tcccgggtga cctgacggcg 780
gtgttcaact tccgtttttc taccgagtcc accgtcgagg gcctgcaaca acgggtcgcg 840

```
gccattctcg acaagcatgg cctggactgg catgtggagt gggcgctgtc gggcctgccg    900

ttcctcaccg agccgggcgc tctgctcgat gcggtgtcgg ccagcattct ggcgatcacc    960

gggcgtgaga cccaggcatc caccagcggc ggcacctccg atgggcgctt cattgcgacg   1020

ctgggcaccc aggtggtcga actggggccg gtcaacgcga cgatccacca ggtcaacgaa   1080

cgcatcctgg ccagcgacct cgatgtgctg accgaaatct actaccagac cctgatcaag   1140

ttgctcgcc                                                           1149

<210> SEQ ID NO 55
<211> LENGTH: 1311
<212> TYPE: DNA
<213> ORGANISM: Pseudomonas fluorescens

<400> SEQUENCE: 55

atgctgcatt tgtcccgcct cacttcgctg gccctgacga tcgccctggt gatcggcgcg     60

cctctggctt ttgccgacca ggccgcaccg gctgcacccg ccacggctgc gacgaccaag    120

gcgccattgc cgctggacga gctgcgtacc tttgccgagg tcatggaccg gatcaaggca    180

gcgtatgtcg aacccgtaga cgacaaggcc ctgctggaaa atgccatcaa gggcatgctc    240

agcaacctcg acccgcactc cgcctacctg ggcccggaag atttcgccga gctgcaggaa    300

agcaccagcg gtgagttcgg cggcctgggc atcgaagtgg gctccgaaga cggccagatc    360

aaagtggtct cgcctatcga cgacaccccg gcgtccaagg ccggtatcca ggccggcgac    420

ctgatcgtga agatcaacgg ccagccaacc cgcggccaga ccatgaccga agccgtcgac    480

aagatgcgcg gcaagctcgg ccagaagatc accctgaccc tggtacgcga cggcggcaac    540

ccgtttgacg tgaccctggc ccgcgcgacc atcacggtca agagcgtgaa aagccagctg    600

ctggagtcgg gctacggtta tatccgtatc acccagttcc aggtcaagac cggcgacgaa    660

gtggccaagg ccctggccaa gctgcgcaaa gacaacggca agaagctcaa cggcatcgtg    720

cttgacctgc gcaacaaccc aggcggcgtg ttgcagtcgg cggtcgaggt ggtcgaccac    780

ttcgtcacca agggcctgat cgtctacacc aagggccgta tcgccaactc agagttgcgc    840

ttctcggcca ccggcaacga cctcagcgag aacgtgccac tggcggtatt gatcaacggt    900

ggcagcgcct cggcttcgga aatcgtcgcc ggtgccctgc aagacctcaa gcgcggcgtg    960

ctgatgggca ccaccagctt cggcaaaggc tcggtgcaga ccgtattgcc gctgaacaac   1020

gagcgtgcgc tgaagatcac cacggcgctg tactacacgc ccaacggccg ctcgatccag   1080

gcccagggca tcgtgccgga catcgaagta cgccgcgcca agatcaccaa cgagatcgac   1140

ggcgaatact acaaagaggc cgacctgcaa ggtcacctgg gcaatggcaa cggcggtgcc   1200

gaccagccaa ccggcagccg cgccaaggcc aagccgatgc cgcaggacga tgactaccaa   1260

ctggcccagg cactcagcct gctcaagggc ttgagcatca cccgcagccg t            1311

<210> SEQ ID NO 56
<211> LENGTH: 852
<212> TYPE: DNA
<213> ORGANISM: Pseudomonas fluorescens

<400> SEQUENCE: 56

atgtcactaa atttcccgct gttgctggtc attgccgttg ccgtctgtgg tctcctggcg     60

ttgctcgatc tggtgttctt cgccccgcgt cgtcgggcgg ccattgcttc ctatcagggc    120

agcgtcagcc agcccgatgc ggtggtggtc gagaagctga acaaagagcc cttgctggtt    180

gagtacggca agtcgttctt cccggtgttg ttcatcgtgc tggtgttgcg ctcgtttctg    240
```

-continued

```
gtagagccgt tccagatccc ttcggggtcg atgaaaccga ccctggacgt gggcgacttc    300

atcctggtga acaagttttc ctacggcatt cgtctgccgg tgatcgacaa gaaagtcatc    360

cccgtgggtg acccgcagcg cggcgatgtg atggtgttcc gctacccaag cgacccgaac    420

gtcaactaca tcaagcgtgt ggtcggcctg ccgggcgacg tggtgcgcta caccagtgac    480

aagcgcctgt tcatcaacgg tgagtcggtg gccgagaagc tgctgggcgc cgagccgaac    540

accctgggca gcgccgagct gtaccaggaa aaactcggcg cggtggagca ccaaatccgc    600

aaggaaatga gccgctaccg tgcgatgccg gatggccagt ggaaagtgcc tgccgggcac    660

tactttatga tgggcgacaa ccgcgacaac tccaacgaca gccgctactg ggatgacccc    720

aacattccca aagacctgct gggcatggtg cccgacgaga acattgtcgg caaagccttc    780

gcggtctgga tgagttggcc ggaacccaag ctcagccacc tgccgaactt ctcgcgggtc    840

gggctgatca ag                                                        852
```

<210> SEQ ID NO 57
<211> LENGTH: 1158
<212> TYPE: DNA
<213> ORGANISM: Pseudomonas fluorescens

<400> SEQUENCE: 57

```
atgctcaagg cactgcgttt ttttggatgg ccattgttgg ctggcgtgct gatcgcgatg     60

ctgattatcc agcgttatcc ccagtgggtg ggcctgccca cactggatgt gaacctgcaa    120

caggcgccgc agaccaacac ggtggtgcag ggcccggtga cctatgccga tgccgtggtc    180

attgccgcgc cggcggtggt caacctgtac accaccaagg tcatcaacaa gcccgcgcat    240

ccgttgtttg aagacccgca atttcgccgc tatttcggtg acaacggccc caagcagcgc    300

cgcatggaat ccagcctcgg ctccggtgtg atcatgagcc ccgagggcta catcctcacc    360

aacaaccacg tgaccaccgg cgccgaccag atcgtggtgg ccctgcgtga cggccgcgaa    420

accctggccc gcgtggtggg cagcgacccg gaaacggatc tggcggtact caagattgat    480

ctgaagaacc taccggccat caccctcggc cgctccgacg gtttgcgcgt gggcgatgtg    540

gcgctggcca tcggcaaccc gttcggggtg ggccagacgg tgaccatggg catcatcagc    600

gccaccgggc gcaaccagct gggccttaac agctacgaag atttcatcca gaccgacgcg    660

gcgatcaacc ccggcaactc cggcggtgcg ctggtggacg ccaatggcaa cctgaccggc    720

atcaacaccg cgatttttc caagtccggc ggttcacagg gcattgggtt tgcgatcccg    780

gtgaagctgg cgatggaagt gatgaagtcg atcatcgagc acggccaggt gattcgcggc    840

tggctgggca ttgaagtaca gcccttgacc aaggaactgg ccgaatcatt cggcctgacc    900

gggcgtccag gcatcgtggt agcggggatc ttccgcgacg gcccggcgca gaaggccggc    960

ctgcaactgg gcgatgtgat cctcagcatc gacggcgccc cggcgggtga tggccgcaag   1020

tcgatgaacc aggtggctcg gatcaagccg accgacaagg tggcgatcct ggtgatgcgc   1080

aacggcaagg agatcaaact gtcggcggaa atcggcctgc gcccaccacc ggcgaccgcg   1140

ccagtgaaag aagagcaa                                                 1158
```

<210> SEQ ID NO 58
<211> LENGTH: 1449
<212> TYPE: DNA
<213> ORGANISM: Pseudomonas fluorescens

<400> SEQUENCE: 58

-continued

```
atgtcattca tcttttccat ttcatcttca aagtcaaaat tacttatgac cactgaaccg      60
tctaaagcgc cgccgcttta cccgaagacc cacctgctcg ccgcaagtgg tatcgccgcc     120
cttctcagcc tggcactgct ggtattccct tccagtgacg ttgaagccaa acgaacatcc     180
ctgagccttg atctggaaag cccagttgaa caactgacac aagatcaaga cgcttccgac     240
gctcaacaag ccacaaacac tgcaactgaa tcacctttcg cccagatcga aagcacaccc     300
gaagacaccc agcaagccgc ccaggaagca cctgcagcag ccaagagtcc ccagcatcgc     360
gaagtcatcg tgggcaaagg cgacacactc tcgaccctgt tcgaaaaagt tgggttgcct     420
gccgccgctg taaatgacgt gctcgccagc gataagcaag ccaagcaatt cactcagctc     480
aaacgtggtc aaaagcttga atttgagctg acgccagacg gccagttgaa caacctgtac     540
accagcatca gtgacttgga aagcatcagc ctgagcaaag gcgccaaagg cttcgcattc     600
aacagaatca ccaccaaacc cgtcatgcgt tccgcctacg tacatggcgt gatcaacagc     660
tccctgtcgc agtcggccgc gcgtgcgggc ctgtcgcata gcatgaccat ggacatggcc     720
agcgtatttg gctacgacat cgacttcgcc caggacatcc gtcaaggcga cgaattcgac     780
gtgatctacg aacagaaagt agccaacgga aaagtggtcg gcactggcaa cattctttct     840
gcacgcttca caaaccgtgg caaaacctac accgccgtgc gctacaccaa caaacaaggc     900
aacagcagct actacacggc tgatggcaac agcatgcgta aggccttcat ccgtacaccc     960
gttgactttg cccgtattag ctcgcgtttc tccatgggcc gcaagcatcc aattctgaac    1020
aaaattcgcg cacacaaggg cgtcgactat gccgcgccgc gtggcacgcc aatcaaagca    1080
gcgggcgacg gcaaggtctt gttggcgggg cgccgtggtg gttacggcaa tacggtgatc    1140
atccagcacg gcaacactta ccgcacgctg tacggccaca tgcaagggtt cgccaagggc    1200
gtcaagacag gcggcaacgt gaaacagggc caagtgatcg gctacatcgg taccaccggc    1260
ctctccaccg gcccgcactt gcactacgag ttccaggtca acggcgtaca cgtcgaccca    1320
ttgggccaga agctgccgat ggccgacccg attgccaagg ccgaacgcgc gcgcttcatg    1380
caacagagcc agccgctgat ggcacggatg gatcaagagc gctccacctt gctggcttcg    1440
gcgaagcgt                                                            1449
```

<210> SEQ ID NO 59
<211> LENGTH: 996
<212> TYPE: DNA
<213> ORGANISM: Pseudomonas fluorescens

<400> SEQUENCE: 59

```
atgagtgacg agtggaaagc gcctgaaaag gccgagagca gtgatgataa aagctggaag      60
ctgctggaaa agaccctcct ggccagcgtc caggaacagc ggcgttcgcg gcgctggggg     120
attttcttca agctgctgac ctttgtgtac ctgcttggga tgctggcgct gttcagcccg     180
ctgatggaca tggaaaagag cgccacccgc ggcagtcatt acaccgcctt gatcgaggtg     240
cgcggcgtga ttgccgacaa ggagcccgcc agtgccgaca atatcgtcac cagcctgcgc     300
gcggcctttg aggaccccaa ggtcaaaggc gtggtcctgc gtatcaacag cccaggcggc     360
agcccggtgc agtcgggcta tgtgtatgac gagattcgtc gtctgcgcgc cttgcatccg     420
gataccaagc tctatgccgt gatctccgac ctgggtgcct cgggcgccta ttacattgcc     480
agtgccgcag accagatcta tgccgacaag gccagcctgg tgggttctat tggtgtgacc     540
gcggccggtt acggttttgt cggtgctatg gagaagctgg ggatagagcg tcgcacctac     600
acctcgggtg agcacaagtc gttcctcgat cctttccagc cgcagaaggc ggatgaaacc     660
```

```
gcgttctggc agggcgttct cgacactact catcgtcagt tcatcgccag cgtcaagcag    720

ggccgtgggg atcgtctgaa ggataaagac catccagagc tgttctccgg cctggtctgg    780

tcgggtgaac aggcgttgcc gctgggcctg atcgatggcc tgggcagtgc cagttcggtg    840

gcgcgggatg tggtgggtga gaagaagttg gtgtatttta cggttgagga atcgccgttt    900

gatcgcttct ccaagaagct cggtgccagt gtggcggaga agctagctct gtatatgggc    960

ttccaggggg ccgtccctgc gctgaaacct gaaggc                              996
```

<210> SEQ ID NO 60
<211> LENGTH: 1365
<212> TYPE: DNA
<213> ORGANISM: Pseudomonas fluorescens

<400> SEQUENCE: 60

```
atgcgacttt ccaatacgct gcaaagtttt catgcgccgc ttgctggcga tcagcaatca     60

gcggtggccg atgcgaccct aaggcccaac gacccctctg aatcgaacgt tgataaaccc    120

tctttcacgg ttgatcaggc cgcgcgtcaa atcactcgaa ccggccatcg ttggtttgac    180

gccaatcgcg acggcatcac gcagatctcc tattcattca acaagcacgc aagagggcac    240

acggcgttca atgcgaccca gaaagagcag gcccggcgct cgatgcaatc gtgggaggat    300

gtcgcgaatg tttcattcca ggaaggcagt cgtcgccccg aggggcttct agcgttctcc    360

aatagcacgg actacgaggt cgccttcggc cagtatccgg gccaggaagg taaagtgctg    420

atcaatcccc gattcggcac caatactaac ccggccctgc acaatcatgg gcgaatgacc    480

ctgacccatg aaattgggca caacctgggc ctgttacacc caggcaccta taattttggt    540

aatcccaatt accgcgatca cgccttatat gctcaggata cgcgggctta cagcgtgatg    600

agctacttcg atgcacctga agcgggtaaa cacttcaatg gaaagttacc gtcggcgccg    660

atgatggatg atatcgccgc tgcgcagcgg gtttatggtg ccaataacac gacgcgcaat    720

tcagatacca cctatggctt caactccaat gcgggacgag actatctgga gttgaactcg    780

cgtcacgata cggccttgtt ttgtgtatgg gacggtggtg gtgtcgatac gttggacttt    840

tccaagtatc accaaaacca gactatcaat ttgcgggcgg agtccttttc ggatgttggc    900

ggcctggtgg ggaatgtttc cattgccaag gggcttacgc tggagaatgc aatcggcggc    960

tccgggcatg actcgatcat tggtaaccaa gcaaacaacg tgcttaaagg tggggcgggt   1020

gcggatcgac tccgaggtgc ggggggcgct gacaccttcg cttacgacaa tgccagcgac   1080

tccacgccgg aatatcccga tcagattatg gattttgtca cgggtgtgga cagaatcgat   1140

ctgtcgaacc tgctgggcaa cgcgggggtt gatgccctga ggttcgtcag gcggctgacg   1200

ggcaaaccag gtgaagcgat tctggattac aaccgtacga ctaacctgtc taggctggcc   1260

atcgacctca cagggaatgg ccgatttgat tttttcctca aggcttacgg cccgatcaat   1320

gtgcccgaca tcatcaccgc caatcctggc aggcagcgct acgcc                   1365
```

<210> SEQ ID NO 61
<211> LENGTH: 558
<212> TYPE: DNA
<213> ORGANISM: Pseudomonas fluorescens

<400> SEQUENCE: 61

```
atgagctcgc aactcaacgg caagcacatc ctcgtcatca cctccaacac cggtatcgag     60

cgcgacgaac tgctcaagcc gctggagacg ctgcgtggct acggcgcgac cgtgacgcac    120
```

gcctccagca aagggggcac tacccagaca tttgtcggcg acacggaaaa agaccagacc 180
gtggaatccg acgtgcaact gtcggatgtt gtcagcgccg acttcgatgc gctggtcatc 240
ccgggcggca cggtcaatgc cgatacgctg cgccaggatg ccgccgcgtt gcgcttgatc 300
aatgagttcg tgcaggccgg caagaccatc gcggcaatct gtcacgggcc atggaccctg 360
atcgacgctg gcgtggtcaa gggcaaaacc ctgactgcct ataaaagcgt gcgcatcgac 420
cttgaaaacg ccggcgctgc cggcgtggtg gatgccgagg ttaaagagtg ccaggccaat 480
ggctggacct tgatcacctc gcgcacgccg gacgatctac cggcgttcaa tgaggcgatt 540
gccaaggccg tcggcggc 558

<210> SEQ ID NO 62
<211> LENGTH: 1227
<212> TYPE: DNA
<213> ORGANISM: Pseudomonas fluorescens

<400> SEQUENCE: 62
atgctcttca ccttcccgcg taccctgttg gccgctaccc tggccttgtc tttcagcctg 60
ccggcctaca gcgccgagcc tcataaacag atccagcaac aggccgaaca atacaaggcc 120
gaagccttga agctgctgga gcgcctggtg aatatcgact cgggctcagg ctacgagccc 180
ggcttgactc aagtgcgcga tatcgccgtg gatgagttga aacagttggg tttcaccatc 240
gaactggtgc cggataaagc cgccaacaac agccatgtgg tcgccaccct caaaggcact 300
ggcaaggcca agatcctgct gatggcccat atggacaccg tattcaagga aggctcggcc 360
gccgagcgcc ccttccacat caaggacggc cgcgcctacg gccccggcgt gatggatgac 420
aagggcggca tagtcgccgg catctatgcg ctcaaagtcc tcaaaagcca gggcttcaag 480
gactacgcgc agatcacctt cctgctcgac gccagcgaag aaaccgggtc cgacgccgct 540
tccgaactga tccgcaacac tgccaagggc cacgatgtaa ccctgaacct ggaacccggt 600
cgccccgccg acggcctggt ggtgtggcgc aaaggcagcg ctaccgccgt ggtcgaagtc 660
aaaggcaagg ccgcccacgc cggcgtcgcc ccggaactgg gacgcaacgc cgccatggaa 720
gccgcgcacc agatcctgca actgggcaaa ctcggcgacg aagacaagaa aaccaccatc 780
aacttcaccg tgctcaaggc tggcgaccgc accaacgtca tccctgacca ggccaccgcc 840
aaggccgacg tgcgtgcggc cttgccggaa gaattcgacc ggatcgagaa agacctggcc 900
cgggtttcag ccaacaaatt gatcccggaa accgaagtga aaaccagcct gcagcgcggc 960
ctgccgccga tgccgcagac ggccgagtcg gataaattgg tggcgatggc ccaagggatt 1020
tatggcgaac tgggacgcaa gttgaccatc gaaggcagcg gcggcgcggc ggatgccagc 1080
ttgtccgccg gtgtaggcac gccgacgttg gatgggtttg ggatagtggg gggcaatatt 1140
cacacggcgg aggaatatgc cgaggtggag agtgttgcgc cgcgggttta tttgttgagt 1200
cggatgatca tggagttgtc caagcgc 1227

<210> SEQ ID NO 63
<211> LENGTH: 1488
<212> TYPE: DNA
<213> ORGANISM: Pseudomonas fluorescens

<400> SEQUENCE: 63
atgagtgatc gcaaaaacag ccgcctgatc ctgcccggcc tgatcgccgt caccctgatg 60
gcggccagcg ccgtttactt cttgcgcccc agcgagtcgg tcgccagcca ggccctggac 120
aaggctcaaa cggccagcac cctgcaatcc ctggcggaac tggatggcaa ggcaccgacc 180

```
aaccgcaagc tcgacgtaca aacctggacc accgccgaag gcgccaaggt gctgttcgtc    240
gaagcccatg agttgccgat gttcgacatg cgcctgctgt tcgccgccgg cagcagccag    300
gatggcgacg tgccaggcct ggcgctgatg accaacgcca tgctcaacga aggcgtgccg    360
ggcaaggacg tcagccagat cgccagtggc ttcgaaggcc tgggggccga ctttggcaac    420
ggcgcctacc gcgacatggc gctggtgacc ctgcgcagcc tgagcgacag cgccaagcgc    480
gacgccgccc tgtcactgtt caaccaggtg atcggccagc cgactttccc ggcagactca    540
ctggcacgca tcaagaacca gatcctggcc ggtttcgagt accagaagca gaaccccggc    600
aaactggcga gcatcgaact gttcaagcgc ctgtacggcg accaccctta cgcacacccg    660
agcgaaggca cccccgagag cgtgccgaag attaccctgg cgcagttgca ggcgttccac    720
gccaaggcct atgcagcggg taacgcggtg attgcagtgg tgggcgacct gacccgcgcc    780
gaagctgaag ccatgacggc caaggtgtcc gcgtcgctgc ccaaaggccc ggctatggcc    840
aagatcgccc agccgaccga gccaaaagcc ggcctgagcc gtatcgagtt cccgtccaag    900
caaacccacc tgctgtttgc gcagttgggc atcgaccgtg ccgacccgga ttacgcagcc    960
ttgtccctgg gtaaccagat cctcggcggc ggtggcttcg gcacccgctt gatgagcgaa   1020
gtgcgtgaaa agcgcggcct gacctacggc gtgtattccg gtttctcacc aatgcaggcg   1080
cgcggcccgt tcatgatcaa cctgcagacc cgcgccgaaa tgagcggtgg caccttgcgc   1140
ctggtggagg acgtactggc tgactacctc aagaccggcc cgacgcaaaa ggaactggat   1200
gacgccaagc gcgagctggc cggcagcttc ccgctgtcca ccgccagcaa cgccgatatc   1260
gtcgggcagt tgggcgccat gggtttctac aacctgccgc tgagctatct ggaagatttc   1320
atgaaacaat cccaggccct gaccgtcgat caggtcaagg ctgcaatgaa taaacacttg   1380
agcgccgaca agatggtcat cgtgaccgcc ggcccgacga ttgcgcaaaa gccactaccg   1440
ccccccactg ataaacctgc cgagcagccg ctcggggttc cggagcat                1488
```

<210> SEQ ID NO 64
<211> LENGTH: 1353
<212> TYPE: DNA
<213> ORGANISM: Pseudomonas fluorescens

<400> SEQUENCE: 64

```
atgaatgctc tagcccgccg cgccgcaggc ctgctgttca gcacagtttg tctgcctctc     60
tcagctttgg ctgccgatcc acaacccacc catgaattca ccctcgataa cggcctcaag    120
gtggtcgtgc gcgaagatca tcgtgcgccg gtggtggttt cccaggtctg gtacaaggtt    180
ggctcaagct acgaaacccc gggccagacc ggtttgtccc acgccctgga acacatgatg    240
ttcaaaggca gcgccaaggt tggccccggc gaagcctcgc tgatcctgcg cgacctgggc    300
gccgaagaaa atgcgttcac cagcgacgac tacaccgcgt actaccaggt attggcccgt    360
gaccgcctgg gcgtggcctt tgagctggaa gccgaccgca tggccagcct gcgcctgccg    420
gccgacgagt tcagccgtga aatcgaggta atcaaggaag aacgccgcct gcgcaccgac    480
gataacccca tgtccaaggc gttcgagcgc ttcaaggcca tggcgttccc ggccagtggc    540
taccacacgc cgaccattgg ctggatggcc gacctggacc gcatgaaggt cgaggaactg    600
cgccactggt accaatcctg gtacgtgccg aacaacgcca ccctggtggt ggtcggcgac    660
gtgaccccgg acgaggtgaa aaacctcgcc caacgttact tcgggccgat ccccaagcgt    720
gacgtgccac cggcaaaaat cccgatggaa ctggccgagc ccggcgagcg cctgctgacc    780
```

-continued

```
ctgcacgtgc agacccaact gccgagcgtg atcctgggct tcaacgtgcc cggcctggcc    840

accgccgaag acaaacgctc ggtacaggcc ctgcgcctga tctcggccct gctggacggc    900

ggctacagtg cacggatctc cgagcaactg gaacgcggtg aggagctggt gtccgccgct    960

tccaccaact acgacgccta cacccgtggc gacagcctgt tcaccctctc ggccacgccg   1020

aaccagcaga agaagaaaac cgtcgcccaa gccgaagccg gcctgtggcg cctgctcgat   1080

gagctgaagg ccaagccgcc gaccgccgaa gagctggagc gcatccgcgc ccaagtgatt   1140

gccggcctgg tgtaccagcg tgattccatc accagccagg ccacggccat tggctccctg   1200

gaaaccgtcg gcctgtcctg gaaactcatg gacaccgagc ttgccgacct gcaaagcgtg   1260

accccggaag acatccagaa ggctgcacgc acctatttca cccgcgaacg tctgagcgtc   1320

gcccatgttt tgcctgagga gaccgctcat gag                                1353
```

<210> SEQ ID NO 65
<211> LENGTH: 528
<212> TYPE: DNA
<213> ORGANISM: Pseudomonas fluorescens

<400> SEQUENCE: 65

```
ttgaccacca tcgtttcagt acgtcgccac ggcaaagttg tcatgggcgg cgacggccag     60

gtttccctgg gcaacaccgt gatgaaaggc aacgccaaga aagtgcgccg cctgtaccac    120

ggccaggtgc ttgccggctt cgcaggcgca accgccgacg cctttaccct gttcgagcgt    180

ttcgaaggcc agcttgagaa acaccagggc cacctggtgc gcgccgctgt ggaactagcc    240

aaagaatggc gcaccgaccg ctccctcagc cgcctggagg ccatgctcgc ggttgcgaac    300

aaagacgctt ccctgatcat cactggcaac ggcgacgtgg ttgaacccga gcatggcctg    360

atcgccatgg gttccggcgg cggctacgcc caggctgcgg ccagcgcgct gttgaagaaa    420

accgacctgt cggcccgtga aatcgtcgag accgccctgg gtatcgctgg cgatatctgc    480

gtgttcacca accacaacca gaccattgag gagcaggacc tcgccgag                 528
```

<210> SEQ ID NO 66
<211> LENGTH: 636
<212> TYPE: DNA
<213> ORGANISM: Pseudomonas fluorescens

<400> SEQUENCE: 66

```
atgcgaccat ttttcaagac atggctaacc atttgcctat taatgccact ggccgcccac     60

gccaccaatc gtgagcaacg acttccgaac gttaacggtt tcacccctaa agtccatagc    120

acgcccagca ctgccaaagc ggcaaagccg accgtcagcc gcccgactca actgagcaag    180

gcccacggca aagtgctttc cacccagctg gccgtgaaca ccaagcaaag cagcaacgtc    240

ttgagccgtg ccgtcaacgt gctcggtaca ccttatcgtt ggggcggcag cagcccaagt    300

aaagggttcg actgcagcgg gctggtgaaa tatgcattta acgatgtaaa agcggtggac    360

ctgccacgca cctccaacgc catggcggcc ggccatgggt tgaaggttga ccgcaaagac    420

ctgaagccgg gcgatctgtt gttcttcaag ttgaagagcc gccaggtgaa ccacgttgcc    480

atctacctgg gcaatgaccg ctttattcac gcaccgcgcc gtggcaagtc ggtgagcatc    540

gacacgctga aaaagccgtt ctgggacaag aactacgtga ttgccaagcg ggtactgcct    600

aaagagcaga acagcaacct gcggatcgtg cagcgc                              636
```

<210> SEQ ID NO 67
<211> LENGTH: 2040

<212> TYPE: DNA
<213> ORGANISM: Pseudomonas fluorescens

<400> SEQUENCE: 67

```
atgcctattt ccaccgcacc gattgcccgc aaggccccag gcccagaccc gtacgcctgg     60
ctgcaagaac gcgacaaccc tgaggtgctc gactacctca aggtcgaaaa cgcttggcag    120
gaagcgcaac tggccgatca gcaggcgttg cgcgagaccc tgttcgacga gatcaagggc    180
cgcattttgg aaaccgacct gtccctgccc tccccttggg gcccgtattt gtattacacc    240
cgcaccaccg ccggcgacga atacgcccgc cactaccgct gccgccgccc ggccgatgac    300
agcaaccacg tggacgccag cagcgaagaa ctgttgctgg accctaacgt actggccaat    360
ggcggctttt tctccctggg cgcattcagc atcagccccg accaccaacg cctggcctac    420
agcctcgaca ccagtggcga agagatttac accctgttcg tgaaggaatt ggcgtccgac    480
aaggtcagcg aactggcgtt cgacaactgc gacggcagca tgacctgggc caatgacagc    540
ctgacgctgt ttttcggtga gctggacgac acccatcgtc cgcacaaact gtatcgctat    600
cgcctggacg gcaccgccgc gcaggaagtc ttccacgagc ccgacggccg tttcttcctg    660
cattgctacc gctcaagctc cgaacgccaa ctgttgctgg ccctgggcag caagaccacc    720
agcgaagtct gggcgctgga cgccgagcaa ccgcacctgg ccttcgcctg cctggcgccg    780
cgggtcgaag accacgaata cgatgtcgac cacggcaagc gcaatggcca gtggacctgg    840
tttatccgca gcaaccgcga cggcatcaac catgcactgt acgtggccgc cgacaccggc    900
acgccgccca ccgaagccga ctggcagaac ctgatccccc acagcgatga ggtcatgctc    960
gacggcgtga gcctgaacgc caacgccatg accttgagcc tgcgcattgg tggcctgccg   1020
gttatcgaag tacaccccga gaacgtgccg gcctatcggg tgcaattgcc tgacgccgcc   1080
tacagccttt acgtgcagaa cagcctggag tttcccagcg acaagatccg cctgcgctat   1140
gaagccttga accgtcccgc ccaagtgcgc cagctcgacc tggcgacagg cgcgcaggtt   1200
gtgctcaagg aaaccccggt gctgggcgtc ttcaacgccg atgattacgt cagccaacgc   1260
ctgtgggcca cgtccgccga cggcacccag gtgcccatca gcctggtggt caaacgtgac   1320
cagctcggca agccgacgcc gctgtacctg tatggctacg ggcctacggg ctcaagcctg   1380
gacccgtggt tttcccatgc gcgcctgagc ttgctcgacc gcggggtggc gtttgccatc   1440
gcccatgtgc gcggcggcgg tgagctgggg gaagcctggt atcgcaacgg caagcaggaa   1500
cacaagcaga ataccttcag cgactttatc gcctgcgccg agcatttgat cgcccagggc   1560
ctgaccacct cccggcaact ggcgatcagc ggcggcagtg ccggcggcct gttgatcggc   1620
gcggtgctca accagcgccc ggaattgttc caggcggcga ttgccgaagt accgttcgtc   1680
gacgtgctca acaccatgct cgacccggaa ctgccgctga ccatcaccga gtacgacgaa   1740
tggggcaacc ccgaagaccc cgaggtgtac gcgcgcatca aggcctacgc gccctacgag   1800
aacgtcagcg cccaggctta cccggccacg ctggtgatcg ccggctataa cgacagccgt   1860
gtgcaatatt gggaagccgc caagtgggtg gccaagctgc gtgataccaa gacggacgac   1920
aacctgctgc tgctcaagac cgaactgggc gccggccatg gcggcatgag cgggcgctat   1980
caggggctac gtgacgtcgc cctcgaatat gcctttgtgt tcaaggccct cggcctggtc   2040
```

<210> SEQ ID NO 68
<211> LENGTH: 1311
<212> TYPE: DNA
<213> ORGANISM: Pseudomonas fluorescens

<400> SEQUENCE: 68
atgcgcccga taactgcccc cgaactgctc gctcccgccg gcaccctgaa aaacatgcgc 60
tacgccttcg cctacggtgc cgacgcggtc tatgccggcc agccgcgcta cagcctgcgg 120
gtgcgcaata acgagttcga ccacgccaac ctggccctcg gcatccagga agcccatgac 180
cagggcaagc gcttttacgt ggtggtgaac attgcgccgc acaacgccaa gctcaagacc 240
ttcctcaaag accttgcgcc cgtgatcgct atgggcccgg atgcgctgat catgtccgac 300
ccggggttga tcatgctggt gcgcgagcac ttcccgcaga tgccaatcca cctgtcggta 360
caggccaata cggtgaactg ggccagcgtg gcgttctggc agcaacaagg catttgcagg 420
gtgattctgt cgcgggagct gtccctggaa gagatcggcg aaatccgcca gcaggtgccg 480
gccatggagt tggaggtgtt tgtacatggc gccttgtgca tggcctattc cgggcggtgc 540
ctgctgtcgg gctatatgaa caagcgcgat gccaaccagg gcagttgcac caatgcctgc 600
cgctggaaat accaggccac gccggcagtg gagaatgtca cgggggatat cgtccatgaa 660
tatcaaccca cattgggcat cggcgcgccc accgatcagg tgttcctgct acaagaggcc 720
aatcgccccg atgaccccat gcccgctttc gaagacgaac acggcaccta catcatgaac 780
gccaaggacc tgcgcgccgt gcagcatgtg gagcgcctgg cacagatggg cgtgcattcg 840
ttaaagatcg aaggccgcac caaatcgcac ttctactgcg cacgcaccac ccaggtgtat 900
cgccaggcca tcgatgacgc tgtggccggc cgtgcgtttg accgcggctt gatgaccaac 960
ctcgagtccc tggcccaacg tggctacaca gaaggtttcc tgcgccgcca cgtgcatgac 1020
gaataccaga actaccagaa cggcagctcg gtttccgagc gccagcagtt tgtcggggag 1080
ctgaccggcg agcgccgtgg tgcgttggcc gaggtgaagg tgaagaatcg ctttgcgctg 1140
ggcgaccacc tggagttgat gacgcccgcc ggcaactttc actttgactt gccgagcctg 1200
cataacgcca agggcgaagc catcgaggtg gcgccggggg acgggcatac ggtgtatgtg 1260
ccgattccgg cgcagatgga cctgcgtttt ggcttgctga tgcgcgacgt t 1311

<210> SEQ ID NO 69
<211> LENGTH: 627
<212> TYPE: DNA
<213> ORGANISM: Pseudomonas fluorescens

<400> SEQUENCE: 69
gtgcaaagcg tattgctgac gggcttcgag ccctttgata acgccccgat taacccctcg 60
tgggaggctg tgcgtcggtt ggatggcgtg cagttgagcg aaggtgtgca aattgttgcg 120
cgttgtttgc cctgcgcatt tgcctccgct gccgagacct tactgcaatt gatcaacgaa 180
ctgcagccgg caatggtcat cgccacgggc ttggggcctg ggcgcggtga tatttccatc 240
gagcgcgttg cgatcaacgt taacgatgcg cgtattcccg acaatctggg cgcgcagccg 300
attgatatcg cggtagtgga tggcggcccg gcggcgtatt tctcgacgtt gccgatcaag 360
ggcatggtca aggcggtgcg tgaggccggt attacgtcct cggtgtcgca gacggcgggg 420
acgtttgtgt gtaaccaggt gttttaccgc ttgcagcatg cgttggcggg gactggggtg 480
cgcagtgggt ttattcacgt tcccggcttg cctggatcgg gcgagccgtc gatggcgtta 540
tcgatgaccg tggaagggtt gcgtgtagcg gcgttggccg cctggcaaac ccaggcggat 600
atcgttctta ccggtggcca gatcagc 627

<210> SEQ ID NO 70
<211> LENGTH: 1722

<212> TYPE: DNA
<213> ORGANISM: Pseudomonas fluorescens

<400> SEQUENCE: 70
atgaaatacc aacccttgag tcacacgttg attgcgaccg cgctggtctt gacggtcaac 60
ggtgtgcacg cagcttccca agccccggtt gcgggtgaaa atggcatggt ggtcacggcc 120
cagcacctgg caacccacgt gggtgtcgat gtgctcaagg ccggcggcaa cgcggtcgat 180
gcggcggtgg cggtaggtta cgcgctggcg gtggtgtacc cggcggcggg caacctgggc 240
ggcggtggtt tcatgaccgt gcaactggcg gacgggcgca agaccttcct cgacttccgc 300
gaaaaagccc cgttggcggc aacggccgac atgtacctcg acaaggccgg caatgtggtc 360
gaaggcctca gcgccaaagg ccatttggcg gtcggcgtac cgggcacggt gtctggcatg 420
gagctggccc tgagcaagta cggcaccctc aagcgcgcgc aagtgattgc cccggcgatc 480
aagttggccg aaaacggctt tgcgctggag cagggcgata tcgacctgtt gcacactgcc 540
accggtgagt tcgaaaaaga ccaggacatg cgcgggatct tcctgcacaa cggaaaaccg 600
atgcaggtgg gtcagaagct ggtgcagaag gacctggcca agaccctcaa ggaaatctcg 660
gccaagggca ccgacggttt ctataaaggc tgggttgcca aggcggtggt ggattccagc 720
caggccggca aaggcatcat cacccaggcc gacctcgacg cctacaaaac ccgcgaactg 780
gcccccatcg agtgcgacta ccgtggctac catgtggtct cggcaccgcc acccagctcg 840
ggcggtgtag tgatctgcca gatcatgaac atcctcgaag gctacccgat ggccgatctg 900
ggctatcact cggcccaggg cctgcactac cagatcgaag cgatgcgcca tgcctacgtg 960
gaccgcaaca gctacctggg tgatccggac ttcgtgaaga accccatcga gcatctgctg 1020
gacaagaact acgcggccaa gctacgcgct gccatcgagc cgcagaaggc cggtgactcc 1080
caggcgatca agccaggtgt gtcgccccac gaaggcaata acaccaccca ctattccatc 1140
gtcgacaagt ggggcaacgc ggtctcggtg acctataccc tcaatgactg gtttggcgcc 1200
ggggtgatgg ccagcaagac cggggtgatt ctcaacgatg aaatggatga cttcaccgtc 1260
aaggtcggcg tgccgaatat gtatgggctg gtgcagggcg aagccaacgc catcgcaccg 1320
ggcaaggcgc cgttgtcatc gatgagcccg accatcgtca ccaaggacgg taaggcagta 1380
atggtcgttg gcacaccggg gggcagccgc attatcaccg cgaccttgct gaccatcctg 1440
aatgtcatcg actacaagat gaacatccag gaagccgtgg acgcaccgcg cttccaccag 1500
caatggatgc cggaaaccac caaccttgag acctttgcgg tcagcccgga cacccagaag 1560
atcctcgaaa gctggggcca caagtttgcc ggcccgcaag atgccaacca cctggccgcc 1620
atcctggtag gcgcgccttc cctggacggc aagccggtgg gtaacaaccg tttctatggg 1680
gccaatgacc cgcggcgcaa cacgggcttg tcgttgggct ac 1722

<210> SEQ ID NO 71
<211> LENGTH: 579
<212> TYPE: DNA
<213> ORGANISM: Pseudomonas fluorescens

<400> SEQUENCE: 71
atgtctttta cgctcaccgg cttttgcgag tttcgtgaag aaatacgcaa aagtcgcttt 60
atcaccttgg cggcgccgat taccagcccg caggacgccc aagcgttttt cgagcagcac 120
agcgacctca acgccacaca caactgctgg gcctggaagc tgggcgatca ataccgcagc 180
agcgatgacg gcgaacccgg aggcaccgcc gggcgcccga ttcttgcggc catcgaggcc 240
cagggctttg atcaggtggc cgtcttggtg atccgctggt acggcggcat tcaactgggc 300
acgggtggat tggcccgggc ctatggcggc ggggccaata aatgcctgca gaatgccgaa 360
cgcatcgagc tgatcagccg cgtccccctg cgttgcgcct gcgggttctc cgaactgaac 420
ctggtgaagc tgcgtgtcgc tgaactcggc gggcttttgg tggaagaaac cttcaccgcc 480
aacggcgtag agctgcagct cgccctgggg gaggcgcaca tcgacaccct gcaaacccag 540
ctcgccgacc tgagccgtgg gcgcatcctg ctcgaacgc 579

<210> SEQ ID NO 72
<211> LENGTH: 975
<212> TYPE: DNA
<213> ORGANISM: Pseudomonas fluorescens

<400> SEQUENCE: 72
atgagcccag ccgagttgca cgccgacagc atcgttatcg acggtctgat tattgccaag 60
tggaaccgcg acctgttcga agacatgcgc aaaggtggcc tcaccgccgc caattgcacg 120
gtgtcggtgt gggaaggctt ccaggccacg atcaataaca tcgttgccag ccagaccctg 180
atccgcgaaa acagcgacct ggtgatcccg gtgaaaacca ccgccgacat ccgccgcgcc 240
aaggagctgg gcaagactgg catcatcttc ggcttccaga atgcccatgc ctttgaggac 300
cagctcggct atgtcgagat cttcaagcag ctcggcgtgg gcgtggtgca gatgtgctac 360
aacacccaga acctggtggg caccggttgc tacgagcgcg atggcggcct gtcgggtttc 420
gggcgtgaga tcgtcggcga gatgaaccgc gtcggcatca tgtgcgacct gtcccacgtg 480
ggctccaaga ccagcgaaga ggtcatcctc gaatcgaaaa agccggtgtg ctactcccac 540
tgtctgccgt ccgggcttaa agagcacccg cgcaacaagt ccgatgaaga gctgaagttc 600
atcgccgacc atggcggatt tgtcggtgtg accatgttcg cgccgttttt ggccaagggc 660
atcgactcga ctatcgacga ctatgccgaa gccatcgaat acaccatgaa catcgtcggc 720
gaagacgcca tcggcatcgg caccgacttc acccagggcc atggccagga tttcttcgaa 780
atgctcaccc atgacaaggg ctacgcccgc cgcctgacca gcttcggcaa gatcatcaac 840
ccgctgggca tccgcaccgt gggtgagttc cccaacctca ccgagaccct gctcaagcgc 900
ggccacagcg agcgcgtggt gcgcaagatc atgggcgaga actgggtcaa cgtgctcaag 960
gacgtctggg gcgaa 975

<210> SEQ ID NO 73
<211> LENGTH: 1353
<212> TYPE: DNA
<213> ORGANISM: Pseudomonas fluorescens

<400> SEQUENCE: 73
atggcaatga caaaatcacg ttcgaaaaag gcgctgtata tcggcctgcc gctggccctg 60
gctatcggcg ccggggcggg ctttctggtc tgggatcagt ggttcaaggg caacgccggc 120
tacccgctgg aggtgatcaa gcaggccaat gaaatgcagg atcgcctgtt gtcattcgac 180
agccacatca ccctgcccct ggatttcggc acggcgggca acgaggccga caaggatggc 240
agcggccagt tcgacctggc caaggccgcc cgcgggcgat tgtcgggcgc cgcgctgacg 300
atattcggct ggccggaaat ctggaacggc gccaacgccc cgcacaagcc caccgacggt 360
tttgtcgagg aggcccgcca cgagcaggag gtgcgctata agatcatctc cggcatggtg 420
cgcgactttc ccaaccaggt gggcatcgcc tacaccccgg acgatatgcg acgcctacac 480
ggcgaaggca agttcgcgat ttttatcagc atgctcaacg cctacccccct gggcaatgac 540

-continued

```
ctgaaccagc tggacctgtg ggccgcacgc ggcatgcgca tgttcgggtt cagctacatc    600

ggcaataacg cctggtccga ctcgtcgcgc ccgctgccgt ttttcaatga ctcccccgac    660

gcccttgaag gcctgtcgcc gatcggccag caagcggtgc atcgcctcaa tgacctgggg    720

gtgatcatcg acgtgtcgca gatgtcgacc aaggccctgg aacaagtcgc gcagttgagc    780

cgtacgccga tggtggcgtc ccactcggcg ccacgggcat cggtggacat cccgcgcaac    840

ctcagtgaca aggaactgca actgatcaag aacagcggcg gcgtggtgca agtggtgggc    900

ttccccgcct acctgcggcc cttgagccag ccgacccagg acaagctcaa cgccctgcgc    960

gcacgcttcg acctgccgcc actgcccaat ctggccatgg ctctgatgcc cggcgacgcg   1020

atcattgccg cctggcccga gcaacgcttc ggccagtacg ccagcgcgct gtacggcatc   1080

ctcgaggaag aacccaaggc caccctcaag gacctgggcg acgccatcga ctacaccgtg   1140

cgcaagatcg gcatcgatca tgtcggtatt gcctcggact tcaacgacgg cggcggcctc   1200

cagggctggg agaacgtcgg cgaagtgcgc aacgtcaccg ccgaactgat ccagcgcggc   1260

tactccgaag ccgatatcgc caaactgtgg ggaggcaact tcctgcgggt gtgggagcag   1320

gtacaaaaat ccgccaagcc attggccaat cgc                                1353
```

<210> SEQ ID NO 74
<211> LENGTH: 2064
<212> TYPE: DNA
<213> ORGANISM: Pseudomonas fluorescens

<400> SEQUENCE: 74

```
atgtcagcca ttacaaatta tcatccctcg tacgtaaaac ctcaaactta cccgctctcg     60

gccgacgccc caacagccga tccacttgca ccttcgttat cggacaaggt tgcacgagac    120

cttactcgcg acaatttgaa attaaaagat aaaaatggcg acggcaaact aacagtttca    180

tataaatttt tagaccaggg cgcaggtgag ttcagccagg ccagaaagaa agcgttcaag    240

agcgccatca aggcttggga agacgtggtc aaagtcaagt tcaccgaaaa cgccaaggag    300

gctgatgcgt tttttgtact tcatgccaat ccgggcgttg gtggatatgc cgtcatgcca    360

aatgaccaag gaactgcaag cattggcatc ggcgtcggcg ataagaactc gcccctgcac    420

tctgccatga tccatgagct tggtcatagt ttgggattag accatccaac cggagattac    480

ccagaaaaca accatactca tactgccatg agttacagta acaaatggtg gctacccaca    540

gacaatccta ggcttcgtat ttcggactat aacttgactc cagcaatgca cgacatcgca    600

ggcattcatc gcttatacga acccaattat gaaacccgaa aagataatac aacctacggc    660

tttaactcca acactgagcg cgatcattat acgttgacct ccgccgacga cctgaccaac    720

ttttgtgtct gggacaacgg cggcgaagac acgttggact tttccggctt caagcagaac    780

caaaagataa acctggccgc cgagacactc tcggatgtgg gcggccgcgt gggcaacgtg    840

tccatcgcca agggcgttgt gatggagaac gccatcggtg gctcagggca tgacgtactg    900

atcggcaatc acgtcaataa cagactaacc ggcggagccg gtcgcgacaa actgataggc    960

ggcggtggtg ctgatacctt tgtttataac aaagccagcg actccacccc tgggaatccg   1020

gacatacttg aagactttac cagcggcgtc gacaagatcg acctgtccag ggtgctcaac   1080

gacgccggca ttgaaaagcc ggagctggtt agcgtactca ccggtcgcaa aggcgagctg   1140

acgctcagct acgatgaaaa tgccaagatg cacaaactgg ttctgaatgt gagcggcaaa   1200

cctgactctg cactactgat tctgagcaaa ggacctatag cgctggacga catcctggcc   1260
```

```
cacgcggatt caaagcccga gcctgggccc gagccagaac ctgagccagc ccccaaaccc   1320
aggcctgaac cagaaccgaa gcccaggccc aagcgtgaac ccaagcccaa gccagaacca   1380
gagcccaggc ccaccccagt atcatgcccc cgacccgaca cgcgcgacac ggtctatggt   1440
ttcaatgcaa ataccggacg ccccagtaca accctcacct ctgcctgcga caaaccttat   1500
ttcagcgtgg acgacagaaa aggcaacgac accgtggact tctctggttt ctatcaagac   1560
caacagattg atctgacacc cggtactcgc tccagcgtag gtgggctacg cgacaatgtg   1620
tttattacgc aaacaaccgt catcgaaaac gccataggtg gcaagggtaa cgaccgtatc   1680
agcggaaata gcgccgataa catcctgatc ggtggtgcag gcgcggacca tctgaccggc   1740
aatggaggct ttaatacctt cagctaccat tttgcctgcg attctccacg caacaacgcg   1800
gacaccctct tggacttcac cacgggcaaa gacaagattg atttgagaaa aatgagcgaa   1860
aatgcccaag tcaaactcaa ctatgtcaac cagtaccgca accagcccgg cgacacgatc   1920
atcgtgcaca acccattcac cggcaggtac ttcctgggcg ttgacctgac gggcgatggc   1980
aagaccgatt ttctgatcaa gagtacccgc cccatcagca acgaagacgt gatcggactg   2040
aacatccagg atgacggtta cctg                                          2064
```

<210> SEQ ID NO 75
<211> LENGTH: 1320
<212> TYPE: DNA
<213> ORGANISM: Pseudomonas fluorescens

<400> SEQUENCE: 75

```
atgatccata tccccaaagc ggaatacacc cggcgccgca aggcgctcat ggcgcagatg     60
gaacccaaca gcatcgcgat cctgccggcc gccgccgtgg ccatccgcaa ccgtgatgtc    120
gagcatgttt accgccagga cagcgatttc caatacctga gcggtttccc cgagcccgaa    180
gcggtgatcg tgctgatgcc cggtcgccag cacggcgagt acgtgctgtt ctgccgcgag    240
cgcaatgccg agcgcgaatt gtgggacggc ctgcgtgccg gcaccgaggg cgcgattcgc    300
gactttggcg ctgacgacgc attccccatt accgatatcg acgacatcct gcccggcctg    360
atcgaaggtc gcgaccgcgt gtactcggcc atgggcagca atgccgagtt cgaccggcat    420
gtgatggagt ggatcaacgt gatccgttcc aaagcgcacc tgggcgccca gccgccgaac    480
gaattcgttg ccctggatca tttgcttcac gatatgcgcc tgtataaatc ggcggcagaa    540
gtgagggtga tgcgcgaggc ggcgcgaata tcctgtgcag cccatgtacg ggcgatgcag    600
gccagccgtg ccggcctgca tgagttcagc ctggaagccg agctggatta cgagtttcgc    660
aaaggcggtg cgaaaatgcc ggcctatggc tccatcgtcg ccgctgggcg caacagctgc    720
atcctgcatt accagcagaa tgacgcggtg ctcaaagacg gcgacctggt gctgatcgat    780
gctgggtgcg agatcgattg ctacgccagc gacatcaccc gtacctggcc ggtcaatggc    840
aagttctcgc ccgagcagaa ggcgatctac gagattgtgc tggcctccca ggaagccgcc    900
ttcaagcaga tcgcgccgaa caaacattgg aaccaggccc acgaggcgac cgtgcaggtc    960
atcaccgccg gcttggtaaa gctggggttg ttgcaaggtg acgttgacga actgatcgcc   1020
agcgaagcct accgcgcctt ctacatgcac cgtgccggcc actggctggg catggatgtg   1080
catgatgtgg gcgagtacaa agtgggcggt gaatggcgcg tgctggaagt gggcatggcc   1140
ttgaccgtgg agccgggcat ctatatttcc ccggacaacc agaacgtggc aaagaaatgg   1200
cgtggcattg gcgtgcgcat cgaggacgac gtggtagtga ccaagcaagg ctgtgaaatc   1260
ctgaccggcg gcgtgcccaa gaccgttgcc gagatcgaag cgttgatggc ggctgcccga   1320
```

<210> SEQ ID NO 76
<211> LENGTH: 684
<212> TYPE: DNA
<213> ORGANISM: Pseudomonas fluorescens

<400> SEQUENCE: 76
atgagcaccc tgctggccct ggacaccgcg actgaagctt gctccgttgc cttgctgcac 60
gatggcaagg tcacgagcca ctacgaggtg atcccgcgcc tgcacgcgca gaaattgttg 120
ccgatgatca agcaactgct tgaagacgcc ggtaccaccc tggcggcggt ggatgccatc 180
gcgtttggcc gtggccccgg tgcattcact ggcgtgcgca tcgccattgg cgtggtgcag 240
ggcctggctt ttgccctgga gcgtccggtg ttgccagtgt ccaaccttgc ggtactggcc 300
cagcgcgcgt tgcgtgagca cggggcgtcg caggtggcag cggcgattga tgcacgcatg 360
gatgaagtct actggggttg ctaccgtgag atcgcaggcg aaatgcgcct ggtcggtgcc 420
gaagcggtgc tggcccccga agcggcgcag ttgcccgctg atgccagcgg cgattggttc 480
ggtgccggca cgggctgggg ttatggcgaa cgcatcaaga tgacgtgtac gcagcaggac 540
gcggcgatgt tgccccacgc tgaagacctg ctggcgttgg cgcgtttcgc attcgagcgc 600
ggcgaagcga ttgcggcgga ccaggcagca ccggtgtatc tgcgcgataa agtcgcacaa 660
accaaggccg agcgcgggat tatt 684

<210> SEQ ID NO 77
<211> LENGTH: 588
<212> TYPE: DNA
<213> ORGANISM: Pseudomonas fluorescens

<400> SEQUENCE: 77
atgagtctgg cgctattccc cctcaacact gtgctgttcc caggctgcac cctcgacctg 60
cagatattcg aggcgcgcta cctggacatg atcggccgtt gcatgaaaaa gggcgaaggc 120
tttggtgtgg tgtgcatcct ggatggctca gaggtgggcg cggcccctga cggttatgcg 180
cttgtcggtt gtgaagcgct gattcgtgac ttcaaacagc aggagaacgg cctgctgggc 240
attcgcgtcg aaggtggccg tcgtttccgc gtgcgtgaag ctggcgtgca aaaagaccag 300
ttgctggtgg ccgacgtgca atggctgcaa gagttgccgg accagccgct gggcgaagaa 360
gacgccgact tgctggcgtt gcttgaggcc ctggccgagc acccgatggt ggcttcgctg 420
gacatgggcg gtgacgtcga aggccagcaa gccctgggca accggttggc ctatctgctg 480
ccgtttaccg aggccgacaa aatcgacttg ctgcaactgg acgacccaca gcaacggctg 540
gatgcgatcc agatgttgct cgatgaactg cagggcgagc tgttcacc 588

<210> SEQ ID NO 78
<211> LENGTH: 768
<212> TYPE: DNA
<213> ORGANISM: Pseudomonas fluorescens

<400> SEQUENCE: 78
atgatcaaga cccccgcaca gttggccgta atgcgtgaag ccgggcgcct gttggcgcag 60
gtcttcgaca tgctcgacgg cttcgtcgcc gccggccgct ctaccctgga gctggacagc 120
gccgtcgaag ccttcatccg caatgacctc aaggcccgcc ctgccagcct ggggcagtac 180
gactacccct tctgcatcaa cacctcgatc aacgaagtgg tgtgccacgg catgcccagc 240
gccaagcaat tgctcaagga cggcgacatc atcaacatcg acatcaccct ggaaaaaggc 300
ggcttcattg ccgactccag caagatgtac atgatcggca acgtgacgcc caaggccagg 360
cgcctggtgg acatgacctt cgaggcgatg tgggccggta tccgccaggt caagcccggc 420
gcgcgcctgg gcgatatcgg ccatgcgatc cagagccacg cgcaagccaa tggctacagc 480
gtggtgcgcg aatactgcgg ccacggcatc ggccggcaaa tgcacgaaga accgcaaatc 540
ctgcacttcg gccgccccgg caccggcctg gaactgcgcg aaggcatggt gtttaccatc 600
gagccgatgc tcaaccaggg cagcgccaaa acccgcagcc tgaaagacgg ttggacggtg 660
gtcaccaagg acaacagcct ctcggcgcaa tgggaacata ccgtggcggt gacggcggat 720
gggtttgaag tgctgacctt gcaaacccct caaaaccttc acaccctg 768

<210> SEQ ID NO 79
<211> LENGTH: 606
<212> TYPE: DNA
<213> ORGANISM: Pseudomonas fluorescens

<400> SEQUENCE: 79
atgctaaaac tgacgccacg ccaagctgag attctggctt ttatcaagcg ctgccttgat 60
gacaatggtt acccgcctac ccgtgcggag attgccctgg agctggggtt caaatccccg 120
aacgccgccg aggaacacct caaggccctc gctcgcaaag gtgcgatcga gatgacccca 180
ggtgcttcgc ggggtattcg tatccctggc ttcgaagcca aggccgacga gtcgacattg 240
ccgatcatcg gccgcgtcgc cgcaggtgcg ccgatcctgg cgcagcagca cgtcgaggaa 300
tcctgcaaca tcaacccgac cttcttccat ccccgcgccg actacctgtt gcgcgttcac 360
ggcatgagca tgaaggacgt gggcatcttt gacggtgacc tgctggcggt ccataccacc 420
cgcgaagctc gcaatggcca gatcgtcgtg gcccgtatcg gcgacgaggt cacggtcaaa 480
cgcttcaaac gcgaaggcag caaggtctgg ctcctggccg aaaaccctga gtttgccccg 540
atcgaagtca acctgaaaga ccaggacctg gtgatcgaag gcttgagtgt cggcgtcatt 600
cgccgc 606

<210> SEQ ID NO 80
<211> LENGTH: 2373
<212> TYPE: DNA
<213> ORGANISM: Pseudomonas fluorescens

<400> SEQUENCE: 80
atgcctgcgc cggttcaccc tcatcccgtt cacctgaccc tcgccaatgg cctgcgggtt 60
tgcctgcgcc atgcgccgcg cttgaagcgc tgcgccgccg ttttacaggt ggctgccggc 120
agccatgacg tgccattggc ctggcctggg ctggcgcatt ttcttgagca cttgctgttt 180
ctcggtaccg agcgctttcc agccggcgaa gggctgatgg cctacgtgca acgacacggt 240
gggcaggtca atgccagcac ccgtgagcgc accaccgagt tttctttgga actgccggtg 300
ccggttttta cagacgggct gatgcggttg gcggatatgc tgactcaccc acgcctggcc 360
ctcgacgatc aacagcgtga gcgcgaagtg ctcgacgcgg agttcatcgc ctggtcccag 420
gatgccaagg cccaacaaca agtggcgctg ctgcaaggct tggcagcaga tcatccgttg 480
cgcggttttc atgccggcaa ccgcgacagc ctgccggtgg aaagcgaggc ctttcagcaa 540
gccttgcgcg ggttccacgc acacttttat caaagcgggc agatgacttt gagccttgcc 600
ggcccacaat cgctgaccga cctgcaggcc atggcccagc agttcagtga ccaactgaca 660
cccgggccat tgcacccgca ggccgctcca ccggccttga tgcaaggctc cgcacgctgc 720
tatcaacacg ccgccgatcg ccacctgcat caggtcatta cctgtgacgc accacgggaa 780

```
gcgttggcgt ttctctgcac ctggctcaac gcctcggccc ccggcgggtt gctcgccgaa    840
ctgcaagctc gacgactggc caccgcgctg caggcgtccg tgctgtacca gtttgcggat    900
caagccgtgc tggatatcca cttcactctc ggcagcgagc gcgaaccggc cacgcagatc    960
gaagagttac tgcacgactg gctgagcttc ttcgcacaca gcgactggac agcgttacgc   1020
gaagaattcg ccttgctcaa tgctcgccag caacaggtcc aaggcgccct ggccttggcg   1080
cgcaacgacg cccacgatct gtcggaacaa ggcgccgctg ccctcaaggc catgctcgat   1140
tcactgcacc tgcccgcctc ccggcaccct tggcaactgc cgcctaacaa tcctttgctt   1200
cgtgcgcccg ccaaggaaga acgcgccggc ctgattcgcg gccaaaccag cgcccatcgt   1260
ggcttgcgta cctttgccca ggatcgctca cggggccgac gggagctgtc ggcgctgacc   1320
ttcagccagg cgttggcgga tgacacgggc gaaggtgcgc tgtacctgca ctggcggttt   1380
gactcggcgg tacccaccgg gctggaaagc ctgttgcggc cgttgtgcga acaggcacgg   1440
caggcgggcg tcgagttgtc ttgcgaaacg atcgccactg actggcaggt aaagatgcac   1500
ggcctccacg agcccatgcc ggcggtgctc gaagcgttgg cgcggtgtct gagtgactcg   1560
aatggacctt tgccaccgcc cgctcccgtg ccgatgatcg ccatccggga actgctcaag   1620
gcgttgcctg cttgctgtgc cggtgttcaa cccgagcctc aggggacgac agcgtcctgg   1680
gccacagcac gctggcaggg gctggtcaca ggcttgcccg ccagctgtga agcggcgatc   1740
aaagccgcag cggcccggtt gcctgggcaa ccggcaactc tgcctttcac acctcaggcc   1800
cttgacgggc aaaagcgctg gcacgcagtc aacaccgaat ccagcgaggc ggcgctactg   1860
ctattttgcc caacgcctgt gcaaaccctc gccgatgaag ccaactggcg gttactcggg   1920
cacgtgctgc aagggccgtt ctaccagcgc ttgagagtcg aactgcaaat cggctacgcc   1980
gtgttcagtg gcatccgaca aatcaacggc caaaccggcc tgctgtttgg ggtgcaatcg   2040
cccagcactt ctctggacgg catcgtcgaa cagttgcagg ccttcctcga acaactgccg   2100
tcgttgatcg agcgctgccc cgacttgggt aaccaggccc ttgcgcagca gttcgcggcc   2160
caggcgctac ccgtcaacca ggctgccgag ttgctctggc atgcgcactt ggcaggtcat   2220
tcgtcgggtt atctggatca gcttcaacag ttgattcaac agcgcacacg cgaggatgtg   2280
cagcacgccg cgcagcaact caatgacgcc gcaggcggct ggcaatgcgt ggccaacggg   2340
cggtgtatca acgacgactg gcaagcgacg tcg                                2373
```

<210> SEQ ID NO 81
<211> LENGTH: 2007
<212> TYPE: DNA
<213> ORGANISM: Pseudomonas fluorescens

<400> SEQUENCE: 81

```
atgaggcgcg cattgtgcaa agggtctggg cttgaacgtc cccctcacct caaggaagac     60
cttgtgataa agcctctagc cctcgccatc agcgttgccg gtgccctgtt gcccacccat    120
agccaggcgt acgattacgg ccagcacgcc aacaccaccc tggaaaagct gatcaacgat    180
taccctggcc gttatcgcgg cacggccaat tttgccgggg cagccgactg gatgcagagc    240
cagatgggca cggcctataa catcagccgc caggatttca cctggaacaa cggcagccgg    300
gcttcgcaaa acgtggtggc ctctgccgct ggcaccaagg cccagtacgt ggtgattggc    360
gcgcatttcg atacctactt cggccgcccg accctacaag gcctggatga caacggttcc    420
ggcgccagcg tgttgactga ggtggcgaag aacctcggcg gcctgtcact ggaaaatggc    480
```

ctgcaaatcg ttggcttcgg cgccgaagaa gaaggcctgc gtggctcgcg ggcctttgtc 540
gactcactca gcgccagcca gcgcgccaac atgctcgcga tgatcaacct cgacagcctg 600
atcaccggtg acatgatgta tgcccacgcc ggccagaaca gcaccgctaa cccggcgttg 660
gcctccttgc gtgagcacac cttccagatc gccagggaac tgaacatccc cttgttcagc 720
aaccccggcc tggacccgca gtacccaaag ggcaccggct gctgcagcga tggtgaagcg 780
ttcgaaccgc tgaatatccc gatcctttat atagaggcca ccaactggga actgggcgac 840
ctggacggtt acacccagac cgacaacccg aaaatccccg gcggctcgac ctggcacgac 900
cccaccgaag acaacaaagc cgtgctgacc gatgcattcg gccaggcgcg catcgaccag 960
cgcctgcgtg actattcacg cctgctcagc cgcctggtgc tggaactgac caacgccgac 1020
ctgatggcct cgaccgcttc cggcggtgcc gttgcgcgca atatgcaaga caacctgcaa 1080
cgccagcatc aggccctggt acgcctgcat gatcgccgct ggctgaccct gcaagcggcc 1140
agccgcgagg tgggcagctt tgatggcgag atcggcgtgg atggcgaata caacccggac 1200
agcggcttcg acagcgcccc caaccccgaa gcccggcgct tgggcctgca tgccctcggc 1260
gactaccaac tgacttcaag cctgaatatg ggcgccagcc tcagctacct caatgggcgc 1320
gacaaactgg agcatcgcgg caagctcgac agcgacacct ggcaggcagc cgtctatgca 1380
ctgctcaacg atggtgggcc aagctggctg gccggtgacc tgagcgtggg ccacacgcgc 1440
ttcgattcca agcgcaacct ggtcatccag gccaatggcg ggccgatcct gctcaaccag 1500
caactgacgg gcgacaccga tgccctggcg ctgggcgcac gggtgctggg tggctatgac 1560
tttgactttg gcgcgatcaa gagcgggccg ttcgccggcc tggactacag ccattaccgc 1620
atcgacaagt tccacgaaaa gcagaacctg cgcacggccc tggaatacga agagcagtct 1680
ttcgactccc tggaagccag cctcggctgg cgcgtgcgcg gcgctgttgc cctgccctat 1740
ggcctgaacc tgatgcccta cggcgacatc gcctgggtca aggaattggc cgacggccgc 1800
ctggacgacc tgcaactcac cgcgcacgcc gatggccagg cccgcaacgc caggctgggc 1860
tcagtggata agagctttgc tcgtgcacaa ctcggcagcc aactggcgat caccccacag 1920
ttgggcgtgt ttgccgaggt caatggccgc ctcgggcatg ctgaaggcag ccagaccggt 1980
tattcgctgg gtgtgcagtg gatgttc 2007

<210> SEQ ID NO 82
<211> LENGTH: 1380
<212> TYPE: DNA
<213> ORGANISM: Pseudomonas fluorescens

<400> SEQUENCE: 82
atgcgtcgcc tgttactcgc ctgcctgctc ttgggctcgg cacacgcctt tgcctttgac 60
cgtctgcaag tcgagggcta caccttgccc aacggcctgc aactgctgct caaaccgggc 120
accgagcgtg ggcatgtcgc tattcgcctg gtggttggtg tgggcctgga cgacttcggt 180
tgcgaagaaa aagaactgcc gcacttgttc gagcacttgc tgttcagcgg catcgacggc 240
ggcggcgagg gcgacctcga agaccgcatg caagccctgg gcggcgagtg gaacgcctac 300
accagcaacg ccgataccac cttcgtgatc gaggcgcccg cgcagaacca acgcaaggtg 360
ctggacctgc tgctggcaat cctcacgcgc acgcaactga ccgacgccca tatcaacgcc 420
gccaaacagg tggtggagcg cgaagacggc ggccattact cacacttgca acgcctgctg 480
gaccgccagg acctcggtca cagcgccagc aaccaattgg ccgtggagtt gggcctcaag 540
tgcgccgaac gcgccgaggt cagccacctc acccgcgatc agttggagaa gctgcgcaac 600

```
gaatggtacg cgccgaacaa catgaccctg atcgtcgtcg gcgatctcga caaactgctg    660

cctgcctacc tggaacgcac ctatggtcaa ctcgaccccg tggagccgag cgaacatcgc    720

ccgcttccgg aaatccagca caccgccgcc agccaccgcg acctgatccg cggctgggtg    780

ggcgatggcg ccaagctgca ctggctgttc cccgagccgg tgttggatga ccagcatgat    840

gaaacctaca acctgctcaa ggattacctc gactgggcac tgtaccggca actgcgcctc    900

aagcacggtt tgtcctacgg cccctgggta gaacgcgaag tgctcggcgg cgttggattc    960

ctcagcttga atgccgacct tgagcgagaa aacctccctg aagctgagca ggtcttgcaa   1020

gacctcaagg cccaactgct caaggacggc ctcgacccaa cagtattcac acgcctgcag   1080

caagccgcca ttgcccggca ggcttgggcg gtgcagggca acagcgcgct ggccgactat   1140

tattggagtg cggccggcga ctacagcaac gggcgtttca gcgatccggt caaacgcatc   1200

aaggctgtaa gcctggcgca aaccaaccag gccatgcgcg aagcgttcca gcagccgggc   1260

tactggcgca tcgaaaaacc gctgttgagt tatgacgcgt tgacctggat cggtgcgggc   1320

gtgctgggcc tgatcatcct tggtttgatc ggcttgaggc tttatcgcaa acctgttgag   1380
```

<210> SEQ ID NO 83
<211> LENGTH: 819
<212> TYPE: DNA
<213> ORGANISM: Pseudomonas fluorescens

<400> SEQUENCE: 83

```
atgccacgcc tactgagcct gttgatgctg ttgtgcctca cgtttaacgc ccacgccgac     60

agctacatca cgcgaaccct gaacaaaccc gtgcctggcg gcgtggccgt cgtcgaacta    120

ggcccttcgg ccacagcgcc gaaagccacc taccagggca agccggtgct ggtggtcaag    180

gagcaggaca actggctggc gattgtcggc atcccgttga cggtcaagcc tggcaacgag    240

cgcatcagca gcgggggcgg caacctgccg tttatcgtcg gctacaagaa gtatccggaa    300

caacgcatca ccttgaagaa caaaagccag gtcaaccccg acccggccca gctcaagcgc    360

atcgaaggcg aattggcagt gcagctcaag gcttaccgca gcttcagccc gaatttgccg    420

agcaatctgg tgctggataa accggtgaac gggccgctgt cgagcaagtt cggggtgcga    480

cgcttcttca acggcgaaga gcgcaacccg cactcgggcc tggacttcgc cgtaccggcc    540

ggcacaccga tcaagacacc cgccaatggc aaggtgattc tggtcggcaa ttacttcttc    600

aacggcaata ccgtgtttgt cgaccatggc caggggttta tcagcatgtt ctgccatatg    660

tcgaagatcg atgtgagggt gggtcagcaa ctggtgcgcg gtgcggtagt cggcaaagta    720

ggctcgacag gccgggccac tgggccgcat atgcactgga acgtcagcct gaacgatgca    780

cgggtagatc cggcgatttt tatcggcgcg tttcaaccc                          819
```

<210> SEQ ID NO 84
<211> LENGTH: 789
<212> TYPE: DNA
<213> ORGANISM: Pseudomonas fluorescens

<400> SEQUENCE: 84

```
atgattgctt tgccctggct gtacctcacc ctactttcca ttggctatgt cgtggccttg     60

atctacggcc aactgggcgt actggcggcg gtctccatcg cactgctgct ggtggccggg    120

tacgccgtgc gccagcaacg caacccttgg gcgcgctacc tgggtcacgg cttgtttatt    180

gtcctggccc tgggcctggc gatgcactgg ctgccgggtt tctataacgg ccgcggtatt    240
```

```
gcgccccagc gttttactcc ggactcagtg cccttctcga tgtacctgaa ccaggacaaa    300

cccctgatcg gcttctggct gttgctggcc tgcccatgga ttgtggcgcg acgctcattg    360

cgcctgtcga tctgcgtcac ggccgtggcc ctgaccctgg ccgccatcgc cgccctgggt    420

ggcgcagcgc tgctagggat gatcagttgg gcgccgaaat ggccggacga ggcgtggctg    480

tgggtgttga ataacctgct gctggtgacg ttggtcgaag aagcgctgtt tcgcgggtat    540

atccagggcg gcctgagccg acgcttcaaa cacctgccct atggcgagaa cctcgcgctg    600

ctgctggcct cactgttatt cggcctggtg cattttgctg cgggttggca gtggatgctg    660

ctggcgagta ttgctggcgt gggttacggc ctggcctatc gctttggtgg cttgggcgcg    720

gcgattgcca cgcactttgg cttgaatctg ctgcacttcg gcctgttcac ctacccgatg    780

ctcgccggc                                                             789
```

<210> SEQ ID NO 85
<211> LENGTH: 1737
<212> TYPE: DNA
<213> ORGANISM: Pseudomonas fluorescens

<400> SEQUENCE: 85

```
atgcactttc cactgaaaaa actggtggct gccaccttgt tcgccgcgag cctgtcggca     60

gttgccactc ccgcatccgc taacatcacc gcagaccaaa gcgcagccat cttgaagcag    120

ttcagcgaga cctcggtcac cgattttcgc agtttcctcg gcaccctggc taagggcgag    180

ttcggcaaat cggctgacac cggcactgct atcagcgcgt ttctgggcaa caaaaccctg    240

agcgccgagc agcagaacga gatcaatcgc ctgctgggca tttacacccg cgttaaatat    300

ggcaaagccg cgctcgaaac cctgcgtgaa ctggtggaga tccctacgtt taacgtagac    360

ggcctgccgc aatacaataa cccggaattc ctcaagatcg ccgcgaagat cgaggccctg    420

gccaagtcct tcaacctgaa cttccgtaac gtcgataacc gcgtctacga aatctccctg    480

gaaggcagcg gtgatgaagt cgtgggggtg catgctcacg ccgacgtggt gccggtcacc    540

ccggaaaact gggtgctgca agacggcacc aaactcgacc cgttcaaggt cacgctgatc    600

ggcgaccgca tgtatggccg cggtaccgag gatgacaaga acggcatcgt ggtgacgatg    660

tacgccatga aggtgatcaa ggaagaaaag ctgccactgg cgcgcacgtt caagctgctg    720

gtggacacca ccgaagaaac ttccggtgag gctattcctt actatttcga gcgcaatccc    780

gtgccgcaat acaacctggc gctggatggc ggttacccgg tggtgattgc cgagaaaggc    840

tcggggacgg tcatggccac cttcccggtg cgcaaaggcg aaggcaaagg cgcagagatc    900

atcgcgatga ccggcggcaa ggcgaacaac cagatcccat cggcctcggt agccacgctg    960

gtcagcgata cacccgccga attggccgcc agcctgcaac aggccggtgc cgactatgcc   1020

aagcgcaacg gtggcaattt ccaggtgacg gccaaggtcg atggcaagga cgtcaaactc   1080

acggtgaccg gcgtgtccgc gcactcctcc gagcccgaaa ccggagtcaa cccggtggcg   1140

cgcatgctgg agttgatcca tagcctggat ggcaaggtcg ccctcaagca caaccacatc   1200

accgacgccg cgcggtatgc cgccgacaac tggggcctgg attacctggg cggcaaattg   1260

ggtgtgggct acgcggatga tttcatgggc ccgctgacca cctcgctgac gtttgtgggc   1320

caagatgaca aagccttcaa actggcagtg aacctgcgcg cgccgaaagg taaaacccct   1380

gattcactca aggcgcagat tgagcagaag ctcactgcct ggaaccagga tgccaaggtc   1440

aaggtgaact tcacgtactc gctcgacacg ccgatgtacc gcaaccctga aggcgagtgg   1500

gtcaaggcct tgttggcggt ggccacggaa aacctgggga tggcacacaa gttcggcact   1560
```

tcagccggcg caacctccgt gcatgacctg cccaacggcg tgcaattcgg cctggcgcgc 1620
ccggaagaga agtacaccgg gcacacggac agcgagttca agacggttga gcagttcttg 1680
ctggacctgc agatcgtcac cgaaatgatg ggccgcgtcg ggcaattgcc gaagctc 1737

<210> SEQ ID NO 86
<211> LENGTH: 1431
<212> TYPE: DNA
<213> ORGANISM: Pseudomonas fluorescens

<400> SEQUENCE: 86
atgtcaaaag taaaagacaa agctattgta tctgccgcgc aagccagcac tgcttactcg 60
caaatcgata gcttcagcca tttgtatgac cgtggcggta acctcacagt caatggcaaa 120
ccgtcctaca ccgtggacca ggcagcgacc cagctgctgc gggatggtgc tgcgtaccgg 180
gactttgatg gcaacggcaa gatcgatctg acctacacct tcctcacctc ggctacccag 240
agcaccatga acaaacatgg catctcgggg ttcagccagt tcaacaccca gcagaaagca 300
caggccgcac tggccatgca atcctgggcg gatgttgcca acgtgacctt taccgaaaag 360
gcttccggcg gtgacggcca catgacgttc ggtaactaca gcagtggcca ggacggcgcc 420
gcggccttcg cttacctgcc cggtaccggt gcaggctacg acggcacctc gtggtacctg 480
acaaacaaca gctacacgcc gaacaagacc ccggacctga acaactatgg ccggcagacc 540
ctgacccacg aaatcggcca caccctgggc ctggctcacc ctggcgacta caacgccggg 600
aacggcaacc cgacctataa cgacgcaacc tatggacagg acacgcgtgg ttatagcctc 660
atgagttact ggagcgagag caacaccaac cagaacttca gcaaaggcgg cgtcgaagct 720
tacgcttccg gcccgctgat cgacgacatt gccgcgatcc agaagctcta cggtgccaac 780
ctcagcaccc gcgccacgga caccacctac gggttcaact ccaacaccgg gcgtgatttc 840
ctcagcgcca cgtccaacgc cgacaagctg gtgttctcgg tatgggacgg tggcggcaac 900
gacaccctgg acttctccgg tttcacccag aaccagaaga tcaacctcac ggccacctcg 960
ttctctgatg tgggcggcct ggtgggcaac gtgtccatcg ccaagggcgt caccatcgag 1020
aacgcgttcg gcggcgcggg caacgacctg attattggta accaagttgc caacaccatc 1080
aagggcgggg ccggcaacga cctcatctac ggcggcggcg gtgcggacca actgtggggc 1140
ggcgcgggca gcgatacatt cgtgtacggt gccagttccg actccaagcc aggggctgcg 1200
gataagatct tcgacttcac gtccggttcg gacaagatcg acctgtctgg tatcaccaag 1260
ggtgcgggcg tgaccttcgt caacgccttt accgggcatg ccggcgatgc tgtactgagc 1320
tatgcctcgg gtaccaacct gggcaccttg gccgtggact tttccgggca cggcgtggcg 1380
gatttcctcg tcaccaccgt tggccaggcg gctgccagtg acatcgtagc c 1431

<210> SEQ ID NO 87
<211> LENGTH: 1827
<212> TYPE: DNA
<213> ORGANISM: Pseudomonas fluorescens

<400> SEQUENCE: 87
atgaacggag ttcagcgcgt gtttttgatt tcccgccgca gcctgacagt catcgccgca 60
gccctggccc tcgccgcctg ccacacgccg gtcaacgaac agccaccggc cccggagctg 120
ggctcgggct atcgcaccga cctgagcacc cgccacgccg agcgccatat ggccgccgcc 180
gccaaccctc tggccgctga agccgggcgt gagatgttgc gccaaggcgg ttcggctatt 240

-continued

```
gatgctgcga ttgctatgca agcgatattg accctggtgg aaccgcagtc gtccggcatc    300
ggcggcggtg cattcatcat gctgtgggat gggcacaacg tgcaggctta cgacggccgc    360
gaaactgcgc cggccggggc gacggagcgc ttgttcctga agggcgacgg tacgccgatg    420
gcgttcacgg atgcgcagat tggcgggcgc tcggtgggca cgccaggggt attgcgcgcc    480
ctggagatgg cgcacaaaaa gagcggccac ttgccatggg ccaagctgtt cgagccggcg    540
attcgcttgt cggagcaagg cttcgccatt tccccgcgct tgcacagctt gatcgccgca    600
gaccgcttta tcgcgcaatc gcccgacatg gcggcgtact tcctgaatgc cgatggctcg    660
ccaaaagcca ccggcacgct gctgaaaaac ccggcactgg ccgtcgtgtt caagcgcatc    720
gccaaggaag ggccggacgc gctgtaccaa ggcccgattg ccgaggagat cgcacgcaag    780
gtgcagggcc atcgcaatgc cggcagcctg tcccaggctg atctcaaggg ctacaccgcc    840
aagcaacgcg caccgctgtg caccgactac aaacaatgga aggtctgcgg catgccaccg    900
ccgtcctcgg gcgggattgc cgtggcgcag atcctcggga cactgcaggc gctggaaacc    960
cgcaccccgc gcctggccat cgcccctatg acaccggtca agagtgcctc gccggccggg   1020
cttgagccga cacccgaggc cgtgcacctg ctcgccgaag ccgggcgcct ggcctttgcc   1080
gaccgcgcgc tgtacgtggc cgatgcagac ttcacccccg tacccgtcgc cggcctcgtc   1140
gcaccgagtt acctggcgca gcgcgccacg ctgatcggcg aacgcagcat gggcatcgcc   1200
aagcccggcc aacccgccgg tattcaggta gcgtatgcgc cagaccgctc gccgctgcgc   1260
atctccacct cacaggtggt ggcggtggac gaccagggcg gcgccgtgtc gatgaccacc   1320
acggttgaag cggcattcgg ctctcatgtg atggtccagg gctttttgct caacaaccag   1380
atgaccgact tctccttcat ccccgaagaa aacggccagc ctgtggccaa ccgcgtgcaa   1440
ccgggcaaac gcccacgctc ggccatggcg ccgaccttgg tgttcgaccg caactcgggc   1500
gaactgctgg ctaccgtcgg ctcccccggc ggctcgcaga tcatcgagta cgtgagtaaa   1560
tccctggtgg ccatgctcga ctggaagctc gacccgcagg cggccatcag cctgcccaac   1620
ttcggcagtc gcaatggtgc taccgagttg gaagctgggc tgttcagccc ggcgcttaaa   1680
caggcgctca aggacaaggg ccacgccctg agcgagatcg agatgaccag cggcgtgcag   1740
gccatcgtgc gcacacggga tgcccaaggc aaggtgacgc tcagtggtgg cgcggaccct   1800
cggcgtgaag gtgaggcgtt gggtgat                                       1827
```

<210> SEQ ID NO 88
<211> LENGTH: 1647
<212> TYPE: DNA
<213> ORGANISM: Pseudomonas fluorescens

<400> SEQUENCE: 88

```
atgacggtgg tgaaggtctt ttcaatgtgg gagctttatc gggctgacaa cggagcagtc     60
ggcatcggta actcgcatat atggacggtt aactttccac tgttcagagt atcaaagcac    120
atgcatatcc ctgttaggca gtcttcttac tcgcgtcctt cagataagtt acagcccgat    180
ctttcacccg atgaacacca agttgttctc tgggccaaca ataaaaaatc tttcaccacg    240
gatcaggccg cgaaacacat cacccgcggt ggcttcaagt ttcatgatcg caacaatgat    300
ggaaaaatcg tcgtgggtta taactttgcg ggcggcttca atgcggctca gaaagaacgg    360
gccaggcaag cccttcagta ctgggcggat gttgctaata tcgaatttgt tgaaaatggc    420
ccgaacacgg atggcacaat aagcatcaag ggtgttccgg gttcggcagg cgtcgcgggg    480
ttgcccaaca aatataattc gaacgtccag gccaatatag gcacccaggg tgggcaaaac    540
```

```
ccggcgatgg gcagtcactt cctgggctta ttgatccatg aactggggca taccctgggg    600

ctgagtcatc caggtaaata cgacggccag ggtttcaatt acgatcgggc tgccgaatat    660

gcccaggaca ccaaggctcg cagtgtcatg agctattgga cggagactca tcagccgggg    720

cacaattttg ccgggcgcag cccgggtgcc ccgatgatgg acgatatcgc cgccgcccag    780

cggctctacg gcgccaacac caaaacccgg aataccgaca ccacctacgg cttcaattcc    840

aattcaggcc gggaggctta tagcctcaag caggggagcg acaagccgat cttcaccgtc    900

tgggacggtg gaggtaatga cacgctcgac ttctccgggt tcacccagaa ccaaaccatc    960

aacctcaagg ctgagtcatt ctcggacgtg gggggcttgc gaggaaatgt gtcgattgcc   1020

aagggtgtga gtgtggaaaa cgccattggc ggtacaggca acgatacctt gacggggaac   1080

gagggcaaca atcggctcac gggcggcaag gggggccgata agctgcacgg cggagctgga  1140

gcagacacgt ttgtttaccg ccgcgccagc gattcaacgc cgcaggcacc ggacatcatc   1200

caggacttcc agagcgggag cgacaagatc gacctgaccg gtgttgttca ggaggcgggg   1260

ctcaagtcgc tgagcttcgt cgagaaattc agcggcaagg cgggcgaggc cgtgctcggc   1320

caagacgcga aaaccggccg tttcacgttg gcggtggaca caacgggaaa tggtacggcg   1380

gatctactgg ttgccagcca aagccagatc aaacaggcgg atgtgatctg gaacggtcag   1440

gcgccgacag tgacgccaac gcctgaaccc actgtggtgc ctgtgtcaga tcccgtgccg   1500

acccctactt cagagccgac tgaacctgaa cccacgcctg agcccgcccc tttgcccgtc   1560

ccgactccac ggcctggagg agggtttatc gggaaaattt tttcatcatt caaggggttc   1620

ataaaaaaag tgtggtcgat attcagg                                       1647
```

<210> SEQ ID NO 89
<211> LENGTH: 2577
<212> TYPE: DNA
<213> ORGANISM: Pseudomonas fluorescens

<400> SEQUENCE: 89

```
atgagagtgc caggaccaac cgcaacgaat tctaatgcag ggcaggtgcc agatccgagg     60

agtggcatca gcccggaggg ccctacgcag gtatatacac taaacagcaa aaaaaccgtc    120

ttcactacgg aacaggccgg gaaacatatc acccgcagcg gtttcaagtt tcatgacagt    180

aacggtgatg gcaaaaccac gttgtcctat cgtgtttcca agggctttac cccacagcag    240

gcagatcaag ccaggcaggc actgcaatcc tggcaggatg tcgctaacgt cacattcact    300

gaaaaaaggc agggggctga cggccatata gatatcaatg agatgcacgg aacctctggg    360

ggtatggcct cactccccaa ccgctatatg agtcaaactt tcgcaaatgt cggaacagcg    420

aatgcaggtg caaaccctcc acggggtcat tattttcgcg aagttctagt tcacgaaata    480

ggccacacca ttgggctgga acacccgggg gactatgatg gctctggtaa ctatggacgg    540

gacgcagcgt atgccgggga tactcgagcg cgttctgtga tgagttacta ttcggaaaaa    600

aaccagccgg gacatgattt caaatcattg aacccctctg cgccgatgat ggatgatata    660

tcggccgttc agaaactcta tggggcgaat actaaaacgc gtaataccga tacgacgtat    720

ggatttaatt ccaatacaaa ccgtgaagcc tatagtttga agtcggctaa cgacacaccc    780

attttctgtg tgtgggatgg tggtggtaat gacacattgg atttctctgg gtattcacac    840

catcagaaaa tcaacctcaa tgccgagtcc ttttcggatg taggggcgtt gaaaggtaac    900

gtttccgttg ccaagggcgt cacgctggaa aatgcagtgg gcggtaaggg cgacgacaca    960
```

cttatcggta atcatgttgc caatcgcctc aaaggggggg cgggagccga cagactgtct 1020 gggggggggcg gcgcagatac ctttgtttac gaccatgcca gtgattccac cccggataac 1080
cctgatgtca tcctggattt tgcgagtggc gcagataaga ttgatgtatc cgcagtcctt 1140
aaaagagcga atgtcagtgc tctcaagttc gtcgatcgct taactggcca acccggccag 1200
gctgtgatga gttatgacga gggccgcaac gagggggggc tggccctgga tctgacaggc 1260
aacggcaagg ctgatctatt aataaaaagc attggccaga taaaagctgc tgatatcttg 1320
gcgcacggcg atacaaccgc gccaaaccct gaacccaaag atcccaagcc gcagccgcgt 1380
cctcaacccg aggagcccaa acccaagcct gaatccaaac cgaaggagcc aaaaccggag 1440
gaaccaaaac cgcgtccgga ctcgtgtgaa ccaaagccgc gtccggatcc gtgtgagccg 1500
aagccgcgtc cggatccgtg cgagccgaag ccgcgtccgg attcgtgtga gccaaagccg 1560
cgtccggatc cgtgcgagcc gaagccgcgt ccagatccac gcgaaccgca gccacgtccg 1620
gacccgcgcg agccgcagcc gcgtccagat ccacgcgaac cgcagccacg tccggacccg 1680
cgcgagccgc agccgcgtcc ggacccgcgc gagccgcagc cgcgtccaga tccacgcgaa 1740
ccgcagccac gtccggaccc gcgcgagccg cagccgcgtc cagatccacg cgaaccgcag 1800
ccacgtccag acccacgtga accgcagcca tgtccggatc cacgcgaacc gcagccgcgt 1860
ccggacccgt gtgagccgca gccgcgtccg gacccgtgtg agccacagcc gcgtccagac 1920
ccacgtgaac cgaggccgcg tccgaaccca cgtgaaccgc agccacgtcc ggacccacgc 1980
gagccgcagc cgcagccgcg tccggaccca cgtgaaccgt acccacgtcc agacccacgt 2040
gaaccgaggc cgcgcccgaa cccacgtgag ccgaggccgc gtccgaaccc acgtgaacca 2100
cagccgcgtc cagacccacg tgagccgagg ccgcgtccgg acccgtgtga gccacagccg 2160
cgtccagacc cacgtgagcc gaggccgcgt ccgaacccac gtgaaccaca gccgcgtcca 2220
gacccacgtg aaccgcagcc acgcccggac ccgcgtgagc cgaggccgcg tccggaccca 2280
cgtgaaccgc agccacgccc ggacccgtgt gagccacagc cgcgtccgga accatgtgag 2340
ccgagaccgc gtccgaaccc acgtgaaccg caaccacgtc cggacccgtg cgagcctaaa 2400
ccaacccctc gcacagatcc ttgcgagccg aaagctgtca ctcgaaacgt aaggccagcc 2460
tatggcttga gtgcccattc aggcgagtac cgggcgatgc aggcgccagc ctttgatagt 2520
cgtcatttcc agggcgggct tgcaggggaa ttcattcgac gtcagaagcg cgctgaa 2577

<210> SEQ ID NO 90
<211> LENGTH: 549
<212> TYPE: DNA
<213> ORGANISM: Pseudomonas fluorescens

<400> SEQUENCE: 90
atgcctttac acattatcaa cttcaccgca ccggtcaccg cctccacgtg cagccaactg 60
atcgaaaaag cctcattagc cgtgcagcaa ggtgcccaag gcctggtact gaatatcgcc 120
accatgggcg gcgaatgcag ctacggcttt acgatgtaca actttttatt gtccctgccg 180
atcccggtgc atacccataa cctcggcacc gtggaatcca tgggcaatat catcttcctg 240
gccggtgagc gcaggaccgc ctgcaaacac agcaaattcc tgttccaccc ctttcattgg 300
catgtgcaag gcgcggttga ccactcgcgc atgtctgaat acgcaatgag cctcgactat 360
gacttgcagt tgtacgcacg catcgtcgcc gagcgcaccg ccgatgccgt cgaaaaactg 420
gagaccgaaa aatacctgat cgccgcgcca cgcattctcg acccgcaaca agcgctcatc 480
gccggcttga tccatgggat cgaacttccc gtggtcaagg cggaattcgt gagcagcttc 540
attcattcc 549

<210> SEQ ID NO 91
<211> LENGTH: 2022
<212> TYPE: DNA
<213> ORGANISM: Pseudomonas fluorescens

<400> SEQUENCE: 91
atgcctgaaa gcaatccact gttactgccc tacgacctgc caccgttctc tgccatccga 60
gcagagcact tggtgcccgc cattgagcag atcatcactg aaagtcgcaa caccaccgcc 120
acgatcattg ccagccagac gccattcccc acctgggacg acctggtgca agcagtggag 180
gcgttggagg ctcgcctgga tggcgttctc aaaatcatcg agctgcttga ctcccacccc 240
caagggcctg catggacgct ggcatcacac cgcagttatg agctggccat gcagtacagg 300
gttgagttgg ccgggaacaa cgacctgtat caactgcacc gacaacttgc cgacagcccg 360
atcgcgaccc ttttcaatga acaacgccac agcgcgttgc gtaaaatatt gcgcaagtac 420
cacttggctg gccttgatct ttctcctgaa aagcagcgac ggctgaaagc gttgaacctg 480
caaatcgatg aattcagcca cgagttcctg cgtcgtgtga gcgactccag tgacgcatgg 540
cgtaagcaca ttcaagacaa ggcgctgctg agcggactac ctgacgcagc cctggcgcgc 600
ctggagttcg cggctcggga cgcaggcctg gggggatggt tattaaccct ttcgaagcaa 660
tcctttcagg aggtgatgag ctacgccgac catagagcct tgcgccagga aatgatgctg 720
gcttactaca gccgtgccgt gggcacgggg cctgacgcca ttgccactga caatgaagcg 780
gttctgaccg tgttgctcga cagtcgtcac cagaaagcac aattgctggg ctatgccaac 840
ttcgccgagc tggcgctggt ggaacaaatg gctgagacga ccgatgaggt cactgcctgt 900
gtgcatcaac agattgatca ggcacgcacg acatttgccc atgatgcaca acaactgcaa 960
cgctatgccg cgcaacgggg agtcgatgcg ctagaaccgt gggattacga ctttttcgcg 1020
gaaaaaattc gccaggacgt ggcgggtgtc tcccaggacg cagtgcgcct ctacttcccg 1080
ttggagacag tgctgcaacg cttgtgcacg ttcacccaaa cgctgttcgg cgttgagctg 1140
attgaacaag ccacggtcga tacctggcac ccggatgtgc gggtatttga actcagggag 1200
tacgcgcagc cgattggaca tttgtttatt gacccttatc gccgcgtggc gggcggcgaa 1260
attggcgccg ccatgggctt gcgcaatcac cgaatgactg ccgaggggcg cccacaacgg 1320
cccatagccg tgctgcgcag ccagttgcca cgacctacgg cggcccagcc ttgcttgctg 1380
gatcacctgc aattgagggt cctattgcat gagttcggac actgcctgca gcatctgttg 1440
tccgccgccc cctaccgggc gatttcgggc atgggccaat taagccacga tacgacggag 1500
ttcttcggcc tagtgctgga gcagttctgc cttacgccgt cgttcctgat ctatctatcc 1560
gggcatgtgc agacgggaga tcccttgcct gacaaaatgg cgacgcaaat gagccgattt 1620
gctcataccc agaccagtca ggaaaccgcc agtattttgc tcacgggcct cgttgacttc 1680
gagttgcacc gcacctatgg cgacgggcgc acaccgcatg aagtattcac cgacgccaat 1740
gttgaagtcg ggcatttgca gtggcctgat ggcgctcgtc cgatcaacag tttcgaacaa 1800
ccgatgggta gctatggcgc caaactgtat tcctacacgt ggtccggcgt tctggcccgc 1860
caggcgtttg agcggtttga gcgtgatggc ctgttcaacc cgcagaccgg gaaagccttc 1920
cgggacgcgt tcatcactga gggcgatacc ggtactctgt tgagcgcact tgcgcttttc 1980
cggggggacg gcgcgggatg tgtcgggcat tccaccgggg ta 2022

<210> SEQ ID NO 92
<211> LENGTH: 2394
<212> TYPE: DNA
<213> ORGANISM: Pseudomonas fluorescens

<400> SEQUENCE: 92
atgaagacaa ccatcgaatt gcctctcctg ccgttgcgtg atgtcgtcgt ctatccgcac 60
atggttatcc cgctgttcgt ggggcgcgag aagtctatcg aagccctcga ggccgcgatg 120
acgggcgaca agcaaatcct gctgttggcc cagaagaatc ctgctgatga tgatccgggc 180
gaagatgccc tgtatcgcgt cggcaccatt gccactgtcc tgcaattgct caagctgccc 240
gatggcaccg tcaaggtgct ggtcgaaggc gagcagcgcg gtgccgtaga gcgctttatg 300
gaggtggacg gccacctgcg cgcggaagtg gcactgatcg aagaagtcga agccccggag 360
cgtgaatccg aggtgttcgt gcgcagcctg ctgtcgcagt tcgagcagta tgtgcagttg 420
ggcaagaaag tcccggctga agtcctgtcg tccctcaaca gcattgatga gccaagccgc 480
ctggtcgaca ccatggccgc gcacatggcg ctgaaaatcg agcagaagca agacatcctc 540
gaaatcatcg acctgtcggc ccgtgtcgaa cacgtactgg cgatgctgga tggcgaaatc 600
gacctgttgc aggttgaaaa acgcatccgt ggtcgcgtga aaaagcagat ggagcgtagc 660
cagcgcgagt actacctgaa tgagcagatg aaggccattc agaaggaact cggcgacggc 720
gaggaaggcc acaacgaaat cgaagagctg aaaaagcgca tcgatgccgc tggcctgccc 780
aaagacgccc tgaccaaggc caccgccgag ctgaacaagc tcaagcagat gtcgccgatg 840
tcggctgaag ccaccgtggt gcgctcgtat atcgactggc tggtgcaagt gccgtggaag 900
gcccagacca aggtgcgtct ggacctggcc cgtgctgaag agattctcga cgctgaccat 960
tacggcctgg aagaggtcaa ggagcgcatc cttgagtacc tcgctgtaca aaaacgcgtg 1020
aagaaaatcc gcggcccggt gttgtgcctg gttgggcctc cgggcgtggg taaaacctcc 1080
ctggcggaat caattgccag cgcgaccaac cgcaaattcg tgcgcatggc cttgggtggc 1140
gtgcgtgacg aagcggaaat tcgcggtcat cgccgtacct acatcggttc gatgccggga 1200
agattgattc aaaagatgac aaaagtgggt gtacgcaacc cgctgttcct gctcgatgaa 1260
atcgacaaaa tgggcagcga catgcgtggc gacccggcgt cggctttgct cgaagtgctg 1320
gaccctgagc agaaccataa tttcaacgac cattacctgg aagtcgacta cgacttgtct 1380
gacgtaatgt tcctgtgcac ctccaactcc atgaacattc cgccagcctt gctggaccgg 1440
atggaggtga ttcgtctgcc gggctacacc gaagacgaga agatcaacat cgcggtcaag 1500
tacttggcgc ccaagcagat ttcggccaac ggcctgaaga agggcgagat cgaattcgag 1560
gtcgaggcga tccgcgacat cgtgcgctac tacactcgcg aggccggtgt gcggggcctt 1620
gagcgccaga tcgcgaagat ctgccgcaaa gcggtgaagg aacacgcgtt ggaaaaacgc 1680
ttctcggtga aagtggttgc cgactccctg gagcacttcc tgggcgtgaa gaaattccgc 1740
tacggcctgg ccgagcaaca ggaccaggtc ggccaggtga ctggcctggc gtggacccag 1800
gtgggtggcg aattgctcac catcgaagct gcggtgattc cgggcaaagg ccagttgatc 1860
aagaccggct ccctgggtga cgtgatggtc gaatccatta ccgccgcgca gaccgtggta 1920
cgcagccgcg cccgcagcct gggcatcccg ctggacttcc acgagaagca cgacacccat 1980
atccacatgc cggaaggggc gacccccaaa gacggcccta gcgcgggcgt aggcatgtgc 2040
acggccctcg tgtcggcctt gaccggcatt cccgtgcgcg ccgatgtggc gatgaccggg 2100
gaaatcaccc tgcgtggcca ggtattggcg atcggtggtc tcaaagagaa attgctcgcc 2160
gcgcaccggg gtggaatcaa gactgtgatc attcctgaag agaatgttcg cgacttgaag 2220
gaaattcctg acaacatcaa gcaggatctt cagattaaac cggttaaatg gattgacgag 2280
gtcctgcaaa ttgcgctgca atacgcgccg gagcccttgc cggatgtggc cccggagatt 2340
gtcgcgaagg acgaaaaacg cgagtccgat tccaaggaaa gaattagcac gcat 2394

<210> SEQ ID NO 93
<211> LENGTH: 921
<212> TYPE: DNA
<213> ORGANISM: Pseudomonas fluorescens

<400> SEQUENCE: 93
gtgaaaattc gtctttctat tgtcagcctg ttttttgctt tggcaggcac cttcgcccac 60
gccgccgaat ccaccctggc cccgcgtgac gcctccaagc ttcaaatcgc ctccggcagc 120
gccatgctgg tcgatttgca gaccaataaa gtcatttatt ccagcaaccc cgacgtggtg 180
gtacctatcg cctcggtgag caagctgatg accggcctga tcgtcctcga agccaagcag 240
aatatggacg agtacatcga catcaacatc accgacacgc ccgagatgaa aggcgtgttc 300
tcccgggtga agatcggcag ccagatgccg cgcaaggaaa tgctgctgat cgcgctgatg 360
tcttcggaaa accgcgccgc tgcgagcctg gcccaccatt atcctggcgg ttacgcagcc 420
tttatcgcgg cgatgaacgc caaggccaag tccttgggca tgaccagcac ccactacgtg 480
gagcccaccg gcctgtcgat ccataacgtg tcgaccgccc gcgacctgag caagctgctg 540
gcctatgcgc gtaaattccc gatgctgagc cagctgagca ccaccaagga aaagaccgtg 600
tcgttccgca agcccaacta caccttgggc ttctccaaca ccgaccacct gatcaaccgc 660
gccaactggg atatcaagct gaccaagacc ggcttcacca accaggccgg ccactgcctg 720
gtgctggtga cgagcatggg caatcgcccg gtgtcgctgg tgatcctgga tgcctttggc 780
aagttcaccc attttgccga tgccagccgt attcgtagct gggtcgagac cggcaaaggc 840
ggcgcagtgc cggatgtggc gctgcgttac aaggccgata aaaacctcaa gaatcgagcg 900
accgctacgg aagtacgtcg a 921

<210> SEQ ID NO 94
<211> LENGTH: 633
<212> TYPE: DNA
<213> ORGANISM: Pseudomonas fluorescens

<400> SEQUENCE: 94
atgttccgta attcctatat tcagcagaac tctgatatcc aggccgcagg cggcctggtc 60
ccgatggttg tcgagcagtc cgctcgtggc gaacgcgcct acgacatcta ctcgcgcctg 120
ctcaaggagc gagtgatctt tctggttggc ccggtagagg actacatggc caacctgatc 180
tgtgcgcagc tgctgttcct tgaagcggaa aacccggaca aggacatcca tctctacatt 240
aattcgccgg gtggttcggt gactgcgggc atgtcgatct acgacaccat gcagttcatc 300
aagccaaacg tgtcgaccac ctgtattggc caggcgtgca gcatgggcgc cttcctgctg 360
accgcgggtg ccgaaggcaa gcgtttctgc ctgccgaact cgcgcgtgat gattcaccag 420
ccactgggcg gtttccaggg ccaggcgtcg gacatcgaaa tccacgccaa ggaaatcctc 480
ttcattcgtg agcgtctcaa cacgctgatg gccaagcaca gcgggcgcac cctggaagaa 540
atcgagcgcg ataccaaccg tgacaatttc atgagcgctg aagccgccaa ggaatacggg 600
ttgatcgacg cagtgatcga caagcgcccc gca 633

<210> SEQ ID NO 95
<211> LENGTH: 1350
<212> TYPE: DNA
<213> ORGANISM: Pseudomonas fluorescens

<400> SEQUENCE: 95
atgagtgcgc tctacatgat tgtcggcacc ctggttgctc tgggtgtgtt ggtgaccttc 60
cacgaattcg gccacttctg ggtcgcgcgt cgttgcggcg tcaaggtatt gcgcttttcc 120
gtcggtttcg gcatgccgtt gttgcgctgg catgaccgcc gcggcactga gtttgtcatt 180
gctgctatcc cgttgggcgg ctacgtcaag atgctcgatg agcgcgaagg cgaagtgcct 240
gcagaccagt tggaccaatc cttcaatcgc aagaccgttc gtcagcgtat tgcgattgtt 300
gcggcggggc cgattgccaa ctttctgttg gcgatggtgt tcttctgggt cttggccatg 360
ctgggcagcc agcaggtgcg cccggtcatt ggcgcggtcg aagcggacag catcgcggcc 420
aaggctggcc tgacggctgg gcaggaaatt gtatccattg atggcgaacc caccacgggc 480
tggggcgcgg tcaacttgca gttggtgcgt cgcctgggcg agagcggcac cgtcaatgtg 540
gtggtgcgcg accaggattc cagcgccgaa accccgcggg cattggcgct ggaccattgg 600
ctcaagggcg ctgatgagcc cgatccgatc aagtccctgg ggatccgccc ttggcgtccg 660
gccttgccgc cggtgctggc cgagctcgat ccgaaaggcc cagcccaggc tgctggcctg 720
aaaaccggtg atcgcttgct ggccctcgat ggccaggcgc tgggtgactg gcagcaggtg 780
gtcgacctgg tgcgtgtacg ccctgatacc aaaattgtgc tgaaagttga gcgcgagggt 840
gctcaaatcg acgtccccgt gaccttgtcg gtgcgaggcg aagccaaggc agccgggggc 900
tacctgggtg caggggtcaa aggtgtcgag tggccgccat cgatggtgcg agaggtcagc 960
tacgggcctt tggccgcgat tggcgagggt gcgaaacgca cctggaccat gagcgtgctg 1020
accctcgaat ccctcaagaa aatgttgttc ggtgagctct cggtaaaaaa cttgagtgga 1080
ccgataacca ttgctaaagt ggcgggcgct tctgcccagt cgggtgtcgc ggatttcctg 1140
aatttcctgg cttatctgag tattagcctt ggggttctga atttgctgcc cattccagta 1200
ttggatgggg ggcatctgct gttttatctg gtcgagtggg tgcgtggtcg ccccttgtcg 1260
gatcgggtgc agggttgggg gatacagatc ggtatcagtt tggtggtcgg ggtgatgttg 1320
ttagccctgg tcaacgatct gggacgtctg 1350

<210> SEQ ID NO 96
<211> LENGTH: 780
<212> TYPE: DNA
<213> ORGANISM: Pseudomonas fluorescens

<400> SEQUENCE: 96
atgaccgtta ccttgaaaac cgccgaagac atcgcaggca tgcgcgttgc cggcaaactg 60
gctgccgacg tgctggaaat gatcgccgaa cacgtcaagc ccggcgtcac caccgaagcg 120
ctggaccgca tctgccacaa ctatatagtc gacgtgcaaa aagccatccc tgccccgctg 180
aattacaaag gcttccccaa gtcgatctgc acctcgatca accacgtggt ctgccacggc 240
attcccggtg acaagccact gaaggacggc gacaccctga acatcgacgt cacggtgatc 300
aaggacggct accacggcga caccagccgc atgttccacg tcggcaatgt accggtgtgg 360
gccgagcgcc tgtcccaggt cacccaggaa tgcatgtaca aggccatcga aatcgtcaag 420
cccggctgcc gcctgggtga catcggtgaa gtgatccaga agcacgcgga aaagaacggt 480
ttctcggtgg tgcgcgaatt ctgcggccac ggtatcggca aagtgttcca cgaagagccg 540

```
cagatcctgc actacggccg cgccggaacc ggcatggaac tcaaggcagg catgaccttc    600

accatcgagc cgatgatcaa ccagggcaag gccgacacca aggtgctggg cgacggctgg    660

accgccatca ccaaggaccg caagctctcg gcccagtggg aacacaccct gctggtcacc    720

gacaccggct atgagatttt caccctgcgc gccgacgaca ccatcccacg cgtttcggcc    780
```

<210> SEQ ID NO 97
<211> LENGTH: 918
<212> TYPE: DNA
<213> ORGANISM: Pseudomonas fluorescens

<400> SEQUENCE: 97

```
atgaccgccg ccgtacccgc actgcccccc gaaggcaccc tcggcctgat cgcccccgcc     60

ggccccgccg agctggatgt tgaaaaagcc aggcaatgga tgcgtgcccg tggctacgac    120

ctgcatattt tccccggcgt gtacgagcgc gacggctacc tggccggtag cgatgaagtg    180

cgcctgcggg atttgcatgc cgcctttgcc aaccccgata tcgatgccat cctttgcctg    240

cgtggcggct atggcacgcc ccgtttgctc gacgcgctgg acttcgacct gctgcgtgcc    300

aaccccaagc cgttcgtggg ctacagcgat atcaccgcct tgcacctggc gatcaaccgc    360

tacgcgggct ttgtgacatt ccacggcccg atgctcaatg ccgacctgct cggcggcaaa    420

cagccgccca ccgagtcctc cttgttcagc ctgctacgtg gccaaagggg cgccggcagt    480

gtgctgccgc acccgatggc ctgcccgctg accacaatcg agccaggagt ggcctgtggg    540

cgcttgctgg gcggtaactt gtcgatgatc gccgcggtca tgggcacgcc gtacgaaata    600

gacgctgacg gcatcatcct gtttatcgaa gacgtcaacg aaccgctcta tcgcatcgac    660

cgtctgctga ccaacctgcg cctggctggc aagctggctc aggtcgccgg tgtgctggta    720

ggggatgtgg ctggtgtgga tagcggggca ttggcacgtc tgctgaagca gacctttgag    780

ccgctgtgcg ttccagtgct ggcaggctgg agcagtgggc attgcgaccc gaacctgaca    840

ttgccgatgg gcgccttggt gcgcctggat gcgggggagc agcgggtggt gttggagcag    900

gatgtagtgt tcaaggcc                                                  918
```

<210> SEQ ID NO 98
<211> LENGTH: 930
<212> TYPE: DNA
<213> ORGANISM: Pseudomonas fluorescens

<400> SEQUENCE: 98

```
atggaattca tcgaaaaagt tcgcgaaggc tacgcgccct ttggcgccta tcagacctgg     60

tatcgcgtca cgggtgacct gagcacaggc cgcacgccct tggtgatcat ccatggcggc    120

cctggttgca cccacgatta cgtcgacgcc ttcaaagacg tcgccgccag cggccatgcg    180

gtcatccact acgatcagtt gggcaacggc cgctccacgc acttgccgga aaaagacgcg    240

tcgttctgga ccatcggcct gttcctcgac gagttgaaca acctgctgga ccacctgcaa    300

atcagcgaga actacgcgat cctcgggcaa tcctggggcg gcatgctcgg cagcgaacac    360

gcgatcttgc aacccaaggg cctgcgcgcg tttatccctg ccaactcccc cacctgcatg    420

cgcacctggg tcagcgaagc caaccgcctg cgcaagctgt tgcctgaagg cgtgcatgaa    480

accctgctca agcacgagca ggccggcacc taccaagacc cggcatacct ggcggcctca    540

cggattttct atgaccagca tgtgtgccga gtcaacccgt ggcccgaaga agtggcgcgc    600

accttcgccc aggtggatgc cgacccgacg gtgtaccacg ccatgagcgg cccgaccgaa    660
```

```
ttccacgtga tcggcagctt gaaggactgg aacgtgatcg gtcggctgtc agcgatcaag    720

gtgccaaccc tggtgatttc cggccggcac gacgaagcca caccgttggt ggtcaagccg    780

ttcctggatg agatagagaa cgtgcgctgg gcactgtttg aagactccag ccacatgtcc    840

catgtggaag aacgccaggc gtgcatgggg acggtggtga agtttctgga tgaggcgtgt    900

tcgttgccgc acaaagccct caaggccggc                                     930


<210> SEQ ID NO 99
<211> LENGTH: 885
<212> TYPE: DNA
<213> ORGANISM: Pseudomonas fluorescens

<400> SEQUENCE: 99

atgtggcgtg aaattgcccc cgaccagcag tacaacgtgc aagtcgacgg ccataacctc     60

gtggtctaca gctttggcga aggcgatgag gtgctgctgt gtctcaacgg cgggccgggc    120

ctgccgtgtg actatctgcg tgacacccat ggctggctca aagcacataa cctgcgagtg    180

gttgcattcg accagcttgg cacaggcgca tcagccagac cggccgatgc cgcactgtgg    240

gaaatccgcc gttatgtcga agaagtcgag accgtgcgcc aggcgctggg cctgggccgc    300

gtgcatttgc tcgggcattc ctggggcggt tggctgggca tcgaatatgc cgtgcattat    360

cccggtgcgc tcaaaagcct gatcctggaa aacaccgtcg gcgacattcc ccacctgtcc    420

caggaactgg agcgcctgcg cggcgccctg ggcagcgaaa ccgtggccat gatgcaacgc    480

cacgaagcca tgggcaccct cgaccacccg cagtaccagg ccgccatcac cttgctcaac    540

taccgccacg tgtgccggct cgacgaatgg cccgagccgg tcaagcgctc cctgggcgac    600

tggaacatgg ggccttacga aaccatgcaa ggccccaacg agttcctcta tatcggcaac    660

ctcaaggact ggaaccgcct caaggaaatg gccgagttca cgatgccgat cctgatcacc    720

accggccagc acgacgaact cacccccgcc tgtgcgatgc gcatgaaact tgcagcaccc    780

catgccgagt tgcatgtgtt ccccaacagc agccatatgc cgttttacga ggagccgcag    840

gcgtacttcc cggtgctgct ggactttctc gctcgccacc gaggc                    885


<210> SEQ ID NO 100
<211> LENGTH: 537
<212> TYPE: DNA
<213> ORGANISM: Pseudomonas fluorescens

<400> SEQUENCE: 100

atgtcgacct cggcccgcct gatgcttatt gtttgcgccg cgctgctcag cgcctgcgcc     60

agtcgcacac cgccgcccgc gcccgtcgcg gtcaagccta agccggtgtt caactatgcc    120

acccagaatt tctcgccagc tgccgaagac gtgctctttc gtgcgctggg cctggtcggc    180

acgccttatc gctggggcgg caacacaccg gactcgggtt ttgattgcag cggcctgatc    240

ggctttgtat tccgcgacgc tgctggcatc tcattgccgc gcaccacccg tgaactgatc    300

gtgatgcgtg cccaggacgt cagcgaacaa aacctgcaga ccggcgacct gctgttcttc    360

gccaccggtg gtggttcgcg ggtcagccat gcgggtattt atgtggggga ggggcgcttc    420

gtacacgcgc cgcaaaccgg cggtacggtg aagctggata cgctatccaa agcgtattgg    480

cagaatgcct acctgagtgc caaacgcgtg ttgccaggga atctggcgcg taacccc       537


<210> SEQ ID NO 101
<211> LENGTH: 633
<212> TYPE: DNA
<213> ORGANISM: Pseudomonas fluorescens
```

<400> SEQUENCE: 101
gtgcccatgc taaatcgctt cgcacccctc gtgcctctcg cactcgttac cctgttgttt 60
ggttgcgcct cccaccctca gcaggtggca gaacagcaaa aaccacaggt tcaaaatcag 120
gcaaagttcg ttgctgcaca gtctgcttct gtttatgaag aagaggtggc aaccgaaaaa 180
gaactcgccg agttctccga cagcaagcct taccagctgc cacttctggc cgacagcatc 240
cttgagcgcg gcatgtcctt gatcggtacc cgttaccgtt tcggcggcac ctcggaagcc 300
ggttttgatt gcagcggttt cattggctac ctgtttcgtg aagaagccgg tatgaacctg 360
ccgcgctcca cgcgcgagat gatcaacgtg aatgcaccgt tggtcgcacg aaacaacctc 420
aagcccggtg atctgctttt ctttagtacc agtggccgcg gtcgtgtcag ccacgccggt 480
atctacctgg gcgataacca gtttattcat tccagcagcc gccgcagtgg tggtgttcgg 540
gtcgataacc tcggtgacag ctactggagc aaaaccttca tcgaagccaa gcgcgcactc 600
gccatggccc cgacgacggt taccgctagt aag 633

<210> SEQ ID NO 102
<211> LENGTH: 1458
<212> TYPE: DNA
<213> ORGANISM: Pseudomonas fluorescens

<400> SEQUENCE: 102
atgatcaaat ctttgcgttc agtgttactt gccagtgttg tcttgcccct ggccttttcc 60
gtttgcgccg ctcccgtcaa taacaccctg ccacccagcg ttgcccaggc cttgcagaag 120
gccaagctgc aaaataccgc gctgtccctg gtgatgctgc ccctgaacgg ccctggtacc 180
cctacggttt tcaacgccga cgtctcggtg aacccggcct ccaccatgaa gctggtcacc 240
acttacgcgg ccctggaaat gctcggcccc aaccatcagt ggaagaccga gttctacacc 300
gatggcaccc tcagcggcgg cgtgttgcgc ggcaacctgt acctcaaggg cggcggcgac 360
cccaagctga acatagaaaa actctggctg ctgatgcggg acctgcgcgc caatggcgtg 420
cagcaagtca ccggcgacct ggtgctggac cgtaacttct tcaaccagcc gcaattgccc 480
gagttcaacg acgacggcaa cgatgagaac aagccgttcc tggtcaagcc cgacgccttg 540
ctggtcaacc tcaaggccct gcgcttcgtg acccgcaatg attcggggcg ggtgatcgta 600
tcggtcgagc cgccgattgc cagcattcgc atcgacaacc aggtgaaagt caccaacgcc 660
aaacagtgca ccggtgacgt gcgctacagc ccggtgaccg ccgccgacgg cagcgtgacc 720
gtgaccgtca gcggccaact gggtgatggc tgcagctcgc agacctacct gtcgctgctc 780
gaccacgcca cctacaccgc aggcgccgtg cgggcgatct ggaaggagtt gggcggcacc 840
atccagggcc gtgatatcca ggcaccggtg cccaaggatg ccaaagtcct ggcccgggcc 900
ttctcgccgg acctggcgga gatcatccgc gacatcaaca aatacagtaa caacaccatg 960
gcccagcagt tgttcctgag cctgggtgcg cagtttcgca acgatgccga tggcgacgat 1020
gccaaggctg cgcaacgtgt cgtgcgccag tggctagcca agaaaggcat caccgcgccg 1080
cacctggtga tggaaaacgg ctccggcctg tcccgcgccg aacgggtcag cgcccgcgag 1140
atggcggcca tgctgcaagc cgcgtggaaa agcccttatg cggcggagta catcagctcg 1200
atgccgatcg ccggcaccga cggcaccatg cgtaaacgcc tgaaaaccac cgccctgcgc 1260
ggcgaagccc atgtgaagac cggcaccttg aacaccgtac gcgccatcgc cggttacagc 1320
cgcgacaaca atggcaatac ctgggcggtg gtggcgattc tcaacgactc caagccttgg 1380
ggagcctcgt cggtgctgga tcaggtgctg ctggacctgt atcgccagcc gaaggccgtt 1440
gcagccgcac cggttctc 1458

<210> SEQ ID NO 103
<211> LENGTH: 1440
<212> TYPE: DNA
<213> ORGANISM: Pseudomonas fluorescens

<400> SEQUENCE: 103
atgagcgagt tgttgtcctc agtcagtgat cacctcctgg cacccggtgg cgtgaccatc 60
gaaagcctgc aaaccgtgct cggcgatctg gccgggccgg gtatcgatgc ggctgacctg 120
tatttccagg ggcagatttc cgagtcatgg gcgctggaag atgggatcgt caaggaaggc 180
agtttcaacc ttgaccaggg cgtaggcgtt cgcgcgcaat cgggtgagaa gaccggcttt 240
gcctacagca atgcgatcac cctggaggcc ttgggcctgg cggcgcgtgc cgcccgttcg 300
atttcccgtg ccggccagaa tggcacggtg caggcattca gtacccagga cgtggcccag 360
ttgtatgcgc cggataaccc cttggaagtg atcagccgtg cggaaaaagt cgagctgctc 420
aagcgtatcg acgcagctac ccgcgctctg gacccgcgta tccagcaagt gaccgtaagc 480
atggccggcg tgtgggagcg catccttgtg gcgtccaccg acggtgggct ggcggcggat 540
gtgcggccgc tggtgcgttt caatgtgagc gtgatcgtcg aacagaacgg gcgccgcgag 600
cgcggtggcc atggcggcgg cgggcgcacc gactaccgtt atttcctcgc tgacgaccgt 660
gccatgggct atgcccgtga ggcgctgcgc caggcattgg tcaacctgga ggcgataccg 720
gcaccggccg gcaccttgcc ggtggtgctg ggctcgggtt ggtctggcgt gttgctccac 780
gaagccgtgg gccatggcct ggaaggcgat ttcaaccgca agggcagttc cgcctatagc 840
gggcgcatgg gcgaaatggt tgcgtccaag ctgtgcacca ttgtcgatga cggcaccctg 900
gccggccgcc gtggttcgct gagtgtcgat gacgaaggta cgccgaccga atgcaccacc 960
ctgatcgaga acggcgtgct caagggctac atgcaagaca agctcaacgc ccgcctgatg 1020
ggcgtggcgc gcaccggtaa tggtcgccgt gaatcctatg cgcacctgcc aatgccgcgt 1080
atgaccaaca cctacatgct cggtggccaa agcgatccgg cagaaatcat tgcctcggtc 1140
aaacgcggta tctactgcgc caacctcggc ggcggccagg ttgatatcac cagcggcaag 1200
ttcgtgttct ccaccagcga ggcgtacctg atcgaagacg gcaagattac cgcgccggtc 1260
aaaggggcga cgttgattgg taacgggccg gaagccatga gcaaagtgtc gatggtcggt 1320
aacgacctgt cgctggacag cggcgtgggc acgtgcggca aggatgggca gtcggtgccg 1380
gtaggtgtcg gccagccaac cttgaaaatt gatgcgatta ccgtgggtgg cacgggatcg 1440

<210> SEQ ID NO 104
<211> LENGTH: 1344
<212> TYPE: DNA
<213> ORGANISM: Pseudomonas fluorescens

<400> SEQUENCE: 104
atgagtgcag cccaaagcgt cggtccacaa gcgttaccgg cactgcagga acaagtcgag 60
cagatccttg ccgaggccaa gcgccagggg gccagcgcct gtgaagtggc ggtgtcgctg 120
gagcaagggt tgtcgacttc ggtgcgccag cgggaagtgg aaacggttga attcaatcgt 180
gaccaagggt ttggcattac cttgtatgcg ggccagcgca aaggctcggc cagcacttcc 240
gccagtggcc ctgaggcaat tcgcgagacc gtcgccgcag cactggcgat tgccaagcac 300
acctccgagg atgaaagctc gggcctggcc gacaaggcgc tgatggccaa ggaggtgcag 360

```
gattttgacc tgttccatgc ctgggatatc acccctgagc aagccatcga gctggcgctg    420

acctgcgaag cggcagcctt cgatgccgat gcccgcatca agaatgcgga cggcaccacc    480

ttgagcaccc atcagggttg tcgcgtctac ggcaacagcc atggctttat cggtggttat    540

gcctccacgc gtcacagcct cagttgcgtg atgattgccg aagccaacgg gcagatgcag    600

cgtgattact ggtacgacgt aaaccgccaa ggcgatttac tggcagaccc tgcaagcatt    660

ggccagcgtg cggcgcaacg ggctgcgagc cgcctgggcg cgcgcccggt gccgacctgc    720

gaagtgcctg tgctgttttc cgcagagttg gccggtggtt tattcggcag cttcctgggg    780

gcgatttccg gaggcaacct gtatcgcaag tcttcgttcc tggaaggcgc catcggccag    840

aagctgtttc ctgagtggct gaccatcgac gagcgcccgc atttgatgcg cgccatgggc    900

agttcgtcgt tcgacggcga tggcttggcg acctatgcca agccgtttgt cgagaaaggt    960

gagctggtgt cttatgtgct gggcacttat gccggtcgca agttgggcct gcccagtacc   1020

gccaacgcgg gcggcgttca taacctgttc gtgacccatg gcgatgaaga ccaggccgcg   1080

ttgttgcggc gtatggggcg tgggttgctg gtgactgaat tgatgggcca tggcctgaac   1140

atggtcaccg gtgactactc gcgcggtgcg gcgggcttct gggtggagaa cggcgaaatt   1200

cagttcgccg tccaggaagt gaccatcgcc ggcaatatgc gcgatatgtt caagcagatc   1260

gttgccgtgg gtaacgacct ggaactgcgc agcaatatcc gtacgggttc ggtgctgatc   1320

gaacgcatga cggtcgctgg cagc                                          1344
```

<210> SEQ ID NO 105
<211> LENGTH: 1431
<212> TYPE: DNA
<213> ORGANISM: Pseudomonas fluorescens

<400> SEQUENCE: 105

```
atgacttttt tgcgccctac cctgctgacg ctggcctgcc tgctggcctc cccggccttc     60

gctgacgacc tgccgtcact tggtgacgcc agctctgcca ttgtctcgcc gcaacaggaa    120

taccaactgg gccgcgcctg gctggcttac ctgcgcggcc aggtctcgca actcaatgac    180

ccgcaactca aggattacgt cgaaaccagc gtgtacaagc tggtggagac cagccaggtc    240

aatgaccggc gcctggaatt tatcctgatc aacagcccac agctcaacgc ctttgcggca    300

ccgggtggga tcgtcggggt caacggcggc ctgtttctca atgcacagac cgaaggcgaa    360

tacgcgtcgg tactggccca cgaactggcg cacttgtccc aacgccactt cgcccgaggc    420

gtggaagcgc aatcacgcat gcaactgccg atgatggccg ccctgcttgg cggcattatc    480

gccgccgctg cgggtgccgg ggatgccggt atcgccgcga ttgccggttc acaagccgcc    540

gcgatccagg agcagcgccg attctcgcgc cagaacgagc aggaggctga ccgcatcggc    600

atcctcaatc tggaaaaagc aggctacgac ccgcgctcca tgcccaccat gttcgaacgg    660

ctgatgcgcc aataccgctt cgacgccaag ccgccagagt tcctgctgac tcacccggtc    720

accgaatcgc gtatcgccga cacccgcaac cgcgccgaac aagccaaacc cggcggcaag    780

gaagacagcc tgcgctatca actgattcgc gcacgggtac agctcaagta cgaagacaca    840

ccaggcctgg ctgccaagcg cttccaggca cagctggatg aaaaccctaa aaatgacgtg    900

gcgcgctatg gcctggccat cgcccagatc aagggcactc aactcaagga agcacgggaa    960

agcctggcgc cgctgttggc caaggcgccc aacgacatca cctacaacct ggcccaaatc   1020

gaactggaca ttaccagcaa ccgcatgccc gatgcgcagc aacgcaccga ccgaatgctc   1080
```

```
acccaatacc ccagcaacta tccgctgaat caggtgcggg tagacctgtt gcttaaacag   1140

aaccgtaccg ccgatgcaga aaaggcgctg gacgggctgc tcaaatcgcg cccggacgat   1200

ccggacgtgt ggtatcaggt cgccgaaaca cgcggcttgt ccggcaacat cattggcctg   1260

catcaggccc gtgccgaata tttcgcactg gtgggggatt tccagcaagc catccagcag   1320

ttggactttg ccaagcggcg tgctggcaat aacttcccgc tgtcctcgcg catcgacgcc   1380

cgtcagcgtg aactgatcga acaggagcgc ctggtgaaag gcatgatgag c             1431
```

<210> SEQ ID NO 106
<211> LENGTH: 1059
<212> TYPE: DNA
<213> ORGANISM: Pseudomonas fluorescens

<400> SEQUENCE: 106

```
atgtgtgttc gccaaccgcg caacccgatt ttttgcctga tcccgccgta catgctcgac     60

cagatcgcac gccacggcga caaagcccaa cgggaagtcg cattacgcac gcgtgccaag    120

gacagcacgt ttcgttcgtt gcgcatggtc gcggtacccg ccaaggggcc ggcccgcatg    180

gcactggccg tgggcgccga gaagcaacgc tcgatctaca gtgccgaaaa caccgacagc    240

ctgcccggca agctgatccg cggcgaaggg cagcccgcca gtggcgatgc cgcggtggac    300

gaagcctatg acggcctggg cgcgaccttc gatttttttg accaggtctt tgatcgcaat    360

tccatcgacg atgcgggcat ggcgctggac gccacggtgc acttcggcca ggactacaac    420

aatgcgttct ggaattcgac ccagatggtg ttcggcgatg gcgaccagca gttgttcaac    480

cgctttaccg tggcactcga cgtcattggg catgagttgg cccatggcgt gactgaggat    540

gaggccaagc tgatgtactt caaccagtcc ggtgcgctga acgagtcgtt gtcggacgtg    600

ttcggttcgc tgatcaagca gtacgcgtta aagcaaacgg ccgaggatgc cgactggttg    660

atcggcaagg ggttgtttac caaaaagatc aagggcacgg cgctgcgctc gatgaaggcg    720

ccaggcactg cgtttgatga caagctgctg ggcaaagacc cgcagcctgg gcacatggat    780

gattttgtgc aaacttacga ggacaatggg ggcgtgcata tcaattccgg cattcccaac    840

catgcgttct accaggtggc gatcaatata ggcgggttcg cctgggagcg tgccgggcgt    900

atctggtatg acgcactgcg cgattcgcgg ttgcggccca attccgggtt cttgcgtttt    960

gcgcgcatta cccacgatat tgccggccag ctttatggcg tgaacaaagc tgagcagaag   1020

gcagtcaagg aaggctggaa agcggtgggc ataaacgtt                          1059
```

<210> SEQ ID NO 107
<211> LENGTH: 885
<212> TYPE: DNA
<213> ORGANISM: Pseudomonas fluorescens

<400> SEQUENCE: 107

```
atgatgcgca tcctgctgtt cttggccact aacctggcgg tcgtactgat tgccagcgtc     60

accctgagcc tttttggctt caacgggttc atggcggcca atggggttga tctgaacctc    120

aatcagctgc tgattttctg tgcggtcttt ggttttgccg gctcgctgtt ctcgctgttc    180

atctccaagt ggatggcgaa gatgagcacc agcacccaga tcatcactca accccgcact    240

cgccatgaac aatggctgat gcaaaccgtg gagcagttgt ctcaagaagc aggcatcaaa    300

atgcccgaag tggggatttt tcctgcttat gaggccaacg cctttgccac cggctggaac    360

aagaacgacg cactggtggc tgtgagccag ggcctgctgg agcggttttc gcccgatgaa    420

gtcaaggcgg tgctggccca cgagatcggc cacgtagcca acggcgacat ggtcaccctg    480
```

gcactggtac agggcgtggt gaacaccttc gtgatgttct ttgcgcggat catcggcaac 540
tttgtcgaca aggtcatctt caagaacgaa gaaggccgtg gcattgccta cttcgtggcg 600
accattttcg ccgagttggt cctgggcttc ctggccagcg ccatcgtgat gtggttctcg 660
cgcaaacgcg agttccgcgc agatgaagcc ggcgcacgcc tggcgggcac cagcgcaatg 720
atcggcgcgc tgcaacgcct gcgctccgaa cagggcctgc cggtgcatat gccggacagc 780
ctgaccgcct tcggcatcaa cggcggcatc aagcagggcc tggctcgctt gttcatgagc 840
cacccgccgc tggaagagcg gattgacgca ctgcgtcgcc ggggc 885

<210> SEQ ID NO 108
<211> LENGTH: 969
<212> TYPE: DNA
<213> ORGANISM: Pseudomonas fluorescens

<400> SEQUENCE: 108
atgcagactt ggtacccgca gatcaaaccc tacgcccggc acgatctggc tgtcgatgac 60
acccacaccc tgtatgtcga tgaaagtggc tcccccgaag gattgcctgt cgtgttcatc 120
catggcggcc ccggttccgg ttgcgacgcc cagagccgct gctatttcga cccgaacctc 180
taccatattg tcaccttcga ccagcgtggc tgtggccgct ccacgccaag ggcgagcctg 240
gagaacaaca ccacttggga cctggtcgcc gaccttgaac gcatccgcga gcacctgggc 300
atcgacaagt gggtgctgtt cggcggctcc tggggctcga ccctggccct ggcctacgcg 360
caaacccatc ccgagcgtgt gctcggcctg atcgtgcgcg gcatcttcct cgcccggccc 420
caggatattc gctggttcta ccaggagggc gcgagccgtc tgttcccgga ttactggcag 480
gactacgtgg ccccgatccc ggtggaggag cgccacgata tgattgccgc ttaccacaag 540
cggctgaccg gcaatgacca gatcgcccag atgcacgcgg ccaaagcctg gtctggctgg 600
gaaggccgca tgctgggcct gtgcccgagc ccacaacatg tggagcggtt ttccgagccg 660
cagcgcgccc tgtccatcgc acgtatcgag tgccattact tcaccaacaa ctccttcctg 720
gaacccaacc agctgattcg cgatatgcac aagatcgccc atctgcctgg cgtcatcatc 780
catggccgct acgatatgat ctgcacgctg gataacgcct gggagttgca ccaggcctgg 840
cccaacagcg agttgcaggt gatccgcgag gcggggcatg cggcatccga gccgggtatc 900
actgacgcgc tggtacgcgc gaccggcgaa atggcccggc gcttgctcga cctgccgcct 960
gaagaagca 969

<210> SEQ ID NO 109
<211> LENGTH: 864
<212> TYPE: DNA
<213> ORGANISM: Pseudomonas fluorescens

<400> SEQUENCE: 109
ttgagcctgc tgctgagtga gtatccctgg gcgtttgtcg gcgtggcgct ggtgttgggc 60
ctgatcgtcg gcagctttct caatgtgttg gcgtggcgcc tgcccaaaat gctcgagcgg 120
gagtggcgtg cccaggccca tgagattctc gacttgccag ccgagcccgg tgggccggcc 180
tataacctga tgcatccgaa ctcttgctgc ccgcgctgca atcatccgat tcggccttgg 240
gaaaatatcc cggtgctcag ctacctgctg ctccgggggc attgtgccca ctgccgtgag 300
cccatcggcc tgcgttaccc tctcaccgaa ctggcctgcg cgctgatctg cgccgctgtc 360
gcctggcact tcggcttcgg ctggcaagcc ggcgcggtga tgctgctgag ctggggcttg 420

```
ctggggatga gcctgattga tctggaccac caattgctgc cggatgtgct ggtgctgccg    480

ctgctatggc tggggctgat cctcaacagc gctgacctgc tgacgccact gcccgatgca    540

gtatggggcg cggtcatcgg ctacatgagc ttgtggtgcc tgttctggct gttcaagctg    600

gccaccggca aagacggcat gggccatggc gacttcaaat tattggcctt gctgggagcc    660

tggggcggct ggcagattct gccgatgacc ctgctgatgg cctcgctgct gggcgtgttt    720

gccgggctga ttttgctgcg tttgcgtaag gcccaggtgt cagcgccaat gccgttcggc    780

ccctgcctgg caattgccgg ctggattgca ttgctctggg gtggtcaaat aaccgacttc    840

tatttgcagt ctgtcggttt caga                                            864


<210> SEQ ID NO 110
<211> LENGTH: 510
<212> TYPE: DNA
<213> ORGANISM: Pseudomonas fluorescens

<400> SEQUENCE: 110

atgcctaatg cagccagtcg tttcggacgt ctgggctggc tcgtactgag cctgctggta     60

ctggtcatcg accaggtcag caaggctcac ttcgagggct ccctggaaat gttccagcaa    120

atcgtggtga tcccggatta cttcagttgg accctggcct acaacaccgg cgccgccttc    180

agcttcctgg ctgacggcgg tggctggcag cgctggctgt tcgcggtgat cgccgtggtg    240

gtcagtgccg tgctggtggt gtggctaaag cgtctgggcc gcgacgacac ctggctggcc    300

attgcgctgg cgctggtgct gggtggcgcg ctgggtaacc tgtatgaccg catcgccctg    360

ggccatgtga tcgacttcat cctggtgcat tggcagaacc gccactactt cccggcgttc    420

aactttgccg acagcgccat taccgttggt gcaatcatgc tggcgctgga tatgttcaag    480

agcaagaaaa ccggagaaac cgtcaatgac                                      510


<210> SEQ ID NO 111
<211> LENGTH: 1908
<212> TYPE: DNA
<213> ORGANISM: Pseudomonas fluorescens

<400> SEQUENCE: 111

atggcaaaga atctgatcct gtggttgatc atcgcggctg tcctggtgac ggtgatgaac     60

aacttctcca gccctaacga gccgcagacc ctcaactatt ccgacttcat ccagcaagtt    120

aaggatggca aggtcgagcg cgtagcggtt gatggctacg tgattaccgg taagcgcaac    180

gatggcgaca gcttcaagac cattcgtcct gccattcagg acaacggtct catcggtgac    240

ctggtggata acaaggtcgt tgtggaaggc aagcagcctg aacagcaaag catctggacc    300

cagctcctgg tggccagctt cccgatcctg gtgattatcg ccgtgttcat gttcttcatg    360

cgccagatgc aaggcggtgc gggaggcaag ggcgggccga tgagcttcgg caaaagcaag    420

gcgcgcctgc tctccgaaga ccaggtgaag accaccctgg ctgacgtcgc aggttgcgac    480

gaagccaagg aagaagtcgg tgagttggtc gagttcctgc gtgatccggg caagttccag    540

cgcctgggtg gccgtattcc tcgcggtgtg ctgatggtgg ggcctccggg taccggtaaa    600

accttgctgg ccaaggcgat tgccggcgaa gccaaggtgc ctttcttcac gatttccggt    660

tctgacttcg tcgagatgtt tgtcggcgtc ggcgccagcc gtgttcgcga tatgttcgag    720

caggccaaga agcacgcgcc atgcatcatc ttcatcgacg aaatcgatgc cgttggtcgc    780

catcgtggcg cgggcatggg gggtggtcac gatgagcgtg agcagaccct caaccagttg    840

ctggtagaga tggatggttt cgagatgaat gacggcatta tcgtcatcgc cgcaaccaac    900
```

cgtcccgacg ttctcgaccc tgcgttgctg cgtccgggcc gtttcgaccg tcaggttgtg 960
gtcggcctgc cggacattcg tggtcgtgag cagatcctga aagtacacat gcgcaaggtg 1020
ccaatgggtg acgacgtggc tccggctgtg atcgcccgtg gtactcccgg tttctccggt 1080
gctgatctgg cgaacctggt caacgaggct tcgctgttcg ctgcccgtac tggcaagcgc 1140
atcgttgaga tgaaagagtt cgaattggcg aaagacaaga tcatgatggg cgccgagcgc 1200
aaatccatgg tcatgtccga gaaagagaag cagaacaccg cttatcacga ggccggtcac 1260
gccattgtag gtcgcgttgt gcctgagcat gaccccgtct acaaagtgtc gatcattcct 1320
cgtggtcggg cactgggtgt gaccatgttc ctgccggaag aagatcgcta cagcctctcc 1380
aagcgtgcgc tgatcagcca gatctgctcg ctgtatggcg gtcgtattgc tgaggaaatg 1440
acccttggct tcgacggtgt gaccactggt gcctccaatg acatcatgcg tgccagccag 1500
atcgcacgaa acatggtgac caagtggggc ttgtcggaaa aactcggccc attgatgtac 1560
gccgaagagg aaggcgaagt gttcctgggg cgtggcggcg gtgggcaaag cgccagcttc 1620
tcgggtgaga cagccaagct gatcgactcc gaagttcgca gcatcattga ccagtgctat 1680
ggcacggcca agcagatttt gactgacaac cgtgacaagc tggacgccat ggctgatgcg 1740
ttgatgaagt acgaaaccat cgatgccgac cagatcgacg acatcatggc gggccgtacg 1800
ccgcgtgagc cgcgcgactg ggaaggtggt tcgggtactt cgggcactcc gcctgtggtg 1860
cagaatgagc gccctgaaac gcctatcggc ggcccggcag ctgatcac 1908

<210> SEQ ID NO 112
<211> LENGTH: 1182
<212> TYPE: DNA
<213> ORGANISM: Pseudomonas fluorescens

<400> SEQUENCE: 112
atgacccgaa ccattcccga acccgatctc gcgtatctgc aaaaagtgct gctggaaatg 60
ctcgccattc ccagccccac cggttttacc gacaccatcg tgcgctacgt cgccgagcgc 120
ctggaagaac tcggcatccc gtttgaaatg acccggcgcg gcacgattcg cgccaccctc 180
aagggccaga aaaacagccc tgaccgcgcc gtctccgcgc acctggacac catcggcgcc 240
gccgtgcgcg cgatcaagga caacggccgt ctgaccctgg cgccagtggg ctgctggtcg 300
agccgctttg ccgaaggcag ccgtgtcagc ctgttcaccg ataacggcgt gattcgcggc 360
agcgtgttgc cgctgatggc ttccgggcac gcgttcaaca ccgccgtgga tgaaatgccg 420
gtgagctggg accatgtgga actgcgcctg gacgcctact gcgccacgcg cgccgactgc 480
gattccctgg gaatcagcgt cggtgactac gtggcgttcg acccgctgcc cgagttcacc 540
gaaagcgggc atatcagcgc ccgccacttg gacgacaagg ccggcgtcgc cgcactgctc 600
gctgcgctca aggccatcgt tgacagtggc gaacccttgc tgatcgactg ccacccgctg 660
ttcaccatca ctgaggaaac cggcagtggc gcagcggccg ccctgccctg ggatgtgagt 720
gagtttgtcg gcatcgatat cgccccggtc gcccctggcc agcagtccag cgaacatgcg 780
gtgagcgtgg ccatgcagga ctccggcggc ccctatgact atcacctgtc ccgccacttg 840
ctgcgcctgg cgtcagacaa cgagctgccg gtgcgccgcg atctgttccg ctattacttc 900
agcgatgccc actcggcggt caccgccggc catgatattc gcaccgcgct gctggccttc 960
ggttgcgatg ccacccatgg ctatgagcgt acccacatcg acagcctcgc cgccctgagc 1020
cgcttgctgg gcgcttacat cctcagcccg ccggtgtttg ccagcgatgc gcaaccggcc 1080

-continued cagggttccc tggaccggtt cagccatcag atcgagcatg aaacgcaaat ggagagcgac 1140
acccgtgtgc cgtcggtgga cagcttggtc ggccagaagt cc 1182

<210> SEQ ID NO 113
<211> LENGTH: 1023
<212> TYPE: DNA
<213> ORGANISM: Pseudomonas fluorescens

<400> SEQUENCE: 113
atgctagtac tgggacttga aacctcctgc gacgaaaccg gagtcgcact atacgacagt 60
gaacgcgggc ttttggccga tgcactgttc agtcagatcg acctgcatcg cgcctatggc 120
ggcgtggtgc cggagcttgc cagccgcgat cacgtcaagc gcatgctgcc gctgatccgc 180
caggtgctgg atgaggccgg ctgtgtggca accgagatcg atgccatcgc ctacacggca 240
gggcccggat tggtcggagc cctgctggtt ggggcctctt gcgcccaggc gctggccttt 300
gcctggggca ttcctgccct cggcgtgcac catatggaag gccatttatt ggcgcccatg 360
ctggaaaaaa caccgccaga gttcccgttc gtcgctttgt tggtttcggg ggggcatacg 420
cagctggttc aggtggatgg gatcggccaa tacacgctgt tgggcgagtc gctggacgat 480
gctgccggcg aagcgttcga caaaaccgcg aagatgatgg ggcttaatta tcctggcggt 540
ccggaaatcg cccgcctggc tgagaacggc gttgccggtc gctatacctt tccgcggccg 600
atgtgtgatc gtcctggctt gatgttcagt ttcagcggct tgaaaacctc tgccttgaac 660
acctggcagc acagcgttag cgccggggac gacggccaac aagcccgttg cgacatcgcg 720
ctggcgttcc agcaggctgt ggtggagact ttgaccatca agtgcaagcg cgccctgaaa 780
caggcgggca tgaagcggct ggtgatcgca ggcggcgtca gcgccaacaa ggcgttgcgc 840
agttccctgg aaaaaatgct cggtgacatg aatggcaatg tgttctacgc acgccctgag 900
ttctgcactg acaacggcgc gatgatcgcc tacgccggtt gccagcgcct gcaggccgga 960
cagcacgaaa gcctggcgat cagcgtgcag gcgcgctggc cgatggagca attgccgccg 1020
ttg 1023

<210> SEQ ID NO 114
<211> LENGTH: 2436
<212> TYPE: DNA
<213> ORGANISM: Pseudomonas fluorescens

<400> SEQUENCE: 114
atgcctgatc ctgttgctgc cagcttgcgt ctagcgcccg aagcgctgac tcgccctttc 60
tccgctgaac agttcagctt ctcgaccacc aatgatttgg agccctttcg cggtgtgctt 120
ggccaggaac gtgcggttga agccttgcag ttcggcgtgg ccatgccacg ccccggttac 180
aacgtgtttg tcatgggcga gccgggcacc ggccgctttt cgttcgtcaa acgctacctg 240
aaagccgaag gcaagcgcct gcaaaccccg gcggactggg tttatgtgaa taatttcgat 300
gagccccgcg agccccgcgc cctggaatta ccgggtggcg ccgccgcggc gtttattgcc 360
gatatcaacg ccttggtgga taacctggtc gccaccttcc cggcggtgtt cgaacacccg 420
acttatcaac agcgtaaaag cgccatcgac cgggcgttca accagcgcta cgacaaagcg 480
ctggacgtga tcgaacgcct ggccttggaa aaagacgtgg cgctgtaccg cgacagctcc 540
aacatcgcct tcacgccgat gctcgacggc aaggcgctgg atgaagccga gttttcgcaa 600
ctgccggaag ccgatcgcga gcgcttccac accgatatct ccgagctgga agaacgcctc 660
aacgaagagc tggccagcct gccgcagtgg aagcgcgagt ccaacaacca gctgcgccag 720

```
ttcaacgaag aaaccatcac cctggccctg cagccgttgc tggcaccgtt gtcggaaaag    780
tatgcagaaa acgccggggt ctgtggctat ctgcaggcca tgcaggtgta cttgctcaaa    840
accgtggtcg agcaattggt ggacgacgcc aagaccgacg cccaggcgcg caagctgctt    900
gaggagcaat actgcccgag cctggtggtg ggccactcgg tcaacggtgg cgcgccggtg    960
gtgtttgaac cgcacccgac ctacgacaac ctgttcggcc gtatcgaata cagcaccgac   1020
cagggcgcgc tctataccac ctaccgccag ctgcgtcccg gcgcgttgca ccgcgccaat   1080
ggcggcttcc tgattctgga agccgaaaaa atgctcagcg agccctttgt gtgggatgcg   1140
ctcaagcgtt ccctgcaatc gcgcaagctg aagatggaat cgcccctggg cgaactcggc   1200
cgcctggcca ccgtgaccct caacccgcag atgattccct tgcaggtcaa ggtgatcatc   1260
atcggttcgc gccagttgta ttacgccctg caagacgccg acccggactt ccaggagatg   1320
ttccgcgtat tggtggactt cgacgaagac atccccatgg tcgacgagag cctggagcag   1380
ttcgcccagt tgctcaaaac ccgtacttcg gaagaaggca tggcgccgct gacctcggac   1440
gcggtggcgc gcctggcgac ttacagcgca cgcctggccg aacatcaagg ccgcttgtct   1500
gcgcgtattg gtgatttgtt ccagttggtc agcgaggcgg actttattcg ccacctggcg   1560
ggcgatgaga tgaccgatgc cggcatatc gagcgcgccc tcaaggccaa ggccacgcgc   1620
accggccgtg tgtcggcgcg gattctcgac gacatgctcg ccggcgtcat cctcatcgac   1680
accgccggtg cggccgtggg caagtgcaac ggcctgacgg tgctggaagt gggcgactcg   1740
gcattcggcg tgccggcgcg gatttccgcc acggtgtacc cgggcggcag cggcattgtc   1800
gacatcgagc gcgaagttaa cctcggccag ccaattcact ccaagggcgt gatgatcctc   1860
accggttacc tgggcagccg ttatgcccag gaattcccgt tggccatctc cgccagtatt   1920
gccctggagc agtcctacgg ctatgtggac ggcgacagtg cgtccctggg cgaggcgtgc   1980
accttgatct cggccttgtc gaagacgccg ctcaagcaat gttttgccat caccggctcg   2040
atcaaccagt ttggtgaagt gcaggcggtg ggcggggtca acgagaagat cgaaggcttc   2100
ttccgcctct gcgaagcccg cgggttgacc ggtgagcagg gggcgatcat ccctcaggct   2160
aacgtcgcca cgctgatgct cgacgagaaa gtgttgcagg ctgtgcgtgc cgggcaattc   2220
catatctatg cggtgcgcca ggccgatgag gccttgagcc tgctggtggg cgaggatgcc   2280
ggcgagccgg acgccgaggg gcagttcccg gaaggcaccg tgaatgcgcg ggtggtggag   2340
cgcttgcggg cgattgccga gatgatcagt gaggaggatt tgaaggaggc ggagaaagag   2400
ctggcgcagc aggcgttggc agaagccaag ccgacc                             2436
```

<210> SEQ ID NO 115
<211> LENGTH: 8679
<212> TYPE: DNA
<213> ORGANISM: Pseudomonas fluorescens

<400> SEQUENCE: 115

```
gtggcagtcg gcggcggttt gaacctcacg gtgggtggcg tcagcaccag cagtaccttt     60
gacggtgatc tcagcggcgc tggcggcttg atcaaggtcg gcaccggcac cctcacgctc    120
aacggaatca atggcatcac cggtaacacg gcgatcaacg cgggtaccct ggatgtcgag    180
ggttctctgg gcagcgcgtt ggtcaacgtg aatagcggcg gcactctcac cggcagtggc    240
tcgctattgg gtacggcgaa tatcaatagc ggcgggcacc tggcgctggg cagtggcacg    300
accttgtcgg ctggcggcct gaacatgagt gccggggcca gtctggatgt ggcgcttggc    360
```

-continued

```
gcaccgtcgc tgacttcgct gatgaatgtc ggtggcaacg tgaacctggc cggcgacctc    420
aatgtgagcg atgccggtgg cttcggcgct ggtgtgtatc gcatgatcaa ctacaccggc    480
ggcttgaccg gtgcgttgaa cgtcaacacg gtgccgctgg gttatggcct gggtgatcta    540
ctggtacaaa cctccgtggg cagccaggtc aacctggtgg tagcggcgcc gaatattcgt    600
ttctgggacg gcagcaacac ccttgccaac ggcactgttg acggtggcag cggcacctgg    660
acagcggggg gcaccaactg gacctcggcc gacggccttt ccaaccagac ctggggcggt    720
ggctttgcgg tgttccaagg tgctgcgggc actgtcagcg tggatggcgt acaaaccatc    780
accggtctgc aattcgtcac cgatggctac agcctggtca atggcaccgg tgggcagttg    840
agcaccggca gcggcaactt cgccgtgcgc gtcgacccac tggcgactgc caccctcggc    900
gtcgatatca ccggcgcggg cgtgctgaac aaactcgata ccggcacgct ggtgctcaat    960
ggcgccaaca gctacaccgg cggcaccttg ctcaatggcg gtacggtggt ggtcggcagc   1020
aacaccgcgc tgggcactgg cacgctgacc gctgcggcgg gcaccaccct ggacagcaac   1080
gcctctgtaa ccctgggcaa tgatgcggta ctcaacggca gcctgacggt cggcggcagc   1140
aacgcattgg cgctcaatgg cgccatcagc ggcaccggtg gcctggtcaa gaatggcacg   1200
gcaggcctga cactcggcgg caccaatacc ttcctgggcc ctgtggcctt gaacgcaggc   1260
gggctgatcc tggcccgcaa tacggcgctg ggcgcgggcg tgttgaatgc cgcaggcggt   1320
accaccttgg acgcgagcac ggcggtcacc actaccaacg cgatcaatct ggcgggcaac   1380
ctgggcatcg gcggcaccgc tgacctgacc ctcggcggcg caatcaacgg tgcaggcagc   1440
ctgaccaagg agggcacggc caatctgatc ctcagcggcg ccaacgccta cctgggtggc   1500
accaccctga acgccggtac gctgaccttg ggcagcgcca ccgcccttgg cctgggcaac   1560
ctcaccgttg gcggcgcggc gaccctggat aactcggcag cgctgagtgt gggcaatggc   1620
gtcgtgcttg acgccaacct cgccgtcacc ggcagcaacg acctgaccct gggtggcctg   1680
gtcaccggca cggctggcct gagcaaagac ggcgcggcca acctgaccct caatggcgtc   1740
aacaccttcc aaggcggcac cagcctcaac gccggcacgc tgaccctggg cacggcagca   1800
gccctgggta ccggcgcctt gaacgtaaac ggtgcagcta ctctggccaa cagcacaccg   1860
ctggtattgg ccaatgcggt caacctcaac gctgggctga ccgtgggcgg tctcaacaac   1920
aacctgaccc tggccggcgt gctggccggc agcggcagcc tggtcaaaac cggcacggcg   1980
gatgtgagcc tcaccggtac taacaccttc aacggcctgt tcgatgtgca atcaggcagc   2040
ctcaccacgc tgggcaacgg agcactgggt gtcggcgccg gggtcaacct ggcgagcggt   2100
acctccttga acctgggcgg cagcgccagc ctgggcgccc tcacgggtac cggtattgcc   2160
accgtaggcg ccggcagcac cttgagcgtc ggcaacaata atctggacag caccttcgac   2220
ggcatcgtgg caggcctcgg cgacctggcc aaagacggca caggcgcctt gaccctcggt   2280
ggcctcagcg tggtgaccgg ggacgcccag gtcaacgccg gcagcttgct cgtcaatggt   2340
tccctggcca gcgccaacgt ggcggtgggc agtggtgcca ccctcggtgg taccggtact   2400
ttgttgggca acgtgagcat cgccgacggc ggccacctgg ccgtcaattc cggcgcgacc   2460
ctgaccaccg gttcgctgct gctcaatgcc aactccaacc tggatgcggg cctcggcgcg   2520
cccgcgacgg gcggcaccgc gctggtgcag gtcaacggca acctgaccct ggacggcacc   2580
ctcaacgtca ccgatatcgg cggcttcggt gcgggtatct accgcctgat cgactacacc   2640
ggcggcctga ccaacaacgg cctgctgctg ggcagcctgc cggtgaacat cccggccagc   2700
gacctggacc tgcaaaccgc gatcggcaac cagatcaacc tgctggtcaa cggcagcacc   2760
```

-continued

```
aacgtgcagt tctgggacgg cagccaaacc acgggcaatg gcaccatcga aggcggcagc   2820
ggcacctgga gtgcaggcgg cagccaatgg accggcgtca acggcgcatt caacaccgcc   2880
tggaccccga acagctttgc cgtgttccaa ggctcggcag gcaccgtcac ggttgacggc   2940
gcgcaagccg tcaccggttt gcagttcgtc acggatggct acaccctggc gggcggcgca   3000
gcgggcgcct tgaccctgtt caatggtgtg ggtggcaaca ccgccgtacg tgtcgatccc   3060
ggcgtcaccg ccaccctggg cgtcgcgctt aacggcggcg gcactctggc caagctcgac   3120
accggtaccc tggtgcttaa cggtgccaac agctacaccg gcggcaccgc cctggatggc   3180
ggcaccctgg tggtcggcaa taacagtgcc ctgggcagcg gcctcttgac caccgccaac   3240
ggcaccaccc tggacagcaa caccgcggtc agtctggcca atgcgctcaa cgtcaacggc   3300
agcctcaccc tcggcggcag caacgccctg accctggccg gcaccgtggc gggcacgggc   3360
agcctgatca agaatggcat cgccaacctg accctcagtg gcaacaacac ctatgccggc   3420
ccaaccgcac tcaacgcagg cggcctgatc ctggcctcca acacggccct gggcagtggc   3480
gctctgaacg cggccgctgg caccaccctc gacagcagca cggcggtcgc cctggccaac   3540
acggtcaatc tggccggcaa cctgggcatt ctgggcaccg ccgacctgag cctgaacggc   3600
ctggtcagcg gtagcggtgg gctgaccaaa accggcgcgg gcaacctcac gctcaacggc   3660
gccaacgcct acctgggcgg cacgcaattg aatgccggct ccctgaccct gggcaatgcg   3720
tcggccttgg gcagcggtgc cttggcggtc aatggggcaa ctaccctgga caccaacacg   3780
gcgttggccc tggccaataa caccagcctg aatgccgcgc tcaccgtcgg cggcagcaac   3840
gatctgagcc tcaacggtgt agtggacggc agtggttcgt tgatcaaggc cggtggcgcc   3900
aacctgacgc tcaacggcgc caacacctac agcggcggca cggcgctcag tgccggcacg   3960
ctgaccctcg gcagcaccac agccctgggc tcgggcgcgt tgaccgtcgg cggtacggcg   4020
accctggcca acagcacgcc gctggtgctg gccaatgcgg tcaatctcaa tggcgacctc   4080
actatcgctg gtagcaacaa cctgaccctg gccggtgtgc tcgctggcaa tgcggcgctg   4140
atcaaaaatg gcgcggcgga cctgctgctg accggcaaca acagcttcag cggcccgctg   4200
accgtggcgg cgggcagcgt gaccacgacg ggtaatggtg cactgggcac cacctccggc   4260
gtcactgtcg gcagcggcgc cagcctcaac ctgggtggca atgccaacct caacagcctg   4320
gccggcgacg gcgtggtaca ggtggctggc ggcaacacgc tggcggtggg tggcagcaac   4380
ctggataaca gctttggcgg cgcgctgaac ggtgccggca acctggataa aaacggcagc   4440
ggggtgctca acttgagcgg taccaacgcc atcagcggtg cggccaacgt caacggcggt   4500
accttgaatg tcaccggttc cctggccagc ggcacggtgg cagtgagcag cggcgcgacc   4560
ctggccggca gcggttcatt ggccggcgcg gtgaccgtgg ccgacggtgg gcacatcggc   4620
ctggcctccg gcagcacgtt gtcggtgggc tcgttggtgc tgggcggcaa ctcgaacctg   4680
gatgtcggtc tcggcactcc ggtgctgggt ggcggcacgg gcctgctgaa tgtcggcggc   4740
aatctgaccc tggacggcaa cctcaatgtc accgatatcg gtggttttgg cagcggcgtc   4800
tacaacctta tcaactacac cggggccttg accgataacg gcctggctct gggcacactg   4860
ccaggcagcg tggtgccggg cgacctgcaa gtgcagaccg cgatcaccaa caaggtcaac   4920
ctgctggtga ccgcgcccaa caccaccgtg cagttctggg atggcaacag cctgatcggc   4980
aacggtgcga ttgacggcgg caacggcacc tggagcgccg gcaataccaa ctggaccaat   5040
gtcgacggca ccctcaacca gggctgggtc aacagctttg cggtgttcca aggcgcggca   5100
```

-continued

```
ggcaacgtga cggtggacgg cacgcagaac atcaccggca tgcagttcgt caccgacggc   5160
tacaccctgg gcgccggcac ggcgggggtg ctcaacctgg tcaatggcgg caccggcaac   5220
accgcggtgc gcgtcgaccc gaacgctacc gcgaccctgg gcgtaaccct caacggcgcc   5280
ggcaccctgg ccaagctcga cagcggcacc ctggtgctca acggcagcaa tggctacacc   5340
ggcggtaccg cgctcaatgg cggcaccctg gtggtgggca ataacagtgc cctgggcaca   5400
ggcgtcctga cggcggccgg tggtaccacc ctggacagca acgcggcggt cagcctggcc   5460
aatgcggccg tgctcaacgg tgcgttgacg gtgggtggca gcaacgcgct ggccctcaat   5520
ggtggcgtca gcggcagcgg cagcctggtg aaaaacggtg ccgccgcgct gacgcttaat   5580
ggcgtcaaca gctacagcgg cggcactggc ctgaacgccg gtcaattgat cctcggcaat   5640
aaagctgccc tgggcagtgg agcattgacg gtgggcggcg cggcgcaact ggatggcagc   5700
accgatctgc aactgaccaa tgccctcaac ctgggcggcc cgctgaccct ggccggcagc   5760
cacgacctgg ccctcaacgg cgtggtcagc ggcagcggca gcctggtgaa aaatggcaac   5820
ggcgccttgt tgctgaccgc tgccaacacc tacagcggcg gtaccacgct caacggcggc   5880
agcaccaccg gcaacaccac cagcctgcaa ggcgctatcg ccaacaacgc ggcattgacc   5940
tttgagcaag ccagcgacgg cacctacacc ggcaacctca ccggtaccgg cgtgttgaac   6000
aaaaccggca ccggcgcatt gttgctcagc ggcaacaaca cctttaccgg caacaccaac   6060
gtcaacaccg gcagcctgct ggtcaacggc accttgaaca gcgccgcggt gcaagtcgcc   6120
agcggtgcga ccctcggcgg cagcggtacc ctgggcggtg cggtgaacat ggctgacggc   6180
tcggtgctcc aggccggtgc cgcgacacca ctgtcggtgg ggtcgctggc cttgtcttcg   6240
ggcaccaccc tggacttcgc cctcggtgcg ccgggtgcct ccagtacagc ggtgaacgtg   6300
gcgggcaacc tgaccctgga cggcacgctc aacgtcagcg acacgggcgg cttcggtgtc   6360
ggtgtgtacc agctgttccg ctacggcggc agcttgaccg ataacggcct cacctttggc   6420
accttgccgg tggcgctggg caacctgagc ctgcaaacgg cgctggccaa ccagctcaac   6480
ctggtggtgc aaaccactcc agggcagatc cagttctgga acggcggcac caccaacccc   6540
gatggcagca tcagcggcgg cagcggtacc tggggcccag gcaccaactg gaccgacccc   6600
accggcaccc aagggcaggc gtccaccaat cagttcgcgg tatttggcgg gcagggcggc   6660
accgtgaccg tggtcggcaa ccaaggcttc actggcctgc aagtgctgga cgccggctac   6720
acgctggtcg ccggcgcagg cggcagcttg agcccgacca atgcggcgga tggcagcctg   6780
gcgccggtgc gggtcaattc cggcgtgacc gctcagattg atgcaccgct ggtgggaacc   6840
ggcggcatca acaagctgga tgcgggcacc ttgctgctga ctggcgccaa tacctacacc   6900
ggcggcacca ccgtcagtgg cggtacgctg gcgggcacca ccaccagcct gcgtggcagg   6960
atcctcaaca acgcgcggtt gttgttcgcc caacgcacca atggccagtt cagcggtacc   7020
ttgagcggca cgggtgcgct gatcaagcaa ggcgcaggcg cgctgttgct gaccggcaac   7080
cagccgttca gcggcaccgt ggcagtggaa gagggcgtgt tgcaagtggg taacgcggcc   7140
aacccaggcg cggtgcttgg cggccaagtc actgtggcca acggtgcggg gctgaccggt   7200
aacggcagtg tcggttcgct ggtcaacaac ggctcggtga cgcccgacgg tggcaagctg   7260
accgtggccg gcaacttcac caacgccagc accggtgcgc tgaacctggt gatcacccca   7320
tccaccaccg gctccctggc cgtgggcggc accgccaacc tgggcggtac cttgaatgtg   7380
gtcaacctgg ctccctatgc cggcgccacc acctacaccc tgctgacagc cggcgcggtc   7440
aacggcacct ttgccaccac caacctggag aacctggcgt tcctcacgac cgcgttgaac   7500
```

```
tacagcccaa cccaagtggc cctggcggtc agccgcaaca acgtcagcta cgccagcgtg   7560

gcggccaccg gtaaccaacg cggcgtggcg gcggcgttgg gcacaggtac cgcagtcggt   7620

ggcgcagcgg tgcaaaatgc actgcttaac ggtaatgcag cggcggcacg tgcggccttc   7680

gacagcttgt ccggcgaaat ccacgccagc accgccagcg ccatgcttga agattcgcgt   7740

tatgtgcgtg acgcggtcaa cgagcgcctg cgccaacccg gttgctaccg cgaggacgac   7800

ccgcgcaatg ctctggcccc cagcgagaac cacctgagca gcgccggttg ccacggcgag   7860

atggtcggtt ggatgcgcgt gctcggcacc tggggccata tgggcggtga cagcaacagc   7920

gccaagctgg accgcaacct cagtggcttc ctgctcggta ccgacaagca agtggacgac   7980

gcctggcgcg tgggcgtggc cgccggctac acccgcagcg acctggacgc caagcgccgc   8040

aattccagcg ccgatgtgga cagctaccac ctgatggcct acaccgccta ccagcaagaa   8100

gccttcgccg cacgcatggg cgtggcgtac agctggcatg acgttgaaag caaacgcaac   8160

gtggccgtcg gtgccgaagg ccaacgcctc aaagccgatt acaaggcacg cagtgcgcag   8220

gtgttcggtg aagtcggcta caccattcaa acccctaccg tggccctgga accgttcgcc   8280

ggcctggcct acgtcaacta tgacagcgac acgatcaagg aaaaaggcgg ctcggcagcc   8340

ctgcgtggcg atgccgacca gggcatcacc tactcgacct tgggcgtgcg cattggccag   8400

accatcaccc tgggcaacgg ctcgaaaatc accccacggg gcagcatcgg ctggcgccat   8460

gccttcggtg acaccaagcc cgacgccgac ctgagcttta tcaatggcgg tggctcgttc   8520

agcacccagg gcgtgccgat tgccaaagac agcgcggtgg tggaagcggg cctggactac   8580

cagatcagcc agaacggcag actgggcctg ggctattcgg gccagctctc gcgcaacgac   8640

aaggaccacg ccgtgacggt aagtttctcc ctcggtttc                          8679
```

<210> SEQ ID NO 116
<211> LENGTH: 1101
<212> TYPE: DNA
<213> ORGANISM: Pseudomonas fluorescens

<400> SEQUENCE: 116

```
atgcgtgcac gtcaattggg cattacgttg ggttgggca tgcccggcga attgaatgcc      60

atcaccgatg ttcccggggt tcgcgtcggc catgccacgc tcaaggcgca ggtcgacggc    120

aagcaggtgc gtaccggcgt tacgctgatc cagccgcgtg ccggggaagc gcggcatcaa    180

ccgtgttttg ccggctacca cgtgctcaac ggcaatggtg acgccacggg gcttgaatgg    240

atcagcgagg cggggctgtt gaccacgccg atggcgatca ccaacactca cagtatcggg    300

gtggtacgcg acagcctgat cgccctggag cgcgagcggc tggcggaccc ggcggtgtac    360

tggtgtatgc cggtggtcat ggaaacctac gatggcctgc tcaacgatat ctggggccag    420

cacgtgcgcc cagagcatgt gcgccaggcc ctggaccagg cggaaagcgg cccggttcag    480

gaaggcgcgg tgggcggtgg caccggcatg atttgtcatg agttcaaggg cggcatcggc    540

accgcgtcac ggcggttgcc agcggagcag ggcggctgga ccgtcggcgt actggtgcag    600

gccaaccatg gcaagcgcca ggagctgcgg gtcgatggct acccggtggg ccgtcacttg    660

atggacattg cttcgccctt tgccgagcaa ggtacccccg gcatgggctc catcgtggtg    720

atcatcgcca cggacgcccc cttgctgccc caccagtgcc agcgcctggc acagcgtgcg    780

tccatcggca tcgcgcgcac cggtggaggc accgaggatt ccagtggtga cctgttcctg    840

gcctttgcca ccggtaacca ggatttgcca ccggccgact atgggcgcaa ggacctgccg    900
```

```
ctcagcaccg gcttgcagat ggtcaacaat gatcatattt cgccgctgtt cagcgcggcg    960

gcagaggcgg tggaggaggc gatcatcaac gccattctgg cgggtgaaga catgaccacc   1020

caagacggcg tcaaggtgcc gggcctggct ggcgaaaccc tcttggcagc cctgcaacag   1080

tgtggctgga gtatgtcccg g                                             1101
```

<210> SEQ ID NO 117
<211> LENGTH: 2352
<212> TYPE: DNA
<213> ORGANISM: Pseudomonas fluorescens

<400> SEQUENCE: 117

```
atgaagcgcg tcttgcaggt ttttgcggtg ctgattgtgc tggtcgccct gggcgccggt     60

tggtacgtct acagcaaaca acctacgcgc cagggcacgg tgacgctggc gcacctgcaa    120

ggctcggtca cggtgcgtta cgacgaccgt ggcgtaccgc atatccgcgc cgagaacgaa    180

gccgacctgt accgcgccct gggctatgtg cacgcccagg accgcctgtt ccagatggag    240

atcatgcggc gcctggcccg tggcgaactg gccgaggtgc tggggcccaa gctgctggac    300

accgataagc tctttcgcag cctgcgcatc cgcgagcgtg ccttaagcta tgtggagcat    360

atggaccctg gctcagcctc gtccaaggcc ctgcaagcct acctggacgg gatcaatcag    420

tatcaggaca gccacgccag ccccatggag ttcgatgtgc tgggcatcgc caagcgcccg    480

tttaccgccg aagacagcat cagcgtcgcc gggtacatgg cctacagctt tgccgcggcc    540

tttcgcaccg agccggtgct gacctatgtg cgtgaccggc tgggcagcga ctacttgaag    600

gtcttcgatc tcgactggca acccaagggc gcactcaacc tggcggccag cgattggcag    660

acccttggcg ccatcgccgc cctgagcgaa caggccctgg ccgacaacgg cctgccgcag    720

ttcgaaggca gcaatgcctg ggccgtcagc ggcagccata cccaaagtgg caagccgttg    780

ctggcgggtg accctcatat ccgtttttcg gtgccttcgg tctggtacga ggcgcaactg    840

tcggcgccag gcttcgagct atacggctac cacaacgcgc tggtaccggt ggcgttcctg    900

gggcacaacc tggacttcgg ctggagcctg accatgttcc agaacgacga cctcgacctg    960

gtcgccgaga aggtcaaccc aaacaacccc aaccaggtct ggtatcacga ccaatgggtg   1020

gacatgagca gcagcgagca gcagatccag gtcaagggcc aggcgccggt gaccctcacc   1080

ctgcgccgct cgccccacgg cccgatcatc aacgatgtgc tcggtgagaa cgccggcagc   1140

acaccgattg ccatgtggtg ggcgttcctc gacagcgaaa acccgatcct cgatggtttc   1200

tatcagctca accgtgccga taccctggcc aaggcgcgtg ccgcggccgc gaaggtctcg   1260

gcgccgggcc tgaacatcgt gtgggcaaac gccaagggcg atatcggctg gtgggcggcg   1320

gcgcagttgc cgatccgccc ggccggcgtc aacccggcgt tcatcctcga cggcagtacc   1380

gcccaggccg acaagctggg tttctacccc ttcagtgcca acccccagga agaaaacccg   1440

ccgcgcggct atgtggtgtc cgccaatgcc cagccagcat cgcccaccgg catgccgatc   1500

cccggctatt acaacctggc ggatcgtggc cagcagttga acgtgcagtt gagcgacaaa   1560

agcgtgaagt gggatgtgac caacagccag gccctgcaac tgggcaccac caccgcctac   1620

ggcacgcgcc tgctggcgcc gctgttgccg gtgctgcgcg aggtggtcaa ggacccggcg   1680

caactcaaat tggtggaaca gcttgccaac tggaagggtg actacccgct ggactccacc   1740

agcgccacgc tgttcaacca gttgctgttc aacctcagcg acgcgacctt tcaccccaaa   1800

ctcggcgatg ccttgttcaa gaccttgctc ggcacccgcg tgatcgacgc cgcattgccc   1860

cgcctggccg catcggcaga ctcgccctgg tggaacggca accgcgccga taccgtcaag   1920
```

ctcgcctggg acaacagcct ggcccacctc aaggcgacgt tcggcgatga cccggcgcaa 1980
tggcagtggg gcaaggcgca caccctgacc cacggccacc cgctgggcct gcaaaagccg 2040
ctggataaaa ttttcaacgt cggcccgttc ccggcgccgg gcagccatga ggttccgaac 2100
aaccagaccg cgctgattgg cccggcaccg tggccggtga cctacggccc gtcgacacgg 2160
cgcctgatcg acttcgccga cccgacccac gccctcacca tcaacccggt ggggcaaagc 2220
ggtgtgccgt ttgatacgca ctatggcgac caggcgcaga gctatatcga gggaaggtac 2280
gagcaggcgc acttcagtga tgaggaagtg acggccaata cccgcggcac cttgaaactg 2340
ctgcccgccc ga 2352

<210> SEQ ID NO 118
<211> LENGTH: 2964
<212> TYPE: DNA
<213> ORGANISM: Pseudomonas fluorescens

<400> SEQUENCE: 118 atgccccgt ctccacaacg cctcgcgctc gccatcaccc tgttggccgg cggtggtttc 60
atcgaagcag ccgcagccaa gaccctgcag atcgacacgc ctaccaccca ggggcaaacc 120
ctgggtggca gtgatacgtt gaccacgtcg gcgcctggca gcattacaac ctccggggta 180
gcagtgacgc tcaaggacgg cacccgcagt gcgggggtgg tggtgactaa cgcgggcaag 240
ctggtctcca gtggcggccg gggtatcgac agttcgggca gtgtcagcgg ggagcgcagg 300
tacagcattt acaaccttgc cggtggggtg atccaaggcg ccaatgatgc gttgcgcatc 360
aacagtaacg ttgccagcgg cagcgtgctg atcgacaaca gcggcaccat tcgctcggcc 420
accggccaag ggctggacct ggatgcgctg cgcagcagta acgtcaccac cacgatcatc 480
aaccgtgccg gtggcttgat tcgcggggag gccagcgacg gcatgaagac cggcgccaac 540
gcttctatca ctaactacgg cgagatctcc actggcgaca ccttctcccg cgatgacaag 600
ttcgatggcg tggacatcga ctccgccagc ggcgtgacgg tcaccaatta cggcctgatt 660
tccggtggcc gccatggcat caccacggac gagggcgcca cgctgaccaa ctacggcacg 720
gtgatcggcc gcaacggctc gggctttggt tccgatggcg acggcactgt ggtcaaccac 780
ggcaccatca taggcgcgtt ctccggcctg caaccggatg gcgacggtga cggtgtggac 840
atcgacaaga tcgcccatat cgaaaattac ggtgttatcc agggtgtagg cgccgggggt 900
gtcgacaaga acggcttcgc caacggcagc gaagggatcg ccctgggcgg tggctctctc 960
tacaacgcca aggcgcgct gatcagtggt gccagcaatg ccatcctggt ggacgacggc 1020
agcgacgggc cggggctcgc ggccaccacc ctggagaacc acggcacgat tgaaggcctg 1080
gatggctttg gcgtgaagtt cgtcggcaac tatgccgaca cggtcatcaa cagcggcacc 1140
ataagcggca gtaatggcct ggctctggat ttgggcggcg gcgatgacca gctgatcttg 1200
cgtaacggca gccgctttat cggcacggtg gacggcggca gcggttacga ccgactgacc 1260
ctggacgacg tcgccggtgg cagttttggc gacagccgca acctcgaacg gttggaggtc 1320
aagcaaggca cctggacgtt gaccggccag ggtgacttca gcgacggcgg cgagatttcc 1380
agcggtgcca cgctggtcaa ccaaggcggc attgccggta acgtgacggt cgacgcaggc 1440
ggtgtgtatg ccggcggcgg ctcggtgggc agcctgctgg tcaacggcac tctgcagacc 1500
aacaccgtat tgggtaccgc cagcatcagc cgtgacttgc gcatgggcag cggctcgacc 1560
ctcgcctatg gcgtcaacgc cgacggcagt agcgcaccga tcaaggtcgg cggcaccgct 1620

```
taccttaatg gggcgacgct gacggtcaac cccggcgaag gcacctaccc ctggcaaagc   1680
cactacagcg tgctgcaagc cggcagcatc aatggcacgt ttggcaaggt caccagcgac   1740
tacgccttcc tgaccccgac cctggattac agcgccactc aggtcggcct tacgtacacc   1800
cgtaacgaca tcgccttcaa ccagttcgcc agcaccggca acggcgccag cgccgccaac   1860
agcctggcgg gcctgggcac gaccaacccg ctgtacaacg ccctgctcaa taccaccacc   1920
ggcacagccg gtgccgctat cgagcaactg gcgggcagca gcaccgccaa cctcaccagc   1980
gccaccctca atgccagtgc gcaagtgggc aacagcatgc tcgccgccat gcacaaggtg   2040
ggcggcggtg cgggactgct ggtagggctc aatgacaaag atacaccggt actggccgcc   2100
accggcgtgc ccgccgaggt gcgcaacctc aatgacccga atgcccgcgg ccgactgtgg   2160
ctgcaaggca tcggcagcta cggcaagctt gatggcgagc acggcagcaa cggcttgacc   2220
caacgcacca aaggcacagt gctcggcgcc gattgggcgc tggacagcga ctggcgcttg   2280
ggtgtgctag gggttactc caagaccgac ctggacacca ccggtgtcga cggcagcgtc   2340
gacagctggc acgccggcgt ctatgccctg cgccagagcg gcccattggc gttgcgactg   2400
ggtgcggcct acagcgggca ccagggcgac agtaaacgca cgctggcctt cagcggtttt   2460
aacgaccgcg ccaaaggcga ctatgacgcc aacagccagc aggcttttgc ggaactgggc   2520
tacgccctgg gcagcggtcg cttgagcgca gaaccgttcg ccaacctcgg ctaccagcgc   2580
taccagcgcg acggctataa cgaaaaaggc ggcgccgctg cgttgcatgt cgacggccag   2640
acccaggaca acttcagcag caccttcggc ctgcgcctgg cccacctgag ccagctgaac   2700
aacggtgtca gcctcacacc ccgtgccagc gtcggctgga agcacaccta tggcgatgtc   2760
gacagcacca cacgccaggc tttcctggcc ggtggcacag ccttcaatgt gcaaggcagc   2820
gctctggatc gggatagcct gctgctggag gcgagcctgg atgtaggttt atccgcccgc   2880
catcgcctgg gcctgggcta taccggtgaa gtgggcagca acagccgcaa ccacgcgctc   2940
acaggccaat ggcagatgag tttt                                          2964
```

<210> SEQ ID NO 119
<211> LENGTH: 1806
<212> TYPE: DNA
<213> ORGANISM: Pseudomonas fluorescens

<400> SEQUENCE: 119

```
atgagtacgc agcctttgac ccatggaacg gttccccagc gcctggcgca cacccgtgaa     60
ctgatgcgcc gcgaaggcat tcatgccctg ctggtgccat cggcggaccc gcacctgtcc    120
gaatatttgc cgggttactg gcaagggcgt cagtggttgt ccggctttca tggttcggtg    180
ggcaccctga tcgtcacggc ggagtttgcc ggggtctggg cggacagccg ttactgggaa    240
caggcgacca aggaactcaa gggcagcggt atcgagttgg tgaagctgca accgggtcag    300
cctgggccgc tggagtggtt ggcggagcaa acccctgagg gtggcgtggt ggcggtggac    360
ggcgcggtca tggccgtggc ctcggcacgc accctgggtg gcaagttggc cgagcgtggc    420
gcgcgtctgc gtaccgatat cgatgtactc aatgatgtct ggcaagaccg cccggcgctg    480
ccgaaccagc cgatctatca gcatctgccg ccccaggcca cggtcagtcg tggcgagaaa    540
ctggccgctt tgcgcgccag tttgaaagac aagggcgccg actggcattt catcgcgacg    600
ctggatgaca tcgcctggct attcaacctg cgcggcgctg atgtgtcgtt caatccggtg    660
tttgtgtcct ttgccttgat caatcagcag caggcgactt tgtttgtggc gttgggcaag    720
gtcgatgcgc ctctgcgggc ggtgcttgag caggatggcg tgaccctgcg tgattacagc    780
```

```
gaggtggcgc acgcgctgcg agcggtaccg gcgggcgcaa gcttgcaagt agacccggcc    840
cgcgtcaccg ccggcttgct ggaaaacctc gacgcgggcg tcaagctggt tgaaagcctc    900
aaccccacca cactggccaa atcccgcaag agcctggcag acgcggaaca tatccgccaa    960
gccatggagc aggatggtgc ggcgctgtgc gaattctttg cctggctcga cagtgccctg   1020
ggccgcgagc gcattaccga actgacgatt gacgaacacc tgaccgctgc gcgtacccgc   1080
cgcccaggct atgtatcgct aagcttcaac accattgccg ccttcaatgc caacggcgcg   1140
atgccgcatt accacgccac cgaagaagag catgcgctga tcgaaggtga tggcttgctg   1200
ttgatcgact cgggcggcca gtacctgggc ggaaccacgg acatcacgcg gatggtgccc   1260
atcggtagac cgagtgagga acagaagcgc gattgcacgc gggtactcaa gggcgtgatt   1320
gccctgtccc gtgcgcagtt ccccaaaggc attctttcac cgttgctgga tgccattgcc   1380
cgggcaccga tctgggcaga aggcgtggac tacggtcacg gtacaggcca cggcgtaggt   1440
tatttcctca acgtgcatga gggcccgcag gtgattgcct atcaagccgc tgcggcgcca   1500
caaacggcga tgcagccagg gatgattacg tcaattgagc cgggtactta tcgccctggc   1560
cgttggggcg tgcgcattga gaacctggtg ttgaaccgtg aagcgggcaa gaccgagttt   1620
ggcgaattcc tcaagttcga aaccctgacc ctgtgcccga ttgatacccg gtgcttggag   1680
ccgtcgttgc tgacggcgga tgagcgtgaa tggttcaacg cgtatcacgc ccaggtgcgt   1740
gagcgtttga gcccgctgct caatggtgca gcgcttgagt ggttgcaggt gcgcactgcg   1800
gcgatt                                                              1806
```

<210> SEQ ID NO 120
<211> LENGTH: 2112
<212> TYPE: DNA
<213> ORGANISM: Pseudomonas fluorescens

<400> SEQUENCE: 120

```
atgcgttatc aattgccccc gcgtcgaatc agcatgaagc atctgttccc cagcaccgcc     60
ctcgcttttt tcattggtct cggcttcgcg tcgatgtcga ccaatacgtt cgcagccaat    120
agctgggaca accttcagcc tgatcgcgat gaggtgattg ccagccttaa cgtcgtcgag    180
ttgcttaagc gccatcacta cagcaagccg ccgctggacg acgctcgctc agtgatcatc    240
tacgacagct acctcaagct gctggacccg tcgcgcagct acttcctggc cagcgatatc    300
gctgagttcg acaagtggaa gacgcaattc gacgacttcc tcaagagcgg cgacctgcag    360
cctggcttca ccatctacaa gcgctaccta gaccgcgtca aagcgcgtct ggacttcgcc    420
ctgggtgagc tgaacaaagg cgtcgacaag ctcgatttca cccagaaaga aacccttctg    480
gtggaccgca aggacgcccc ttggctgacc agcaccgcag ccctagacga cctgtggcgc    540
aaacgcgtca aggacgaagt gctgcgcttg aagatcgccg gcaaagagcc caaggccatt    600
caagagctgt tgaccaagcg ctacaaaaac cagctggcgc gcctggacca gacccgtgcc    660
gaggatatct tccaggccta catcaacacc tttgcgatgt cctacgaccc gcacaccaat    720
tatctgtcgc cagataacgc ggaaaatttc gatatcaata tgagtctgtc cctggaaggc    780
atcggtgccg tcctgcaaag cgacaatgac caggtgaaga ttgtacgtct ggtgccggca    840
ggcccggctg acaaaaccaa gcaagtggca ccggccgaca agatcatcgg cgtggcccag    900
gccgacaaag agatggtcga tgtggtcggc tggcgcctgg acgaagtggt caagctgatc    960
cgtgggccta aaggcagcgt ggtgcgcctg gaagtgattc cgcacaccaa tgcaccgaac   1020
```

```
gaccagacca gcaagatcgt gtccatcacc cgtgaagcgg tgaagctcga agaccaggcc   1080
gtgcagaaga aagtcctcaa cctcaagcag gatggcaagg actacaagct gggggtgatt   1140
gaaatcccgg ccttctacct ggacttcaag gcgttccgtg ccggtgatcc ggactacaag   1200
tccaccaccc gcgacgtgaa gaaaatcctc acagaactgc agaaagagaa agtcgacggc   1260
gtggtcatcg acctgcgcaa caacggcggc ggctccctgc aggaagccac cgagctgacc   1320
agcctgttta tcgacaaggg cccgaccgtg ttggtacgca acgctgacgg ccgtgtcgac   1380
gtgctcgaag acgagaaccc gggggccttc tacaaagggc cgatggcgct gctggtcaac   1440
cgcctctcgg cctcggcctc ggagattttc gccggtgcca tgcaggacta ccaccgtgca   1500
ctgatcatcg gcggccagac cttcggcaaa ggcaccgtgc agaccatcca gccgctgaac   1560
catggcgagc ttaagctgac actggccaag ttctaccggg tctccgggca gagcacccag   1620
catcagggcg tactgccgga tatcgatttc ccgtcgatca tcgacaccaa ggaaattggc   1680
gaaagcgccc tgcctgaagc catgccgtgg gacaccatcc gccctgcgat caagccggcg   1740
tcggatccgt tcaagccgtt cctggcacag ctgaaggctg accacgacac ccgctctgcc   1800
aaggatgccg agttcgtgtt tatccgcgac aagctggccc tggccaagaa gctgatggaa   1860
gagaagaccg tcagcctcaa cgaagcggat cgccgtgcac agcactccag catcgagaat   1920
cagcaactgg tgctggaaaa cacccgccgc aaggccaaag gtgaagaccc gctcaaagag   1980
ctgaagaaag aagatgaaga cgcgctgccg accgaggcgg ataaaaccaa gccggaagac   2040
gacgcctact tggccgagac tggccggatc ctgctggatt acctgaagat caccaagcag   2100
gtggccaagc ag                                                        2112
```

<210> SEQ ID NO 121
<211> LENGTH: 3072
<212> TYPE: DNA
<213> ORGANISM: Pseudomonas fluorescens

<400> SEQUENCE: 121

```
ttgctcgcga aaaacgtcaa cgataacgcg ggcaacctgg atgcacgcgg cgtctgtgag     60
tgcttcgcga gcaagctcgc tcctacaggg ggaataacaa taatagggag tgtgcacatg    120
atcaccgatt caccacgttt caaacccttc accgcaggtt ccttgctctt gctgtccgtt    180
gcggcacagg cgcaatacat cgagaccggc caaccgggta accctgccag ctggcgctcg    240
gccgagtacc agagcgactg gggcctgggc cgtatgaaag ccgatgaagc ctacgccgcc    300
gggatcagcg gccagggcgt gaaaatcggc gcgctggact cagggttcga tgccaatcac    360
cccgaagccg ccaaagaccg tttccacccg gtcaccgcca ctggcaccta tgtcgatggc    420
agcgccttca gcaccaccgg cgcgctcaac ccgaacaacg attcccacgg cacccacgtc    480
accggcacca tgggcgccgc ccgcgacggc gtgggtatgc atggcgttgc ttacaacgcg    540
caagtctttg tgggcaacac caacgccaac gacagcttcc tgttcggccc cacgccagac    600
cccaaatact tcaagaccgt gtacaccgca ctggtggatt ccggcgtgcg cgccatcaac    660
aacagctggg gcagccagcc caaggacgtc agctaccaga ccctggacaa catgcatgcg    720
gcgtacgccc agcattacaa ccgcggcacc tggcttgacg cggcagcgga cgtggccaag    780
gcgggcgtga tcaacgtgtt cagcgccggc aacagcggct atgccaacgc cagcgtgcgc    840
tcggccttgc cgtatttcca gccggaactg gaaggccact ggctggccgt atccgggctg    900
gataaagcca ataaccagaa atacaacaag tgcggcgttg ccaagtactg gtgtatttct    960
acccccggcg cgctgatcaa cagcactatt cccgacgggg ggtatggggt gaagtccggc   1020
```

acctcgatgt cagcgcccca tgccactggc gcgttggcgc tggtgatgga acgttatccc 1080
tacatgacca acgagcaagc cttgcaggtg ctgctgacca ccgccacgca gctcgacggc 1140
tcgatcaccc aggcgcctaa cgccatcgtc ggctggggcg tgcctgacct gggccgggcg 1200
atgcacggtc ctgggcaatt gctcgggccc atggaggtca acctggccgc cgggcagggc 1260
gatgtgtgga gcaacggcat ctccgaccag gcgctgcttc agcgccaggc cgaggaccgc 1320
gccgagcaca cggcctggca gcaaaccctg atcgacaagg gctggcaaaa cggcgtgggc 1380
gccactgcca gccagcagga ccagaccgac tacgccatcg gcaatgcccg cgaccaggcc 1440
gccgccaacc gcgtgtacga aggcagcctg atcaaggccg gtgccggcag tctggtgctc 1500
agcggcgaca gcacctatcg cggtgcgacc ctggtcaacg gcggtctgtt ggccgtcaat 1560
ggctcgttga cttcggcggt gacggtcaat gacagcggca ccctgggtgg ttccggacgt 1620
atcgccgcgt tgtcggtaaa cagtggcggc cgtgtggcgc caggcaattc ggtgggtaca 1680
ttgcaggtgg cgggggatgt aaacctcggc gccggctcga cctatgccgt ggaactgacg 1740
cccaccagca gcgaccgcat tgtcgccggc ggccaggcta ttctgggcgg cggtaccgtt 1800
acgctggcgc tggaaaacag ccccaccttg ctcagccaga gcgaggccca aagcctgatc 1860
ggccggcagt actcgattct cgaggcggcg ggcggcattc agggccagtt cgggcaagtg 1920
ctgcccaact acctgttcct cggtggcact ctggactacg ccgccaatgc cgtgcaactg 1980
aacgtggggc gcaacgacgc cagcttcgcc agcgtcggcg ccacccgcaa ccagcgcaac 2040
gtcgcagccg ccgccgagca attgggcgcc ggcaactcgg tgtatgaaag cctgctgcag 2100
tcgcaatcgg tcgccgtggc ccagcagggc ttgcagcaac tgtccgggga aatctacccg 2160
gctgtgggtg cgatgctgat caacgacagc ctgcaactgc gtaatgccgt gggcgagcgc 2220
ctgcgccatg tgccagtgac cggtgaaagc aacctgtggt tcaaagcact gggcgcctgg 2280
ggcaagaccg acagacgcac tgaaacggcg ggttccacta cctccatcgg tggcctgttg 2340
gcgggcgtgg atggcgcgct ggatgagcag acccgcgtgg gtgtggtcgc cggttacagc 2400
gacagctcct tgaacatggg cagcggtacc cattcatcgg catccatcga cagctaccac 2460
tttggcgcgt acgccgggcg cgagctgggt gattggcgcc tgagcgtcgg cggtgcctac 2520
agctggcatc gcggcgatgt gaagcgcgac ctgcaatggg gggatgtcag cggcaagcaa 2580
aaaaccaagc tggacgcgac cacggcgcag gtcttcaccg aagccgcgta ccgcatccgc 2640
ctgcaagcgg tggccctgga gccgttcgcc aacctggcct atgtgcatct gaacagcgag 2700
tccttccacg aaaaaggcga tgccgcggcc ctggagcgcg gcagcgaccg gcgtgacgcg 2760
gtgctcagca cccttggcgt acgtgccctg aaaaccctgg ctctcaatga ccaccagcaa 2820
ctagacctgt ccggttcgtt gggctggcaa cacagcctga cggcggtgga gtccgaagag 2880
cacttggcgt ttgtcgcggg cgggccttca tttgccgtgc gcagtgcgcc attgctgcgc 2940
gacgctgcct tggtgggcgt gcaggccagc ctggcgctga atgcatcgac acgggtcaac 3000
ctggattaca acggccaact gggtgggcgc gcgaaaaccc agggcgtggg tttgagcttg 3060
aactggcagt tc 3072

<210> SEQ ID NO 122
<211> LENGTH: 1023
<212> TYPE: DNA
<213> ORGANISM: Pseudomonas fluorescens

<400> SEQUENCE: 122

```
atggattttc tggccgaata cgcgagcttt ctggcgaaga ccgtcaccct ggtggtcgct      60

attctggtgg tactgatcag ctttgcagcc ttgcgcagta aaggtcgtcg taaatccgcc     120

ggccaattgc aggtcagcaa gctgaatgat ttttacaagg gattgcgcga gcgcctggag     180

tcgagcctgc tcgacaaaga ccagctcaag gccctgcgca agtccgaaag caaagccgaa     240

aagaagaaag acaagaagaa gcccgaggcc aagccacggg tattcgtgct ggatttcgac     300

ggtgacatca aggcctcggc caccgaaagc ctgcgccatg aaatcaccgc gctgctgagc     360

ctggccacgc ccaaggatga agtggtgctg cgcctggaaa gcggcggcgg catggtgcac     420

agctatggcc tggcctcttc gcaattggcg cgtatccgcc aggccggcgt gccattgact     480

gtgtgcatcg acaaagtggc ggccagcggc ggctacatga tggcgtgcat cggcgagaag     540

atcatcagcg ctcccttcgc cattctcggt tccattggcg tggtggcgca gttgcccaac     600

gtcaatcgcc tgctgaaaaa gcacgacatc gactttgaag tgctgactgc cggtgaatac     660

aagcgcacgc tcacagtgtt cggcgaaaac accgagaagg gccgggagaa gttccaggaa     720

gacctggaca ttacccacca gttgttcaag aacttcgttt cgcgctaccg cccacagttg     780

gcgattgacg aggtggctac cggtgaagtg tggctgggcg tcgccgcact cgacaagcaa     840

ctggtcgatg agctgcaaac cagcgacgaa tacctggcca ccaaggccaa gaccgccgaa     900

gtgttccacc tgcactatgc cgagcgtaag agcctgcaag agcgcgtagg cctggcagcc     960

agcggttcgg tggaccgggt gctgttgacc tggtggagcc gcttgaccca gcaacggttc    1020

tgg                                                                  1023


<210> SEQ ID NO 123
<211> LENGTH: 2439
<212> TYPE: DNA
<213> ORGANISM: Pseudomonas fluorescens

<400> SEQUENCE: 123

atggcctcgc cagccctctt acattttctt ccccggttcg gcgttgccgc ggcagtggtc      60

agtgccttgg gcctggccgg ttgccagctc cagaacaccc aggacaccct gccgcccgtt     120

gctggcgtgc agccgatcaa gggcctggca cagaatgtgt cggtgcgccg caatgcccaa     180

ggcatgccgc tgatcgaaag caacactttc cacgacgctc tgttcagcct cggttacgtg     240

cacgccagcg accgcatcac ccagatggtc actctgcgcc tgctggctca gggccgtctg     300

gcggaaatgt cgggcccgca agtgctggat gtcgaccgct tcatgcgggc ggtcaacctc     360

aagaaaagcg ctggcgagtt gtacaatgcc tcatcgccac gcctcagacg cttctttgaa     420

gtgtatgccc gaggcgtcaa cgcctacctg ttccgctacc gcgacaagct gccggcggac     480

ctggcccaga gcggctacaa gcccgagtac tggaagccgg aagattcggc gctgctgttc     540

tgcctgctca atttcagcca gtcgagcaac ctgcaggggg agctctcgtc cctggtgctg     600

gcgcaaaagg tcggcgtcga caaactcgcc tggctcaccc caagcgcacc ggacgaacct     660

gtcccgctgg ccgaagccga caagctcaaa ggcgtcaacc tgagccagat caccggcctc     720

gccgggctgg aaaccgtagg ccagcaattg cgcagcctca acgccctgag cgtcaccacc     780

tcaagcaact gggccattgg cccgcaacgc agccgcagcg ccaagagcct gttggccaac     840

gacatcgccg cgcagccaca agcaccgtcg ccgtggaact acgtgcagat tcgtgcgccc     900

aaataccagg ccgccggtgc ttcgattgcc ggcctgccga ccctgctctc cggtttcaac     960

ggcaaagtgg cgtggagcat gagcgcggtc aagggcgaca cccaggacct gttcctggag    1020

aaggtcaaac gccagggcaa cgcgctgtac tacgagaaca acggcaaatg gctgccggcc    1080
```

ggcgtgcgca acgaaacctt cttcatcaag ggccagcgct cgattcgcga agtggtgtac 1140
gaaacccgcc acggcgccct gctcaacagc agccaggcgc tcaccagcgg tcttggcctg 1200
gccttgcaaa ccgccgactt caaggacgac aagagcctgg atgcattctt cgacctgtcc 1260
cgcgcacaaa acgctggcaa agcctcggat gccacccgcg agattcgcgc catagccttg 1320
aacatgatct tcgccgacgc cagcaacatc ggctggcaag tcaccggccg cttccccaac 1380
cgccgagaag gcgaaggcct gttgccatcg ccgggctggg acacgcgctt tgactgggac 1440
ggctacgccg acgcgatgct gcacccgtac gaccaagacc cggcccaggg ctggatcggc 1500
accgccaacc agcgcaccgc accgcgtggc tacggcatgc aactgtccaa cgcctgggat 1560
gcaccggagc gcagcgaacg cctggcgcaa ctggccaacg ctggcaagca tgacagccgc 1620
agcctgatcg ccatgcaata cgaccagacc accctcttcg ccgccaagct caagaacatg 1680
ttccaggcgc cgggtatggc cctgcccctc aagcaggcca tcgatgcatt gccggcagcg 1740
gaacgcgcca aggcccgcga agcgctcgac cgcctgatgg ccttcgatgg tcgactggcg 1800
accacctcgg ctgacgcggc gatctatgaa ctgttcctgc aagaaagcgc ccggcagatc 1860
ttcctcgaca aactcggccc ggaaaacagc gccagctgga aagccttcgt cagcaacgtc 1920
agcctgtcct actcggccat cgccgaccac ctgctgggcc gtgaagacag cccattctgg 1980
gatgacacgc gtaccgcgca aaaagaagac aaacccgcga tcctggcccg caccctggcc 2040
gccgccatca ctactggcga cagccaattg ggcgccgatc acaaggcctg gcagtggggc 2100
aagctgcaca gcaccacatg gaaaaatacc agcggccagg tcatccgcgg ccccttcgcc 2160
agcggtggcg atcacaacac cctgaacccg gcaccgtaca cctggggcca ggatttcaac 2220
gcgacccaag tatcggcgct gcgcatgatc atcgacttcg gccaggcgga accaatgatg 2280
ggccagagcg gcatcggcca atccggcaac ccggccagcc cgaactatgc caacggcatc 2340
gacccgtcgt tgaaggcgca atatctgagc tttccgatgc agccgcagaa ctttgagaag 2400
gtgtacggca agacaaggtt gaccctgacg cctggtaag 2439

<210> SEQ ID NO 124
<211> LENGTH: 1434
<212> TYPE: DNA
<213> ORGANISM: Pseudomonas fluorescens

<400> SEQUENCE: 124
atgtcgatac cacgtttgaa gtcttactta tccatagtcg ccacagtgct ggtgctgggt 60
caggccttac ctgcgcaagc ggtcgagttg cctgacttca cccaactggt ggagcaggcc 120
tcgcctgccg tggtgaacat cagtaccacg cagaagctgc cggatcgcaa agtctcgaac 180
cagcagatgc ccgacctgga aggcttgccg cccatgctgc gcgagttctt cgaacgaggg 240
atgccgcaac cacgctcccc ccgtggcggc ggtggccagc gcgaagccca atccctgggc 300
tccggcttca tcatttcgcc tgacggctat atcctcacca acaaccacgt gattgccgat 360
gccgacgaga ttctcgtgcg cctggccgac cgcagtgaac tcaaggccaa gctgattggc 420
accgatccac gttccgacgt ggccttgctt aaaatcgagg gcaaggactt gccggtgctt 480
aagctgggca agtcccagga cctgaaggcc ggtcagtggg tggtcgcgat cggttcgccg 540
ttcggctttg accacaccgt tacccaaggc atcgtcagcg ccatcggtcg cagcctgccg 600
aacgaaaact acgtaccgtt catccagacc gacgtgccga tcaacccggg taactccggt 660
ggcccgctgt tcaacctggc cggcgaagtg gtggggatca actcgcagat ctacacccgc 720

```
tccggcggct tcatgggcgt gtctttcgcg atcccaatcg atgtggccat ggacgtctcc    780
aatcagctca aaagcggcgg caaggtcagc cgcggctggt tgggcgtggt aatccaggaa    840
gtgaacaagg acctggctga gtccttcggt ctcgacaagc cggccggtgc cctggttgcg    900
cagattcagg acaatggccc tgcggccaaa ggcggcctga aagtcggtga cgtcatcctg    960
agcatgaacg gccagccgat catcatgtcg gcagacttgc ctcatttggt cggcgcgctc   1020
aaggccggcg gcaaagccaa gctggaagtg attcgtgatg gcaagcgcca gaacgtcgaa   1080
ctgaccgtag gtgccatccc ggaagaaggc gcgaccctgg atgccctggg caacgccaag   1140
cccggtgccg agcgcagcag taaccgcctg ggtatcgccg tggttgaact gaccgccgag   1200
cagaagaaaa ccttcgacct gcaaagcggt gtggtgatca aggaagttca ggacggccca   1260
gccgccttga tcggcctgca accgggtgac gtgatcactc acttgaacaa ccaggcaatc   1320
gataccacca aggaattcgc cgacatcgcc aaggcgttgc cgaagaatcg ctcggtgtcg   1380
atgcgcgtcc tgcgtcaagg ccgtgccagc ttcattacct tcaagctggc tgag         1434
```

<210> SEQ ID NO 125
<211> LENGTH: 1287
<212> TYPE: DNA
<213> ORGANISM: Pseudomonas fluorescens

<400> SEQUENCE: 125

```
atgcgcgaag cgttgaatca aggcctgatc gacttcctca aggcctcccc tactcctttt     60
catgccactg ccgccctggc ccagcgcctg gaagccgccg gctaccagcg tctcgacgag    120
cgcgacacct gggccaccga ggccaacggt cgctactacg tgacccgcaa cgattcctcg    180
atcatcgcct tcaagctcgg ccgccaatcg ccgctgcaag atggtatccg catggtcggc    240
gcccacaccg acagcccgtg cctgcgggtc aagccccagc cggagctgca acgccagggc    300
ttctggcaac tgggtgtgga agtctacggc ggcgcgctgc tggcaccctg gttcgaccgc    360
gacctgtccc tggccgggcg tgtcaccttc cgccgcgatg gcaaggtcga gagccaactg    420
atcgacttca agctgccgat cgccatcatt cccaacctgg ccattcacct caaccgtgaa    480
gccaaccaag gctgggcgat caatgcccag accgagctgc cgccgatcct cgcgcagttt    540
gccggtgacg agcgcgtgga ctttcgcgcc gtgctcaccg agcagttggc ccgcgagcat    600
gggttgaacg ccgatgtggt gctcgactac gagctgagtt tctacgacac ccaaagtgcc    660
gccgtgatcg gcctcaatgg cgactttatc gctggtgcgc gcctggacaa cctgctgtcg    720
tgctacgccg gtttgcaggc cttgctcacc agcgacaccg atgaaacctg cgtgctggtg    780
tgcaacgacc acgaagaagt cggttcctgc tcagcctgcg gtgccgatgg cccgatgctg    840
gaacagaccc tgcgtcgcct gctgcccgaa ggtgaagaat tcgtacgcac cattcagaaa    900
tccctgctgg tgtcggcaga caacgcccac ggcgtgcacc ccaactacgc cgagaaacac    960
gacgccaacc acggtccgaa actcaacgcc ggcccggtga tcaaggtcaa cagcaaccag   1020
cgctacgcca ccaacagcga aaccgccggg ttcttccgcc acctgtgcat ggcccaggaa   1080
gtgccagtgc agagcttcgt ggtgcgcagc gacatgggct gtggctcgac catcggcccc   1140
atcaccgcca gccacctagg cgtgcgcacg gtggacatcg gcttgccgac ctttgccatg   1200
cactctatcc gcgagctgtg cggcagccat gacctggcgc acctggtcaa ggtgttgggg   1260
gcgttctacg ccagtcgcga tttgccc                                       1287
```

<210> SEQ ID NO 126
<211> LENGTH: 3288

<212> TYPE: DNA
<213> ORGANISM: Pseudomonas fluorescens

<400> SEQUENCE: 126
gtgtcgattc atgtcgcgtt gcaccacgtt acgcattacc gctacgaccg tgctgttgaa 60
ctcggcccac agatcgttcg gctacgcccg gcggcccata gccgtacgcg gatcttgtct 120
tacgcgctca aagtgctgcc tgagcagcac ttcatcaatt ggcagcagga cccgcagggc 180
aactacctgg cgcgcttggt attcccggaa aagaccgatg agttgcgcat tgaggtcgac 240
ctcgtcgccg aaatggcggt attcaacccg ttcgattttt tcctcgaacc ctacgccgaa 300
aaaatcccct tcagctacgc cgccgatgag cagcgcgagt tggcgccata cttggaaacc 360
ttgccgctga cgccaaagtt tgccgcctat ttggccggca tcgaccgcac gccgctgccc 420
gctgtggatt tcctggtggg cctcaatcag cgtctggccg cggatatcgg ttacctgatc 480
cgcatggaac cgggcgtaca aaccccggaa ttcaccttgg gcgccgcatc cggctcctgc 540
cgggattcgg cctggctgct ggtgcaattg ctgcgcaacc tggggttggc ggcgcggttt 600
gtgtcgggct atttgatcca gctcaccgcc gacgtcaaag cccttgatgg cccgtccggc 660
accgaagtcg acttcaccga cctgcacgcc tggtgcgagg tgtacttgcc cggcgcgggc 720
tggatcggcc tggacgccac ctccgggctg ttcgccggtg aagggcatat ccccttggcc 780
tgtagccctg atccttcgtc cgccgcaccg atcagcgggc tggtggaacc ctgcgagtgc 840
gaattcaccc acgagatgtc ggtggagcgc atttgggaag cgccacgggt gaccaagccc 900
tataccgaag aacaatggct ggcgatccag gccctgggcc ggcagattga tggcgacctg 960
ctcaaggacg acgtacgcct gaccatgggc ggcgagccaa ccttcgtctc tatcgacgac 1020
cccgacggtg ccgagtggaa caccgcagcc ctgggcccgg acaagcgtcg cctgtcggcc 1080
gagctgttcc agcgcctgcg ccagcactat gcgcccaagg gcctggtgca tttcggccaa 1140
ggcaagtggt accccggcga gcaactgccg cgctggtcgc tcaattgcta ctggcgccgc 1200
gacggcgtgc cgatctggca caacagtgcg ctgattgccg atgagcaaga ggactatggc 1260
gccgatgggg tgatggccgg gcgtttcctg gccagcgtcg ccgagcgcct caaactaccg 1320
gcgcgctttg tgttcccggc gttcgaagac aatttctact acctatggcg cgaaggggcg 1380
ctgccccaga acgtcactgc ccaggacccg cgcctgagcg acgacctgga gcgtgaacgc 1440
ctgcgtaaag tgttcagcca gggcctggat aaagtcatcg gccaggtgct gccgctggca 1500
cgtactgcgg ccaatgaccg ctggcagagt gggcgttggt acctgcgcga taaccattgc 1560
cgcctggtgc cgggggattc gccgctgggc tatcgcctgc cgctcgcctc gcagccctgg 1620
gtgactgcgg cggagtatcc gtttgtgcat ccgaccgacc ctaaccagga tcagccggat 1680
ctgccgacca gcgcccagtt gcaaaaccat ggcgagcccg cgccggttga tgatcgtgtg 1740
cccaagattg acgagtccgc cgactggctg acccgtaccg cgctgtgcgc cgaagcacgg 1800
gaagggcgcc tgtatctgtt tatgccgccg ctggagcgcg tcgaggacta cctggaactg 1860
gtgaccgcta tcgaggccac cgccgaagag ctgcattgcc cggtactgct ggagggctac 1920
gagccgccag cggatacgcg cctgagcaat ttccgagtga cgccagaccc tggtgtcatc 1980
gaggtcaacg tacagccgtc cgccacctgg gacgagttgg tagaacgcac cgaattcctc 2040
tacgaagagg cccggcaaac ccgcctgacc accgagaagt tcatgatcga cgggcgccat 2100
accggcaccg gtggcggtaa ccacttcgtg ctcggcggcg cgacgcccaa ggattcgccc 2160
ttcctgcgcc ggccggacct gctacgcagc ctgatcagct actggcacaa ccacccgtcg 2220

```
ttgtcctatt tgttctccgg cctgtttatc ggccccacct cccaggcgcc ccgggtagat   2280
gaggcgcgca acgatgcgct gtatgaactg gaaatcgcct tcgcgcagat gccggagcca   2340
ggcgaggagt gcccgccgtg gctggtggac cgcctgttgc gcaacctgct gatcgacgtg   2400
acgggtaata cccatcgcgc cgaattctgt atcgacaaac tttactcacc cgacggcgcc   2460
actggccgcc tggggctgct ggaactgcgc gcctttgaaa tgcccccccca tgcgcgcatg   2520
agcctgaccc agcagttgtt gctgcgggcg ctggtcgcgc ggttctggcg cgagccctat   2580
gcgccgccga agctggcgcg ctggggcact gagctgcatg accgtttcct gttgccgcac   2640
tttatcgagc aggactttgc cgacgtgatc gtcgagctga acgcggccgg ctatccgctg   2700
cgggccgaat ggttcgcggc gcatctggag tttcgtttcc ccaaggtggg cgactacgcc   2760
gtcagcggta tcgaactgga actgcgccag gccttggagc cttggcatgt gctgggcgag   2820
gagggggcgg tgggtggcac ggtgcgctat gtggattcgt ccctggagcg cctgcaagtg   2880
aagttgagcg ggttgccgcc gcaacgctac ctgctgacct gcaatggcgt gccggtgccg   2940
ctgcaagcga ccggccgcgt cggcgagttc gtggcgggcg tgcgttaccg cgcctggcag   3000
ccggccaact gcctgcaacc gaccatcccc gtgcatgcgc cactggtatt tgacctgctc   3060
gacacctgga tgcagcgttc gttgggcggc tgccaatacc atgtggcgca cccaggcggg   3120
cgcaattacg acagcctgcc ggtgaatgcc aatgaggcgg agagccggcg catggcgcgg   3180
tttttccgct tggggcatag cccgggcaag ctgccagtgc cgactgtaac ggtaaacgat   3240
gaattgccaa tgacgctgga tttgcggcgt ttcaaaaaaa ataaggaa                3288
```

<210> SEQ ID NO 127
<211> LENGTH: 1974
<212> TYPE: DNA
<213> ORGANISM: Pseudomonas fluorescens

<400> SEQUENCE: 127

```
atggcgcgtt gttgtgttgc ctggcaagcc tggggaccgc ccaggctgca ccctatgtgg     60
aaaccggcaa actgggcgac gccgccagct ggcgcagcaa tgagttcaag gccgactggg    120
ggcctgggcg ccgtgcacgc cgacaccgcc tatgcggctg gctataccgg caagggcgtc    180
aagctgggga tcttcgacca gccggtatac gcccagcacc cggagttcgc cagccctgac    240
aaggtggtga cgattgtcac cgagggcatt cgccaataca ccgacccata tatcccggtg    300
aaggcgggcg acgcgttccg ctacgacggc acgccgtcca aggactccaa cggcaaactg    360
ggtaaccacg gcacccacgt cggcggcatt gcggccggta accgcgatgg cgggccgatg    420
catggcgtgg cgttcaacgc acagatcctc accgccgaaa acggtgaccc ggggccggaa    480
gacgggatca tccttggcaa cgacggcgcc gtgtacaagg ccggttggga tgggctggtc    540
gccagtggcg cacgcatcat caacaacagt tggggcatcg gcatcggtga tcagtacgcc    600
aaaggcggcc gtgatccggc gttccccaac ttcaccgtca acgaggccca ggcgcagttc    660
aataccatcc ggccgatcct tggcacccta gcaggtggtg cgtaccaagg cgccatcgac    720
gcggcccgca gcggtgtgct gaccatcttt gccgcaggca atgactacaa cctcaacaac    780
ccggatgcga tttccggcct tgcgtatttt gtgccagaga tcgcgcctaa ctggctgtcc    840
gtcgcggccc tccagcagaa cccgaatacc gccagccccg atccgtacgt gatcagtacg    900
ttctcctcgc gttgtggtta tgcggcgagc ttttgcgtgt cggcacccgg caccaagatc    960
tacagttcga tcatcaacgg taccgacctg agcaacctca ccaccgactg ggccaacaaa   1020
aacggcacct ccatggccgc acctcacgtg gcgggcgccg cagcggtgct gatggagcgc   1080
```

ttccagtaca tgagcggcga ccagatttcc accgtgctca agaccaccgc caccgacctc 1140
ggcgcgccgg gcatcgactc gttgtacggc tggggcatga tcaacctggg caaagcggtc 1200
aacggcccag ggatgtttat caccgctgag gatatcccgg ccgagttccg tatcgacggc 1260
gcctacggca gcggccagtt cgtcgcggac ctgccgggtg tcggcgcggt ggtggatgcc 1320
ggcaaaccca ctcagcgtgt gtgcgacgac gtgcactgcg ggcgggatgt gtggagcaat 1380
gacatctcgg gccatggcgg cctgaccaag cagggcatcg gtaccttggt gctcaccggc 1440
gccaatacct acagcgggcc gacgcgggtc aaccagggct tgctggcgat caacggttcg 1500
gttacctccg acgtcactgt gagccagagc ggcgtggtcg gtggttcggg gcgtatcggt 1560
tcgctgagcg cgaacagcgg cggcaccgtg gcgccgggca attccatcgg caccttgaac 1620
gtggcgggca acgtcaactt tgaaccgggt tccacctacg cggtagaact gtcgcccacc 1680
agcagcgatc gcatcgtcgc cggcggcacg gccaccctca acggcggcac cgtgaccctg 1740
gccctggaaa atagcccgac cttgttgagc gccacccagg cccaaagcct gatcggccgt 1800
cagtacaaca tcctgcaagc ggcaggtggc gtcaccggca gtttcgcggc agtggtgccc 1860
aactacctgt ttgtcggcgg caccttgaac tacgccgcca acggtgtgca actggatgtg 1920
gacgcacaac gctcgccatg tggcgcagcc aacaagcgcc aggcgcgcgt gaga 1974

<210> SEQ ID NO 128
<211> LENGTH: 3726
<212> TYPE: DNA
<213> ORGANISM: Pseudomonas fluorescens

<400> SEQUENCE: 128
atggacgtag caggtaatgg cttcactgtg tcgcaacgca atcgcacccc ccgtttcaag 60
accacacccc tcacacccat agcactcggc ctggccttat ggctgggcca cggttccgtg 120
gccagggcag acgacaaccc ttacaccccg caggtactgg aatcggcgtt caggacagcc 180
gtcgcctcat tcggccctga gactgccgtg tacaaaaacc tcaggtttgc ctacgccgat 240
atcgtcgatc ttgcggccaa ggacttcgcg gcccagtccg gcaagttcga ttcggccctc 300
aagcaaaact atgagctgca acccgagaac ctgaccatcg gcgccatgct cggcgacacc 360
cgtcggccac tggactacgc ctcgcgcctg gattactacc gcagccggct gttcagcaac 420
agcggccgct acaccaccaa tatcctggac ttttccaagg ccattatcgc caacttgccg 480
gccgccaagc cttacaccta cgtagagcca ggcgttagca gcaacctcaa tgggcagttg 540
aacgccggcc agtcctgggc tggcgcaacc cgtgactgga gcgccaacgc gcaaacctgg 600
aagaccccgg aagctcaggt caactctggc ctggaccgca ccaacgcgta ctacgcctat 660
gccttgggca tcaccggtaa gggggtgaat gtcggcgtgc tggactcggg catcttcacc 720
gaacactccg agttccaggg caagaatgcc cagggccagg accgggtgca ggcggtgacc 780
tccacgggcg agtactacgc cacccatccg cgctaccgcc ttgaagtgcc cagtggtgag 840
ttcaagcagg gtgagcattt cagtatccca ggggaatacg acccggcgtt caacgacggg 900
catggcacgg agatgtccgg ggtgctggcc gccaaccgca acggcacggg tatgcacggc 960
attgccttcg acgccaacct gtttgtcgcc aacactggcg gcagcgacaa cgaccgctac 1020
caaggctcca acgacctcga ctacaacgca ttcatggcca gctacaacgc cctggcggcg 1080
aagaacgtgg cgatcgtcaa ccagagttgg gggcagagtt cgcgcgatga cgtggagaac 1140
cacttcggca acgtcggcga cagcgccgcg caaaacctgc gcgacatgac cgccgcctat 1200

-continued

```
cgcccgttct gggacaaggc ccatgccggg cacaaaacct ggatggacgc catggccgat   1260
gcggcccggc aaaacacgtt catccagatc atctcggcgg gcaacgacag ccacggtgcc   1320
aacccggaca ccaattcgaa cctgccgttc ttcaaaccgg atatcgaagc taagttcctc   1380
tccatcactg gctacgacga aactagcgcc caggtctaca accgctgcgg tacgtccaag   1440
tggtggtgcg tgatgggcat atcgggcatt ccatctgccg gccccgaggg cgaaatcatc   1500
ccgaatgcca acggcacctc ggccgccgca ccgagcgttt ccggggcctt ggcgctagtg   1560
atgcaacgct tcccctacat gaccgccagc caggcgcggg acgtgttgct gaccacctcc   1620
agcctgcaag cgccggatgg cccggacacg ccggttggca cgctgaccgg tggccgcacc   1680
tacgacaacc tgcaaccggt gcatgatgcc gcgccgggtt tgccgcaagt gccgggtgtg   1740
gtcagtggct ggggcttgcc caacctgcaa aaagccatgc aagggccggg gcagttcctc   1800
ggtgcggtgg cagtggcgtt gcccagtggt acccgcgata tctgggccaa cccgatttcc   1860
gatgaagcca ttcgcgcccg ccgcgtagaa gacgctgccg aacaggctac ctgggccgcc   1920
accaagcagc aaaaaggctg gctcagtggc ctgcccgcca atgcctcggc cgacgatcag   1980
tttgaatacg acatcggtca tgcccgggag caggcaacac tcacccgcgg ccaggacgtg   2040
ctcaccggca gcacctacgt cggtagcctg gtcaagtccg gggatggcga gttggtgctg   2100
gaaggccaga acacctattc gggcagtact tgggtacgcg gaggcaaatt gtcggtggac   2160
ggcgcattga cctctgccgt gacggtagat agcagcgccg tgggcacgcg caatgccgat   2220
aacggcgtga tgaccacact gggcggcacc ctggccggca acggcacggt gggcgccttg   2280
accgtcaaca acggtgggcg agtggcccct gggcattcga taggcacact gcgcaccggc   2340
gatgtcacgt tcaacccggg ttcggtgtat gccgtcgaag tcggggccga tggccgcagc   2400
gaccagttgc agagcagcgg ggtggcgacc ctcaatggcg gtgtggtgag cgtgtcccta   2460
gagaacagcc ccaacctgtt gaccgccacc gaggcgcgca gcttgctggg ccagcagttc   2520
aatatcctca gcgccagcca aggtatccag gggcagtttg cagcgttcgc ccccaactac   2580
ctgttcattg gcactgcgct gaactatcaa ccgaaccagt tgaccctggc gatagcccgc   2640
aaccagacca ccttcgccag cgtcgcgcaa acccgcaatg agcggtcggt ggcgacggta   2700
gccgagacat tgggcgctgg cagcccggtc tacgaaagcc tgctggcgtc ggattccgct   2760
gcccaggcgc gggagggctt caaacaactt tcagggcaac tgcattcgga cgtggctgca   2820
gcgcaaatgg ctgacagccg ctacctgcgt gaagcggtca acgctcgcct gcaacaggcg   2880
caggcactgg actccagcgc gcagatcgac agccgtgaca acggcggctg ggtacagctg   2940
cttggtggac gcaacaacgt cagtggtgac aacaacgcca gcggctactc ctcgtccacc   3000
agcggcgtac tgctgggcct ggacaccgag gtgaacgacg gctggcgcgt gggcgcggcg   3060
accggttata cccaaagcca cctcaacggc cagtcggcgt cggcggacag cgacaactat   3120
cacctgtcgg tctatggcgg caaacgcttc gaggcgattg ccctgcgcct gggcggtgcc   3180
agcacctggc accgtctgga cacttcgcga cgggtggcct atgccaatca gtcggaccat   3240
gccaaggccg actacaacgc gcgtaccgac caagtgtttg ccgagatcgg ttacacccag   3300
tggaccgtgt ttgaaccctt cgccaacctc acgtacctga actatcaaag cgactcgttc   3360
aaggaaaaag gcggtgccgc agccttgcat gccagccagc aaagccagga cgcgacactc   3420
tccaccctgg gcgtgcgtgg tcacactcag ttgccgctca cgtccacctc ggcggtgacc   3480
ctgcgcggtg agctgggttg ggagcaccag ttcggtgata ccgatcgtga agcttctctg   3540
aagtttgccg gtagtgacac ggccttcgcc gtaaacagcg tgcctgtggc cagggatggt   3600
```

```
gcggtgatca aagccagtgc ggagatggcc ttgaccaagg acacccttgt gtcgttgaac   3660
tacagtggct tgctctccaa ccggggtaac aacaacggga tcaatgccgg gtttaccttc   3720
ctgttc                                                              3726
```

<210> SEQ ID NO 129
<211> LENGTH: 2418
<212> TYPE: DNA
<213> ORGANISM: Pseudomonas fluorescens

<400> SEQUENCE: 129

```
atgagcgacc agcaagaatt tccagattac gacctcaacg attacgccga ccccgaaaac     60
gctgaagccc cctcgtccaa tactggcctg gccttgcctg ggcaaaacct gccggacaag    120
gtttacatca tcccgatcca caaccggccg tttttcccgg cccaagtgtt gccggtgatc    180
gtcaatgaag aaccctgggc cgaaaccctg gagctggtga gcaaatccga ccaccattcc    240
cttgcgctgt ttttcatgga cacgccgccc gatgacccac ggcacttcga cacctccgcc    300
ctgccgctgt acggcaccct ggtgaaggtg caccacgcca gccgcgagaa cggcaagctg    360
cagttcgtgg ctcagggcct gacccgcgtg cgcatcaaga cctggctcaa gcaccaccgc    420
ccaccgtacc tggtggaggt tgaatacccg caccagccca gcgagccgac cgatgaggtc    480
aaggcctacg gcatggcgct gatcaatgcg atcaaggaac tgctgcccct caacccgctg    540
tacagcgaag agttgaagaa ctacctcaac cgcttcagcc ccaacgaccc gtcgccgctt    600
accgacttcg ccgccgccct cacctcggcg accggtaatg agctgcagga agtgctggac    660
tgcgtgccca tgctcaagcg catggaaaaa gtgctgccga tgttgcgcaa agaggtagaa    720
gtcgcgcgcc tgcaaaaaga actctccgcc gaggtaaacc gcaagatcgg cgagcaccag    780
cgagagttct tcctcaagga acaactcaaa gtcatccaac aggagctggg cctgaccaag    840
gacgatcgca gcgccgacgt cgaacagttc gaacagcgcc tgcaaggcaa ggtgttgccg    900
gcccaggcac agaagcgcat cgatgaagag ctgaacaaac tgtcgatcct ggaaaccggt    960
tcgccggaat acgccgtcac gcgcaactac ctggactggg ccacctcggt gccgtggggc   1020
gtgtacggcg cagacaaact cgacctcaag cacgcgcgca aagtgctcga caagcaccat   1080
gcgggcctgg atgacatcaa gagccgcatc ctcgaattcc tcgccgtggg cgcctacaag   1140
ggcgaagtcg ccggttccat cgtgttgctg gtgggcccgc cgggcgtggg caagaccagt   1200
gtgggcaagt ccatcgccga atccctgggg cggccgttct atcgcttcag tgtcggcggc   1260
atgcgcgacg aggccgagat caagggccac cggcgcacct acatcggcgc cctgcccggc   1320
aagctggtgc aggcgttgaa agacgtggaa gtgatgaacc cggtgatcat gctcgacgag   1380
atcgataaga tgggccagag cttccagggc gacccggcgt cggcgctgct ggaaaccctg   1440
gacccggaac agaacgtcga attcctcgac cactacctgg atctgcgcct ggacctgtcc   1500
aaagtgctgt tcgtgtgcac cgccaacacc ctggactcga tcccgggccc gttgctggac   1560
cgcatggaag tgattcgcct gtcgggctat atcaccgaag aaaaagtcgc catcgccaag   1620
cgccacctgt ggcccaagca gttggaaaaa gccggcgtgg ccaaaaacag cctgaccatc   1680
agtgatggtg ccttgcgcgc gttgatcgac ggttatgcgc gagaggccgg cgtgcgtcag   1740
ttggagaagc aactgggcaa gctggtgcgc aaggcggtgg tcaagctgct ggatgaaccg   1800
gactcggtga tcaagatcgg caacaaggac ctggaaagct ccctgggcat gcccgtgttc   1860
cgtaatgaac aagtgctgtc cggcaccggc gtgattaccg gcctggcctg gaccagcatg   1920
```

ggcggcgcca ccttgccgat cgaagcgacg cgcatccaca cgctcaaccg cggcttcaag 1980
ctcaccgggc agttgggtga agtgatgaaa gagtccgccg aaatcgccta cagctacatc 2040
agttcaaacc ttaagtcgtt tggcggcgat gcgaagttct tcgatgaagc cttcgtccac 2100
ttgcacgtac cggaaggcgc cacccccaaa gacggcccga gtgctggcgt gaccatggcc 2160
agtgcgttgc tgtccctggc ccgcaaccaa ccgccgaaaa aaggcgtggc gatgaccggc 2220
gaactgacct tgaccgggca tgtactgccg attggcggag tgcgcgagaa ggtgattgcg 2280
gcgcggcgcc agaagattca cgagttgatc ttgccggagc ccaaccgtgg cagctttgag 2340
gagttgccgg attatttgaa ggaaggcatg acggtgcact ttgccaagcg gtttgcggat 2400
gtggcgaagg tgctcttc 2418

<210> SEQ ID NO 130
<211> LENGTH: 2655
<212> TYPE: DNA
<213> ORGANISM: Pseudomonas fluorescens

<400> SEQUENCE: 130
atgcgcaccg aacaaccgaa gatgatttac ctgaaggact atcaggcgcc ggactacctg 60
atcgacgaga cgcacctgac cttcgagttg ttcgaggacc acagcctggt ccacgcgcag 120
ctggtgatgc gccgcaaccc cgagcgtggt accggcctgc caccgctggt gctcgatggc 180
cagcagcttg agttgctgag cgtcaccctc gcggatcagg aactgaccgc cgccgattac 240
cagctgaccg acagccacct gaccctgcag cccccgagtg aaaccttcac cctggacacc 300
acggtcaaga tccacccgga aaccaacacc gcactggaag gcttgtacaa atccagcggt 360
atgttctgca cccagtgcga ggccgaaggt ttccgcaaga tcacctatta cctcgaccgc 420
ccggatgtga tgagcgtgtt caccaccacg gtgatcgccg agcaacacag ctacccggtg 480
ctgctgtcca acggcaaccc gattgccagc ggccctggtg aagacggccg gcactgggcg 540
acctgggaag acccgttcaa aaagccggcc tacctgtttg cgctggtggc cggtgacctg 600
tggtgcgtcg aagacagctt taccaccatg accaaccgcg aagtcgcgct gcgcatctac 660
gtcgagccgg aaaatatcga caagtgccag cacgccatga ccagcctgaa aaaatccatg 720
cgctgggacg aagagaccta cggccgcgag tacgacctcg acatcttcat gatcgttgcg 780
gtcaacgact tcaacatggg cgccatggag aacaagggcc tcaacatctt caactccagc 840
gccgtgctgg cccgcgccga aaccgctaca gacgccgctc accagcgcgt cgaagccatc 900
gtcgcccacg aatacttcca caactggtcg ggtaaccgcg tgacctgccg cgactggttc 960
cagctgtcgc tcaaggaagg cttcaccgtg ttccgtgact cgggcttctc tgccgacatg 1020
aactcggcca cggtcaagcg catccaggac gtggcgtact tgcgtaccca tcagttcgct 1080
gaagatgccg gccccatggc ccatgccgtg cgccccgaca gctttatcga gatctccaac 1140
ttctacaccc tgaccgtgta tgaaaagggc tcggaagtgg tcggcatgat ccacaccttg 1200
ctcggcgccg agggctttcg caaaggcagc gacctgtatt tcgaacgcca tgacggccag 1260
gccgtgacct gcgacgactt catcaaggcc atggaagacg ccaatggcgc cgacctcagc 1320
cagttcaagc gctggtacag ccaggccggc accccgcgcc tggcggtcag cgaggcctac 1380
gacgcagcgg ccaagaccta cagcctgacc ttccgccaga gttgcccgcc cactccggac 1440
aaggtcgaga aactgccctt tgtgatcccg gtggagctgg gcttgctgga cgggcagggc 1500
gccggcattg ccttgcgcct ggccggtgaa gcgacggcgg gcgacacttc gcgggtaatc 1560
tcggtgaccg aagcggagca gacgtttacc ttcgtcgaca tcgctgaaaa acccttgcct 1620
tcgttgctgc gtggtttctc ggcgccggtg aagctcagct tcccctacag ccgtgatcaa 1680
ctgatgttcc tgatgcagca cgacagcgac ggtttcaacc gctgggatgc cggccagcaa 1740
ttggccgtgc aggtgctgca ggagctgatc ggccagcatc aggcgggcca gccgctgaag 1800
ctcgatcaac gcttgatcga cgcgctgcgc acggtgttga gcgatgaaag cctggaccag 1860
gccatggtcg ccgaaatgct ctcgctgccg agcgaagcct acctcaccga aatcagcgaa 1920
gtggcggatg tggacgccat ccacgctgcc cgcgagtttg cccgcaagca actggccgac 1980
aacctgttcg aagggttgtg gctgcgctac caggccaacc gcgagctgtc caagcaaacg 2040
ccatatgtgg cagaggccga gcacttcgcc cggcgtgcgc tgcagaacat cgcgctgtcg 2100
tacttgatgc tcagcggcaa gccagaagta ttggcggcca ccctggatca gttcgacacc 2160
agcgataaca tgaccgaacg cctgacggcg ttggcggtgc tggtgaactc gccgtttgaa 2220
gcagagaaag cccaggcctt ggcggtgttt gccgaaaact tcaaggacaa cccgctggtc 2280
atggaccaat ggttcagcgt acaggccggc agcaccttgc cgggcgggct ggcgcgggtc 2340
aaggcgttga tgcagcaccc ggcgttcacc atcaagaacc ccaacaaggt acgcgcgctg 2400
gtgggcgcat ttgccgggca gaacctgatc aacttccatg cggcggatgg ctcgggttac 2460
cggttcctgg cggatctggt gatccagctc aataccttga acccgcagat tgcctcgcgc 2520
caactggcgc cgctgacccg ctggcgtaaa tacgacagcg cacggcaggc gctgatgaaa 2580
gcggagctgg agcgcatcct gggcgcgggt gagctgtcca gcgatgtgtt tgaggtggtc 2640
agcaagagcc tggcg 2655

<210> SEQ ID NO 131
<211> LENGTH: 1080
<212> TYPE: DNA
<213> ORGANISM: Pseudomonas fluorescens

<400> SEQUENCE: 131
gtggccgtca cgccgaacca gcgcgccgtg gccggcgccg tcgagcaatt gggcgcgggc 60
aacggtgtgt atgaaagctt gctgctggca cccacggccg cctcggccca gggcgcgttc 120
cagcaactga gcggcgaggt ttacccggcg ctggaaaccg cgctggtcaa tgacagccgc 180
tacgtgcgcg aagccgtggg cgaacgcctg cgcaacggtg aaatgggcgc tgccagccaa 240
gccatcgaca gccgtggcaa cgtgtgggtc aaggcactgg gcgcatgggg caagaccgac 300
agccgcaacg acaccgcggg ctacaccacc tccatcggcg gcatgctcgc cggtgtggac 360
ggtgccctcg atgacgccac acgcattggc ctggtggccg gctacagcga cacgtcgctg 420
aacatgggca gcggcaccca cagccgcgct tcggtcgaca gctaccattt cggcgcctat 480
gccgggcatg aaatcggcgc ctggcgcctg agtggcggcg cgacctacag ctggcaccgc 540
gccgatgtca aacgcgacct gcaatacggc gacgtcagcg gcaagcaaaa ggccaaggtc 600
gatgcccaca gcacccaggt gttcaccgaa gctgcgtacc gcatcaacct gcaaccgctg 660
gccctggagc cgttcgccaa tctggcctac gtgcacctgg caactgacag cttcaaagag 720
aagggcgacg ccgccgcgct gagaagtggc gatgacagcc gtgacctggt gctcagcacc 780
ctgggtatgc gcgccttgaa gaccttcaat atcaacgatc accagcaact ggaagtctcc 840
ggcaccctgg gctggcagca caacctgagc agcaccgatt cggagcagca cctggcgttt 900
gcctcgggcg gcccttcgtt cgctgtggaa agtgcgccaa tggtgcgcga tgctgcgttg 960
gtcggggcac gggtcagcct ggcattgagc aaggatgcgc gggtgaactt cgattacaac 1020
ggcctgctgg ccagcaagga gaaggtgcac ggcgtcggct tgagcctgga ttgggcgttc 1080

<210> SEQ ID NO 132
<211> LENGTH: 1149
<212> TYPE: DNA
<213> ORGANISM: Pseudomonas fluorescens

<400> SEQUENCE: 132
atgaccgtgg ccttgacctc catcaagatc agcaccgact tcgacagcgg caacattcag 60
gtcctggatg ccagcgacgc ttatcagttg ttgctggcaa tcaaacccga cacccgcagc 120
gatcactacc aatggttcca cttcaaggcc gaaggcatgc acgtggggca cacccacacc 180
tttcgcttga gcaacgcagg gcgctcgtcc tacaagcatg cctggagcgg ttacaacgcc 240
gtggcgtcct atgaccatat caactggttc cgggtaccga cacgttttga tggcgagatc 300
ctgcacatca ctctccagac ccggcaaaag tacgcctggt ttgcctactt cgagccctac 360
agccgtgaac gccacgactg gttgatcgag caagccctga agtacgccgg agtcaccctg 420
ctggccaccg gcaagagcgc tgaaggccgc gatatccaac tgctgcgccg tggcaaaggg 480
atcgaaggcc ggcgcaaggt gtggatcatc gcccagcagc accccggcga acacatggcc 540
gaatggttta tggagggcgt gattgagcgc ctgcaaaaag acggcgacga cgaactgaaa 600
aaactgctgg ccgtcgccga tctgtacctg gtgccgaacg tgaacccgga cggtgccttc 660
catggccacc tgcgcaccaa tgccatgggc caggacctca accgcgcctg gcaaagcgcc 720
agccaggaac tcagccccga agtcctgttc gtccagcaac agatggaaaa atacggcgtg 780
gatatgttcc tcgacataca cggcgatgaa gaaatcccct acgtgttcac cgccggctgc 840
gaaggcaacc ctggctacac cccgcgtatc gaagccctgg aaaaacactt ccgcagccat 900
ttgagccacc tgacccggga cttccagacc acccacggct acacccgcga cctgcctggc 960
caagccaaca tgaccctggc ctgcaacgcg gtgggggaaa agtacgactg cctgtccctg 1020
accctggaaa tgcccttcaa ggacaacgac gacgcgccca acctgcgaac tggctggtca 1080
ggcgatcgtt cgaaacagtt gggcaaggac gtattgagca gcatcgccga tatcgtcggg 1140
cgtttgcgc 1149

<210> SEQ ID NO 133
<211> LENGTH: 1293
<212> TYPE: DNA
<213> ORGANISM: Pseudomonas fluorescens

<400> SEQUENCE: 133
atgcttcgcg ccttgataac ccttgctctt gtctgcctgc tccaaccggc gtttgccgat 60
gagcgcgcac aaacccaaca acagttggac gctacgcgtc aggacattac cgagctgaaa 120
aagctgctcg gcaagctcca ggaagaaaaa tccggggtgc agaaagacct gcgcggcacg 180
gaaaccgaaa tgggcaagct ggagaagcag gtccaggagc tgcaaaaaga actaaagaag 240
agcgagtcgg aactggagcg actcgacgct gagaaaaaaa aactccagag cgcacgcgtt 300
gaacagcaac gtctgatcgc gatccaggcc cgtgccgcgt accagagcgg ccgccaggag 360
tacctcaagc tgctgctcaa ccagcagaat ccggaaaaat tcgcccgtac cctcacctat 420
tacgattacc tgagccaggc gcgcctggcg caattgaagg ggtttaacga aaccctgcgc 480
caattggcca atgtcgaaca ggaaatcgcc gaccagcaat cccagctgct cgaccagaaa 540
accgccctgg acacccagcg cgaccagctc gataaagtac gcaaggaacg ccagcaggcc 600
ctggccaagc tcaacagcga cgtaaaagcc cgcgacgcca agctccaggc ccgcgagcag 660

-continued

```
gaccaggccg acctggccaa agtcctcaag accatcgaag aaaccctggc ccgccaggca    720

cgcgaggccg aagaagcgcg gcaaaaagcg ctgatcgccc agcaggaagc cgaaaaaaag    780

cgtcagcgtg aggctgaact ggctgccacc accgacgctc cggccccgcg caaacccgcg    840

cgcgcagccc ctggcccgct ggtttccagc agtggcgagt cgttcggcgg cccttttgct    900

tcagcgcgcg gcaaacttcc atggccggtt gatggtcgat tactggcacg ctttggggaa    960

acccgtggcg atgacacccg cgccaagtgg gatggcgtga tgatcagcgc ctctgccggc   1020

agccaggtcc acgccgtgca tggtggccgc gtggtgtttg ccgattggtt gcggggcgcc   1080

ggcttgctgg tgattcttga ccacggtaat ggctatttga gcctttacgg ccacaatcag   1140

acattactca agtcggcagg tgatgttgta aaagccggtg aatccatctc cactgtcggt   1200

aacagtggtg gccaggacac cccggcgctg tacttcgcta ttcgtcagca gggccgcccg   1260

agcgaccctg cacaatggtg ccggtcccaa gga                                 1293
```

<210> SEQ ID NO 134
<211> LENGTH: 1440
<212> TYPE: DNA
<213> ORGANISM: Pseudomonas fluorescens

<400> SEQUENCE: 134

```
atgttcgaac accacgccac gctcaagaaa cacttcagcg ccctgcgcac caccgccgaa     60

tttttctccc tgcgctacgt acgcgaatcc ggccagtacc tgtcggtgcg caagaacgtc    120

gccgagccgc ctcacctggg ccatgacgaa ggcgcgatgc tcaccgtgcg tctcaacggg    180

gtagaagcct acgccgcgac caacgatatt tcccttgccg gcctgcaagc cgcccttgag    240

cgtgctgaac agcaagcccg gttgatcaag ccccacgccc tgctcgacct gcaccagcag    300

ccggtgtcca gcgacgtcgc cgactacctg tcgcccgacc tcgaccagcc cttcccatcc    360

ctgagcgact gctaccaatt gctcggcgat gagtccgccg ccgtgcccaa ggatgagcgc    420

ctggtgagct gggaagtcag cctgggaacc acgcgggtcg aacagatcta cctcaacagc    480

gccggcgcgc aattgcgtca ggcccagcgc tttgtctttc cgggcctgag tgtgaccgcc    540

ttcgacggca acgacagcca gacccgtacc ctgggcggca ccaacttcgg ccagcaaggc    600

agtgccggcg tgatccagcg ctttggcctg gtgggcgccg cccgcaaagt ggccgacgaa    660

gccctgcaat tgctgctcgc accgaatacg ccccacggcc cgcgtgacct gctgctgatg    720

cccgaccaga tgatcctgca gatccacgag tccatcggcc atccgctgga gctggatcgc    780

atcctcggtg acgagcgcaa ttacgccggc accagttttg tgaaagccag cgacttcggc    840

cacctgcaat atggctcacc gctgcttaat gtcaccttcg acccggacat ccccgaacag    900

cttgccagtt acggccatga cgacgacggc acgcctgcca gcaagcaatt tctgattcgc    960

gagggcctgc tgctcaagcc attgggcggg gccttgtcgc aatttcgcgc caacctgcca   1020

ggcgttgcca acagccgcgc ctgcggctgg aaccgtgcgc ccatcgaccg catggccaac   1080

ctgaatatcg agcctggcga taaaagcctc gcgcaactgg tgggcggcat cgagaacggc   1140

atcctgatgt cgaccaaccg ttcgtggtcc atcgacgatg cgcgcaacaa gttccagttc   1200

ggctgcgagt ggggccagtt gatcgaaaac ggcgaactca agggcgtggt gaagaacccc   1260

aactaccggg cgatttccgc gcagttctgg cgcaagctca gcgcggtggg cgacgccagc   1320

accttcaagg tgttgggcac gccaaactgc ggcaaaggcg aacccaacca ggtgatccgc   1380

gtcggccatg cgtcgccggc ctgtgtattc agcaatgtcg atgtatttgg gggagatgcc   1440
```

<210> SEQ ID NO 135
<211> LENGTH: 711
<212> TYPE: DNA
<213> ORGANISM: Pseudomonas fluorescens

<400> SEQUENCE: 135
atgcgaatga acggtcttac acaccaatgg gttttggggt tgctcggcgc ggttgcgagc 60
agtgccgtgg ttgccgccag cagcggccag gacagtgccc gggaggaaat tgccgcccag 120
gcaaaaatcc tcgaacccag cctgttggaa acccgccgcg atatccacgc ccatcccgaa 180
ctgggcaata ccgaaacccg caccgccgag ttggtcgcca aacagttgcg cgaactcggc 240
cttgaagtaa agaccggggt ggcccgcact ggcgtcgtcg ccatcttgaa aggtgccctg 300
cccggcccga ccgtggccct gcgcgccgac atggatgcgc tgccggtcaa ggaagtcgcc 360
gacctgccct tcgcctccaa agccaagggc acctacctgg gcaaggaagt cgacgtgatg 420
cacgcctgcg gccacgacgc acataccgct atcctgctga gcactgcgaa gattcttacg 480
gggatgcgcg agcgcctgcc cggcaccgtg gtgttttatt tccaaccggc cgaagaaggc 540
cccagcgact ttatccccga cggcaagaac acttggggcg cgaagatgat ggtgcaggaa 600
ggcgtaatga aagcgcccaa gccggatgcg gtgtttggcc tgcacgtatg ggccggtgtg 660
cctgccgggg caaatcgcct atcgcccggg cccgactttg gccagctccg a 711

<210> SEQ ID NO 136
<211> LENGTH: 720
<212> TYPE: DNA
<213> ORGANISM: Pseudomonas fluorescens

<400> SEQUENCE: 136
atgcggtgtt tggcctgcac gtatgggccg gtgtgcctgc cggggcaaat cgcctatcgc 60
ccgggcccga ctttggccag ctccgatgac ctgcgcatca aaatcctcgg caaacagacc 120
cacgccggcc gcccctggga cggtatcgac ccgatcaccg tcggcgcgca aaccattgtc 180
ggcctgcaga ccgtggtcag ccgccgtacc gatatttcgt cattcccctc tgtggtgagc 240
atcggcacca tcaacggtgg cactcgctac aacatcatcc ccgagtcggt ggacatgagc 300
ggcacccttc gctcctacga ctacggcatt cgtcagaagc tgcatgcaga cgtgcgtcaa 360
accgtagaga aaatcgccga aagcggtggc gccaaggccg aagtgacaat catcgagaag 420
tacgacccca ccatcaacaa cccggcgctg accgagaaaa tgctgccgag cctgcgttgg 480
gcggctcagg atgatgtggt gcaaggccca ttggtaggtg gcgccgaaga cttctcgttc 540
tatgccaagg aagcgccggg gctgtttgtg ttcctggggg tgaccccaag ggaccaggac 600
atgagcaagg cggcgccgaa tcacaaccca gggttctttg tggatgagtc ggcattggtg 660
gtgggcgtga ggacactggc gtcgttggcg acggattacc tttacaccca cacccccctg 720

<210> SEQ ID NO 137
<211> LENGTH: 870
<212> TYPE: DNA
<213> ORGANISM: Pseudomonas fluorescens

<400> SEQUENCE: 137
ctggcgactc tggttgtgaa caacatgcgt ggtatcgtca aggttgcagc cgtcaaggct 60
ccaggcttcg gcgaccgtcg caaggccatg ctgcaggaca tcgccgtatt gactggcggt 120
accgttatct ccgaagagat cggcctgagc ctggaaagcg ccaccctgga aaacctgggt 180
agcgccaagc gcgtgaccat ctccaaggaa aacaccatca tcgttgacgg tgctggcgtt 240
gaaggcgaca tcgagtcccg catcgcgcag atccgtgccc aggttgctga aacctcctcg 300
gactacgacc gtgaaaaact gcaagagcgc ctggccaagc tgtccggcgg cgttgcggtg 360
atcaaggttg gcgctggttc cgaagttgaa atgaaagaga agaaggcccg cgttgaagac 420
gccttgcacg caacccgtgc agccgttgaa gaaggcgtgg tacctggcgg tggcgttgcg 480
ctgatccgtg ctctggaagc cctgaccaac ctgaccggcg acaatgccga ccagaacgtt 540
ggtatcgctg tgctgcgtcg tgccgttgaa gcaccgctgc gccagatcgc tgccaactcc 600
ggcgacgagc caagcgttgt ggtcaacgaa gtcaagaacg gcaaaggtaa ctacggttac 660
aacgctgcga ctggcgtcta cggcgacatg atcgaaatgg gcatcctgga tccaaccaag 720
gtgactcgtt cggcgctgca agcagcagcc tccatcggtg gcttgatcct gaccaccgaa 780
gctgccatcg ctgacaagcc gaaggctgaa ggcgcagctg gcggcggtat gccagacatg 840
ggcggcatgg gtggcatggg cggcatgatg 870

<210> SEQ ID NO 138
<211> LENGTH: 855
<212> TYPE: DNA
<213> ORGANISM: Pseudomonas fluorescens

<400> SEQUENCE: 138
atgtcactaa atttcccgct gttgctggtc attgccgttg ccgtctgtgg tctcctggcg 60
ttgctcgatc tggtgttctt cgccccgcgt cgtcgggcgg ccattgcttc ctatcagggc 120
agcgtcagcc agcccgatgc ggtggtggtc gagaagctga acaaagagcc cttgctggtt 180
gagtacggca agtcgttctt cccggtgttg ttcatcgtgc tggtgttgcg ctcgtttctg 240
gtagagccgt tccagatccc ttcggggtcg atgaaaccga ccctggacgt gggcgacttc 300
atcctggtga acaagttttc ctacggcatt cgtctgccgg tgatcgacaa gaaagtcatc 360
cccgtgggtg acccgcagcg cggcgatgtg atggtgttcc gctacccaag cgacccgaac 420
gtcaactaca tcaagcgtgt ggtcggcctg ccgggcgacg tggtgcgcta caccagtgac 480
aagcgcctgt tcatcaacgg tgagtcggtg gccgagaagc tgctgggcgc cgagccgaac 540
accctgggca gcgccgagct gtaccaggaa aaactcggcg cggtggagca ccaaatccgc 600
aaggaaatga gccgctaccg tgcgatgccg gatggccagt ggaaagtgcc tgccgggcac 660
tactttatga tgggcgacaa ccgcgacaac tccaacgaca gccgctactg ggatgacccc 720
aacattccca aagacctgct gggcatggtg cccgacgaga acattgtcgg caaagccttc 780
gcggtctgga tgagttggcc ggaacccaag ctcagccacc tgccgaactt ctcgcgggtc 840
gggctgatca agtaa 855

<210> SEQ ID NO 139
<211> LENGTH: 771
<212> TYPE: DNA
<213> ORGANISM: Pseudomonas fluorescens

<400> SEQUENCE: 139
atgatcaaga cccccgcaca gttggccgta atgcgtgaag ccgggcgcct gttggcgcag 60
gtcttcgaca tgctcgacgg cttcgtcgcc gccggccgct ctaccctgga gctggacagc 120
gccgtcgaag ccttcatccg caatgacctc aaggcccgcc ctgccagcct ggggcagtac 180
gactacccct tctgcatcaa cacctcgatc aacgaagtgg tgtgccacgg catgcccagc 240
gccaagcaat tgctcaagga cggcgacatc atcaacatcg acatcaccct ggaaaaaggc 300

-continued

```
ggcttcattg ccgactccag caagatgtac atgatcggca acgtgacgcc caaggccagg    360

cgcctggtgg acatgacctt cgaggcgatg tgggccggta tccgccaggt caagcccggc    420

gcgcgcctgg gcgatatcgg ccatgcgatc cagagccacg cgcaagccaa tggctacagc    480

gtggtgcgcg aatactgcgg ccacggcatc ggccggcaaa tgcacgaaga accgcaaatc    540

ctgcacttcg gccgccccgg caccggcctg gaactgcgcg aaggcatggt gtttaccatc    600

gagccgatgc tcaaccaggg cagcgccaaa acccgcagcc tgaaagacgg ttggacggtg    660

gtcaccaagg acaacagcct ctcggcgcaa tgggaacata ccgtggcggt gacggcggat    720

gggtttgaag tgctgacctt gcaaacccct caaaaccttc acaccctgta g             771
```

<210> SEQ ID NO 140
<211> LENGTH: 1863
<212> TYPE: DNA
<213> ORGANISM: Pseudomonas fluorescens

<400> SEQUENCE: 140

```
atggctctac tgcaaatcgc cgaacccggc caaagccctc aaccgcacca gcgtcgcctg     60

gcggtcggga ttgacctggg caccaccaat tccctggttg ctgccttgcg cagcggcctg    120

tccgagccac tgcctgacgc cgatgggcag gtgatcctgc cgtccgccgt gcgttatcac    180

gccgaccgca ctgaagtggg cgaatcggcc aaattggccg cgtccgcaga ccctttgaac    240

acggtgttgt cggtcaagcg cttgatgggt cgtgggttgt ccgacgtcaa gcaattgggc    300

gaccaactgc cgtaccgctt tgtcggcggt gaatcccata tgccgttcat cgacaccgtc    360

caggggccca agagcccggt ggaagtgtcg gctgatatcc tcaaggtgct gcgccagcgt    420

gcagaaagca ccctgggcgg tgagctggta ggggcggtga tcactgttcc ggcgtatttc    480

gatgacgccc agcgccaagc caccaaggat gcggcgaaac ttgccggctt gaacgtgctg    540

cgcttgctca acgaaccgac tgcggcggcg gtggcctacg gcctcgatca gcacgctgaa    600

ggcctggtcg ctatttatga cctgggcggc ggcaccttcg atatttcgat cctgcgcctg    660

accggcggtg tgttcgaagt gctcgcgacc ggcggcgaca gcgccctggg tggcgatgat    720

ttcgatcacg ctattgctgg ctggatcatc agcagtgctg gcttatcggc cgacctggac    780

ccaggcgcgc agcgcaacct gctgcaaact gcctgcgcgg ccaaagaggc gctgactgac    840

gctgcttctg ttgaagtgtc ctacggtgac tggtcggcac agctgacccg cgaagccttt    900

gatgcgctga tcgagccgat ggtcgcccgc agcctcaaag cctgtcgtcg tgctgtgcgt    960

gattccggta tcgagttgga agacgtcggt gcagtggtca tggtcggcgg ttccacccgc   1020

gtgccgcgcg tgcgcgaagc ggtcgccgaa gcctttgggc gccaaccgct gaccgaaatc   1080

gacccggatc aagtggtcgc catcggcgct gccatccagg ccgataccct ggctggtaac   1140

aaacgcgatg gcggcgaatt gctgttgctc gacgtgatcc cgttgtccct gggcctggaa   1200

accatgggtg gcctgatgga gaaggtgatt ccgcgcaaca ccaccattcc cgtcgcccgt   1260

gcccaggact tttctaccta caaagacggc cagacagcga tgatgattca tgtgctgcaa   1320

ggtgagcgcg agctgatcag cgactgccgt tccctggcgc gctttgaatt gcgtggcatt   1380

ccggcgatgg tggccggtgc cgccaagatt cgcgtgacct tccaggtcga tgccgatggc   1440

ttgctcagcg tggctgcgcg tgagctggct tcgggcgtgg aggccagcat ccaggtcaag   1500

ccgtcctacg gcctcaccga tggcgaaatc gccaagatgc tcaaggattc gttccagtat   1560

gccggtgacg ataaggtcgc ccgtgtatta cgcgagcagc aagtagatgc ccagcgcctg   1620

ctcgaagcgg tgcagggtgc ccttgaagcc gatggcgagc gcctgctgga tgccgaagaa   1680
```

cgcatggtca ttgacctgca aatgcaggaa ctggccgaac tgatgaaagg caacgatggc 1740
tacgccatcg agcaacagac caagcgcctg tcgcaagtga ctgatgcctt tgccgcccgc 1800
cgtatggatc agacggttaa agccgcgctg gcgggccgca acctgaatga aattgaggaa 1860
taa 1863

<210> SEQ ID NO 141
<211> LENGTH: 783
<212> TYPE: DNA
<213> ORGANISM: Pseudomonas fluorescens

<400> SEQUENCE: 141
atgaccgtta ccttgaaaac cgccgaagac atcgcaggca tgcgcgttgc cggcaaactg 60
gctgccgacg tgctggaaat gatcgccgaa cacgtcaagc ccggcgtcac caccgaagcg 120
ctggaccgca tctgccacaa ctatatagtc gacgtgcaaa aagccatccc tgccccgctg 180
aattacaaag gcttccccaa gtcgatctgc acctcgatca accacgtggt ctgccacggc 240
attcccggtg acaagccact gaaggacggc gacaccctga acatcgacgt cacggtgatc 300
aaggacggct accacggcga caccagccgc atgttccacg tcggcaatgt accggtgtgg 360
gccgagcgcc tgtcccaggt cacccaggaa tgcatgtaca aggccatcga aatcgtcaag 420
cccggctgcc gcctgggtga catcggtgaa gtgatccaga agcacgcgga aaagaacggt 480
ttctcggtgg tgcgcgaatt ctgcggccac ggtatcggca aagtgttcca cgaagagccg 540
cagatcctgc actacggccg cgccggaacc ggcatggaac tcaaggcagg catgaccttc 600
accatcgagc cgatgatcaa ccagggcaag gccgacacca aggtgctggg cgacggctgg 660
accgccatca ccaaggaccg caagctctcg gcccagtggg aacacaccct gctggtcacc 720
gacaccggct atgagatttt caccctgcgc gccgacgaca ccatcccacg cgtttcggcc 780
tga 783

<210> SEQ ID NO 142
<211> LENGTH: 1182
<212> TYPE: DNA
<213> ORGANISM: Pseudomonas fluorescens

<400> SEQUENCE: 142
atgcaaaaaa ccagtgccac gctgctgata atcgatgacg acgaagtagt gcgcgcgagc 60
ctcgcggcct acttggaaga cagtggcttc agcgtcctgc aggccagtaa tggccaacag 120
ggtctccagg tattcgagcg cgacaagccc gaccttgtga tctgcgacct tcgcatgccc 180
cagatgggcg gcctggagct gattcgccag gtgaccgacc ttgccccgca aacgccggtg 240
attgtcgtgt ccggtgccgg tgtcatgaac gatgccgttg aagccttgcg cctgggcgcc 300
gccgattacc tgatcaaacc cctggaagac ctggccgtgc tggagcactc ggtgcgccgc 360
gccctggacc gtgcacgcct gctcctggaa aaccagcgct accgcgaaaa gctcgagacc 420
gccaaccgcg aacttgaagc cagcctgaac ctgctgcagg aagaccagaa cgccggtcgc 480
caggtgcaga tgaacatgct gccggtcagc ccctggacca ccgacgaatt caagttcgcc 540
caccagatca tcccgtcgtt gtacctgtcg ggtgattttg tcgactattt ccgcgtcgat 600
gagcggcgcg tagcgttcta cctggccgac gtttccggcc acggcgcgtc ttcagcgttt 660
gtgaccgtgt tgttgaagtt catgaccaca cggctgttgg tcgagtccaa gcgcaatggc 720
accttgccgg agttcacccc ctccgaggtg ctgggccaca tcaaccgagg cctgatcagc 780

```
tgcaagctgg gcaagcacgt gacgatggtc ggcggcgtga tcgacgaaga aaccggtctt    840

ttgacctaca gtattggcgg tcacctgccg atgcctgttt tatacactcc tgacagtgtg    900

cgctacctgg aagggcgtgg cctgcccgta ggcttgttta acgaagccac gtacgaagac    960

cacatcctag aattgccgcc gaccttcagc ctgacgctgc tgtccgacgg aattctggac   1020

cttcttccag agcctacact caaagagaaa gaagccgcct tgccccaaaa ggtcaagtcg   1080

gcgggcggca gcctggatgg cctgcggcag gtttttggat tggccacgct aggggagatg   1140

ccggatgata tcgccctatt ggtgttgagc aggaatcttt ga                      1182
```

<210> SEQ ID NO 143
<211> LENGTH: 339
<212> TYPE: DNA
<213> ORGANISM: Pseudomonas fluorescens

<400> SEQUENCE: 143

```
atgagctttt ttatctctaa cgccatggct gacgccgctg cgcctgctgc tgccggccct     60

atgggcggtg gtttcgagtg gattttcctg gtcggcttcc tggtcatctt ctacctgatg    120

atctggcgtc cacaggccaa gcgcgccaaa gagcagaaaa acctgctggg cagcctgcaa    180

aaaggcgacg aagtcgtgac cactggcggc atcgccggca agatcaccaa ggtttccgat    240

gctttcgtgg tactggaagt ctccgacacc gtggaaatga agttccagaa gggcgccatc    300

gccgccacgc tgcctaaagg cacgctcaaa gcgatctaa                           339
```

<210> SEQ ID NO 144
<211> LENGTH: 435
<212> TYPE: DNA
<213> ORGANISM: Pseudomonas fluorescens

<400> SEQUENCE: 144

```
atgtccgcac ctcttgtaat cccctgccca cattgcaacg gcctcaaccg catccccggc     60

gaacgcctgg gtgacgcgcc caagtgtggg cgttgcaagc agtcggtgtt gctgagcaaa    120

ccctttgatt tgaaacaggg tgactatgcc agccagatca agggcgacct gccgcttttg    180

gtcgatgtgt gggccgactg gtgcgggccg tgcaagtcgt ttgcgccggt attcgaacag    240

gccgccgggc agttggaagg caagtgccgg ctggcgaagc tggacagtga agctaaccag    300

cacctgtcgg cgcagttggg gattcgctcg attcccagtt tgattctgtt caagaacggc    360

cgcgaagtgg cgcgccagag tggggcattc ccgttgccgc agttgatgag ctggttgcgt    420

agccaggggg tgtaa                                                     435
```

<210> SEQ ID NO 145
<211> LENGTH: 1359
<212> TYPE: DNA
<213> ORGANISM: Pseudomonas fluorescens

<400> SEQUENCE: 145

```
atggcctacg attttgacct gtatgtaatt ggcgccggtt ctggcggtgt tcgcgcggcg     60

cgctttgccg ctggctttgg cgccaaggtg gccgtggcgg agagccgcta cctgggtggc    120

acctgcgtga acgtcggctg tgtgccaaag aagctgttgg tgtatggcgc gcattttgcc    180

gaggattttg agcaggccag tggctttggc tggtccctgg gcgaggcgaa ctttgattgg    240

gcgaccttga tcgccaacaa ggatcgcgag atcaaccgcc tcaatggcat ctatcgcaac    300

ctgttggtca acagcggcgt gaccctgcat gaagggcatg cacgcctggt tgatgcccac    360

caggtggaga ttaacggtga gcgcttcact gccaagcaca tcctgatcgc caccggcggc    420
```

tggccgcaga tccctgagat tccagggcgc gagcacgcca ttggttccaa tgaggcattc 480
ttcctcaaag agctacctaa gcgcgtgctg gtagtgggcg gtggctatat cgccgtcgag 540
ttcgccggca tcttccacgg cttgggtgca caaacttcat tgctgtatcg cggcgacttg 600
ttcttgcgcg gctttgatgg ctcggtgcgc aagcatctgc aagaagagct gaccaagcgc 660
ggcctggact tgcagttcaa tgccgacatc gagcgcatcg ataagcaagc cgacggcagc 720
ctcaaggcca cgttgaagga tggtcgcgtg ctggaagccg attgtgtgtt ctacgccacc 780
ggccgccgcc caatgctgga taacctgggc ctggaaaaca ccggggtcaa actggacgag 840
cgcggtttcg tcgcggtgga tgatctctac cagaccgccg agccgtcgat cctggcgatt 900
ggcgatgtga ttggtcgtgt gcagctgacg ccggtggctc tggctgaagg catggccgtg 960
gcgcggcggt tgttcaagcc cgagcaatac cggccggtgg attacgccaa tatcgcgacg 1020
gcggtgttca gcctgccaaa tatcggcaca gtcggtctga cggaagagga tgcacgcaag 1080
cacggccaca acgtgcagat ctttgaaagc cgtttccggc cgatgaagct gaccctcacc 1140
gattgccagg aaaagaccct gatgaagctg gtggtcgacg ccgacaccga caaagtgctg 1200
ggttgccaca tggtcggccc ggatgcgggt gaaatcgtgc aagggctggc gatcgcgctc 1260
aaggcgggcg cgactaagca gcatttcgac gaaaccatcg gcgtgcatcc tacggcggcg 1320
gaagaattcg tcaccatgcg cacgcccgtg gcggactga 1359

<210> SEQ ID NO 146
<211> LENGTH: 1584
<212> TYPE: DNA
<213> ORGANISM: Pseudomonas fluorescens

<400> SEQUENCE: 146
ttgagcgaac ttctcaaccg ccgcctggcc ctgctcggca agcgcgaaca cctctccctg 60
ctagagcagt gcttgcacgg catcgagcgc gaatgcctgc gcgtcaccag tgagggtcgc 120
ctggcacaaa cgccacaccc cgaagcattg ggcgccgcgt tgaccaacga acagatcacc 180
actgactact cggaatctct gctggagttc atcaccccag ccctgcccaa cccggccgag 240
accctgagca gcctggacaa gatccatcgc tttgcctact ccaagctggg cagcgaatac 300
ctctggagcc cctcgatgcc gtgcccgttg ccggccgagg aagatatacc gattgcctac 360
tacggcacct ccaatatcgg tcagctcaag tacgtgtacc gcaagggcct ggccctgcgt 420
tacggcaaga ccatgcagtg catcgcaggc atccactaca acttttccct cccggaagcg 480
ttgtggccgt tgctcaagga aacagaaggg tttgtcggca ccgaccgtga ctatcagtcc 540
acggcctaca tcgcgctgat ccgtaatttc cgacgctaca gttggctgtt gatgtacctg 600
ttcggtgcct cgccagccct ggacgccggc ttcctgcggg ggcgctcgca ccagcttgaa 660
gtcctcgacg ccgacaccct gtacctgccc tacgccacca gcctgcgcat gagcgacctg 720
ggttaccaga gcaatgccca ggccggcctg acgccgtgct acaacgactt ggccagctac 780
accgatagcc tgcgcgaagc ggtggcaacg ccctacgcgc cgtacgttga agtcggcacg 840
cacaaggatg gcgagtgggt gcagctgaac accaacatcc tgcagatcga aaacgagtac 900
tactccaaca tccgtcccaa gcgcgtgacc tacactggcg agcggccgat ccaggcgttg 960
atggcccgcg gcatccagta catcgaagtg cgctgcctgg acatcaaccc gttcttgccg 1020
atgggtatcg acctgccgga atcacgtttc ctcgacgcgt tcctgctgta ctgcgcactg 1080
aacgacagcc cgctgttcgc caacaacgag tgcggcaacg ccagctccaa cttcctcagc 1140

```
gtggtcaagg aaggccgccg tccgggcctg caattgcagc gtgacggcca gccggtggac   1200

atgaaggagt gggcggccga gttgctggag aagattgccc cgctggccgc cctgctcgat   1260

cagagccatg gcatcactga gcacagcgag gcactggacg cccagttggc caaggtcaag   1320

gacccgtccc tgacgccgtc ggcccaggta ttggcggcca tggccgagcg caaggatagc   1380

tttgcgcagt tctccctgca tcaaagcgaa gtgcatgctg aatacttccg caaggagcct   1440

ttggcgcctg aggaacaagc gcactttgaa gaactggccc gtgcgtcgct ggcgcaacag   1500

gcggagctgg agcagaacga agtgggcgat ttcgacgtgt ttgtcggctc gtaccaggca   1560

agcatcctgg ccatcagcaa ctaa                                          1584
```

<210> SEQ ID NO 147
<211> LENGTH: 507
<212> TYPE: DNA
<213> ORGANISM: Pseudomonas fluorescens

<400> SEQUENCE: 147

```
atgattgacg acatgcgttt aggcagggag cggcgctttc tggtgttgct gggcatcatc     60

tgcctggcgc tgattggcgg ggcgctgtac atgcaagtgg tgctgggaga agcaccgtgc    120

ccgctgtgca ttctgcagcg ctacgccttg ctgctgattg cgctcttcgc gttcatcggc    180

gccgccatgc gcaccaaggg cgcgctgacg ttctttgaag ggttggtggt gctcagcgcc    240

ttgggtggcg tggctgcggc cggccatcac gtgtacaccc agttcttccc ccaggtcagc    300

tgcggtatcg atgtgttgca accgatcgtc gacgacctgc ccctggccaa ggtgtttccc    360

ctgggcttcc aggtcgacgg cttctgcagc accccctacc caccgattct cggcctgtct    420

ctggcccaat gggcactggt ggcattcgtg ctgacggcga tcctggtgcc cctatgcatc    480

tatcgcaacc gtcaccccaa agcctga                                        507
```

<210> SEQ ID NO 148
<211> LENGTH: 1728
<212> TYPE: DNA
<213> ORGANISM: Pseudomonas fluorescens

<400> SEQUENCE: 148

```
atgcggcatc tgtttacctt tctgctggtg ttgttcgcgg gattcgccca ggcagcgccg     60

ggcagcccct tcgaaaccaa acccgacttc ctcccggtgg gcaaagcctt cgcctttacc    120

tccgaacgtc ttgaaagcgg cgaaacccag ctgttttggc agattgccga cggttactac    180

ctgtaccagc agcgcatgaa gttcgacggc ctggccgaaa agcccgtgct gcccgagggt    240

gaagcccata gcgacgagtt ctttggcgag cagcaagtgt atcgccaggg cctggaagtg    300

aagatccccg ccggcaccac cggccaggtc aagctcggct ggcagggctg cgccgatgcg    360

ggcctgtgct atccaccgca gtcgatcacc gtggacctgg gcggcaaccc ggccgtcgcc    420

gccaccgcgc aagcccagga tcaaagcctg gccagcggcc tgcaacagcg cagcctgggg    480

tggagcctgc tggtgttctt cggcctgggc ctgctgttgg cgtttgcgcc ttgctcgttg    540

ccgatgctgc cgatcctcgc cggcctggtg gtgggcagtg gcgccagccc gcgccgtggc    600

tttgccctgg ccggcagcta cgtcgtgtgc atggcgctgg tatatgccgc cttgggggtg    660

atggccgcgt tgctcggcgc caaccttgcc gcacttttgc aaacgccgtg gatcctcggc    720

agctttgcgg cgttgttcgt gctgctcgct ctgccgatgt tcggcttctt tgaattgcaa    780

ctgcccgcct tcctgcgcga ccgcctcgat aacgtcagcc gccagcaaag cggtggcagc    840

ctggtgggtg ccggtgtgct cggcgcgttg tccggcctgc tggtgggacc gtgcatgacc    900
```

```
gcgcccctgg ctggcgccct gctgtacatc gcccagagcg gcaatgcgct gcacggtggc    960
ctgatcctgt ttgccatggg catcggtatc ggcattcccc tgttgttgct ggtgaccgtg   1020
ggcaatcgct tcctgcccaa gccgggcacc tggatgaacg tgctcaaggg catcttcggt   1080
ttcctgttcc tgggcactgc ggtgctgatg attcgcccgg tggtcggcga cagcctgtgg   1140
atcggcctgt ggggcgcctt ggcgctggtg atggcgtact gtggctgggc gctggcccgt   1200
gagtccggcc tggcggccaa ggtatttggc gccggttccc tggtgctggg cctgtggggc   1260
gcggtgctgg tggtgggtgc ggccggtggc agcgatgagc tgtggcaacc gttgaaggtc   1320
tacagcggct ctcgggtcgc cgatgcaccc agcgctcacg atgccttcac cacggtcagc   1380
gatccggcag tattgcaaag ccaactcgac agcgccaagg cccagggcca gtgggtgctg   1440
ttggactact acgccgactg gtgcgtgtcg tgcaagatca tggaaaaaca ggtgttcggc   1500
aaacccgagg tgatggacgc gctcaaagac gtgcgcctgt tacgcctgga cgtcaccgcc   1560
gacaacgccg ccagccgcga gctgctgggc cgctacaaag tgccggggcc accgagcttc   1620
gtgtggatcg gcccggacgg tgaagaacgc cgcgcccaac gcatcaccgg cgaagtagac   1680
gccgccgcct tcctgcaacg ctggacacaa acccgagacg cgcgctga                1728
```

<210> SEQ ID NO 149
<211> LENGTH: 1869
<212> TYPE: DNA
<213> ORGANISM: Pseudomonas fluorescens

<400> SEQUENCE: 149

```
atgctgaaca aataccctct gtggaaatac gtactgatcc tggcggtgct ggcgatcggc     60
tttatttatt ccgctcccaa tctctatcct gatgacccgg cgatccagat ctctggcgcc    120
agcacttcgc tgcaggtcaa tcaggctgat ctggaccgtg cgagcaaagc gctcaacgac    180
gcgggtatcc aggttaaagc ggcaaccttg gcagctggtt ccaaaggcgg cttgttgcgc    240
ctgaccaagc aagaagacca attgccggcc aaagatgtcg tacgcaaggt catgggtgat    300
gactacgttg tcgcgctcaa cctggcccag accacgccac aatggctgcg cagcattggc    360
gcgcacccga tgaagctggg tctggacttg tccggtggtg tgcacttcct gctggaagtc    420
gacatggaca aggccctgga cgcacgtctg aaagtctacg aaggcgacgt gaagagcctg    480
ctgcgcaaag agaagctgcg ctatcgcagc ctgccgcagc tcaacggtgc cattcagctg    540
ggctttgctg acgaagcatc ccgcgaacag gcccgtgcgc ttatccgcaa gaacttcaat    600
gatttcgaca tcgtgcctgc cgacctcaat ggtcaagcgg tactgcgtct ggcgatgagc    660
ccggccaaga tcgccgaaat ccgcgaatac tccatcaagc agaacttgac cacggtgcgt    720
aaccgcgtca acgagctggg tgtggccgag ccgatcgtgc agcgccaggg cgccaaccgt    780
atcgtggttg agttgccggg cgtacaggac accgctgaag ccaagcgtat cctcggcaag    840
accgccaacc tggagttccg tctcgcggca gacccaggcg ctacgcgtgc cacttccgaa    900
gagttcgaat tccgtgaagg caaccgtcct cctgcgttga tcgagcgtgg tttgatcatc    960
accggtgacc aggtgaccga cgccaaggcc ggtttcggcg agcacggtac gcctgaagtg   1020
aacatccgcc tggatggcca tggcggcgaa ctgatgagcc gcgccacgcg cagcaacgtc   1080
ggtcgcagca tggcagtgat cttcatcgag cagcgcccgg tgaccaccta caccaagcag   1140
atggtcaacg gcgtcgagaa agacgtgccg gtgcagacct tcaaggaaga gaagaagatc   1200
atcagcctgg cgaccatcca gtcgccgctg ggtgctcagt tccgtatcac tggcctgaac   1260
```

ggccagggcg agtcgtccga gctggcgttg ctgctgcgtg ccggtggcct ggctgcaccg 1320
atgtacttcg ctgaagagcg taccattggc ccgagcctgg gtgccgacaa catcaccaag 1380
ggtgtcgatg cggcgctgtg gggcatgttg ttcgtgtcgc tgttcatcat cgccatctac 1440
cgcttctttg gtgtgatcgc caccgttgcc ctggcgggca acatggtgat gttgctggct 1500
ctgatgtcgt tgctgggtgc cacactgacc ctgccaggta ttgccggtat cgtactcacc 1560
atgggtatgg cggtggatgc caacgtgctg atcttctcgc ggattcgtga agagatcgcc 1620
gccggcatga ccgtgcagcg tgcaatcaac gaaggcttcg gccgggcatt taccgcgatc 1680
ctcgactcca acctgaccac gctgttggtc ggcgggattc tcttcgccat gggcacaggc 1740
ccggtgaaag gctttgcggt gaccatgtcc ctcgggatct ttacctcgat gttcacggcc 1800
atcatggtga cccgcgcaat ggtcaacctg atctttggcg ggcgtgactt caagaagttg 1860
tggatttaa 1869

<210> SEQ ID NO 150
<211> LENGTH: 915
<212> TYPE: DNA
<213> ORGANISM: Pseudomonas fluorescens

<400> SEQUENCE: 150
atgttacgta caatcaactt catgggcgtt cgcaacgttg cgttcggcgt caccgtgctc 60
cttaccgttc tggcgttgtt cagctggttc cataagggtc tgaactacgg cctggacttc 120
accggcggta cgctcatcga gctgacctac gagaagccgg ccgacgttac cctggtgcgc 180
agcgagctgg tcaaggccgg ctatcacgaa gccgtggtac agagctttgg tgccaccacc 240
gacctgctgg tgcgtatgcc tggcgaagac ccgcaactgg gtcaccaggt agccgaggcc 300
ttgcaaaagg tcggcggcga taaccctgcg tcggtcaaac gcgtcgagtt cgtcggcccg 360
caagtgggtg aagaactgcg cgatcagggc ggcctcggca tgctgatggc gctggtcggc 420
atcatgatct acctggcgtt ccgctttcag tggaagttcg gtgtcggcgc cattgtgtcg 480
ctgatccacg acgtggtcgt caccgtgggt atcctggcct acttccagat caccttcgac 540
ctgaccgtat tggcagctgt gctggcgatc attggttact cgctcaacga caccatcgtg 600
gtattcgacc gagttcgtga gaacttccgt gtactgcgca aggcgacgtt gatcgagaac 660
atcaacatct ccaccaccca gaccctgctg cggaccatgg cgacgtcgat ctccaccttg 720
ctggcgattg ctgcgctgat gatcttcggc ggcgacaacc tgtggggctt ctccctggcg 780
ctgtttatcg gcgttctggc gggtacctac tcgtcgatct acatcgccaa cgtggtgctg 840
atctggctga acctcaacag cgaagacttg atccctcctg ccgctaccga caaggaggtc 900
gacgaccgtc cttga 915

<210> SEQ ID NO 151
<211> LENGTH: 906
<212> TYPE: DNA
<213> ORGANISM: Pseudomonas fluorescens

<400> SEQUENCE: 151
atgagaatcc tcggcatttt atgcctgcta ctcacattga acggctgcag ctccttactg 60
ttctaccccg agcccggcct gcccttcact ccggaaaaag cccacctgca ataccgcgac 120
gtcacgctca ccaccgcaga cggggtgaag ctgcacgctt ggtggttgcc agccaaagcg 180
ggtgtgccac tcaaaggcac catcctgcat ttgcacggca acggcggtaa cctcgcctgg 240
cacctggggg gcagttggtg gttgccggag cagggttatc aagtgttgtt gctggactat 300

```
cgcggctatg ggctgtcgga aggcaagcca tcgttgccgg cggtctacca ggatatcgac    360

gccgcattcg gctggatcga caaggcgcct gaaacccagg gtaaaccgct gattattctc    420

gggcaaagcc tgggcggtgc actggcggtg cattacctgg cagcccaccc ggagcgtcaa    480

gcccaactca aagctctggt actggacggc gtgccagcca gttatcgtga cgtaggacaa    540

ttcgccttga gcacttcctg gttaacctgg ccgttgcagg tgccgctgtc atggctggtg    600

cccgacgccg acagtgcgat caatgccatg ccccgcgtga ccggcgtgcc caagctgctg    660

ttccacagcc tggatgatcc catcgtgccg gtggccaatg gcatccgcct gtatcaggcc    720

gcaccgccgc ccagggtgtt gcaactgacc cgtggcggcc atgtgcagac ctttgccgat    780

aaaacctggc agaccgtgat gctgcgttac ctggacgacc cgcagcactt caacggcttg    840

cgccgcctgg gcgaaattcc gaattaccct attcctaaag ttgattcatc agagagcccg    900

caatga                                                               906
```

<210> SEQ ID NO 152
<211> LENGTH: 1338
<212> TYPE: DNA
<213> ORGANISM: Pseudomonas fluorescens

<400> SEQUENCE: 152

```
atgtccatga ctccccgcga aatcgtccat gaactcaatc gccatatcat cggccaggac     60

gatgccaagc gcgccgttgc cattgcgctg cgtaaccgct ggcgccggat gcaactgccg    120

gaagaactgc gcgttgaagt aacgcccaag aacatcctga tgatcggccc caccggcgtg    180

ggtaaaaccg agatcgcccg gcgcctggcc aaactggcca atgcaccgtt catcaaggtc    240

gaagcgacca agttcaccga agtcggctat gtgggccgcg atgtcgagtc gatcattcgt    300

gacctggctg acgccgccct gaagatgctg cgcgaacagg aagtaaccaa ggtcagccac    360

cgcgccgaag acgccgctga agagcgcatc ctcgacgccc tgttgccacc ggcacgcatg    420

ggtttcaacg aagacgccgc accggctacc gattccaaca ctcgccagct gttccgcaag    480

cgcctgcgtg aaggccagct ggatgacaag gaaatcgaga tcgaagtggc tgaagtgtcc    540

ggcgtggata tttctgcccc gcctggcatg gaagaaatga ccagccagct gcagaacctg    600

ttcgccaaca tgggcaaggg caagaagaaa agccgcaagc tcaaggtgaa agaggcgctc    660

aagctcgtgc gcgacgaaga agccgggcgc ctggtcaatg aggaagaact caaggccaag    720

gccctggaag cggtcgagca acatggcatc gtgtttatcg acgagatcga caaagtggcc    780

aagcgaggca actcaggcgg cgtggatgtg tcccgcgaag gcgtgcagcg cgatttgctg    840

ccgctgatcg agggctgcac ggtcaacacc aagctgggca tggtcaagac tgaccacatc    900

ctgtttatcg cttccggtgc tttccacctg agcaagccca gcgacctggt gcccgagctg    960

caaggccgct tgccgattcg ggtggagctc aaggcgctga cgccgggcga cttcgagcgc   1020

atcctcagcg agccgcatgc ctcgctcacc gagcagtacc gcgagttgct gaaaaccgaa   1080

gggctgggta tcgaattcca ggcagacggg atcaagcgcc tggcggagat cgcctggcag   1140

gtcaacgaga agaccgagaa catcggtgcc cgtcgcctgc ataccttgct tgagcgcctg   1200

ctggaggaag tgtccttcag tgccggcgac atggccggtg cgcagaatgg cgaagcgatc   1260

aagatcgatg ctgattacgt caacagccac ttgggcgaat tggcgcagaa cgaagatctg   1320

tctcgttata tcctgtaa                                                 1338
```

<210> SEQ ID NO 153

<211> LENGTH: 1533
<212> TYPE: DNA
<213> ORGANISM: Pseudomonas fluorescens

<400> SEQUENCE: 153

```
gtgaagtcct ctcatgccga tgcgaactcg gcggcagaca accaggcctc gacaggatcc     60
aagttgctta atctttccgc tccgctggta ggtgaccgca ctggcctgca gcgactgtat    120
ggatcgagcc tgaactccgg actgcttcaa ctaggggaag tgaattctgg caaagtggtt    180
atcgctcgtt gttccccgaa ggcagaggaa gataccaaac cggcagcgga tgagcccaag    240
ccgaatggtg acaccaagcc agtaacggat aagcccaagc cgggcggctt ctccacgcca    300
gtaacagata ggcccaagcc acgcggcggc accaaggagc cggtggttga gcagcccaag    360
ccagagggca ccaagcagcc agtggttgag cagcccaagc cagagggcac caagcagcca    420
gtggtagatc agcccaagcc agaaggtacc aaggggccgg tggttgagca gcccaagccc    480
gagggcacca aacagccagt ggtagatcag cccaagccag cgggcactaa gcagccagtg    540
gtagatcagc ccaagccagc gggcactaag cagccagtgg tagatcagcc caagccagcg    600
ggcactaagc agccagtggt agatcagccc aagccagcgg gcactaagca gccagtggta    660
gatcagccca agccagcagg cactaagcag ccagtggtag agcagcccaa gccagagggc    720
accaagcagc cagtggttga ccggcccaag ccagagggca ccaagcagcc agtggtagat    780
cagcccaagc cagaaggcac caagcagcca gtggtagatc agcccaagcc agaaggcacc    840
aagcagccag tcgttgaccg gcccaggcca ggcggcgacc cccggaccga tgacaccacc    900
tacggattca attcaaatac tggcaagcgg gaaaccaccc tgacgtccgc gtccgataag    960
ccagagttca acatctggga tgagcgtggg aacgatacgt ttgatttctc tggcttcaag   1020
caggatcaaa tcatcaactt gcgtggcggt gcgttttcca gtgtaggcgg gatgagggaa   1080
aacgttcgca tcggtgagaa gacggtgatc gaaaatgccg tgggtggcca cggtaacgac   1140
cgcatcatag gtaacagtgc cgataacgtg cttaccggtg gcgcgggagc cgatacgttg   1200
gtgggcggcg gcggctggaa taccttcaag ttcaatgcct ttagtgattc aacccgcgcc   1260
aatgccgact tgctgttgga cttcaacaca gggcaagaca agatcgacct ctcgcagatg   1320
gcgctcgacg gcaaggtatc gttgaacttc gtcgataact acacggggaa ggcgggcgac   1380
accatcatca agtttaaccc gctgtctggc cgttatttgc tggcgataga cttggacgga   1440
gatggcaaga ccgacttcct gatcaagagt acccgaatga tcagtccgga agatgtcata   1500
gggctcaaca ttaaagatgg cggttatctt tga                                1533
```

<210> SEQ ID NO 154
<211> LENGTH: 2271
<212> TYPE: DNA
<213> ORGANISM: Pseudomonas fluorescens

<400> SEQUENCE: 154

```
atgttaaacc gcgagctcga agtcaccctc aatcttgcct tcaaggaggc tcgttcgaag     60
cgtcatgaat tcatgaccgt cgaacacctt ttgctggcac ttttggataa cgaagctgcc    120
gccaccgttc tacgtgcgtg cggcgccaac cttgacaagc tcaagcatga cctgcaggag    180
tttatcgact ccaccacgcc actgatcccc gtgcatgacg aggaccgcga aacccagcca    240
accctgggct tccagcgggt attgcagcgt gctgtgttcc acgtacagag ctccggtaag    300
cgtgaggtca caggcgcgaa tgtacttgtg gcaattttca gcgaacagga aagccaggcc    360
gtgtttctgc tcaagcagca gagcgttgcc cgtattgatg tggtcaacta catcgcccac    420
```

```
ggtatctcca aggtgcctgg gcacggcgat cattccgagg gtgagcagga catgcaggac    480

gaggagggcg gcgagtcttc ttcttccagc aacccgctgg atgcctatgc aagtaacctc    540

aatgaaatgg cgcgccaggg gcggatcgat ccgctagtgg ggcgtgagca tgaggttgag    600

cgtgtagcgc agatcctggc gcgtcgtcgc aagaacaacc cattgctggt gggcgaggcg    660

ggcgtgggta aaaccgcgat tgccgaaggc ctggccaagc gcattgtcga caaccaggtg    720

ccagacctgc tggccagcag tgtcgtctac tcccttgacc tgggcgcgtt gctcgccggg    780

accaagtacc gtggcgattt cgagaagcgc ttcaaggcgt tgctcggcga gctgaaaaaa    840

cgcccgcagg ccatcctgtt catcgacgag atccatacca tcattggcgc cggtgcggct    900

tccggtgggg tgatggacgc ttccaacctg ctcaagccac tgctgtcctc cggtgatatc    960

cgctgcattg gttcgaccac gttccaggaa tttcgcggca tcttcgagaa agaccgcgcc   1020

ctggcgcgtc gcttccagaa agttgacgtg tccgagccct cggttgaaga caccatcggc   1080

atcctgcgcg ggctcaaggg gcgttttgaa gcgcaccatg gcatcgagta caccgatgag   1140

gccctgcgtg cggcggctga gctggcgtcg cgctacatca acgaccggca catgccagac   1200

aaagccatcg atgtgatcga cgaggcgggt gcctaccagc gcctgcagcc ggtcgagaag   1260

cgcgtgaagc gcatcgacgt gcctcaggtc gaggacatcg tggccaagat cgcgcggatt   1320

ccgccaaaac acgtcaccag ttccgacaag gagttgctgc gtaacctgga gcgcgacctc   1380

aagctcaccg tgtttggtca ggatgcggcc atcgactcgc tgtccacggc gatcaagttg   1440

tcccgtgcgg gcctcaagtc gccggacaag ccagtcggtt cgttcctgtt cgcaggcccg   1500

accggcgtcg gcaagaccga ggcggctcgc cagttggcca aggccatggg catcgagctg   1560

gtgcgtttcg acatgtccga gtacatggag cgccacacgg tgtcgcgttt gatcggcgcg   1620

cctccgggct atgtcggctt cgatcagggc ggcctgttga ccgaggcgat caccaagcag   1680

ccacactgcg tattgctgct cgacgaaatc gaaaaggctc acccggaagt cttcaacctg   1740

ctgttgcagg tcatggacca cggcaccctg accgacaaca acgggcgcaa ggcagacttc   1800

cgcaacgtga tcgtgatcat gaccaccaac gccggtgctg aaaccgcggc gcgtgcttcg   1860

atcggcttta cgcatcagga tcactcgtct gatgccatgg aagtgatcaa gaagagcttc   1920

acgccggagt tccgcaaccg cctggacacc attatccagt ttggtcgcct cagccatgag   1980

gtcatcaaaa gcgtggtgga caagttcctc accgagcttc aagcgcagtt ggaagacaag   2040

cgcgtgcagc tggatgtgac ggaagcggcc cgcagttgga tcgcagaggg cggctacgat   2100

gcggcaatgg gcgcacgccc aatggcgcgt ctgatccagg acaagatcaa gcggccattg   2160

gccgaagaga tcctgttcgg cgaactctcc gaccatggcg gcgtggtgca catcgacctg   2220

aaggacggcg agctgacctt cgagttcgag accacggcgg aaatggcctg a            2271
```

<210> SEQ ID NO 155
<211> LENGTH: 1284
<212> TYPE: DNA
<213> ORGANISM: Pseudomonas fluorescens

<400> SEQUENCE: 155

```
atgactgaca cccgcaacgg cgaggacaac ggcaagctgc tctattgctc cttctgtggc     60

aaaagccagc atgaagtacg caaattgatt gccggcccct cggtgtttat ctgcgacgaa    120

tgcgtcgacc tgtgcaatga catcatccgt gaggaggtgc aggaagccca ggccgagagc    180

agtgcgcata aattaccttc gcctaaagaa atcagtggca tccttgacca atacgtcatt    240
```

ggtcaagagc gtgcaaaaaa ggttctggcc gtagcggtgt acaaccacta caagcgcttg 300
aaccagcgtg acaagaaagg tgacgaggtt gaactcggca agagcaacat cttgctgatc 360
ggtcctacag gctcgggtaa aaccctgctt gcagaaaccc tcgctcgcct gctgaacgtt 420
ccgttcacca tcgccgacgc caccaccctc accgaggctg gctacgtggg tgaagatgtc 480
gagaacatca ttcagaaact gctgcagaag tgcgactacg acgtagagaa agcccagatg 540
ggtattgtct acatcgacga gatcgacaag atctcgcgca agtcggacaa cccgtcgatc 600
actcgggacg tttccggtga aggcgtgcag caggccctgt tgaagctgat cgaaggcacg 660
gttgcgtccg taccgccgca aggtggtcgc aagcacccgc agcaggaatt ccttcaggtt 720
gatacgcgca acatcctgtt catttgtggc ggtgcgttct cgggtctcga gaaggtgatt 780
cagcagcgtt ccacccgtgg cggcattggt ttcagtgcgg aagtgcgtag caaggaagaa 840
ggcaagaagg tgggcgagtc cctgcgtgaa gtcgagcctg acgatttggt caagttcggt 900
ctgatcccgg aattcgttgg ccgtctgccg gtcctggcca cgttggacga gttggatgag 960
gcggctttga tccagatcct caccgaaccg aaaaacgccc tgaccaagca atacggcaaa 1020
ttgttcgaga tggaaggtgt agacctggag ttccgtaccg acgcgctgaa atcggtggcc 1080
aagcgggcac tggagcgcaa gaccggtgca cgtggtctgc gttctatcct cgaaggcgtg 1140
ttgctcgaca ccatgtacga aatcccctcg cagtccgagg tgagtaaagt ggtgatcgac 1200
gaaagcgtta tcgaaggcaa gtccaagccg ctgtatatct atgaaaacag tgagccggct 1260
gccaaggctg cacccgacgc gtaa 1284

<210> SEQ ID NO 156
<211> LENGTH: 723
<212> TYPE: DNA
<213> ORGANISM: Pseudomonas fluorescens

<400> SEQUENCE: 156
atgcggtgtt tggcctgcac gtatgggccg gtgtgcctgc cggggcaaat cgcctatcgc 60
ccgggcccga ctttggccag ctccgatgac ctgcgcatca aaatcctcgg caaacagacc 120
cacgccggcc gcccctggga cggtatcgac ccgatcaccg tcggcgcgca aaccattgtc 180
ggcctgcaga ccgtggtcag ccgccgtacc gatatttcgt cattcccctc tgtggtgagc 240
atcggcacca tcaacggtgg cactcgctac aacatcatcc ccgagtcggt ggacatgagc 300
ggcacccttc gctcctacga ctacggcatt cgtcagaagc tgcatgcaga cgtgcgtcaa 360
accgtagaga aaatcgccga aagcggtggc gccaaggccg aagtgacaat catcgagaag 420
tacgacccca ccatcaacaa cccggcgctg accgagaaaa tgctgccgag cctgcgttgg 480
gcggctcagg atgatgtggt gcaaggccca ttggtaggtg gcgccgaaga cttctcgttc 540
tatgccaagg aagcgccggg gctgtttgtg ttcctggggg tgaccccaag ggaccaggac 600
atgagcaagg cggcgccgaa tcacaaccca gggttctttg tggatgagtc ggcattggtg 660
gtgggcgtga ggacactggc gtcgttggcg acggattacc tttacaccca caccccccctg 720 tag 723

<210> SEQ ID NO 157
<211> LENGTH: 398
<212> TYPE: DNA
<213> ORGANISM: Pseudomonas fluorescens

<400> SEQUENCE: 157
ggggccgttt aggattcgac gccggtcgcg aaactttagg tgcatgccga gttggtaaca 60
gaactcgtaa atccactgtt gcaacttctt atagttgcca atgacgaaaa ctacggccag 120
gaattcgctc tcgctgcgta agcagcctta gccctgagct tctggtacct tcgggtccag 180
caatcaccag gggatgtctg taaacccaaa gtgattgtca tatagaacag aatcgccgtg 240
cagtacgttg tggacgaagc ggctaaaact tacacaactc gcccaaagca ccctgcccctt 300 cgggtcgctg agggttaact taatagaaac ggctacgcat gtagtaccga cagcggagta 360
ctggcggacg ggggttcaaa tccccccggc tccaccac 398

<210> SEQ ID NO 158
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 158

His His His His His His
1               5

<210> SEQ ID NO 159
<211> LENGTH: 72
<212> TYPE: DNA
<213> ORGANISM: Artificial Sequence
<220> FEATURE:
<223> OTHER INFORMATION: Description of Artificial Sequence: Synthetic
      mutant phosphate binding protein leader sequence (pbp*)
<220> FEATURE:
<221> NAME/KEY: CDS
<222> LOCATION: (1)..(72)

<400> SEQUENCE: 159 atg aaa ctg aaa cgt ttg atg gcg gca atg act ttt gtc gct gct ggc 48
Met Lys Leu Lys Arg Leu Met Ala Ala Met Thr Phe Val Ala Ala Gly
1               5                   10                  15 gtt gcg acc gtc aac gcg gtg gcc 72
Val Ala Thr Val Asn Ala Val Ala
            20

<210> SEQ ID NO 160
<211> LENGTH: 24
<212> TYPE: PRT
<213> ORGANISM: Artificial Sequence
<220> FEATURE:
<223> OTHER INFORMATION: Description of Artificial Sequence: Synthetic
      mutant phosphate binding protein leader sequence (pbp*)

<400> SEQUENCE: 160

Met Lys Leu Lys Arg Leu Met Ala Ala Met Thr Phe Val Ala Ala Gly
1               5                   10                  15

Val Ala Thr Val Asn Ala Val Ala
            20

<210> SEQ ID NO 161
<211> LENGTH: 66
<212> TYPE: DNA
<213> ORGANISM: Pseudomonas fluorescens
<220> FEATURE:
<221> NAME/KEY: CDS
<222> LOCATION: (1)..(66)

<400> SEQUENCE: 161 atg cgt aat ctg atc ctc agc gcc gct ctc gtc act gcc agc ctc ttc 48
Met Arg Asn Leu Ile Leu Ser Ala Ala Leu Val Thr Ala Ser Leu Phe

```
1               5                   10                  15

ggc atg acc gca caa gct                                               66
Gly Met Thr Ala Gln Ala
            20


<210> SEQ ID NO 162
<211> LENGTH: 22
<212> TYPE: PRT
<213> ORGANISM: Pseudomonas fluorescens

<400> SEQUENCE: 162

Met Arg Asn Leu Ile Leu Ser Ala Ala Leu Val Thr Ala Ser Leu Phe
1               5                   10                  15

Gly Met Thr Ala Gln Ala
            20


<210> SEQ ID NO 163
<211> LENGTH: 63
<212> TYPE: DNA
<213> ORGANISM: Pseudomonas fluorescens
<220> FEATURE:
<221> NAME/KEY: CDS
<222> LOCATION: (1)..(63)

<400> SEQUENCE: 163

atg cgc ttg acc cag att att gcc gcc gca gcc att gcg ttg gtt tcc       48
Met Arg Leu Thr Gln Ile Ile Ala Ala Ala Ala Ile Ala Leu Val Ser
1               5                   10                  15

acc ttt gcg ctc gcc                                                   63
Thr Phe Ala Leu Ala
            20


<210> SEQ ID NO 164
<211> LENGTH: 21
<212> TYPE: PRT
<213> ORGANISM: Pseudomonas fluorescens

<400> SEQUENCE: 164

Met Arg Leu Thr Gln Ile Ile Ala Ala Ala Ala Ile Ala Leu Val Ser
1               5                   10                  15

Thr Phe Ala Leu Ala
            20


<210> SEQ ID NO 165
<211> LENGTH: 99
<212> TYPE: DNA
<213> ORGANISM: Bacillus coagulans
<220> FEATURE:
<221> NAME/KEY: CDS
<222> LOCATION: (1)..(99)

<400> SEQUENCE: 165

atg agc aca cga atc ccc cgc cga caa tgg ctg aaa ggc gcc tcg ggc       48
Met Ser Thr Arg Ile Pro Arg Arg Gln Trp Leu Lys Gly Ala Ser Gly
1               5                   10                  15

ctg ctg gcc gcc gcg agc ctg ggc cgg ttg gcc aac cgc gag gcg cgc       96
Leu Leu Ala Ala Ala Ser Leu Gly Arg Leu Ala Asn Arg Glu Ala Arg
            20                  25                  30

gcc                                                                   99
Ala


<210> SEQ ID NO 166
<211> LENGTH: 33
<212> TYPE: PRT
```

<213> ORGANISM: Bacillus coagulans

<400> SEQUENCE: 166

Met Ser Thr Arg Ile Pro Arg Arg Gln Trp Leu Lys Gly Ala Ser Gly
1 5 10 15

Leu Leu Ala Ala Ala Ser Leu Gly Arg Leu Ala Asn Arg Glu Ala Arg
20 25 30

Ala

<210> SEQ ID NO 167
<211> LENGTH: 75
<212> TYPE: DNA
<213> ORGANISM: Pseudomonas fluorescens
<220> FEATURE:
<221> NAME/KEY: CDS
<222> LOCATION: (1)..(75)

<400> SEQUENCE: 167 atg tcg tgc aca cgt gca ttc aaa cca ctg ctg ctg atc ggc ctg gcc 48
Met Ser Cys Thr Arg Ala Phe Lys Pro Leu Leu Leu Ile Gly Leu Ala
1 5 10 15 aca ctg atg tgt tcc cat gca ttc gct 75
Thr Leu Met Cys Ser His Ala Phe Ala
20 25

<210> SEQ ID NO 168
<211> LENGTH: 25
<212> TYPE: PRT
<213> ORGANISM: Pseudomonas fluorescens

<400> SEQUENCE: 168

Met Ser Cys Thr Arg Ala Phe Lys Pro Leu Leu Leu Ile Gly Leu Ala
1 5 10 15

Thr Leu Met Cys Ser His Ala Phe Ala
20 25

<210> SEQ ID NO 169
<211> LENGTH: 72
<212> TYPE: DNA
<213> ORGANISM: Pseudomonas fluorescens
<220> FEATURE:
<221> NAME/KEY: CDS
<222> LOCATION: (1)..(72)

<400> SEQUENCE: 169 atg ctt ttt cgc aca tta ctg gcg agc ctt acc ttt gct gtc atc gcc 48
Met Leu Phe Arg Thr Leu Leu Ala Ser Leu Thr Phe Ala Val Ile Ala
1 5 10 15 ggc tta ccg tcc acg gcc cac gcg 72
Gly Leu Pro Ser Thr Ala His Ala
20

<210> SEQ ID NO 170
<211> LENGTH: 24
<212> TYPE: PRT
<213> ORGANISM: Pseudomonas fluorescens

<400> SEQUENCE: 170

Met Leu Phe Arg Thr Leu Leu Ala Ser Leu Thr Phe Ala Val Ile Ala
1 5 10 15

Gly Leu Pro Ser Thr Ala His Ala
20

<210> SEQ ID NO 171
<211> LENGTH: 69
<212> TYPE: DNA
<213> ORGANISM: Pseudomonas fluorescens
<220> FEATURE:
<221> NAME/KEY: CDS
<222> LOCATION: (1)..(69)

<400> SEQUENCE: 171

```
atg ccg cct cgt tct atc gcc gca tgt ctg ggg ctg ctg ggc ttg ctc       48
Met Pro Pro Arg Ser Ile Ala Ala Cys Leu Gly Leu Leu Gly Leu Leu
1               5                   10                  15

atg gct acc cag gcc gcc gcc                                           69
Met Ala Thr Gln Ala Ala Ala
            20
```

<210> SEQ ID NO 172
<211> LENGTH: 23
<212> TYPE: PRT
<213> ORGANISM: Pseudomonas fluorescens

<400> SEQUENCE: 172

```
Met Pro Pro Arg Ser Ile Ala Ala Cys Leu Gly Leu Leu Gly Leu Leu
1               5                   10                  15

Met Ala Thr Gln Ala Ala Ala
            20
```

<210> SEQ ID NO 173
<211> LENGTH: 63
<212> TYPE: DNA
<213> ORGANISM: Pseudomonas fluorescens
<220> FEATURE:
<221> NAME/KEY: CDS
<222> LOCATION: (1)..(63)

<400> SEQUENCE: 173

```
atg cgc ctc gct gcc cta ccg cta ttg ctt gcc cct ctc ttt att gcg       48
Met Arg Leu Ala Ala Leu Pro Leu Leu Leu Ala Pro Leu Phe Ile Ala
1               5                   10                  15

ccg atg gcc gtt gcg                                                   63
Pro Met Ala Val Ala
            20
```

<210> SEQ ID NO 174
<211> LENGTH: 21
<212> TYPE: PRT
<213> ORGANISM: Pseudomonas fluorescens

<400> SEQUENCE: 174

```
Met Arg Leu Ala Ala Leu Pro Leu Leu Leu Ala Pro Leu Phe Ile Ala
1               5                   10                  15

Pro Met Ala Val Ala
            20
```

<210> SEQ ID NO 175
<211> LENGTH: 63
<212> TYPE: DNA
<213> ORGANISM: Pseudomonas fluorescens
<220> FEATURE:
<221> NAME/KEY: CDS
<222> LOCATION: (1)..(63)

<400> SEQUENCE: 175

```
atg aag ttc aaa cag ctg atg gcg atg gcg ctt ttg ttg gcc ttg agc       48
Met Lys Phe Lys Gln Leu Met Ala Met Ala Leu Leu Leu Ala Leu Ser
1               5                   10                  15
```

```
gct gtg gcc cag gcc                                                63
Ala Val Ala Gln Ala
            20


<210> SEQ ID NO 176
<211> LENGTH: 21
<212> TYPE: PRT
<213> ORGANISM: Pseudomonas fluorescens

<400> SEQUENCE: 176

Met Lys Phe Lys Gln Leu Met Ala Met Ala Leu Leu Leu Ala Leu Ser
1               5                   10                  15

Ala Val Ala Gln Ala
            20


<210> SEQ ID NO 177
<211> LENGTH: 63
<212> TYPE: DNA
<213> ORGANISM: Pseudomonas fluorescens
<220> FEATURE:
<221> NAME/KEY: CDS
<222> LOCATION: (1)..(63)

<400> SEQUENCE: 177

atg aat aga tct tcc gcg ttg ctc ctc gct ttt gtc ttc ctc agc ggc       48
Met Asn Arg Ser Ser Ala Leu Leu Leu Ala Phe Val Phe Leu Ser Gly
1               5                   10                  15

tgc cag gcc atg gcc                                                63
Cys Gln Ala Met Ala
            20


<210> SEQ ID NO 178
<211> LENGTH: 21
<212> TYPE: PRT
<213> ORGANISM: Pseudomonas fluorescens

<400> SEQUENCE: 178

Met Asn Arg Ser Ser Ala Leu Leu Leu Ala Phe Val Phe Leu Ser Gly
1               5                   10                  15

Cys Gln Ala Met Ala
            20


<210> SEQ ID NO 179
<211> LENGTH: 99
<212> TYPE: DNA
<213> ORGANISM: Pseudomonas fluorescens
<220> FEATURE:
<221> NAME/KEY: CDS
<222> LOCATION: (1)..(99)

<400> SEQUENCE: 179

atg caa aac cgc act gtg gaa atc ggt gtc ggc ctt ttc ttg ctg gct       48
Met Gln Asn Arg Thr Val Glu Ile Gly Val Gly Leu Phe Leu Leu Ala
1               5                   10                  15

ggc atc ctg gct tta ctg ttg ttg gcc ctg cga gtc agc ggc ctt tcg       96
Gly Ile Leu Ala Leu Leu Leu Leu Ala Leu Arg Val Ser Gly Leu Ser
            20                  25                  30

gcc                                                                99
Ala


<210> SEQ ID NO 180
<211> LENGTH: 33
<212> TYPE: PRT
<213> ORGANISM: Pseudomonas fluorescens
```

<400> SEQUENCE: 180

Met Gln Asn Arg Thr Val Glu Ile Gly Val Gly Leu Phe Leu Leu Ala
1 5 10 15

Gly Ile Leu Ala Leu Leu Leu Leu Ala Leu Arg Val Ser Gly Leu Ser
20 25 30

Ala

<210> SEQ ID NO 181
<211> LENGTH: 117
<212> TYPE: DNA
<213> ORGANISM: Pseudomonas fluorescens
<220> FEATURE:
<221> NAME/KEY: CDS
<222> LOCATION: (1)..(117)

<400> SEQUENCE: 181 atg tct ctt cgt aat atg aat atc gcc ccg agg gcc ttc ctc ggc ttc 48
Met Ser Leu Arg Asn Met Asn Ile Ala Pro Arg Ala Phe Leu Gly Phe
1 5 10 15 gcg ttt att ggc gcc ttg atg ttg ttg ctc ggt gtg ttc gcg ctg aac 96
Ala Phe Ile Gly Ala Leu Met Leu Leu Leu Gly Val Phe Ala Leu Asn
20 25 30 cag atg agc aaa att cgt gcg 117
Gln Met Ser Lys Ile Arg Ala
35

<210> SEQ ID NO 182
<211> LENGTH: 39
<212> TYPE: PRT
<213> ORGANISM: Pseudomonas fluorescens

<400> SEQUENCE: 182

Met Ser Leu Arg Asn Met Asn Ile Ala Pro Arg Ala Phe Leu Gly Phe
1 5 10 15

Ala Phe Ile Gly Ala Leu Met Leu Leu Leu Gly Val Phe Ala Leu Asn
20 25 30

Gln Met Ser Lys Ile Arg Ala
35

<210> SEQ ID NO 183
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 183
aattactagt aggaggtaca ttatgcgctt 30

<210> SEQ ID NO 184
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 184
tatactcgag ttatttaacc tgtttcagta 30

<210> SEQ ID NO 185

<211> LENGTH: 5
<212> TYPE: PRT
<213> ORGANISM: Artificial Sequence
<220> FEATURE:
<223> OTHER INFORMATION: Description of Artificial Sequence: Synthetic
First 5 amino acids of the predicted protein sequence for the
processed form of dsbC-Skp

<400> SEQUENCE: 185

Ala Asp Lys Ile Ala
1 5

<210> SEQ ID NO 186
<211> LENGTH: 10
<212> TYPE: PRT
<213> ORGANISM: Artificial Sequence
<220> FEATURE:
<223> OTHER INFORMATION: Description of Artificial Sequence: Synthetic
First 10 amino acids of the predicted protein sequence for the
unprocessed form of dsbC-Skp

<400> SEQUENCE: 186

Met Arg Leu Thr Gln Ile Ile Ala Ala Ala
1 5 10

<210> SEQ ID NO 187
<211> LENGTH: 10
<212> TYPE: PRT
<213> ORGANISM: Artificial Sequence
<220> FEATURE:
<223> OTHER INFORMATION: Description of Artificial Sequence: Synthetic
First 10 amino acids of the predicted protein sequence for the
processed form of dsbC-Skp

<400> SEQUENCE: 187

Ala Asp Lys Ile Ala Ile Val Asn Met Gly
1 5 10

<210> SEQ ID NO 188
<211> LENGTH: 63
<212> TYPE: DNA
<213> ORGANISM: Pseudomonas fluorescens
<220> FEATURE:
<221> NAME/KEY: CDS
<222> LOCATION: (1)..(63)

<400> SEQUENCE: 188 atg aag aag tcc acc ttg gct gtg gct gta acg ttg ggc gca atc gcc 48
Met Lys Lys Ser Thr Leu Ala Val Ala Val Thr Leu Gly Ala Ile Ala
1 5 10 15 cag caa gca ggc gct 63
Gln Gln Ala Gly Ala
20

<210> SEQ ID NO 189
<211> LENGTH: 21
<212> TYPE: PRT
<213> ORGANISM: Pseudomonas fluorescens

<400> SEQUENCE: 189

Met Lys Lys Ser Thr Leu Ala Val Ala Val Thr Leu Gly Ala Ile Ala
1 5 10 15

Gln Gln Ala Gly Ala
20

<210> SEQ ID NO 190
<211> LENGTH: 72

<212> TYPE: DNA
<213> ORGANISM: Pseudomonas fluorescens
<220> FEATURE:
<221> NAME/KEY: CDS
<222> LOCATION: (1)..(72)

<400> SEQUENCE: 190

```
atg aaa ctg aaa aac acc ttg ggc ttg gcc att ggt tct ctt att gcc       48
Met Lys Leu Lys Asn Thr Leu Gly Leu Ala Ile Gly Ser Leu Ile Ala
1               5                   10                  15

gct act tct ttc ggc gtt ctg gca                                       72
Ala Thr Ser Phe Gly Val Leu Ala
            20
```

<210> SEQ ID NO 191
<211> LENGTH: 24
<212> TYPE: PRT
<213> ORGANISM: Pseudomonas fluorescens

<400> SEQUENCE: 191

```
Met Lys Leu Lys Asn Thr Leu Gly Leu Ala Ile Gly Ser Leu Ile Ala
1               5                   10                  15

Ala Thr Ser Phe Gly Val Leu Ala
            20
```

<210> SEQ ID NO 192
<211> LENGTH: 72
<212> TYPE: DNA
<213> ORGANISM: Pseudomonas fluorescens
<220> FEATURE:
<221> NAME/KEY: CDS
<222> LOCATION: (1)..(72)

<400> SEQUENCE: 192

```
atg aaa ctg aaa cgt ttg atg gcg gca atg act ttt gtc gct gct ggc       48
Met Lys Leu Lys Arg Leu Met Ala Ala Met Thr Phe Val Ala Ala Gly
1               5                   10                  15

gtt gcg acc gcc aac gcg gtg gcc                                       72
Val Ala Thr Ala Asn Ala Val Ala
            20
```

<210> SEQ ID NO 193
<211> LENGTH: 24
<212> TYPE: PRT
<213> ORGANISM: Pseudomonas fluorescens

<400> SEQUENCE: 193

```
Met Lys Leu Lys Arg Leu Met Ala Ala Met Thr Phe Val Ala Ala Gly
1               5                   10                  15

Val Ala Thr Ala Asn Ala Val Ala
            20
```

<210> SEQ ID NO 194
<211> LENGTH: 60
<212> TYPE: DNA
<213> ORGANISM: Pseudomonas fluorescens
<220> FEATURE:
<221> NAME/KEY: CDS
<222> LOCATION: (1)..(60)

<400> SEQUENCE: 194

```
atg ttt gcc aaa ctc gtt gct gtt tcc ctg ctg act ctg gcg agc ggc       48
Met Phe Ala Lys Leu Val Ala Val Ser Leu Leu Thr Leu Ala Ser Gly
1               5                   10                  15

cag ttg ctt gct                                                       60
```

```
Gln Leu Leu Ala
            20


<210> SEQ ID NO 195
<211> LENGTH: 20
<212> TYPE: PRT
<213> ORGANISM: Pseudomonas fluorescens

<400> SEQUENCE: 195

Met Phe Ala Lys Leu Val Ala Val Ser Leu Leu Thr Leu Ala Ser Gly
1               5                   10                  15

Gln Leu Leu Ala
            20


<210> SEQ ID NO 196
<211> LENGTH: 51
<212> TYPE: DNA
<213> ORGANISM: Pseudomonas fluorescens
<220> FEATURE:
<221> NAME/KEY: CDS
<222> LOCATION: (1)..(51)

<400> SEQUENCE: 196

atg atc aaa cgc aat ctg ctg gtt atg ggc ctt gcc gtg ctg ttg agc       48
Met Ile Lys Arg Asn Leu Leu Val Met Gly Leu Ala Val Leu Leu Ser
1               5                   10                  15

gct                                                                   51
Ala


<210> SEQ ID NO 197
<211> LENGTH: 17
<212> TYPE: PRT
<213> ORGANISM: Pseudomonas fluorescens

<400> SEQUENCE: 197

Met Ile Lys Arg Asn Leu Leu Val Met Gly Leu Ala Val Leu Leu Ser
1               5                   10                  15

Ala


<210> SEQ ID NO 198
<211> LENGTH: 69
<212> TYPE: DNA
<213> ORGANISM: Pseudomonas fluorescens
<220> FEATURE:
<221> NAME/KEY: CDS
<222> LOCATION: (1)..(69)

<400> SEQUENCE: 198

atg cag aac tat aaa aaa ttc ctt ctg gcc gcg gcc gtc tcg atg gcg       48
Met Gln Asn Tyr Lys Lys Phe Leu Leu Ala Ala Ala Val Ser Met Ala
1               5                   10                  15

ttc agc gcc acg gcc atg gca                                           69
Phe Ser Ala Thr Ala Met Ala
            20


<210> SEQ ID NO 199
<211> LENGTH: 23
<212> TYPE: PRT
<213> ORGANISM: Pseudomonas fluorescens

<400> SEQUENCE: 199

Met Gln Asn Tyr Lys Lys Phe Leu Leu Ala Ala Ala Val Ser Met Ala
1               5                   10                  15

Phe Ser Ala Thr Ala Met Ala
```

```
            20


<210> SEQ ID NO 200
<211> LENGTH: 93
<212> TYPE: DNA
<213> ORGANISM: Pseudomonas fluorescens
<220> FEATURE:
<221> NAME/KEY: CDS
<222> LOCATION: (1)..(93)

<400> SEQUENCE: 200

atg atc cgt gac aac cga ctc aag aca tcc ctt ctg cgc ggc ctg acc       48
Met Ile Arg Asp Asn Arg Leu Lys Thr Ser Leu Leu Arg Gly Leu Thr
1               5                   10                  15

ctc acc cta ctc agc ctg acc ctg ctc tcg ccc gcg gcc cat tct           93
Leu Thr Leu Leu Ser Leu Thr Leu Leu Ser Pro Ala Ala His Ser
            20                  25                  30


<210> SEQ ID NO 201
<211> LENGTH: 31
<212> TYPE: PRT
<213> ORGANISM: Pseudomonas fluorescens

<400> SEQUENCE: 201

Met Ile Arg Asp Asn Arg Leu Lys Thr Ser Leu Leu Arg Gly Leu Thr
1               5                   10                  15

Leu Thr Leu Leu Ser Leu Thr Leu Leu Ser Pro Ala Ala His Ser
            20                  25                  30


<210> SEQ ID NO 202
<211> LENGTH: 5
<212> TYPE: PRT
<213> ORGANISM: Artificial Sequence
<220> FEATURE:
<223> OTHER INFORMATION: Description of Artificial Sequence: Synthetic
      N-terminal amino acid sequence of processed azurin and ibp

<400> SEQUENCE: 202

Ala Gln Val Gln Leu
1               5


<210> SEQ ID NO 203
<211> LENGTH: 1317
<212> TYPE: DNA
<213> ORGANISM: Bacillus coagulans
<220> FEATURE:
<221> NAME/KEY: CDS
<222> LOCATION: (1)..(1317)

<400> SEQUENCE: 203

atg agc aca cga atc ccc cgc cga caa tgg ctg aaa ggc gcc tcg ggc       48
Met Ser Thr Arg Ile Pro Arg Arg Gln Trp Leu Lys Gly Ala Ser Gly
1               5                   10                  15

ctg ctg gcc gcc gcg agc ctg ggc cgg ttg gcc aac cgc gag gcg cgc       96
Leu Leu Ala Ala Ala Ser Leu Gly Arg Leu Ala Asn Arg Glu Ala Arg
            20                  25                  30

gcc gcc gaa gcg agc gcc gcc gcg ccg ctc gac act ggc tcg ctg ggc      144
Ala Ala Glu Ala Ser Ala Ala Ala Pro Leu Asp Thr Gly Ser Leu Gly
        35                  40                  45

gcc tcg ccg cgc gcg acg ctc gac gcc tgc ctg caa aaa gcc gtc gac      192
Ala Ser Pro Arg Ala Thr Leu Asp Ala Cys Leu Gln Lys Ala Val Asp
    50                  55                  60

gac ggc acg ctc aag agc gtg gtg gcg atg gcc gcc acc gag cgc ggg      240
Asp Gly Thr Leu Lys Ser Val Val Ala Met Ala Ala Thr Glu Arg Gly
65                  70                  75                  80
```

-continued

```
ctc gcc tac cag ggc gcg cgc ggc ccg gcc aac gcg gcc ggc gag ccg      288
Leu Ala Tyr Gln Gly Ala Arg Gly Pro Ala Asn Ala Ala Gly Glu Pro
                85                  90                  95

atc ggc ccc gat acg gtg ttc tgg atg ctg tcg atg acc aag gcg atc      336
Ile Gly Pro Asp Thr Val Phe Trp Met Leu Ser Met Thr Lys Ala Ile
            100                 105                 110

acc gcc acc gcc tgc atg cag ctg atc gag cag ggc cgg ctc ggg ctc      384
Thr Ala Thr Ala Cys Met Gln Leu Ile Glu Gln Gly Arg Leu Gly Leu
        115                 120                 125

gac cag ccc gcc gcc gag atc ctg ccg caa ctg aag gcg ccg cag gtg      432
Asp Gln Pro Ala Ala Glu Ile Leu Pro Gln Leu Lys Ala Pro Gln Val
    130                 135                 140

ctg gag ggc ttc gac gcc gcc ggc cag ccc agg ctg cgc ccg gcg cgc      480
Leu Glu Gly Phe Asp Ala Ala Gly Gln Pro Arg Leu Arg Pro Ala Arg
145                 150                 155                 160

cgc gcg atc acg gtg cgc cac ctg ctc acg cat acc tcg ggc tat acc      528
Arg Ala Ile Thr Val Arg His Leu Leu Thr His Thr Ser Gly Tyr Thr
                165                 170                 175

tac agc atc tgg agc gag gcg ctg ggc cgc tac gaa cag gtc acg ggc      576
Tyr Ser Ile Trp Ser Glu Ala Leu Gly Arg Tyr Glu Gln Val Thr Gly
            180                 185                 190

atg ccc gac atc ggc tac tcg ctg aac ggc gcc ttc gcg gcc ccg ctc      624
Met Pro Asp Ile Gly Tyr Ser Leu Asn Gly Ala Phe Ala Ala Pro Leu
        195                 200                 205

gaa ttc gag ccc ggc gag cgc tgg caa tac ggc atc ggc atg gat tgg      672
Glu Phe Glu Pro Gly Glu Arg Trp Gln Tyr Gly Ile Gly Met Asp Trp
    210                 215                 220

gtg ggc aag ctg gtg gag gcg gtg acc gac cag tcg ctg gaa gtg gcg      720
Val Gly Lys Leu Val Glu Ala Val Thr Asp Gln Ser Leu Glu Val Ala
225                 230                 235                 240

ttc cgc gag cgg atc ttc gcg ccg ctc ggc atg cac gat acg ggc ttc      768
Phe Arg Glu Arg Ile Phe Ala Pro Leu Gly Met His Asp Thr Gly Phe
                245                 250                 255

ctg atc ggc agc gcg caa aag cgc cgc gtc gcc acg ctg cat cgg cgc      816
Leu Ile Gly Ser Ala Gln Lys Arg Arg Val Ala Thr Leu His Arg Arg
            260                 265                 270

cag gcc gat ggc tcg ctg acg ccg gaa ccc ttc gag acc aac cag cgg      864
Gln Ala Asp Gly Ser Leu Thr Pro Glu Pro Phe Glu Thr Asn Gln Arg
        275                 280                 285

ccc gag ttc ttc atg ggc ggc ggc ggg ctg ttc agc acc ccg cgc gac      912
Pro Glu Phe Phe Met Gly Gly Gly Gly Leu Phe Ser Thr Pro Arg Asp
    290                 295                 300

tac ctc gcc ttc ctg cag atg ctg ctg aac ggc ggc gcc tgg cgc ggc      960
Tyr Leu Ala Phe Leu Gln Met Leu Leu Asn Gly Gly Ala Trp Arg Gly
305                 310                 315                 320

gag cgg ctg ctg cgg ccc gac acc gtg gcg agc atg ttc cgc aac cag     1008
Glu Arg Leu Leu Arg Pro Asp Thr Val Ala Ser Met Phe Arg Asn Gln
                325                 330                 335

atc ggc gat ctt cag gtt cgc gaa atg aag acc gcc cag ccg gcc tgg     1056
Ile Gly Asp Leu Gln Val Arg Glu Met Lys Thr Ala Gln Pro Ala Trp
            340                 345                 350

tcg aac agc ttc gac caa ttc ccc ggc gcg acg cac aag tgg ggg ctg     1104
Ser Asn Ser Phe Asp Gln Phe Pro Gly Ala Thr His Lys Trp Gly Leu
        355                 360                 365

tcc ttc gat ctc aac agc gag ccg ggg ccg cac ggg cgc ggc gcc ggc     1152
Ser Phe Asp Leu Asn Ser Glu Pro Gly Pro His Gly Arg Gly Ala Gly
    370                 375                 380

tcg ggt agc tgg gcc ggc ctg ctg aac acc tac ttc tgg atc gat ccc     1200
Ser Gly Ser Trp Ala Gly Leu Leu Asn Thr Tyr Phe Trp Ile Asp Pro
```

```
385                 390                 395                 400

gcc aag cgc gtg acg ggg gcg ctg ttc acg cag atg ctg ccg ttc tac      1248
Ala Lys Arg Val Thr Gly Ala Leu Phe Thr Gln Met Leu Pro Phe Tyr
                405                 410                 415

gac gcg cgc gtg gtc gat ctc tac ggg cgc ttc gag cgc ggg ctc tac      1296
Asp Ala Arg Val Val Asp Leu Tyr Gly Arg Phe Glu Arg Gly Leu Tyr
            420                 425                 430

gac ggg ctg ggc cgc gcc tga                                          1317
Asp Gly Leu Gly Arg Ala
        435


<210> SEQ ID NO 204
<211> LENGTH: 438
<212> TYPE: PRT
<213> ORGANISM: Bacillus coagulans

<400> SEQUENCE: 204

Met Ser Thr Arg Ile Pro Arg Arg Gln Trp Leu Lys Gly Ala Ser Gly
1               5                   10                  15

Leu Leu Ala Ala Ala Ser Leu Gly Arg Leu Ala Asn Arg Glu Ala Arg
            20                  25                  30

Ala Ala Glu Ala Ser Ala Ala Ala Pro Leu Asp Thr Gly Ser Leu Gly
        35                  40                  45

Ala Ser Pro Arg Ala Thr Leu Asp Ala Cys Leu Gln Lys Ala Val Asp
    50                  55                  60

Asp Gly Thr Leu Lys Ser Val Val Ala Met Ala Ala Thr Glu Arg Gly
65                  70                  75                  80

Leu Ala Tyr Gln Gly Ala Arg Gly Pro Ala Asn Ala Ala Gly Glu Pro
                85                  90                  95

Ile Gly Pro Asp Thr Val Phe Trp Met Leu Ser Met Thr Lys Ala Ile
            100                 105                 110

Thr Ala Thr Ala Cys Met Gln Leu Ile Glu Gln Gly Arg Leu Gly Leu
        115                 120                 125

Asp Gln Pro Ala Ala Glu Ile Leu Pro Gln Leu Lys Ala Pro Gln Val
    130                 135                 140

Leu Glu Gly Phe Asp Ala Ala Gly Gln Pro Arg Leu Arg Pro Ala Arg
145                 150                 155                 160

Arg Ala Ile Thr Val Arg His Leu Leu Thr His Thr Ser Gly Tyr Thr
                165                 170                 175

Tyr Ser Ile Trp Ser Glu Ala Leu Gly Arg Tyr Glu Gln Val Thr Gly
            180                 185                 190

Met Pro Asp Ile Gly Tyr Ser Leu Asn Gly Ala Phe Ala Ala Pro Leu
        195                 200                 205

Glu Phe Glu Pro Gly Glu Arg Trp Gln Tyr Gly Ile Gly Met Asp Trp
    210                 215                 220

Val Gly Lys Leu Val Glu Ala Val Thr Asp Gln Ser Leu Glu Val Ala
225                 230                 235                 240

Phe Arg Glu Arg Ile Phe Ala Pro Leu Gly Met His Asp Thr Gly Phe
                245                 250                 255

Leu Ile Gly Ser Ala Gln Lys Arg Arg Val Ala Thr Leu His Arg Arg
            260                 265                 270

Gln Ala Asp Gly Ser Leu Thr Pro Glu Pro Phe Glu Thr Asn Gln Arg
        275                 280                 285

Pro Glu Phe Phe Met Gly Gly Gly Gly Leu Phe Ser Thr Pro Arg Asp
    290                 295                 300
```

```
Tyr Leu Ala Phe Leu Gln Met Leu Leu Asn Gly Gly Ala Trp Arg Gly
305                 310                 315                 320

Glu Arg Leu Leu Arg Pro Asp Thr Val Ala Ser Met Phe Arg Asn Gln
                325                 330                 335

Ile Gly Asp Leu Gln Val Arg Glu Met Lys Thr Ala Gln Pro Ala Trp
            340                 345                 350

Ser Asn Ser Phe Asp Gln Phe Pro Gly Ala Thr His Lys Trp Gly Leu
        355                 360                 365

Ser Phe Asp Leu Asn Ser Glu Pro Gly Pro His Gly Arg Gly Ala Gly
    370                 375                 380

Ser Gly Ser Trp Ala Gly Leu Leu Asn Thr Tyr Phe Trp Ile Asp Pro
385                 390                 395                 400

Ala Lys Arg Val Thr Gly Ala Leu Phe Thr Gln Met Leu Pro Phe Tyr
                405                 410                 415

Asp Ala Arg Val Val Asp Leu Tyr Gly Arg Phe Glu Arg Gly Leu Tyr
            420                 425                 430

Asp Gly Leu Gly Arg Ala
        435


<210> SEQ ID NO 205
<211> LENGTH: 324
<212> TYPE: DNA
<213> ORGANISM: Escherichia coli
<220> FEATURE:
<221> NAME/KEY: CDS
<222> LOCATION: (1)..(324)

<400> SEQUENCE: 205

agc gat aaa att att cac ctg act gac gac agt ttt gac acg gat gta       48
Ser Asp Lys Ile Ile His Leu Thr Asp Asp Ser Phe Asp Thr Asp Val
1               5                   10                  15

ctc aaa gcg gac ggg gcg atc ctc gtc gat ttc tgg gca gag tgg tgc       96
Leu Lys Ala Asp Gly Ala Ile Leu Val Asp Phe Trp Ala Glu Trp Cys
            20                  25                  30

ggt ccg tgc aaa atg atc gcc ccg att ctg gat gaa atc gct gac gaa      144
Gly Pro Cys Lys Met Ile Ala Pro Ile Leu Asp Glu Ile Ala Asp Glu
        35                  40                  45

tat cag ggc aaa ctg acc gtt gca aaa ctg aac atc gat caa aac cct      192
Tyr Gln Gly Lys Leu Thr Val Ala Lys Leu Asn Ile Asp Gln Asn Pro
    50                  55                  60

ggc act gcg ccg aaa tat ggc atc cgt ggt atc ccg act ctg ctg ctg      240
Gly Thr Ala Pro Lys Tyr Gly Ile Arg Gly Ile Pro Thr Leu Leu Leu
65                  70                  75                  80

ttc aaa aac ggt gaa gtg gcg gca acc aaa gtg ggt gca ctg tct aaa      288
Phe Lys Asn Gly Glu Val Ala Ala Thr Lys Val Gly Ala Leu Ser Lys
                85                  90                  95

ggt cag ttg aaa gag ttc ctc gac gct aac ctg gcg                      324
Gly Gln Leu Lys Glu Phe Leu Asp Ala Asn Leu Ala
            100                 105


<210> SEQ ID NO 206
<211> LENGTH: 108
<212> TYPE: PRT
<213> ORGANISM: Escherichia coli

<400> SEQUENCE: 206

Ser Asp Lys Ile Ile His Leu Thr Asp Asp Ser Phe Asp Thr Asp Val
1               5                   10                  15

Leu Lys Ala Asp Gly Ala Ile Leu Val Asp Phe Trp Ala Glu Trp Cys
            20                  25                  30
```

```
Gly Pro Cys Lys Met Ile Ala Pro Ile Leu Asp Glu Ile Ala Asp Glu
        35                  40                  45

Tyr Gln Gly Lys Leu Thr Val Ala Lys Leu Asn Ile Asp Gln Asn Pro
    50                  55                  60

Gly Thr Ala Pro Lys Tyr Gly Ile Arg Gly Ile Pro Thr Leu Leu Leu
65                  70                  75                  80

Phe Lys Asn Gly Glu Val Ala Ala Thr Lys Val Gly Ala Leu Ser Lys
                85                  90                  95

Gly Gln Leu Lys Glu Phe Leu Asp Ala Asn Leu Ala
            100                 105


<210> SEQ ID NO 207
<211> LENGTH: 63
<212> TYPE: DNA
<213> ORGANISM: Pseudomonas fluorescens
<220> FEATURE:
<221> NAME/KEY: CDS
<222> LOCATION: (1)..(63)

<400> SEQUENCE: 207

atg aga aac ctt ctt cga gga atg ctt gtc gtt att tgc tgt atg gca       48
Met Arg Asn Leu Leu Arg Gly Met Leu Val Val Ile Cys Cys Met Ala
1               5                   10                  15

ggg ata gcg gcg gcg                                                   63
Gly Ile Ala Ala Ala
            20


<210> SEQ ID NO 208
<211> LENGTH: 21
<212> TYPE: PRT
<213> ORGANISM: Pseudomonas fluorescens

<400> SEQUENCE: 208

Met Arg Asn Leu Leu Arg Gly Met Leu Val Val Ile Cys Cys Met Ala
1               5                   10                  15

Gly Ile Ala Ala Ala
            20


<210> SEQ ID NO 209
<211> LENGTH: 20
<212> TYPE: PRT
<213> ORGANISM: Pseudomonas fluorescens

<400> SEQUENCE: 209

Asn Thr Leu Gly Leu Ala Ile Gly Ser Leu Ile Ala Ala Thr Ser Phe
1               5                   10                  15

Gly Val Leu Ala
            20


<210> SEQ ID NO 210
<211> LENGTH: 22
<212> TYPE: PRT
<213> ORGANISM: Pseudomonas sp.

<400> SEQUENCE: 210

Met Arg Pro Ser Ile His Arg Thr Ala Ile Ala Ala Val Leu Ala Thr
1               5                   10                  15

Ala Phe Val Ala Gly Thr
            20


<210> SEQ ID NO 211
```

<211> LENGTH: 72
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: CDS
<222> LOCATION: (1)..(72)

<400> SEQUENCE: 211

```
atg aaa ctg aaa cgt ttg atg gcg gca atg act ttt gtc gct gct ggc       48
Met Lys Leu Lys Arg Leu Met Ala Ala Met Thr Phe Val Ala Ala Gly
1               5                   10                  15

gtt gcg acc gcc aac gcg gtg gcc                                       72
Val Ala Thr Ala Asn Ala Val Ala
            20
```

<210> SEQ ID NO 212
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 212

```
Met Lys Leu Lys Arg Leu Met Ala Ala Met Thr Phe Val Ala Ala Gly
1               5                   10                  15

Val Ala Thr Ala Asn Ala Val Ala
            20
```

<210> SEQ ID NO 213
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: CDS
<222> LOCATION: (1)..(63)

<400> SEQUENCE: 213

```
atg aag aag tcc acc ttg gct gtg gct gta acg ttg ggc gca atc gcc       48
Met Lys Lys Ser Thr Leu Ala Val Ala Val Thr Leu Gly Ala Ile Ala
1               5                   10                  15

cag caa gca ggc gct                                                   63
Gln Gln Ala Gly Ala
            20
```

<210> SEQ ID NO 214
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 214

```
Met Lys Lys Ser Thr Leu Ala Val Ala Val Thr Leu Gly Ala Ile Ala
1               5                   10                  15

Gln Gln Ala Gly Ala
            20
```

<210> SEQ ID NO 215
<211> LENGTH: 60

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(60)

<400> SEQUENCE: 215

atg ttt gcc aaa ctc gtt gct gtt tcc ctg ctg act ctg gcg agc ggc       48
Met Phe Ala Lys Leu Val Ala Val Ser Leu Leu Thr Leu Ala Ser Gly
1               5                   10                  15

cag ttg ctt gct                                                       60
Gln Leu Leu Ala
            20


<210> SEQ ID NO 216
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Met Phe Ala Lys Leu Val Ala Val Ser Leu Leu Thr Leu Ala Ser Gly
1               5                   10                  15

Gln Leu Leu Ala
            20


<210> SEQ ID NO 217
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(69)

<400> SEQUENCE: 217

atg cag aac tat aaa aaa ttc ctt ctg gcc gcg gcc gtc tcg atg gcg       48
Met Gln Asn Tyr Lys Lys Phe Leu Leu Ala Ala Ala Val Ser Met Ala
1               5                   10                  15

ttc agc gcc acg gcc atg gca                                           69
Phe Ser Ala Thr Ala Met Ala
            20


<210> SEQ ID NO 218
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Met Gln Asn Tyr Lys Lys Phe Leu Leu Ala Ala Ala Val Ser Met Ala
1               5                   10                  15

Phe Ser Ala Thr Ala Met Ala
            20


<210> SEQ ID NO 219
<211> LENGTH: 96
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(96)

<400> SEQUENCE: 219

atg atg atc cgt gac aac cga ctc aag aca tcc ctt ctg cgc ggc ctg       48
Met Met Ile Arg Asp Asn Arg Leu Lys Thr Ser Leu Leu Arg Gly Leu
1               5                   10                  15

acc ctc acc cta ctc agc ctg acc ctg ctc tcg ccc gcg gcc cat tct       96
Thr Leu Thr Leu Leu Ser Leu Thr Leu Leu Ser Pro Ala Ala His Ser
            20                  25                  30


<210> SEQ ID NO 220
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Met Met Ile Arg Asp Asn Arg Leu Lys Thr Ser Leu Leu Arg Gly Leu
1               5                   10                  15

Thr Leu Thr Leu Leu Ser Leu Thr Leu Leu Ser Pro Ala Ala His Ser
            20                  25                  30


<210> SEQ ID NO 221
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(51)

<400> SEQUENCE: 221

atg atc aaa cgc aat ctg ctg gtt atg ggc ctt gcc gtg ctg ttg agc       48
Met Ile Lys Arg Asn Leu Leu Val Met Gly Leu Ala Val Leu Leu Ser
1               5                   10                  15

gct                                                                   51
Ala


<210> SEQ ID NO 222
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Met Ile Lys Arg Asn Leu Leu Val Met Gly Leu Ala Val Leu Leu Ser
1               5                   10                  15

Ala


<210> SEQ ID NO 223
<211> LENGTH: 22
<212> TYPE: PRT
<213> ORGANISM: Artificial Sequence
<220> FEATURE:
<223> OTHER INFORMATION: Description of Artificial Sequence: Synthetic
```

peptide

<400> SEQUENCE: 223

Leu Lys Arg Leu Met Ala Ala Met Thr Phe Val Ala Ala Gly Val Ala
1 5 10 15

Thr Ala Asn Ala Val Ala
20

<210> SEQ ID NO 224
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 224

Met Lys Leu Lys Arg Leu Met Ala Ala Met Thr Phe Val Ala Ala Gly
1 5 10 15

Val Ala Thr Ala Asn Ala Val
20

<210> SEQ ID NO 225
<211> LENGTH: 22
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 225

Met Lys Leu Lys Arg Leu Met Ala Ala Met Thr Phe Val Ala Ala Gly
1 5 10 15

Val Ala Thr Ala Asn Ala
20

<210> SEQ ID NO 226
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 226

Met Lys Leu Lys Arg Leu Met Ala Ala Met Thr Phe Val Ala Ala Gly
1 5 10 15

Val Ala Thr Ala Asn
20

<210> SEQ ID NO 227
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 227

Met Lys Leu Lys Arg Leu Met Ala Ala Met Thr Phe Val Ala Ala Gly
1 5 10 15

Val Ala Thr Ala
20

<210> SEQ ID NO 228
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 228

Met Lys Leu Lys Arg Leu Met Ala Ala Met Thr Phe Val Ala Ala Gly
1 5 10 15

Val Ala Thr

<210> SEQ ID NO 229
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 229

Met Lys Leu Lys Arg Leu Met Ala Ala Met Thr Phe Val Ala Ala Gly
1 5 10 15

Val Ala

<210> SEQ ID NO 230
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 230

Met Lys Leu Lys Arg Leu Met Ala Ala Met Thr Phe Val Ala Ala Gly
1 5 10 15

Val

<210> SEQ ID NO 231
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 231

Met Lys Leu Lys Arg Leu Met Ala Ala Met Thr Phe Val Ala Ala Gly
1 5 10 15

<210> SEQ ID NO 232
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 232

Met Lys Leu Lys Arg Leu Met Ala Ala Met Thr Phe Val Ala Ala
1 5 10 15

<210> SEQ ID NO 233
<211> LENGTH: 14
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 233

Met Lys Leu Lys Arg Leu Met Ala Ala Met Thr Phe Val Ala
1               5                   10

<210> SEQ ID NO 234
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Lys Ser Thr Leu Ala Val Ala Val Thr Leu Gly Ala Ile Ala Gln Gln
1               5                   10                  15

Ala Gly Ala

<210> SEQ ID NO 235
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Met Lys Lys Ser Thr Leu Ala Val Ala Val Thr Leu Gly Ala Ile Ala
1               5                   10                  15

Gln Gln Ala Gly
            20

<210> SEQ ID NO 236
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Met Lys Lys Ser Thr Leu Ala Val Ala Val Thr Leu Gly Ala Ile Ala
1               5                   10                  15

Gln Gln Ala

<210> SEQ ID NO 237
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Met Lys Lys Ser Thr Leu Ala Val Ala Val Thr Leu Gly Ala Ile Ala
1               5                   10                  15

Gln Gln

<210> SEQ ID NO 238
<211> LENGTH: 17
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 238

Met Lys Lys Ser Thr Leu Ala Val Ala Val Thr Leu Gly Ala Ile Ala
1               5                   10                  15

Gln

<210> SEQ ID NO 239
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Met Lys Lys Ser Thr Leu Ala Val Ala Val Thr Leu Gly Ala Ile Ala
1               5                   10                  15

<210> SEQ ID NO 240
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Met Lys Lys Ser Thr Leu Ala Val Ala Val Thr Leu Gly Ala Ile
1               5                   10                  15

<210> SEQ ID NO 241
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Met Lys Lys Ser Thr Leu Ala Val Ala Val Thr Leu Gly Ala
1               5                   10

<210> SEQ ID NO 242
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Met Lys Lys Ser Thr Leu Ala Val Ala Val Thr Leu Gly
1               5                   10

<210> SEQ ID NO 243
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

-continued

Met Lys Lys Ser Thr Leu Ala Val Ala Val Thr Leu
1 5 10

<210> SEQ ID NO 244
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 244

Met Lys Lys Ser Thr Leu Ala Val Ala Val Thr
1 5 10

<210> SEQ ID NO 245
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 245

Met Tyr Lys Ser Thr Leu Ala Val Ala Val Thr Leu Gly Ala Ile Ala
1 5 10 15

Gln Gln Ala Gly Ala
20

<210> SEQ ID NO 246
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 246

Met Lys Lys Ser Ser Leu Ala Val Ala Val Thr Leu Gly Ala Ile Ala
1 5 10 15

Gln Gln Ala Gly Ala
20

<210> SEQ ID NO 247
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 247

Met Lys Lys Ser Thr Leu Ala Leu Ala Val Thr Leu Gly Ala Ile Ala
1 5 10 15

Gln Gln Ala Gly Ala
20

<210> SEQ ID NO 248
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 248

```
Met Lys Lys Ser Thr Leu Ala Val Ala Val Arg Thr Leu Gly Ala Ile
1               5                   10                  15

Ala Gln Gln Ala Gly Ala
            20


<210> SEQ ID NO 249
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Met Lys Lys Ser Thr Leu Ala Val Ala Val Thr Leu Gly Val Ile Ala
1               5                   10                  15

Gln Gln Ala Gly Ala
            20


<210> SEQ ID NO 250
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Met Lys Lys Ser Thr Leu Ala Val Ala Val Thr Leu Gly Ala Leu Ala
1               5                   10                  15

Gln Gln Ala Gly Ala
            20


<210> SEQ ID NO 251
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Ala Lys Leu Val Ala Val Ser Leu Leu Thr Leu Ala Ser Gly Gln Leu
1               5                   10                  15

Leu Ala


<210> SEQ ID NO 252
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Met Phe Ala Lys Leu Val Ala Val Ser Leu Leu Thr Leu Ala Ser Gly
1               5                   10                  15

Gln Leu Leu


<210> SEQ ID NO 253
<211> LENGTH: 18
<212> TYPE: PRT
<213> ORGANISM: Artificial Sequence
<220> FEATURE:
<223> OTHER INFORMATION: Description of Artificial Sequence: Synthetic
```

peptide

<400> SEQUENCE: 253

Met Phe Ala Lys Leu Val Ala Val Ser Leu Leu Thr Leu Ala Ser Gly
1               5                   10                  15

Gln Leu

<210> SEQ ID NO 254
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 254

Met Phe Ala Lys Leu Val Ala Val Ser Leu Leu Thr Leu Ala Ser Gly
1               5                   10                  15

Gln

<210> SEQ ID NO 255
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 255

Met Phe Ala Lys Leu Val Ala Val Ser Leu Leu Thr Leu Ala Ser Gly
1               5                   10                  15

<210> SEQ ID NO 256
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 256

Met Phe Ala Lys Leu Val Ala Val Ser Leu Leu Thr Leu Ala Ser
1               5                   10                  15

<210> SEQ ID NO 257
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 257

Met Phe Ala Lys Leu Val Ala Val Ser Leu Leu Thr Leu Ala
1               5                   10

<210> SEQ ID NO 258
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 258

Met Phe Ala Lys Leu Val Ala Val Ser Leu Leu Thr Leu 1 5 10

<210> SEQ ID NO 259
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 259

Met Phe Ala Lys Leu Val Ala Val Ser Leu Leu Thr
1 5 10

<210> SEQ ID NO 260
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 260

Met Phe Ala Lys Leu Val Ala Val Ser Leu Leu
1 5 10

<210> SEQ ID NO 261
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 261

Met Phe Ala Lys Leu Val Ala Val Ser Leu
1 5 10

<210> SEQ ID NO 262
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 262

Met Leu Arg Lys Leu Val Ala Val Ser Leu Leu Thr Leu Ala Ser Gly
1 5 10 15

Gln Leu Leu Ala
20

<210> SEQ ID NO 263
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 263

Met Ile Arg Lys Leu Val Ala Val Ser Leu Leu Thr Leu Ala Ser Gly
1 5 10 15

Gln Leu Leu Ala
20

<210> SEQ ID NO 264
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

```
Met Phe Ala Lys Ala Val Ala Val Ser Leu Leu Thr Leu Ala Ser Gly
1               5                   10                  15

Gln Leu Leu Ala
            20
```

<210> SEQ ID NO 265
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

```
Met Phe Ala Lys Leu Ala Ala Val Ser Leu Leu Thr Leu Ala Ser Gly
1               5                   10                  15

Gln Leu Leu Ala
            20
```

<210> SEQ ID NO 266
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

```
Met Phe Ala Lys Leu Ile Ser Ala Ser Leu Leu Thr Leu Ala Ser Gly
1               5                   10                  15

Gln Leu Leu Ala
            20
```

<210> SEQ ID NO 267
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

```
Met Phe Ala Lys Leu Val Ala Val Ser Leu Ile Thr Leu Ala Ser Gly
1               5                   10                  15

Gln Leu Leu Ala
            20
```

<210> SEQ ID NO 268
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

```
Met Phe Ala Lys Leu Val Ala Val Ser Leu Leu Ser Leu Ala Ser Gly
```

-continued

```
1               5                   10                  15

Gln Leu Leu Ala
            20


<210> SEQ ID NO 269
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Met Phe Ala Lys Leu Val Ala Val Ser Leu Leu Thr Leu Leu Ser Gly
1               5                   10                  15

Gln Leu Leu Ala
            20


<210> SEQ ID NO 270
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Met Phe Ala Lys Leu Val Ala Val Ser Leu Leu Thr Leu Phe Ser Gly
1               5                   10                  15

Gln Leu Leu Ala
            20


<210> SEQ ID NO 271
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Met Phe Ala Lys Leu Val Ala Val Ser Leu Leu Thr Leu Ala Ser Ala
1               5                   10                  15

Gln Leu Leu Ala
            20


<210> SEQ ID NO 272
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Met Phe Ala Lys Leu Val Ala Val Ser Leu Leu Thr Leu Ala Ser Gly
1               5                   10                  15

Ser Leu Leu Ala
            20


<210> SEQ ID NO 273
<211> LENGTH: 20
<212> TYPE: PRT
<213> ORGANISM: Artificial Sequence
<220> FEATURE:
```

<223> OTHER INFORMATION: Description of Artificial Sequence: Synthetic peptide

<400> SEQUENCE: 273

Met Phe Ala Lys Leu Val Ala Val Ser Leu Leu Thr Leu Ala Ser Gly
1 5 10 15

Pro Leu Leu Ala
20

<210> SEQ ID NO 274
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 274

Met Phe Ala Lys Leu Val Ala Val Ser Leu Leu Thr Leu Ala Ser Gly
1 5 10 15

Gln Val Leu Ala
20

<210> SEQ ID NO 275
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 275

Met Phe Ala Lys Leu Val Ala Val Ser Leu Leu Thr Leu Ala Ser Gly
1 5 10 15

Gln Val Phe Ala
20

<210> SEQ ID NO 276
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 276

Asn Tyr Lys Lys Phe Leu Leu Ala Ala Ala Val Ser Met Ala Phe Ser
1 5 10 15

Ala Thr Ala Met Ala
20

<210> SEQ ID NO 277
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 277

Met Gln Asn Tyr Lys Lys Phe Leu Leu Ala Ala Ala Val Ser Met Ala
1 5 10 15

Phe Ser Ala Thr Ala Met
20

<210> SEQ ID NO 278
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 278

```
Met Gln Asn Tyr Lys Lys Phe Leu Leu Ala Ala Ala Val Ser Met Ala
1               5                   10                  15

Phe Ser Ala Thr Ala
            20
```

<210> SEQ ID NO 279
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 279

```
Met Gln Asn Tyr Lys Lys Phe Leu Leu Ala Ala Ala Val Ser Met Ala
1               5                   10                  15

Phe Ser Ala Thr
            20
```

<210> SEQ ID NO 280
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 280

```
Met Gln Asn Tyr Lys Lys Phe Leu Leu Ala Ala Ala Val Ser Met Ala
1               5                   10                  15

Phe Ser Ala
```

<210> SEQ ID NO 281
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 281

```
Met Gln Asn Tyr Lys Lys Phe Leu Leu Ala Ala Ala Val Ser Met Ala
1               5                   10                  15

Phe Ser
```

<210> SEQ ID NO 282
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 282

```
Met Gln Asn Tyr Lys Lys Phe Leu Leu Ala Ala Ala Val Ser Met Ala
1               5                   10                  15
```

Phe

<210> SEQ ID NO 283
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Met Gln Asn Tyr Lys Lys Phe Leu Leu Ala Ala Ala Val Ser Met Ala
1               5                   10                  15

<210> SEQ ID NO 284
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Met Gln Asn Tyr Lys Lys Phe Leu Leu Ala Ala Ala Val Ser Met
1               5                   10                  15

<210> SEQ ID NO 285
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Met Gln Asn Tyr Lys Lys Phe Leu Leu Ala Ala Ala Val Ser
1               5                   10

<210> SEQ ID NO 286
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Met Gln Asn Tyr Lys Lys Phe Leu Leu Ala Ala Ala Val
1               5                   10

<210> SEQ ID NO 287
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Ile Arg Asp Asn Arg Leu Lys Thr Ser Leu Leu Arg Gly Leu Thr Leu
1               5                   10                  15

Thr Leu Leu Ser Leu Thr Leu Leu Ser Pro Ala Ala His Ser
            20                  25                  30

<210> SEQ ID NO 288
<211> LENGTH: 31

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 288

Met Met Ile Arg Asp Asn Arg Leu Lys Thr Ser Leu Leu Arg Gly Leu
1 5 10 15

Thr Leu Thr Leu Leu Ser Leu Thr Leu Leu Ser Pro Ala Ala His
20 25 30

<210> SEQ ID NO 289
<211> LENGTH: 30
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 289

Met Met Ile Arg Asp Asn Arg Leu Lys Thr Ser Leu Leu Arg Gly Leu
1 5 10 15

Thr Leu Thr Leu Leu Ser Leu Thr Leu Leu Ser Pro Ala Ala
20 25 30

<210> SEQ ID NO 290
<211> LENGTH: 29
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 290

Met Met Ile Arg Asp Asn Arg Leu Lys Thr Ser Leu Leu Arg Gly Leu
1 5 10 15

Thr Leu Thr Leu Leu Ser Leu Thr Leu Leu Ser Pro Ala
20 25

<210> SEQ ID NO 291
<211> LENGTH: 28
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 291

Met Met Ile Arg Asp Asn Arg Leu Lys Thr Ser Leu Leu Arg Gly Leu
1 5 10 15

Thr Leu Thr Leu Leu Ser Leu Thr Leu Leu Ser Pro
20 25

<210> SEQ ID NO 292
<211> LENGTH: 27
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 292

Met Met Ile Arg Asp Asn Arg Leu Lys Thr Ser Leu Leu Arg Gly Leu
1 5 10 15

```
Thr Leu Thr Leu Leu Ser Leu Thr Leu Leu Ser
            20                  25


<210> SEQ ID NO 293
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Met Met Ile Arg Asp Asn Arg Leu Lys Thr Ser Leu Leu Arg Gly Leu
1               5                   10                  15

Thr Leu Thr Leu Leu Ser Leu Thr Leu Leu
            20                  25


<210> SEQ ID NO 294
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Met Met Ile Arg Asp Asn Arg Leu Lys Thr Ser Leu Leu Arg Gly Leu
1               5                   10                  15

Thr Leu Thr Leu Leu Ser Leu Thr Leu
            20                  25


<210> SEQ ID NO 295
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Met Met Ile Arg Asp Asn Arg Leu Lys Thr Ser Leu Leu Arg Gly Leu
1               5                   10                  15

Thr Leu Thr Leu Leu Ser Leu Thr
            20


<210> SEQ ID NO 296
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Met Met Ile Arg Asp Asn Arg Leu Lys Thr Ser Leu Leu Arg Gly Leu
1               5                   10                  15

Thr Leu Thr Leu Leu Ser Leu
            20


<210> SEQ ID NO 297
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 297

Met Met Ile Arg Asp Asn Arg Leu Lys Thr Ser Leu Leu Arg Gly Leu
1 5 10 15

Thr Leu Thr Leu Leu Ser
20

<210> SEQ ID NO 298
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 298

Lys Arg Asn Leu Leu Val Met Gly Leu Ala Val Leu Leu Ser Ala
1 5 10 15

<210> SEQ ID NO 299
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 299

Met Ile Lys Arg Asn Leu Leu Val Met Gly Leu Ala Val Leu Leu Ser
1 5 10 15

<210> SEQ ID NO 300
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 300

Met Ile Lys Arg Asn Leu Leu Val Met Gly Leu Ala Val Leu Leu
1 5 10 15

<210> SEQ ID NO 301
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 301

Met Ile Lys Arg Asn Leu Leu Val Met Gly Leu Ala Val Leu
1 5 10

<210> SEQ ID NO 302
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 302

Met Ile Lys Arg Asn Leu Leu Val Met Gly Leu Ala Val
1 5 10

<210> SEQ ID NO 303
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Met Ile Lys Arg Asn Leu Leu Val Met Gly Leu Ala
1               5                   10

<210> SEQ ID NO 304
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Met Ile Lys Arg Asn Leu Leu Val Met Gly Leu
1               5                   10

<210> SEQ ID NO 305
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Met Ile Lys Arg Asn Leu Leu Val Met Gly
1               5                   10

<210> SEQ ID NO 306
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Met Ile Lys Arg Asn Leu Leu Val Met
1               5

<210> SEQ ID NO 307
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Met Ile Lys Arg Asn Leu Leu Val
1               5

<210> SEQ ID NO 308
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Met Ile Lys Arg Asn Leu Leu
1               5

<210> SEQ ID NO 309
<211> LENGTH: 834
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(834)

<400> SEQUENCE: 309

```
atg aaa ctg aaa cgt ttg atg gcg gca atg act ttt gtc gct gct ggc       48
Met Lys Leu Lys Arg Leu Met Ala Ala Met Thr Phe Val Ala Ala Gly
1               5                   10                  15

gtt gcg acc gcc aac gcg gtg gcc gcc cag gtg cag ctg cag gag tcg       96
Val Ala Thr Ala Asn Ala Val Ala Ala Gln Val Gln Leu Gln Glu Ser
            20                  25                  30

ggc cca gga ctg gtg aag cct tcg gag acc ctg tcc ctc acc tgc act      144
Gly Pro Gly Leu Val Lys Pro Ser Glu Thr Leu Ser Leu Thr Cys Thr
        35                  40                  45

gtc tct ggt ggt tcc atc agt agt tat cac tgg agc tgg atc cgg cag      192
Val Ser Gly Gly Ser Ile Ser Ser Tyr His Trp Ser Trp Ile Arg Gln
    50                  55                  60

ccc cca ggg aag gga ctg gag tgg att ggg tat atc tat tac agt ggg      240
Pro Pro Gly Lys Gly Leu Glu Trp Ile Gly Tyr Ile Tyr Tyr Ser Gly
65                  70                  75                  80

agc acc aac tac aac ccc tcc ctc aag aat cga gtc acc ata tct gta      288
Ser Thr Asn Tyr Asn Pro Ser Leu Lys Asn Arg Val Thr Ile Ser Val
                85                  90                  95

gac acg tcc aag aac cag ttc tcc ctg aac ctg agg tct gtg acc gct      336
Asp Thr Ser Lys Asn Gln Phe Ser Leu Asn Leu Arg Ser Val Thr Ala
            100                 105                 110

gca gac acg gcc gtg tat tac tgt gcg cga gga acg tat ggc cca gcc      384
Ala Asp Thr Ala Val Tyr Tyr Cys Ala Arg Gly Thr Tyr Gly Pro Ala
        115                 120                 125

gga gat gct ttt gat atc tgg ggg caa ggg acc acg gtc acc gtc tcg      432
Gly Asp Ala Phe Asp Ile Trp Gly Gln Gly Thr Thr Val Thr Val Ser
    130                 135                 140

agt ggt gga ggc ggt tca ggc gga ggt ggc agc ggc ggt ggc gga tcg      480
Ser Gly Gly Gly Gly Ser Gly Gly Gly Gly Ser Gly Gly Gly Gly Ser
145                 150                 155                 160

gac atc cag atg acc cag tct cct tcc acc ctg tct gca tct att gga      528
Asp Ile Gln Met Thr Gln Ser Pro Ser Thr Leu Ser Ala Ser Ile Gly
                165                 170                 175

gac aga gtc acc atc acc tgc cgg gcc agt gag ggt att tat cac tgg      576
Asp Arg Val Thr Ile Thr Cys Arg Ala Ser Glu Gly Ile Tyr His Trp
            180                 185                 190

ttg gcc tgg tat cag cag aag cca ggg aaa gcc cct aaa ctc ctg atc      624
Leu Ala Trp Tyr Gln Gln Lys Pro Gly Lys Ala Pro Lys Leu Leu Ile
        195                 200                 205

tat aag gcc tct agt tta gcc agt ggg gcc cca tca agg ttc agc ggc      672
Tyr Lys Ala Ser Ser Leu Ala Ser Gly Ala Pro Ser Arg Phe Ser Gly
    210                 215                 220

agt gga tct ggg aca gat ttc act ctc acc atc agc agc ctg cag cct      720
Ser Gly Ser Gly Thr Asp Phe Thr Leu Thr Ile Ser Ser Leu Gln Pro
225                 230                 235                 240
```

```
gat gat ttt gca act tat tac tgc caa caa tat agt aat tat ccg ctc      768
Asp Asp Phe Ala Thr Tyr Tyr Cys Gln Gln Tyr Ser Asn Tyr Pro Leu
                245                 250                 255

act ttc ggc gga ggg acc aag ctg gag atc aaa cgt gcg gcc gca cat      816
Thr Phe Gly Gly Gly Thr Lys Leu Glu Ile Lys Arg Ala Ala Ala His
            260                 265                 270

cac cat cat cac cat taa                                              834
His His His His His
        275


<210> SEQ ID NO 310
<211> LENGTH: 277
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 310

Met Lys Leu Lys Arg Leu Met Ala Ala Met Thr Phe Val Ala Ala Gly
1               5                   10                  15

Val Ala Thr Ala Asn Ala Val Ala Ala Gln Val Gln Leu Gln Glu Ser
            20                  25                  30

Gly Pro Gly Leu Val Lys Pro Ser Glu Thr Leu Ser Leu Thr Cys Thr
        35                  40                  45

Val Ser Gly Gly Ser Ile Ser Ser Tyr His Trp Ser Trp Ile Arg Gln
    50                  55                  60

Pro Pro Gly Lys Gly Leu Glu Trp Ile Gly Tyr Ile Tyr Tyr Ser Gly
65                  70                  75                  80

Ser Thr Asn Tyr Asn Pro Ser Leu Lys Asn Arg Val Thr Ile Ser Val
                85                  90                  95

Asp Thr Ser Lys Asn Gln Phe Ser Leu Asn Leu Arg Ser Val Thr Ala
            100                 105                 110

Ala Asp Thr Ala Val Tyr Tyr Cys Ala Arg Gly Thr Tyr Gly Pro Ala
        115                 120                 125

Gly Asp Ala Phe Asp Ile Trp Gly Gln Gly Thr Thr Val Thr Val Ser
    130                 135                 140

Ser Gly Gly Gly Gly Ser Gly Gly Gly Gly Ser Gly Gly Gly Gly Ser
145                 150                 155                 160

Asp Ile Gln Met Thr Gln Ser Pro Ser Thr Leu Ser Ala Ser Ile Gly
                165                 170                 175

Asp Arg Val Thr Ile Thr Cys Arg Ala Ser Glu Gly Ile Tyr His Trp
            180                 185                 190

Leu Ala Trp Tyr Gln Gln Lys Pro Gly Lys Ala Pro Lys Leu Leu Ile
        195                 200                 205

Tyr Lys Ala Ser Ser Leu Ala Ser Gly Ala Pro Ser Arg Phe Ser Gly
    210                 215                 220

Ser Gly Ser Gly Thr Asp Phe Thr Leu Thr Ile Ser Ser Leu Gln Pro
225                 230                 235                 240

Asp Asp Phe Ala Thr Tyr Tyr Cys Gln Gln Tyr Ser Asn Tyr Pro Leu
                245                 250                 255

Thr Phe Gly Gly Gly Thr Lys Leu Glu Ile Lys Arg Ala Ala Ala His
            260                 265                 270

His His His His His
        275


<210> SEQ ID NO 311
```

<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 311
gctctagagg aggtaactta tgaaactgaa acg 33

<210> SEQ ID NO 312
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 312
ctgcacctgg gcggccaccg cgtt 24

<210> SEQ ID NO 313
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 313
aacgcggtgg ccgcccaggt gcag 24

<210> SEQ ID NO 314
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 314
acgcgtcgac ttattaatgg tgatgatggt gatgtgcggc cgcacgttga tc 52

<210> SEQ ID NO 315
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 315
gggaatggtt gggaaggcca ccgcgttggc 30

<210> SEQ ID NO 316
<211> LENGTH: 50
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 316
agagaactag taaaaaggag aaatccatgg ctacaggctc ccggacgtcc 50

<210> SEQ ID NO 317
<211> LENGTH: 38

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 317
agagactcga gtcattagaa gccacagctg ccctccac 38

<210> SEQ ID NO 318
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 318
gccaacgcgg tggccttccc aaccattccc 30

<210> SEQ ID NO 319
<211> LENGTH: 48
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 319
agagactcga gtcattagaa gccacagctg ccctccacag agcggcac 48

<210> SEQ ID NO 320
<211> LENGTH: 645
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: CDS
<222> LOCATION: (1)..(645)

<400> SEQUENCE: 320

```
atg aaa ctg aaa cgt ttg atg gcg gca atg act ttt gtc gct gct ggc       48
Met Lys Leu Lys Arg Leu Met Ala Ala Met Thr Phe Val Ala Ala Gly
1               5                   10                  15

gtt gcg acc gcc aac gcg gtg gcc ttc cca acc att ccc tta tcc agg       96
Val Ala Thr Ala Asn Ala Val Ala Phe Pro Thr Ile Pro Leu Ser Arg
            20                  25                  30

cct ttt gac aac gct atg ctc cgc gcc cat cgt ctg cac cag ctg gcc      144
Pro Phe Asp Asn Ala Met Leu Arg Ala His Arg Leu His Gln Leu Ala
        35                  40                  45

ttt gac acc tac cag gag ttt gaa gaa gcc tat atc cca aag gaa cag      192
Phe Asp Thr Tyr Gln Glu Phe Glu Glu Ala Tyr Ile Pro Lys Glu Gln
    50                  55                  60

aag tat tca ttc ctg cag aac ccc cag acc tcc ctc tgt ttc tca gag      240
Lys Tyr Ser Phe Leu Gln Asn Pro Gln Thr Ser Leu Cys Phe Ser Glu
65                  70                  75                  80

tct att ccg aca ccc tcc aac agg gag gaa aca caa cag aaa tcc aac      288
Ser Ile Pro Thr Pro Ser Asn Arg Glu Glu Thr Gln Gln Lys Ser Asn
                85                  90                  95

cta gag ctg ctc cgc atc tcc ctg ctg ctc atc cag tcg tgg ctg gag      336
Leu Glu Leu Leu Arg Ile Ser Leu Leu Leu Ile Gln Ser Trp Leu Glu
            100                 105                 110

ccc gtg cag ttc ctc agg agt gtc ttc gcc aac agc ctg gtg tac ggc      384
```

-continued

```
Pro Val Gln Phe Leu Arg Ser Val Phe Ala Asn Ser Leu Val Tyr Gly
        115                 120                 125

gcc tct gac agc aac gtc tat gac ctc cta aag gac cta gag gaa ggc      432
Ala Ser Asp Ser Asn Val Tyr Asp Leu Leu Lys Asp Leu Glu Glu Gly
    130                 135                 140

atc caa acg ctg atg ggg agg ctg gaa gat ggc agc ccc cgg act ggg      480
Ile Gln Thr Leu Met Gly Arg Leu Glu Asp Gly Ser Pro Arg Thr Gly
145                 150                 155                 160

cag atc ttc aag cag acc tac agc aag ttc gac aca aac tca cac aac      528
Gln Ile Phe Lys Gln Thr Tyr Ser Lys Phe Asp Thr Asn Ser His Asn
                165                 170                 175

gat gac cta ctc aag aac tac ggg ctg ctc tac tgc ttc agg aag gac      576
Asp Asp Leu Leu Lys Asn Tyr Gly Leu Leu Tyr Cys Phe Arg Lys Asp
            180                 185                 190

atg gac aag gtc gag aca ttc ctg cgc atc gtg cag tgc cgc tct gtg      624
Met Asp Lys Val Glu Thr Phe Leu Arg Ile Val Gln Cys Arg Ser Val
        195                 200                 205

gag ggc agc tgt ggc ttc taa                                          645
Glu Gly Ser Cys Gly Phe
    210


<210> SEQ ID NO 321
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 321

Met Lys Leu Lys Arg Leu Met Ala Ala Met Thr Phe Val Ala Ala Gly
1               5                   10                  15

Val Ala Thr Ala Asn Ala Val Ala Phe Pro Thr Ile Pro Leu Ser Arg
            20                  25                  30

Pro Phe Asp Asn Ala Met Leu Arg Ala His Arg Leu His Gln Leu Ala
        35                  40                  45

Phe Asp Thr Tyr Gln Glu Phe Glu Glu Ala Tyr Ile Pro Lys Glu Gln
    50                  55                  60

Lys Tyr Ser Phe Leu Gln Asn Pro Gln Thr Ser Leu Cys Phe Ser Glu
65                  70                  75                  80

Ser Ile Pro Thr Pro Ser Asn Arg Glu Glu Thr Gln Gln Lys Ser Asn
                85                  90                  95

Leu Glu Leu Leu Arg Ile Ser Leu Leu Leu Ile Gln Ser Trp Leu Glu
            100                 105                 110

Pro Val Gln Phe Leu Arg Ser Val Phe Ala Asn Ser Leu Val Tyr Gly
        115                 120                 125

Ala Ser Asp Ser Asn Val Tyr Asp Leu Leu Lys Asp Leu Glu Glu Gly
    130                 135                 140

Ile Gln Thr Leu Met Gly Arg Leu Glu Asp Gly Ser Pro Arg Thr Gly
145                 150                 155                 160

Gln Ile Phe Lys Gln Thr Tyr Ser Lys Phe Asp Thr Asn Ser His Asn
                165                 170                 175

Asp Asp Leu Leu Lys Asn Tyr Gly Leu Leu Tyr Cys Phe Arg Lys Asp
            180                 185                 190

Met Asp Lys Val Glu Thr Phe Leu Arg Ile Val Gln Cys Arg Ser Val
        195                 200                 205

Glu Gly Ser Cys Gly Phe
    210
```

<210> SEQ ID NO 322
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 322

Ala Asp Lys Ile Ala Ile Val Asn Met Gly Ser Leu Phe
1 5 10

<210> SEQ ID NO 323
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 323

Gln Gln Val Ala Gln Lys Thr Gly Val Ser Asn Thr Leu Glu Asn Glu
1 5 10 15

Phe

<210> SEQ ID NO 324
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 324

Phe Pro Thr Ile Pro Leu Ser Arg Pro Phe
1 5 10

<210> SEQ ID NO 325
<211> LENGTH: 277
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 325

Met Lys Leu Lys Asn Thr Leu Gly Leu Ala Ile Gly Ser Leu Ile Ala
1 5 10 15

Ala Thr Ser Phe Gly Val Leu Ala Ala Gln Val Gln Leu Gln Glu Ser
20 25 30

Gly Pro Gly Leu Val Lys Pro Ser Glu Thr Leu Ser Leu Thr Cys Thr
35 40 45

Val Ser Gly Gly Ser Ile Ser Ser Tyr His Trp Ser Trp Ile Arg Gln
50 55 60

Pro Pro Gly Lys Gly Leu Glu Trp Ile Gly Tyr Ile Tyr Tyr Ser Gly
65 70 75 80

Ser Thr Asn Tyr Asn Pro Ser Leu Lys Asn Arg Val Thr Ile Ser Val
85 90 95

Asp Thr Ser Lys Asn Gln Phe Ser Leu Asn Leu Arg Ser Val Thr Ala
100 105 110

Ala Asp Thr Ala Val Tyr Tyr Cys Ala Arg Gly Thr Tyr Gly Pro Ala
115 120 125

```
Gly Asp Ala Phe Asp Ile Trp Gly Gln Gly Thr Thr Val Thr Val Ser
    130                 135                 140

Ser Gly Gly Gly Gly Ser Gly Gly Gly Gly Ser Gly Gly Gly Gly Ser
145                 150                 155                 160

Asp Ile Gln Met Thr Gln Ser Pro Ser Thr Leu Ser Ala Ser Ile Gly
                165                 170                 175

Asp Arg Val Thr Ile Thr Cys Arg Ala Ser Glu Gly Ile Tyr His Trp
            180                 185                 190

Leu Ala Trp Tyr Gln Gln Lys Pro Gly Lys Ala Pro Lys Leu Leu Ile
        195                 200                 205

Tyr Lys Ala Ser Ser Leu Ala Ser Gly Ala Pro Ser Arg Phe Ser Gly
    210                 215                 220

Ser Gly Ser Gly Thr Asp Phe Thr Leu Thr Ile Ser Ser Leu Gln Pro
225                 230                 235                 240

Asp Asp Phe Ala Thr Tyr Tyr Cys Gln Gln Tyr Ser Asn Tyr Pro Leu
                245                 250                 255

Thr Phe Gly Gly Gly Thr Lys Leu Glu Ile Lys Arg Ala Ala Ala His
            260                 265                 270

His His His His His
        275
```

<210> SEQ ID NO 326
<211> LENGTH: 277
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 326

```
Met Lys Leu Lys Arg Leu Met Ala Ala Met Thr Phe Val Ala Ala Gly
1               5                   10                  15

Val Ala Thr Ala Asn Ala Val Ala Ala Gln Val Gln Leu Gln Glu Ser
            20                  25                  30

Gly Pro Gly Leu Val Lys Pro Ser Glu Thr Leu Ser Leu Thr Cys Thr
        35                  40                  45

Val Ser Gly Gly Ser Ile Ser Ser Tyr His Trp Ser Trp Ile Arg Gln
    50                  55                  60

Pro Pro Gly Lys Gly Leu Glu Trp Ile Gly Tyr Ile Tyr Tyr Ser Gly
65                  70                  75                  80

Ser Thr Asn Tyr Asn Pro Ser Leu Lys Asn Arg Val Thr Ile Ser Val
                85                  90                  95

Asp Thr Ser Lys Asn Gln Phe Ser Leu Asn Leu Arg Ser Val Thr Ala
            100                 105                 110

Ala Asp Thr Ala Val Tyr Tyr Cys Ala Arg Gly Thr Tyr Gly Pro Ala
        115                 120                 125

Gly Asp Ala Phe Asp Ile Trp Gly Gln Gly Thr Thr Val Thr Val Ser
    130                 135                 140

Ser Gly Gly Gly Gly Ser Gly Gly Gly Gly Ser Gly Gly Gly Gly Ser
145                 150                 155                 160

Asp Ile Gln Met Thr Gln Ser Pro Ser Thr Leu Ser Ala Ser Ile Gly
                165                 170                 175

Asp Arg Val Thr Ile Thr Cys Arg Ala Ser Glu Gly Ile Tyr His Trp
            180                 185                 190

Leu Ala Trp Tyr Gln Gln Lys Pro Gly Lys Ala Pro Lys Leu Leu Ile
```

```
        195                 200                 205

Tyr Lys Ala Ser Ser Leu Ala Ser Gly Ala Pro Ser Arg Phe Ser Gly
    210                 215                 220

Ser Gly Ser Gly Thr Asp Phe Thr Leu Thr Ile Ser Ser Leu Gln Pro
225                 230                 235                 240

Asp Asp Phe Ala Thr Tyr Tyr Cys Gln Gln Tyr Ser Asn Tyr Pro Leu
                245                 250                 255

Thr Phe Gly Gly Gly Thr Lys Leu Glu Ile Lys Arg Ala Ala Ala His
            260                 265                 270

His His His His His
        275


<210> SEQ ID NO 327
<211> LENGTH: 161
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 327

Met Lys Lys Trp Leu Leu Ala Ala Gly Leu Gly Leu Ala Leu Ala Thr
1               5                   10                  15

Ser Ala Gln Ala Ala Asp Lys Ile Ala Ile Val Asn Met Gly Ser Leu
            20                  25                  30

Phe Gln Gln Val Ala Gln Lys Thr Gly Val Ser Asn Thr Leu Glu Asn
        35                  40                  45

Glu Phe Lys Gly Arg Ala Ser Glu Leu Gln Arg Met Glu Thr Asp Leu
    50                  55                  60

Gln Ala Lys Met Lys Lys Leu Gln Ser Met Lys Ala Gly Ser Asp Arg
65                  70                  75                  80

Thr Lys Leu Glu Lys Asp Val Met Ala Gln Arg Gln Thr Phe Ala Gln
                85                  90                  95

Lys Ala Gln Ala Phe Glu Gln Asp Arg Ala Arg Arg Ser Asn Glu Glu
            100                 105                 110

Arg Gly Lys Leu Val Thr Arg Ile Gln Thr Ala Val Lys Ser Val Ala
        115                 120                 125

Asn Ser Gln Asp Ile Asp Leu Val Val Asp Ala Asn Ala Val Ala Tyr
    130                 135                 140

Asn Ser Ser Asp Val Lys Asp Ile Thr Ala Asp Val Leu Lys Gln Val
145                 150                 155                 160

Lys


<210> SEQ ID NO 328
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 328

Ala Asp Lys Ile Ala Ile Val Asn Met Gly Ser Leu Phe Gln Gln Val
1               5                   10                  15

Ala Gln Lys Thr Gly Val Ser Asn Thr Leu Glu Asn Glu Phe Lys Gly
            20                  25                  30

Arg Ala Ser Glu Leu Gln Arg Met Glu Thr Asp Leu Gln Ala Lys Met
        35                  40                  45
```

-continued

```
Lys Lys Leu Gln Ser Met Lys Ala Gly Ser Asp Arg Thr Lys Leu Glu
    50                  55                  60

Lys Asp Val Met Ala Gln Arg Gln Thr Phe Ala Gln Lys Ala Gln Ala
65                  70                  75                  80

Phe Glu Gln Asp Arg Ala Arg Arg Ser Asn Glu Glu Arg Gly Lys Leu
                85                  90                  95

Val Thr Arg Ile Gln Thr Ala Val Lys Ser Val Ala Asn Ser Ala Asp
            100                 105                 110

Ile Asp Leu Val Val Asp Ala Asn Ala Val Ala Tyr Asn Ser Ser Asp
        115                 120                 125

Val Lys Asp Ile Thr Ala Asp Val Leu Lys Gln Val
    130                 135                 140


<210> SEQ ID NO 329
<211> LENGTH: 93
<212> TYPE: DNA
<213> ORGANISM: Pseudomonas fluorescens

<400> SEQUENCE: 329

atgatccgtg acaaccgact caagacatcc cttctgcgcg gcctgaccct caccctactc      60

agcctgaccc tgctctcgcc cgcggcccat gcc                                    93


<210> SEQ ID NO 330
<211> LENGTH: 31
<212> TYPE: PRT
<213> ORGANISM: Pseudomonas fluorescens

<400> SEQUENCE: 330

Met Ile Arg Asp Asn Arg Leu Lys Thr Ser Leu Leu Arg Gly Leu Thr
1               5                   10                  15

Leu Thr Leu Leu Ser Leu Thr Leu Leu Ser Pro Ala Ala His Ala
            20                  25                  30
```

That which is claimed:

1. A method of assembling an array and using the array to simultaneously screen at least 10 nonidentical expression systems for testing expression of at least one heterologous recombinant protein, said method comprising:

placing Pseudomonad or *E. coli* host cell populations in separate addressable locations of the array;

introducing at least one expression vector encoding the at least one heterologous recombinant protein into each host cell population in the array to produce each of the at least 10 nonidentical expression systems in the array, wherein the array of at least 10 nonidentical expression systems includes at least 5 different host cell populations and at least 2 different expression vectors, wherein at least 3 of said at least 5 different host cell populations are deficient in their expression of at least one host cell protease, wherein the at least 10 nonidentical test expression systems in the array each comprises a different combination of a) a Pseudomonad or *E. coli* host cell population, and b) at least one of the at least 2 different expression vectors encoding the at least one heterologous recombinant protein, and simultaneously screening the at least 10 nonidentical test expression systems on the array;

wherein at least one expression system in the array of the at least 10 nonidentical test expression systems over-expresses the at least one heterologous recombinant protein.

2. The method of claim 1, wherein the at least 2 different expression vectors each encode a different heterologous recombinant protein.

3. The method of claim 2, wherein the array includes at least 5 different expression vectors, and wherein each of said at least 5 different expression vectors encodes a different heterologous recombinant protein.

4. The method of claim 1, wherein at least one expression vector encodes 2 different heterologous recombinant proteins.

5. The method of claim 1, wherein at least 20 nonidentical test expression systems are placed in separate addressable locations, and wherein the array includes at least 10 different host cell populations and at least 2 different expression vectors, and further wherein at least 5 of said at least 10 different host cell populations are deficient in their expression of at least one host cell protease.

6. The method of claim 1, wherein at least 50 nonidentical test expression systems are placed in separate addressable locations, and wherein the array includes at least 20 different host cell populations and at least 3 different expression vectors, and further wherein at least 10 of said at least 20 different host cell populations are deficient in their expression of at least one host cell protease.

7. The method of claim 1 wherein the overexpression of the heterologous recombinant protein by the at least one expression system in the array of the at least 10 nonidentical test expression systems is an increase in yield of the heterologous recombinant protein, of about 1.5-fold to about 100-fold, relative to the yield in an indicator expression system.

8. The method of claim 1 wherein the overexpression is a yield of the heterologous recombinant protein by the at least one expression system in the array of the at least 10 nonidentical test expression systems of about 10 mg/liter to about 2000 mg/liter.

9. The method of claim 7 wherein the increase in yield is about 1.5-fold to about 100-fold.

10. The method of claim 1 wherein the overexpression is a yield of the heterologous recombinant protein by the at least one expression system in the array of the at least 10 nonidentical test expression systems of about 0.1 mg/ml to about 50 mg/ml, wherein the heterologous recombinant protein is correctly processed protein.

11. The method of claim 7 wherein the indicator expression system comprises a second expression system in the array of the at least 10 nonidentical test expression systems in the array, or a standard expression system.

12. The method of claim 7, wherein the yield of the heterologous recombinant protein is a measure of the amount of soluble heterologous recombinant protein, the amount of recoverable heterologous recombinant protein, the amount of properly processed heterologous recombinant protein, the amount of properly folded heterologous recombinant protein, the amount of active heterologous recombinant protein, and/or the total amount of heterologous recombinant protein.

13. The method of claim 7, further comprising selecting an optimal expression system from among the at least 10 nonidentical test expression systems based on the increased yield of the heterologous recombinant protein in the optimal expression system relative to that in the indicator expression system.

14. The method of claim 8, further comprising selecting an optimal expression system from among the at least ten nonidentical test expression systems based on the yield of the heterologous recombinant protein in the optimal expression system.

15. The method of claim 1, wherein at least 2 of said at least 5 different host cell populations overexpress at least one folding modulator.

16. The method of claim 15, wherein the at least one folding modulator is encoded by a nucleic acid sequence selected from the group consisting of: SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, and SEQ ID NO: 150.

17. The method of claim 15, wherein the at least one folding modulator is expressed from a plasmid.

18. The method of claim 1, wherein at least one host cell population in the array is defective in at least one to about eight host cell proteases.

19. The method of claim 18, wherein the at least one to about eight host cell proteases are selected from the proteases encoded by a nucleic acid sequence selected from the group consisting of: SEQ ID NO: 110, SEQ ID NO: 109, SEQ ID NO: 69, SEQ ID NO: 66, SEQ ID NO: 100, SEQ ID NO: 101, SEQ ID NO: 61, SEQ ID NO: 130, SEQ ID NO: 52, SEQ ID NO: 91, SEQ ID NO: 106, SEQ ID NO: 111, SEQ ID NO: 86, SEQ ID NO: 89, SEQ ID NO: 60, SEQ ID NO: 88, SEQ ID NO: 74, SEQ ID NO: 132, SEQ ID NO: 80, SEQ ID NO: 63, SEQ ID NO: 64, SEQ ID NO: 82, SEQ ID NO: 47, SEQ ID NO: 125, SEQ ID NO: 54, SEQ ID NO: 85, SEQ ID NO: 62, SEQ ID NO: 81, SEQ ID NO: 112, SEQ ID NO: 113, SEQ ID NO: 76, SEQ ID NO: 58, SEQ ID NO: 83, SEQ ID NO: 133, SEQ ID NO: 96, SEQ ID NO: 78, SEQ ID NO: 75, SEQ ID NO: 119, SEQ ID NO: 107, SEQ ID NO: 105, SEQ ID NO: 95, SEQ ID NO: 57, SEQ ID NO: 124, SEQ ID NO: 121, SEQ ID NO: 127, SEQ ID NO: 128, SEQ ID NO: 115, SEQ ID NO: 131, SEQ ID NO: 118, SEQ ID NO: 67, SEQ ID NO: 51, SEQ ID NO: 93, SEQ ID NO: 53, SEQ ID NO: 46, SEQ ID NO: 102, SEQ ID NO: 90, SEQ ID NO: 94, SEQ ID NO: 92, SEQ ID NO: 129, SEQ ID NO: 114, SEQ ID NO: 50, SEQ ID NO: 79, SEQ ID NO: 56, SEQ ID NO: 108, SEQ ID NO: 98, SEQ ID NO: 99, SEQ ID NO: 120, SEQ ID NO: 55, SEQ ID NO: 123, SEQ ID NO: 117, SEQ ID NO: 122, SEQ ID NO: 59, SEQ ID NO: 116, SEQ ID NO: 19, SEQ ID NO: 70, SEQ ID NO: 87, SEQ ID NO: 49, SEQ ID NO: 68, SEQ ID NO: 97, SEQ ID NO: 104, SEQ ID NO: 103, SEQ ID NO: 48, SEQ ID NO:72, SEQ ID NO: 73, SEQ ID NO: 77, SEQ ID NO: 71, SEQ ID NO: 84, SEQ ID NO: 126, SEQ ID NO: 134, SEQ ID NO: 135, SEQ ID NO: 136, SEQ ID NO: 151, SEQ ID NO: 152, SEQ ID NO: 153, SEQ ID NO: 154, SEQ ID NO: 155, SEQ ID NO: 156, and SEQ ID NO: 157.

20. The method of claim 1, further comprising determining the number of cysteine residues in, the presence of clustered prolines in, the requirement of an N terminal methionine for activity of, or the presence of a small amino acid in the plus two position of, the heterologous recombinant protein.

21. The method of claim 20, wherein when the heterologous recombinant protein has more than two cysteine residues, at least one of said at least 2 different expression systems overexpressing a folding modulator overexpresses a disulfide isomerase/oxidoreductase.

22. The method of claim 21, wherein the disulfide isomerase/oxidoreductase is encoded on a plasmid.

23. The method of claim 20, wherein when the heterologous recombinant protein has more than four cysteine residues, at least one of said at least 2 different expression vectors encoding the heterologous recombinant protein contains a periplasmic secretion leader coding sequence.

24. The method of claim 20, wherein when the heterologous recombinant protein has more than four cysteine residues, at least one of said at least 2 different expression vectors encoding the heterologous recombinant protein contains a high or medium ribosome binding sequence.

25. The method of claim 23, further wherein said at least one of said at least 2 different expression vectors encoding the heterologous recombinant protein and containing a periplasmic secretion leader coding sequence is included in at least one expression system that overexpresses at least one periplasmic chaperone, and at least one expression system that overexpresses at least one cytoplasmic chaperone.

26. The method of claim 20, wherein when the heterologous protein has fewer than four cysteine residues, at least one of said at least 2 different expression vectors encoding the heterologous recombinant protein does not contain a periplasmic secretion leader coding sequence, and further wherein said at least one of said at least 2 different expression vectors encoding the heterologous recombinant protein and not containing a periplasmic secretion leader coding sequence is included in at least one expression system that overexpresses at least one cytoplasmic chaperone.

27. The method of claim 20, wherein when clustered prolines are present, at least one expression system that overexpresses at least one 2+ peptidyl-prolyl cis-trans isomerase (PPIase) is included in the array.

28. The method of claim 27, wherein the 2+ peptidyl-prolyl cis-trans isomerase (PPIase) is encoded on a plasmid.

29. The method of claim 20, wherein when the N-terminal methionine is required, at least one expression system comprising a host cell population that has at least one defect in at least one host cell methionyl amino peptidase, is included in the array.

30. The method of claim 20 wherein when a small amino acid is present in the plus two position of the heterologous recombinant protein, at least one expression system comprising a host cell population that has at least one defect in at least one amino peptidase, is included in the array.

31. The method of claim 20, wherein the small amino acid is selected from the group consisting of: glycine, alanine, valine, serine, threonine, aspartic acid, asparagine, and proline.

32. The method of claim 1, wherein the heterologous recombinant protein is selected from the group consisting of: a toxin; a cytokine, growth factor or hormone, or receptor thereof; an antibody or antibody derivative; a human therapeutic protein or therapeutic enzyme; a non-natural protein or a fusion protein; a chaperone; a pathogen protein or pathogen-derived antigen; a lipoprotein; a reagent protein; and a biocatalytic enzyme.

33. The method of claim 32, wherein the toxin is a vertebrate or invertebrate animal toxin, a plant toxin, a bacterial toxin, a fungal toxin, or variant thereof.

34. The method of claim 32, wherein the antibody or antibody derivative is a humanized antibody, modified antibody, nanobody, bispecific antibody, single-chain antibody, Fab, Domain antibody, shark single domain antibody, camelid single domain antibody, linear antibody, diabody, or BiTE molecule.

35. The method of claim 1, wherein at least 10% of the heterologous recombinant protein is insoluble when expressed in an indicator strain, or wherein the heterologous recombinant protein is predicted to be insoluble using a protein solubility prediction tool.

36. The method of claim 8, wherein the yield of the heterologous recombinant protein is a measure of the amount of soluble heterologous recombinant protein, the amount of recoverable heterologous recombinant protein, the amount of properly processed heterologous recombinant protein, the amount of properly folded heterologous recombinant protein, the amount of active heterologous recombinant protein, and/or the total amount of heterologous recombinant protein.

37. The method of claim 1, wherein at least one of said at least 2 different expression vectors encodes a periplasmic secretion leader sequence operably linked to the heterologous recombinant protein.

38. The method of claim 1, wherein the overexpression is a yield of the heterologous recombinant protein of about 10 mg/ml to about 25 mg/ml in the periplasmic compartment of the host cell of the at least one nonidentical test expression system.

* * * * *